US007767418B2

(12) United States Patent
Lee et al.

(10) Patent No.: US 7,767,418 B2
(45) Date of Patent: Aug. 3, 2010

(54) POLYNUCLEOTIDE ENCODING A NOVEL TRP CHANNEL FAMILY MEMBER, LTRPC3, AND SPLICE VARIANTS THEREOF

(75) Inventors: Ning Lee, Hillsborough, NJ (US); Jian Chen, Princeton, NJ (US); John N. Feder, Belle Mead, NJ (US); Shujian Wu, Langhorne, PA (US); Liana M. Lee, San Francisco, CA (US); Michael A. Blanar, Malvern, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 81 days.

(21) Appl. No.: 12/152,547

(22) Filed: May 15, 2008

(65) Prior Publication Data

US 2008/0274505 A1 Nov. 6, 2008

Related U.S. Application Data

(63) Continuation-in-part of application No. 10/210,152, filed on Aug. 1, 2002, now abandoned.

(60) Provisional application No. 60/309,544, filed on Aug. 2, 2001.

(51) Int. Cl.
*C12P 21/06* (2006.01)
*C12N 15/00* (2006.01)
*C07K 1/00* (2006.01)
*C07H 21/02* (2006.01)

(52) U.S. Cl. .................... 435/69.1; 536/23.1; 536/23.6; 435/320.1; 530/350

(58) Field of Classification Search ........................ None
See application file for complete search history.

(56) References Cited

U.S. PATENT DOCUMENTS

| 7,344,882 B2 | 3/2008 | Lee et al. |
| 2004/0229315 A1 | 11/2004 | Lee et al. |

FOREIGN PATENT DOCUMENTS

| WO | WO 01/32870 | 5/2001 |
| WO | WO02/46415 A2 | 6/2002 |
| WO | WO 02/077237 | 10/2002 |
| WO | WO03/012063 A2 | 3/2003 |

OTHER PUBLICATIONS

NCBI Entrez Accession No. gi|NP_066003, Grimm, C. et al., Dec. 21, 2003.
NCBI Entrez Accession No. gi|26336493, Carninci, P. et al., Dec. 5, 2002.
NCBI Entrez Accession No. gi|27597205, Okabayashi, K. et al., Jan. 10, 2003.
NCBI Entrez Accession No. gi|28626249, Lee, N. et al., Jun. 3, 2003.
Carninci, P. et al., "High-Efficiency Full-Length cDNA Cloning", Methods in Enzymology, vol. 303, pp. 19-44 (1999).
Carninci, P. et al., "Normalization and Subtraction of Cap-Trapper-Selected cDNAs to Prepare Full-Length cDNA Libraries for Rapid Discovery of New Genes", Genome Research, vol. 10, pp. 1617-1630 (2000).
Lee, N. et al., "Expression and Characterization of Human Transient Receptor Potential Melastatin 3 (hTRPM3)", The Journal of Biological Chemistry, vol. 278, No. 23, pp. 20890-20897 (2003).
Nagase, T. et al., "Prediction of the Coding Sequences of Unidentified Human Genes. XVIII. The Complete Sequences of 100 New cDNA Clones from Brain Which Code for Large Proteins in vitro", DNA Research, vol. 7, pp. 273-281 (2000).
Shibata, K. et al., "RIKEN Integrated Sequence Analysis (RISA) System—384-Format Sequencing Pipeline with 384 Multicapillary Sequencer", Genome Research, vol. 10, pp. 1757-1771 (2000).
The FANTOM Consortium and the RIKEN Genome Exploration Research Group Phase I & II Team, "Analysis of the mouse transcriptome based on functional annotation of 60,770 full-length cDNAs", Nature, vol. 420, pp. 563-573 (2002).
The RIKEN Genome Exploration Research Group Phase II Team and the FANTOM Consortium, "Functional annotation of a full-length mouse cDNA collection", Nature, vol. 409, pp. 685-690 (2001).
Wiemann, S. et al., "Toward a Catalog of Human Genes and Proteins: Sequencing and Analysis of 500 Novel Complete Protein Coding Human cDNAs", Genome Research, vol. 11, pp. 422-435 (2001).
Jin, et al., The 3'→5' exonuclease of DNA polymerase δ can substitute for the 5' flap endonuclease Rad27/Fen1 in processing Okazaki fragments and preventing genome instability, PNAS, vol. 98(9), pp. 5122-5127 (2001).
Negritto, et al., "Novel Function of Rad27 (FEN-1) in Restricting Short-Sequence Recombination", Molec. Cell. Biol., vol. 21(7), pp. 2349-2358 (2001).
Stucki, et al., "In Eukaryotic Flap Endonuclease 1, the C Terminus Is Essential for Substrate Binding", J. Biol Chem., vol. 276(11), pp. 7843-7849 (2001).
Tom, et al., "Mechanism Whereby Proliferating Cell Nuclear Antigen Stimulates Flap Endonuclease 1", J. of Biol. Chem., vol. 275(14), pp. 10498-10505 (2000).
Oberwinkler, et al., "Alternative Splicing Switches the Divalent Cation Selectivity of TRPM3 Channels", J. Biol. Chem., vol. 280(23), pp. 22540-22548, 2005.
NCBI Entrez Accession No. Q9HCF6 (gi:59803113), Grimm, et al., Oct. 17, 2006.

(Continued)

*Primary Examiner*—Olga N Chernyshev
(74) *Attorney, Agent, or Firm*—Stephen C. D'Amico

(57) ABSTRACT

The present invention provides novel polynucleotides encoding LTRPC3 polypeptides, fragments and homologues thereof. The present invention also provides polynucleotides encoding variants and splice variants of LTRPC3 polypeptides, LTRPC3b, LTRPC3c, LTRPC3d, LTRPC3e, and LTRPC3f, respectively. Also provided are vectors, host cells, and recombinant and synthetic methods for producing said polypeptides. The invention further relates to diagnostic and therapeutic methods for applying these novel LTRPC3, LTRPC3b, LTRPC3c, LTRPC3d, LTRPC3e, and LTRPC3f polypeptides to the diagnosis, treatment, and/or prevention of various diseases and/or disorders related to these polypeptides. The invention further relates to screening methods for identifying agonists and antagonists of the polynucleotides and polypeptides of the present invention.

16 Claims, 53 Drawing Sheets

Figure 6:
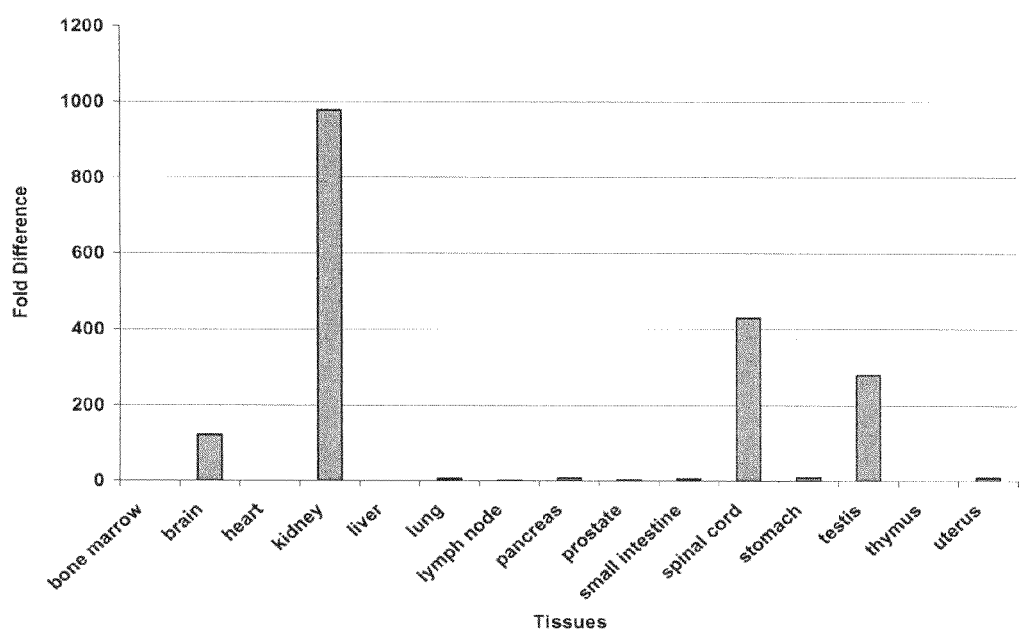

(2 of 53 Drawing Sheet(s) Filed in Color)

OTHER PUBLICATIONS

NCBI Entrez Accession No. AF536749 (gi:28626248), Lee, et al., Jun. 3, 2003.
NCBI Entrez Accession No. AB099661 (gi:27597204), Okabayashi, et al., Jan. 10, 2003.
Grimm, et al., "Activation of the Melastatin-Related Cation Channel TRPM3 by D-*erythro*-Sphingosine", Molecular Pharm., vol. 67 (3), pp. 798-805 (2005).
Grimm, et al., "Molecular and Functional Characterization of the Melastatin-related Cation Channel TRPM3", JBC, vol. 278 (24), pp. 21493-21501 (2003).
Tishkoff, et al., "A Novel Mutation Avoidance Mechanism Dependent on *S. cerevisiae RAD27* is Distinct from DNA Mismatch Repair", Cell, vol. 88, pp. 253-263 (1997).
Umar, et al., "DNA-replication fidelity, mismatch repair and genome instability in cancer cells", Eur. J. Biochem., vol. 238, pp. 297-307 (1996).
Ma, et al., "Single Nucleotide Polymorphism Analyses of the Human Proliferating Cell Nuclear Antigen (PCNA) and Flap Endonuclease (FEN1) Genes", Int. J. Cancer, vol. 88, pp. 938-942 (2000).
Henricksen, et al., "Inhibition of Flap Endonuclease 1 by Flap Secondary Structure and Relevance to Repeat Sequence Expansion", JBC, vol. 275 (22), pp. 16420-16427 (2000).
NCBI Entrez Accession No. AJ505026 (gi:30141362), Grimm, et al., Apr. 15, 2005.
Hosfieled et al., Prog. Nucleic Acid Res. Mol. Biol., vol. 68, pp. 315-347 (2001).
Skolnick, et al., TIBTECh, vol. 18, pp. 34-39 (2000).
Bork, et al., Curr. Opin. Struc. Biol., vol. 8, pp. 331-332 (1998).
Duncan, et al., "Down-Regulation of the Novel Gene Melastatin Correlates with Potential for Melanoma Metastasis", Cancer Research, vol. 58, pp. 1515-1520 (1998).
Hara, et al., "LTRPC2 $Ca^{2+}$-Permeable Channel Activated by Changes in Redox Status Confers Susceptibility to Cell Death", Molecular Cell., vol. 9, pp. 163-173 (2002).
Heymann, et al., "Conformations of the rhodopsin third cytoplasmic loop grafted onto bacteriorhodopsin", Neuron (Structure), vol. 8(6), pp. 643-653 (2000).
Harteneck, et al., "From worm to man: three subfamilies of TRP channels", TINS, vol. 23 (4), pp. 159-166 (2000).
Hendricksen, et al., "Inhibition of Flap Endonuclease 1 by Flap Secondary Structure and Relevance to Repeat Sequence Expansion", J. of Biol. Chem., vol. 275 (22) pp. 16420-16427 (2000).
Launay, et al., "TRPM4 Is a $Ca^{2+}$-Activated Nonselective Cation Channel Mediating Cell Membrane Depolarization", Cell, vol. 109, pp. 397-407 (2002).
Ma, et al., "Single Nucleotide Polymorphism Analyses of the Human Proliferating Cell Nuclear Antigen (PCNA) and Flap Endonuclease (FEN1) Genes", Int. J. Cancer, vol. 88, pp. 938-942 (2000).
McKemy, et al., "Identification of a cold receptor reveals a general role for TRP channels in thermosensation", Nature, vol. 416, pp. 52-58 (2002).
Montell, et al., "A Unified Nomenclature for the Superfamily of TRP Cation Channels", Molecular Cell, vol. 9, pp. 229-231 (2002).
Nadler, et al., "LTRPC7 is a Mg-ATP- regulated divalent cation channel required for cell viability", Nature, vol. 411, pp. 590-595 (2001).
Nagamine, et al., "Molecular Cloning of a Novel Putative $Ca^{2+}$ Channel Protein (TRPC7) Highly Expressed in Brain", Genomics, vol. 54, pp. 124-131 (1988).
Okazaki, et al., "Analysis of the mouse transcriptome based on functional annotation of 60,770 full-length cDNAs", Nature, vol. 420, pp. 563-573 (2002).
Peier, et al., "A TRP Channel that Senses Cold Stimuli and Menthol", Cell, vol. 108, pp. 705-715 (2002).
Perraud, et al., "ADP-ribose gating of the calcium-permeable LTRPC2 channel revealed by Nudix motif homology", Nature, vol. 411, pp. 595-599 (2001).
Philipp, et al., "A novel capacitative calcium entry channel expressed in excitable cells", EMBO J., vol. 17(15), pp. 4274-4282 (1998).
Prasad, et al., "FEN1 Stimulation of DNA Polymerase β Mediates an Excision Step in Mammalian Long Patch Base Excision Repair", J. Biol. Chem., vol. 275(6), pp. 4460-4466 (2000).
Runnels, et al., "The TRPM7 channel is inactivated by $PIP_2$ hydrolysis", Nature Cell Biol., vol. 4, pp. 329-336 (2002).
Runnels, et al., "TRP-PLIK, a Bifunctional Protein with Kinase and Ion Channel Activities", Science, vol. 291, pp. 1043-1047 (2001).
Sano, et al., "Immunocyte $Ca^{2+}$ Influx System Mediated by LTRPC2", Science, vol. 293, pp. 1327-1330 (2001).
Silve, et al., "The Immunosuppressant SR 31747 Blocks Cell Proliferation by Inhibiting a Steriod Isomerase in *Saccharomyces cerevisiae*", Molecular Cell Biol., vol. 16(6), pp. 2719-2727 (1996).
Tsavaler, et al., "Trp-p8, a Novel Prostate-specific Gene, Is Up-Regulated in Prostate Cancer and Other Malignancies and Shares High Homology with Transient Receptor Potential Calcium Channel Proteins", Cancer Research, vol. 61, pp. 3760-3769 (2001).
Xu, et al., "Regulation of melastatin, a TRP-related protein, through interaction with a cystoplasmic isoform", PNAS, vol. 98(19), pp. 10692-10697 (2001).
Warbrick, et al., "FEN1 Expression: A Novel Marker for Cell Proliferation", J. of Pathology, vol. 186, pp. 319-324 (1998).
NCBI Entrez Accession. No. AL358786 (gi:13990071), G. Laird, May 2, 2001.
NCBI Entrez Accession No. AAB50622 (gi:1911245, H. Sakura, Mar. 27, 1997.
NCBI Entrez Accession No. AAC06146 (gi:2979524), Boulay, et al., Mar. 20, 1998.
NCBI Entrez Accession No. AAD10167 (gi:4200415), Zhu, et al., Jan. 28, 1999.
NCBI Entrez Accession No. AAD17196 (gi:4324938), Vannier, et al., Mar. 15, 1999.
NCBI Entrez Accession No. AAD42069 (gi:5326854), Okada, et al., Sep. 21, 1999.
NCBI Entrez Accession No. AAF02200 (gi:6048344), Zhu, et al., Oct. 16, 1999.
NCBI Entrez Accession No. AAF01468 (gi:6014703), Mori, et al., Oct. 7, 1999.
NCBI Entrez Accession No. AAF01468 (gi:7328583), Walker, et al., Mar. 25, 2000.
NCBI Entrez Accession No. CAC14420 (gi:11065673), J.E. Sulston., Oct. 12, 2004.
NCBI Entrez Accession No. NP_113747 (gi:13928756), Napal, et al., Aug. 21, 2004.
NCBI Entrez Accession No. NT_008306 (gi:14740344), NCBI Annotation Project, Jul. 16, 2001.

Fig. 1A

```
  1  atgtatgtgcgagtatcttttgatacaaaacctgatctcctcttacacctgatgaccaag   60
  1  M  Y  V  R  V  S  F  D  T  K  P  D  L  L  L  H  L  M  T  K    20

61  gaatggcagttggagcttcccaagcttctcatctctgtccatggggcctgcagaacttt   120
 21  E  W  Q  L  E  L  P  K  L  L  I  S  V  H  G  G  L  Q  N  F    40

121  gaactccagccaaaactcaagcaagtctttgggaagggctcatcaaagcagcaatgaca   180
 41  E  L  Q  P  K  L  K  Q  V  F  G  K  G  L  I  K  A  A  M  T    60

181  actggagcgtggatattcactggagggggttaacacaggtgttattcgtcatgttggcgat  240
 61  T  G  A  W  I  F  T  G  G  V  N  T  G  V  I  R  H  V  G  D    80

241  gccttgaaggatcatgcctctaagtctcgaggaaagatatgcaccataggtattgcccc   300
 81  A  L  K  D  H  A  S  K  S  R  G  K  I  C  T  I  G  I  A  P   100

301  tggggaattgtggaaaaccaggaggacctcattggaagagatgttgtccggccataccag  360
101  W  G  I  V  E  N  Q  E  D  L  I  G  R  D  V  V  R  P  Y  Q   120

361  accatgtccaatcccatgagcaagctcactgttctcaacagcatgcattcccacttcatt  420
121  T  M  S  N  P  M  S  K  L  T  V  L  N  S  M  H  S  H  F  I   140

421  ctggctgacaacgggaccactggaaaatatggagcagaggtgaaacttcgaagacaactg  480
141  L  A  D  N  G  T  T  G  K  Y  G  A  E  V  K  L  R  R  Q  L   160

481  gaaaagcatatttcactccagaagataaacacaagaatcggtcaaggtgttcctgtggtg  540
161  E  K  H  I  S  L  Q  K  I  N  T  R  I  G  Q  G  V  P  V  V   180

541  gcactcatagtggaaggaggacccaatgtgatctcgattgttttggagtaccttcgagac  600
181  A  L  I  V  E  G  G  P  N  V  I  S  I  V  L  E  Y  L  R  D   200

601  acccctcccgtgccagtggttgtctgtgatgggagtggacgggcatcggacatcctggcc  660
201  T  P  P  V  P  V  V  V  C  D  G  S  G  R  A  S  D  I  L  A   220

661  tttgggcataaatactcagaagaaggcggactgataaatgaatctttgagggaccagctg  720
221  F  G  H  K  Y  S  E  E  G  G  L  I  N  E  S  L  R  D  Q  L   240

721  ttggtgactatacagaagactttcacatacactcgaacccaagctcagcatctgttcatc  780
241  L  V  T  I  Q  K  T  F  T  Y  T  R  T  Q  A  Q  H  L  F  I   260

781  atcctcatggagtgcatgaagaagaaggaattgattacggtatttcggatgggatcagaa  840
261  I  L  M  E  C  M  K  K  K  E  L  I  T  V  F  R  M  G  S  E   280

841  ggacaccaggacattgatttggctatcctgacagctttactcaaaggagccaatgcctcg  900
281  G  H  Q  D  I  D  L  A  I  L  T  A  L  L  K  G  A  N  A  S   300
```

Fig. 1B

```
 901  gccccagaccaactgagcttagctttagcctggaacagagtcgacatcgctcgcagccag  960
 301   A  P  D  Q  L  S  L  A  L  A  W  N  R  V  D  I  A  R  S  Q   320

961  atctttatttacgggcaacagtggccggtgggatctctggagcaagccatgttggatgcc  1020
 321   I  F  I  Y  G  Q  Q  W  P  V  G  S  L  E  Q  A  M  L  D  A   340

1021  ttagttctggacagagtggattttgtgaaattactcatagagaatggagtaagcatgcac  1080
 341   L  V  L  D  R  V  D  F  V  K  L  L  I  E  N  G  V  S  M  H   360

1081  cgttttctcaccatctccagactagaggaattgtacaatacgagacatgggccctcaaat  1140
 361   R  F  L  T  I  S  R  L  E  E  L  Y  N  T  R  H  G  P  S  N   380

1141  acattgtaccacttggtcagggatgtcaaaaaggggaacctgcccccagactacagaatc  1200
 381   T  L  Y  H  L  V  R  D  V  K  K  G  N  L  P  P  D  Y  R  I   400

1201  agcctgattgacatcggcctggtgatcgagtacctgatgggcggggcttatcgctgcaac  1260
 401   S  L  I  D  I  G  L  V  I  E  Y  L  M  G  G  A  Y  R  C  N   420

1261  tacacgcgcaagcgcttccggacccctctaccacaacctcttcggccccaagaggcccaaa  1320
 421   Y  T  R  K  R  F  R  T  L  Y  H  N  L  F  G  P  K  R  P  K   440

1321  gccttgaaactgctgggaatggaggatgatattcccttgaggcgaggaagaaagacaacc  1380
 441   A  L  K  L  L  G  M  E  D  D  I  P  L  R  R  G  R  K  T  T   460

1381  aagaaacgtgaagaagaggtggacattgacttggatgatcctgagatcaaccacttcccc  1440
 461   K  K  R  E  E  E  V  D  I  D  L  D  D  P  E  I  N  H  F  P   480

1441  ttccctttccatgagctcatggtgtgggctgttctcatgaagcggcagaagatggccctg  1500
 481   F  P  F  H  E  L  M  V  W  A  V  L  M  K  R  Q  K  M  A  L   500

1501  ttcttctggcagcacggtgaggaggccatggccaaggccctggtggcctgcaagctctgc  1560
 501   F  F  W  Q  H  G  E  E  A  M  A  K  A  L  V  A  C  K  L  C   520

1561  aaagccatggctcatgaggcctctgagaacgacatggttgacgacatttcccaggagctg  1620
 521   K  A  M  A  H  E  A  S  E  N  D  M  V  D  D  I  S  Q  E  L   540

1621  aatcacaattccagagactttggccagctggctgtggagctcctggaccagtcctacaag  1680
 541   N  H  N  S  R  D  F  G  Q  L  A  V  E  L  L  D  Q  S  Y  K   560

1681  caggacgaacagctggccatgaaactgctgacgtatgagctgaagaactggagcaacgcc  1740
 561   Q  D  E  Q  L  A  M  K  L  L  T  Y  E  L  K  N  W  S  N  A   580

1741  acgtgcctgcagcttgccgtggctgccaaacaccgcgacttcatcgcgcacacgtgcagc  1800
 581   T  C  L  Q  L  A  V  A  A  K  H  R  D  F  I  A  H  T  C  S   600
```

Fig. 1C

```
1801 cagatgctgctcaccgacatgtggatgggccggctccgcatgcgcaagaactcaggcctc 1860
 601  Q  M  L  L  T  D  M  W  M  G  R  L  R  M  R  K  N  S  G  L   620

1861 aaggtaattctgggaattctacttcctccttcaattctcagcttggagttcaagaacaaa 1920
 621  K  V  I  L  G  I  L  L  P  P  S  I  L  S  L  E  F  K  N  K   640

1921 gacgacatgccctatatgtctcaggcccaggaaatccacctccaagagaaggaggcagaa 1980
 641  D  D  M  P  Y  M  S  Q  A  Q  E  I  H  L  Q  E  K  E  A  E   660

1981 gaaccagagaagcccacaaaggaaaaagaggaagaggacatggagctcacagcaatgttg 2040
 661  E  P  E  K  P  T  K  E  K  E  E  D  M  E  L  T  A  M  L      680

2041 ggacgaaacaacggggagtcctccaggaagaaggatgaagaggaagttcagagcaagcac 2100
 681  G  R  N  N  G  E  S  S  R  K  K  D  E  E  E  V  Q  S  K  H   700

2101 cggttaatccccctcggcagaaaaatctatgaattctacaatgcacccatcgtgaagttc 2160
 701  R  L  I  P  L  G  R  K  I  Y  E  F  Y  N  A  P  I  V  K  F   720

2161 tggttctacacactggcgtatatcggatacctgatgctcttcaactatatcgtgttagtg 2220
 721  W  F  Y  T  L  A  Y  I  G  Y  L  M  L  F  N  Y  I  V  L  V   740

2221 aagatggaacgctggccgtccacccaggaatggatcgtaatctcctatatttttcaccctg 2280
 741  K  M  E  R  W  P  S  T  Q  E  W  I  V  I  S  Y  I  F  T  L   760

2281 ggaatagaaaagatgagagagattctgatgtcagagccagggaagttgctacagaaagtg 2340
 761  G  I  E  K  M  R  E  I  L  M  S  E  P  G  K  L  L  Q  K  V   780

2341 aaggtatggctgcaggagtactggaatgtcacggacctcatcgccatcctctgttttct 2400
 781  K  V  W  L  Q  E  Y  W  N  V  T  D  L  I  A  I  L  L  F  S   800

2401 gtcggaatgatccttcgtctccaagaccagcccttcaggagtgacgggagggtcatctac 2460
 801  V  G  M  I  L  R  L  Q  D  Q  P  F  R  S  D  G  R  V  I  Y   820

2461 tgcgtgaacatcatttactggtatatccgtctcctagacatcttcggcgtgaacaagtat 2520
 821  C  V  N  I  I  Y  W  Y  I  R  L  L  D  I  F  G  V  N  K  Y   840

2521 ttgggcccgtatgtaatgatgattggaaaaatgatgatagacatgatgtactttgtcatc 2580
 841  L  G  P  Y  V  M  M  I  G  K  M  M  I  D  M  M  Y  F  V  I   860

2581 attatgctggtggttctgatgagctttggggtcgccaggcaagccatccttttttcccaat 2640
 861  I  M  L  V  V  L  M  S  F  G  V  A  R  Q  A  I  L  F  P  N   880

2641 gaggagccatcatggaaactggccaagaacatcttctacatgccctattggatgatttat 2700
 881  E  E  P  S  W  K  L  A  K  N  I  F  Y  M  P  Y  W  M  I  Y   900
```

Fig. 1D

```
2701  ggggaagtgtttgcggaccagatagaccctccctgtggacagaatgagacccgagaggat  2760
901   G  E  V  F  A  D  Q  I  D  P  P  C  G  Q  N  E  T  R  E  L   920

2761  ggtaaaataatccagctgcctcccctgcaagacaggagcttggatcgtgccggccatcatg  2820
921   G  K  I  I  Q  L  P  P  C  K  T  G  A  W  I  V  P  A  I  M   940

2821  gcctgctacctcttagtggcaaacatcttgctggtcaacctcctcattgctgtctttaac  2880
941   A  C  Y  L  L  V  A  N  I  L  L  V  N  L  L  I  A  V  F  N   960

2881  aatacatttttgaagtaaaatcgatatccaaccaagtctggaagtttcagaggtatcag  2940
961   N  T  F  F  E  V  K  S  I  S  N  Q  V  W  K  F  Q  R  Y  Q   980

2941  ctcatcatgactttccatgaaaggccagttctgccccaccactgatcatcttcagccac  3000
981   L  I  M  T  F  H  E  R  P  V  L  P  P  P  L  I  I  F  S  H   1000

3001  atgaccatgatattccagcacctgtgctgccgatggaggaaacacgagagcgacccggat  3060
1001  M  T  M  I  F  Q  H  L  C  C  R  W  R  K  H  E  S  D  P  D   1020

3061  gaaagggactacggcctgaaactcttcataaccgatgatgagctcaagaaagtacatgac  3120
1021  E  R  D  Y  G  L  K  L  F  I  T  D  D  E  L  K  K  V  H  D   1040

3121  tttgaagagcaatgcatagaagaatacttcagagaaaaggatgatcggttcaactcatct  3180
1041  F  E  E  Q  C  I  E  E  Y  F  R  E  K  D  D  R  F  N  S  S   1060

3181  aatgatgagaggatacgggtgacttcagaaagggtggagaacatgtctatgcggctggag  3240
1061  N  D  E  R  I  R  V  T  S  E  R  V  E  N  M  S  M  R  L  E   1080

3241  gaagtcaacgagagagagcactccatgaaggcttcactccagaccgtggacatccggctg  3300
1081  E  V  N  E  R  E  H  S  M  K  A  S  L  Q  T  V  D  I  R  L   1100

3301  gcgcagctggaagaccttatcgggcgcatggccacggccctggagcgcctgacaggtctg  3360
1101  A  Q  L  E  D  L  I  G  R  M  A  T  A  L  E  R  L  T  G  L   1120

3361  gagcgggccgagtccaacaaaatccgctcgaggacctcgtcagactgcacggacgccgcc  3420
1121  E  R  A  E  S  N  K  I  R  S  R  T  S  S  D  C  T  D  A  A   1140

3421  tacattgtccgtcagagcagcttcaacagccaggaagggaacaccttcaagctccaagag  3480
1141  Y  I  V  R  Q  S  S  F  N  S  Q  E  G  N  T  F  K  L  Q  E   1160

3481  agtatagaccctgcaggtgaggagaccatgtccccaacttctccaaccttaatgccccgt  3540
1161  S  I  D  P  A  G  E  E  T  M  S  P  T  S  P  T  L  M  P  R   1180

3541  atgcgaagccattctttctattcagtcaatatgaaagacaaaggtggtatagaaaagttg  3600
1181  M  R  S  H  S  F  Y  S  V  N  M  K  D  K  G  G  I  E  K  L   1200
```

Fig. 1E

```
3601  gaaagtattttttaaagaaaggtccctgagcctacaccgggctactagttcccactctgta  3660
1201  E   S   I   F   K   E   R   S   L   S   L   H   R   A   T   S   S   H   S   V   1220

3661  gcaaaagaacccaaagctcctgcagcccctgccaacaccttggccattgttcctgattcc  3720
1221  A   K   E   P   K   A   P   A   A   P   A   N   T   L   A   I   V   P   D   S   1240

3721  agaagaccatcatcgtgtatagacatctatgtctctgctatggatgagctccactgtgat  3780
1241  R   R   P   S   S   C   I   D   I   Y   V   S   A   M   D   E   L   H   C   D   1260

3781  atagaccctctggacaattccgtgaacatccttgggctaggcgagccaagcttttcaact  3840
1261  I   D   P   L   D   N   S   V   N   I   L   G   L   G   E   P   S   F   S   T   1280

3841  ccagtaccttccacagcccttcaagtagtgcctatgcaacacttgcacccacagacaga  3900
1281  P   V   P   S   T   A   P   S   S   S   A   Y   A   T   L   A   P   T   D   R   1300

3901  cctccaagccggagcattgattttgaggacatcacctccatggacactagatcttttct  3960
1301  P   P   S   R   S   I   D   F   E   D   I   T   S   M   D   T   R   S   F   S   1320

3961  tcagactacacccacctcccagaatgccaaaacccctgggactcagagcctccgatgtac  4020
1321  S   D   Y   T   H   L   P   E   C   Q   N   P   W   D   S   E   P   P   M   Y   1340

4021  cacaccattgagcgttccaaaagtagccgctacctagccaccacacccttcttctagaa  4080
1341  H   T   I   E   R   S   K   S   S   R   Y   L   A   T   T   P   F   L   L   E   1360

4081  gaggctcccattgtgaaatctcatagctttatgttttcccctcaaggagctattatgcc  4140
1361  E   A   P   I   V   K   S   H   S   F   M   F   S   P   S   R   S   Y   Y   A   1380

4141  aactttggggtgcctgtaaaaacagcagaatacacaagtattacagactgtattgacaca  4200
1381  N   F   G   V   P   V   K   T   A   E   Y   T   S   I   T   D   C   I   D   T   1400

4201  aggtgtgtcaatgcccctcaagcaattgcggacagagctgccttccctggaggtcttgga  4260
1401  R   C   V   N   A   P   Q   A   I   A   D   R   A   A   F   P   G   G   L   G   1420

4261  gacaaagtggaggacttaacttgctgccatccagagcgagaagcagaactgagtcacccc  4320
1421  D   K   V   E   D   L   T   C   C   H   P   E   R   E   A   E   L   S   H   P   1440

4321  agctctgacagtgaggagaatgaggccaaaggccgcagagccaccattgcaatatcctcc  4380
1441  S   S   D   S   E   E   N   E   A   K   G   R   R   A   T   I   A   I   S   S   1460

4381  caggagggtgataactcagagagaaccctgtccaacaacatcactgttcccaagatagag  4440
1461  Q   E   G   D   N   S   E   R   T   L   S   N   N   I   T   V   P   K   I   E   1480

4441  cgcgccaacagctactcggcagaggagccaagtgcgccatatgcacacaccaggaagagc  4500
1481  R   A   N   S   Y   S   A   E   E   P   S   A   P   Y   A   H   T   R   K   S   1500
```

Fig. 1F

```
4501  ttctccatcagtgacaaactcgacaggcagcggaacacagcaagcctgcaaaatcccttc  4560
1501   F  S  I  S  D  K  L  D  R  Q  R  N  T  A  S  L  Q  N  P  F   1520

4561  cagagaagcaagtcctccaagccggagggccgagggacagcctgtccatgaggagactg  4620
1521   Q  R  S  K  S  S  K  P  E  G  R  G  D  S  L  S  M  R  R  L   1540

4621  tccagaacatcggctttccaaagctttgaaagcaagcacacctaa  4665
1541   S  R  T  S  A  F  Q  S  F  E  S  K  H  T         1554
```

Fig. 2A

```
  1 atgtatgtgcgagtatcttttgatacaaaacctgatctcctcttacacctgatgaccaag   60
  1  M  Y  V  R  V  S  F  D  T  K  P  D  L  L  L  H  L  M  T  K    20

61 gaatggcagttggagcttcccaagcttctcatctctgtccatggggcctgcagaacttt  120
 21  E  W  Q  L  E  L  P  K  L  L  I  S  V  H  G  G  L  Q  N  F    40

121 gaactccagccaaaactcaagcaagtctttgggaaagggctcatcaaagcagcaatgaca  180
 41  E  L  Q  P  K  L  K  Q  V  F  G  K  G  L  I  K  A  A  M  T    60

181 actggagcgtggatattcactggaggggttaacacaggtgttattcgtcatgttggcgat  240
 61  T  G  A  W  I  F  T  G  G  V  N  T  G  V  I  R  H  V  G  D    80

241 gccttgaaggatcatgcctctaagtctcgaggaaagatatgcaccataggtattgccccc  300
 81  A  L  K  D  H  A  S  K  S  R  G  K  I  C  T  I  G  I  A  P   100

301 tggggaattgtggaaaaccaggaggacctcattggaagagatgttgtccggccataccag  360
101  W  G  I  V  E  N  Q  E  D  L  I  G  R  D  V  V  R  P  Y  Q   120

361 accatgtccaatcccatgagcaagctcactgttctcaacagcatgcattcccacttcatt  420
121  T  M  S  N  P  M  S  K  L  T  V  L  N  S  M  H  S  H  F  I   140

421 ctggctgacaacgggaccactggaaaatatggagcagaggtgaaacttcgaagacaactg  480
141  L  A  D  N  G  T  T  G  K  Y  G  A  E  V  K  L  R  R  Q  L   160

481 gaaaagcatatttcactccagaagataaacacaagaatcggtcaaggtgttcctgtggtg  540
161  E  K  H  I  S  L  Q  K  I  N  T  R  I  G  Q  G  V  P  V  V   180

541 gcactcatagtggaaggaggacccaatgtgatctcgattgttttggagtaccttcgagac  600
181  A  L  I  V  E  G  G  P  N  V  I  S  I  V  L  E  Y  L  R  D   200

601 accctcccgtgccagtggttgtctgtgatgggagtggacgggcatcggacatcctggcc  660
201  T  P  P  V  P  V  V  V  C  D  G  S  G  R  A  S  D  I  L  A   220

661 tttgggcataaatactcagaagaaggcggactgataaatgaatctttgagggaccagctg  720
221  F  G  H  K  Y  S  E  E  G  G  L  I  N  E  S  L  R  D  Q  L   240

721 ttggtgactatacagaagactttcacatacactcgaacccaagctcagcatctgttcatc  780
241  L  V  T  I  Q  K  T  F  T  Y  T  R  T  Q  A  Q  H  L  F  I   260

781 atcctcatggagtgcatgaagaagaaggaattgattacggtatttcggatgggatcagaa  840
261  I  L  M  E  C  M  K  K  K  E  L  I  T  V  F  R  M  G  S  E   280
```

Fig. 2B

```
 841 ggacaccaggacattgatttggctatcctgacagctttactcaaaggagccaatgcctcg  900
 281  G  H  Q  D  I  D  L  A  I  L  T  A  L  L  K  G  A  N  A  S   300

901 gccccagaccaactgagcttagctttagcctggaacagagtcgacatcgctcgcagccag  960
 301  A  P  D  Q  L  S  L  A  W  N  R  V  D  I  A  R  S  Q        320

961 atctttatttacgggcaacagtggccggtgggatctctggagcaagccatgttggatgcc 1020
 321  I  F  I  Y  G  Q  Q  W  P  V  G  S  L  E  Q  A  M  L  D  A   340

1021 ttagttctggacagagtggattttgtgaaattactcatagagaatggagtaagcatgcac 1080
 341  L  V  L  D  R  V  D  F  V  K  L  L  I  E  N  G  V  S  M  H   360

1081 cgttttctcaccatctccagactagaggaattgtacaatacgagacatgggccctcaaat 1140
 361  R  F  L  T  I  S  R  L  E  E  L  Y  N  T  R  H  G  P  S  N   380

1141 acattgtaccacttggtcagggatgtcaaaaagcgagagtatccaggtttcggttggatc 1200
 381  T  L  Y  H  L  V  R  D  V  K  K  R  E  Y  P  G  F  G  W  I   400

1201 tattttaaggggaacctgcccccagactacagaatcagcctgattgacatcggcctggtg 1260
 401  Y  F  K  G  N  L  P  P  D  Y  R  I  S  L  I  D  I  G  L  V   420

1261 atcgagtacctgatgggcggggcttatcgctgcaactacacgcgcaagcgcttccggacc 1320
 421  I  E  Y  L  M  G  G  A  Y  R  C  N  Y  T  R  K  R  F  R  T   440

1321 ctctaccacaacctcttcggccccaagagacccaaagccttgaaactgctgggaatggag 1380
 441  L  Y  H  N  L  F  G  P  K  R  P  K  A  L  K  L  L  G  M  E   460

1381 gatgatattcccttgaggcgaggaagaaagacaaccaagaaacgtgaagaagaggtggac 1440
 461  D  D  I  P  L  R  R  G  R  K  T  T  K  K  R  E  E  V  D      480

1441 attgacttggatgatcctgagatcaaccacttccccttcccttccatgagctcatggtg 1500
 481  I  D  L  D  D  P  E  I  N  H  F  P  F  P  F  H  E  L  M  V   500

1501 tgggctgttctcatgaagcggcagaagatggccctgttcttctggcagcacggtgaggag 1560
 501  W  A  V  L  M  K  R  Q  K  M  A  L  F  F  W  Q  H  G  E  E   520

1561 gccatggccaaggccctggtggcctgcaagctctgcaaagccatggctcatgaggcctct 1620
 521  A  M  A  K  A  L  V  A  C  K  L  C  K  A  M  A  H  E  A  S   540

1621 gagaacgacatggttgacgacatttcccaggagctgaatcacaattccagagactttggc 1680
 541  E  N  D  M  V  D  D  I  S  Q  E  L  N  H  N  S  R  D  F  G   560

1681 cagctggctgtggagctcctggaccagtcctacaagcaggacgaacagctggccatgaaa 1740
 561  Q  L  A  V  E  L  L  D  Q  S  Y  K  Q  D  E  Q  L  A  M  K   580
```

Fig. 2C

```
1741  ctgctgacgtatgagctgaagaactggagcaacgccacgtgcctgcagcttgccgtggct  1800
 581   L  L  T  Y  E  L  K  N  W  S  N  A  T  C  L  Q  L  A  V  A    600

1801  gccaaacaccgcgacttcatcgcgcacacgtgcagccagatgctgctcaccgacatgtgg  1860
 601   A  K  H  R  D  F  I  A  H  T  C  S  Q  M  L  L  T  D  M  W    620

1861  atgggccggctccgcatgcgcaagaactcaggcctcaaggtaattctgggaattctactt  1920
 621   M  G  R  L  R  M  R  K  N  S  G  L  K  V  I  L  G  I  L  L    640

1921  cctccttcaattctcagcttggagttcaagaacaaagacgacatgccctatatgtctcag  1980
 641   P  P  S  I  L  S  L  E  F  K  N  K  D  D  M  P  Y  M  S  Q    660

1981  gcccaggaaatccacctccaagagaaggaggcagaagaaccagagaagcccacaaaggaa  2040
 661   A  Q  E  I  H  L  Q  E  K  E  A  E  E  P  E  K  P  T  K  E    680

2041  aaagaggaagaggacatggagctcacagcaatgttgggacgaaacaacggggagtcctcc  2100
 681   K  E  E  D  M  E  L  T  A  M  L  G  R  N  N  G  E  S  S      700

2101  aggaagaaggatgaagaggaagttcagagcaagcaccggttaatccccctcggcagaaaa  2160
 701   R  K  K  D  E  E  V  Q  S  K  H  R  L  I  P  L  G  R  K      720

2161  atctatgaattctacaatgcacccatcgtgaagttctggttctacacactggcgtatatc  2220
 721   I  Y  E  F  Y  N  A  P  I  V  K  F  W  F  Y  T  L  A  Y  I    740

2221  ggatacctgatgctcttcaactatatcgtgttagtgaagatggaacgctggccgtccacc  2280
 741   G  Y  L  M  L  F  N  Y  I  V  L  V  K  M  E  R  W  P  S  T    760

2281  caggaatggatcgtaatctcctatatttttcaccctgggaatagaaaagatgagagagatt  2340
 761   Q  E  W  I  V  I  S  Y  I  F  T  L  G  I  E  K  M  R  E  I    780

2341  ctgatgtcagagccagggaagttgctacagaaagtgaaggtatggctgcaggagtactgg  2400
 781   L  M  S  E  P  G  K  L  L  Q  K  V  K  V  W  L  Q  E  Y  W    800

2401  aatgtcacggacctcatcgccatccttctgttttctgtcggaatgatccttcgtctccaa  2460
 801   N  V  T  D  L  I  A  I  L  L  F  S  V  G  M  I  L  R  L  Q    820

2461  gaccagcccttcaggagtgacggggagggtcatctactgcgtgaacatcatttactggtat  2520
 821   D  Q  P  F  R  S  D  G  E  V  I  Y  C  V  N  I  I  Y  W  Y    840

2521  atccgtctcctagacatcttcggcgtgaacaagtatttgggcccgtatgtaatgatgatt  2580
 841   I  R  L  L  D  I  F  G  V  N  K  Y  L  G  P  Y  V  M  M  I    860

2581  ggaaaaatgatgatagacatgatgtactttgtcatcattatgctggtggttctgatgagc  2640
 861   G  K  M  M  I  D  M  M  Y  F  V  I  I  M  L  V  V  L  M  S    880
```

Fig. 2D

```
2641 tttggggtcgccaggcaagccatccttttttcccaatgaggagccatcatggaaactggcc 2700
 881  F  G  V  A  R  Q  A  I  L  F  P  N  E  E  P  S  W  K  L  A   900

2701 aagaacatcttctacatgccctattggatgatttatggggaagtgtttgcggaccagata 2760
 901  K  N  I  F  Y  M  P  Y  W  M  I  Y  G  E  V  F  A  D  Q  I   920

2761 gaccctccctgtggacagaatgagacccgagaggatggtaaaataatccagctgcctccc 2820
 921  D  P  P  C  G  Q  N  E  T  R  E  D  C  K  I  I  Q  L  P  P   940

2821 tgcaagacaggagcttggatcgtgccggccatcatggcctgctacctcttagtggcaaac 2880
 941  C  K  T  G  A  W  I  V  P  A  I  M  A  C  Y  L  L  V  A  N   960

2881 atcttgctggtcaacctcctcattgctgtctttaacaatacatttttttgaagtaaaatcg 2940
 961  I  L  L  V  N  L  L  I  A  V  F  N  N  T  F  F  E  V  K  S   980

2941 atatccaaccaagtctggaagtttcagaggtatcagctcatcatgactttccatgaaagg 3000
 981  I  S  N  Q  V  W  K  F  Q  R  Y  Q  L  I  M  T  F  H  E  R  1000

3001 ccagttctgcccccaccactgatcatcttcagccacatgaccatgatattccagcacctg 3060
1001  P  V  L  P  P  P  L  I  I  F  S  H  M  T  M  I  F  Q  H  L  1020

3061 tgctgccgatggaggaaacacgagagcgacccggatgaaagggactacggcctgaaactc 3120
1021  C  C  R  W  R  K  H  E  S  D  P  D  E  R  D  Y  G  L  K  L  1040

3121 ttcataaccgatgatgagctcaagaaagtacatgactttgaagagcaatgcatagaagaa 3180
1041  F  I  T  D  D  E  L  K  K  V  H  D  F  E  E  Q  C  I  E  E  1060

3181 tacttcagagaaaaggatgatcggttcaactcatctaatgatgagaggatacgggtgact 3240
1061  Y  F  R  E  K  D  D  R  F  N  S  S  N  D  E  R  I  R  V  T  1080

3241 tcagaaagggtggagaacatgtctatgcggctggaggaagtcaacgagagagagcactcc 3300
1081  S  E  R  V  E  N  M  S  M  R  L  E  E  V  N  E  R  E  H  S  1100

3301 atgaaggcttcactccagaccgtggacatccggctggcgcagctggaagaccttatcggg 3360
1101  M  K  A  S  L  Q  T  V  D  I  R  L  A  Q  L  E  D  L  I  G  1120

3361 cgcatggccacggccctggagcgcctgacaggtctggagcgggccgagtccaacaaaatc 3420
1121  R  M  A  T  A  L  E  R  L  T  G  L  E  R  A  E  S  N  K  I  1140

3421 cgctcgaggacctcgtcagactgcacggacgccgcctacattgtccgtcagagcagcttc 3480
1141  R  S  R  T  S  S  D  C  T  D  A  A  Y  I  V  R  Q  S  S  F  1160

3481 aacagccaggaagggaacaccttcaagctccaagagagtatagaccctgcaggtgaggag 3540
1161  N  S  Q  E  G  N  T  F  K  L  Q  E  S  I  D  P  A  G  E  E  1180
```

Fig. 2E

```
3541  accatgtccccaacttctccaaccttaatgccccgtatgcgaagccattctttctattca  3600
1181   T  M  S  P  T  S  P  T  L  M  P  R  M  R  S  H  S  F  Y  S   1200

3601  gtcaatatgaaagacaaaggtggtatagaaaagttggaaagtattttaaagaaaggtcc   3660
1201   V  N  M  K  D  K  G  G  I  E  K  L  E  S  I  F  K  E  R  S   1220

3661  ctgagcctacaccgggctactagttcccactctgtagcaaaagaacccaaagctcctgca  3720
1221   L  S  L  H  R  A  T  S  S  H  S  V  A  K  E  P  K  A  P  A   1240

3721  gcccctgccaacaccttggccattgttctgattccagaagaccatcatcgtgtatagac   3780
1241   A  P  A  N  T  L  A  I  V  P  D  S  R  R  P  S  S  C  I  D   1260

3781  atctatgtctctgctatggatgagctccactgtgatatagaccctctggacaattccgtg  3840
1261   I  Y  V  S  A  M  D  E  L  H  C  D  I  D  P  L  D  N  S  V   1280

3841  aacatccttgggctaggcgagccaagcttttcaactccagtaccttccacagccccttca  3900
1281   N  I  L  G  L  G  E  P  S  F  S  T  P  V  P  S  T  A  P  S   1300

3901  agtagtgcctatgcaacacttgcacccacagacagacctccaagccggagcattgatttt  3960
1301   S  S  A  Y  A  T  L  A  P  T  D  R  P  P  S  R  S  I  D  F   1320

3961  gaggacatcacctccatggacactagatcttttttcttcagactacacccacctcccagaa  4020
1321   E  D  I  T  S  M  D  T  R  S  F  S  S  D  Y  T  H  L  P  E   1340

4021  tgccaaaaccccctgggactcagagcctccgatgtaccacaccattgagcgttccaaaagt  4080
1341   C  Q  N  P  W  D  S  E  P  P  M  Y  H  T  I  E  R  S  K  S   1360

4081  agccgctacctagccaccacaccctttcttctagaagaggctcccattgtgaaatctcat  4140
1361   S  R  Y  L  A  T  T  P  F  L  L  E  E  A  P  I  V  K  S  H   1380

4141  agctttatgttttccccctcaaggagctattatgccaactttggggtgcctgtaaaaaca  4200
1381   S  F  M  F  S  P  S  R  S  Y  Y  A  N  F  G  V  P  V  K  T   1400

4201  gcagaatacacaagtattacagactgtattgacacaaggtgtgtcaatgcccctcaagca  4260
1401   A  E  Y  T  S  I  T  D  C  I  D  T  R  C  V  N  A  P  Q  A   1420

4261  attgcggacagagctgccttccctggaggtcttggagacaaagtggaggacttaacttgc  4320
1421   I  A  D  R  A  A  F  P  G  G  L  G  D  K  V  E  D  L  T  C   1440

4321  tgccatccagagcgagaagcagaactgagtcaccccagctctgacagtgaggagaatgag  4380
1441   C  H  P  E  R  E  A  E  L  S  H  P  S  S  D  S  E  E  N  E   1460

4381  gccaaaggccgcagagccaccattgcaatatcctcccaggagggtgataactcagagaga  4440
1461   A  K  G  R  R  A  T  I  A  I  S  S  Q  E  G  D  N  S  E  R   1480
```

Fig. 2F

```
4441  accctgtccaacaacatcactgttcccaagatagagcgcgccaacagctactcggcagag  4500
1481   T   L   S   N   N   I   T   V   P   K   I   E   R   A   N   S   Y   S   A   E   1500

4501  gagccaagtgcgccatatgcacacaccaggaagagcttctccatcagtgacaaactcgac  4560
1501   E   P   S   A   P   Y   A   H   T   R   K   S   F   S   I   S   D   K   L   D   1520

4561  aggcagcggaacacagcaagcctgcaaaatcccttccagagaagcaagtcctccaagccg  4620
1521   R   Q   R   N   T   A   S   L   Q   N   P   F   Q   R   S   K   S   S   K   P   1540

4621  gagggccgaggggacagcctgtccatgaggagactgtccagaacatcggctttccaaagc  4680
1541   E   G   R   G   D   S   L   S   M   R   R   L   S   R   T   S   A   F   Q   S   1560

4681  tttgaaagcaagcacacctaa   4701
1561   F   E   S   K   H   T   1566
```

Fig. 3A

```
  1  atgtatgtgcgagtatcttttgatacaaaacctgatctcctcttacacctgatgaccaag   60
  1   M  Y  V  R  V  S  F  D  T  K  P  D  L  L  L  H  L  M  T  K    20

61  gaatggcagttggagcttcccaagcttctcatctctgtccatggggcctgcagaacttt  120
 21   E  W  Q  L  E  L  P  K  L  L  I  S  V  H  G  G  L  Q  N  F    40

121  gaactccagccaaaactcaagcaagtctttgggaaagggctcatcaaagcagcaatgaca  180
 41   E  L  Q  P  K  L  K  Q  V  F  G  K  G  L  I  K  A  A  M  T    60

181  actggagcgtggatattcactggaggggttaacacaggtgttattcgtcatgttggcgat  240
 61   T  G  A  W  I  F  T  G  G  V  N  T  G  V  I  R  H  V  G  D    80

241  gccttgaaggatcatgcctctaagtctcgaggaaagatatgcaccataggtattgccccc  300
 81   A  L  K  D  H  A  S  K  S  R  G  K  I  C  T  I  G  I  A  P   100

301  tggggaattgtggaaaaccaggaggacctcattggaagagatgttgtccggccataccag  360
101   W  G  I  V  E  N  Q  E  D  L  I  G  R  D  V  V  R  P  Y  Q   120

361  accatgtccaatcccatgagcaagctcactgttctcaacagcatgcattcccacttcatt  420
121   T  M  S  N  P  M  S  K  L  T  V  L  N  S  M  H  S  H  F  I   140

421  ctggctgacaacgggaccactggaaaatatggagcagaggtgaaacttcgaagacaactg  480
141   L  A  D  N  G  T  T  G  K  Y  G  A  E  V  K  L  R  R  Q  L   160

481  gaaaagcatatttcactccagaagataaaacacaagaatcggtcaaggtgttcctgtggtg  540
161   E  K  H  I  S  L  Q  K  I  N  T  R  I  G  Q  G  V  P  V  V   180

541  gcactcatagtggaaggaggacccaatgtgatctcgattgttttggagtaccttcgagac  600
181   A  L  I  V  E  G  G  P  N  V  I  S  I  V  L  E  Y  L  R  D   200

601  accccctcccgtgccagtggttgtctgtgatgggagtggacgggcatcggacatcctggcc  660
201   T  P  P  V  P  V  V  C  D  G  S  G  R  A  S  D  I  L  A   220

661  tttgggcataaatactcagaagaaggcggactgataaatgaatctttgagggaccagctg  720
221   F  G  H  K  Y  S  E  E  G  G  L  I  N  E  S  L  R  D  Q  L   240

721  ttggtgactatacagaagactttcacatacactcgaacccaagctcagcatctgttcatc  780
241   L  V  T  I  Q  K  T  F  T  Y  T  R  T  Q  A  Q  H  L  F  I   260

781  atcctcatggagtgcatgaagaagaaggaattgattacggtatttcggatgggatcagaa  840
261   I  L  M  E  C  M  K  K  K  E  L  I  T  V  F  R  M  G  S  E   280
```

Fig. 3B

```
 841  ggacaccaggacattgatttggctatcctgacagctttactcaaaggagccaatgcctcg   900
 281   G  H  Q  D  I  D  L  A  I  L  T  A  L  L  K  G  A  N  A  S   300

901  gccccagaccaactgagcttagctttagcctggaacagagtcgacatcgctcgcagccag   960
 301   A  P  D  Q  L  S  L  A  W  N  R  V  D  I  A  R  S  Q         320

961  atctttatttacgggcaacagtggccggtgggatctctggagcaagccatgttggatgcc  1020
 321   I  F  I  Y  G  Q  Q  W  P  V  G  S  L  E  Q  A  M  L  D  A   340

1021  ttagttctggacagagtggattttgtgaaattactcatagagaatggagtaagcatgcac  1080
 341   L  V  L  D  R  V  D  F  V  K  L  L  I  E  N  G  V  S  M  H   360

1081  cgttttctcaccatctccagactagaggaattgtacaatacgagacatgggccctcaaat  1140
 361   R  F  L  T  I  S  R  L  E  E  L  Y  N  T  R  H  G  P  S  N   380

1141  acattgtaccacttggtcagggatgtcaaaaaggggaacctgcccccagactacagaatc  1200
 381   T  L  Y  H  L  V  R  D  V  K  K  G  N  L  P  P  D  Y  R  I   400

1201  agcctgattgacatcggcctggtgatcgagtacctgatgggcggggcttatcgctgcaac  1260
 401   S  L  I  D  I  G  L  V  I  E  Y  L  M  G  G  A  Y  R  C  N   420

1261  tacacgcgcaagcgcttccggaccctctaccacaacctcttcggccccaagaggcccaaa  1320
 421   Y  T  R  K  R  F  R  T  L  Y  H  N  L  F  G  P  K  R  P  K   440

1321  gccttgaaactgctgggaatggaggatgatattcccttgaggcgaggaagaaagacaacc  1380
 441   A  L  K  L  L  G  M  E  D  D  I  P  L  R  R  G  R  K  T  T   460

1381  aagaaacgtgaagaagaggtggacattgacttggatgatcctgagatcaaccacttcccc  1440
 461   K  K  R  E  E  V  D  I  D  L  D  D  P  E  I  N  H  F  P      480

1441  ttccctttccatgagctcatggtgtgggctgttctcatgaagcggcagaagatggccctg  1500
 481   F  P  F  H  E  L  M  V  W  A  V  L  M  K  R  Q  K  M  A  L   500

1501  ttcttctggcagcacggtgaggaggccatggccaaggccctggtggcctgcaagctctgc  1560
 501   F  F  W  Q  H  G  E  E  A  M  A  K  A  L  V  A  C  K  L  C   520

1561  aaagccatggctcatgaggcctctgagaacgacatggttgacgacatttcccaggagctg  1620
 521   K  A  M  A  H  E  A  S  E  N  D  M  V  D  D  I  S  Q  E  L   540

1621  aatcacaattccagagactttggccagctggctgtggagctcctggaccagtcctacaag  1680
 541   N  H  N  S  R  D  F  G  Q  L  A  V  E  L  L  D  Q  S  Y  K   560
```

Fig. 3C

```
1681 caggacgaacagctggccatgaaactgctgacgtatgagctgaagaactggagcaacgcc 1740
 561  Q   D   E   Q   L   A   M   K   L   L   T   Y   E   L   K   N   W   S   N   A    580

1741 acgtgcctgcagcttgccgtggctgccaaacaccgcgacttcatcgcgcacacgtgcagc 1800
 581  T   C   L   Q   L   A   V   A   A   K   H   R   D   F   I   A   H   T   C   S    600

1801 cagatgctgctcaccgacatgtggatgggccggctccgcatgcgcaagaactcaggcctc 1860
 601  Q   M   L   L   T   D   M   W   M   G   R   L   R   M   R   K   N   S   G   L    620

1861 aaggtaattctgggaattctacttcctccttcaattctcagcttggagttcaagaacaaa 1920
 621  K   V   I   L   G   I   L   L   P   P   S   I   L   S   L   E   F   K   N   K    640

1921 gacgacatgccctatatgtctcaggcccaggaaatccacctccaagagaaggaggcagaa 1980
 641  D   D   M   P   Y   M   S   Q   A   Q   E   I   H   L   Q   E   K   E   A   E    660

1981 gaaccagagaagcccacaaaggaaaaagaggaagaggacatggagctcacagcaatgttg 2040
 661  E   P   E   K   P   T   K   E   K   E   E   D   M   E   L   T   A   M   L    680

2041 ggacgaaacaacggggagtcctccaggaagaaggatgaagaggaagttcagagcaagcac 2100
 681  G   R   N   N   G   E   S   S   R   K   K   D   E   E   V   Q   S   K   H    700

2101 cggttaatccccctcggcagaaaaatctatgaattctacaatgcacccatcgtgaagttc 2160
 701  R   L   I   P   L   G   R   K   I   Y   E   F   Y   N   A   P   I   V   K   F    720

2161 tggttctacacactggcgtatatcggatacctgatgctcttcaactatatcgtgttagtg 2220
 721  W   F   Y   T   L   A   Y   I   G   Y   L   M   L   F   N   Y   I   V   L   V    740

2221 aagatggaacgctggccgtccacccaggaatggatcgtaatctcctatatttttcaccctg 2280
 741  K   M   E   R   W   P   S   T   Q   E   W   I   V   I   S   Y   I   F   T   L    760

2281 ggaatagaaaagatgagagagattctgatgtcagagccaggaagttgctacagaaagtg 2340
 761  G   I   E   K   M   R   E   I   L   M   S   E   P   G   K   L   L   Q   K   V    780

2341 aaggtatggctgcaggagtactggaatgtcacggacctcatcgccatccttctgttttct 2400
 781  K   V   W   L   Q   E   Y   W   N   V   T   D   L   I   A   I   L   L   F   S    800

2401 gtcggaatgatccttcgtctccaagaccagcccttcaggagtgacgggagggtcatctac 2460
 801  V   G   M   I   L   R   L   Q   D   Q   P   F   R   S   D   G   R   V   I   Y    820

2461 tgcgtgaacatcatttactggtatatccgtctcctagacatcttcggcgtgaacaagtat 2520
 821  C   V   N   I   I   Y   W   Y   I   R   L   L   D   I   F   G   V   N   K   Y    840
```

Fig. 3D

```
2521  ttgggcccgtatgtaatgatgattggaaaaatgatgatagacatgatgtactttgtcatc  2580
 841  L  G  P  Y  V  M  M  I  G  K  M  M  L  D  M  M  Y  F  V   860

2581  attatgctggtggttctgatgagctttggggtcgccaggcaagccatccttttccccaat  2640
 861  I  M  L  V  V  L  M  S  F  G  V  A  R  Q  A  I  L  F  P  N  880

2641  gaggagccatcatggaaactggccaagaacatcttctacatgccctattggatgattat   2700
 881  E  E  P  S  W  K  L  A  K  N  I  F  Y  M  P  Y  W  M  I  Y  900

2701  ggggaagtgtttgcggaccagatagaccgtaagcaagtttatgattctcatacaccaaag  2760
 901  G  E  V  F  A  D  Q  I  D  R  K  Q  V  Y  D  S  H  T  P  K  920

2761  tcagctccctgtggacagaatgagacccgagaggatggtaaaataatccagctgcctccc  2820
 921  S  A  P  C  G  Q  N  E  T  R  E  D  G  K  I  Q  L  P  P    940

2821  tgcaagacaggagcttggatcgtgccggccatcatggcctgctacctcttagtggcaaac  2880
 941  C  K  T  G  A  W  I  V  P  A  L  M  A  C  Y  L  L  V  A  N  960

2881  atcttgctggtcaacctcctcattgctgtctttaacaatacatttttgaagtaaaatcg   2940
 961  I  L  L  V  N  L  L  I  A  V          N  N  T  F  F  E  V  K  S  980

2941  atatccaaccaagtctggaagtttcagaggtatcagctcatcatgactttccatgaaagg  3000
 981  I  S  N  Q  V  W  K  F  Q  R  Y  Q  L  I  M  T  F  H  E  R  1000

3001  ccagttctgcccccaccactgatcatcttcagccacatgaccatgatattccagcacctg  3060
1001  P  V  L  P  P  P  L  I  I  F  S  H  M  T  M  I  F  Q  H  L  1020

3061  tgctgccgatggaggaaacacgagagcgacccggatgaaagggactacggcctgaaactc  3120
1021  C  C  R  W  R  K  H  E  S  D  P  D  E  R  D  Y  G  L  K  L  1040

3121  ttcataaccgatgatgagctcaagaaagtacatgactttgaagagcaatgcatagaagaa  3180
1041  F  I  T  D  D  E  L  K  K  V  H  D  F  E  E  Q  C  I  E  E  1060

3181  tacttcagagaaaaggatgatcggttcaactcatctaatgatgagaggatacgggtgact  3240
1061  Y  F  R  E  K  D  D  R  F  N  S  S  N  D  E  R  I  R  V  T  1080

3241  tcagaaagggtggagaacatgtctatgcggctggaggaagtcaacgagagagagcactcc  3300
1081  S  E  R  V  E  N  M  S  M  R  L  E  E  V  N  E  R  E  H  S  1100

3301  atgaaggcttcactccagaccgtggacatccggctggcgcagctggaagaccttatcggg  3360
1101  M  K  A  S  L  Q  T  V  D  I  R  L  A  Q  L  E  D  L  I  G  1120
```

Fig. 3E

```
3361  cgcatggccacggccctggagcgcctgacaggtctggagcgggccgagtccaacaaaatc  3420
1121   R   M   A   T   A   L   E   R   L   T   G   L   E   R   A   E   S   N   K   I   1140

3421  cgctcgaggacctcgtcagactgcacggacgccgcctacattgtccgtcagagcagcttc  3480
1141   R   S   R   T   S   S   D   C   T   D   A   A   Y   I   V   R   Q   S   S   F   1160

3481  aacagccaggaagggaacaccttcaagctccaagagagtatagaccctgcaggtgaggag  3540
1161   N   S   Q   E   G   N   T   F   K   L   Q   E   S   I   D   P   A   G   E   E   1180

3541  accatgtccccaacttctccaaccttaatgccccgtatgcgaagccattctttctattca  3600
1181   T   M   S   P   T   S   P   T   L   M   P   R   M   R   S   H   S   F   Y   S   1200

3601  gtcaatatgaaagacaaaggtggtatagaaaagttggaaagtattttttaaagaaaggtcc  3660
1201   V   N   M   K   D   K   G   G   I   E   K   L   E   S   I   F   K   E   R   S   1220

3661  ctgagcctacaccgggctactagttcccactctgtagcaaaagaacccaaagctcctgca  3720
1221   L   S   L   H   R   A   T   S   S   H   S   V   A   K   E   P   K   A   P   A   1240

3721  gcccctgccaacaccttggccattgttcctgattccagaagaccatcatcgtgtatagac  3780
1241   A   P   A   N   T   L   A   I   V   P   D   S   R   R   P   S   S   C   I   D   1260

3781  atctatgtctctgctatggatgagctccactgtgatatagaccctctggacaattccgtg  3840
1261   I   Y   V   S   A   M   D   E   L   H   C   D   I   D   P   L   D   N   S   V   1280

3841  aacatccttgggctaggcgagccaagcttttcaactccagtaccttccacagcccttca   3900
1281   N   I   L   G   L   G   E   P   S   F   S   T   P   V   P   S   T   A   P   S   1300

3901  agtagtgcctatgcaacacttgcaccacagacagacctccaagccggagcattgatttt  3960
1301   S   S   A   Y   A   T   L   A   P   T   D   R   P   P   S   R   S   I   D   F   1320

3961  gaggacatcacctccatggacactagatcttttttcttcagactacacccacctcccagaa  4020
1321   E   D   I   T   S   M   D   T   R   S   F   S   S   D   Y   T   H   L   P   E   1340

4021  tgccaaaaccccctgggactcagagcctccgatgtaccacaccattgagcgttccaaaagt  4080
1341   C   Q   N   P   W   D   S   E   P   P   M   Y   H   T   I   E   R   S   K   S   1360

4081  agccgctacctagccaccacacccttcttctagaagaggctcccattgtgaaatctcat  4140
1361   S   R   Y   L   A   T   T   P   F   L   E   E   A   P   I   V   K   S   H   1380

4141  agctttatgttttcccctcaaggagctattatgccaactttggggtgcctgtaaaaaca  4200
1381   S   F   M   F   S   P   S   R   S   Y   Y   A   N   F   G   V   P   V   K   T   1400
```

Fig. 3F

```
4201 gcagaatacacaagtattacagactgtattgacacaaggtgtgtcaatgcccctcaagca 4260
1401  A  E  Y  T  S  I  T  D  C  I  D  T  R  C  V  N  A  P  Q  A  1420

4261 attgcggacagagctgccttccctggaggtcttggagacaaagtggaggacttaacttgc 4320
1421  I  A  D  R  A  A  F  P  G  G  L  G  D  K  V  E  D  L  T  C  1440

4321 tgccatccagagcgagaagcagaactgagtcacccagctctgacagtgaggagaatgag 4380
1441  C  H  P  E  R  E  A  E  L  S  H  P  S  S  D  S  E  E  N  E  1460

4381 gccaaaggccgcagagccaccattgcaatatcctcccaggagggtgataactcagagaga 4440
1461  A  K  G  R  R  A  T  I  A  I  S  S  Q  E  G  D  N  S  E  R  1480

4441 accctgtccaacaacatcactgttcccaagatagagcgcgccaacagctactcggcagag 4500
1481  T  L  S  N  N  I  T  V  P  K  I  E  R  A  N  S  Y  S  A  E  1500

4501 gagccaagtgcgccatatgcacacaccaggaagagcttctccatcagtgacaaactcgac 4560
1501  E  P  S  A  P  Y  A  H  T  R  K  S  F  S  I  S  D  K  L  D  1520

4561 aggcagcggaacacagcaagcctgcaaaatcccttccagagaagcaagtcctccaagccg 4620
1521  R  Q  R  N  T  A  S  L  Q  N  P  F  Q  R  S  K  S  S  K  P  1540

4621 gagggccgagggacagcctgtccatgaggagactgtccagaacatcggctttccaaagc 4680
1541  E  G  R  G  D  S  L  S  M  R  R  L  S  R  T  S  A  F  Q  S  1560

4681 tttgaaagcaagcacacctaa  4701
1561  F  E  S  K  H  T         1566
```

Fig. 4A

```
  1  atgtatgtgcgagtatcttttgatacaaaacctgatctcctcttacacctgatgaccaag   60
  1  M  Y  V  R  V  S  F  D  T  K  P  D  L  L  L  H  L  M  T  K    20

61  gaatggcagttggagcttcccaagcttctcatctctgtccatggggcctgcagaacttt   120
 21  E  W  Q  L  E  L  P  K  L  L  I  S  V  H  G  G  L  Q  N  F    40

121  gaactccagccaaaactcaagcaagtctttgggaaaggctcatcaaagcagcaatgaca   180
 41  E  L  Q  P  K  L  K  Q  V  F  G  K  G  L  I  K  A  A  M  T    60

181  actggagcgtggatattcactggagggggttaacacaggtgttattcgtcatgttggcgat  240
 61  T  G  A  W  I  F  T  G  G  V  N  T  G  V  I  R  H  V  G  D    80

241  gccttgaaggatcatgcctctaagtctcgaggaaagatatgcaccataggtattgccccc   300
 81  A  L  K  D  H  A  S  K  S  R  G  K  I  C  T  I  G  I  A  P   100

301  tggggaattgtggaaaaccaggaggacctcattggaagagatgttgtccggccataccag   360
101  W  G  I  V  E  N  Q  E  D  L  I  G  R  D  V  V  R  P  Y  Q   120

361  accatgtccaatcccatgagcaagctcactgttctcaacagcatgcattcccacttcatt   420
121  T  M  S  N  P  M  S  K  L  T  V  L  N  S  M  H  S  H  F  I   140

421  ctggctgacaacgggaccactggaaaatatggagcagaggtgaaacttcgaagacaactg   480
141  L  A  D  N  G  T  T  G  K  Y  G  A  E  V  K  L  R  R  Q  L   160

481  gaaaagcatatttcactccagaagataaacacaagaatcggtcaaggtgttcctgtggtg   540
161  E  K  H  I  S  L  Q  K  I  N  T  R  I  G  Q  G  V  P  V  V   180

541  gcactcatagtggaaggaggacccaatgtgatctcgattgttttggagtaccttcgagac   600
181  A  L  I  V  E  G  G  P  N  V  I  S  I  V  L  E  Y  L  R  D   200

601  acccctccgtgccagtggttgtctgtgatgggagtggacgggcatcggacatcctggcc   660
201  T  P  P  V  P  V  V  V  C  D  G  S  G  R  A  S  D  I  L  A   220

661  tttgggcataaatactcagaagaaggcggactgataaatgaatctttgagggaccagctg   720
221  F  G  H  K  Y  S  E  E  G  G  L  I  N  E  S  L  R  D  Q  L   240

721  ttggtgactatacagaagactttcacatacactcgaacccaagctcagcatctgttcatc   780
241  L  V  T  I  Q  K  T  F  T  Y  T  R  T  Q  A  Q  H  L  F  I   260

781  atcctcatggagtgcatgaagaagaaggaattgattacggtatttcggatgggatcagaa   840
261  I  L  M  E  C  M  K  K  K  E  L  I  T  V  F  R  M  G  S  E   280

841  ggacaccaggacattgatttggctatcctgacagctttactcaaaggagccaatgcctcg   900
281  G  H  Q  D  I  D  L  A  I  L  T  A  L  L  K  G  A  N  A  S   300
```

Fig. 4B

```
 901   gccccagaccaactgagcttagctttagcctggaacagagtcgacatcgctcgcagccag   960
 301    A  P  D  Q  L  S  L  A  L  A  W  N  R  V  D  I  A  R  S  Q    320

961   atctttatttacgggcaacagtggccggtgggatctctggagcaagccatgttggatgcc  1020
 321    I  F  I  Y  G  Q  Q  W  P  V  G  S  L  E  Q  A  M  L  D  A    340

1021   ttagttctggacagagtggattttgtgaaattactcatagagaatggagtaagcatgcac  1080
 341    L  V  L  D  R  V  D  F  V  K  L  L  I  E  N  G  V  S  M  H    360

1081   cgtttTctcaccatctccagactagaggaattgtacaatacgagacatgggccctcaaat  1140
 361    R  F  L  T  I  S  R  L  E  E  L  Y  N  T  R  H  G  P  S  N    380

1141   acattgtaccacttggtcagggatgtcaaaaagcgagagtatccaggtttcggttggatc  1200
 381    T  L  Y  H  L  V  R  D  V  K  K  R  E  Y  P  G  F  G  W  I    400

1201   tattttaaggggaacctgcccccagactacagaatcagcctgattgacatcggcctggtg  1260
 401    Y  F  K  G  N  L  P  P  D  Y  R  I  S  L  I  D  I  G  L  V    420

1261   atcgagtacctgatgggcggggcttatcgctgcaactacacgcgcaagcgcttccggacc  1320
 421    I  E  Y  L  M  G  G  A  Y  R  C  N  Y  T  R  K  R  F  R  T    440

1321   ctctaccacaacctcttcggccccaagagggatgatattcccttgaggcgaggaagaaag  1380
 441    L  Y  H  N  L  F  G  P  K  R  D  D  I  P  L  R  R  G  R  K    460

1381   acaaccaagaaacgtgaagaagaggtggacattgacttggatgatcctgagatcaaccac  1440
 461    T  T  K  K  R  E  E  V  D  I  D  L  D  D  P  E  I  N  H    480

1441   ttccccttcccttTccatgagctcatggtgtgggctgttctcatgaagcggcagaagatg  1500
 481    F  P  F  P  F  H  E  L  M  V  W  A  V  L  M  K  R  Q  K  M    500

1501   gccctgttcttctggcagcacggtgaggaggccatggccaaggccctggtggcctgcaag  1560
 501    A  L  F  F  W  Q  H  G  E  E  A  M  A  K  A  L  V  A  C  K    520

1561   ctctgcaaagccatggctcatgaggcctctgagaacgacatggttgacgacatttcccag  1620
 521    L  C  K  A  M  A  H  E  A  S  E  N  D  M  V  D  D  I  S  Q    540

1621   gagctgaatcacaattccagagactttggccagctggctgtggagctcctggaccagtcc  1680
 541    E  L  N  H  N  S  R  D  F  G  Q  L  A  V  E  L  L  D  Q  S    560

1681   tacaagcaggacgaacagctggccatgaaactgctgacgtatgagctgaagaactggagc  1740
 561    Y  K  Q  D  E  Q  L  A  M  K  L  L  T  Y  E  L  K  N  W  S    580

1741   aacgccacgtgcctgcagcttgccgtggctgccaaacaccgcgacttcatcgcgcacacg  1800
 581    N  A  T  C  L  Q  L  A  V  A  A  K  H  R  D  F  I  A  H  T    600
```

Fig. 4C

```
1801  tgcagccagatgctgctcaccgacatgtggatgggccggctccgcatgcgcaagaactca  1860
 601   C   S   Q   M   L   L   T   D   M   W   M   G   R   L   R   M   R   K   N   S    620

1861  ggcctcaaggtaattctgggaattctacttcctccttcaattctcagcttggagttcaag  1920
 621   G   L   K   V   I   L   G   I   L   L   P   P   S   I   L   S   L   E   F   K    640

1921  aacaaagacgacatgccctatatgtctcaggcccaggaaatccacctccaagagaaggag  1980
 641   N   K   D   D   M   P   Y   M   S   Q   A   Q   E   I   H   L   Q   E   K   E    660

1981  gcagaagaaccagagaagcccacaaaggaaaaagaggaagaggacatggagctcacagca  2040
 661   A   E   E   P   E   K   P   T   K   E   K   E   E   D   M   E   L   T   A    680

2041  atgttgggacgaaacaacggggagtcctccaggaagaaggatgaagaggaagttcagagc  2100
 681   M   L   G   R   N   N   G   E   S   S   R   K   K   D   E   E   V   Q   S    700

2101  aagcaccggttaatcccctcggcagaaaaaatctatgaattctacaatgcacccatcgtg  2160
 701   K   H   R   L   I   P   L   G   R   K   I   Y   E   F   Y   N   A   P   I   V    720

2161  aagttctggttctacacactggcgtatatcggatacctgatgctcttcaactatatcgtg  2220
 721   K   F   W   F   Y   T   L   A   Y   I   G   Y   L   M   L   F   N   Y   I   V    740

2221  ttagtgaagatggaacgctggccgtccacccaggaatggatcgtaatctcctatatttc  2280
 741   L   V   K   M   E   R   W   P   S   T   Q   E   W   I   V   I   S   Y   I   F    760

2281  accctgggaatagaaaagatgagagagattctgatgtcagagccagggaagttgctacag  2340
 761   T   L   G   I   E   K   M   R   E   I   L   M   S   E   P   G   K   L   L   Q    780

2341  aaagtgaaggtatggctgcaggagtactggaatgtcacggacctcatcgccatccttctg  2400
 781   K   V   K   V   W   L   Q   E   Y   W   N   V   T   D   I   I   A   I   L   L    800

2401  ttttctgtcggaatgatccttcgtctccaagaccagcccttcaggagtgacgggagggtc  2460
 801   F   S   V   G   M   I   L   R   L   Q   D   Q   P   F   R   S   D   G   R   V    820

2461  atctactgcgtgaacatcatttactggtatatccgtctcctagacatcttcggcgtgaac  2520
 821   I   Y   C   V   N   I   I   Y   W   Y   I   R   L   L   D   I   F   G   V   N    840

2521  aagtatttgggcccgtatgtaatgatgattggaaaaatgatgatagacatgatgtacttt  2580
 841   K   Y   L   G   P   Y   V   M   M   I   G   K   M   M   I   D   M   M   Y   F    860

2581  gtcatcattatgctggtggttctgatgagctttggggtcgccaggcaagccatccttttt  2640
 861   V   I   I   M   L   V   V   L   M   S   F   G   V   A   R   Q   A   I   L   F    880

2641  cccaatgaggagccatcatggaaactggccaagaacatcttctacatgccctattggatg  2700
 881   P   N   E   E   P   S   W   K   L   A   K   N   I   F   Y   M   P   Y   W   M    900
```

Fig. 4D

```
2701  atttatggggaagtgtttgcggaccagatagaccctccctgtggacagaatgagacccga  2760
 901   I  Y  G  E  V  F  A  D  Q  I  D  P  P  C  G  Q  N  E  T   920

2761  gaggatggtaaaataatccagctgcctccctgcaagacaggagcttggatcgtgccggcc  2820
 921   E  D  G  K  I  I  Q  L  P  P  C  K  T  G  A  W  I  V  P  A  940

2821  atcatggcctgctacctcttagtggcaaacatcttgctggtcaacctcctcattgctgtc  2880
 941   I  M  A  C  Y  L  L  V  A  N  I  L  L  V  N  L  L  I  A  V  960

2881  tttaacaatacatttttgaagtaaaatcgatatccaaccaagtctggaagtttcagagg  2940
 961   F  N  N  T  F  F  E  V  K  S  I  S  N  Q  V  W  K  F  Q  R  980

2941  tatcagctcatcatgactttccatgaaaggccagttctgccccaccactgatcatcttc  3000
 981   Y  Q  L  I  M  T  F  H  E  R  P  V  L  P  P  P  L  I  I  F   1000

3001  agccacatgaccatgatattccagcacctgtgctgccgatggaggaaacacgagagcgac  3060
1001   S  H  M  T  M  I  F  Q  H  L  C  C  R  W  R  K  H  E  S  D  1020

3061  ccggatgaaagggactacggcctgaaactcttcataaccgatgatgagctcaagaaagta  3120
1021   P  D  E  R  D  Y  G  L  K  L  F  I  T  D  D  E  L  K  K  V  1040

3121  catgactttgaagagcaatgcatagaagaatacttcagagaaaaggatgatcggttcaac  3180
1041   H  D  F  E  E  Q  C  I  E  E  Y  F  R  E  K  D  D  R  F  N  1060

3181  tcatctaatgatgagaggatacgggtgacttcagaaagggtggagaacatgtctatgcgg  3240
1061   S  S  N  D  E  R  I  R  V  T  S  E  R  V  E  N  M  S  M  R  1080

3241  ctggaggaagtcaacgagagagagcactccatgaaggcttcactccagaccgtggacatc  3300
1081   L  E  E  V  N  E  R  E  H  S  M  K  A  S  L  Q  T  V  D  I  1100

3301  cggctggcgcagctggaagacctatcgggcgcatggccacggccctggagcgcctgaca  3360
1101   R  L  A  Q  L  E  D  L  I  G  R  M  A  T  A  L  E  R  L  T  1120

3361  ggtctggagcgggccgagtccaacaaaatccgctcgaggacctcgtcagactgcacggac  3420
1121   G  L  E  R  A  E  S  N  K  I  R  S  R  T  S  S  D  C  T  D  1140

3421  gccgcctacattgtccgtcagagcagcttcaacagccaggaagggaacaccttcaagctc  3480
1141   A  A  Y  I  V  R  Q  S  S  F  N  S  Q  E  G  N  T  F  K  L  1160

3481  caagagagtatagaccctgcaggtgaggagaccatgtccccaacttctccaaccttaatg  3540
1161   Q  E  S  I  D  P  A  G  E  E  T  M  S  P  T  S  P  T  L  M  1180

3541  ccccgtatgcgaagccattctttctattcagtcaatatgaaagacaaaggtggtatagaa  3600
1181   P  R  M  R  S  H  S  F  Y  S  V  N  M  K  D  K  G  G  I  E  1200
```

Fig. 4E

```
3601 aagttggaaagtattttaaagaaaggtccctgagcctacaccgggctactagttcccac 3660
1201  K  L  E  S  I  F  K  E  R  S  L  S  L  H  R  A  T  S  S  H  1220

3661 tctgtagcaaaagaacccaaagctcctgcagcccctgccaacaccttggccattgttcct 3720
1221  S  V  A  K  E  P  K  A  P  A  A  P  A  N  T  L  A  I  V  P  1240

3721 gattccagaagaccatcatcgtgtatagacatctatgtctctgctatggatgagctccac 3780
1241  D  S  R  R  P  S  S  C  I  D  I  Y  V  S  A  M  D  E  L  H  1260

3781 tgtgatatagaccctctggacaattccgtgaacatccttgggctaggcgagccaagcttt 3840
1261  C  D  I  D  P  L  D  N  S  V  N  I  L  G  L  G  E  P  S  F  1280

3841 tcaactccagtaccttccacagccccttcaagtagtgcctatgcaacacttgcacccaca 3900
1281  S  T  P  V  P  S  T  A  P  S  S  S  A  Y  A  T  L  A  P  T  1300

3901 gacagacctccaagccggagcattgattttgaggacatcacctccatggacactagatct 3960
1301  D  R  P  P  S  R  S  I  D  F  E  D  I  T  S  M  D  T  R  S  1320

3961 ttttcttcagactacacccacctcccagaatgccaaaaccctgggactcagagcctccg 4020
1321  F  S  S  D  Y  T  H  L  P  E  C  Q  N  P  W  D  S  E  P  P  1340

4021 atgtaccacaccattgagcgttccaaaagtagccgctacctagccaccacacccttctt 4080
1341  M  Y  H  T  I  E  R  S  K  S  S  R  Y  L  A  T  T  P  F  L  1360

4081 ctagaagaggctcccattgtgaaatctcatagctttatgttttccccctcaaggagctat 4140
1361  L  E  E  A  P  I  V  K  S  H  S  F  M  F  S  P  S  R  S  Y  1380

4141 tatgccaactttggggtgcctgtaaaaacagcagaatacacaagtattacagactgtatt 4200
1381  Y  A  N  F  G  V  P  V  K  T  A  E  Y  T  S  I  T  D  C  I  1400

4201 gacacaaggtgtgtcaatgcccctcaagcaattgcggacagagctgccttccctggaggt 4260
1401  D  T  R  C  V  N  A  P  Q  A  I  A  D  R  A  A  F  P  G  G  1420

4261 cttggagacaaagtggaggacttaacttgctgccatccagagcgagaagcagaactgagt 4320
1421  L  G  D  K  V  E  D  L  T  C  C  H  P  E  R  E  A  E  L  S  1440

4321 caccccagctctgacagtgaggagaatgaggccaaaggccgcagagccaccattgcaata 4380
1441  H  P  S  S  D  S  E  E  N  E  A  K  G  R  R  A  T  I  A  I  1460

4381 tcctcccaggagggtgataactcagagagaaccctgtccaacaacatcactgttcccaag 4440
1461  S  S  Q  E  G  D  N  S  E  R  T  L  S  N  N  I  T  V  P  K  1480

4441 atagagcgcgccaacagctactcggcagaggagccaagtgcgccatatgcacacaccagg 4500
1481  I  E  R  A  N  S  Y  S  A  E  E  P  S  A  P  Y  A  H  T  R  1500
```

Fig. 4F

```
4501 aagagcttctccatcagtgacaaactcgacaggcagcggaacacagcaagcctgcaaaat  4560
1501   K  S  F  S  I  S  D  K  L  D  R  Q  R  N  T  A  S  L  Q  N   1520

4561 cccttccagagaagcaagtcctccaagccggagggccgaggggacagcctgtccatgagg  4620
1521   P  F  Q  R  S  K  S  S  K  P  E  G  R  G  D  S  L  S  M  R   1540

4621 agactgtccagaacatcggctttccaaagctttgaaagcaagcacacctaa  4671
1541   R  L  S  R  T  S  A  F  Q  S  F  E  S  K  H  T   1556
```

Fig. 5A

```
                        50
LTRPC3       (1)  MYVRVSFDTKPDLLLHLMTKEWQLELPKLLISVHGGLQNFELQPKLKQVF
LTRPC3b      (1)  MYVRVSFDTKPDLLLHLMTKEWQLELPKLLISVHGGLQNFELQPKLKQVF
LTRPC3c      (1)  MYVRVSFDTKPDLLLHLMTKEWQLELPKLLISVHGGLQNFELQPKLKQVF
LTRPC3e      (1)  MYVRVSFDTKPDLLLHLMTKEWQLELPKLLISVHGGLQNFELQPKLKQVF
melastatin1  (1)  MYIRVSYDTKPDSLLHLMVKDWQLELPKLLISVHGGLQNFEMQPKLKQVF 51                                            100
LTRPC3       (51) GKGLIKAAMTTGAWIFTGGVNTGVIRHVGDALKDHASKSRGKICTIGIAP
LTRPC3b      (51) GKGLIKAAMTTGAWIFTGGVNTGVIRHVGDALKDHASKSRGKICTIGIAP
LTRPC3c      (51) GKGLIKAAMTTGAWIFTGGVNTGVIRHVGDALKDHASKSRGKICTIGIAP
LTRPC3e      (51) GKGLIKAAMTTGAWIFTGGVNTGVIRHVGDALKDHASKSRGKICTIGIAP
melastatin1  (51) GKGLIKAAMTTGAWIFTGGVSTGVISHVGDALKDHSSKSRGRVCAIGIAP 101                                           150
LTRPC3      (101) WGIVENQEDLIGRDVVRPYQTMSNPMSKLTVLNSMHSHFILADNGTTGKY
LTRPC3b     (101) WGIVENQEDLIGRDVVRPYQTMSNPMSKLTVLNSMHSHFILADNGTTGKY
LTRPC3c     (101) WGIVENQEDLIGRDVVRPYQTMSNPMSKLTVLNSMHSHFILADNGTTGKY
LTRPC3e     (101) WGIVENQEDLIGRDVVRPYQTMSNPMSKLTVLNSMHSHFILADNGTTGKY
melastatin1 (101) WGIVENKEDLVGKDVTRVYQTMSNPLSKISVLNNSHTHPILADNGTLGKY 151                                           200
LTRPC3      (151) GAEVKLRRQLEKHISLQKINTR--------------------IGQ
LTRPC3b     (151) GAEVKLRRQLEKHISLQKINTR--------------------IGQ
LTRPC3c     (151) GAEVKLRRQLEKHISLQKINTR--------------------IGQ
LTRPC3e     (151) GAEVKLRRQLEKHISLQKINTR--------------------IGQ
melastatin1 (151) GAEVKLRRLLEKHISLQKINTR--------------------LGQ 201                                           250
LTRPC3      (176) GVPVVALIVEGGPNVISIVLEYLRDTPPVPVVVCDGSGRASDILAFGHKY
LTRPC3b     (176) GVPVVALIVEGGPNVISIVLEYLRDTPPVPVVVCDGSGRASDILAFGHKY
LTRPC3c     (176) GVPVVALIVEGGPNVISIVLEYLRDTPPVPVVVCDGSGRASDILAFGHKY
LTRPC3e     (176) GVPVVALIVEGGPNVISIVLEYLRDTPPVPVVVCDGSGRASDILAFGHKY
melastatin1 (176) GVPLVCLVVEGGPNVVSIVLEYLQEEPPIPVVICDGSGRASDILSFAHKY 251                                           300
LTRPC3      (226) SEEGGLINESLRDQLLVTIQKTFTYTRTQAQHLFIILMECMKKKELITVF
LTRPC3b     (226) SEEGGLINESLRDQLLVTIQKTFTYTRTQAQHLFIILMECMKKKELITVF
LTRPC3c     (226) SEEGGLINESLRDQLLVTIQKTFTYTRTQAQHLFIILMECMKKKELITVF
LTRPC3e     (226) SEEGGLINESLRDQLLVTIQKTFTYTRTQAQHLFIILMECMKKKELITVF
melastatin1 (226) CEEGGTINESLREQLLVTIQKTFNYNKAQSHQLFAILMECMKKKELVTVF 301                                           350
LTRPC3      (276) RMGSEGHQDIDLAILTALLKGANASAPDQLSLALAWNRVDIARSQIFIYG
LTRPC3b     (276) RMGSEGHQDIDLAILTALLKGANASAPDQLSLALAWNRVDIARSQIFIYG
LTRPC3c     (276) RMGSEGHQDIDLAILTALLKGANASAPDQLSLALAWNRVDIARSQIFIYG
LTRPC3e     (276) RMGSEGHQDIDLAILTALLKGANASAPDQLSLALAWNRVDIARSQIFIYG
melastatin1 (276) RMGSEGQQDIEMAILTALLKGINVSAPDQLSLALAWNRVDIARSQIFVFG 351                                           400
LTRPC3      (326) QQWP---------------------------------------------
LTRPC3b     (326) QQWP---------------------------------------------
LTRPC3c     (326) QQWP---------------------------------------------
LTRPC3e     (326) QQWP---------------------------------------------
melastatin1 (326) PHWTPLGSLAPPTDSKATEKEKKPPMATTKGGRGKGKGKKKGKVKEEVEE 401                                           450
LTRPC3      (330) ----------VGSLEQAMLDALVLDRVDFVKLLIENGVSMHRFLTISR
LTRPC3b     (330) ----------VGSLEQAMLDALVLDRVDFVKLLIENGVSMHRFLTISR
LTRPC3c     (330) ----------VGSLEQAMLDALVLDRVDFVKLLIENGVSMHRFLTISR
LTRPC3e     (330) ----------VGSLEQAMLDALVLDRVDFVKLLIENGVSMHRFLTISR
melastatin1 (376) ETDPRKIELLNWVNALEQAMLDALVLDRVDFVKLLIENGVNMQHFLTIPR
```

Fig. 5B

```
              451                                                500
LTRPC3     (368) LEELYNTRHGPSNTLYHLVRDVKK-----------GNLPPDYRISLIDI
LTRPC3b    (368) LEELYNTRHGPSNTLYHLVRDVKKREYPGFGWIYFKGNLPPDYRISLIDI
LTRPC3c    (368) LEELYNTRHGPSNTLYHLVRDVKK-----------GNLPPDYRISLIDI
LTRPC3e    (368) LEELYNTRHGPSNTLYHLVRDVKKREYPGFGWIYFKGNLPPDYRISLIDI
melastatin1(426) LEELYNTRLGPPNTIHHLVRDVKK-----------SNLPPDYHISLIDI 501                                                550
LTRPC3     (406) GLVIEYLMGGAYRCNYTRKRFRTLYHNLFGPKRPKALKLLGMEDDIPLRR
LTRPC3b    (418) GLVIEYLMGGAYRCNYTRKRFRTLYHNLFGPKRPKALKLLGMEDDIPLRR
LTRPC3c    (406) GLVIEYLMGGAYRCNYTRKRFRTLYHNLFGPKRPKALKLLGMEDDIPLRR
LTRPC3e    (418) GLVIEYLMGGAYRCNYTRKRFRTLYHNLFGPKR---------DDIPLRR
melastatin1(464) GLVIEYLMGGAYRCNYTRKNFRTLYMNLFGPKRPKALKLLGMEDDEPPAK 551                                                600
LTRPC3     (456) GRKTTKKR-EEEVDIDLDDPEINHPFPFHELMVWAVLMKRQKMALFFWQ
LTRPC3b    (468) GRKTTKKR-EEEVDIDLDDPEINHPFPFHELMVWAVLMKRQKMALFFWQ
LTRPC3c    (456) GRKTTKKR-EEEVDIDLDDPEINHPFPFHELMVWAVLMKRQKMALFFWQ
LTRPC3e    (458) GRKTTKKR-EEEVDIDLDDPEINHPFPFHELMVWAVLMKRQKMALFFWQ
melastatin1(514) GKKKKKKKKEEEIDIDVDDPAVSRFQYPPHELMVWAVLMKRQKMAVFLWQ 601                                                650
LTRPC3     (505) HGEEAMAKALVACKLCKAMAHEASENDMVDDISQELNHNSRDFGQLAVEL
LTRPC3b    (517) HGEEAMAKALVACKLCKAMAHEASENDMVDDISQELNHNSRDFGQLAVEL
LTRPC3c    (505) HGEEAMAKALVACKLCKAMAHEASENDMVDDISQELNHNSRDFGQLAVEL
LTRPC3e    (507) HGEEAMAKALVACKLCKAMAHEASENDMVDDISQELNHNSRDFGQLAVEL
melastatin1(564) RGEESMAKALVACKLYKAMAHESSESDLVDDISQDLDNNSKDFGQLAIEL 651                                                700
LTRPC3     (555) LDQSYKQDEQLAMKLLTYELKNWSNATCLQLAVAAKHRDFIAHTCSQMLL
LTRPC3b    (567) LDQSYKQDEQLAMKLLTYELKNWSNATCLQLAVAAKHRDFIAHTCSQMLL
LTRPC3c    (555) LDQSYKQDEQLAMKLLTYELKNWSNATCLQLAVAAKHRDFIAHTCSQMLL
LTRPC3e    (557) LDQSYKQDEQLAMKLLTYELKNWSNATCLQLAVAAKHRDFIAHTCSQMLL
melastatin1(614) LDQSYKHDEQIAMKLLTYELKNWSNTCLKLAVAAKHRDFIAHTCSQMLL 701                                                750
LTRPC3     (605) TDMWMGRLRMRKNSGLKVILGILLPPSILSLEFKNKDDMPYMSQAQEIHL
LTRPC3b    (617) TDMWMGRLRMRKNSGLKVILGILLPPSILSLEFKNKDDMPYMSQAQEIHL
LTRPC3c    (605) TDMWMGRLRMRKNSGLKVILGILLPPSILSLEFKNKDDMPYMSQAQEIHL
LTRPC3e    (607) TDMWMGRLRMRKNSGLKVILGILLPPSILSLEFKNKDDMPYMSQAQEIHL
melastatin1(664) TDMWMGRLRMRKNPGLKVIMGILLPPTILFLEFRTYDDFSYQTS------

751                                                800
LTRPC3     (655) QEKEAEEPEKPTKEKEEEDMELTAMLGRNNGESSRKKDEEEVQSKHRLIP
LTRPC3b    (667) QEKEAEEPEKPTKEKEEEDMELTAMLGRNNGESSRKKDEEEVQSKHRLIP
LTRPC3c    (655) QEKEAEEPEKPTKEKEEEDMELTAMLGRNNGESSRKKDEEEVQSKHRLIP
LTRPC3e    (657) QEKEAEEPEKPTKEKEEEDMELTAMLGRNNGESSRKKDEEEVQSKHRLIP
melastatin1(708) --KENEDG----KEKEEENTDANADAC------SRKGDEENEHKKQRSIP 801                                                850
LTRPC3     (705) LGRKIYEFYNAPIVKFWFYTLAYIGYLMLFNYIVLVKMERWPSTQEWIVI
LTRPC3b    (717) LGRKIYEFYNAPIVKFWFYTLAYIGYLMLFNYIVLVKMERWPSTQEWIVI
LTRPC3c    (705) LGRKIYEFYNAPIVKFWFYTLAYIGYLMLFNYIVLVKMERWPSTQEWIVI
LTRPC3e    (707) LGRKIYEFYNAPIVKFWFYTLAYIGYLMLFNYIVLVKMERWPSTQEWIVI
melastatin1(746) IGTKICEFYNAPIVKFWFYTISYLGYILLFNYVILVRMDGWPSLQEWIVI 851                                                900
LTRPC3     (755) SYIFTLGIEKMREILMSEPGKLLQKVKVWLQEYWNVTDLIAILLFSVGMI
LTRPC3b    (767) SYIFTLGIEKMREILMSEPGKLLQKVKVWLQEYWNVTDLIAILLFSVGMI
LTRPC3c    (755) SYIFTLGIEKMREILMSEPGKLLQKVKVWLQEYWNVTDLIAILLFSVGMI
LTRPC3e    (757) SYIFTLGIEKMREILMSEPGKLLQKVKVWLQEYWNVTDLIAILLFSVGMI
melastatin1(796) SYIVSLALEKIREILMSEPGKLSQKIKVWLQEYWNITDLVAISTFMIGAI
```

Fig. 5C

```
                    901                                                950
     LTRPC3   (805) LRLQDQPFRSDGRVIYCVNIIYWYIRLLDIFGVNKYLGPYVMMIGKMMID
     LTRPC3b  (817) LRLQDQPFRSDGRVIYCVNIIYWYIRLLDIFGVNKYLGPYVMMIGKMMID
     LTRPC3c  (805) LRLQDQPFRSDGRVIYCVNIIYWYIRLLDIFGVNKYLGPYVMMIGKMMID
     LTRPC3e  (807) LRLQDQPFRSDGRVIYCVNIIYWYIRLLDIFGVNKYLGPYVMMIGKMMID
  melastatin1 (846) LRLQNQPYMGYGRVIYCVDIIFWYIRVLDIFGVNKYLGPYVMMIGKMMID 951                                               1000
     LTRPC3   (855) MMYFVIIMLVVLMSFGVARQAILFPNEEPSWKLAKNIFYMPYWMIYGEVF
     LTRPC3b  (867) MMYFVIIMLVVLMSFGVARQAILFPNEEPSWKLAKNIFYMPYWMIYGEVF
     LTRPC3c  (855) MMYFVIIMLVVLMSFGVARQAILFPNEEPSWKLAKNIFYMPYWMIYGEVF
     LTRPC3e  (857) MMYFVIIMLVVLMSFGVARQAILFPNEEPSWKLAKNIFYMPYWMIYGEVF
  melastatin1 (896) MLYFVVIMLVVLMSFGVARQAILHPEEKPSWKLARNIFYMPYWMIYGEVF 1001                                              1050
     LTRPC3   (905) ADQID-----------PPCGQNETREDGKIIQLPPCKTGAWIVPAIMAC
     LTRPC3b  (917) ADQID-----------PPCGQNETREDGKIIQLPPCKTGAWIVPAIMAC
     LTRPC3c  (905) ADQIDRKQVYDSHTPKSAPCGQNETREDGKIIQLPPCKTGAWIVPAIMAC
     LTRPC3e  (907) ADQID-----------PPCGQNETREDGKIIQLPPCKTGAWIVPAIMAC
  melastatin1 (946) ADQIDLYAMEIN-----PPCGENLYDEEG--KRLPPCIPGAWDTPALMAC 1051                                              1100
     LTRPC3   (943) YLLVANILLVNLLIAVFNNTFFEVKSISNQVWKFQRYQLIMTFHERPVLP
     LTRPC3b  (955) YLLVANILLVNLLIAVFNNTFFEVKSISNQVWKFQRYQLIMTFHERPVLP
     LTRPC3c  (955) YLLVANILLVNLLIAVFNNTFFEVKSISNQVWKFQRYQLIMTFHERPVLP
     LTRPC3e  (945) YLLVANILLVNLLIAVFNNTFFEVKSISNQVWKFQRYQLIMTFHERPVLP
  melastatin1 (989) YLLVANILLVNLLIAVFNNTFFEVKSISNQVWKFQRYQLIMTFHDRPVLP 1101                                              1150
     LTRPC3   (993) PPLIIFSHMTMIFQHLCCRWR-KHESDPDERDYGLKLFITDDELKKVHDF
     LTRPC3b  (1005)PPLIIFSHMTMIFQHLCCRWR-KHESDPDERDYGLKLFITDDELKKVHDF
     LTRPC3c  (1005)PPLIIFSHMTMIFQHLCCRWR-KHESDPDERDYGLKLFITDDELKKVHDF
     LTRPC3e  (995) PPLIIFSHMTMIFQHLCCRWR-KHESDPDERDYGLKLFITDDELKKVHDF
  melastatin1 (1039)PPMIILSHIYIIIMRLSGRCRKKREGDQEERDRGLKLFLSDEELKRLHEF 1151                                              1200
     LTRPC3   (1042)EEQCIEEYFREKDDRFNSSNDERIRVTSERVENMSMRLEEVNEREHSMKA
     LTRPC3b  (1054)EEQCIEEYFREKDDRFNSSNDERIRVTSERVENMSMRLEEVNEREHSMKA
     LTRPC3c  (1054)EEQCIEEYFREKDDRFNSSNDERIRVTSERVENMSMRLEEVNEREHSMKA
     LTRPC3e  (1044)EEQCIEEYFREKDDRFNSSNDERIRVTSERVENMSMRLEEVNEREHSMKA
  melastatin1 (1089)EEQCVQEHFREKEDEQQSSSDERIRVTSERVENMSMRLEEINERETFMKT 1201                                              1250
     LTRPC3   (1092)SLQTVDIRLAQLEDLIGRMATALERLTGLERAESNKIRSRTSSDCTDAAY
     LTRPC3b  (1104)SLQTVDIRLAQLEDLIGRMATALERLTGLERAESNKIRSRTSSDCTDAAY
     LTRPC3c  (1104)SLQTVDIRLAQLEDLIGRMATALERLTGLERAESNKIRSRTSSDCTDAAY
     LTRPC3e  (1094)SLQTVDIRLAQLEDLIGRMATALERLTGLERAESNKIRSRTSSDCTDAAY
  melastatin1 (1139)SLQTVDIRLAQLEEISNRMVNALENLAGIDRSDLIQARSRASSECEATYL 1251                                              1300
     LTRPC3   (1142)IVRQSSFNSQEGNTFKLQESIDPAGEETMSPTSPTLMPRMRSHSFYSVNM
     LTRPC3b  (1154)IVRQSSFNSQEGNTFKLQESIDPAGEETMSPTSPTLMPRMRSHSFYSVNM
     LTRPC3c  (1154)IVRQSSFNSQEGNTFKLQESIDPAGEETMSPTSPTLMPRMRSHSFYSVNM
     LTRPC3e  (1144)IVRQSSFNSQEGNTFKLQESIDPAGEETMSPTSPTLMPRMRSHSFYSVNM
  melastatin1 (1189)LR-QSSINSADG--------------------------YSLYRYHF 1301                                              1350
     LTRPC3   (1192)KDKGGIEKLESIFKERSLSLHRATSSHSVAKEPKAPAAPANTLAIVPDSR
     LTRPC3b  (1204)KDKGGIEKLESIFKERSLSLHRATSSHSVAKEPKAPAAPANTLAIVPDSR
     LTRPC3c  (1204)KDKGGIEKLESIFKERSLSLHRATSSHSVAKEPKAPAAPANTLAIVPDSR
     LTRPC3e  (1194)KDKGGIEKLESIFKERSLSLHRATSSHSVAKEPKAPAAPANTLAIVPDSR
  melastatin1 (1208)NGEELLFEDTSLSTSPGTGVRKKTCSFRIKEEK----------DVKTHL
```

Fig. 5D

```
              1351                                               1400
LTRPC3    (1242) RPSSCIDIYVSAMDELHCDIDPLDNSVNILGLGEPSFSTPVPSTAPSSSA
LTRPC3b   (1254) RPSSCIDIYVSAMDELHCDIDPLDNSVNILGLGEPSFSTPVPSTAPSSSA
LTRPC3c   (1254) RPSSCIDIYVSAMDELHCDIDPLDNSVNILGLGEPSFSTPVPSTAPSSSA
LTRPC3e   (1244) RPSSCIDIYVSAMDELHCDIDPLDNSVNILGLGEPSFSTPVPSTAPSSSA
melastatin1 (1247) VPECQNSLHLSLGTSTSATPDGSHLAVDDLKNAEESKLGEDIGISKEDDE 1401                                              1450
LTRPC3    (1292) YATLAPTDRPPSRSIDFEDITSMDTRSFSSDYTHLPECQNPWDSEPPMYH
LTRPC3b   (1304) YATLAPTDRPPSRSIDFEDITSMDTRSFSSDYTHLPECQNPWDSEPPMYH
LTRPC3c   (1304) YATLAPTDRPPSRSIDFEDITSMDTRSFSSDYTHLPECQNPWDSEPPMYH
LTRPC3e   (1294) YATLAPTDRPPSRSIDFEDITSMDTRSFSSDYTHLPECQNPWDSEPPMYH
melastatin1 (1297) RQIDSKKEETISPSLNKTDVIHGQDKSDVQNTQLTVETTNIEG---TISY 1451                                              1500
LTRPC3    (1342) TIERSKSSRYLATTPFLLEEAPIVKSHSFMFSPSRSYYANFGVPVKTAEY
LTRPC3b   (1354) TIERSKSSRYLATTPFLLEEAPIVKSHSFMFSPSRSYYANFGVPVKTAEY
LTRPC3c   (1354) TIERSKSSRYLATTPFLLEEAPIVKSHSFMFSPSRSYYANFGVPVKTAEY
LTRPC3e   (1344) TIERSKSSRYLATTPFLLEEAPIVKSHSFMFSPSRSYYANFGVPVKTAEY
melastatin1 (1344) PLEETKITRYFP--DETINACKTMKSRSFVYSRGRKLVGGVNQDVEYSSI 1501                                              1550
LTRPC3    (1392) TSITDCIDTRCVNAPQAIADRAAFPGGLGDKVEDLTCCHPEREAELSHPS
LTRPC3b   (1404) TSITDCIDTRCVNAPQAIADRAAFPGGLGDKVEDLTCCHPEREAELSHPS
LTRPC3c   (1404) TSITDCIDTRCVNAPQAIADRAAFPGGLGDKVEDLTCCHPEREAELSHPS
LTRPC3e   (1394) TSITDCIDTRCVNAPQAIADRAAFPGGLGDKVEDLTCCHPEREAELSHPS
melastatin1 (1392) TDQQLTTEWQCQVQKITRSHSTDIEYIVSEAAVQAEQKE---------Q 1551                                              1600
LTRPC3    (1442) SDSEENEAKGRRATIAISSQEGDNSERTLSNNITVPKIERANSYSAEEPS
LTRPC3b   (1454) SDSEENEAKGRRATIAISSQEGDNSERTLSNNITVPKIERANSYSAEEPS
LTRPC3c   (1454) SDSEENEAKGRRATIAISSQEGDNSERTLSNNITVPKIERANSYSAEEPS
LTRPC3e   (1444) SDSEENEAKGRRATIAISSQEGDNSERTLSNNITVPKIERANSYSAEEPS
melastatin1 (1432) FADMQDEHHVAEAIPRIPRLSLTITDRNGMENLLSVKPDQTLGFPSLRSK 1601                                              1650
LTRPC3    (1492) APYAHTRKSFSISDKLDRQRNTASLQNPFQRSKSSKPEGRGDSLSMRRLS
LTRPC3b   (1504) APYAHTRKSFSISDKLDRQRNTASLQNPFQRSKSSKPEGRGDSLSMRRLS
LTRPC3c   (1504) APYAHTRKSFSISDKLDRQRNTASLQNPFQRSKSSKPEGRGDSLSMRRLS
LTRPC3e   (1494) APYAHTRKSFSISDKLDRQRNTASLQNPFQRSKSSKPEGRGDSLSMRRLS
melastatin1 (1482) SLHGHPRNVKSIQCKLDRSGHASSVSSLVIVSGMTAEE--------KKVK 1651     1663
LTRPC3    (1542) RTSAFQSFESKHT
LTRPC3b   (1554) RTSAFQSFESKHT
LTRPC3c   (1554) RTSAFQSFESKHT
LTRPC3e   (1544) RTSAFQSFESKHT
melastatin1 (1524) KEKASTETEC---
```

Fig. 8.

LTRPC3

| Protein | Genbank ID | Identities | Similarities |
|---|---|---|---|
| human melastatin 1 | gi|3243075 | 65.7% | 73.5% |

LTRPC3b

| Protein | Genbank ID | Identities | Similarities |
|---|---|---|---|
| human melastatin 1 | gi|3243075 | 65.7% | 73.5% |

LTRPC3c

| Protein | Genbank ID | Identities | Similarities |
|---|---|---|---|
| human melastatin 1 | gi|3243075 | 65.4% | 73.1% |

LTRPC3e

| Protein | Genbank ID | Identities | Similarities |
|---|---|---|---|
| human melastatin 1 | gi|3243075 | 65.5% | 73.3% |

Fig. 9A

```
               1                                                  50
LTRPC3    (1)  MYVRVSFDTKPDLLLHLMTKEWQLELPKLLISVHGGLQNFELQPKLKQVF
LTRPC3b   (1)  MYVRVSFDTKPDLLLHLMTKEWQLELPKLLISVHGGLQNFELQPKLKQVF
LTRPC3c   (1)  MYVRVSFDTKPDLLLHLMTKEWQLELPKLLISVHGGLQNFELQPKLKQVF
LTRPC3d   (1)  MYVRVSFDTKPDLLLHLMTKEWQLELPKLLISVHGGLQNFELQPKLKQVF
LTRPC3e   (1)  MYVRVSFDTKPDLLLHLMTKEWQLELPKLLISVHGGLQNFELQPKLKQVF
LTRPC3f   (1)  MYVRVSFDTKPDLLLHLMTKEWQLELPKLLISVHGGLQNFELQPKLKQVF 51                                                 100
LTRPC3    (51) GKGLIKAAMTTGAWIFTGGVNTGVIRHVGDALKDHASKSRGKICTIGIAP
LTRPC3b   (51) GKGLIKAAMTTGAWIFTGGVNTGVIRHVGDALKDHASKSRGKICTIGIAP
LTRPC3c   (51) GKGLIKAAMTTGAWIFTGGVNTGVIRHVGDALKDHASKSRGKICTIGIAP
LTRPC3d   (51) GKGLIKAAMTTGAWIFTGGVNTGVIRHVGDALKDHASKSRGKICTIGIAP
LTRPC3e   (51) GKGLIKAAMTTGAWIFTGGVNTGVIRHVGDALKDHASKSRGKICTIGIAP
LTRPC3f   (51) GKGLIKAAMTTGAWIFTGGVNTGVIRHVGDALKDHASKSRGKICTIGIAP 101                                                150
LTRPC3   (101) WGIVENQEDLIGRDVVRPYQTMSNPMSKLTVLNSMHSHFILADNGTTGKY
LTRPC3b  (101) WGIVENQEDLIGRDVVRPYQTMSNPMSKLTVLNSMHSHFILADNGTTGKY
LTRPC3c  (101) WGIVENQEDLIGRDVVRPYQTMSNPMSKLTVLNSMHSHFILADNGTTGKY
LTRPC3d  (101) WGIVENQEDLIGRDVVRPYQTMSNPMSKLTVLNSMHSHFILADNGTTGKY
LTRPC3e  (101) WGIVENQEDLIGRDVVRPYQTMSNPMSKLTVLNSMHSHFILADNGTTGKY
LTRPC3f  (101) WGIVENQEDLIGRDVVRPYQTMSNPMSKLTVLNSMHSHFILADNGTTGKY 151                                                200
LTRPC3   (151) GAEVKLRRQLEKHISLQKINTR-------------------------IGQ
LTRPC3b  (151) GAEVKLRRQLEKHISLQKINTR-------------------------IGQ
LTRPC3c  (151) GAEVKLRRQLEKHISLQKINTR-------------------------IGQ
LTRPC3d  (151) GAEVKLRRQLEKHISLQKINTR-------------------------IGQ
LTRPC3e  (151) GAEVKLRRQLEKHISLQKINTR-------------------------IGQ
LTRPC3f  (151) GAEVKLRRQLEKHISLQKINTRCLPFFSLDSRLFYSFWGSCQLDSVGIGQ 201                                                250
LTRPC3   (176) GVPVVALIVEGGPNVISIVLEYLRDTPPVPVVVCDGSGRASDILAFGHKY
LTRPC3b  (176) GVPVVALIVEGGPNVISIVLEYLRDTPPVPVVVCDGSGRASDILAFGHKY
LTRPC3c  (176) GVPVVALIVEGGPNVISIVLEYLRDTPPVPVVVCDGSGRASDILAFGHKY
LTRPC3d  (176) GVPVVALIVEGGPNVISIVLEYLRDTPPVPVVVCDGSGRASDILAFGHKY
LTRPC3e  (176) GVPVVALIVEGGPNVISIVLEYLRDTPPVPVVVCDGSGRASDILAFGHKY
LTRPC3f  (201) GVPVVALIVEGGPNVISIVLEYLRDTPPVPVVVCDGSGRASDILAFGHKY 251                                                300
LTRPC3   (226) SEEGGLINESLRDQLLVTIQKTFTYTRTQAQHLFIILMECMKKKELITVF
LTRPC3b  (226) SEEGGLINESLRDQLLVTIQKTFTYTRTQAQHLFIILMECMKKKELITVF
LTRPC3c  (226) SEEGGLINESLRDQLLVTIQKTFTYTRTQAQHLFIILMECMKKKELITVF
LTRPC3d  (226) SEEGGLINESLRDQLLVTIQKTFTYTRTQAQHLFIILMECMKKKELITVF
LTRPC3e  (226) SEEGGLINESLRDQLLVTIQKTFTYTRTQAQHLFIILMECMKKKELITVF
LTRPC3f  (251) SEEGGLINESLRDQLLVTIQKTFTYTRTQAQHLFIILMECMKKKELITVF 301                                                350
LTRPC3   (276) RMGSEGHQDIDLAILTALLKGANASAPDQLSLALAWNRVDIARSQIFIYG
LTRPC3b  (276) RMGSEGHQDIDLAILTALLKGANASAPDQLSLALAWNRVDIARSQIFIYG
LTRPC3c  (276) RMGSEGHQDIDLAILTALLKGANASAPDQLSLALAWNRVDIARSQIFIYG
LTRPC3d  (276) RMGSEGHQDIDLAILTALLKGANASAPDQLSLALAWNRVDIARSQIFIYG
LTRPC3e  (276) RMGSEGHQDIDLAILTALLKGANASAPDQLSLALAWNRVDIARSQIFIYG
LTRPC3f  (301) RMGSEGHQDIDLAILTALLKGANASAPDQLSLALAWNRVDIARSQIFIYG
```

Fig. 9B

```
              351                                                    400
LTRPC3  (326) QQWPVGSLEQAMLDALVLDRVDFVKLLIENGVSMHRFLTISRLEELYNTR
LTRPC3b (326) QQWPVGSLEQAMLDALVLDRVDFVKLLIENGVSMHRFLTISRLEELYNTR
LTRPC3c (326) QQWPVGSLEQAMLDALVLDRVDFVKLLIENGVSMHRFLTISRLEELYNTR
LTRPC3d (326) QQWPVGSLEQAMLDALVLDRVDFVKLLIENGVSMHRFLTISRLEELYNTR
LTRPC3e (326) QQWPVGSLEQAMLDALVLDRVDFVKLLIENGVSMHRFLTISRLEELYNTR
LTRPC3f (351) QQWPVGSLEQAMLDALVLDRVDFVKLLIENGVSMHRFLTISRLEELYNTR 401                                                    450
LTRPC3  (376) HGPSNTLYHLVRDVKK-------------GNLPPDYRISLIDIGLVIEYLM
LTRPC3b (376) HGPSNTLYHLVRDVKKREYPGFGWIYFKGNLPPDYRISLIDIGLVIEYLM
LTRPC3c (376) HGPSNTLYHLVRDVKKREYPGFGWIYFKGNLPPDYRISLIDIGLVIEYLM
LTRPC3d (376) HGPSNTLYHLVRDVKK-------------GNLPPDYRISLIDIGLVIEYLM
LTRPC3e (376) HGPSNTLYHLVRDVKKREYPGFGWIYFKGNLPPDYRISLIDIGLVIEYLM
LTRPC3f (401) HGPSNTLYHLVRDVKK-------------GNLPPDYRISLIDIGLVIEYLM 451                                                    500
LTRPC3  (414) GGAYRCNYTRKRFRTLYHNLFGPKRPKALKLLGMEDDIPLRRGRKTTKKR
LTRPC3b (426) GGAYRCNYTRKRFRTLYHNLFGPKRPKALKLLGMEDDIPLRRGRKTTKKR
LTRPC3c (414) GGAYRCNYTRKRFRTLYHNLFGPKRPKALKLLGMEDDIPLRRGRKTTKKR
LTRPC3d (414) GGAYRCNYTRKRFRTLYHNLFGPKR----------DDIPLRRGRKTTKKR
LTRPC3e (426) GGAYRCNYTRKRFRTLYHNLFGPKR----------DDIPLRRGRKTTKKR
LTRPC3f (439) GGAYRCNYTRKRFRTLYHNLFGPKRPKALKLLGMEDDIPLRRGRKTTKKR 501                                                    550
LTRPC3  (464) EEEVDIDLDDPEINHFPFPFHELMVWAVLMKRQKMALFFWQHGEEAMAKA
LTRPC3b (476) EEEVDIDLDDPEINHFPFPFHELMVWAVLMKRQKMALFFWQHGEEAMAKA
LTRPC3c (464) EEEVDIDLDDPEINHFPFPFHELMVWAVLMKRQKMALFFWQHGEEAMAKA
LTRPC3d (454) EEEVDIDLDDPEINHFPFPFHELMVWAVLMKRQKMALFFWQHGEEAMAKA
LTRPC3e (466) EEEVDIDLDDPEINHFPFPFHELMVWAVLMKRQKMALFFWQHGEEAMAKA
LTRPC3f (489) EEEVDIDLDDPEINHFPFPFHELMVWAVLMKRQKMALFFWQHGEEAMAKA 551                                                    600
LTRPC3  (514) LVACKLCKAMAHEASENDMVDDISQELNHNSRDFGQLAVELLDQSYKQDE
LTRPC3b (526) LVACKLCKAMAHEASENDMVDDISQELNHNSRDFGQLAVELLDQSYKQDE
LTRPC3c (514) LVACKLCKAMAHEASENDMVDDISQELNHNSRDFGQLAVELLDQSYKQDE
LTRPC3d (504) LVACKLCKAMAHEASENDMVDDISQELNHNSRDFGQLAVELLDQSYKQDE
LTRPC3e (516) LVACKLCKAMAHEASENDMVDDISQELNHNSRDFGQLAVELLDQSYKQDE
LTRPC3f (539) LVACKLCKAMAHEASENDMVDDISQELNHNSRDFGQLAVELLDQSYKQDE 601                                                    650
LTRPC3  (564) QLAMKLLTYELKNWSNATCLQLAVAAKHRDFIAHTCSQMLLTDMWMGRLR
LTRPC3b (576) QLAMKLLTYELKNWSNATCLQLAVAAKHRDFIAHTCSQMLLTDMWMGRLR
LTRPC3c (564) QLAMKLLTYELKNWSNATCLQLAVAAKHRDFIAHTCSQMLLTDMWMGRLR
LTRPC3d (554) QLAMKLLTYELKNWSNATCLQLAVAAKHRDFIAHTCSQMLLTDMWMGRLR
LTRPC3e (566) QLAMKLLTYELKNWSNATCLQLAVAAKHRDFIAHTCSQMLLTDMWMGRLR
LTRPC3f (589) QLAMKLLTYELKNWSNATCLQLAVAAKHRDFIAHTCSQMLLTDMWMGRLR 651                                                    700
LTRPC3  (614) MRKNSGLKVILGILLPPSILSLEFKNKDDMPYMSQAQEIHLQEKEAEEPE
LTRPC3b (626) MRKNSGLKVILGILLPPSILSLEFKNKDDMPYMSQAQEIHLQEKEAEEPE
LTRPC3c (614) MRKNSGLKVILGILLPPSILSLEFKNKDDMPYMSQAQEIHLQEKEAEEPE
LTRPC3d (604) MRKNSGLKVILGILLPPSILSLEFKNKDDMPYMSQAQEIHLQEKEAEEPE
LTRPC3e (616) MRKNSGLKVILGILLPPSILSLEFKNKDDMPYMSQAQEIHLQEKEAEEPE
LTRPC3f (639) MRKNSGLKVILGILLPPSILSLEFKNKDDMPYMSQAQEIHLQEKEAEEPE
```

Fig. 9C

```
              701                                              750
LTRPC3  (664) KPTKEKEEEDMELTAMLGRNNGESSRKKDEEEVQSKHRLIPLGRKIYEFY
LTRPC3b (676) KPTKEKEEEDMELTAMLGRNNGESSRKKDEEEVQSKHRLIPLGRKIYEFY
LTRPC3c (664) KPTKEKEEEDMELTAMLGRNNGESSRKKDEEEVQSKHRLIPLGRKIYEFY
LTRPC3d (654) KPTKEKEEEDMELTAMLGRNNGESSRKKDEEEVQSKHRLIPLGRKIYEFY
LTRPC3e (666) KPTKEKEEEDMELTAMLGRNNGESSRKKDEEEVQSKHRLIPLGRKIYEFY
LTRPC3f (689) KPTKEKEEEDMELTAMLGRNNGESSRKKDEEEVQSKHRLIPLGRKIYEFY 751                                              800
LTRPC3  (714) NAPIVKFWFYTLAYIGYLMLFNYIVLVKMERWPSTQEWIVISYIFTLGIE
LTRPC3b (726) NAPIVKFWFYTLAYIGYLMLFNYIVLVKMERWPSTQEWIVISYIFTLGIE
LTRPC3c (714) NAPIVKFWFYTLAYIGYLMLFNYIVLVKMERWPSTQEWIVISYIFTLGIE
LTRPC3d (704) NAPIVKFWFYTLAYIGYLMLFNYIVLVKMERWPSTQEWIVISYIFTLGIE
LTRPC3e (716) NAPIVKFWFYTLAYIGYLMLFNYIVLVKMERWPSTQEWIVISYIFTLGIE
LTRPC3f (739) NAPIVKFWFYTLAYIGYLMLFNYIVLVKMERWPSTQEWIVISYIFTLGIE 801                                              850
LTRPC3  (764) KMREILMSEPGKLLQKVKVWLQEYWNVTDLIAILLFSVGMILRLQDQPFR
LTRPC3b (776) KMREILMSEPGKLLQKVKVWLQEYWNVTDLIAILLFSVGMILRLQDQPFR
LTRPC3c (764) KMREILMSEPGKLLQKVKVWLQEYWNVTDLIAILLFSVGMILRLQDQPFR
LTRPC3d (754) KMREILMSEPGKLLQKVKVWLQEYWNVTDLIAILLFSVGMILRLQDQPFR
LTRPC3e (766) KMREILMSEPGKLLQKVKVWLQEYWNVTDLIAILLFSVGMILRLQDQPFR
LTRPC3f (789) KMREILMSEPGKLLQKVKVWLQEYWNVTDLIAILLFSVGMILRLQDQPFR 851                                              900
LTRPC3  (814) SDGRVIYCVNIIYWYIRLLDIFGVNKYLGPYVMMIGKMMIDMMYFVIIML
LTRPC3b (826) SDGRVIYCVNIIYWYIRLLDIFGVNKYLGPYVMMIGKMMIDMMYFVIIML
LTRPC3c (814) SDGRVIYCVNIIYWYIRLLDIFGVNKYLGPYVMMIGKMMIDMMYFVIIML
LTRPC3d (804) SDGRVIYCVNIIYWYIRLLDIFGVNKYLGPYVMMIGKMMIDMMYFVIIML
LTRPC3e (816) SDGRVIYCVNIIYWYIRLLDIFGVNKYLGPYVMMIGKMMIDMMYFVIIML
LTRPC3f (839) SDGRVIYCVNIIYWYIRLLDIFGVNKYLGPYVMMIGKMMIDMMYFVIIML 901                                              950
LTRPC3  (864) VVLMSFGVARQAILFPNEEPSWKLAKNIFYMPYWMIYGEVFADQID----
LTRPC3b (876) VVLMSFGVARQAILFPNEEPSWKLAKNIFYMPYWMIYGEVFADQID----
LTRPC3c (864) VVLMSFGVARQAILFPNEEPSWKLAKNIFYMPYWMIYGEVFADQIDRKQV
LTRPC3d (854) VVLMSFGVARQAILFPNEEPSWKLAKNIFYMPYWMIYGEVFADQID----
LTRPC3e (866) VVLMSFGVARQAILFPNEEPSWKLAKNIFYMPYWMIYGEVFADQID----
LTRPC3f (889) VVLMSFGVARQAILFPNEEPSWKLAKNIFYMPYWMIYGEVFADQID----

951                                             1000
LTRPC3  (910) --------PPCGQNETREDGKIIQLPPCKTGAWIVPAIMACYLLVANILL
LTRPC3b (922) --------PPCGQNETREDGKIIQLPPCKTGAWIVPAIMACYLLVANILL
LTRPC3c (914) YDSHTPKSAPCGQNETREDGKIIQLPPCKTGAWIVPAIMACYLLVANILL
LTRPC3d (900) --------PPCGQNETREDGKIIQLPPCKTGAWIVPAIMACYLLVANILL
LTRPC3e (912) --------PPCGQNETREDGKIIQLPPCKTGAWIVPAIMACYLLVANILL
LTRPC3f (935) --------PPCGQNETREDGKIIQLPPCKTGAWIVPAIMACYLLVANILL 1001                                            1050
LTRPC3  (952) VNLLIAVFNNTFFEVKSISNQVWKFQRYQLIMTFHERPVLPPPLIIFSHM
LTRPC3b (964) VNLLIAVFNNTFFEVKSISNQVWKFQRYQLIMTFHERPVLPPPLIIFSHM
LTRPC3c (964) VNLLIAVFNNTFFEVKSISNQVWKFQRYQLIMTFHERPVLPPPLIIFSHM
LTRPC3d (942) VNLLIAVFNNTFFEVKSISNQVWKFQRYQLIMTFHERPVLPPPLIIFSHM
LTRPC3e (954) VNLLIAVFNNTFFEVKSISNQVWKFQRYQLIMTFHERPVLPPPLIIFSHM
LTRPC3f (977) VNLLIAVFNNTFFEVKSISNQVWKFQRYQLIMTFHERPVLPPPLIIFSHM
```

Fig. 9D

```
              1051                                               1100
LTRPC3  (1002) TMIFQHLCCRWRKHESDPDERDYGLKLFITDDELKKVHDFEEQCIEEYFR
LTRPC3b (1014) TMIFQHLCCRWRKHESDPDERDYGLKLFITDDELKKVHDFEEQCIEEYFR
LTRPC3c (1014) TMIFQHLCCRWRKHESDPDERDYGLKLFITDDELKKVHDFEEQCIEEYFR
LTRPC3d  (992) TMIFQHLCCRWRKHESDPDERDYGLKLFITDDELKKVHDFEEQCIEEYFR
LTRPC3e (1004) TMIFQHLCCRWRKHESDPDERDYGLKLFITDDELKKVHDFEEQCIEEYFR
LTRPC3f (1027) TMIFQHLCCRWRKHESDPDERDYGLKLFITDDELKKVHDFEEQCIEEYFR 1101                                              1150
LTRPC3  (1052) EKDDRFNSSNDERIRVTSERVENMSMRLEEVNEREHSMKASLQTVDIRLA
LTRPC3b (1064) EKDDRFNSSNDERIRVTSERVENMSMRLEEVNEREHSMKASLQTVDIRLA
LTRPC3c (1064) EKDDRFNSSNDERIRVTSERVENMSMRLEEVNEREHSMKASLQTVDIRLA
LTRPC3d (1042) EKDDRFNSSNDERIRVTSERVENMSMRLEEVNEREHSMKASLQTVDIRLA
LTRPC3e (1054) EKDDRFNSSNDERIRVTSERVENMSMRLEEVNEREHSMKASLQTVDIRLA
LTRPC3f (1077) EKDDRFNSSNDERIRVTSERVENMSMRLEEVNEREHSMKASLQTVDIRLA 1151                                              1200
LTRPC3  (1102) QLEDLIGRMATALERLTGLERAESNKIRSRTSSDCTDAAYIVRQSSFNSQ
LTRPC3b (1114) QLEDLIGRMATALERLTGLERAESNKIRSRTSSDCTDAAYIVRQSSFNSQ
LTRPC3c (1114) QLEDLIGRMATALERLTGLERAESNKIRSRTSSDCTDAAYIVRQSSFNSQ
LTRPC3d (1092) QLEDLIGRMATALERLTGLERAESNKIRSRTSSDCTDAAYIVRQSSFNSQ
LTRPC3e (1104) QLEDLIGRMATALERLTGLERAESNKIRSRTSSDCTDAAYIVRQSSFNSQ
LTRPC3f (1127) QLEDLIGRMATALERLTGLERAESNKIRSRTSSDCTDAAYIVRQSSFNSQ 1201                                              1250
LTRPC3  (1152) EGNTFKLQESIDPAGEETMSPTSPTLMPRMRSHSFYSVNMKDKGGIEKLE
LTRPC3b (1164) EGNTFKLQESIDPAGEETMSPTSPTLMPRMRSHSFYSVNMKDKGGIEKLE
LTRPC3c (1164) EGNTFKLQESIDPAGEETMSPTSPTLMPRMRSHSFYSVNMKDKGGIEKLE
LTRPC3d (1142) EGNTFKLQESIDPAGEETMSPTSPTLMPRMRSHSFYSVNMKDKGGIEKLE
LTRPC3e (1154) EGNTFKLQESIDPAGEETMSPTSPTLMPRMRSHSFYSVNMKDKGGIEKLE
LTRPC3f (1177) EGNTFKLQESIDPAGEETMSPTSPTLMPRMRSHSFYSVNMKDKGGIEKLE 1251                                              1300
LTRPC3  (1202) SIFKERSLSLHRATSSHSVAKEPKAPAAPANTLAIVPDSRRPSSCIDIYV
LTRPC3b (1214) SIFKERSLSLHRATSSHSVAKEPKAPAAPANTLAIVPDSRRPSSCIDIYV
LTRPC3c (1214) SIFKERSLSLHRATSSHSVAKEPKAPAAPANTLAIVPDSRRPSSCIDIYV
LTRPC3d (1192) SIFKERSLSLHRATSSHSVAKEPKAPAAPANTLAIVPDSRRPSSCIDIYV
LTRPC3e (1204) SIFKERSLSLHRATSSHSVAKEPKAPAAPANTLAIVPDSRRPSSCIDIYV
LTRPC3f (1227) SIFKERSLSLHRATSSHSVAKEPKAPAAPANTLAIVPDSRRPSSCIDIYV 1301                                              1350
LTRPC3  (1252) SAMDELHCDIDPLDNSVNILGLGEPSFSTPVPSTAPSSSAYATLAPTDRP
LTRPC3b (1264) SAMDELHCDIDPLDNSVNILGLGEPSFSTPVPSTAPSSSAYATLAPTDRP
LTRPC3c (1264) SAMDELHCDIDPLDNSVNILGLGEPSFSTPVPSTAPSSSAYATLAPTDRP
LTRPC3d (1242) SAMDELHCDIDPLDNSVNILGLGEPSFSTPVPSTAPSSSAYATLAPTDRP
LTRPC3e (1254) SAMDELHCDIDPLDNSVNILGLGEPSFSTPVPSTAPSSSAYATLAPTDRP
LTRPC3f (1277) SAMDELHCDIDPLDNSVNILGLGEPSFSTPVPSTAPSSSAYATLAPTDRP 1351                                              1400
LTRPC3  (1302) PSRSIDFEDITSMDTRSFSSDYTHLPECQNPWDSEPPMYHTIERSKSSRY
LTRPC3b (1314) PSRSIDFEDITSMDTRSFSSDYTHLPECQNPWDSEPPMYHTIERSKSSRY
LTRPC3c (1314) PSRSIDFEDITSMDTRSFSSDYTHLPECQNPWDSEPPMYHTIERSKSSRY
LTRPC3d (1292) PSRSIDFEDITSMDTRSFSSDYTHLPECQNPWDSEPPMYHTIERSKSSRY
LTRPC3e (1304) PSRSIDFEDITSMDTRSFSSDYTHLPECQNPWDSEPPMYHTIERSKSSRY
LTRPC3f (1327) PSRSIDFEDITSMDTRSFSSDYTHLPECQNPWDSEPPMYHTIERSKSSRY
```

Fig. 9E

```
              1401                                                  1450
 LTRPC3  (1352) LATTPFLLEEAPIVKSHSFMFSPSRSYYANFGVPVKTAEYTSITDCIDTR
 LTRPC3b (1364) LATTPFLLEEAPIVKSHSFMFSPSRSYYANFGVPVKTAEYTSITDCIDTR
 LTRPC3c (1364) LATTPFLLEEAPIVKSHSFMFSPSRSYYANFGVPVKTAEYTSITDCIDTR
 LTRPC3d (1342) LATTPFLLEEAPIVKSHSFMFSPSRSYYANFGVPVKTAEYTSITDCIDTR
 LTRPC3e (1354) LATTPFLLEEAPIVKSHSFMFSPSRSYYANFGVPVKTAEYTSITDCIDTR
 LTRPC3f (1377) LATTPFLLEEAPIVKSHSFMFSPSRSYYANFGVPVKTAEYTSITDCIDTR 1451                                                  1500
 LTRPC3  (1402) CVNAPQAIADRAAFPGGLGDKVEDLTCCHPEREAELSHPSSDSEENEAKG
 LTRPC3b (1414) CVNAPQAIADRAAFPGGLGDKVEDLTCCHPEREAELSHPSSDSEENEAKG
 LTRPC3c (1414) CVNAPQAIADRAAFPGGLGDKVEDLTCCHPEREAELSHPSSDSEENEAKG
 LTRPC3d (1392) CVNAPQAIADRAAFPGGLGDKVEDLTCCHPEREAELSHPSSDSEENEAKG
 LTRPC3e (1404) CVNAPQAIADRAAFPGGLGDKVEDLTCCHPEREAELSHPSSDSEENEAKG
 LTRPC3f (1427) CVNAPQAIADRAAFPGGLGDKVEDLTCCHPEREAELSHPSSDSEENEAKG 1501                                                  1550
 LTRPC3  (1452) RRATIAISSQEGDNSERTLSNNITVPKIERANSYSAEEPSAPYAHTRKSF
 LTRPC3b (1464) RRATIAISSQEGDNSERTLSNNITVPKIERANSYSAEEPSAPYAHTRKSF
 LTRPC3c (1464) RRATIAISSQEGDNSERTLSNNITVPKIERANSYSAEEPSAPYAHTRKSF
 LTRPC3d (1442) RRATIAISSQEGDNSERTLSNNITVPKIERANSYSAEEPSAPYAHTRKSF
 LTRPC3e (1454) RRATIAISSQEGDNSERTLSNNITVPKIERANSYSAEEPSAPYAHTRKSF
 LTRPC3f (1477) RRATIAISSQEGDNSERTLSNNITVPKIERANSYSAEEPSAPYAHTRKSF 1551                                                  1600
 LTRPC3  (1502) SISDKLDRQRNTASLQNPFQRSKSSKPEGRGDSLSMRRLSRTSAFQSFES
 LTRPC3b (1514) SISDKLDRQRNTASLQNPFQRSKSSKPEGRGDSLSMRRLSRTSAFQSFES
 LTRPC3c (1514) SISDKLDRQRNTASLQNPFQRSKSSKPEGRGDSLSMRRLSRTSAFQSFES
 LTRPC3d (1492) SISDKLDRQRNTASLQNPFQRSKSSKPEGRGDSLSMRRLSRTSAFQSFES
 LTRPC3e (1504) SISDKLDRQRNTASLQNPFQRSKSSKPEGRGDSLSMRRLSRTSAFQSFES
 LTRPC3f (1527) SISDKLDRQRNTASLQNPFQRSKSSKPEGRGDSLSMRRLSRTSAFQSFES

1601
 LTRPC3  (1552) KHT
 LTRPC3b (1564) KHT
 LTRPC3c (1564) KHT
 LTRPC3d (1542) KHT
 LTRPC3e (1554) KHT
 LTRPC3f (1577) KHT
```

Fig. 10

>AL358786 Encoding internal segment of LTRPC3
ATTACGGTATTTCGGATGGGATCAGAAGGACACCAGGACATTGATTTGGCTATCCTGACA
GCTTTACTCAAAGGTAAAAGANNN (SEQ ID NO:12).

>AL358786 Encoding internal segment of LTRPC3
CCTTTCCATGAGCTCATGGTGTGGGCTGTTCTCATGAAGCGGCAGAAGATGGCCCTGTTC
TTCTGGCAGCACGGTGAGGAGGCCATGGCCAAGGCCCTGGTGGCCTGCAAGCTCTGCAAA
GCCATGGCTCATGAGGCCTCTGAGAACGACATGGTTGACGACATTTCCCAGGAGCTGAAT
CACAATTCCAGAGACTTTGGCCAGCTGGCTGTGGAGCTCCTGGACCAGTCCTACAAGCAG
GACGAACAGCTGGCCATGAAACTGCTGACGTATGAGCTGAAGAACTGGAGCAACGCCACG
TGCCTGCAGCTTGCCGTGGCTGCCAAACACCGCGACTTCATCGCGCACACGTGCAGCCAG
ATGCTGCTCACCGACATGTGGATGGGCCGGCTCNNN   (SEQ ID NO:13).

>AL358786 Encoding internal segment of LTRPC3
CTGGCGTATATCGGATACCTGATGCTCTTCAACTATATCGTGTTAGTGAAGATGGAACGC
TGGCCGTCCACCCAGGAATGGATCGTAATCTCCTATATTTTCACCCTGGGAATAGAAAAG
ATGAGAGAGATTCTGATGTCAGAGCCAGGGAAGTTGCTACAGAAAGTGAAGGTATGGCTG
CAGGAGTACTGGAATGTCACGGACCTCATCGCCATCCTTCTGTTTTCTGTCGGAATGATC
CTTCGTCTCCAAGACCAGCCCTTCAGGAGTGACGGGAGGGTCATCTACTGCGTGAACATC
ATTTACTGGTATATCCGTCTCCTAGACATCTTCGGCGTGAACAAGTATTTGGGCCCGTAT
GTAATGATGATTGGAAAAATGATGATAGACATGATGTACTTTGTCATCATTATGCTGGTG
GTTCTGATGAGCTTTGGGGTCGCCAGGCAAGCCATCCTTTTTCCCAATGAGGAGCCATCA
TGGAAACTGGCCAAGAACATCTTCTACATGCCCTATTGGATGATTTATGGGGAAGTG (SEQ
ID NO:14).

>NT_008306 Encoding 5' end of novel LTRPC3
ATATTTAATCACTTAAATTAGCAGAATACATGCCCTCTAGCTCTATGAAGCAGGAACATGA
ACCAAACACATTTAGGATGTTGCAAAAACTAAAGGCATAGCTGTATACAGAGACTGTTCG
GAGTTATTTACATAAAATGCAAAGCTGACTTCTGTAGACTGTTCGGAGTTATTTCCATAAA
ACACAAAGTTTACTTCTGTAATAAGAAGCAGCTTTGCCACATGCCACACACACACGCACA
CTTTGCCCCATGCTGGGGCCATCGCCAGTTCTGCCCCTGCTTGCCTGGTGTTGCTGTGGGC
GTCTGATAGGCCAGCATGTTGGCCTCACCCCAGTATCTCCGTGCTTCAGAATGAGAAAA
ATGAAAGTCGCCTCTCCCGAAATGACATCCAGTCTGAAAAGTGGTCCATCAGCAAACACA
CTCAACTCAGCCCTACGGATGCTTTTGGGACCATTGAGTTCCAAGGAGGTGGCCATTCCAA
CAAAGCCATGTATGTGCGAGTATCTTTTGATACAAAACCTGATCTCCTCTTACACCTGATG
ACCAAGGAATGGCAGTTGGAGCTTCCCAAGCTTCTCATCTCTGTCCATGGGGGCCTGCAG
AACTTTGAACTCCAGCCAAAACTCAAGCAAGTCTTTGGGAAAGGGCTCATCAAAGCAGCA
ATGACAACTGGAGCGTGGATATTCACTGGAGGGGTTAACACAGGTGTTATTCGTCATGTT
GGCGATGCCTTGAAGGATCATGCCTCTAAGTCTCGAGGAAAGATATGCACCATAGGTATT
GCCCCCTGGGGAATTGTGGAAAACCAGGAGGACCTCATTGGAAGAGATGTTGTCCGGCCA
TACCAGACCATGTCCAATCCCATGAGCAAGCTCACTGTTCTCAACAGCATGCATTCCCACT
TCATTCTGGCTGACAACGGGACCACTGGAAAATATGGAGCAGAGGTGAAACTTCGAAGAC
AACTGGAAAAGCATATTTCACTCCAGAAGATAAACACAGATGCCTGCCGTTTTTCTCTCT
TGACTCCCGCTTGTTTTATTCATTTTGGGGTAGTTGCCAGTTAGACTCAGTTGGAATCGGTC
AAGGTGTTCCTGTGGTGGCACTCATAGTGGAAGGAGGACCCAATGTGATCTCGATTGTTTT
GGAGTACCTTCGAGACACCCCTCCCGTGCCAGTGGTTGTCTGTGATGGGAGTGGACGGGC
ATCGGACATCCTGGCCTTTGGGCATAAATACTCAGAAGAAGGCGGACTGATAAATGAATC
TTTGAGGGACCAGCTGTTGGTGACTATACAGAAGACTTTCACATACACTCGAACCCAAGC
TCAGCATCTGTTCATCATCCTCATGGAGTGCATGAAGAAGAAGGAATTGATTACGGTATTT
CGGATGGGATCAGAAGGACACCAGGACATTGATTTGGCTATCCTGACAGCTTTACTCAAA
GGTAAAAGAGTC (SEQ ID NO:15).

Fig. 11A

```
>cele-cterm-nompc (Genbank Accession No. gi|11065673)
KFIFDLMVCGKTNDNEPLQEFILQSPAPIETAVKLSALYRDMSEKEKERAKDLLNVAVFSENMAVELLGI
TATEYNAALLLKAKDNRGRPLLDVLIENEQKEVVSYASVQRYLTEVWTARVDWSFGKFVAFSLFVLICPP
AWFYFSLPLDSRIGRAPIIKFVCHIVSHVYFTILLTIVVLNITHKMYEVTSVVPNPVEWLLLLWLSGNLV
SELSTVGGGSGLGIVKVLILVLSAMAIAVHVLAFLLPAVFLTHLDNDEKLHFARTMLYLKNQLFAFALLF
AFVEYLDFLTVHHLFGPWAIIIRDLMYDLARFLVILMLFVAGFTLHVTSIFQPAYQPVDEDSAELMRLAS
PSQTLEMLFFSLFGLVEPDSMPPLHLVPDFAKIILKLLFGIYMMVTLIVLINLLIAMMSDTYQRIQAQSD
KEWKFGRAILIRQMNKKSATPSPINMLTKLIIVLRVAWRNR (SEQ ID NO:16).

>droso-nompc-cterm-long (Genbank Accession No. gi|7328583)
RFVYNLMVVSKNHNNKPIQEFVLVSPAPVDTAAKLSNIYIVLSTKEKERAKDLVAAGKQCEAMATELLAL
AAGSDSAGKILQATDKRNVEFLDVLIENEQKEVIAHTVVQRYLQELWHGSLTWASWKILLLLVAFIVCPP
VWIGFTFPMGHKFNKVPIIKFMSYLTSHIYLMIHLSIVGITPIYPVLRLSLVPYWYEVGLLIWLSGLLLF
ELTNPSDKSGLGSIKVLVLLLGMAGVGVHVSAFLFVSKEYWPTLVYCRNQCFALAFLLACVQILDFLSFH
HLFGPWAIIIGDLLKDLARFLAVLAIFVFGFSMHIVALNQSFANFSPEDLRSFEKKNRNRGYFSDVRMHP
INSFELLFFAVFGQTTTEQTQVDKIKNVATPTQPYWVEYLFKIVFGIYMLVSVVVLINLLIAMMSDTYQR
IQVVLLNALLSNSTLFINSYFNHKYINFILHCVLIILYFSIRSKFTYEDDLYFLDI (SEQ ID NO:17).

>trrp8(trp7)-m (Genbank Accession No. gi|14548296)
MLGSNTFKNMQRRHTTLREKGRRQAIRGPAYMFNEKGTSLTPEEERFLDSAEYGNIPVVRKMLEESKTLN
FNCVDYMGQNALQLAVGNEHLEVTELLLKKENLARVGDALLLAISKGYVRIVEAILSHPAFAQGQRLTLS
PLEQELRDDDFYAYDEDGTRFSHDITPIILAAHCQEYEIVHILLLKGARIERPHDYFCKCNECTEKQRKD
SFSHSRSRMNAYKGLASAAYLSLSSEDPVLTALELSNELARLANIETEFKNDYRKLSMQCKDFVVGVLDL
CRDTEEVEAILNGDVNLQVWSDHHRPSLSRIKLAIKYEVKKFVAHPNCQQQLLTMWYENLSGLRQQSIAV
KFLAVFGVSIGLPFLAIAYWIAPCSKLGQTLRSPFMKFVAHAVSFTIFLGLLVVNASDRFEGVKTLPNET
FTDYPKQIFRVKTTQFSWTEMLIMKWVLGMIWSECKEIWEEGPREYVLHLWNLLDFGMLSIFVASFTARF
MAFLKASEAQLYVDQYVQDVTLHNVSLPPEVAYFTYARDKWWPSDPQIISEGLYAIAVVLSFSRIAYILP
ANESFGPLQISLGRTVKDIFKFMVIFIMVFVAFMIGMFNLYSYYRGAKYNPAFTTVEESFKTLFWSIFGL
SEVISVVLKYDHKFIENIGYVLYGVYNVTMVVVLLNMLIAMINNSYQEIEEDADVEWKFARAKLWLSYFD
EGRTLPAPFNLVPSPKSFYYLIMRIKMCLIELCQSKAKRCENDLEMGMLNSKFRKTRYQAGMRNSENLTA
NSTFSKPTRYQKIMKRLIKRYVLKAQVDRENDEVNEGELKEIKQDISSLRYELLEEKSQATGELADLIQQ
LSEKFGKNLNKDHLRVNQGKDI (SEQ ID NO:18).

>trrp6-m (Genbank Accession No. gi|7305597)
MSQSPRFVTRRGGSLKAAPGAGTRRNESQDYLLMDELGDDGYPQLPLPPYGYYPSFRGNENRLTHRRQTI
LREKGRRLANRGPAYMFNDHSTSLSIEEERFLDAVEYGNIPVVWKMLEECHSLNVNCVDYMGQNALQLAV
ANEHLEITELLLKKENLSRVGDALLLAISKGYVRIVEAILNHPSFAEGKRLATSPSQSELQQDDFYAYDE
DGTRFSHDVTPIILAAHCQEYEIVHTLLRKGARIERPHDYFCKCTECSQKQKHDSFSHSRSRINAYKGLA
SPAYLSLSSEDPVMTALELSNELAVLANIEKEFKNDYRKLSMQCKDFVVGLLDLCRNTEEVEAILNGDAE
TRQPGDFGRPNLSRLKLAIKDEVKKFVAHPNCQQQLLSIWYENLSGLRQQTMAVKFLVVLAVAIGLPFLA
LIYWCAPCSKMGKILPRPFMKFVAHAASFTIFLGLLVMNAADRFEGTKLLPNETSTDNARQLFRMKTSCF
SWMEMLIISWVIGMIWAECKEIWTQGPKEYLFELWMLDFGMLAIFAASFIARFMAFWHASKAQSIIDAN
DTLKDLTKVTLGDNVKYYNLARIKWDPTDPQIISEGLYAIAVVLSFSRIAYILPANESFGPLQISLGRTV
KDIFKFMVIFIMVFVAFMIGMPNLYSYYIGAKQNEAFTTVEESFKTLFWAIFGLSEVKSVVINYNHKFIE
NIGYVLYGVYNVTMVIVLLNMLIAMINSSFQEIEDDADVEWKFARAKLWFSYFEEGRTLPVPFNLVPSPK
SLLYLLLKFKKWMCELIQGGQKQGFQEDAEMNKRNEEKKFGISGSHEDLSKFSLDKNQLAHNKQSSTRSSE
DYHLNSFSNPPRQYQKIMKRLIKRYVLQAQIDKESDEVNEGELKEIKQDISSLRYELLEEKSQNSEDLAE
LIRKLGERLSLEPKLEESRR (SEQ ID NO:19).

>trp3-m (Genbank Accession No. gi|6014703)
MRDKGRRQAVRGPAFMFGARGPSLTAEEERFLDAAEYGNIPVVRKMLEESRTLNVNCVDYMGQNALQLAV
GNEHLEVTELLLKKENLARIGDALLLAISKGYVRIVEAILGHPGFAASRRLTLSPCEQELRDDDFYAYDE
DGTRFSPDITPIILAAHCHKYEVVHLLLLKGARIERAHDYFCRCSDCAEKQRLDAFSHSRSRINAYKGLA
SPAYLSLSSEDPVLTALELSNELAKLANIEKEFKNDYRKLSMQCKDFVVGVLDLCRDSEEVEAILNGDLE
SAEPLERHGHKASLSRVKLAIKYEVKKFVAHPNCQQQLLTIWYENLSGLREQTIAIKCLVVLVVALGLPF
LAIGYWIAPCSRLGKILRSPFMKFVAHAASFIIFLGLLVFNASDRFEGITTLPNITVIDYPKQIFRVKTT
QFTWTEMLIMVWVLGMMWSECKELWLEGPREYIVQLWNVLDFGMLSIFIAAFTARFLAFLQATKAQQYVD
SHVQESDLSEVTLPPEVQYFTYARDKWLPSDPQIISEGLYAIAVVLSFSRIAYILPANESFGPLQISLGR
TVKDIFKFMVLFIMVFLAFMIGMFILYSYYLGAKVNPAFTTVEESFKTLFWSIFGLSEVTSVVLKYDHKF
IENIGYVLYGIYNVTMVVVLLNMLIAMINSSYQEIEDDSDVEWKFARSKLWLSYFDDGKTLPPPFSLVPS
PKSFVYFIMRITNFSKCRRRRLQKDLELGMGNSKSRLNLFTQSNSRVFESHSFNSILNQPTRYQQIMKRL
IKRYVLKAQVDKENDEVNEGELKEIKQDISSLRYELLEDKSQATEELAILIHKLSEKLNPSVLRCE (SEQ ID NO:20).
```

Fig. 11B

>trpc7 (Genbank Accession No. gi|6686045)
MEPSALRKAGSEQEEGFEGLPRRVTDLGMVSNLRRSNSSLFKSWRLQCPFGNNDKQESLSSWIPENIKKK
ECVYFVESSKLSDAGKVVCQCGYTHEQHLEEATKPHTFQGTQWDPKKHVQEMPTDAFGDIVFTGLSQVK
KYVRVSQDTPSSVIYHLMTQHWGLDVPNLLISVTGGAKNFNMKPRLKSIFRRGLVKVAQTTGAWIITGGS
HTGVMKQVGEAVRDFSLSSSYKEGELITIGVATWGTVHRREGLIHPTGSFPAEYILDEDGQGNLTCLDSN
HSHFILVDDGTHGQYGVEIPLRTRLEKFISEQTKERGGVAIKIPIVCVVLEGGPGTLHTIDNATTNGTPC
VVVEGSGRVADVIAQVANLPVSDITISLIQQKLSVFFQEMFETFTESRIVEWTKKIQDIVRRQLLTVFR
EGKDGQQDVDVAILQALLKASRSQDHFGHENWDHQLKLAVAWNRVDIARSEIFMDEWQWKPSDLHPTMTA
ALISNKPEFVKLFLENGVQLKEFVTWDTLLYLYENLDPSCLFHSKLQKVLVEDPERPACAPAAPRLQMHH
VAQVLRELLGDFTQPLYPRPRHNDRLRLLLPVPHVKLNVQGVSLRSLYKRSSGHVTFTMDPIRDLLIWAI
VQNRRELAGIIWAQSQDCIAAALACSKILKELSKEEEDTDSSEEMLALAEEYEHRAIGVFTECYRKDEER
AQKLLTRVSEAWGKTTCLQLALEAKDMKFVSHGGIQAFLTKVWWGQLSVDNGLWRVTLCMLAFPLLLTGL
ISFREKRLQDVGTPAARARAFFTAPVVVFHLNILSYFAFLCLFAYVLMVDFQPVPSWCECAIYLWLFSLV
CEEMRQLFYDPDECGLMKKAALYFSDFWNKLDVGAILLFVAGLTCRLIPATLYPGRVILSLDFILFCLRL
MHIFTISKTLGPKIIIVKRMMKDVFFFLFLLAVWVVSFGVAKQAILIHNERRVDWLFRGAVYHSYLTIFG
QIPGYIDGVNFNPEHCSPNGTDPYKPKCPESDATQQRPAFPEWLTVLLLCLYLLFTNILLLNLLIAMFNY
TFQQVQEHTDQIWKFQRHDLIEEYHGRPAAPPPFILLSHLQLFIKRVVLKTPAKRHKQLKNKLEKNEEAA
LLSWEIYLKENYLQNRQFQQKQRPEQKIEDISNKVDAMVDLLDLDPLKRSGSMEQRLASLEEQVAQTARA
LHWIVRTLRASGFSSEADVPTLASQKAAEEPDAEPGGRKKTEEPGDSYHVNARHLLYPNCPVTRFPVPNE
KVPWETEFLIYDPPFYTAERKDAAAMDPMGDTLEPLSTIQYNVVDGLRDRRSFHGPYTVQAGLPLNPMGR
TGLRGRGSLSCFGPNHTLYPMVTRWRRNEDGAICRKSIKKMLEVLVVKLPLSEHWALPGGSREPGEMLPR
KLKRILRQEHWPSFENLLKCGMEVYKGYMDDPRNTDNAWIETVAVSVHFQDQNDVELNRLNSNLHACDSG
ASIRWQVVDRRIPLYANHKTLLQKAAAEFGAHY (SEQ ID NO:21).

>trp5-mouse (Genbank Accession No. gi|14548292)
MAQLYYKKVNYSPYRDRIPLQIVRAETELSAEEKAFLSAVEKGDYATVKQALQEAEIYYNVNINCMDPLG
RSALLIAIENENLEIMELLLNHSVYVGDALLYAIRKEVVGAVELLLSYRKPSGEKQVPTLMMDTQFSEFT
PDITPIMLAAHTNNYEIIKLLVQKRVTIPRPHQIRCNCVECVSSSEVDSLRHSRSRLNIYKALASPSLIA
LSSEDPILTAFRLGWELKELSKVENEFKAEYEELSQQCKLFAKDLLDQARSSRELEIILNHRDDHSEELD
PQKYHDLAKLKVAIKYHQKEFVAQPNCQQLLATLWYDGFPGWRRKHWVVKLLTCMTIGFLFPMLSIAYLI
SPRSNLGLFIKKPFIKFICHTASYLTFLFMLLLASQHIVRTDLHVQGPPPTVVEWMILPWVLGFIWGEIK
EMWDGGFTEYIHDWWNLMDFAMNSLYLATISLKIVAYVKYNGSRPREEWEMWHPTLIAEALFAISNILSS
LRLISLFTANSHLGPLQISLGRMLLDILKFLFIYCLVLLAFANGLNQLYFYYETRAIDEPNNCKGIRCEK
QNNAFSTLFETLQSLFWSVFGLLNLYVTNVKARHEFTEFVGATMFGTYNVISLVVLLNMLIAMMNNSYQL
IADHADIEWKFARTKLWMSYFDEGGTLPPPFNIIPSPKSFLYLGNWFNNTFCPKRDPDGRRRRHNLRSFT
ERHADSLIQNQHYQEVIRNLVKRYVAAMIRNSKTNEGLTEENFKELKQDISSFRYEVLDLLGNRKHPRRS
LSTSSADFSQRDDTNDGSGGARAKSKSVSFNVGCKKKACHGAPLIRTVPRASGAQGKPKSESSSKRSFMG
PSFKKLGLFFSKFNGQTSEPTSEPMYTISDGIAQQHCMWQDIRYSQMEKGKAEACSQSQMNLGEVELGEI
RGAAARSSECPLACSSSLHCASGICSSNSKLLDSSEDVFETWGEACDLLMHKWGDG (SEQ ID NO:22).

>trp4-m (Genbank Accession No. gi|14548291)
MAQFYYKRNVNAPYRDRIPLRIVRAESELSPSEKAYLNAVEKGDYASVKKSLEEAEIYFKININCIDPLG
RTALLIAIENENLELIELLLSFNVYVGDALLHAIRKEVVGAVELLLNHKKPSGEKQVPPILLDKQFSEFT
PDITPIILAAHTNNYEIIKLLVQKGVSVPRPHEVRCNCVECVSSSDVDSLRHSRSRLNIYKALASPSLIA
LSSEDPFLTAFQLSWELQSKVENEFKSEYEELSRQCKQFAKDLLDQTRSSRELEIILNYRDDNSLIEE
QSGNDLARLKLAIKYRQKEFVAQPNCQQLLASRWYDEFPGWRRHWAVKMVTCFIIGLLFPVFSVCYLIA
PKSPLGLFIRKPFIKFICHTASYLTFLFLLLLASQHIDRSDLNRQGPPPTIVEWMILPWVLGFIWGEIKQ
MWDGGLQDYIHDWWNLMDFVMNSLYLATISLKIVAFVKYSALNPRESWDMWHPTLVAEALFAIANIFSSL
RLISLFTANSHLGPLQISLGRMLLDILKFLFIYCLVLLAFANGLNQLYFYYEETKGLSCKGIRCEKQNNA
FSTLFETLQSLFWSIFGLINLYVTNVKAQHEFTEFVGATMFGTYNVISLVVLLNMLIAMMNNSYQLIADH
ADIEWKFARTKLWMSYFEEGGTLPTPFNVIPSPKSLWYLVKWIWTHLCKKKMRRKPESFGTIGRRAADNL
RRHHQYQEVMRNLVKRYVAAMIREAKTEEGLTEENVKELKQDISSFRFEVLGLLRGSKLSTIQSANAASS
ADSDEKSQSEGNGKDKRKNLSLFDLTTLIHPRSAAIASERHNLSNGSALVVQEPPREKQRKVNFVADIKN
FGLFHRRSKQNAAEQNANQIFSVSEEITRQQAAGALERNIELESKGLASRGDRSIPGLNEQCVLVDHRER
NTDTLGLQVGKRVCSTFKSEKVVVEDTVPIIPKEKHAHEEDSSIDYDLSPTDTAAHEDYVTTRL (SEQ ID NO:23).

Fig. 11C

>trp2-m (Genbank Accession No. gi|4324938)
MGTKTHPVVPWSTKEISELKGMLKQLQPGPLGRAARMVLSAARKAPPASVVSPNNSHGEPGPSRAESAEP
RAEEPNRKTAVGRRKRRKVQEPRRSLSNSSSQPNRRTGRTRQRQHRPQTKSDDGGVQAAGQCPICAGFFS
IETLPQHAATCGESPPPQPASPASLSSSESVLRRHHVALTPVPLVPKPQPNWTEIVNKKLKFPPTLLRAI
QEGQLGLVQQLLESSSDASGAGPGGPLRNVEESEDRSWREALNLAIRLGHEVITDVLLANVKFDFRQIHE
ALLVAVDTNQPAVVRRLLARLEREKGRKVDTKSFSLAFFDSSIDGSRFAPGVTPLTLACQKDLYEIAQLL
MDQGHTIARPHPVSCACLECSNARRYDLLKFSLSRINTYRGIASRAHLSLASEDAMLAAFQLSRELRRLA
RKEPEFKPQYIALESLCQDYGFELLGMCRNQSEVTAVLNDLGEDSETEPEAEGLGQAFEEGIPNLARLRL
AVNYNQKQFVAHPICQQVLSSIWCGNLAGWRGSTTIWRLFVASLIFLTMPFLCIGYWLAPKSQLGRLLKI
PVLKFLLHSASYLWFLIFLLGESLVMETQLSTFKGRSQSVWETSLHMIWVTGFLWPECKEVWIEGLRSYL
LDWWNFLDVVILSLYLASFALRLLLAGLAYMHCRDASDSTTCRCFTTAERSEWRTEDPQFLAEVLFTVTS
MLSFTRLAYILPAHESLGTLQISIGKMIDDMIRFMFILMIILTAFLCGLNNIYVPYQESEKLGNFNETFQ
FLFWTMFGMEEHTVVDMPQFLVPEFVGRAMYGIFTIVMVIVLLNMLIAMITNSFQKIEDDADVEWKFARS
KLYLSYFREGLTLPVPFNILPSPKAAFYLVRRIPRFLCCGSSCCKAKKSDYPPIGTFTNPGARAGSAGEG
ERVSYRLRVIKALVQRYIETARREFEETRRKDLGNRLTELTKTVSRLQSEVASVQKNLAAGGAPRPPDGA
SILSRYITRVRNSFQNLGPPTSDTPAELTMPGIVETEVSLGDGLDGTGEAGAPAPGEPGSSSSAHVLVHR
EQEAEGSGDLLLEGDLETKGES (SEQ ID NO:24).

>trp1a-m (Genbank Accession No. gi|1911245)
MGAPPPSPGLPPSWAAMMAALYPSTDLSGVSSSSLPSSPSSSSPNEVMALKDVREVKEENTLNEKLFLLA
CDKGDYYMVKKILEENSSGDLNINCVDVLGRNAVTITIENESLDILQLLLDYGCQSADALLVAIDSEVVG
AVDILLNHRPKRSSRPTIVKLMERIQNPEYSTTMDVAPVILAAHRNNYEILTMLLKQDVSLPKPHAVGCE
CTLCSAKNKKDSLRHSRFRLDIYRCLASPALIMLTEEDPILRAFELSADLKELSLVEVEFRNDYEELARQ
CKMFAKDLLAQARNSRELEVILNHTSSDEPLDKRGLLEERMNLSRLKLAIKYNQKEFVSQSNCQQFLNTV
WFGQMSGYRRKPTCKKIMTVLTVGIFWPVLSLCYLIAPKSQFGRIIHTPFMKFIIHGASYFTFLLLLNLY
SLVYNEDKKNTMGPALERIDYLLILWIIGMIWSDIKRLWYEGLEDFLEESRNQLSFVMNSLYLATFALKV
VAHNKFHDFADRKDWDAFHPTLVAEGLFAFANVLSYLRLFFMYTTSSILGPLQISMGQMLQDFGKFLGMF
LLVLPSFTIGLTQLYDKGYTSKEQKDCVGIFCEQQSNDTFHSFIGTCFALFWYIFSLAHVAIFVTRFSYG
EELQSFVGAVIVGTYNVVVVIVLTKLLVAMLHKSFQLIANHEDKEWKFARAKLWLSYFDDKCTLPPPFNI
IPSPKTICYMISSLSKWICSHTSKGKVKRQNSLKEWRNLKQKRDENYQKVMCCLVHRYLTSMRQKMQSTD
QATVENLNELRQDLSKFRNEIRDLLGFRTSKYAMFYPRN (SEQ ID NO:25).

Fig. 14A

LTRPC3d
ATGTATGTGCGAGTATCTTTTGATACAAAACCTGATCTCCTCTTACACCTGATGACCAAGG
AATGGCAGTTGGAGCTTCCCAAGCTTCTCATCTCTGTCCATGGGGGCCTGCAGAACTTTGA
ACTCCAGCCAAAACTCAAGCAAGTCTTTGGGAAAGGGCTCATCAAAGCAGCAATGACAAC
TGGAGCGTGGATATTCACTGGAGGGGTTAACACAGGTGTTATTCGTCATGTTGGCGATGCC
TTGAAGGATCATGCCTCTAAGTCTCGAGGAAAGATATGCACCATAGGTATTGCCCCCTGG
GGAATTGTGGAAAACCAGGAGGACCTCATTGGAAGAGATGTTGTCCGGCCATACCAGACC
ATGTCCAATCCCATGAGCAAGCTCACTGTTCTCAACAGCATGCATTCCCACTTCATTCTGG
CTGACAACGGGACCACTGGAAAATATGGAGCAGAGGTGAAACTTCGAAGACAACTGGAA
AAGCATATTTCACTCCAGAAGATAAACACAAGAATCGGTCAAGGTGTTCCTGTGGTGGCA
CTCATAGTGGAAGGAGGACCCAATGTGATCTCGATTGTTTTGGAGTACCTTCGAGACACCC
CTCCCGTGCCAGTGGTTGTCTGTGATGGGAGTGGACGGGCATCGGACATCCTGGCCTTTGG
GCATAAATACTCAGAAGAAGGCGGACTGATAAATGAATCTTTGAGGGACCAGCTGTTGGT
GACTATACAGAAGACTTTCACATACACTCGAACCCAAGCTCAGCATCTGTTCATCATCCTC
ATGGAGTGCATGAAGAAGAAGGAATTGATTACGGTATTTCGGATGGGATCAGAAGGACA
CCAGGACATTGATTTGGCTATCCTGACAGCTTTACTCAAAGGAGCCAATGCCTCGGCCCCA
GACCAACTGAGCTTAGCTTTAGCCTGGAACAGAGTCGACATCGCTCGCAGCCAGATCTTT
ATTTACGGGCAACAGTGGCCGGTGGGATCTCTGGAGCAAGCCATGTTGGATGCCTTAGTT
CTGGACAGAGTGGATTTTGTGAATTACTCATAGAGAATGGAGTAAGCATGCACCGTTTT
CTCACCATCTCCAGACTAGAGGAATTGTACAATACGAGACATGGGCCCTCAAATACATTG
TACCACTTGGTCAGGGATGTCAAAAAGGGGAACCTGCCCCCAGACTACAGAATCAGCCTG
ATTGACATCGGCCTGGTGATCGAGTACCTGATGGGCGGGGCTTATCGCTGCAACTACACG
CGCAAGCGCTTCCGGACCCTCTACCACAACCTCTTCGGCCCCAAGAGGGATGATATTCCCT
TGAGGCGAGGAAGAAAGACAACCAAGAAACGTGAAGAAGAGGTGGACATTGACTTGGAT
GATCCTGAGATCAACCACTTCCCCTTCCCTTTCCATGAGCTCATGGTGTGGGCTGTTCTCAT
GAAGCGGCAGAAGATGGCCCTGTTCTTCTGGCAGCACGGTGAGGAGGCCATGGCCAAGGC
CCTGGTGGCCTGCAAGCTCTGCAAAGCCATGGCTCATGAGGCCTCTGAGAACGACATGGT
TGACGACATTTCCCAGGAGCTGAATCACAATTCCAGAGACTTTGGCCAGCTGGCTGTGGA
GCTCCTGGACCAGTCCTACAAGCAGGACGAACAGCTGGCCATGAAACTGCTGACGTATGA
GCTGAAGAACTGGAGCAACGCCACGTGCCTGCAGCTTGCCGTGGCTGCCAAACACCGCGA
CTTCATCGCGCACACGTGCAGCCAGATGCTGCTCACCGACATGTGGATGGGCCGGCTCCG
CATGCGCAAGAACTCAGGCCTCAAGGTAATTCTGGGAATTCTACTTCCTCCTTCAATTCTC
AGCTTGGAGTTCAAGAACAAAGACGACATGCCCTATATGTCTCAGGCCCAGGAAATCCAC
CTCCAAGAGAAGGAGGCAGAAGAACCAGAGAAGCCCACAAAGGAAAAAGAGGAAGAGG
ACATGGAGCTCACAGCAATGTTGGGACGAAACAACGGGGAGTCCTCCAGGAAGAAGGAT
GAAGAGGAAGTTCAGAGCAAGCACCGGTTAATCCCCCTCGGCAGAAAAATCTATGAATTC
TACAATGCACCCATCGTGAAGTTCTGGTTCTACACACTGGCGTATATCGGATACCTGATGC
TCTTCAACTATATCGTGTTAGTGAAGATGGAACGCTGGCCGTCCACCCAGGAATGGATCGT
AATCTCCTATATTTTCACCCTGGGAATAGAAAAGATGAGAGAGATTCTGATGTCAGAGCC
AGGGAAGTTGCTACAGAAAGTGAAGGTATGGCTGCAGGAGTACTGGAATGTCACGGACCT
CATCGCCATCCTTCTGTTTTCTGTCGGAATGATCCTTCGTCTCCAAGACCAGCCCTTCAGGA
GTGACGGGAGGGTCATCTACTGCGTGAACATCATTTACTGGTATATCCGTCTCCTAGACAT
CTTCGGCGTGAACAAGTATTTGGGCCCGTATGTAATGATGATTGGAAAAATGATGATAGA
CATGATGTACTTTGTCATCATTATGCTGGTGGTTCTGATGAGCTTTGGGGTCGCCAGGCAA
GCCATCCTTTTTCCCAATGAGGAGCCATCATGGAAACTGGCCAAGAACATCTTCTACATGC
CCTATTGGATGATTTATGGGGAAGTGTTTGCGGACCAGATAGACCCTCCCTGTGGACAGA
ATGAGACCCGAGAGGATGGTAAAATAATCCAGCTGCCTCCCTGCAAGACAGGAGCTTGGA
TCGTGCCGGCCATCATGGCCTGCTACCTCTTAGTGGCAAACATCTTGCTGGTCAACCTCCT
CATTGCTGTCTTTAACATACATTTTTTGAAGTAAAATCGATATCCAACCAAGTCTGGAAG
TTTCAGAGGTATCAGCTCATCATGACTTTCCATGAAAGGCCAGTTCTGCCCCCACCACTGA
TCATCTTCAGCCACATGACCATGATATTCCAGCACCTGTGCTGCCGATGGAGGAAACACG
AGAGCGACCCGGATGAAAGGGACTACGGCCTGAAACTCTTCATAACCGATGATGAGCTCA
AGAAAGTACATGACTTTGAAGAGCAATGCATAGAAGAATACTTCAGAGAAAAGGATGAT
CGGTTCAACTCATCTAATGATGAGAGGATACGGGTGACTTCAGAAAGGGTGGAGAACATG
TCTATGCGGCTGGAGGAAGTCAACGAGAGAGAGCACTCCATGAAGGCTTCACTCCAGACC
GTGGACATCCGGCTGGCGCAGCTGGAAGACCTTATCGGGCGCATGGCCACGGCCCTGGAG
CGCCTGACAGGTCTGGAGCGGGCCGAGTCCAACAAAATCCGCTCGAGGACCTCGTCAGAC
TGCACGGACGCCGCCTACATTGTCCGTCAGAGCAGCTTCAACAGCCAGGAAGGGAACACC

Fig. 14B

TTCAAGCTCCAAGAGAGTATAGACCCTGCAGGTGAGGAGACCATGTCCCCAACTTCTCCA
ACCTTAATGCCCCGTATGCGAAGCCATTCTTTCTATTCAGTCAATATGAAAGACAAAGGTG
GTATAGAAAAGTTGGAAAGTATTTTTAAAGAAAGGTCCCTGAGCCTACACCGGGCTACTA
GTTCCCACTCTGTAGCAAAAGAACCCAAAGCTCCTGCAGCCCCTGCCAACACCTTGGCCAT
TGTTCCTGATTCCAGAAGACCATCATCGTGTATAGACATCTATGTCTCTGCTATGGATGAG
CTCCACTGTGATATAGACCCTCTGGACAATTCCGTGAACATCCTTGGGCTAGGCGAGCCAA
GCTTTTCAACTCCAGTACCTTCCACAGCCCCTTCAAGTAGTGCCTATGCAACACTTGCACC
CACAGACAGACCTCCAAGCCGGAGCATTGATTTTGAGGACATCACCTCCATGGACACTAG
ATCTTTTTCTTCAGACTACACCCACCTCCCAGAATGCCAAAACCCCTGGGACTCAGAGCCT
CCGATGTACCACACCATTGAGCGTTCCAAAAGTAGCCGCTACCTAGCCACCACACCCTTTC
TTCTAGAAGAGGCTCCCATTGTGAAATCTCATAGCTTTATGTTTTCCCCCTCAAGGAGCTA
TTATGCCAACTTTGGGGTGCCTGTAAAAACAGCAGAATACACAAGTATTACAGACTGTAT
TGACACAAGGTGTGTCAATGCCCCTCAAGCAATTGCGGACAGAGCTGCCTTCCCTGGAGG
TCTTGGAGACAAAGTGGAGGACTTAACTTGCTGCCATCCAGAGCGAGAAGCAGAACTGAG
TCACCCCAGCTCTGACAGTGAGGAGAATGAGGCCAAAGGCCGCAGAGCCACCATTGCAAT
ATCCTCCCAGGAGGGTGATAACTCAGAGAGAACCCTGTCCAACAACATCACTGTTCCCAA
GATAGAGCGCGCCAACAGCTACTCGGCAGAGGAGCCAAGTGCGCCATATGCACACACCA
GGAAGAGCTTCTCCATCAGTGACAAACTCGACAGGCAGCGGAACACAGCAAGCCTGCAA
AATCCCTTCCAGAGAAGCAAGTCCTCCAAGCCGGAGGGCCGAGGGGACAGCCTGTCCATG
AGGAGACTGTCCAGAACATCGGCTTTCCAAAGCTTTGAAAGCAAGCACACCTAA (SEQ ID
NO:317)

Fig. 15A

LTRPC3f
ATGTATGTGCGAGTATCTTTTGATACAAAACCTGATCTCCTCTTACACCTGATGACCAAGG
AATGGCAGTTGGAGCTTCCCAAGCTTCTCATCTCTGTCCATGGGGGCCTGCAGAACTTTGA
ACTCCAGCCAAAACTCAAGCAAGTCTTTGGGAAAGGGCTCATCAAAGCAGCAATGACAAC
TGGAGCGTGGATATTCACTGGAGGGGTTAACACAGGTGTTATTCGTCATGTTGGCGATGCC
TTGAAGGATCATGCCTCTAAGTCTCGAGGAAAGATATGCACCATAGGTATTGCCCCCTGG
GGAATTGTGGAAAACCAGGAGGACCTCATTGGAAGAGATGTTGTCCGGCCATACCAGACC
ATGTCCAATCCCATGAGCAAGCTCACTGTTCTAACAGCATGCATTCCCACTTCATTCTGG
CTGACAACGGGACCACTGGAAAATATGGAGCAGAGGTGAAACTTCGAAGACAACTGGAA
AAGCATATTTCACTCCAGAAGATAAACACAAGATGCCTGCCGTTTTCTCTCTTGACTCCC
GCTTGTTTTATTCATTTTGGGGTAGTTGCCAGCTAGACTCAGTTGGAATCGGTCAAGGTGT
TCCTGTGGTGGCACTCATAGTGGAAGGAGGACCCAATGTGATCTCGATTGTTTTGGAGTAC
CTTCGAGACACCCCTCCCGTGCCAGTGGTTGTCTGTGATGGGAGTGGACGGGCATCGGAC
ATCCTGGCCTTTGGGCATAAATACTCAGAAGAAGGCGGACTGATAAATGAATCTTTGAGG
GACCAGCTGTTGGTGACTATACAGAAGACTTTCACATACACTCGAACCCAAGCTCAGCAT
CTGTTCATCATCCTCATGGAGTGCATGAAGAAGAAGGAATTGATTACGGTATTTCGGATG
GGATCAGAAGGACACCAGGACATTGATTTGGCTATCCTGACAGCTTTACTCAAAGGAGCC
AATGCCTCGGCCCCAGACCAACTGAGCTTAGCTTTAGCCTGGAACAGAGTCGACATCGCT
CGCAGCCAGATCTTTATTTACGGGCAACAGTGGCCGGTGGGATCTCTGGAGCAAGCCATG
TTGGATGCCTTAGTTCTGGACAGAGTGGATTTTGTGAAATTACTCATAGAGAATGGAGTAA
GCATGCACCGTTTTCTCACCATCTCCAGACTAGAGGAATTGTACAATACGAGACATGGGC
CCTCAAATACATTGTACCACTTGGTCAGGGATGTCAAAAAGGGGAACCTGCCCCCAGACT
ACAGAATCAGCCTGATTGACATCGGCCTGGTGATCGAGTACCTGATGGGCGGGGCTTATC
GCTGCAACTACACGCGCAAGCGCTTCCGGACCCTCTACCACAACCTCTTCGGCCCCAAGA
GGCCCAAAGCCTTGAAACTGCTGGGAATGGAGGATGATATTCCCTTGAGGCGAGGAAGAA
AGACAACCAAGAAACGTGAAGAAGAGGTGGACATTGACTTGGATGATCCTGAGATCAAC
CACTTCCCCTTCCCTTTCCATGAGCTCATGGTGTGGGCTGTTCTCATGAAGCGGCAGAAGA
TGGCCCTGTTCTTCTGGCAGCACGGTGAGGAGGCCATGGCCAAGGCCCTGGTGGCCTGCA
AGCTCTGCAAAGCCATGGCTCATGAGGCCTCTGAGAACGACATGGTTGACGACATTTCCC
AGGAGCTGAATCACAATTCCAGAGACTTTGGCCAGCTGGCTGTGGAGCTCCTGGACCAGT
CCTACAAGCAGGACGAACAGCTGGCCATGAAACTGCTGACGTATGAGCTGAAGAACTGG
AGCAACGCCACGTGCCTGCAGCTTGCCGTGGCTGCCAAACACCGCGACTTCATCGCGCAC
ACGTGCAGCCAGATGCTGCTCACCGACATGTGGATGGGCCGGCTCCGCATGCGCAAGAAC
TCAGGCCTCAAGGTAATTCTGGGAATTCTACTTCCTCCTTCAATTCTCAGCTTGGAGTTCA
AGAACAAAGACGACATGCCCTATATGTCTCAGGCCCAGGAAATCCACCTCCAAGAGAAGG
AGGCAGAAGAACCAGAGAAGCCCACAAAGGAAAAAGAGGAAGAGGACATGGAGCTCAC
AGCAATGTTGGGACGAAACAACGGGGAGTCCTCCAGGAAGAAGGATGAAGAGGAAGTTC
AGAGCAAGCACCGGTTAATCCCCCTCGGCAGAAAAATCTATGAATTCTACAATGCACCCA
TCGTGAAGTTCTGGTTCTACACACTGGCGTATATCGGATACCTGATGCTCTTCAACTATAT
CGTGTTAGTGAAGATGGAACGCTGGCCGTCCACCCAGGAATGGATCGTAATCTCCTATATT
TTCACCCTGGGAATAGAAAAGATGAGAGAGATTCTGATGTCAGAGCCAGGGAAGTTGCTA
CAGAAAGTGAAGGTATGGCTGCAGGAGTACTGGAATGTCACGGACCTCATCGCCATCCTT
CTGTTTTCTGTCGGAATGATCCTTCGTCTCCAAGACCAGCCCTTCAGGAGTGACGGGAGGG
TCATCTACTGCGTGAACATCATTTACTGGTATATCCGTCTCCTAGACATCTTCGGCGTGAA
CAAGTATTTGGGCCCGTATGTAATGATGATTGGAAAAATGATGATAGACATGATGTACTTT
GTCATCATTATGCTGGTGGTTCTGATGAGCTTTGGGGTCGCCAGGCAAGCCATCCTTTTTC
CCAATGAGGAGCCATCATGGAAACTGGCCAAGAACATCTTCTACATGCCCTATTGGATGA
TTTATGGGGAAGTGTTTGCGGACCAGATAGACCCTCCCTGTGGACAGAATGAGACCCGAG
AGGATGGTAAAATAATCCAGCTGCCTCCCTGCAAGACAGGAGCTTGGATCGTGCCGGCCA
TCATGGCCTGCTACCTCTTAGTGGCAAACATCTTGCTGGTCAACCTCCTCATTGCTGTCTTT
AACAATACATTTTTTGAAGTAAAATCGATATCCAACCAAGTCTGGAAGTTTCAGAGGTATC
AGCTCATCATGACTTTCCATGAAAGGCCAGTTCTGCCCCCACCACTGATCATCTTCAGCCA
CATGACCATGATATTCCAGCACCTGTGCTGCCGATGGAGGAAACACGAGAGCGACCCGGA
TGAAAGGGACTACGGCCTGAAACTCTTCATAACCGATGATGAGCTCAAGAAAGTACATGA
CTTTGAAGAGCAATGCATAGAAGAATACTTCAGAGAAAAGGATGATCGGTTCAACTCATC
TAATGATGAGAGGATACGGGTGACTTCAGAAAGGGTGGAGAACATGTCTATGCGGCTGGA
GGAAGTCAACGAGAGAGAGCACTCCATGAAGGCTTCACTCCAGACCGTGGACATCCGGCT
GGCGCAGCTGGAAGACCTTATCGGGCGCATGGCCACGGCCCTGGAGCGCCTGACAGGTCT

Fig. 15B

```
GGAGCGGGCCGAGTCCAACAAAATCCGCTCGAGGACCTCGTCAGACTGCACGGACGCCGC
CTACATTGTCCGTCAGAGCAGCTTCAACAGCCAGGAAGGGAACACCTTCAAGCTCCAAGA
GAGTATAGACCCTGCAGGTGAGGAGACCATGTCCCCAACTTCTCCAACCTTAATGCCCCGT
ATGCGAAGCCATTCTTTCTATTCAGTCAATATGAAAGACAAAGGTGGTATAGAAAAGTTG
GAAAGTATTTTTAAAGAAAGGTCCCTGAGCCTACACCGGGCTACTAGTTCCCACTCTGTAG
CAAAAGAACCCAAAGCTCCTGCAGCCCCTGCCAACACCTTGGCCATTGTTCCTGATTCCAG
AAGACCATCATCGTGTATAGACATCTATGTCTCTGCTATGGATGAGCTCCACTGTGATATA
GACCCTCTGGACAATTCCGTGAACATCCTTGGGCTAGGCGAGCCAAGCTTTTCAACTCCAG
TACCTTCCACAGCCCCTTCAAGTAGTGCCTATGCAACACTTGCACCCACAGACAGACCTCC
AAGCCGGAGCATTGATTTTGAGGACATCACCTCCATGGACACTAGATCTTTTTCTTCAGAC
TACACCCACCTCCCAGAATGCCAAAACCCCTGGGACTCAGAGCCTCCGATGTACCACACC
ATTGAGCGTTCCAAAAGTAGCCGCTACCTAGCCACCACACCCTTTCTTCTAGAAGAGGCTC
CCATTGTGAAATCTCATAGCTTTATGTTTTCCCCCTCAAGGAGCTATTATGCCAACTTTGGG
GTGCCTGTAAAAACAGCAGAATACACAAGTATTACAGACTGTATTGACACAAGGTGTGTC
AATGCCCCTCAAGCAATTGCGGACAGAGCTGCCTTCCCTGGAGGTCTTGGAGACAAAGTG
GAGGACTTAACTTGCTGCCATCCAGAGCGAGAAGCAGAACTGAGTCACCCAGCTCTGAC
AGTGAGGAGAATGAGGCCAAAGGCCGCAGAGCCACCATTGCAATATCCTCCCAGGAGGG
TGATAACTCAGAGAGAACCCTGTCCAACAACATCACTGTTCCCAAGATAGAGCGCGCCAA
CAGCTACTCGGCAGAGGAGCCAAGTGCGCCATATGCACACACCAGGAAGAGCTTCTCCAT
CAGTGACAAACTCGACAGGCAGCGGAACACAGCAAGCCTGCAAAATCCCTTCCAGAGAA
GCAAGTCCTCCAAGCCGGAGGGCCGAGGGGACAGCCTGTCCATGAGGAGACTGTCCAGA
ACATCGGCTTTCCAAAGCTTTGAAAGCAAGCACACCTAA (SEQ ID NO:318)
```

Fig. 16
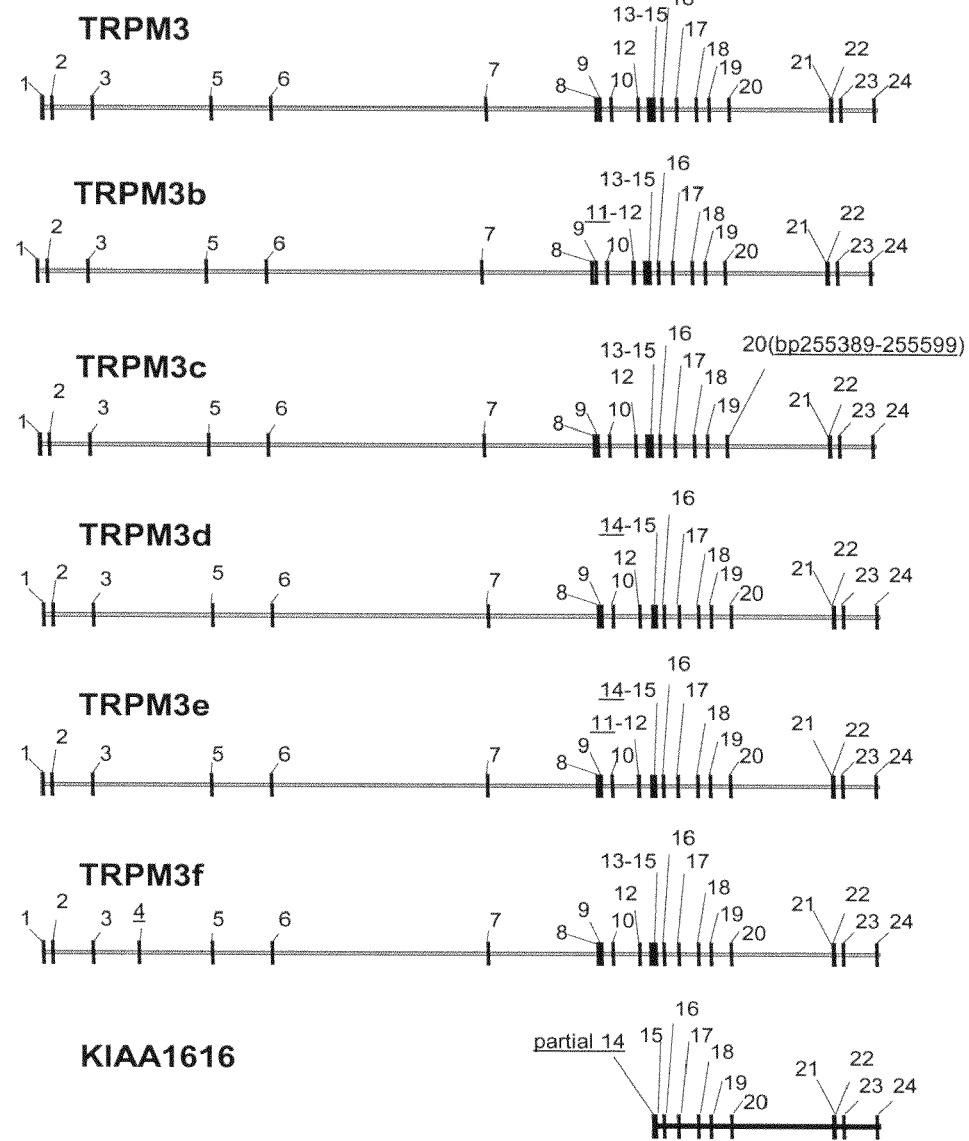
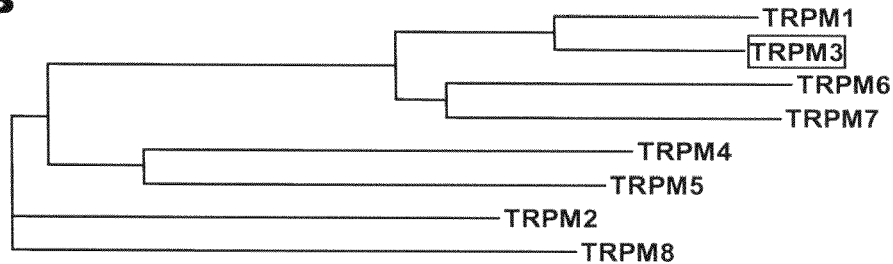

POLYNUCLEOTIDE ENCODING A NOVEL TRP CHANNEL FAMILY MEMBER, LTRPC3, AND SPLICE VARIANTS THEREOF

This application is a continuation-in-part application of non-provisional application U.S. Ser. No. 10/210,152, filed Aug. 1, 2002 now abandoned, which claims benefit to provisional application U.S. Ser. No. 60/309,544 filed Aug. 2, 2001, under 35 U.S.C. 119(e).

FIELD OF THE INVENTION

The present invention provides novel polynucleotides encoding LTRPC3 polypeptides, fragments and homologues thereof. The present invention also provides polynucleotides encoding variants and splice variants of LTRPC3 polypeptides, LTRPC3b, LTRPC3c, and LTRPC3e, respectively. Also provided are vectors, host cells, and recombinant and synthetic methods for producing said polypeptides. The invention further relates to diagnostic and therapeutic methods for applying these novel LTRPC3, LTRPC3b, LTRPC3c, and LTRPC3e polypeptides to the diagnosis, treatment, and/or prevention of various diseases and/or disorders related to these polypeptides. The invention further relates to screening methods for identifying agonists and antagonists of the polynucleotides and polypeptides of the present invention.

BACKGROUND OF THE INVENTION

Intracellular $Ca^{2+}$ plays a pivotal role in various cell functions, ranging from exocytosis and contraction to gene expression and cell differentiation, proliferation and apoptosis. $Ca^{2+}$ entry into cells, particularly in non-excitable cells, can be mediated via store-operated $Ca^{2+}$ channel (s) (SOC). Following $Ca^{2+}$ release from the intracellular stores, SOC mediate $Ca^{2+}$ influx from the extracellular space to generate sustained increases in intracellular $Ca^{2+}$ concentration and replenish the internal $Ca^{2+}$ stores. The molecular mechanism of SOC activation and the molecular identity of SOC remains elusive. Members of TRP (Transient Receptor Potential) channels, an emerging class of $Ca^{2+}$-permeable cation channel superfamily, are likely candidates for SOC (reviewed in *Trends Neurosci*, 23, 159-166, (2000)).

Human mutations in the genes involved in intracellular $Ca^{2+}$ handling result in visual defects, diabetes mellitus, disorders in the skin, skeletal-muscle, nervous, cardiac and vascular systems (reviewed by Missiaen et al., 2000). In addition to the well characterized voltage-dependent $Ca^{2+}$ channels, $Ca^{2+}$ pumps and $Ca^{2+}$-permeable ligand-gated channels, TRPC (Transient Receptor Potential Channels) is an emerging class of $Ca^{2+}$-permeable cation channel superfamily. All of the channels in this family contain a six-trans-membrane domain although various cellular mechanisms have been implicated in their functions.

Following the identification of the founding member of this family, dTRP, from the *Drosophila* mutants trp whose photoreceptors failed to generate a sustained receptor potential in response to intense sustained light (*Neuron* 8, 643-651, (1992)), mammalian homologues have been cloned and all of them contain a six-trans-membrane domain followed by a TRP motif (XWKFXR, SEQ ID NO:), the diagnosed feature of the TRP family of proteins. The mutant fly showed a reduced $Ca^{2+}$ selectivity of the light response and the channel activity of DTRP depended on PLC activation was also demonstrated.

Based on their homology, they are divided into three subfamilies: short (s), osm (o) and long (l). New nomenclature for each subfamily has recently been proposed and is as follows: TRPC (canonical), TRPV (vanilloid), and TRPM (melastatin) (*Mol. Cell.* 9, 229-231, (2002)). The sTRPC subfamily includes TRP1-7. Although the specific physiological function of each isoform remains to be assigned, it is generally believed that they may be involved in $Ca^{2+}$ entry after activation of receptors coupling to PLC. The TRP2 is specifically expressed in vomeronasal organ and involved in pheromone sensory signaling (Liman, et al., 1999). TRP1 and TRP6 are functioned in vascular smooth muscle cells and may play a role in controlling smooth muscle tone, arteriosclerosis and neointimal hypoerplasia (Inoue et al., 2001; Xu & Beech, 2001). It has been shown that TRP4−/− mice lack an endothelial store-operated $Ca^{2+}$ current, which leads to reduced agonist-dependent vasorelaxation (Freichel et al., 2001).

The first member of oTRPC Subfamily is OSM-9 cloned from *C. elegans*. It is involved in responses to odorants, high osmotic strength, and mechanical stimulation. Recently, several mammalian homologues including vanilloid receptor (VR1) and vanilloid receptor-like receptor (VRL-1), which may have functions in pain and heat perception (Caterina, 1999; Caterina et al., 2000). VR1 has also been shown to be the receptor of anandamide and mediating its vasodilation effect (Zygmunt et al., 1999). OTRPC4 is an osmotically activated channel and a candidate osmoreceptor, may be involved in regulation of cellular volume (Strotmann et al., 2000). CaT1 & ECaC1 may be the calcium-release-activated calcium channel and involved in $Ca^{2+}$ reabsorption in intestine and kidney (Peng, et al, 1999; Yu et al., 2001).

The function of the lTRPC is less clear. The cloned mammalian lTRPC includes melastatin1/MLSN1/LTRPC1, MTR1/LTRPC5, TRPC7/LTRPC2 and TRP-P8. It is known that melastatin 1 is down regulated in metastatic melanomas (Duncan et al., 1998) and MTR1 is associated with Beckwith-Wiedemann syndrome and a predisposition to neoplasias (Prawitt et al., 2000). TRPC7 is mapped to the chromosome region linked to bipolar affective disorder, nonsyndromic hereditary deafness, Knobloch syndrome and holosencephaly (Nagamine et al., 1998). TRP-P8 is a prostate-specific gene and up-regulated in prostate cancer and other malignancies (Tsavaler et al., 2001). A recently cloned TRP-PLIK/hSOC-2/hCRAC-1 exhibits a very interesting feature in that it is a bi-functional protein with kinase and ion channel activities (Runnels et al., 2001). Additionally, a very long TRPC homologue NOMPC was found in *Drosophila* and *C. elegans*. NOMPC was identified as a mechanosensitive channel that can detect sound, pressure or movement changes (Walker et al., 2000).

Members of the TRPM subfamily are characteristic of their unusually long cytoplasmic tails at both ends of the channel domain and some of the family members contain an enzyme domain at the C-terminal region. Despite their similarities of structure, TRPMs have been implicated in a variety of biological functions. TRPM1 is found to be down-regulated in metastatic melanomas (*Cancer Res.* 58, 1515-1520, (1998)). TRPM2 is a $Ca^{2+}$-permeable channel that contains an ADP-ribose pyrophosphatase domain and can be activated by ADP-ribose, NAD (*Nature* 411, 595-599, (2001); and *Science* 293, 1327-1330, (2001)) and changes in redox status (*Mol. Cell.* 9, 163-173, (2002)). TRPM2 is mapped to the chromosome region linked to bipolar affective disorder, nonsyndromic hereditary deafness, Knobloch syndrome and holosencephaly (*Genomics* 54, 124-131, (1998)). Two splice variants of TRPM4 have been described. TRPM4a is predominantly a $Ca^{2+}$ permeable channel (*Proc. Natl. Acad. Sci. U.S.A.* 98, 10692-10697, (2001); whereas TRPM4b conducts monovalent cations upon activation by changes in intracellular Ca$^{2+}$ (*Cell* 109, 397-401, (2002)). TRPM5 is associated with Beckwith-Wiedemann syndrome and a predisposition to neoplasias (*Mol. Genet.* 9, 203-216, (2001)). TRPM7, another bifunctional protein, has kinase activity in additional to its ion channel activity. TRPM7 is regulated by Mg$^{2+}$-ATP and/or PIP$_2$, and required for cell viability (*Science* 291, 1043-1047, (2001); *Nature* 411, 690-695, (2001); and *Nat. Cell Biol.* 4, 329-36, (2002)). TRPM8 is up-regulated in prostate cancer and other malignancies (*Cancer Res.* 61, 3760-3769, (2001)). Recently, it has also been shown to be a receptor that senses cold stimuli (*Nature* 416, 52-58, (2002); and *Cell* 108, 705-715, (2002)).

Characterization of the LTRPC3 polypeptide of the present invention led to the determination that it is involved in the modulation of the FEN1 DNA base-excision repair/proliferation modulating protein, either directly or indirectly.

In mammalian cells, single-base lesions, such as uracil and abasic sites, appear to be repaired by at least two base excision repair (BER) subpathways: "single-nucleotide BER" requiring DNA synthesis of just one nucleotide and "long patch BER" requiring multi-nucleotide DNA synthesis. In single-nucleotide BER, DNA polymerase beta (beta-pol) accounts for both gap filling DNA synthesis and removal of the 5'-deoxyribose phosphate (dRP) of the abasic site, whereas the involvement of various DNA polymerases in long patch BER is less well understood.

Flap endonuclease 1 (Fen1) is a structure-specific metallonuclease that plays an essential function in DNA replication and DNA repair (Tom, S., Henricksen, L, A., Bambara, R, A, J. Biol, Chem., 275(14):10498-505, (2000)). It interacts like many other proteins involved in DNA metabolic events with proliferating cell nuclear antigen (PCNA), and its enzymatic activity is stimulated by PCNA in vitro by as much as 5 to 50 fold (Stucki, M., Jonsson, Z, O., Hubscher, U, J. Biol, Chem., 276(11):7843-9, (2001)). Recently, immunodepletion experiments in human lymphoid cell extracts have shown long-patch BER to be dependent upon FEN1 (Prasad, R., Dia, G, L., Bohr, V, A., Wilson, S, H, J. Biol, Chem., 275(6):4460-6, (2000)). In addition, FEN1 has also been shown to cooperate with beta-pol in long patch BER excision and is involved in determining the predominant excision product seen in cell extracts. The substrate for FEN1 is a flap formed by natural 5'-end displacement of the short intermediates of lagging strand replication. FEN1 binds to the 5'-end of the flap, tracks to the point of annealing at the base of the flap, and then cleaves the substrate (Tom, S., Henricksen, L, A., Bambara, R, A, J. Biol, Chem., 275(14):10498-505, (2000)).

The FEN1 is also referred to as Rad27. FEN1 plays a critical role in base-excision repair as evidenced by *Saccharomyces cerevisiae* FEN1 null mutants displaying an enhancement in recombination that increases as sequence length decreases (Negritto, M, C., Qiu, J., Ratay, D, O., Shen, B., Bailis, A, M, Mol, Cell, Biol., 21(7):2349-58, (2001)). The latter suggests that Rad27 preferentially restricts recombination between short sequences. Since wild-type alleles of both RAD27 and its human homologue FEN1 complement the elevated short-sequence recombination (SSR) phenotype of a rad27-null mutant, this function may be conserved from yeast to humans. Furthermore, mutant Rad27 and FEN-1 enzymes with partial flap endonuclease activity but without nick-specific exonuclease activity were shown to partially complement the SSR phenotype of the rad27-null mutant suggesting that the endonuclease activity of Rad27 (FEN-1) plays a role in limiting recombination between short sequences in eukaryotic cells. In addition, preliminary data from yeast suggests the FEN-1 deficiencies may result in genomic instability (Ma, X., Jin, Q., Forsti, A., Hemminki, K., Ku, R, Int, J. Cancer., 88(6):938-42, (2000)). More recently, FEN 1 null mutants results in the expansion of repetitive sequences (Henricksen, L, A., Tom, S., Liu, Y., Bambara, R, A, J. Biol, Chem., 275(22):16420-7, (2000)).

Aside from the role of FEN1 in base-excision repair, FEN1 has also been shown to play a significant role in modulating signal transduction in proliferating cells. This role is intricately associated with the role of FEN1 in DNA replication. Of particular significance is the observation that FEN1 is a nuclear antigen, that it is expressed by cycling cells, and that it co-localizes with PCNA and polymerase alpha during S phase. Fen1 expression is topologically regulated in vivo and is associated with proliferative populations (Warbrick, E., Coates, P, J., Hall, P, A, J. Pathol., 186(3):319-24, (1998)). Antibodies have been described by Warbrick et al. that specifically bind FEN1, the assays of which are hereby incorporated herein by reference.

In addition, experiments in *S. cerevisiae* using the novel immunosuppressant agent SR 31747 have shown that SR 31747 arrests cell proliferation by directly targeting sterol isomerase and that FEN 1 is required to mediate the proliferation arrest induced by ergosterol depletion (Silve, S., Leplatois, P., Josse, A., Dupuy, P, H., Lanau, C., Kaghad, M., Dhers, C., Picard, C., Rahier, A., Taton, M., Le, Fur, G., Caput, D., Ferrara, P., Loison, G, Mol, Cell, Biol., 16(6): 2719-27, (1996)).

Using the above examples, it is clear the availability of a novel cloned transient receptor potential channel family provides an opportunity for adjunct or replacement therapy, and are useful for the identification of transient receptor potential channel agonists, or stimulators (which might stimulate and/or bias transient receptor potential channel function), as well as, in the identification of transient receptor potential channel inhibitors. All of which might be therapeutically useful under different circumstances.

The present invention also relates to recombinant vectors, which include the isolated nucleic acid molecules of the present invention, and to host cells containing the recombinant vectors, as well as to methods of making such vectors and host cells, in addition to their use in the production of LTRPC3, LTRPC3b, LTRPC3c, and LTRPC3e polypeptides using recombinant techniques. Synthetic methods for producing the polypeptides and polynucleotides of the present invention are provided. Also provided are diagnostic methods for detecting diseases, disorders, and/or conditions related to the LTRPC3, LTRPC3b, LTRPC3c, and LTRPC3e polypeptides and polynucleotides, and therapeutic methods for treating such diseases, disorders, and/or conditions. The invention further relates to screening methods for identifying binding partners of the polypeptides.

BRIEF SUMMARY OF THE INVENTION

The present invention provides isolated nucleic acid molecules, that comprise, or alternatively consist of, a polynucleotide encoding the LTRPC3b protein having the amino acid sequence shown in FIGS. 2A-F (SEQ ID NO:4) or the amino acid sequence encoded by the cDNA clone, LTRPC3b (also referred to as AL358786, NT_008306, clone 86, TRPM3, and/or LTRPC6 splice variant).

The present invention provides isolated nucleic acid molecules, that comprise, or alternatively consist of, a polynucleotide encoding the LTRPC3c protein having the amino acid sequence shown in FIGS. 3A-F (SEQ ID NO:6) or the amino acid sequence encoded by the cDNA clone, LTRPC3c (also referred to as AL358786, NT_008306, clone 86, TRPM3, and/or LTRPC6 splice variant).

The present invention provides isolated nucleic acid molecules, that comprise, or alternatively consist of, a polynucleotide encoding the LTRPC3e protein having the amino acid sequence shown in FIGS. 5A-F (SEQ ID NO:9) or the amino acid sequence encoded by the cDNA clone, LTRPC3e (also referred to as AL358786, NT_008306, clone 86, TRPM3, and/or LTRPC6 splice variant).

The present invention also relates to recombinant vectors, which include the isolated nucleic acid molecules of the present invention, and to host cells containing the recombinant vectors, as well as to methods of making such vectors and host cells, in addition to their use in the production of LTRPC3, LTRPC3b, LTRPC3c, and LTRPC3e polynucleotides or polypeptides using recombinant techniques. Synthetic methods for producing the polypeptides and polynucleotides of the present invention are provided. Also provided are diagnostic methods for detecting diseases, disorders, and/or conditions related to the LTRPC3, LTRPC3b, LTRPC3c, and LTRPC3e polypeptides and polynucleotides, and therapeutic methods for treating such diseases, disorders, and/or conditions. The invention further relates to screening methods for identifying binding partners of the polypeptides.

The invention further provides an isolated LTRPC3b polypeptide having an amino acid sequence encoded by a polynucleotide described herein.

The invention further provides an isolated LTRPC3c polypeptide having an amino acid sequence encoded by a polynucleotide described herein.

The invention further provides an isolated LTRPC3e polypeptide having an amino acid sequence encoded by a polynucleotide described herein.

The invention further relates to a polynucleotide encoding a polypeptide fragment of SEQ ID NO:4, 6, 7, 9, which is hybridizable to SEQ ID NO: 3, 5, and/or 8.

The invention further relates to a polynucleotide encoding a polypeptide domain of SEQ ID NO: 4, 6, 7, 9, which is hybridizable to SEQ ID NO: 3, 5, and/or 8.

The invention further relates to a polynucleotide encoding a polypeptide epitope of SEQ ID NO: 4, 6, 7, 9, and/or 10 or a polypeptide epitope encoded by the cDNA sequence included in the deposited clone, which is hybridizable to SEQ ID NO: 3, 5, and/or 8.

The invention further relates to a polynucleotide encoding a polypeptide of SEQ ID NO:4, 6, 7, 9, which is hybridizable to SEQ ID NO: 3, 5, and/or 8, having biological activity.

The invention further relates to a polynucleotide which is a variant of SEQ ID NO: 8.

The invention further relates to a polynucleotide which is an allelic variant of SEQ ID NO: 8.

The invention further relates to a polynucleotide which encodes a species homologue of the SEQ ID NO: 9.

The invention further relates to an isolated nucleic acid molecule of SEQ ID NO:8 wherein the polynucleotide fragment comprises a nucleotide sequence encoding the sequence identified as SEQ ID NO: 9.

The invention further relates to an isolated nucleic acid molecule of SEQ ID NO:8, wherein the polynucleotide fragment comprises the entire nucleotide sequence of SEQ ID NO: 8.

The invention further relates to an isolated nucleic acid molecule of SEQ ID NO: 8, wherein the nucleotide sequence comprises sequential nucleotide deletions from either the C-terminus or the N-terminus.

The invention further relates to an isolated polypeptide comprising an amino acid sequence that comprises a polypeptide fragment of SEQ ID NO: 9

The invention further relates to a polypeptide fragment of SEQ ID NO: 9, having biological activity.

The invention further relates to a polypeptide domain of SEQ ID NO: 9.

The invention further relates to a full length protein of SEQ ID NO: 9.

The invention further relates to a variant of SEQ ID NO: 9.

The invention further relates to an allelic variant of SEQ ID NO: 9. The invention further relates to a species homologue of SEQ ID NO: 9.

The invention further relates to the isolated polypeptide of SEQ ID NO: 9, wherein the full length protein comprises sequential amino acid deletions from either the C-terminus or the N-terminus.

The invention further relates to an isolated antibody that binds specifically to the isolated polypeptide of SEQ ID NO: 9.

BRIEF DESCRIPTION OF THE FIGURES/DRAWINGS

The file of this patent contains at least one Figure executed in color. Copies of this patent with color Figure(s) will be provided by the Patent and Trademark Office upon request and payment of the necessary fee."

FIGS. 1A-F show the polynucleotide sequence (SEQ ID NO:1) and deduced amino acid sequence (SEQ ID NO:2) of the novel human transient receptor potential channel member, LTRPC3, of the present invention. The standard one-letter abbreviation for amino acids is used to illustrate the deduced amino acid sequence. The polynucleotide sequence contains a sequence of 4665 nucleotides (SEQ ID NO:1), encoding a polypeptide of 1554 amino acids (SEQ ID NO:2). An analysis of the LTRPC3 polypeptide determined that it comprised the following features: six transmembrane domains (TM1 thru TM6) located from about amino acid 620 to about amino acid 637 (TM1), from about amino acid 717 to about amino acid 734 (TM2), from about amino acid 790 to about amino acid 803 (TM3), from about amino acid 817 to about amino acid 834 (TM4), from about amino acid 851 to about amino acid 868 (TM5), and/or from about amino acid 938 to about amino acid 958 (TM6) of SEQ ID NO:2 represented by double underlining; a predicted TRP domain (EWKFAR) located from about amino acid 973 to about amino acid 978 of SEQ ID NO:2 represented by light shading; a predicted ion transport signature domain located at about amino acid 748 to about amino acid 959 of SEQ ID NO:2 represented by dark shading; a predicted coiled-coil domain located at about amino acid 1063 to about amino acid 1117 of SEQ ID NO:2 represented by italics; and conserved cysteine residues located at amino acid 94, 209, 265, 419, 517, 582, 598, 821, 912, 929, 942, 1045, 1136, and 1402 of SEQ ID NO:2 represented in bold. Conservation of cysteines at key amino acid residues is indicative of conserved structural features, which may correlate with conservation of protein function and/or activity.

FIGS. 2A-F show the polynucleotide sequence (SEQ ID NO:3) and deduced amino acid sequence (SEQ ID NO:4) of the novel human transient receptor potential channel member splice variant, LTRPC3b, of the present invention. The standard one-letter abbreviation for amino acids is used to illustrate the deduced amino acid sequence. The polynucleotide sequence contains a sequence of 4701 nucleotides (SEQ ID NO:3), encoding a polypeptide of 1566 amino acids (SEQ ID NO:4). An analysis of the LTRPC3b polypeptide determined that it comprised the following features: six transmembrane domains (TM1 thru TM6) located from about amino acid 632 to about amino acid 649 (TM1), from about amino acid 729 to about amino acid 746 (TM2), from about amino acid 802 to about amino acid 815 (TM3), from about amino acid 829 to about amino acid 846 (TM4), from about amino acid 863 to about amino acid 880 (TM5), and/or from about amino acid 950 to about amino acid 970 (TM6) of SEQ ID NO:4 represented by double underlining; a predicted TRP domain (EWKFAR) located from about amino acid 985 to about amino acid 990 of SEQ ID NO:4 represented by light shading; a predicted ion transport signature domain located at about amino acid 760 to about amino acid 971 of SEQ ID NO:4 represented by dark shading; a predicted coiled-coil domain located at about amino acid 1075 to about amino acid 1129 of SEQ ID NO:4 represented by italics; and conserved cysteine residues located at amino acid 94, 209, 265, 431, 529, 594, 611, 833, 924, 941, 954, 1057, 1148, and 1114 of SEQ ID NO:4 represented in bold. Conservation of cysteines at key amino acid residues is indicative of conserved structural features, which may correlate with conservation of protein function and/or activity.

FIGS. 3A-F show the polynucleotide sequence (SEQ ID NO:5) and deduced amino acid sequence (SEQ ID NO:6) of the novel human transient receptor potential channel member splice variant, LTRPC3c, of the present invention. The standard one-letter abbreviation for amino acids is used to illustrate the deduced amino acid sequence. The polynucleotide sequence contains a sequence of 4701 nucleotides (SEQ ID NO:5), encoding a polypeptide of 1566 amino acids (SEQ ID NO:6). An analysis of the LTRPC3c polypeptide determined that it comprised the following features: six transmembrane domains (TM1 thru TM6) located from about amino acid 620 to about amino acid 637 (TM1), from about amino acid 717 to about amino acid 734 (TM2), from about amino acid 790 to about amino acid 803 (TM3), from about amino acid 817 to about amino acid 834 (TM4), from about amino acid 851 to about amino acid 868 (TM5), and/or from about amino acid 950 to about amino acid 970 (TM6) of SEQ ID NO:6 represented by double underlining; a predicted TRP domain (EWKFAR) located from about amino acid 985 to about amino acid 990 of SEQ ID NO:6 represented by light shading; a predicted ion transport signature domain located at about amino acid 760 to about amino acid 971 of SEQ ID NO:6 represented by dark shading; a predicted coiled-coil domain located at about amino acid 1075 to about amino acid 1129 of SEQ ID NO:6 represented by italics; and conserved cysteine residues located at amino acid 94, 210, 265, 419, 517, 582, 599. 821, 941, 1057, 1148, and 1414 of SEQ ID NO:6 represented in bold. Conservation of cysteines at key amino acid residues is indicative of conserved structural features, which may correlate with conservation of protein function and/or activity.

FIGS. 4A-F show the polynucleotide sequence (SEQ ID NO:9) and deduced amino acid sequence (SEQ ID NO:10) of the novel human transient receptor potential channel member splice variant, LTRPC3e, of the present invention. The standard one-letter abbreviation for amino acids is used to illustrate the deduced amino acid sequence. The polynucleotide sequence contains a sequence of 4671 nucleotides (SEQ ID NO:9), encoding a polypeptide of 1556 amino acids (SEQ ID NO:10). An analysis of the LTRPC3e polypeptide determined that it comprised the following features: six transmembrane domains (TM1 thru TM6) located from about amino acid 622 to about amino acid 639 (TM1), from about amino acid 719 to about amino acid 736 (TM2), from about amino acid 792 to about amino acid 805 (TM3), from about amino acid 819 to about amino acid 836 (TM4), from about amino acid 853 to about amino acid 870 (TM5), and/or from about amino acid 940 to about amino acid 960 (TM6) of SEQ ID NO:10 represented by double underlining; a predicted TRP domain (EWKFAR) located from about amino acid 975 to about amino acid 980 of SEQ ID NO:10 represented by light shading; a predicted ion transport signature domain located at about amino acid 750 to about amino acid 961 of SEQ ID NO:10 represented by dark shading; a predicted coiled-coil domain located at about amino acid 1065 to about amino acid 1119 of SEQ ID NO:10 represented by italics; and conserved cysteine residues located at amino acid 94, 209, 265, 431, 519, 584, 601, 823, 914, 931, 944, 1047, 1138, and 1404 of SEQ ID NO:10 represented in bold. Conservation of cysteines at key amino acid residues is indicative of conserved structural features, which may correlate with conservation of protein function and/or activity.

FIGS. 5A-D show the regions of identity and similarity between the LTRPC3 (SEQ ID NO:2), LTRPC3b (SEQ ID NO:4), LTRPC3c (SEQ ID NO:6), and LTRPC3e (SEQ ID NO:10) polypeptides of the present invention to another member of human transient receptor potential channel family, specifically, the human melastatin 1 protein (Melastatin1; Genbank Accession No. gi|3243075; SEQ ID NO:11). The alignment was created using the CLUSTALW algorithm described elsewhere herein using default parameters (CLUSTALW parameters: gap opening penalty: 10; gap extension penalty: 0.5; gap separation penalty range: 8; percent identity for alignment delay: 40%; and transition, weighting: 0). The darkly shaded amino acids represent regions of matching identity. The lightly shaded amino acids represent regions of matching similarity. Dots between residues indicate gapped regions for the aligned polypeptides.

FIG. 6 shows an expression profile of the novel human transient receptor potential channel family member, LTRPC3 (SEQ ID NO:2). The figure illustrates the relative expression level of LTRPC3 amongst various mRNA tissue sources. As shown, transcripts corresponding to LTRPC3 expressed predominately in kidney tissue. The LTRPC3 polypeptide was also expressed significantly in spinal cord, testis, and brain. Expression data was obtained by measuring the steady state LTRPC3 mRNA levels by RT-PCR using the PCR primer pair provided as SEQ ID NO: 375 and 376 as described herein.

Figure 7:
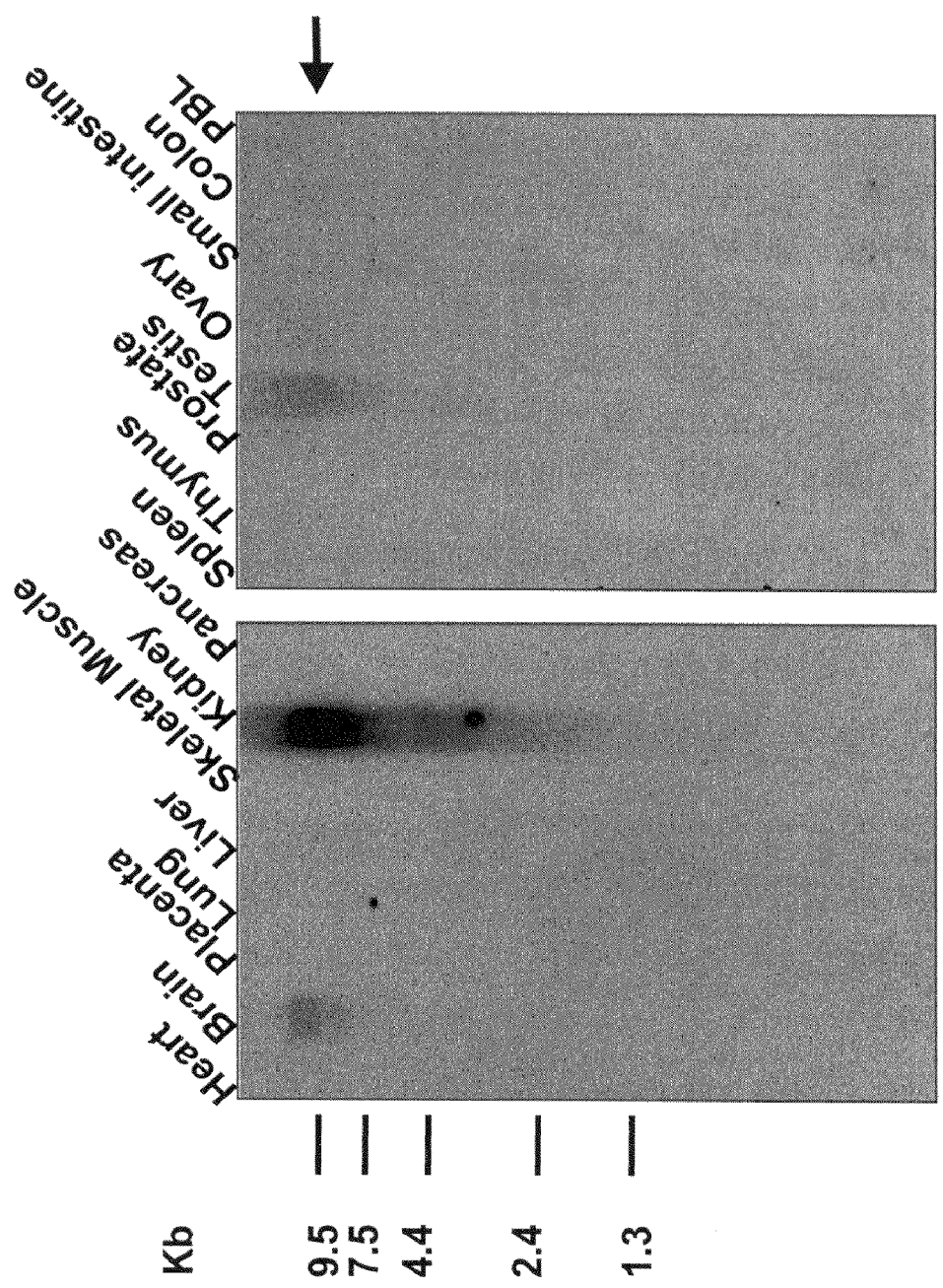

FIG. 7 shows an expression profile of the novel human transient receptor potential channel family member, LTRPC3 (SEQ ID NO:2). The figure illustrates the relative expression level of LTRPC3 amongst various mRNA tissue, and cell sources. As shown, transcripts corresponding to LTRPC3 expressed predominately in kidney tissue. The LTRPC3 polypeptide was also expressed significantly in brain, and testis. Expression data was obtained by probing a Northern blot using a LTRPC3 645-bp PCR amplified fragment as described herein.

FIG. 8 shows a table illustrating the percent identity and percent similarity between the LTRPC3, LTRPC3b, LTRPC3c, and LTRPC3e polypeptides of the present invention with the human melastatin 1 protein (Melastatin1; Genbank Accession No. gi|3243075; SEQ ID NO:11). The percent identity and percent similarity values were determined based upon the GAP algorithm (GCG suite of programs; and Henikoff, S, and Henikoff, J. G., Proc. Natl. Acad. Sci. USA 89: 10915-10919 (1992)).

FIG. 9A-E shows the regions of identity between the LTRPC3 polypeptide (SEQ ID NO:2) of the present invention to its predicted splice variants LTRPC3b (SEQ ID NO:4), LTRPC3c (SEQ ID NO:6), LTRPC3d (SEQ ID NO:7), LTRPC3e (SEQ ID NO:9), and LTRPC3f (SEQ ID NO:10).

The alignment was created using the CLUSTALW algorithm described elsewhere herein using default parameters (CLUSTALW parameters: gap opening penalty: 10; gap extension penalty: 0.5; gap separation penalty range: 8; percent identity for alignment delay: 40%; and transition, weighting: 0). The darkly shaded amino acids represent regions of matching identity. The lightly shaded amino acids represent regions of matching similarity. Dots between residues indicate gapped regions for the aligned polypeptides.

FIG. 10 shows three internal encoding polynucleotide sequences from the human bac AL358786 genomic sequence (Genbank Accession No. gi|AL358786; SEQ ID NOS:12, 13, and 14), in addition to, the human chromosome 9 genomic sequence (Genbank Accession No. gi|NT_008306; SEQ ID NO:15) used to design primers for cloning the LTRPC3, LTRPC3b, LTRPC3c, LTRPC3d, LTRPC3e, and LTRPC3f polynucleotides of the present invention as described herein. Both the BAC AL358786 and human chromosome 9 genomic sequence were predicted to encode portions of the LTRPC3 sequence as described herein. The initiating start codon of LTRPC3 within the human chromosome 9 genomic sequence is denoted in bold and underlined.

FIGS. 11A-C show the polypeptide sequences of several known transient potential receptors that were used to identify the LTRPC3 polypeptide of the present invention (SEQ ID NOS:16-25) via BLAST analysis against the genomic database, as described more specifically herein. The standard one-letter abbreviation for amino acids is used to illustrate the deduced amino acid sequence.

Figure 12:
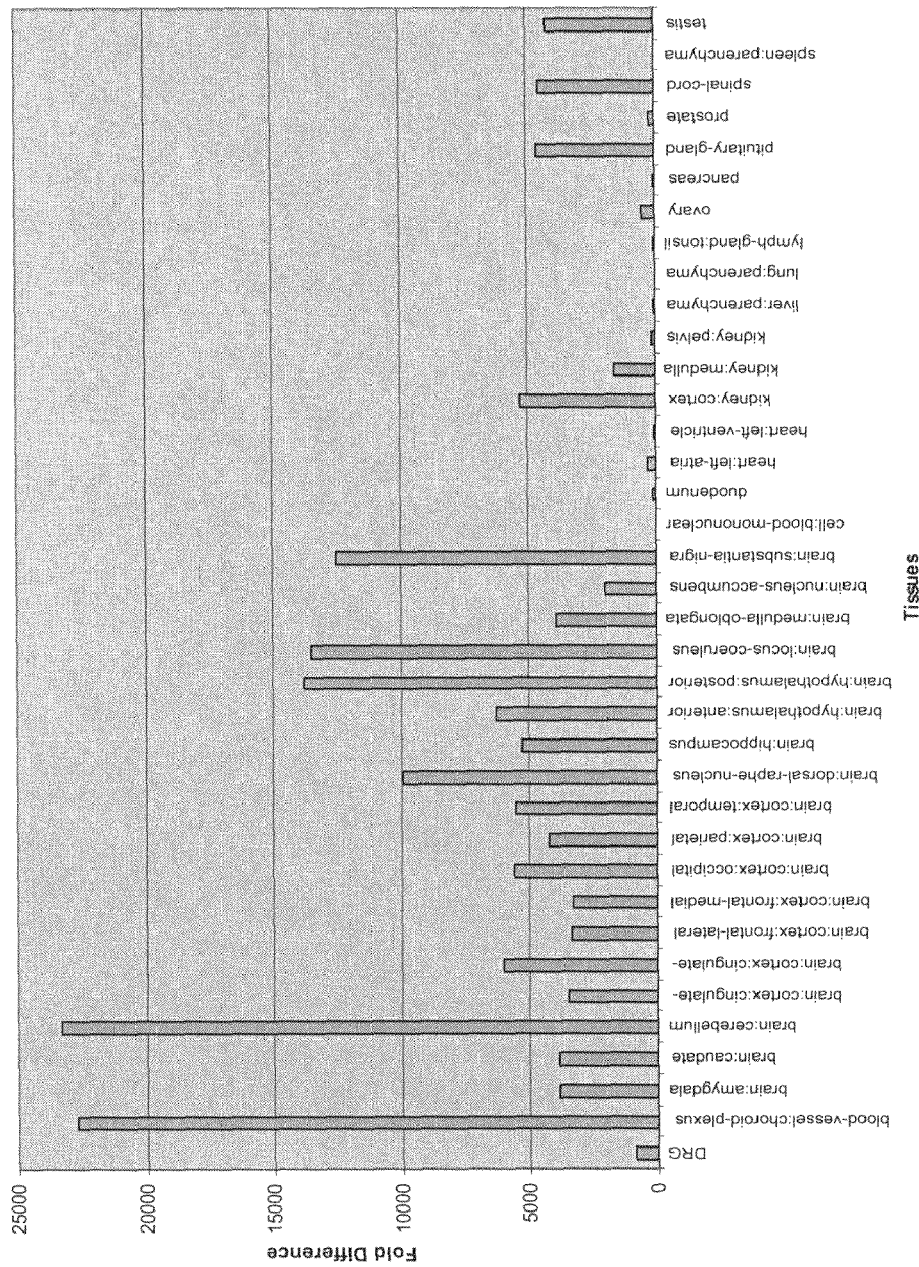

FIG. 12 shows an expanded expression profile of the novel human transient receptor potential channel member, LTRPC3. The figure illustrates the relative expression level of LTRPC3 amongst various mRNA tissue sources. As shown, the LTRPC3 polypeptide was expressed predominately in the brain, specifically the cerebellum, choroid plexus, the locus coeruleus, the posterior hypothalamus and the substantia nigra. Expression of LTRPC3 was also significantly expressed in the kidney, with higher levels observed in the cortex than in the medulla or pelvis. LTRPC3 was also significantly expressed in the spinal cord, testis, and to a lesser extent in other tissues as shown. Expression data was obtained by measuring the steady state LTRPC3 mRNA levels by quantitative PCR using the PCR primer pair provided as SEQ ID NO:270 and 271, and Taqman probe (SEQ ID NO:272) as described in Example 4 herein.

Figure 13:
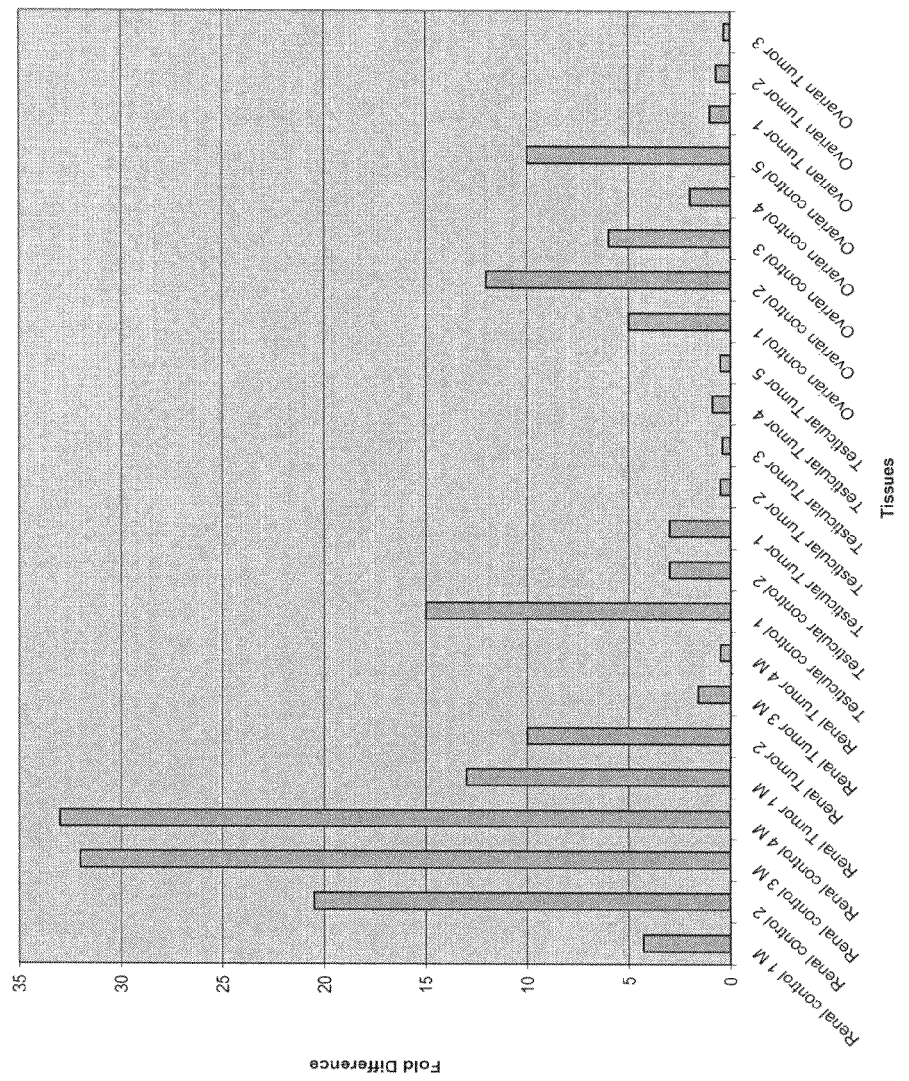

FIG. 13 shows an expanded expression profile of the novel human transient receptor potential channel member, LTRPC3. The figure illustrates the relative expression level of LTRPC3 amongst various mRNA tissue sources isolated from normal and tumor tissues. As shown, the LTRPC3 polypeptide was differentially expressed in renal, testicular, and ovarian cancers compared to each respective normal tissue. Expression data was obtained by measuring the steady state LTRPC3 mRNA levels by quantitative PCR using the PCR primer pair provided as SEQ ID NO:270 and 307, and Taqman probe (SEQ ID NO:272) as described in Example 4 herein.

FIGS. 14A-B show the polynucleotide sequence (SEQ ID NO:281) of the novel human transient receptor potential channel splice variant, LTRPC3d, of the present invention.

FIGS. 15A-B show the polynucleotide sequence (SEQ ID NO:282) of the novel human transient receptor potential channel splice variant, LTRPC3f, of the present invention.

FIG. 16A shows the genomic organization of the novel human transient receptor potential channel, LTRPC3, in addition to LTRPC3 splice variants b, c, d, e, and f, and a known partial sequence of the LTRPC3 gene, KIAA1616 (Genbank Accession No. gi|14743666; SEQ ID NO:283). Differences within the LTRPC3 splice variants b thru f are underlined. The coding exons are shown schematically as boxes, with the exon number indicated as numerals above each exon box. As shown, LTRPC3b contains an extra exon 11; LTRPC3c contains an additional 12 amino acids at exon 20, LTRPC3d does not contain exon 13; LTRPC3e contains an extra exon 11 and does not contain exon 13; and LTRPC3f contains an extra exon 4.

FIG. 16B shows a phylogenetic tree of the TRPM (melastatin) subfamily. As shown, LTRPC3 is most closely related to TRPM1. The phylogenetic tree was created using the CLUSTALW algorithm as provided in the Vector NTI AlignX program.

Figure 17:
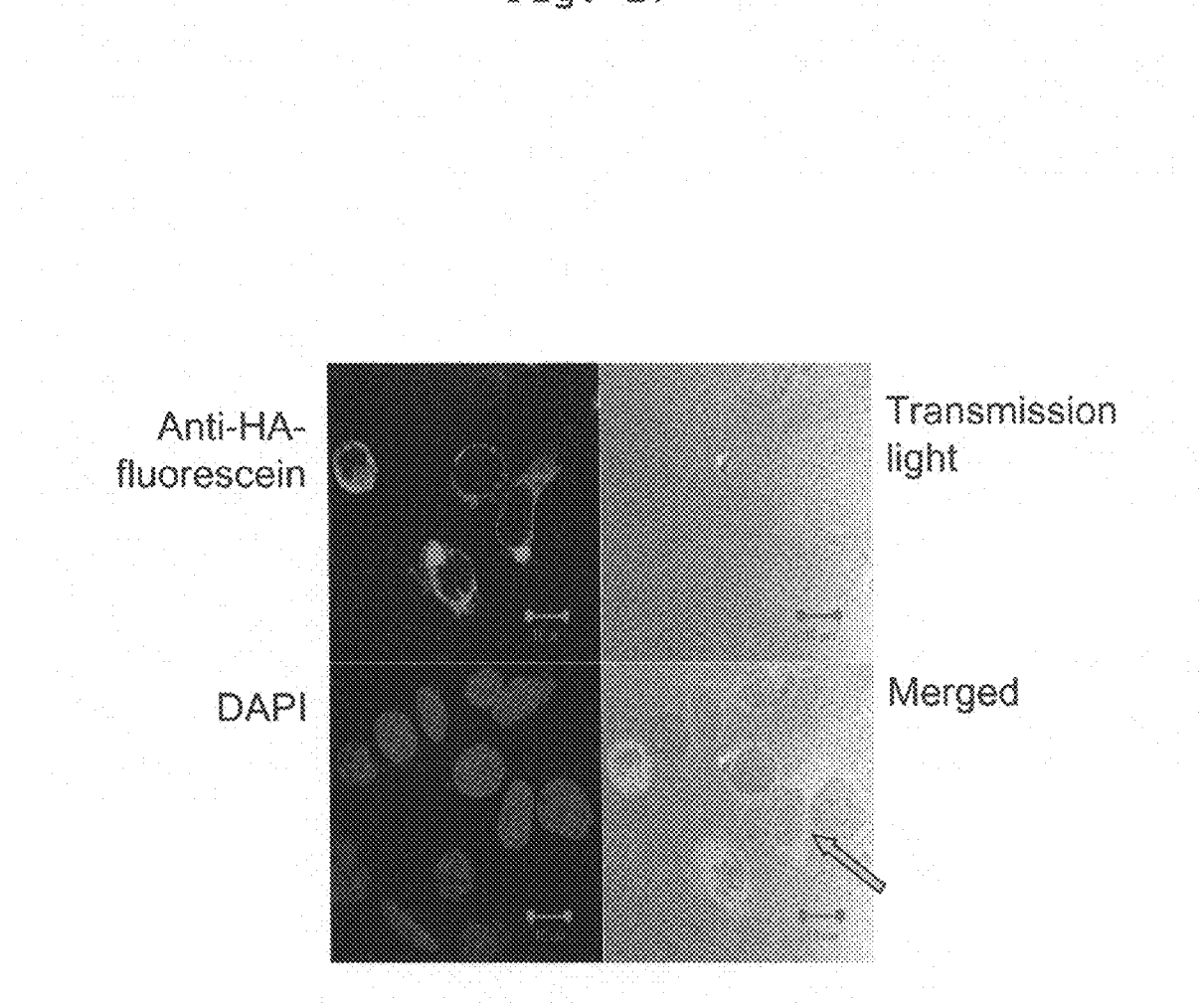

FIG. 17 shows a confocal-image of demonstrating that LTRPC3 is expressed as an integral membrane protein. The left top panel shows the image obtained with a Fluorescein filter; the left bottom panel shows the image obtained with a DAPI filter; the right top panel shows the image obtained using transmitted light; and the right bottom panel is the merged picture of the above three images. One of cells expressing LTRPC3 on the plasma membrane regions is indicated by an arrow. Forty-eight hours after transfection, LTRPC3 expressing HEK 293 cells were fixed with 4% paraformaldehyde, permeabilized with 1% Triton, and labeled with fluorescein conjugated anti-HA (3F10) 48 hours post transfection. The cell nuclei were stained with DAPI. Microscopy was performed as described in Example 6 herein.

Figure 18:
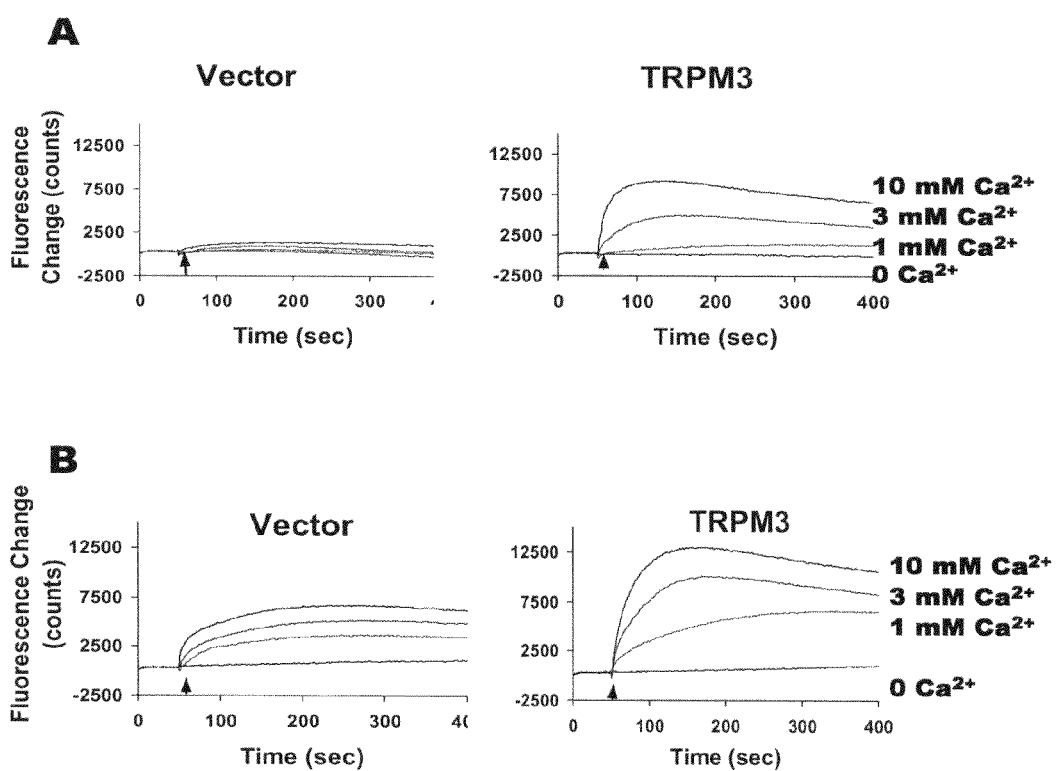

FIG. 18 shows that LTRPC3 mediates concentration-dependent permeability to $Ca^{2+}$. Transfected HEK 293 cells loaded with Fluo-4 were incubated in 1 mM $Ca^{2+}$ solution (A), or a nominally $Ca^{2+}$-free solution (B), and 0, 1, 3 and 10 mM $Ca^{2+}$ solutions were added respectively to cells as indicated. The left panels represent vector-transfected control cells, and the right panels represent LTRPC3-transfected cells. Physiometric methods were performed as described in Example 7 herein.

Figure 19:
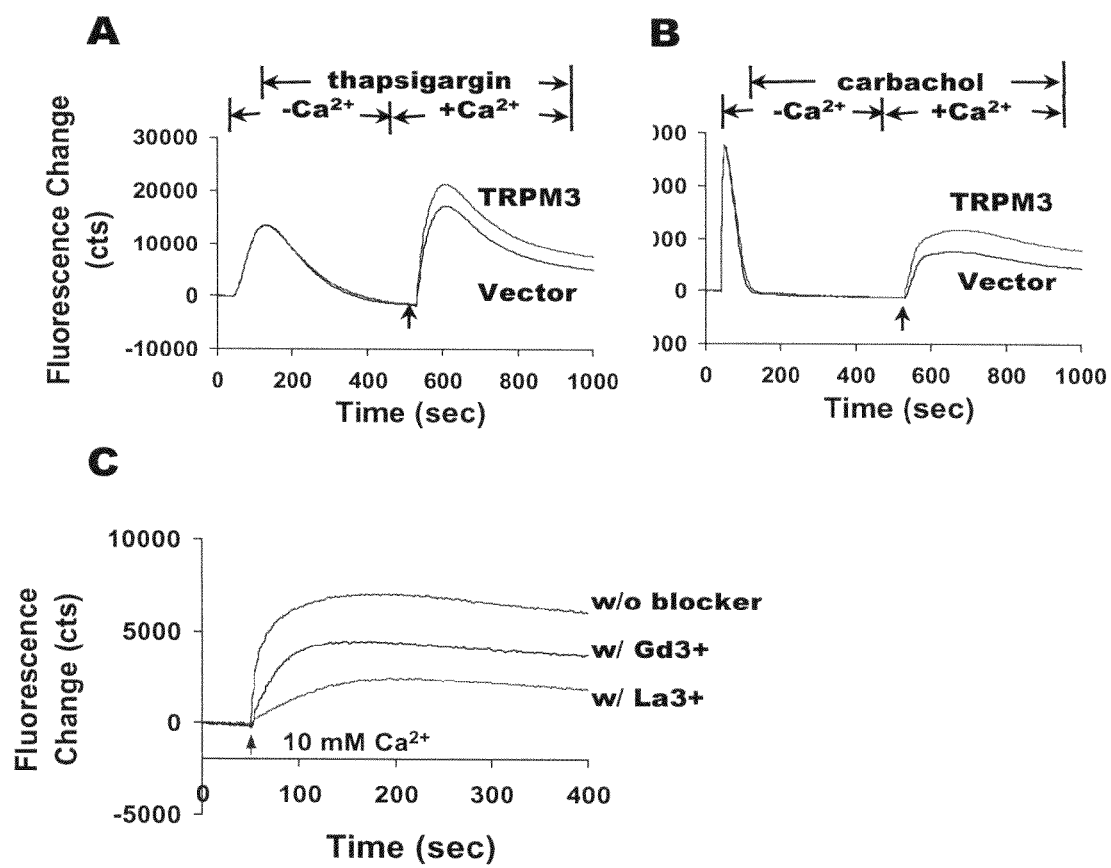

FIG. 19 shows $Ca^{2+}$ entry currents are induced upon store depletion in LTRPC3 expressing HEK 293 cells. 2 mM thapsigargin (A), or 50 μM carbachol (B) was first added to LTRPC3 expressing HEK 293 cells in the absence of external $Ca^{2+}$. After 9 minutes, 2 mM $Ca^{2+}$ solution was added to the cell medium at the indicated times. Currents for vector transfected HEK 293 cells, and LTRPC3 expressing HEK 293 cells are labeled accordingly. Panel (C) shows LTRPC3 mediated $Ca^{2+}$ currents are inhibited by $La^{3+}$ and $Gd^{3+}$. Cells loaded with Fluo-4 were incubated in 1 mM $Ca^{2+}$ solution and treated with 100 μM of $La^{3+}$ ("w/ $La^{3+}$"), $Gd^{3+}$ ("w/ $Gd^{3+}$") or without blockers ("w/o blocker") for 10 min prior to the addition of 10 mM $Ca^{2+}$ to the cell medium as indicated. Curves represent averages of three independent experiments, each involving at least 8 wells per condition. Physiometric methods were performed as described in Example 7 herein.

Figure 20:
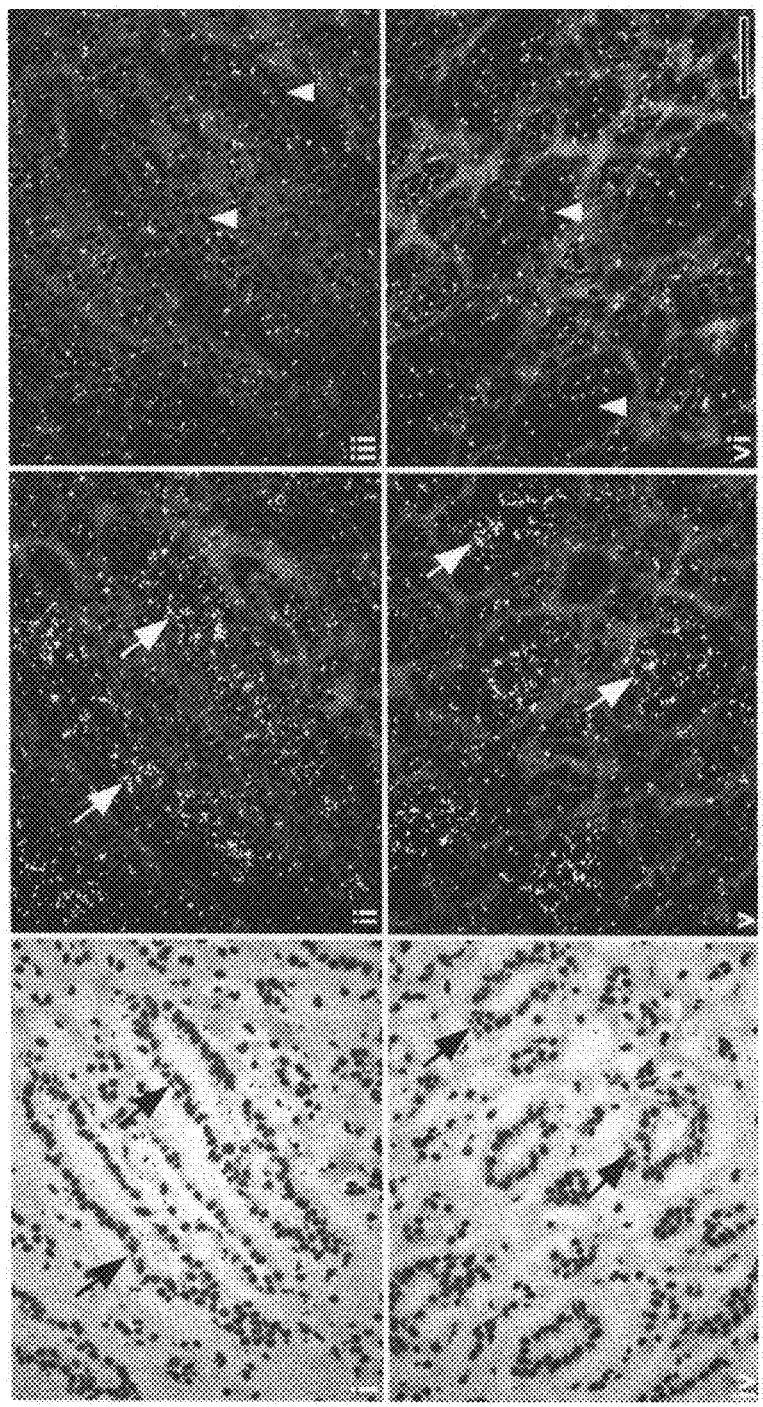

FIG. 20 shows In situ Hybridization (ISH) results of LTRPC3. LTRPC3 mRNA expression was localized in the collecting tubular epithelium of human kidney medulla, medullary rays, and periglomerular regions, with the highest expression localized in medulary tubules. Bright field (i and iv) and dark field (ii and v) photomicrographs show the hybridization signal from antisense hTRMP3 riboprobe as aggregates of fine granules in the cytoplasm of the collecting tubular epithelial cells (arrows) in longitudinal (i and ii) and transverse (iv and v) sections. Low background signal is shown by the control LTRPC3 sense riboprobe in photographs iii and vi (the collecting tubules are indicated by arrowheads). Scale bar denotes 50 µm. ISH methods were performed as described in Example 8 herein.

Figure 21:
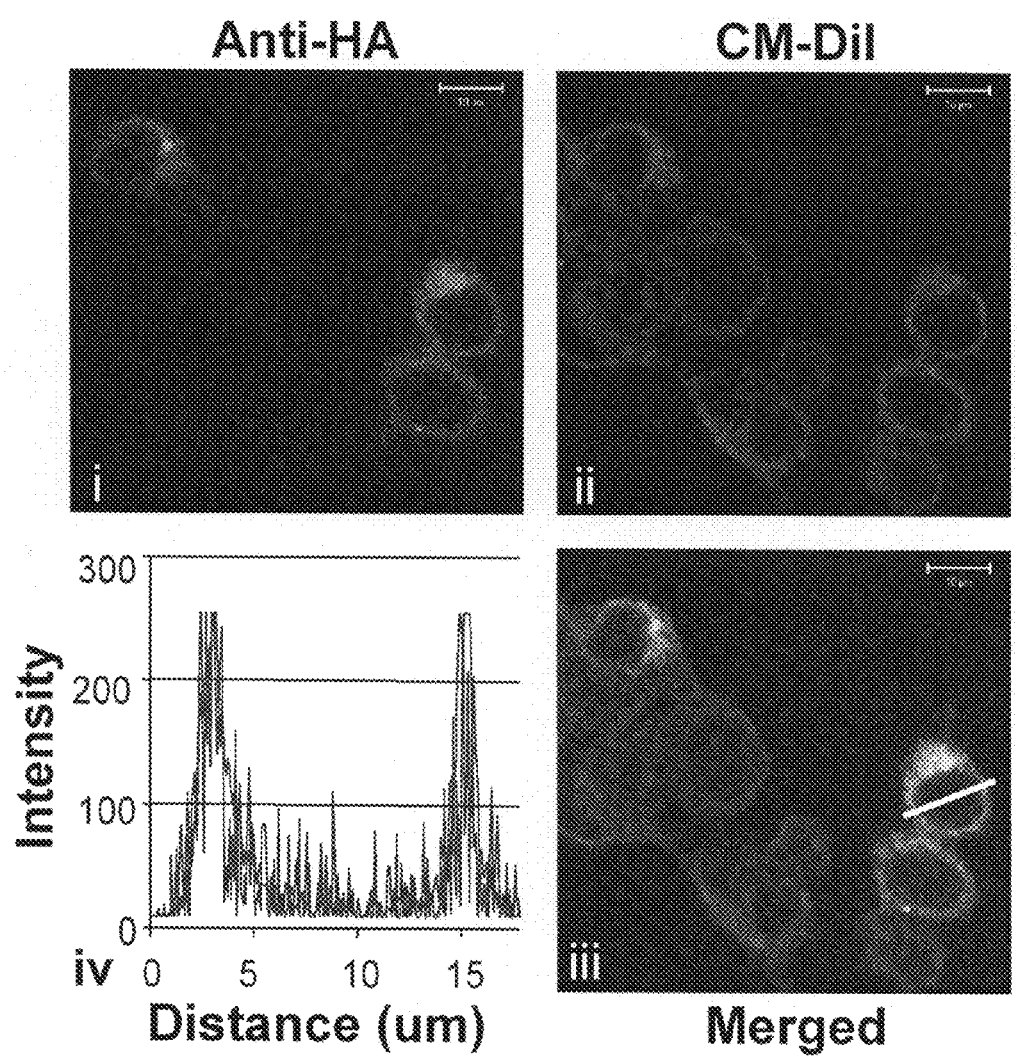

FIG. 21 shows an expanded confocal-image demonstrating that LTRPC3 is expressed as an integral membrane protein. The left top panel (i) shows the image obtained with anti-HA staining (green) which is specific for expressed HA-tagged LTRPC3; the right top panel (ii) shows the image obtained with CM-DiI staining (red), a lipophilic cell membrane marker; the right bottom panel (iii) shows a merged image showing anti-HA, CM-DiI, and DAPI (nuclear stain, blue), with co-localization of LTRPC3 and CM-DiI appearing as yellow; and the left bottom panel (iv) showing the intensity profiles for anti-HA staining (green) and CM-DiI staining (red) along the path indicated by the white line in panel iii, showing overlap of anti-HA staining with CM-DiI staining in a quantitative manner. Scale bar denotes 10 µm. Microscopy was performed as described in Example 9 herein.

Figure 22:
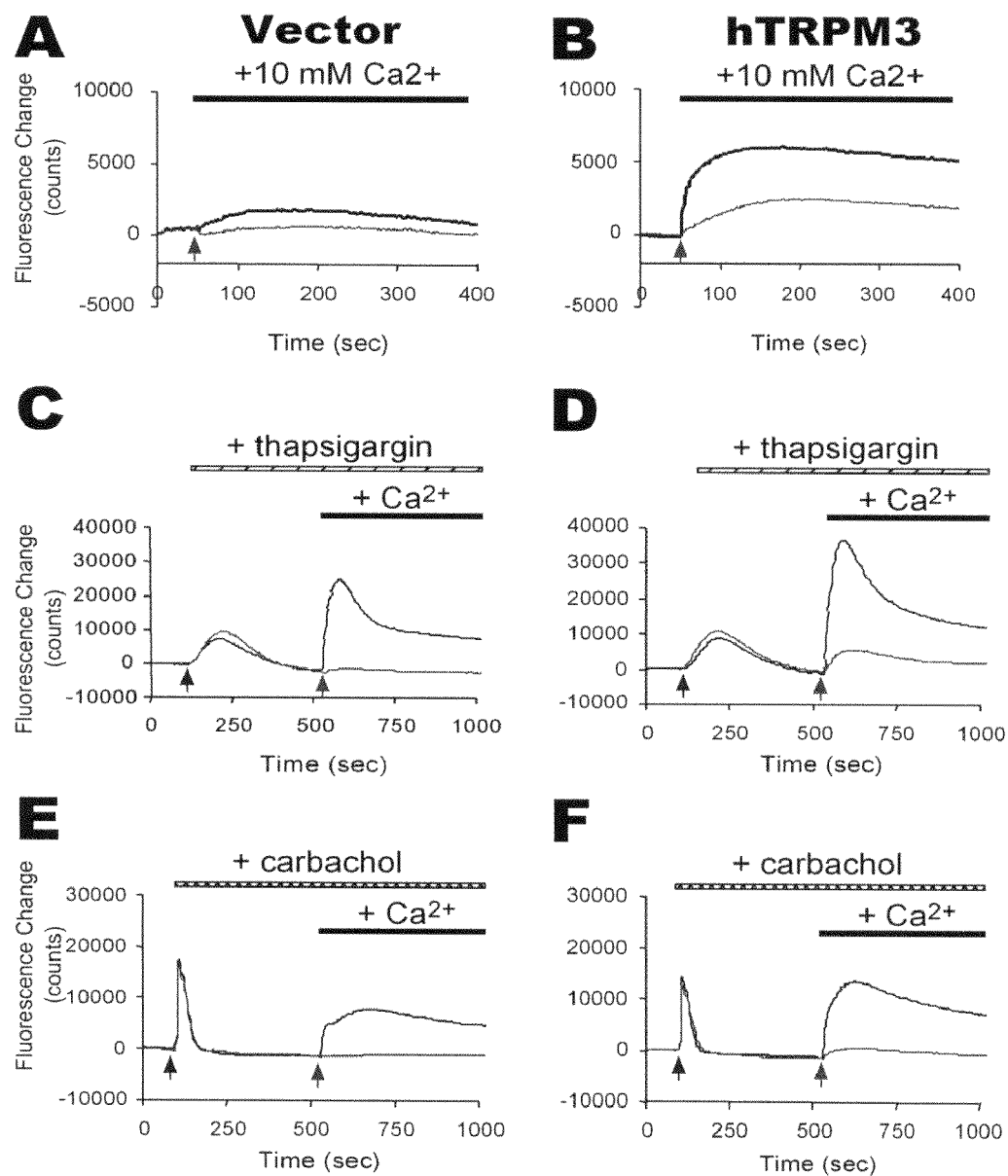

FIG. 22 shows that TRPM3-mediated $Ca^{2+}$ entry can be inhibited by $Gd^{3+}$. Panels A, C and E show results obtained for vector-transfected cells, while Panels B, D and F show results obtained for TRPM3-transfected cells. Panels A and B, show TRPM3-mediated concentration-dependent $Ca^{2+}$ entry was partially inhibited by $Gd^{3+}$. Cells loaded with Fluo-4 were incubated in 1 mM $Ca^{2+}$ solution and treated with 100 µM of $Gd^{3+}$ (red) or without blockers (black) for 10 min prior to the addition of 10 mM $Ca^{2+}$ to the bath solution as indicated. Panels C-F, show that both Tg (Panels C and D) and CCh (Panels E and F) induced LTRPC3-mediated $Ca^{2+}$ entry can be inhibited by $Gd^{3+}$. Cells loaded with Fluo-4 were incubated in a nominally $Ca^{2+}$-free media and treated without blockers (black) or with 100 µM of $Gd^{3+}$ (red) for 10 min prior to the addition of 2 µM TG (Panels C and D, first arrow) or 50 µM CCh (Panels E and F, first arrow), $Ca^{2+}$ entry was stimulated by the bath addition of 10 mM $Ca^{2+}$ (second arrow). Representative traces from one of three independent experiments are shown; each trace is the mean of 12 wells per condition. Physiometric methods were performed as described in Example 10 herein.

Table I provides a summary of the novel polypeptides and their encoding polynucleotides of the present invention.

Table II illustrates the preferred hybridization conditions for the polynucleotides of the present invention. Other hybridization conditions may be known in the art or are described elsewhere herein.

Table III provides a summary of various conservative substitutions encompassed by the present invention.

DETAILED DESCRIPTION OF THE INVENTION

The present invention may be understood more readily by reference to the following detailed description of the preferred embodiments of the invention and the Examples included herein. All references to "LTRPC3" shall be construed to apply to "LTRPC3", "LTRPC3b", "LTRPC3c", "LTRPC3d", "LTRPC3e", and/or "LTRPC3f" unless otherwise specified herein.

The invention provides a novel human sequence that potentially encodes a novel human transient receptor potential channel family member called LTRPC3, in addition to, its splice variants LTRPC3b, LTRPC3c, LTRPC3d, LTRPC3e, and LTRPC3f, which all belong to the lTRPC subfamily. LTRPC3 shares significant homologue with other transient receptor potential channel family members, such as human melatonin receptor 1. Transcripts for LTRPC3 were found predominately in kidney, spinal cord, testis, and brain suggesting that the invention potentially modulates leukocyte proliferation, differentiation, migration, and activation in these tissues. Therefore, the polynucleotide of the present invention has been tentatively named LTRPC3.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:1, SEQ ID NO:3, SEQ ID NO:5, SEQ ID NO:8. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:1, SEQ ID NO:3, SEQ ID NO:5, SEQ ID NO:7, SEQ ID NO:9, and SEQ ID NO:11 was often generated by overlapping sequences contained in multiple clones (contig analysis). A representative clone containing all or most of the sequence for SEQ ID NO:1 was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure. The deposited clone is inserted in the pBSII-SKΔSP-XB plasmid (Strategene) as described herein.

Unless otherwise indicated, all nucleotide sequences determined by sequencing a DNA molecule herein were determined using an automated DNA sequencer (such as the Model 373, preferably a Model 3700, from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded bt the sequenced DNA molecule, beginning at the point of such an insertion or deletion.

Using the information provided herein, such as the nucleotide sequence in FIGS. 1A-F (SEQ ID NO:1), a nucleic acid molecule of the present invention encoding the LTRPC3 polypeptide may be obtained using standard cloning and screening procedures, such as those for cloning cDNAs using mRNA as starting material. Illustrative of the invention, the nucleic acid molecule described in FIGS. 1A-F (SEQ ID NO:1) was discovered in a cDNA library derived from human kidney.

Using the information provided herein, such as the nucleotide sequence in FIGS. 2A-F (SEQ ID NO:3), a nucleic acid molecule of the present invention encoding the LTRPC3b polypeptide may be obtained using standard cloning and screening procedures, such as those for cloning cDNAs using mRNA as starting material. Illustrative of the invention, the nucleic acid molecule described in FIGS. 2A-F (SEQ ID NO:3) was discovered in a cDNA library derived from human kidney.

Using the information provided herein, such as the nucleotide sequence in FIGS. 3A-F (SEQ ID NO:5), a nucleic acid molecule of the present invention encoding the LTRPC3c polypeptide may be obtained using standard cloning and screening procedures, such as those for cloning cDNAs using mRNA as starting material. Illustrative of the invention, the nucleic acid molecule described in FIGS. 3A-F (SEQ ID NO:5) was discovered in a cDNA library derived from human kidney.

Using the information provided herein, such as the nucleotide sequence in FIGS. 5A-F (SEQ ID NO:9), a nucleic acid molecule of the present invention encoding the LTRPC3e polypeptide may be obtained using standard cloning and screening procedures, such as those for cloning cDNAs using mRNA as starting material. Illustrative of the invention, the nucleic acid molecule described in FIGS. 5A-F (SEQ ID NO:9) was discovered in a cDNA library derived human kidney.

A "polynucleotide" of the present invention also includes those polynucleotides capable of hybridizing, under stringent hybridization conditions, to sequences contained SEQ ID NO:3, SEQ ID NO:5, SEQ ID NO:8, the complements thereof, to polynucleotide sequences encoding the sequences contained in SEQ ID NO:4, SEQ ID NO:6, SEQ ID NO:9, the complements thereof. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20× SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, 2nd Ed., T. E. Creighton, W. H. Freeman and Company, New York (1993); Posttranslational Covalent Modification of Proteins, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

As will be appreciated by the skilled practitioner, should the amino acid fragment comprise an antigenic epitope, for example, biological function per se need not be maintained. The terms LTRPC3, LTRPC3b, LTRPC3c, and/or LTRPC3e, polypeptide and LTRPC3, LTRPC3b, LTRPC3c, and/or LTRPC3e protein are used interchangeably herein to refer to the encoded product of the LTRPC3, LTRPC3b, LTRPC3c, and/or LTRPC3e nucleic acid sequence according to the present invention.

"SEQ ID NO:1", "SEQ ID NO:3", "SEQ ID NO:5", and "SEQ ID NO:8", refer to polynucleotide sequences, while "SEQ ID NO:2", "SEQ ID NO:4", "SEQ ID NO:6", and "SEQ ID NO:9", refer to polypeptide sequences, all sequences being identified by an integer specified in Table 1 herein.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about ten-fold less activity, and most preferably, not more than about three-fold less activity relative to the polypeptide of the present invention).

The term "organism" as referred to herein is meant to encompass any organism referenced herein, though preferably to eukaryotic organisms, more preferably to mammals, and most preferably to humans.

As used herein the terms "modulate or modulates" refer to an increase or decrease in the amount, quality or effect of a particular activity, DNA, RNA, or protein.

It is another aspect of the present invention to provide modulators of the LTRPC3, LTRPC3b, LTRPC3c, and/or LTRPC3e protein and LTRPC3, LTRPC3b, LTRPC3c, and/or LTRPC3e peptide targets which can affect the function or activity of LTRPC3, LTRPC3b, LTRPC3c, and/or LTRPC3e in a cell in which LTRPC3, LTRPC3b, LTRPC3c, and/or LTRPC3e function or activity is to be modulated or affected. In addition, modulators of LTRPC3, LTRPC3b, LTRPC3c, and/or LTRPC3e can affect downstream systems and molecules that are regulated by, or which interact with, LTRPC3, LTRPC3b, LTRPC3c, and/or LTRPC3e in the cell. Modulators of LTRPC3, LTRPC3b, LTRPC3c, and/or LTRPC3e include compounds, materials, agents, drugs, and the like, that antagonize, inhibit, reduce, block, suppress, diminish, decrease, or eliminate LTRPC3, LTRPC3b, LTRPC3c, and/or LTRPC3e function and/or activity. Such compounds, materials, agents, drugs and the like can be collectively termed "antagonists". Alternatively, modulators of LTRPC3, LTRPC3b, LTRPC3c, and/or LTRPC3e include compounds, materials, agents, drugs, and the like, that agonize, enhance, increase, augment, or amplify LTRPC3, LTRPC3b, LTRPC3c, and/or LTRPC3e function in a cell. Such compounds, materials, agents, drugs and the like can be collectively termed "agonists".

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that discribed by Ozenberger and Young (Mol. Endocrinol., 9(10):1321-9, (1995); and Ann. N.Y. Acad. Sci., 7; 766:279-81, (1995)).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

Polynucleotides and Polypeptides of the Invention

Features of the Polypeptide Encoded by Gene No:1

The polypeptide of this gene provided as SEQ ID NO:2 (FIGS. 1A-F), encoded by the polynucleotide sequence according to SEQ ID NO:1 (FIGS. 1A-F), and/or encoded by the polynucleotide contained within the deposited clone, LTRPC3, has significant homology at the nucleotide and amino acid level to the human melastatin 1 protein (Melastatin1; Genbank Accession No. gi|3243075; SEQ ID NO:11). An alignment of the LTRPC3 polypeptide with this protein is provided in FIGS. 5A-D.

The LTRPC3 polypeptide was determined to share 65.7% identity and 73.5% similarity with the human melastatin 1 protein (Melastatin1; Genbank Accession No. gi|3243075; SEQ ID NO:11) as shown in FIG. 8.

The LTRPC3 protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain. This family is commonly referred to as the transient receptor potential channel (TRP) family. Melastatin1 defines a separate subfamily of TRP channels referred to as TRPM (melastatin1). TRPM family members are characteristic of their unusually long cytoplasmic tails at both ends of the channel domain and some of the family members contain an enzyme domain at the C-terminal region. Thus, LTRPC3 represents a novel member of the TRPM subfamily.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the melastatin1 protein, in addition to, other transient receptor potential channel family members referenced elsewhere herein or otherwise known in the art.

Most of the known transient receptor potential channel family members, possess one or more transmembrane domains. Likewise, the LTRPC3 polypeptide has been determined to comprise six transmembrane domains (TM1-TM6) as shown in FIGS. 1A-F. The transmembrane domains are located from about amino acid 740 to about amino acid 757 (TM1), from about amino acid 834 to about amino acid 851 (TM2), from about amino acid 908 to about amino acid 920 (TM3), from about amino acid 934 to about amino acid 951 (TM4), from about amino acid 968 to about amino acid 985 (TM5), and/or from about amino acid 1043 to about amino acid 1062 (TM6) of SEQ ID NO:2. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKVILGILLPPSILSLEF (SEQ ID NO:26), IVKFWFYTLAYIGYLMLF (SEQ ID NO:27), VTDLIAILLFSVGM (SEQ ID NO:28), RVIYCVNIIYWYIRLLDI (SEQ ID NO:29), MMIDMMYFVIIMLVVLMS (SEQ ID NO:30), and/or AIMACYLLVANILLVNLLIAV (SEQ ID NO:31). Polynucleotides encoding these polypeptides are also provided. The present invention also encompasses the use of the LTRPC3 transmembrane polypeptides as immunogenic and/or antigenic epitopes as described elsewhere herein.

The present invention also encompasses polypeptides corresponding to the regions between each transmembrane domain of LTRPC3, referred to herein as inter-transmembrane domain polypeptides (inter TM1-2, inter TM2-3, inter TM3-4, inter TM4-5, and inter TM5-6). Such regions are typically solvent accessible (either extracellularly or intracellularly). Therefore, these regions are amenable to the development of agonists and/or antagonists to the LTRPC3 polypeptide, particularly for the development of antibodies specific to these regions.

In preferred embodiments, the following inter-transmembrane domain polypeptides are encompassed by the present invention: KNKDDMPYMSQAQEIHLQEKEAEEPEKPTKEKEEEDMELTAMLGRNNGESS RKKDEEEVQSKHRLIPLGRKIYEFYNAP (SEQ ID NO:50), NYIVLVKMERWPSTQEWIVISYIFTLG-IEKMREILMSEPGKLLQKVKVWLQEY WN (SEQ ID NO:51), ILRLQDQPFRSDG (SEQ ID NO:52), FGVNKY-LGPYVMMIGK (SEQ ID NO:53), and/or FGVARQAILFPNEEPSWKLAKNIFYMPYWMIYGEVFAD-QIDPPCGQNETRED GKIIQLPPCKTGAWIVP (SEQ ID NO:54). Polynucleotides encoding these polypeptides are also provided. The present invention also encompasses the use of the LTRPC3 inter-transmembrane polypeptides as immunogenic and/or antigenic epitopes as described elsewhere herein.

In preferred embodiments, the following N-terminal LTRPC3 inter TM1-2 domain deletion polypeptides are encompassed by the present invention: K1-P79, N2-P79, K3-P79, D4-P79, D5-P79, M6-P79, P7-P79, Y8-P79, M9-P79, S10-P79, Q11-P79, A12-P79, Q13-P79, E14-P79, I15-P79, H16-P79, L17-P79, Q18-P79, E19-P79, K20-P79, E21-P79, A22-P79, E23-P79, E24-P79, P25-P79, E26-P79, K27-P79, P28-P79, T29-P79, K30-P79, E31-P79, K32-P79, E33-P79, E34-P79, E35-P79, D36-P79, M37-P79, E38-P79, L39-P79, T40-P79, A41-P79, M42-P79, L43-P79, G44-P79, R45-P79, N46-P79, N47-P79, G48-P79, E49-P79, S50-P79, S51-P79, R52-P79, K53-P79, K54-P79, D55-P79, E56-P79, E57-P79, E58-P79, V59-P79, Q60-P79, S61-P79, K62-P79, H63-P79, R64-P79, L65-P79, I66-P79, P67-P79, L68-P79, G69-P79, R70-P79, K71-P79, I72-P79, and/or Y73-P79 of SEQ ID NO:50. Polynucleotide sequences encoding these polypeptides are also provided. The present invention also encompasses the use of these N-terminal LTRPC3 inter TM1-2 domain deletion polypeptides as immunogenic and/or antigenic epitopes as described elsewhere herein.

In preferred embodiments, the following C-terminal LTRPC3 inter TM1-2 domain deletion polypeptides are encompassed by the present invention: K1-P79, K1-A78, K1-N77, K1-Y76, K1-F75, K1-E74, K1-Y73, K1-I72, K1-K71, K1-R70, K1-G69, K1-L68, K1-P67, K1-I66, K1-L65, K1-R64, K1-H63, K1-K62, K1-S61, K1-Q60, K1-V59, K1-E58, K1-E57, K1-E56, K1-D55, K1-K54, K1-K53, K1-R52, K1-S51, K1-S50, K1-E49, K1-G48, K1-N47, K1-N46, K1-R45, K1-G44, K1-L43, K1-M42, K1-A41, K1-T40, K1-L39, K1-E38, K1-M37, K1-D36, K1-E35, K1-E34, K1-E33, K1-K32, K1-E31, K1-K30, K1-T29, K1-P28, K1-K27, K1-E26, K1-P25, K1-E24, K1-E23, K1-A22, K1-E21, K1-K20, K1-E19, K1-Q18, K1-L17, K1-H16, K1-I15, K1-E14, K1-Q13, K1-A12, K1-Q11, K1-S10, K1-M9, K1-Y8, and/or K1-P7 of SEQ ID NO:50. Polynucleotide sequences encoding these polypeptides are also provided. The present invention also encompasses the use of these C-terminal LTRPC3 inter TM1-2 domain deletion polypeptides as immunogenic and/or antigenic epitopes as described elsewhere herein.

In preferred embodiments, the following N-terminal LTRPC3 inter TM2-3 domain deletion polypeptides are encompassed by the present invention: F1-N56, N2-N56, Y3-N56, I4-N56, V5-N56, L6-N56, V7-N56, K8-N56, M9-N56, E10-N56, R11-N56, W12-N56, P13-N56, S14-N56, T15-N56, Q16-N56, E17-N56, W18-N56, I19-N56, V20-N56, I21-N56, S22-N56, Y23-N56, I24-N56, F25-N56, T26-N56, L27-N56, G28-N56, I29-N56, E30-N56, K31-N56, M32-N56, R33-N56, E34-N56, I35-N56, L36-N56, M37-N56, S38-N56, E39-N56, P40-N56, G41-N56, K42-N56, L43-N56, L44-N56, Q45-N56, K46-N56, V47-N56, K48-N56, V49-N56, and/or W50-N56 of SEQ ID NO:51. Polynucleotide sequences encoding these polypeptides are also provided. The present invention also encompasses the use of these N-terminal LTRPC3 inter TM2-3 domain deletion polypeptides as immunogenic and/or antigenic epitopes as described elsewhere herein.

In preferred embodiments, the following C-terminal LTRPC3 inter TM2-3 domain deletion polypeptides are encompassed by the present invention: F1-N56, F1-W55, F1-Y54, F1-E53, F1-Q52, F1-L51, F1-W50, F1-V49, F1-K48, F1-V47, F1-K46, F1-Q45, F1-L44, F1-L43, F1-K42, F1-G41, F1-P40, F1-E39, F1-S38, F1-M37, F1-L36, F1-I35, F1-E34, F1-R33, F1-M32, F1-K31, F1-E30, F1-I29, F1-G28, F1-L27, F1-T26, F1-F25, F1-I24, F1-Y23, F1-S22, F1-I21, F1-V20, F1-I19, F1-W18, F1-E17, F1-Q16, F1-T15, F1-S14, F1-P13, F1-W12, F1-R11, F1-E10, F1-M9, F1-K8, and/or F1-V7 of SEQ ID NO:51. Polynucleotide sequences encoding these polypeptides are also provided. The present invention also encompasses the use of these C-terminal LTRPC3 inter TM2-3 domain deletion polypeptides as immunogenic and/or antigenic epitopes as described elsewhere herein.

In preferred embodiments, the following N-terminal LTRPC3 inter TM3-4 domain deletion polypeptides are encompassed by the present invention: I1-G13, L2-G13, R3-G13, L4-G13, Q5-G13, D6-G13, and/or Q7-G13 of SEQ ID NO:52. Polynucleotide sequences encoding these polypeptides are also provided. The present invention also encompasses the use of these N-terminal LTRPC3 inter TM3-4 domain deletion polypeptides as immunogenic and/or antigenic epitopes as described elsewhere herein.

In preferred embodiments, the following C-terminal LTRPC3 inter TM3-4 domain deletion polypeptides are encompassed by the present invention: I1-G13, 1'-D12, I1-S11, I1-R10, I1-F9, I1-P8, and/or I1-Q7 of SEQ ID NO:52. Polynucleotide sequences encoding these polypeptides are also provided. The present invention also encompasses the use of these C-terminal LTRPC3 inter TM3-4 domain deletion polypeptides as immunogenic and/or antigenic epitopes as described elsewhere herein.

In preferred embodiments, the following N-terminal LTRPC3 inter TM4-5 domain deletion polypeptides are encompassed by the present invention: F1-K16, G2-K16, V3-K16, N4-K16, K5-K16, Y6-K16, L7-K16, G8-K16, P9-K16, and/or Y10-K16 of SEQ ID NO:53. Polynucleotide sequences encoding these polypeptides are also provided. The present invention also encompasses the use of these N-terminal LTRPC3 inter TM4-5 domain deletion polypeptides as immunogenic and/or antigenic epitopes as described elsewhere herein.

In preferred embodiments, the following C-terminal LTRPC3 inter TM4-5 domain deletion polypeptides are encompassed by the present invention: F1-K16, F1-G15, F1-I14, F1-M13, F1-M12, F1-V11, F1-Y10, F1-P9, F1-G8, and/or F1-L7 of SEQ ID NO:53. Polynucleotide sequences encoding these polypeptides are also provided. The present invention also encompasses the use of these C-terminal LTRPC3 inter TM4-5 domain deletion polypeptides as immunogenic and/or antigenic epitopes as described elsewhere herein.

In preferred embodiments, the following N-terminal LTRPC3 inter TM5-6 domain deletion polypeptides are encompassed by the present invention: F1-P69, G2-P69, V3-P69, A4-P69, R5-P69, Q6-P69, A7-P69, I8-P69, L9-P69, F10-P69, P11-P69, N12-P69, E13-P69, E14-P69, P15-P69, S16-P69, W17-P69, K18-P69, L19-P69, A20-P69, K21-P69, N22-P69, I23-P69, F24-P69, Y25-P69, M26-P69, P27-P69, Y28-P69, W29-P69, M30-P69, I31-P69, Y32-P69, G33-P69, E34-P69, V35-P69, F36-P69, A37-P69, D38-P69, Q39-P69, I40-P69, D41-P69, P42-P69, P43-P69, C44-P69, G45-P69, Q46-P69, N47-P69, E48-P69, T49-P69, R50-P69, E51-P69, D52-P69, G53-P69, K54-P69, I55-P69, I56-P69, Q57-P69, L58-P69, P59-P69, P60-P69, C61-P69, K62-P69, and/or T63-P69 of SEQ ID NO:54. Polynucleotide sequences encoding these polypeptides are also provided. The present invention also encompasses the use of these N-terminal LTRPC3 inter TM5-6 domain deletion polypeptides as immunogenic and/or antigenic epitopes as described elsewhere herein.

In preferred embodiments, the following C-terminal LTRPC3 inter TM5-6 domain deletion polypeptides are encompassed by the present invention: F1-P69, F1-V68, F1-I67, F1-W66, F1-A65, F1-G64, F1-T63, F1-K62, F1-C61, F1-P60, F1-P59, F1-L58, F1-Q57, F1-I56, F1-I55, F1-K54, F1-G53, F1-D52, F1-E51, F1-R50, F1-T49, F1-E48, F1-N47, F1-Q46, F1-G45, F1-C44, F1-P43, F1-P42, F1-D41, F1-I40, F1-Q39, F1-D38, F1-A37, F1-F36, F1-V35, F1-E34, F1-G33, F1-Y32, F1-I31, F1-M30, F1-W29, F1-Y28, F1-P27, F1-M26, F1-Y25, F1-F24, F1-I23, F1-N22, F1-K21, F1-A20, F1-L19, F1-K18, F1-W17, F1-S16, F1-P15, F1-E14, F1-E13, F1-N12, F1-P11, F1-F10, F1-L9, F1-I8, and/or F1-A7 of SEQ ID NO:54. Polynucleotide sequences encoding these polypeptides are also provided. The present invention also encompasses the use of these C-terminal LTRPC3 inter TM5-6 domain deletion polypeptides as immunogenic and/or antigenic epitopes as described elsewhere herein.

The LTRPC3 polypeptide was determined to comprise several conserved cysteines, at amino acid 94, 209, 265, 419, 517, 582, 598, 821, 912, 929, 942, 1045, 1136, and 1402 of SEQ ID No: 2 (FIGS. 1A-F). Conservation of cysteines at key amino acid residues is indicative of conserved structural features, which may correlate with conservation of protein function and/or activity.

In confirmation of the LTRPC3 representing a member of the transient receptor channel family, the LTRPC3 polypeptide was determined to comprise a predicted TRP domain (EWKFAR) located from about amino acid 973 to about amino acid 978 of SEQ ID NO:2. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following TRP domain polypeptide is encompassed by the present invention: VWKFQR (SEQ ID NO:55). Polynucleotides encoding this polypeptide are also provided. The present invention also encompasses the use of this LTRPC3 TRP domain polypeptide as an immunogenic and/or antigenic epitope as described elsewhere herein.

In further confirmation of the LTRPC3 representing a member of the transient receptor channel family, the LTRPC3 polypeptide was determined to comprise a predicted ion transport signature domain located at about amino acid 748 to about amino acid 959 of SEQ ID NO:2. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following ion transport signature domain polypeptide is encompassed by the present invention: TQEWIVISYIFTLGIEKMREILM-SEPGKLLQKVKVWLQEYWNVTDLIAILLFSV GMIL-RLQDQPFRSDGRVIYCVNIIYWYIRLL-DIFGVNKYLGPYVMMIGKMMID MMYFVIIMLVVLMSFGVARQAILFP-NEEPSWKLAKNIFYMPYWMIYGEVFAD QIDP-PCGQNETREDGKIIQLPPCKTGAWIV-PAIMACYLLVANILLVNLLIAVF (SEQ ID NO:56). Polynucleotides encoding this polypeptide are also provided. The present invention also encompasses the use of this LTRPC3 ion transport signature domain polypeptide as an immunogenic and/or antigenic epitope as described elsewhere herein.

The LTRPC3 polypeptide was determined to comprise a predicted coiled-coil domain located at about amino acid 1063 to about amino acid 1117 of SEQ ID NO:2. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following coiled-coil domain polypeptide is encompassed by the present invention: ERIRVTSERVENMSMRLEEVNEREH-SMKASLQTVDIRLAQLEDLIGRMATAL ERLT (SEQ ID NO:57). Polynucleotides encoding this polypeptide are also provided. The present invention also encompasses the use of this LTRPC3 coiled-coil domain polypeptide as an immunogenic and/or antigenic epitope as described elsewhere herein.

LTRPC3 polypeptides and polynucleotides are useful for diagnosing diseases related to the over and/or under expression of LTRPC3 by identifying mutations in the LTRPC3 gene using LTRPC3 sequences as probes or by determining LTRPC3 protein or mRNA expression levels. LTRPC3 polypeptides will be useful in screens for compounds that affect the activity of the protein. LTRPC3 peptides can also be used for the generation of specific antibodies and as bait in yeast two hybrid screens to find proteins the specifically interact with LTRPC3.

Consistent with LTRPC3 representing a transient receptor potential channel, immunohistochemical experiments have shown that LTRPC3 localizes to the cell membrane (see FIG. 17 and Example 6). Specifically, the complete open reading frame of LTRPC3 with a C-terminal HA tag was transiently transfected into HEK 293 cells to assess its cellular localization. The HA-tagged LTRPC3 was detected using a fluorescein-conjugated anti-HA antibody and a laser scanning confocal microscope which produces a green fluorescent signal. The green fluorescent signal was exclusively detected at the subplasma membrane region of the transfected cells (see FIG. 17), which is consistent with LTRPC3 being an integral membrane protein. Under these conditions approximately ~70% of cells are expressing LTRPC3. The expression of full-length protein was accessed with immunoblot using an anti-HA antibody and detected as the expected size of ~170 kD (data not shown).

Additionally, anti-HA staining was found to be associated with the membrane marker CM-DiI, indicating LTRPC3 protein in or near the plasmalemmal compartment of transfected cells (see FIG. 21). Plasmalemmal localization is consistent with the function of the TRP family as $Ca^{2+}$-permeable cation channels. LTRPC3 was also observed in intracellular compartments, possibly resulting from overexpression in this heterologous expression system, as observed with other ion channels (Marshall, J., et al., (1995) *Neuron* 14, 211-215.).

Moreover, physiometric studies have shown that LTRPC3 is a functional $Ca^{2+}$ permeable channel (see FIGS. 18 and 19, and Example 7). LTRPC3 function was assessed using a Fluorometric Imaging Plate Reader (FLIPR™) that measures real-time intracellular fluorescence changes. Cells transiently transfected with vector or LTRPC3-HA were loaded with the cytoplasmic $Ca^{2+}$ indicator Fluoro-4 in a 1 mM $Ca^{2+}$ solution. Addition of $Ca^{2+}$ to the media resulted in a concentration-dependent influx of $Ca^{2+}$ into LTRPC3-expressing cells (FIG. 18; right panels), indicating that LTRPC3 is a functional $Ca^{2+}$ channel. In contrast, vector-transfected cells showed minimal $Ca^{2+}$ influx under the same experimental conditions (FIG. 18, left panels). The non-transfected cells were indistinguishable from the vector-transfected cells (data not shown). Therefore, LTRPC3 is a constitutively active channel capable of mediating $Ca^{2+}$ influx.

To further address the mechanism of LTRPC3-mediated $Ca^{2+}$ entry, similar $Ca^{2+}$ addition experiments were performed on transfected cells incubated (~30 min) in a nominally $Ca^{2+}$-free solution. Previous studies have shown that lowering extracellular $Ca^{2+}$ concentration below physiological levels can deplete intracellular $Ca^{2+}$ stores in many cell types including HEK 293 (EMBO J. 17, 4274-4282, (1998)). Incubating vector-transfected HEK 293 cells in a nominally $Ca^{2+}$-free solution gave rise to $Ca^{2+}$ entry that was dependent on the concentration of $Ca^{2+}$ added to the buffers, indicating $Ca^{2+}$ influx was mediated through endogenous SOCs in HEK293 cells (FIG. 18, left panels). In LTRPC3 cells, the $Ca^{2+}$ transients triggered by similar $Ca^{2+}$ treatment were much larger (FIG. 18, right panels). This $Ca^{2+}$ entry observed in LTRPC3 cells incubated in $Ca^{2+}$-free media were greater than those observed in 1 mM $Ca^{2+}$ media, indicating that LTRPC3-mediated $Ca^{2+}$ entry can be potentiated by the store-depletion.

The store-operated mechanism of LTRPC3-mediated $Ca^{2+}$ influx was tested further by passively depleting $Ca^{2+}$ stores with thapsigargin (TG), an inhibitor of microsomal $Ca^{2+}$ ATPases that pumps ions from the cytosol back into the stores. Addition of 2 µM thapsigargin equivalently depleted $Ca^{2+}$ stores in LTRPC3-HA- and vector-transfected cells (FIG. 19A). Following store depletion with TG, addition of $Ca^{2+}$ to the buffer induced a much larger $Ca^{2+}$ entry in LTRPC3 cells compared to the vector control cells.

Receptor-mediated $Ca^{2+}$ entry was also more pronounced in LTRPC3-HA-transfected cells. Carbachol (CCh) can activate an endogenous muscarinic receptor and trigger $IP_3$ production, leading to store-depletion in HEK 293 cells. The addition of 50 µM of CCh caused a transient and rapid intracellular $Ca^{2+}$ increase in both LTRPC3- and vector-transfected cells (FIG. 19B). After the store depletion with CCh, adding of $Ca^{2+}$ to the buffer induced a much larger influx of $Ca^{2+}$ into LTRPC3 cells, as compared to vector control cells. These results show that after store depletion with TG or CCh LTRPC3-transfected cells exhibit an increased $Ca^{2+}$ influx when compared to control cells.

The lanthanides, gadolinium ($Gd^{3+}$) and lanthanum ($La^{3+}$), are nonselective $Ca^{2+}$-permeable channel blockers, often used as part of the characterization of overexpressed TRP channels. Both lanthanides blocked LTRPC3 $Ca^{2+}$ conductance, although $La^{3+}$ was more potent (FIG. 19C). In the presence of 1 mM $Ca^{2+}$ in which endogenous SOCs is minimally activated (FIG. 18A), pre-treatment with 100 µM of $La^{3+}$ and $Gd^{3+}$ blocked LTRPC3 $Ca^{2+}$ currents, stimulated by adding 10 mM $Ca^{2+}$, by 67 and 39%, respectively. These results indicated that LTRPC3 mediated currents are not non-specific leak currents resulting from protein overexpression.

Additional experiments were performed to further confirm the $Ca^{2+}$ store-depleted activation of LTRPC3 using $Gd^{3+}$. The effects of 100 μM $Gd^{3+}$ on $Ca^{2+}$ permeability were tested in vector- and LTRPC3-transfected cells. The minimal $Ca^{2+}$ influx observed upon addition of 10 mM $Ca^{2+}$ to the cells (cells were incubated in the presence of 1 mM $Ca^{2+}$) in vector-transfected cells (see FIG. 22A) was strongly inhibited by 100 μM $Gd^{3+}$. In contrast, 100 μM $Gd^{3+}$ inhibited $Ca^{2+}$ entry, induced by adding 10 mM $Ca^{2+}$, by 53% in LTRPC3-transfected cells (see FIG. 22B). $Gd^{3+}$ reduced fluorescence units in vector-transfected cells from 1470±140 to −58±8 and in LTRPC3-transfected cells from 6000±322 to 2080±199 (n=12). Fluorescence values were measured 150 seconds after adding 10 mM $Ca^{2+}$ and percent blockade was calculated as 1 minus $F_{LTRPC3}-F_{Vector}$ in the presence of $Gd^{3+}$ divided by $F_{LTRPC3}-F_{Vector}$ without blocker. The effects of $Gd^{3+}$ on LTRPC3-mediated $Ca^{2+}$ entry, induced by 10 mM $Ca^{2+}$, in the presence of thapsigargin or carbachol was also examined. Cells were incubated in nominally $Ca^{2+}$-free medium for thapsigargin and carbachol experiments. $Gd^{3+}$ inhibited $Ca^{2+}$ entry by 51% after depletion of intracellular stores with thapsigargin (see FIG. 22B). $Gd^{3+}$ reduced peak fluorescence after 10 mM $Ca^{2+}$ addition in vector-transfected cells from 26444±2410 to 1316±60 and in LTRPC3-transfected cells from 37676±2425 to 6783±250 (see FIGS. 22C and D, respectively; n=12). $Gd^{3+}$ inhibited $Ca^{2+}$ entry by 72% after depletion of intracellular stores with carbachol. $Gd^{3+}$ reduced peak $Ca^{2+}$ fluorescence in vector-transfected cells from 9327±466 to 453±15 and in LTRPC3-transfected cells from 14747±988 to 1975±79 (see FIGS. 22E and F, respectively; n=12). These results show that, under identical conditions, the endogenous $Ca^{2+}$ entry pathway was strongly blocked by application of 100 μM $Gd^{3+}$ whereas the LTRPC3-mediated pathway was partially blocked (53%, see FIGS. 22A and B). Stimulation of $Ca^{2+}$ entry in LTRPC3-transfected cells in the presence of thapsigargin or carbachol was also partially blocked by 100 μM $Gd^{3+}$. These results are consistent with the hypothesis that LTRPC3 mediates a $Ca^{2+}$ entry pathway that apparently is distinct from the endogenous $Ca^{2+}$ entry pathways present in HEK 293 cells.

LTRPC3 is constitutively active but can be potentiated by store-depletion and is partially sensitive to $La^{3+}$ and $Gd^{3+}$ blockade. LTRPC3 is believed to represent the first member of the TRPM subfamily that exhibits this store-operated mechanism, although some members of TRPC subfamily have been considered for this role. TRPM1 and TRPM4a are constitutive $Ca^{2+}$ permeable channels but it is unclear whether they can be stimulated by store-depletion (*Proc. Natl. Acad. Sci. U.S.A.* 98, 10692-10697, (2001)). Distinct from TRPM4a, TRPM4b is directly activated by changes in intracellular $Ca^{2+}$ without significant permeation of $Ca^{2+}$ (*Cell* 109, 397-401, (2002)). TRPM2 is activated by ADP-ribose, NAD and changes in redox status (*Nature* 411, 595-599, (2001); *Science* 293, 1327-1330, (2001); and *Mol. Cell.* 9, 163-173, (2002)). TRPM7 is regulated by $Mg^{2+}$-ATP and/or $PIP_2$ (*Science* 291, 1043-1047, (2001); *Nature* 411, 690-695, (2001); and *Nat. Cell Biol.* 4, 329-36 (2002)). TRPM8 is activated by cold temperatures and cooling agents (*Nature* 416, 52-58, (2002); and *Cell* 108, 705-715, (2002)). Therefore, in conjunction with its fairly restricted tissue expression, which is not observed with any other family members, LTRPC3 may have a unique biological function in human.

Expression profiling designed to measure the steady state mRNA levels encoding the LTRPC3 polypeptide showed predominately high expression levels in kidney. The LTRPC3 polypeptide was also significantly expression in spinal cord, testis, and brain (as shown in FIG. 6).

Moreover, Northern hybridizations of the LTRPC3 mRNA confirmed the predominately high expression levels in kidney, and significant expression levels in testis, and brain (as shown in FIG. 7). The Northern hybridization was not performed on spinal cord tissue.

Expanded analysis of LTRPC3 expression levels by Taq-Man™ quantitative PCR (see FIG. 12) confirmed that the LTRPC3 polypeptide is expressed in kidney, brain, testis (FIGS. 6 and 7), although higher expression levels were observed in brain than previously appreciated. LTRPC3 mRNA was expressed predominately in the brain, specifically the cerebellum, choroid plexus, the locus coeruleus, the posterior hypothalamus and the substantia nigra. Expression of LTRPC3 was also significantly expressed in the kidney, with higher levels observed in the cortex than in the medulla or pelvis. LTRPC3 was also significantly expressed in the spinal cord, testis, and to a lesser extent in other tissues as shown.

Therefore, LTRPC3 polynucleotides and polypeptides, including modulators or fragments thereof, may be useful in treating, diagnosing, prognosing, and/or preventing a variety of neurological conditions, in particular various choroid plexus neoplasms, choroid plexus papilloma, Alzheimer's disease, prion disorders and multiple sclerosis and movement disorders that involve the cerebellum. Based upon the expression pattern of LTRPC3 in kidney, this novel TRP family member may also be the cause solitary metastasis in the choroid plexus, a rare type of carcinoma. For example, it has been shown that out of 15 cases of solitary metastasis of the choroid plexus, five originated from renal cell carcinoma (Neurol. Med. Chir. (Tokyo) 1997 December; 37(12):916-9). Additionally, given the rather selective expression of LTRPC3 in the choroid plexus and renal tissues, it may be possible that altered function of LTRPC3 may be responsible for solitary metastasis and renal carcinoma. LTRPC3 polynucleotides and polypeptides, including modulators or fragments thereof, may be useful in treating, diagnosing, prognosing, and/or preventing a variety of renal disorders, particularly solitary metastasis in the choroid plexus, and renal carcinoma.

Moreover, an additional analysis of LTRPC3 expression levels by TaqMan™ quantitative PCR (see FIG. 13) in disease cells and tissues indicated that the LTRPC3 polypeptide is differentially expressed in renal, testicular, and ovarian tumor tissues. In the renal tumor tissue results, an average of 2 out of 3 matched samples, which represent 3 out of 4 samples total, showed a significant decrease in LTRPC3 steady state RNA levels in tumor compared to control samples. In the testicular tumor tissue results, differential expression of LTRPC3 in testicular cancers was observed with all 5 tumor samples showing a significant reduction in steady-state RNA levels compared to two control samples. In the ovarian tumor tissue results, differential expression of LTRPC3 in ovarian cancers was observed with 3 tumor samples showing a significant reduction in steady-state RNA levels compared to five control samples.

The differential expression of LTRPC3 in tumors relative to normal tissues suggests that loss of LTRPC3 expression during tumor progression might contribute to the metastatic process by altering internal calcium stores in a manner that reflects a loss of cellular control on apoptosis. Restoring LTRPC3 function might provide a novel therapeutic approach to treating certain cancers. Therefore, LTRPC3 polynucleotides and polypeptides, including modulators or fragments thereof, particularly agonists of LTRPC3 activity or expression, may be useful in treating, diagnosing, prognosing, ameloriating, and/or preventing a variety of cancers and proliferative conditions, particularly of the kidney, testis, and ovaries.

An additional analysis of LTRPC3 localized expression was assessed using In situ hybridization techniques (ISH). LTRPC3 expression was localized to the cytoplasm of collecting tubular epithelium in the medulla, medullary rays, and periglomerular regions (see FIG. 20, Plates i, ii, iv and v). Tubules in the medulla exhibited the most intense expression. Other tubular epithelia, e.g., proximal convoluted tubular epithelium, exhibited minimal expression. Expression patterns were compared to LTRPC3 sense mRNA-labeled human kidney sections as negative controls (FIG. 20, Plates iii and vi) and to human lysozyme antisense mRNA labeled human kidney sections as positive controls (data not shown).

The observed LTRPC3 mRNA expression in human kidney, suggests that LTRPC3 may play a role in renal handling of calcium and other cations. The kidney plays a major role in $Ca^{2+}$ homeostasis. LTRPC3 could be involved in $Ca^{2+}$ absorption directly due to its $Ca^{2+}$ permeability. Indeed, the in situ hybridization analysis described herein demonstrates that LTRPC3 is predominantly expressed in the connecting tubule, which has frequently been implicated in active transcellular $Ca^{2+}$ reabsorption (see Hoenderop, J. G., et al., (2002) Annu. Rev. Physiol. 64, 529-549; which is hereby incorporated by reference herein in its entirety). Alternatively, LTRPC3 may function as an SOC that regulates $Ca^{2+}$ absorption. In the kidney, $Ca^{2+}$ absorption is regulated by agonists such as calcitonin, parathyroid hormone, and parathyroid hormone-related peptide through their respective G protein-coupled receptors, and downstream SOCs (Friedman, P. A., et al., (1995) Physiol. Rev. 75, 429-471; which is hereby incorporated by reference herein in its entirety).

Potentially, LTRPC3 may involved in the pathogenesis of calcium homeostasis-related disorders such as hypercaliuric nephrolithiasis, certain forms of osteoporosis, Gitelman's disease and Bartter's syndrom.

In preferred embodiments, LTRPC3 polynucleotides and polypeptides, including fragments and modulators thereof, are useful for treating, diagnosing, and/or ameliorating $Ca^{2+}$ reabsorption disorders, disorders associated with aberrant luminal Ca2+ entry via the epithelial Ca2+ channel (ECaC), disorders associated with aberrant cytosolic diffusion of Ca2+ bound to calbindin-D28K, disorders associated with aberrant basolateral extrusion of Ca2+ through the Na+/Ca2+ exchanger (NCX), disorders associated with aberrant plasma membrane Ca2+-ATPase (PMCA) activity and/or activation, disorders associated with the hypocalciuric effect of diuretics, disorders associated with the hypocalciuric effect of thiazide diuretics, disorders associated with hormone insufficiencies that affect the function of the kidney, disorders associated with hormone insufficiencies that affect renal Ca2+ homeostasis, disorders associated with aberrant renal Ca2+ homeostasis as a result of vitamin D deficiency, disorders associated with aberrant renal Ca2+ homeostasis as a result of PTH deficiency, disorders associated with aberrant renal Ca2+ homeostasis as a result of vasopressin deficiency, disorders associated with aberrant renal Ca2+ homeostasis as a result of prostaglandines deficiency, disorders associated with aberrant renal Ca2+ homeostasis as a result of estrogen deficiency, disorders associated with aberrant renal Ca2+ homeostasis as a result of calcitonin deficiency, disorders associated with aberrant renal Ca2+ homeostasis as a result of parathyroid hormone deficiency, disorders associated with aberrant renal Ca2+ homeostasis as a result of atrial natriuretic peptide deficiency, calcium homeostasis-related disorders, hypercaliuric nephrolithiasis, certain forms of osteoporosis, Gitelman's disease, Bartter's syndrom, disorders associated with aberrant function of kidney tubular epithelium, disorders associated with aberrant function of kidney tubular epithelium in the medulla, disorders associated with aberrant function of kidney tubular epithelium in the medullary rays, disorders associated with aberrant function of kidney tubular epithelium in the periglomerular.

In preferred embodiments, LTRPC3 polynucleotides and polypeptides, including fragments and modulators thereof, are useful for treating, diagnosing, and/or ameliorating acute kidney failure, chronic kidney failure, cystic kidney disease, horseshoe kidney, hypertensive kidney disease, kidney atrophy, kidney cancer, kidney disease, kidney failure, kidney infection, kidney metastasis, kidney stone, nephrolithiasis, multicystic dysplastic kidney disease, and polycystic kidney disease.

Characterization of the LTRPC3 polypeptide of the present invention using antisense oligonucleotides led to the determination that LTRPC3 is involved in the negative modulation of the FEN1 DNA base-excision repair/proliferation modulating protein as described in Example 5 herein.

Specifically, antisense inhibition of LTRPC3 resulted in upregulation of Fen1, a marker of proliferation. As such, LTRPC3 behaves in a manner similar to a tumor suppressor, in that loss results in increases in proliferation. While some increases in the proliferation markers p21 and IkB were also observed, they were less significant, and could be a response to the pro-proliferative effect of LTRPC3 antisense inhibition. Interestingly, expression of LTRPC3 was also observed to be significantly reduced in tumor tissues, relative to normal tissues (see FIG. 13). Specifically, renal, testicular, and ovarian tumor samples showed as much as 12 to 30 fold down regulation of LTRPC3 message levels compared to normal tissues. This reduction of LTRPC3 correlating with the tumor state is consistent with the negative FEN1 modulatory activity and suggests this gene may have antiproliferative activities. Therefore, for modulators of LTRPC3 to be useful for treating cancer, it would be necessary to increase the activity of the gene or gene product in order to have the reverse effect on cancerous cells. Thus, an agonist of LTRPC3 activity or a compound that increased LTRPC3 message levels would be a desired invention for cancer therapy.

In preferred embodiments, LTRPC3 polynucleotides and polypeptides, including fragments and modulators thereof, are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrome, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, LTRPC3 polynucleotides and polypeptides, including fragments and modulators thereof, are useful for increasing mammalian base excision repair activity, increasing mammalian single-nucleotide base excision repair activity, and/or increasing mammalian long patch base excision repair activity.

In preferred embodiments, antagonists directed against LTRPC3 are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrome, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, antagonists directed against LTRPC3 are useful for increasing mammalian base excision repair activity, increasing mammalian single-nucleotide base excision repair activity, and/or increasing mammalian long patch base excision repair activity.

In preferred embodiments, agonists directed against LTRPC3 are useful for treating, diagnosing, and/or ameliorating, disorders related to aberrant signal transduction, proliferating disorders, and/or cancers, particularly renal cell carcinomas, testicular cancers, and/or ovarian cancers.

Moreover, agonists directed against LTRPC3 are useful for decreasing mammalian base excision repair activity, decreasing mammalian single-nucleotide base excision repair activity, and/or decreasing mammalian long patch base excision repair activity.

The strong homology to human transient receptor potential channels (TRP), combined with the predominate localized expression in kidney tissue suggests the LTRPC3 polynucleotides and polypeptides, including modulators or fragments thereof, may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention, slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome.for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H., Willems, P, H., Bindels, R, J. J. Biol, Chem., 274(13):8375-8, (1999)).

Thus, the LTRPC3 polynucleotides and polypeptides are expected to share at least some biological activity with TRP family members expressed in kidney cells and tissues, particularly those specifically referenced herein.

The strong homology to human transient receptor potential channels (TRP) proteins, combined with the localized expression in spinal cord and brain suggests the LTRPC3 polynucleotides and polypeptides, including modulators or fragments thereof, may be useful in treating, diagnosing, prognosing, and/or preventing neurodegenerative disease states, behavioral disorders, or inflammatory conditions. Representative uses are described in the "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong homology to human transient receptor potential channels (TRP), combined with the localized expression in testis tissue emphasizes the potential utility for LTRPC3 polynucleotides and polypeptides in treating, diagnosing, prognosing, and/or preventing testicular, in addition to reproductive disorders.

In preferred embodiments, LTRPC3 polynucleotides and polypeptides including agonists and fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The LTRPC3 polynucleotides and polypeptides including agonists and fragments thereof, may also have uses related to modulating testicular development, embryogenesis, reproduction, and in ameliorating, treating, and/or preventing testicular proliferative disorders (e.g., cancers, which include, for example, choriocarcinoma, Nonseminoma, seminona, and testicular germ cell tumors).

Likewise, the localized expression in testis tissue also emphasizes the potential utility for LTRPC3 polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Bimbaumer, L, Lett., 373(3):193-8, (1995)); and TRPC1 (Wes, P, D., Chevesich, J., Jeromin, A., Rosenberg, C., Stetten, G., Montell, C, Proc, Natl, Acad, Sci, U,S,A., 92(21):9652-6, (1995)).

Thus, the LTRPC3 polynucleotides and polypeptides are expected to share at least some biological activity with TRP family members expressed in testis cells and tissues, particularly those specifically referenced herein.

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

In preferred embodiments, LTRPC3 polynucleotides and polypeptides of the present invention, including agonists and/or fragments thereof, have uses that include, modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity.

In more preferred embodiments, LTRPC3 polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

LTRPC3 polynucleotides and polypeptides of the present invention, including agonists and/or fragments may be involved in intracellular $Ca^{2+}$ homeostasis which affects various aspects of biological functions including mechano-regulation, pain transduction, vasorelaxation, gene expression, cell cycle and proliferation/apoptosis. Since LTRPC3 is dominantly expressed in kidney, it may particularly play an important role in regulating cytosolic Ca2+ in the renal system, potentially Ca2+ absorption.

The LTRPC3 gene maps to chromosome 9q21.11-21.31 between the two markers D9S1874 and D9S1807. This region is linked to amyotrophic lateral sclerosis with frontotemporal dementia, early-onset pulverulent cataract, infantile nephronophthisis, hypomagnesemia with secondary hypocalcemia (HSH), and familial hemophagocytic lymphohistiocytosis. Therefore, agonists and/or antagonists of the novel LTRPC3 can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in $Ca^{2+}$ homeostasis including osteoporosis, hypercalciuric stone disease, and chronic renal failure.

Moreover, given the selective expression in kidney, LTRPC3 could be considered a candidate gene for HSH, since the phenotype is a renal insufficiency. LTRPC3 chromosomal location is ~600 kb downstream of a X;9 translocation breakpoint interval described for one patient with HSH (*Hum. Mol. Genet.* 6, 1491-1497, (1997)). Recently, two groups reported that a new member of the TRPM subfamily, TRPM6, expressed in both intestinal tissues and kidney, is associated with HSH (*Nat. Genet.* 31, 166-170, (2002); and *Nat. Genet.* 31, 171-174 (2002)). Indeed, LTRPC3 is ~4 mb 5' to TRPM6 on 9q21. Although TRPM6 is the first component identified for HSH, this should not preclude involvement of LTRPC3 in the disease. Therefore, it is possible that LTRPC3 may co-localize with TRPM6 and/or forms a heteromultimer with TRPM6 in the kidney.

The kidney plays a major role in $Ca^{2+}$ homeostasis (reviewed in *Physiol. Rev.* 75, 429-471, (1995)). LTRPC3 may play a direct role in $Ca^{2+}$ absorption due to its constitutive $Ca^{2+}$ permeability. Alternatively, LTRPC3 may be the SOC that regulates $Ca^{2+}$ absorption. In kidney, $Ca^{2+}$ absorption is regulated by agonists such as calcitonin, parathyroid hormone and parathyroid hormone-related peptide through their respective G protein-coupled receptors, and downstream SOCs. Additionally, in kidney a SOC has been described (*J. Biol. Chem.* 276, 25759-25765, (2001)) for the action of angiotensin II, a vasoactive peptide that plays a major role in regulating blood pressure.

In addition, LTRPC3 polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++ sensitive signaling pathways, the activation of kinase-activatible proteins, and the activation of kinase-dependent signaling pathways.

The LTRPC3 polynucleotides and polypeptides of the present invention, including agonists and/or fragments thereof, have uses that include modulating proliferation, differentiation, migration, and activation in various cells, tissues, and organisms, and particularly in mammalian kidney, spinal cord, testis, and brain, preferably human. LTRPC3 polynucleotides and polypeptides of the present invention, including agonists and/or fragments thereof, may be useful in diagnosing, treating, prognosing, and/or preventing renal, neural, and/or proliferative diseases or disorders, particularly of the renal system.

In addition, antagonists of the LTRPC3 polynucleotides and polypeptides, including modulators or fragments thereof, may have uses that include diagnosing, treating, prognosing, and/or preventing diseases or disorders related to transient receptor potential channel activity, which may include renal, neural, reproductive, and/or proliferative diseases or disorders.

Although it is believed the encoded polypeptide may share at least some biological activities with transient receptor potential channel family members, particularly those melastatin1, a number of methods of determining the exact biological function of this clone are either known in the art or are described elsewhere herein. Briefly, the function of this clone may be determined by applying microarray methodology. Nucleic acids corresponding to the LTRPC3 polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known transient potential receptor inhibitors, which include, but are not limited to the drugs listed herein or otherwise known in the art, might indicate a function in modulating transient potential receptor function, for example. In the case of LTRPC3, kidney, spinal cord, testis, and brain, should be used to extract RNA to prepare the probe.

In addition, the function of the protein may be assessed by applying quantitative PCR methodology, for example. Real time quantitative PCR would provide the capability of following the expression of the LTRPC3 gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:1 (FIGS. 1A-F).

The function of the protein may also be assessed through complementation assays in yeast. For example, in the case of the LTRPC3, transforming yeast deficient in transient receptor potential channel activity with LTRPC3 and assessing their ability to grow would provide convincing evidence the LTRPC3 polypeptide has transient receptor potential channel activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a kidney, spinal cord, testis, and/or brain-specific promoter), or it can be expressed at a specified time of development using an inducible and/or a developmentally regulated promoter.

In the case of LTRPC3 transgenic mice or rats, if no phenotype is apparent in normal growth conditions, observing the organism under diseased conditions (renal, reproductive, neural, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal LTRPC3 deletion polypeptides are encompassed by the present invention: M1-T1554, Y2-T1554, V3-T1554, R4-T1554, V5-T1554, S6-T1554, F7-T1554, D8-T1554, T9-T1554, K10-T1554, P11-T1554, D12-T1554, L13-T1554, L14-T1554, L15-T1554, H16-T1554, L17-T1554, M18-T1554, T19-T1554, K20-T1554, E21-T1554, W22-T1554, Q23-T1554, L24-T1554, E25-T1554, L26-T1554, P27-T1554, K28-T1554, L29-T1554, L30-T1554, I31-T1554, S32-T1554, V33-T1554, H34-T1554, G35-T1554, G36-T1554, L37-T1554, Q38-T1554, N39-T1554, F40-T1554, E41-T1554, L42-T1554, Q43-T1554, P44-T1554, K45-T1554, L46-T1554, K47-T1554, Q48-T1554, V49-T1554, F50-T1554, G51-T1554, K52-T1554, G53-T1554, L54-T1554, I55-T1554, K56-T1554, A57-T1554, A58-T1554, M59-T1554, T60-T1554, T61-T1554, G62-T1554, A63-T1554, W64-T1554, I65-T1554, F66-T1554, T67-T1554, G68-T1554, G69-T1554, V70-T1554, N71-T1554, T72-T1554, G73-T1554, V74-T1554, I75-T1554, R76-T1554, H77-T1554, V78-T1554, G79-T1554, D80-T1554, A81-T1554, L82-T1554, K83-T1554, D84-T1554, H85-T1554, A86-T1554, S87-T1554, K88-T1554, S89-T1554, R90-T1554, G91-T1554, K92-T1554, I93-T1554, C94-T1554, T95-T1554, I96-T1554, G97-T1554, I98-T1554, A99-T1554, P100-T1554, W101-T1554, G102-T1554, I103-T1554, V104-T1554, E105-T1554, N106-T1554, Q107-T1554, E108-T1554, D109-T1554, L110-T1554, I111-T1554, G112-T1554, R113-T1554, D114-T1554, V115-T1554, V116-T1554, R117-T1554, P118-T1554, Y119-T1554, Q120-T1554, T121-T1554, M122-T1554, S123-T1554, N124-T1554, P125-T1554, M126-T1554, S127-T1554, K128-T1554, L129-T1554, T130-T1554, V131-T1554, L132-T1554, N133-T1554, S134-T1554, M135-T1554, H136-T1554, S137-T1554, H138-T1554, F139-T1554, I140-T1554, L141-T1554, A142-T1554, D143-T1554, N144-T1554, G145-T1554, T146-T1554, T147-T1554, G148-T1554, K149-T1554, Y150-T1554, G151-T1554, A152-T1554, E153-T1554, V154-T1554, K155-T1554, L156-T1554, R157-T1554, R158-T1554, Q159-T1554, L160-T1554, E161-T1554, K162-T1554, H163-T1554, I164-T1554, S165-T1554, L166-T1554, Q167-T1554, K168-T1554, I169-T1554, N170-T1554, T171-T1554, R172-T1554, I173-T1554, G174-T1554, Q175-T1554, G176-T1554, V177-T1554, P178-T1554, V179-T1554, V180-T1554, A181-T1554, L182-T1554, I183-T1554, V184-T1554, E185-T1554, G186-T1554, G187-T1554, P188-T1554, N189-T1554, V190-T1554, I191-T1554, S192-T1554, I193-T1554, V194-T1554, L195-T1554, E196-T1554, Y197-T1554, L198-T1554, R199-T1554, D200-T1554, T201-T1554, P202-T1554, P203-T1554, V204-T1554, P205-T1554, V206-T1554, V207-T1554, V208-T1554, C209-T1554, D210-T1554, G211-T1554, S212-T1554, G213-T1554, R214-T1554, A215-T1554, S216-T1554, D217-T1554, I218-T1554, L219-T1554, A220-T1554, F221-T1554, G222-T1554, H223-T1554, K224-T1554, Y225-T1554, S226-T1554, E227-T1554, E228-T1554, G229-T1554, G230-T1554, L231-T1554, I232-T1554, N233-T1554, E234-T1554, S235-T1554, L236-T1554, R237-T1554, D238-T1554, Q239-

T1554, L240-T1554, L241-T1554, V242-T1554, T243-T1554, I244-T1554, Q245-T1554, K246-T1554, T247-T1554, F248-T1554, T249-T1554, Y250-T1554, T251-T1554, R252-T1554, T253-T1554, Q254-T1554, A255-T1554, Q256-T1554, H257-T1554, L258-T1554, F259-T1554, I260-T1554, I261-T1554, L262-T1554, M263-T1554, E264-T1554, C265-T1554, M266-T1554, K267-T1554, K268-T1554, K269-T1554, E270-T1554, L271-T1554, I272-T1554, T273-T1554, V274-T1554, F275-T1554, R276-T1554, M277-T1554, G278-T1554, S279-T1554, E280-T1554, G281-T1554, H282-T1554, Q283-T1554, D284-T1554, I285-T1554, D286-T1554, L287-T1554, A288-T1554, I289-T1554, L290-T1554, T291-T1554, A292-T1554, L293-T1554, L294-T1554, K295-T1554, G296-T1554, A297-T1554, N298-T1554, A299-T1554, S300-T1554, A301-T1554, P302-T1554, D303-T1554, Q304-T1554, L305-T1554, S306-T1554, L307-T1554, A308-T1554, L309-T1554, A310-T1554, W311-T1554, N312-T1554, R313-T1554, V314-T1554, D315-T1554, I316-T1554, A317-T1554, R318-T1554, S319-T1554, Q320-T1554, I321-T1554, F322-T1554, I323-T1554, Y324-T1554, G325-T1554, Q326-T1554, Q327-T1554, W328-T1554, P329-T1554, V330-T1554, G331-T1554, S332-T1554, L333-T1554, E334-T1554, Q335-T1554, A336-T1554, M337-T1554, L338-T1554, D339-T1554, A340-T1554, L341-T1554, V342-T1554, L343-T1554, D344-T1554, R345-T1554, V346-T1554, D347-T1554, F348-T1554, V349-T1554, K350-T1554, L351-T1554, L352-T1554, I353-T1554, E354-T1554, N355-T1554, G356-T1554, V357-T1554, S358-T1554, M359-T1554, H360-T1554, R361-T1554, F362-T1554, L363-T1554, T364-T1554, I365-T1554, S366-T1554, R367-T1554, L368-T1554, E369-T1554, E370-T1554, L371-T1554, Y372-T1554, N373-T1554, T374-T1554, R375-T1554, H376-T1554, G377-T1554, P378-T1554, S379-T1554, N380-T1554, T381-T1554, L382-T1554, Y383-T1554, H384-T1554, L385-T1554, V386-T1554, R387-T1554, D388-T1554, V389-T1554, K390-T1554, K391-T1554, G392-T1554, N393-T1554, L394-T1554, P395-T1554, P396-T1554, D397-T1554, Y398-T1554, R399-T1554, I400-T1554, S401-T1554, L402-T1554, I403-T1554, D404-T1554, I405-T1554, G406-T1554, L407-T1554, V408-T1554, I409-T1554, E410-T1554, Y411-T1554, L412-T1554, M413-T1554, G414-T1554, G415-T1554, A416-T1554, Y417-T1554, R418-T1554, C419-T1554, N420-T1554, Y421-T1554, T422-T1554, R423-T1554, K424-T1554, R425-T1554, F426-T1554, R427-T1554, T428-T1554, L429-T1554, Y430-T1554, H431-T1554, N432-T1554, L433-T1554, F434-T1554, G435-T1554, P436-T1554, K437-T1554, R438-T1554, P439-T1554, K440-T1554, A441-T1554, L442-T1554, K443-T1554, L444-T1554, L445-T1554, G446-T1554, M447-T1554, E448-T1554, D449-T1554, D450-T1554, I451-T1554, P452-T1554, L453-T1554, R454-T1554, R455-T1554, G456-T1554, R457-T1554, K458-T1554, T459-T1554, T460-T1554, K461-T1554, K462-T1554, R463-T1554, E464-T1554, E465-T1554, E466-T1554, V467-T1554, D468-T1554, I469-T1554, D470-T1554, L471-T1554, D472-T1554, D473-T1554, P474-T1554, E475-T1554, I476-T1554, N477-T1554, H478-T1554, F479-T1554, P480-T1554, F481-T1554, P482-T1554, F483-T1554, H484-T1554, E485-T1554, L486-T1554, M487-T1554, V488-T1554, W489-T1554, A490-T1554, V491-T1554, L492-T1554, M493-T1554, K494-T1554, R495-T1554, Q496-T1554, K497-T1554, M498-T1554, A499-T1554, L500-T1554, F501-T1554, F502-T1554, W503-T1554, Q504-T1554, H505-T1554, G506-T1554, E507-T1554, E508-T1554, A509-T1554, M510-T1554, A511-T1554, K512-T1554, A513-T1554, L514-T1554, V515-T1554, A516-T1554, C517-T1554, K518-T1554, L519-T1554, C520-T1554, K521-T1554, A522-T1554, M523-T1554, A524-T1554, H525-T1554, E526-T1554, A527-T1554, S528-T1554, E529-T1554, N530-T1554, D531-T1554, M532-T1554, V533-T1554, D534-T1554, D535-T1554, I536-T1554, S537-T1554, Q538-T1554, E539-T1554, L540-T1554, N541-T1554, H542-T1554, N543-T1554, S544-T1554, R545-T1554, D546-T1554, F547-T1554, G548-T1554, Q549-T1554, L550-T1554, A551-T1554, V552-T1554, E553-T1554, L554-T1554, L555-T1554, D556-T1554, Q557-T1554, S558-T1554, Y559-T1554, K560-T1554, Q561-T1554, D562-T1554, E563-T1554, Q564-T1554, L565-T1554, A566-T1554, M567-T1554, K568-T1554, L569-T1554, L570-T1554, T571-T1554, Y572-T1554, E573-T1554, L574-T1554, K575-T1554, N576-T1554, W577-T1554, S578-T1554, N579-T1554, A580-T1554, T581-T1554, C582-T1554, L583-T1554, Q584-T1554, L585-T1554, A586-T1554, V587-T1554, A588-T1554, A589-T1554, K590-T1554, H591-T1554, R592-T1554, D593-T1554, F594-T1554, I595-T1554, A596-T1554, H597-T1554, T598-T1554, C599-T1554, S600-T1554, Q601-T1554, M602-T1554, L603-T1554, L604-T1554, T605-T1554, D606-T1554, M607-T1554, W608-T1554, M609-T1554, G610-T1554, R611-T1554, L612-T1554, R613-T1554, M614-T1554, R615-T1554, K616-T1554, N617-T1554, S618-T1554, G619-T1554, L620-T1554, K621-T1554, V622-T1554, I623-T1554, L624-T1554, G625-T1554, I626-T1554, L627-T1554, L628-T1554, P629-T1554, P630-T1554, S631-T1554, I632-T1554, L633-T1554, S634-T1554, L635-T1554, E636-T1554, F637-T1554, K638-T1554, N639-T1554, K640-T1554, D641-T1554, D642-T1554, M643-T1554, P644-T1554, Y645-T1554, M646-T1554, S647-T1554, Q648-T1554, A649-T1554, Q650-T1554, E651-T1554, I652-T1554, H653-T1554, L654-T1554, Q655-T1554, E656-T1554, K657-T1554, E658-T1554, A659-T1554, E660-T1554, E661-T1554, P662-T1554, E663-T1554, K664-T1554, P665-T1554, T666-T1554, K667-T1554, E668-T1554, K669-T1554, E670-T1554, E671-T1554, E672-T1554, D673-T1554, M674-T1554, E675-T1554, L676-T1554, T677-T1554, A678-T1554, M679-T1554, L680-T1554, G681-T1554, R682-T1554, N683-T1554, N684-T1554, G685-T1554, E686-T1554, S687-T1554, S688-T1554, R689-T1554, K690-T1554, K691-T1554, D692-T1554, E693-T1554, E694-T1554, E695-T1554, V696-T1554, Q697-T1554, S698-T1554, K699-T1554, H700-T1554, R701-T1554, L702-T1554, I703-T1554, P704-T1554, L705-T1554, G706-T1554, R707-T1554, K708-T1554, I709-T1554, Y710-T1554, E711-T1554, F712-T1554, Y713-T1554, N714-T1554, A715-T1554, P716-T1554, I717-T1554, V718-T1554, K719-T1554, F720-T1554, W721-T1554, F722-T1554, Y723-T1554, T724-T1554, L725-T1554, A726-T1554, Y727-T1554, I728-T1554, G729-T1554, Y730-T1554, L731-T1554, M732-T1554, L733-T1554, F734-T1554, N735-T1554, Y736-T1554, I737-T1554, V738-T1554, L739-T1554, V740-T1554, K741-T1554, M742-T1554, E743-T1554, R744-T1554, W745-T1554, P746-T1554, S747-T1554, T748-T1554, Q749-T1554, E750-T1554, W751-T1554, I752-T1554, V753-T1554, I754-T1554, S755-T1554, Y756-T1554, I757-T1554, F758-T1554, T759-T1554, L760-T1554, G761-T1554, I762-T1554, E763-T1554, K764-T1554, M765-T1554, R766-T1554, E767-T1554, I768-T1554, L769-T1554, M770-T1554, S771-T1554, E772-T1554, P773-T1554, G774-T1554, K775-

T1554, L776-T1554, L777-T1554, Q778-T1554, K779-T1554, V780-T1554, K781-T1554, V782-T1554, W783-T1554, L784-T1554, Q785-T1554, E786-T1554, Y787-T1554, W788-T1554, N789-T1554, V790-T1554, T791-T1554, D792-T1554, L793-T1554, I794-T1554, A795-T1554, I796-T1554, L797-T1554, L798-T1554, F799-T1554, S800-T1554, V801-T1554, G802-T1554, M803-T1554, I804-T1554, L805-T1554, R806-T1554, L807-T1554, Q808-T1554, D809-T1554, Q810-T1554, P811-T1554, F812-T1554, R813-T1554, S814-T1554, D815-T1554, G816-T1554, R817-T1554, V818-T1554, I819-T1554, Y820-T1554, C821-T1554, V822-T1554, N823-T1554, I824-T1554, I825-T1554, Y826-T1554, W827-T1554, Y828-T1554, I829-T1554, R830-T1554, L831-T1554, L832-T1554, D833-T1554, I834-T1554, F835-T1554, G836-T1554, V837-T1554, N838-T1554, K839-T1554, Y840-T1554, L841-T1554, G842-T1554, P843-T1554, Y844-T1554, V845-T1554, M846-T1554, M847-T1554, I848-T1554, G849-T1554, K850-T1554, M851-T1554, M852-T1554, I853-T1554, D854-T1554, M855-T1554, M856-T1554, Y857-T1554, F858-T1554, V859-T1554, I860-T1554, I861-T1554, M862-T1554, L863-T1554, V864-T1554, V865-T1554, L866-T1554, M867-T1554, S868-T1554, F869-T1554, G870-T1554, V871-T1554, A872-T1554, R873-T1554, Q874-T1554, A875-T1554, I876-T1554, L877-T1554, F878-T1554, P879-T1554, N880-T1554, E881-T1554, E882-T1554, P883-T1554, S884-T1554, W885-T1554, K886-T1554, L887-T1554, A888-T1554, K889-T1554, N890-T1554, I891-T1554, F892-T1554, Y893-T1554, M894-T1554, P895-T1554, Y896-T1554, W897-T1554, M898-T1554, I899-T1554, Y900-T1554, G901-T1554, E902-T1554, V903-T1554, F904-T1554, A905-T1554, D906-T1554, Q907-T1554, I908-T1554, D909-T1554, P910-T1554, P911-T1554, C912-T1554, G913-T1554, Q914-T1554, N915-T1554, E916-T1554, T917-T1554, R918-T1554, E919-T1554, D920-T1554, G921-T1554, K922-T1554, I923-T1554, I924-T1554, Q925-T1554, L926-T1554, P927-T1554, P928-T1554, C929-T1554, K930-T1554, T931-T1554, G932-T1554, A933-T1554, W934-T1554, I935-T1554, V936-T1554, P937-T1554, A938-T1554, I939-T1554, M940-T1554, A941-T1554, C942-T1554, Y943-T1554, L944-T1554, L945-T1554, V946-T1554, A947-T1554, N948-T1554, I949-T1554, L950-T1554, L951-T1554, V952-T1554, N953-T1554, L954-T1554, L955-T1554, I956-T1554, A957-T1554, V958-T1554, F959-T1554, N960-T1554, N961-T1554, T962-T1554, F963-T1554, F964-T1554, E965-T1554, V966-T1554, K967-T1554, S968-T1554, I969-T1554, S970-T1554, N971-T1554, Q972-T1554, V973-T1554, W974-T1554, K975-T1554, F976-T1554, Q977-T1554, R978-T1554, Y979-T1554, Q980-T1554, L981-T1554, I982-T1554, M983-T1554, T984-T1554, F985-T1554, H986-T1554, E987-T1554, R988-T1554, P989-T1554, V990-T1554, L991-T1554, P992-T1554, P993-T1554, P994-T1554, L995-T1554, I996-T1554, I997-T1554, F998-T1554, S999-T1554, H1000-T1554, M1001-T1554, T1002-T1554, M1003-T1554, I1004-T1554, F1005-T1554, Q1006-T1554, H1007-T1554, L1008-T1554, C1009-T1554, C110-T1554, R1011-T1554, W1012-T1554, R1013-T1554, K1014-T1554, H1015-T1554, E1016-T1554, S1017-T1554, D1018-T1554, P1019-T1554, D1020-T1554, E1021-T1554, R1022-T1554, D1023-T1554, Y1024-T1554, G1025-T1554, L1026-T1554, K1027-T1554, L1028-T1554, F1029-T1554, I1030-T1554, T1031-T1554, D1032-T1554, D1033-T1554, E1034-T1554, L1035-T1554, K1036-T1554, K1037-T1554, V1038-T1554, H1039-T1554, D1040-T1554, F1041-T1554, E1042-T1554, E1043-T1554, Q1044-T1554, C1045-T1554, I1046-T1554, E1047-T1554, E1048-T1554, Y1049-T1554, F1050-T1554, R1051-T1554, E1052-T1554, K1053-T1554, D1054-T1554, D1055-T1554, R1056-T1554, F1057-T1554, N1058-T1554, S1059-T1554, S1060-T1554, N1061-T1554, D1062-T1554, E1063-T1554, R1064-T1554, I1065-T1554, R1066-T1554, V1067-T1554, T1068-T1554, S1069-T1554, E1070-T1554, R1071-T1554, V1072-T1554, E1073-T1554, N1074-T1554, M1075-T1554, S1076-T1554, M1077-T1554, R1078-T1554, L1079-T1554, E1080-T1554, E1081-T1554, V1082-T1554, N1083-T1554, E1084-T1554, R1085-T1554, E1086-T1554, H1087-T1554, S1088-T1554, M1089-T1554, K1090-T1554, A1091-T1554, S1092-T1554, L1093-T1554, Q1094-T1554, T1095-T1554, V1096-T1554, D1097-T1554, I1098-T1554, R1099-T1554, L1100-T1554, A110-T1554, Q1102-T1554, L1103-T1554, E1104-T1554, D1105-T1554, L1106-T1554, I1107-T1554, G1108-T1554, R1109-T1554, M1110-T1554, A1111-T1554, T1112-T1554, A1113-T1554, L1114-T1554, E1115-T1554, R1116-T1554, L1117-T1554, T1118-T1554, G1119-T1554, L1120-T1554, E1121-T1554, R1122-T1554, A1123-T1554, E1124-T1554, S1125-T1554, N1126-T1554, K1127-T1554, I1128-T1554, R1129-T1554, S1130-T1554, R1131-T1554, T1132-T1554, S1133-T1554, S1134-T1554, D1135-T1554, C1136-T1554, T1137-T1554, D1138-T1554, A1139-T1554, A1140-T1554, Y1141-T1554, I1142-T1554, V1143-T1554, R1144-T1554, Q1145-T1554, S1146-T1554, S1147-T1554, F1148-T1554, N1149-T1554, S1150-T1554, Q1151-T1554, E1152-T1554, G1153-T1554, N1154-T1554, T1155-T1554, F1156-T1554, K1157-T1554, L1158-T1554, Q1159-T1554, E1160-T1554, S1161-T1554, I1162-T1554, D1163-T1554, P1164-T1554, A1165-T1554, G1166-T1554, E1167-T1554, E1168-T1554, T1169-T1554, M1170-T1554, S1171-T1554, P1172-T1554, T1173-T1554, S1174-T1554, P1175-T1554, T1176-T1554, L1177-T1554, M1178-T1554, P1179-T1554, R1180-T1554, M1181-T1554, R1182-T1554, S1183-T1554, H1184-T1554, S1185-T1554, F1186-T1554, Y1187-T1554, S1188-T1554, V1189-T1554, N1190-T1554, M1191-T1554, K1192-T1554, D1193-T1554, K1194-T1554, G1195-T1554, G1196-T1554, I1197-T1554, E1198-T1554, K1199-T1554, L1200-T1554, E1201-T1554, S1202-T1554, I1203-T1554, F1204-T1554, K1205-T1554, E1206-T1554, R1207-T1554, S1208-T1554, L1209-T1554, S1210-T1554, L1211-T1554, H1212-T1554, R1213-T1554, A1214-T1554, T1215-T1554, S1216-T1554, S1217-T1554, H1218-T1554, S1219-T1554, V1220-T1554, A1221-T1554, K1222-T1554, E1223-T1554, P1224-T1554, K1225-T1554, A1226-T1554, P1227-T1554, A1228-T1554, A1229-T1554, P1230-T1554, A1231-T1554, N1232-T1554, T1233-T1554, L1234-T1554, A1235-T1554, I1236-T1554, V1237-T1554, P1238-T1554, D1239-T1554, S1240-T1554, R1241-T1554, R1242-T1554, P1243-T1554, S1244-T1554, S1245-T1554, C1246-T1554, I1247-T1554, D1248-T1554, I1249-T1554, Y1250-T1554, V1251-T1554, S1252-T1554, A1253-T1554, M1254-T1554, D1255-T1554, E1256-T1554, L1257-T1554, H1258-T1554, C1259-T1554, D1260-T1554, I1261-T1554, D1262-T1554, P1263-T1554, L1264-T1554, D1265-T1554, N1266-T1554, S1267-T1554, V1268-T1554, N1269-T1554, I1270-T1554, L1271-T1554, G1272-T1554, L1273-T1554, G1274-T1554, E1275-T1554, P1276-T1554, S1277-T1554, F1278-T1554, S1279-T1554, T1280-T1554, P1281-T1554, V1282-T1554, P1283-T1554, S1284-T1554, T1285-T1554, A1286-T1554, P1287-T1554, S1288-T1554, S1289-T1554, S1290-T1554, A1291-T1554, Y1292-T1554, A1293-T1554, T1294-T1554, L1295-T1554, A1296-T1554, P1297-T1554, T1298-T1554, D1299-T1554, R1300-T1554, P1301-T1554, P1302-T1554, S1303-T1554, R1304-T1554,

S1305-T1554, I1306-T1554, D1307-T1554, F1308-T1554, E1309-T1554, D1310-T1554, I1311-T1554, T1312-T1554, S1313-T1554, M1314-T1554, D1315-T1554, T1316-T1554, R1317-T1554, S1318-T1554, F1319-T1554, S1320-T1554, S1321-T1554, D1322-T1554, Y1323-T1554, T1324-T1554, H1325-T1554, L1326-T1554, P1327-T1554, E1328-T1554, C1329-T1554, Q1330-T1554, N1331-T1554, P1332-T1554, W1333-T1554, D1334-T1554, S1335-T1554, E1336-T1554, P1337-T1554, P1338-T1554, M1339-T1554, Y1340-T1554, H1341-T1554, T1342-T1554, I1343-T1554, E1344-T1554, R1345-T1554, S1346-T1554, K1347-T1554, S1348-T1554, S1349-T1554, R1350-T1554, Y1351-T1554, L1352-T1554, A1353-T1554, T1354-T1554, T1355-T1554, P1356-T1554, F1357-T1554, L1358-T1554, L1359-T1554, E1360-T1554, E1361-T1554, A1362-T1554, P1363-T1554, I1364-T1554, V1365-T1554, K1366-T1554, S1367-T1554, H1368-T1554, S1369-T1554, F1370-T1554, M1371-T1554, F1372-T1554, S1373-T1554, P1374-T1554, S1375-T1554, R1376-T1554, S1377-T1554, Y1378-T1554, Y1379-T1554, A1380-T1554, N1381-T1554, F1382-T1554, G1383-T1554, V1384-T1554, P1385-T1554, V1386-T1554, K1387-T1554, T1388-T1554, A1389-T1554, E1390-T1554, Y1391-T1554, T1392-T1554, S1393-T1554, I1394-T1554, T1395-T1554, D1396-T1554, C1397-T1554, I1398-T1554, D1399-T1554, T1400-T1554, R1401-T1554, C1402-T1554, V1403-T1554, N1404-T1554, A1405-T1554, P1406-T1554, Q1407-T1554, A1408-T1554, I1409-T1554, A1410-T1554, D1411-T1554, R1412-T1554, A1413-T1554, A1414-T1554, F1415-T1554, P1416-T1554, G1417-T1554, G1418-T1554, L1419-T1554, G1420-T1554, D1421-T1554, K1422-T1554, V1423-T1554, E1424-T1554, D1425-T1554, L1426-T1554, T1427-T1554, C1428-T1554, C1429-T1554, H1430-T1554, P1431-T1554, E1432-T1554, R1433-T1554, E1434-T1554, A1435-T1554, E1436-T1554, L1437-T1554, S1438-T1554, H1439-T1554, P1440-T1554, S1441-T1554, S1442-T1554, D1443-T1554, S1444-T1554, E1445-T1554, E1446-T1554, N1447-T1554, E1448-T1554, A1449-T1554, K1450-T1554, G1451-T1554, R1452-T1554, R1453-T1554, A1454-T1554, T1455-T1554, I1456-T1554, A1457-T1554, I1458-T1554, S1459-T1554, S1460-T1554, Q1461-T1554, E1462-T1554, G1463-T1554, D1464-T1554, N1465-T1554, S1466-T1554, E1467-T1554, R1468-T1554, T1469-T1554, L1470-T1554, S1471-T1554, N1472-T1554, N1473-T1554, I1474-T1554, T1475-T1554, V1476-T1554, P1477-T1554, K1478-T1554, I1479-T1554, E1480-T1554, R1481-T1554, A1482-T1554, N1483-T1554, S1484-T1554, Y1485-T1554, S1486-T1554, A1487-T1554, E1488-T1554, E1489-T1554, P1490-T1554, S1491-T1554, A1492-T1554, P1493-T1554, Y1494-T1554, A1495-T1554, H1496-T1554, T1497-T1554, R1498-T1554, K1499-T1554, S1500-T1554, F1501-T1554, S1502-T1554, I1503-T1554, S1504-T1554, D1505-T1554, K1506-T1554, L1507-T1554, D1508-T1554, R1509-T1554, Q1510-T1554, R1511-T1554, N1512-T1554, T1513-T1554, A1514-T1554, S1515-T1554, L1516-T1554, Q1517-T1554, N1518-T1554, P1519-T1554, F1520-T1554, Q1521-T1554, R1522-T1554, S1523-T1554, K1524-T1554, S1525-T1554, S1526-T1554, K1527-T1554, P1528-T1554, E1529-T1554, G1530-T1554, R1531-T1554, G1532-T1554, D1533-T1554, S1534-T1554, L1535-T1554, S1536-T1554, M1537-T1554, R1538-T1554, R1539-T1554, L1540-T1554, S1541-T1554, R1542-T1554, T1543-T1554, S1544-T1554, A1545-T1554, F1546-T1554, Q1547-T1554, and/or S1548-T1554 of SEQ ID NO:2. Polynucleotide sequences encoding these polypeptides are also provided. The present invention also encompasses the use of these N-terminal LTRPC3 deletion polypeptides as immunogenic and/or antigenic epitopes as described elsewhere herein.

In preferred embodiments, the following C-terminal LTRPC3 deletion polypeptides are encompassed by the present invention: M1-T1554, M1-H1553, M1-K1552, M1-S1551, M1-E1550, M1-F1549, M1-S1548, M1-Q1547, M1-F1546, M1-A1545, M1-S1544, M1-T1543, M1-R1542, M1-S1541, M1-L1540, M1-R1539, M1-R1538, M1-M1537, M1-S1536, M1-L1535, M1-S1534, M1-D1533, M1-G1532, M1-R1531, M1-G1530, M1-E1529, M1-P1528, M1-K1527, M1-S1526, M1-S1525, M1-K1524, M1-S1523, M1-R1522, M1-Q1521, M1-F1520, M1-P1519, M1-N1518, M1-Q1517, M1-L1516, M1-S1515, M1-A1514, M1-T1513, M1-N1512, M1-R1511, M1-Q1510, M1-R1509, M1-D1508, M1-L1507, M1-K1506, M1-D1505, M1-S1504, M1-I1503, M1-S1502, M1-F1501, M1-S1500, M1-K1499, M1-R1498, M1-T1497, M1-H1496, M1-A1495, M1-Y1494, M1-P1493, M1-A1492, M1-S1491, M1-P1490, M1-E1489, M1-E1488, M1-A1487, M1-S1486, M1-Y1485, M1-S1484, M1-N1483, M1-A1482, M1-R1481, M1-E1480, M1-I1479, M1-K1478, M1-P1477, M1-V1476, M1-T1475, M1-I1474, M1-N1473, M1-N1472, M1-S1471, M1-L1470, M1-T1469, M1-R1468, M1-E1467, M1-S1466, M1-N1465, M1-D1464, M1-G1463, M1-E1462, M1-Q1461, M1-S1460, M1-S1459, M1-I1458, M1-A1457, M1-I1456, M1-T1455, M1-A1454, M1-R1453, M1-R1452, M1-G1451, M1-K1450, M1-A1449, M1-E1448, M1-N1447, M1-E1446, M1-E1445, M1-S1444, M1-D1443, M1-S1442, M1-S1441, M1-P1440, M1-H1439, M1-S1438, M1-L1437, M1-E1436, M1-A1435, M1-E1434, M1-R1433, M1-E1432, M1-P1431, M1-H1430, M1-C1429, M1-C1428, M1-T1427, M1-L1426, M1-D1425, M1-E1424, M1-V1423, M1-K1422, M1-D1421, M1-G1420, M1-L1419, M1-G1418, M1-G1417, M1-P1416, M1-F1415, M1-A1414, M1-A1413, M1-R1412, M1-D1411, M1-A1410, M1-I1409, M1-A1408, M1-Q1407, M1-P1406, M1-A1405, M1-N1404, M1-V1403, M1-C1402, M1-R1401, M1-T1400, M1-D1399, M1-I1398, M1-C1397, M1-D1396, M1-T1395, M1-I1394, M1-S1393, M1-T1392, M1-Y1391, M1-E1390, M1-A1389, M1-T1388, M1-K1387, M1-V1386, M1-P1385, M1-V1384, M1-G1383, M1-F1382, M1-N1381, M1-A1380, M1-Y1379, M1-Y1378, M1-S1377, M1-R1376, M1-S1375, M1-P1374, M1-S1373, M1-F1372, M1-M1371, M1-F1370, M1-S1369, M1-H1368, M1-S1367, M1-K1366, M1-V1365, M1-I1364, M1-P1363, M1-A1362, M1-E1361, M1-E1360, M1-L1359, M1-L1358, M1-F1357, M1-P1356, M1-T1355, M1-T1354, M1-A1353, M1-L1352, M1-Y1351, M1-R1350, M1-S1349, M1-S1348, M1-K1347, M1-S1346, M1-R1345, M1-E1344, M1-I1343, M1-T1342, M1-H1341, M1-Y1340, M1-M1339, M1-P1338, M1-P1337, M1-E1336, M1-S1335, M1-D1334, M1-W1333, M1-P1332, M1-N1331, M1-Q1330, M1-C1329, M1-E1328, M1-P1327, M1-L1326, M1-H1325, M1-T1324, M1-Y1323, M1-D1322, M1-S1321, M1-S1320, M1-F1319, M1-S1318, M1-R1317, M1-T1316, M1-D1315, M1-M1314, M1-S1313, M1-T1312, M1-I1311, M1-D1310, M1-E1309, M1-F1308, M1-D1307, M1-I1306, M1-S1305, M1-R1304, M1-S1303, M1-P1302, M1-P1301, M1-R1300, M1-D1299, M1-T1298, M1-P1297, M1-A1296, M1-L1295, M1-T1294, M1-A1293, M1-Y1292, M1-A1291, M1-S1290, M1-S1289, M1-S1288, M1-P1287, M1-A1286, M1-T1285, M1-S1284, M1-P1283, M1-V1282, M1-P1281, M1-T1280, M1-S1279, M1-F1278, M1-S1277, M1-P1276, M1-E1275, M1-G1274, M1-L1273, M1-G1272, M1-L1271, M1-I1270, M1-N1269, M1-V1268, M1-S1267, M1-N1266, M1-D1265, M1-L1264, M1-P1263, M1-D1262, M1-I1261, M1-D1260, M1-C1259, M1-H1258, M1-L1257, M1-E1256, M1-D1255, M1-M1254, M1-A1253, M1-S1252, M1-V1251, M1-Y1250, M1-I1249, M1-D1248, M1-I1247, M1-C1246, M1-S1245, M1-S1244, M1-P1243, M1-R1242, M1-R1241, M1-S1240, M1-D1239, M1-P1238, M1-V1237, M1-I1236, M1-A1235, M1-L1234, M1-T1233, M1-N1232, M1-A1231, M1-P1230, M1-A1229, M1-A1228, M1-P1227,
M1-A1226, M1-K1225, M1-P1224, M1-E1223, M1-K1222,
M1-A1221, M1-V1220, M1-S1219, M1-H1218, M1-S1217,
M1-S1216, M1-T1215, M1-A1214, M1-R1213, M1-H1212,
M1-L1211, M1-S1210, M1-L1209, M1-S1208, M1-R1207,
M1-E1206, M1-K1205, M1-F1204, M1-I1203, M1-S1202,
M1-E1201, M1-L1200, M1-K1199, M1-E1198, M1-I1197,
M1-G1196, M1-G1195, M1-K1194, M1-D1193,
M1-K1192, M1-M1191, M1-N1190, M1-V1189,
M1-S1188, M1-Y1187, M1-F1186, M1-S1185, M1-H1184,
M1-S1183, M1-R1182, M1-M1181, M1-R1180, M1-P1179,
M1-M1178, M1-L1177, M1-T1176, M1-P1175, M1-S1174,
M1-T1173, M1-P1172, M1-S1171, M1-M1170, M1-T1169,
M1-E1168, M1-E1167, M1-G1166, M1-A1165, M1-P1164,
M1-D1163, M1-I1162, M1-S1161, M1-E1160, M1-Q1159,
M1-L1158, M1-K1157, M1-F1156, M1-T1155, M1-N1154,
M1-G1153, M1-E1152, M1-Q1151, M1-S1150, M1-N1149,
M1-F1148, M1-S1147, M1-S1146, M1-Q1145, M1-R1144,
M1-V1143, M1-I1142, M1-Y1141, M1-A1140, M1-A1139,
M1-D1138, M1-T1137, M1-C1136, M1-D1135, M1-S1134,
M1-S1133, M1-T1132, M1-R1131, M1-S1130, M1-R1129,
M1-I1128, M1-K1127, M1-N1126, M1-S1125, M1-E1124,
M1-A1123, M1-R1122, M1-E1121, M1-L1120, M1-G1119,
M1-T1118, M1-L1117, M1-R1116, M1-E1115, M1-A1114,
M1-A1113, M1-T1112, M1-A1111, M1-M1110,
M1-R1109, M1-G1108, M1-I1107, M1-L1106, M1-D1105,
M1-E1104, M1-L1103, M1-Q1102, M1-A1101, M1-L1100,
M1-R1099, M1-I1098, M1-D1097, M1-V1096, M1-T1095,
M1-Q1094, M1-L1093, M1-S1092, M1-A1091, M1-K1090,
M1-M1089, M1-S1088, M1-H1087, M1-E1086, M1-R1085,
M1-E1084, M1-N1083, M1-V1082, M1-E1081, M1-E1080,
M1-L1079, M1-R1078, M1-M1077, M1-S1076,
M1-M1075, M1-N1074, M1-E1073, M1-V1072,
M1-R1071, M1-E1070, M1-S1069, M1-T1068, M1-V1067,
M1-R1066, M1-I1065, M1-R1064, M1-E1063, M1-D1062,
M1-N1061, M1-S1060, M1-S1059, M1-N1058, M1-F1057,
M1-R1056, M1-D1055, M1-D1054, M1-K1053, M1-E1052,
M1-R1051, M1-F1050, M1-Y1049, M1-E1048, M1-E1047,
M1-I1046, M1-C1045, M1-Q1044, M1-E1043, M1-E1042,
M1-F1041, M1-D1040, M1-H1039, M1-V1038, M1-K1037,
M1-K1036, M1-L1035, M1-E1034, M1-D1033, M1-D1032,
M1-T1031, M1-I1030, M1-F1029, M1-L1028, M1-K1027,
M1-L1026, M1-G1025, M1-Y1024, M1-D1023, M1-R1022,
M1-E1021, M1-D1020, M1-P1019, M1-D1018, M1-S1017,
M1-E1016, M1-H1015, M1-K1014, M1-R1013,
M1-W1012, M1-R1011, M1-C1010, M1-C1009,
M1-L1008, M1-H1007, M1-Q1006, M1-F1005, M1-I1004,
M1-M1003, M1-T1002, M1-M1001, M1-H1000, M1-S999,
M1-F998, M1-I997, M1-I996, M1-L995, M1-P994,
M1-P993, M1-P992, M1-L991, M1-V990, M1-P989,
M1-R988, M1-E987, M1-H986, M1-F985, M1-T984,
M1-M983, M1-I982, M1-L981, M1-Q980, M1-Y979,
M1-R978, M1-Q977, M1-F976, M1-K975, M1-W974,
M1-V973, M1-Q972, M1-N971, M1-S970, M1-I969,
M1-S968, M1-K967, M1-V966, M1-E965, M1-F964,
M1-F963, M1-T962, M1-N961, M1-N960, M1-F959,
M1-V958, M1-A957, M1-I956, M1-L955, M1-L954,
M1-N953, M1-V952, M1-L951, M1-L950, M1-I949,
M1-N948, M1-A947, M1-V946, M1-L945, M1-L944,
M1-Y943, M1-C942, M1-A941, M1-M940, M1-I939,
M1-A938, M1-P937, M1-V936, M1-I935, M1-W934,
M1-A933, M1-G932, M1-T931, M1-K930, M1-C929,
M1-P928, M1-P927, M1-L926, M1-Q925, M1-I924,
M1-I923, M1-K922, M1-G921, M1-D920, M1-E919,
M1-R918, M1-T917, M1-E916, M1-N915, M1-Q914,
M1-G913, M1-C912, M1-P911, M1-P910, M1-D909,
M1-I908, M1-Q907, M1-D906, M1-A905, M1-F904,
M1-V903, M1-E902, M1-G901, M1-Y900, M1-I899,
M1-M898, M1-W897, M1-Y896, M1-P895, M1-M894,
M1-Y893, M1-F892, M1-I891, M1-N890, M1-K889,
M1-A888, M1-L887, M1-K886, M1-W885, M1-S884,
M1-P883, M1-E882, M1-E881, M1-N880, M1-P879,
M1-F878, M1-L877, M1-I876, M1-A875, M1-Q874,
M1-R873, M1-A872, M1-V871, M1-G870, M1-F869,
M1-S868, M1-M867, M1-L866, M1-V865, M1-V864,
M1-L863, M1-M862, M1-I861, M1-I860, M1-V859,
M1-F858, M1-Y857, M1-M856, M1-M855, M1-D854,
M1-I853, M1-M852, M1-M851, M1-K850, M1-G849,
M1-I848, M1-M847, M1-M846, M1-V845, M1-Y844,
M1-P843, M1-G842, M1-L841, M1-Y840, M1-K839,
M1-N838, M1-V837, M1-G836, M1-F835, M1-I834,
M1-D833, M1-L832, M1-L831, M1-R830, M1-I829,
M1-Y828, M1-W827, M1-Y826, M1-I825, M1-I824,
M1-N823, M1-V822, M1-C821, M1-Y820, M1-I819,
M1-V818, M1-R817, M1-G816, M1-D815, M1-S814,
M1-R813, M1-F812, M1-P811, M1-Q810, M1-D809,
M1-Q808, M1-L807, M1-R806, M1-L805, M1-I804,
M1-M803, M1-G802, M1-V801, M1-S800, M1-F799,
M1-L798, M1-L797, M1-I796, M1-A795, M1-I794,
M1-L793, M1-D792, M1-T791, M1-V790, M1-N789,
M1-W788, M1-Y787, M1-E786, M1-Q785, M1-L784,
M1-W783, M1-V782, M1-K781, M1-V780, M1-K779,
M1-Q778, M1-L777, M1-L776, M1-K775, M1-G774,
M1-P773, M1-E772, M1-S771, M1-M770, M1-L769,
M1-I768, M1-E767, M1-R766, M1-M765, M1-K764,
M1-E763, M1-I762, M1-G761, M1-L760, M1-T759,
M1-F758, M1-I757, M1-Y756, M1-S755, M1-I754,
M1-V753, M1-I752, M1-W751, M1-E750, M1-Q749,
M1-T748, M1-S747, M1-P746, M1-W745, M1-R744,
M1-E743, M1-M742, M1-K741, M1-V740, M1-L739,
M1-V738, M1-I737, M1-Y736, M1-N735, M1-F734,
M1-L733, M1-M732, M1-L731, M1-Y730, M1-G729,
M1-I728, M1-Y727, M1-A726, M1-L725, M1-T724,
M1-Y723, M1-F722, M1-W721, M1-F720, M1-K719,
M1-V718, M1-I717, M1-P716, M1-A715, M1-N714,
M1-Y713, M1-F712, M1-E711, M1-Y710, M1-I709,
M1-K708, M1-R707, M1-G706, M1-L705, M1-P704,
M1-I703, M1-L702, M1-R701, M1-H700, M1-K699,
M1-S698, M1-Q697, M1-V696, M1-E695, M1-E694,
M1-E693, M1-D692, M1-K691, M1-K690, M1-R689,
M1-S688, M1-S687, M1-E686, M1-G685, M1-N684,
M1-N683, M1-R682, M1-G681, M1-L680, M1-M679,
M1-A678, M1-T677, M1-L676, M1-E675, M1-M674,
M1-D673, M1-E672, M1-E671, M1-E670, M1-K669,
M1-E668, M1-K667, M1-T666, M1-P665, M1-K664,
M1-E663, M1-P662, M1-E661, M1-E660, M1-A659,
M1-E658, M1-K657, M1-E656, M1-Q655, M1-L654,
M1-H653, M1-I652, M1-E651, M1-Q650, M1-A649,
M1-Q648, M1-S647, M1-M646, M1-Y645, M1-P644,
M1-M643, M1-D642, M1-D641, M1-K640, M1-N639,
M1-K638, M1-F637, M1-E636, M1-L635, M1-S634,
M1-L633, M1-I632, M1-S631, M1-P630, M1-P629,
M1-L628, M1-L627, M1-I626, M1-G625, M1-L624,
M1-I623, M1-V622, M1-K621, M1-L620, M1-G619,
M1-S618, M1-N617, M1-K616, M1-R615, M1-M614,
M1-R613, M1-L612, M1-R611, M1-G610, M1-M609,
M1-W608, M1-M607, M1-D606, M1-T605, M1-L604,
M1-L603, M1-M602, M1-Q601, M1-S600, M1-C599,
M1-T598, M1-H597, M1-A596, M1-I595, M1-F594,
M1-D593, M1-R592, M1-H591, M1-K590, M1-A589,
M1-A588, M1-V587, M1-A586, M1-L585, M1-Q584,
M1-L583, M1-C582, M1-T581, M1-A580, M1-N579,
M1-S578, M1-W577, M1-N576, M1-K575, M1-L574,
M1-E573, M1-Y572, M1-T571, M1-L570, M1-L569, M1-K568, M1-M567, M1-A566, M1-L565, M1-Q564, M1-E563, M1-D562, M1-Q561, M1-K560, M1-Y559, M1-S558, M1-Q557, M1-D556, M1-L555, M1-L554, M1-E553, M1-V552, M1-A551, M1-L550, M1-Q549, M1-G548, M1-F547, M1-D546, M1-R545, M1-S544, M1-N543, M1-H542, M1-N541, M1-L540, M1-E539, M1-Q538, M1-S537, M1-I536, M1-D535, M1-D534, M1-V533, M1-M532, M1-D531, M1-N530, M1-E529, M1-S528, M1-A527, M1-E526, M1-H525, M1-A524, M1-M523, M1-A522, M1-K521, M1-C520, M1-L519, M1-K518, M1-C517, M1-A516, M1-V515, M1-L514, M1-A513, M1-K512, M1-A511, M1-M510, M1-A509, M1-E508, M1-E507, M1-G506, M1-H505, M1-Q504, M1-W503, M1-F502, M1-F501, M1-L500, M1-A499, M1-M498, M1-K497, M1-Q496, M1-R495, M1-K494, M1-M493, M1-L492, M1-V491, M1-A490, M1-W489, M1-V488, M1-M487, M1-L486, M1-E485, M1-H484, M1-F483, M1-P482, M1-F481, M1-P480, M1-F479, M1-H478, M1-N477, M1-I476, M1-E475, M1-P474, M1-D473, M1-D472, M1-L471, M1-D470, M1-I469, M1-D468, M1-V467, M1-E466, M1-E465, M1-E464, M1-R463, M1-K462, M1-K461, M1-T460, M1-T459, M1-K458, M1-R457, M1-G456, M1-R455, M1-R454, M1-L453, M1-P452, M1-I451, M1-D450, M1-D449, M1-E448, M1-M447, M1-G446, M1-L445, M1-L444, M1-K443, M1-L442, M1-A441, M1-K440, M1-P439, M1-R438, M1-K437, M1-P436, M1-G435, M1-F434, M1-L433, M1-N432, M1-H431, M1-Y430, M1-L429, M1-T428, M1-R427, M1-F426, M1-R425, M1-K424, M1-R423, M1-T422, M1-Y421, M1-N420, M1-C419, M1-R418, M1-Y417, M1-A416, M1-G415, M1-G414, M1-M413, M1-L412, M1-Y411, M1-E410, M1-I409, M1-V408, M1-L407, M1-G406, M1-I405, M1-D404, M1-I403, M1-L402, M1-S401, M1-I400, M1-R399, M1-Y398, M1-D397, M1-P396, M1-P395, M1-L394, M1-N393, M1-G392, M1-K391, M1-K390, M1-V389, M1-D388, M1-R387, M1-V386, M1-L385, M1-H384, M1-Y383, M1-L382, M1-T381, M1-N380, M1-S379, M1-P378, M1-G377, M1-H376, M1-R375, M1-T374, M1-N373, M1-Y372, M1-L371, M1-E370, M1-E369, M1-L368, M1-R367, M1-S366, M1-I365, M1-T364, M1-L363, M1-F362, M1-R361, M1-H360, M1-M359, M1-S358, M1-V357, M1-G356, M1-N355, M1-E354, M1-I353, M1-L352, M1-L351, M1-K350, M1-V349, M1-F348, M1-D347, M1-V346, M1-R345, M1-D344, M1-L343, M1-V342, M1-L341, M1-A340, M1-D339, M1-L338, M1-M337, M1-A336, M1-Q335, M1-E334, M1-L333, M1-S332, M1-G331, M1-V330, M1-P329, M1-W328, M1-Q327, M1-Q326, M1-G325, M1-Y324, M1-I323, M1-F322, M1-I321, M1-Q320, M1-S319, M1-R318, M1-A317, M1-I316, M1-D315, M1-V314, M1-R313, M1-N312, M1-W311, M1-A310, M1-L309, M1-A308, M1-L307, M1-S306, M1-L305, M1-Q304, M1-D303, M1-P302, M1-A301, M1-S300, M1-A299, M1-N298, M1-A297, M1-G296, M1-K295, M1-L294, M1-L293, M1-A292, M1-T291, M1-L290, M1-I289, M1-A288, M1-L287, M1-D286, M1-I285, M1-D284, M1-Q283, M1-H282, M1-G281, M1-E280, M1-S279, M1-G278, M1-M277, M1-R276, M1-F275, M1-V274, M1-T273, M1-I272, M1-L271, M1-E270, M1-K269, M1-K268, M1-K267, M1-M266, M1-C265, M1-E264, M1-M263, M1-L262, M1-I261, M1-I260, M1-F259, M1-L258, M1-H257, M1-Q256, M1-A255, M1-Q254, M1-T253, M1-R252, M1-T251, M1-Y250, M1-T249, M1-F248, M1-T247, M1-K246, M1-Q245, M1-I244, M1-T243, M1-V242, M1-L241, M1-L240, M1-Q239, M1-D238, M1-R237, M1-L236, M1-S235, M1-E234, M1-N233, M1-I232, M1-L231, M1-G230, M1-G229, M1-E228, M1-E227, M1-S226, M1-Y225, M1-K224, M1-H223, M1-G222, M1-F221, M1-A220, M1-L219, M1-I218, M1-D217, M1-S216, M1-A215, M1-R214, M1-G213, M1-S212, M1-G211, M1-D210, M1-C209, M1-V208, M1-V207, M1-V206, M1-P205, M1-V204, M1-P203, M1-P202, M1-T201, M1-D200, M1-R199, M1-L198, M1-Y197, M1-E196, M1-L195, M1-V194, M1-I193, M1-S192, M1-I191, M1-V190, M1-N189, M1-P188, M1-G187, M1-G186, M1-E185, M1-V184, M1-I183, M1-L182, M1-A181, M1-V180, M1-V179, M1-P178, M1-V177, M1-G176, M1-Q175, M1-G174, M1-I173, M1-R172, M1-T171, M1-N170, M1-I169, M1-K168, M1-Q167, M1-L166, M1-S165, M1-I164, M1-H163, M1-K162, M1-E161, M1-L160, M1-Q159, M1-R158, M1-R157, M1-L156, M1-K155, M1-V154, M1-E153, M1-A152, M1-G151, M1-Y150, M1-K149, M1-G148, M1-T147, M1-T146, M1-G145, M1-N144, M1-D143, M1-A142, M1-L141, M1-I140, M1-F139, M1-H138, M1-S137, M1-H136, M1-M135, M1-S134, M1-N133, M1-L132, M1-V131, M1-T130, M1-L129, M1-K128, M1-S127, M1-M126, M1-P125, M1-N124, M1-S123, M1-M122, M1-T121, M1-Q120, M1-Y119, M1-P118, M1-R117, M1-V116, M1-V115, M1-D114, M1-R113, M1-G112, M1-I111, M1-L110, M1-D109, M1-E108, M1-Q107, M1-N106, M1-E105, M1-V104, M1-I103, M1-G102, M1-W10, M1-P100, M1-A99, M1-I98, M1-G97, M1-I96, M1-T95, M1-C94, M1-I93, M1-K92, M1-G91, M1-R90, M1-S89, M1-K88, M1-S87, M1-A86, M1-H85, M1-D84, M1-K83, M1-L82, M1-A81, M1-D80, M1-G79, M1-V78, M1-H77, M1-R76, M1-I75, M1-V74, M1-G73, M1-T72, M1-N71, M1-V70, M1-G69, M1-G68, M1-T67, M1-F66, M1-I65, M1-W64, M1-A63, M1-G62, M1-T61, M1-T60, M1-M59, M1-A58, M1-A57, M1-K56, M1-I55, M1-L54, M1-G53, M1-K52, M1-G51, M1-F50, M1-V49, M1-Q48, M1-K47, M1-L46, M1-K45, M1-P44, M1-Q43, M1-L42, M1-E41, M1-F40, M1-N39, M1-Q38, M1-L37, M1-G36, M1-G35, M1-H34, M1-V33, M1-S32, M1-I31, M1-L30, M1-L29, M1-K28, M1-P27, M1-L26, M1-E25, M1-L24, M1-Q23, M1-W22, M1-E21, M1-K20, M1-T19, M1-M18, M1-L17, M1-H16, M1-L15, M1-L14, M1-L13, M1-D12, M1-P11, M1-K10, M1-T9, M1-D8, and/or M1-F7 of SEQ ID NO:2. Polynucleotide sequences encoding these polypeptides are also provided. The present invention also encompasses the use of these C-terminal LTRPC3 deletion polypeptides as immunogenic and/or antigenic epitopes as described elsewhere herein.

Alternatively, preferred polypeptides of the present invention may comprise polypeptide sequences corresponding to, for example, internal regions of the LTRPC3 polypeptide (e.g., any combination of both N- and C-terminal LTRPC3 polypeptide deletions) of SEQ ID NO:2. For example, internal regions could be defined by the equation: amino acid NX to amino acid CX, wherein NX refers to any N-terminal deletion polypeptide amino acid of LTRPC3 (SEQ ID NO:2), and where CX refers to any C-terminal deletion polypeptide amino acid of LTRPC3 (SEQ ID NO:2). Polynucleotides encoding these polypeptides are also provided. The present invention also encompasses the use of these polypeptides as an immunogenic and/or antigenic epitope as described elsewhere herein.

The LTRPC3 polypeptides of the present invention were determined to comprise several phosphorylation sites based upon the Motif algorithm (Genetics Computer Group, Inc.). The phosphorylation of such sites may regulate some biological activity of the LTRPC3 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the LTRPC3 polypeptide to associate with other potassium channel alpha subunits, beta subunits, or its ability to modulate potassium channel function.

Specifically, the LTRPC3 polypeptide was predicted to comprise two tyrosine phosphorylation sites using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or [RK]-x(3)-[DE]-x(2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Natl. Acad. Sci. U.S.A. 79:973-977 (1982); Hunter T., J. Biol. Chem. 257:4843-4848 (1982), and Cooper J. A., Esch F. S., Taylor S. S., Hunter T., J. Biol. Chem. 259:7835-7841(1984), which are hereby incorporated herein by reference.

In preferred embodiments, the following tyrosine phosphorylation site polypeptides are encompassed by the present invention: LSLEFKNKDDMPYMSQAQ (SEQ ID NO:58), and/or VMMIGKMMIDMMYFVIIM (SEQ ID NO:59). Polynucleotides encoding these polypeptides are also provided. The present invention also encompasses the use of these LTRPC3 tyrosine phosphorylation site polypeptides as immunogenic and/or antigenic epitopes as described elsewhere herein.

The LTRPC3 polypeptide was predicted to comprise twenty three PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. 260: 12492-12499 (1985); which are hereby incorporated by reference herein.

In preferred embodiments, the following PKC phosphorylation site polypeptides are encompassed by the present invention: ADNGTTGKYGAEV (SEQ ID NO:60), VVCDGSGRASDIL (SEQ ID NO:61), GLINESLRDQLLV (SEQ ID NO:62), YRCNYTRKRFRTL (SEQ ID NO:63), RRGRKTTKKREEE (SEQ ID NO:64), RGRKTTKKREEEV (SEQ ID NO:65), ELLDQSYKQDEQL (SEQ ID NO:66), RNNGESSRKKDEE (SEQ ID NO:67), NNGESSRKKDEEE (SEQ ID NO:68), PNEEPSWKLAKNI (SEQ ID NO:69), RIRVTSERVENMS (SEQ ID NO:70), RVENMSMRLEEVN (SEQ ID NO:71), NEREHSMKASLQT (SEQ ID NO:72), LERAESNKIRSRT (SEQ ID NO:73), SQEGNTFKLQESI (SEQ ID NO:74), AIVPDSRRPSSCI (SEQ ID NO:75), ATLAPTDRPPSRS (SEQ ID NO:76), IERSKSSRYLATT (SEQ ID NO:77), QEGDNSERTLSNN (SEQ ID NO:78), APYAHTRKSFSIS (SEQ ID NO:79), KSFSISDKLDRQR (SEQ ID NO:80), FQRSKSSKPEGRG (SEQ ID NO:81), and/or RGDSLSMRRLSRT (SEQ ID NO:82). Polynucleotides encoding these polypeptides are also provided. The present invention also encompasses the use of these LTRPC3 PKC phosphorylation site polypeptides as immunogenic and/or antigenic epitopes as described elsewhere herein.

The present invention also encompasses immunogenic and/or antigenic epitopes of the LTRPC3 polypeptide.

The LTRPC3 polypeptide has been shown to comprise twelve glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine phosphorylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673-702 (1972); Pless D. D., Lennarz W. J., Proc. Natl. Acad. Sci. U.S.A. 74:134-138 (1977); Bause E., Biochem. J. 209:331-336 (1983); Gavel Y., von Heijne G., Protein Eng. 3:433-442 (1990); and Miletich J. P., Broze G. J. Jr., J. Biol. Chem. 265:11397-11404 (1990).

In preferred embodiments, the following asparagine glycosylation site polypeptides are encompassed by the present invention: FILADNGTTGKYGA (SEQ ID NO:83), EGGLINESLRDQLL (SEQ ID NO:84), LLKGANASAPDQLS (SEQ ID NO:85), GAYRCNYTRKRFRT (SEQ ID NO:86), TYELKNWSNATCLQ (SEQ ID NO:87), LKNWSNATCLQLAV (SEQ ID NO:88), LQEYWNVTDLIAIL (SEQ ID NO:89), PPCGQNETREDGKI (SEQ ID NO:90), LIAVFNNTFFEVKS (SEQ ID NO:91), KDDRFNSSNDERIR (SEQ ID NO:92), SERVENMSMRLEEV (SEQ ID NO:93), and/or RTLSNNITVPKIER (SEQ ID NO:94). Polynucleotides encoding these polypeptides are also provided. The present invention also encompasses the use of these LTRPC3 asparagine glycosylation site polypeptides as immunogenic and/or antigenic epitopes as described elsewhere herein.

The LTRPC3 polypeptide has been shown to comprise one RGD cell attachment site domain according to the Motif algorithm (Genetics Computer Group, Inc.). The sequence Arg-Gly-Asp, found in fibronectin, is crucial for its interaction with its cell surface receptor, an integrin. What has been called the 'RGD' tripeptide is also found in the sequences of a number of other proteins, where it has been shown to play a role in cell adhesion. Non-limiting examples of these proteins are the following: some forms of collagens, fibrinogen, vitronectin, von Willebrand factor (VWF), snake disintegrins, and slime mold discoidins. The 'RGD' tripeptide is also found in other proteins where it may serve the same purpose. A consensus pattern for RGD cell attachment sites is the following: R-G-D. Additional information relating to RGD cell attachment site domains may be found in reference to the following publications, which are hereby incorporated by reference herein: Ruoslahti E., Pierschbacher M. D., Cell 44:517-518 (1986); and d'Souza S. E., Ginsberg M. H., Plow E. F., Trends Biochem. Sci. 16:246-250 (1991).

In preferred embodiments, the following RGD cell attachment site domain polypeptide is encompassed by the present invention: SKPEGRGDSLSMR (SEQ ID NO:95). Polynucleotides encoding these polypeptides are also provided. The present invention also encompasses the use of this RGD cell attachment site domain polypeptide as an immunogenic and/or antigenic epitope as described elsewhere herein.

The LTRPC3 polypeptide has been shown to comprise one aminoacyl-transfer RNA synthetases class-II domain according to the Motif algorithm (Genetics Computer Group, Inc.). Aminoacyl-tRNA synthetases (EC 6.1.1.-) are a group of enzymes which activate amino acids and transfer them to specific tRNA molecules as the first step in protein biosynthesis. In prokaryotic organisms there are at least twenty different types of aminoacyl-tRNA synthetases, one for each different amino acid. In eukaryotes there are generally two aminoacyl-tRNA synthetases for each different amino acid: one cytosolic form and a mitochondrial form. While all these enzymes have a common function, they are widely diverse in terms of subunit size and of quaternary structure.

The synthetases specific for alanine, asparagine, aspartic acid, glycine, histidine, lysine, phenylalanine, proline, serine, and threonine are referred to as class-II synthetases and probably have a common folding pattern in their catalytic domain for the binding of ATP and amino acid which is different to the Rossmann fold observed for the class I synthetases.

Class-II tRNA synthetases do not share a high degree of similarity, however at least three conserved regions are present.

The consensus pattern for aminoacyl-transfer RNA synthetases class-II domains are as follows: [FYH]-R-x-[DE]-x(4,12)-[RH]-x(3)-F-x(3)-[DE]; and [GSTALVF]-{DENQHRKP}-[GSTA]-[LIVMF]-[DE]-R-[LIVMF]-x-[LIVMSTAG]-[LIVMFY], where 'x' represents an intervening amino acid residue.

Additional information specific to aminoacyl-transfer RNA synthetases class-II domains may be found in reference to the following publications, Schimmel P., Annu. Rev. Biochem. 56:125-158 (1987); Delarue M., Moras D., BioEssays 15:675-687 (1993); Schimmel P., Trends Biochem. Sci. 16:1-3 (1991); Nagel G. M., Doolittle R. F., Proc. Natl. Acad. Sci. U.S.A. 88:8121-8125 (1991); Cusack S., Haertlein M., Leberman R., Nucleic Acids Res. 19:3489-3498 (1991); Cusack S., Biochimie 75:1077-1081 (1993); Cusack S., Berthet-Colominas C., Haertlein M., Nassar N., Leberman R., Nature 347:249-255 (1990); and Leveque F., Plateau P., Dessen P., Blanquet S., Nucleic Acids Res. 18:305-312 (1990); which are hereby incorporated herein by reference in their entirety.

In preferred embodiments, the following aminoacyl-transfer RNA synthetases class-II domain polypeptide is encompassed by the present invention: LIGRMATALERLTGLERAES (SEQ ID NO:96). Polynucleotides encoding these polypeptides are also provided. The present invention also encompasses the use of this RGD cell attachment site domain polypeptide as an immunogenic and/or antigenic epitope as described elsewhere herein.

The LTRPC3 polypeptide has been shown to comprise three amidation sites according to the Motif algorithm (Genetics Computer Group, Inc.). The precursor of hormones and other active peptides which are C-terminally amidated is always directly followed by a glycine residue which provides the amide group, and most often by at least two consecutive basic residues (Arg or Lys) which generally function as an active peptide precursor cleavage site. Although all amino acids can be amidated, neutral hydrophobic residues such as Val or Phe are good substrates, while charged residues such as Asp or Arg are much less reactive. A consensus pattern for amidation sites is the following: x-G-[RK]-[RK], wherein "X" represents the amidation site. Additional information relating to asparagine glycosylation may be found in reference to the following publications, which are hereby incorporated by reference herein: Kreil G., Meth. Enzymol. 106: 218-223(1984); and Bradbury A. F., Smyth D. G., Biosci. Rep. 7:907-916 (1987).

In preferred embodiments, the following amidation site polypeptides are encompassed by the present invention: DIPLRRGRKTTKKR (SEQ ID NO:97), HRLIPLGRKIYEFY (SEQ ID NO:98), and/or EENEAKGRRATIAI (SEQ ID NO:99). Polynucleotides encoding these polypeptides are also provided. The present invention also encompasses the use of these LTRPC3 amidation site polypeptides as immunogenic and/or antigenic epitopes as described elsewhere herein.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 4651 of SEQ ID NO:1, b is an integer between 15 to 4665, where both a and b correspond to the positions of nucleotide residues shown in SEQ ID NO:1, and where b is greater than or equal to a+14.

Features of the Polypeptide Encoded by Gene No:2

The polypeptide of this gene provided as SEQ ID NO:4 (FIGS. 2A-F), encoded by the polynucleotide sequence according to SEQ ID NO:3 (FIGS. 2A-F), and/or encoded by the polynucleotide contained within the deposited clone, LTRPC3b, has significant homology at the nucleotide and amino acid level to the human melastatin 1 protein (Melastatin1; Genbank Accession No. gi|3243075; SEQ ID NO:11). An alignment of the LTRPC3b polypeptide with this protein is provided in FIGS. 5A-D.

The LTRPC3b polypeptide was determined to share 65.7% identity and 73.5% similarity with the human melastatin 1 protein (Melastatin1; Genbank Accession No. gi|3243075; SEQ ID NO:11) as shown in FIG. 8.

The LTRPC3b protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain. This family is commonly referred to as the transient receptor potential channel (TRP) family. Melastatin1 defines a separate subfamily of TRP channels referred to as TRPM (melastatin1). TRPM family members are characteristic of their unusually long cytoplasmic tails at both ends of the channel domain and some of the family members contain an enzyme domain at the C-terminal region. Thus, LTRPC3 represents a novel member of the TRPM subfamily.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the melastatin1 protein, in addition to, other transient receptor potential channel family members referenced elsewhere herein or otherwise known in the art.

Most of the known transient receptor potential channel family members, possess one or more transmembrane domains. Likewise, the LTRPC3b polypeptide has been determined to comprise six transmembrane domains (TM1-TM6) as shown in FIGS. 2A-F. The transmembrane domains are located from about amino acid 632 to about amino acid 649 (TM1), from about amino acid 729 to about amino acid 746 (TM2), from about amino acid 802 to about amino acid 815 (TM3), from about amino acid 829 to about amino acid 846 (TM4), from about amino acid 863 to about amino acid 880 (TM5), and/or from about amino acid 950 to about amino acid 970 (TM6) of SEQ ID NO:4. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKVILGILLPPSILSLEF (SEQ ID NO:32), IVKFW-FYTLAYIGYLMLF (SEQ ID NO:33), VTDLIAILLFS-VGM (SEQ ID NO:34), RVIYCVNIIYWYIRLLDI (SEQ ID NO:35), MMIDMMYFVIIMLVVLMS (SEQ ID NO:36), and/or AIMACYLLVANILLVNLLIAV (SEQ ID NO:37). Polynucleotides encoding these polypeptides are also provided. The present invention also encompasses the use of the LTRPC3b transmembrane polypeptides as immunogenic and/or antigenic epitopes as described elsewhere herein.

The present invention also encompasses polypeptides corresponding to the regions between each transmembrane domain of LTRPC3b, referred to herein as inter-transmembrane domain polypeptides (inter TM1-2, inter TM2-3, inter TM3-4, inter TM4-5, and inter TM5-6). Such regions are typically solvent accessible (either extracellularly or intracellularly). Therefore, these regions are amenable to the development of agonists and/or antagonists to the LTRPC3b polypeptide, particularly for the development of antibodies specific to these regions.

In preferred embodiments, the following inter-transmembrane domain polypeptides are encompassed by the present invention: KNKDDMPYMSQAQEIHLQEKEAEEPE-KPTKEKEEEDMELTAMLGRNNGESS RKKDEEEVQSKHRLIPLGRKIYEFYNAP (SEQ ID NO:100), NYIVLVKMERWPSTQEWIVISYIFTLG-IEKMREILMSEPGKLLQKVKVWLQEY WN (SEQ ID NO:101), ILRLQDQPFRSDG (SEQ ID NO:102), FGVNKYLGPYVMMIGK (SEQ ID NO:103), and/or FGVARQAILFPNEEPSWKLAKNIFYMPY-WMIYGEVFADQIDPPCGQNETRED GKIIQLPPCKT-GAWIVP (SEQ ID NO:104). Polynucleotides encoding these polypeptides are also provided. The present invention also encompasses the use of the LTRPC3b inter-transmembrane polypeptides as immunogenic and/or antigenic epitopes as described elsewhere herein.

In preferred embodiments, the following N-terminal LTRPC3b inter TM1-2 domain deletion polypeptides are encompassed by the present invention: K1-P79, N2-P79, K3-P79, D4-P79, D5-P79, M6-P79, P7-P79, Y8-P79, M9-P79, S10-P79, Q11-P79, A12-P79, Q13-P79, E14-P79, I15-P79, H16-P79, L17-P79, Q18-P79, E19-P79, K20-P79, E21-P79, A22-P79, E23-P79, E24-P79, P25-P79, E26-P79, K27-P79, P28-P79, T29-P79, K30-P79, E31-P79, K32-P79, E33-P79, E34-P79, E35-P79, D36-P79, M37-P79, E38-P79, L39-P79, T40-P79, A41-P79, M42-P79, L43-P79, G44-P79, R45-P79, N46-P79, N47-P79, G48-P79, E49-P79, S50-P79, S51-P79, R52-P79, K53-P79, K54-P79, D55-P79, E56-P79, E57-P79, E58-P79, V59-P79, Q60-P79, S61-P79, K62-P79, H63-P79, R64-P79, L65-P79, I66-P79, P67-P79, L68-P79, G69-P79, R70-P79, K71-P79, I72-P79, and/or Y73-P79 of SEQ ID NO:100. Polynucleotide sequences encoding these polypeptides are also provided. The present invention also encompasses the use of these N-terminal LTRPC3b inter TM1-2 domain deletion polypeptides as immunogenic and/or antigenic epitopes as described elsewhere herein.

In preferred embodiments, the following C-terminal LTRPC3b inter TM1-2 domain deletion polypeptides are encompassed by the present invention: K1-P79, K1-A78, K1-N77, K1-Y76, K1-F75, K1-E74, K1-Y73, K1-I72, K1-K71, K1-R70, K1-G69, K1-L68, K1-P67, K1-I66, K1-L65, K1-R64, K1-H63, K1-K62, K1-S61, K1-Q60, K1-V59, K1-E58, K1-E57, K1-E56, K1-D55, K1-K54, K1-K53, K1-R52, K1-S51, K1-S50, K1-E49, K1-G48, K1-N47, K1-N46, K1-R45, K1-G44, K1-L43, K1-M42, K1-A41, K1-T40, K1-L39, K1-E38, K1-M37, K1-D36, K1-E35, K1-E34, K1-E33, K1-K32, K1-E31, K1-K30, K1-T29, K1-P28, K1-K27, K1-E26, K1-P25, K1-E24, K1-E23, K1-A22, K1-E21, K1-K20, K1-E19, K1-Q18, K1-L17, K1-H16, K1-I15, K1-E14, K1-Q13, K1-A12, K1-Q11, K1-S10, K1-M9, K1-Y8, and/or K1-P7 of SEQ ID NO:100. Polynucleotide sequences encoding these polypeptides are also provided. The present invention also encompasses the use of these C-terminal LTRPC3b inter TM1-2 domain deletion polypeptides as immunogenic and/or antigenic epitopes as described elsewhere herein.

In preferred embodiments, the following N-terminal LTRPC3b inter TM2-3 domain deletion polypeptides are encompassed by the present invention: F1-N56, N2-N56, Y3-N56, I4-N56, V5-N56, L6-N56, V7-N56, K8-N56, M9-N56, E10-N56, R1'-N56, W12-N56, P13-N56, S14-N56, T15-N56, Q16-N56, E17-N56, W18-N56, I19-N56, V20-N56, I21-N56, S22-N56, Y23-N56, I24-N56, F25-N56, T26-N56, L27-N56, G28-N56, I29-N56, E30-N56, K31-N56, M32-N56, R33-N56, E34-N56, I35-N56, L36-N56, M37-N56, S38-N56, E39-N56, P40-N56, G41-N56, K42-N56, L43-N56, L44-N56, Q45-N56, K46-N56, V47-N56, K48-N56, V49-N56, and/or W50-N56 of SEQ ID NO:101. Polynucleotide sequences encoding these polypeptides are also provided. The present invention also encompasses the use of these N-terminal LTRPC3b inter TM2-3 domain deletion polypeptides as immunogenic and/or antigenic epitopes as described elsewhere herein.

In preferred embodiments, the following C-terminal LTRPC3b inter TM2-3 domain deletion polypeptides are encompassed by the present invention: F1-N56, F1-W55, F1-Y54, F1-E53, F1-Q52, F1-L51, F1-W50, F1-V49, F1-K48, F1-V47, F1-K46, F1-Q45, F1-L44, F1-L43, F1-K42, F1-G41, F1-P40, F1-E39, F1-S38, F1-M37, F1-L36, F1-I35, F1-E34, F1-R33, F1-M32, F1-K31, F1-E30, F1-I29, F1-G28, F1-L27, F1-T26, F1-F25, F1-I24, F1-Y23, F1-S22, F1-I21, F1-V20, F1-I19, F1-W18, F1-E17, F1-Q16, F1-T15, F1-S14, F1-P13, F1-W12, F1-R11, F1-E10, F1-M9, F1-K8, and/or F1-V7 of SEQ ID NO:101. Polynucleotide sequences encoding these polypeptides are also provided. The present invention also encompasses the use of these C-terminal LTRPC3b inter TM2-3 domain deletion polypeptides as immunogenic and/or antigenic epitopes as described elsewhere herein.

In preferred embodiments, the following N-terminal LTRPC3b inter TM3-4 domain deletion polypeptides are encompassed by the present invention: I1-G13, L2-G13, R3-G13, L4-G13, Q5-G13, D6-G13, and/or Q7-G13 of SEQ ID NO:102. Polynucleotide sequences encoding these polypeptides are also provided. The present invention also encompasses the use of these N-terminal LTRPC3b inter TM3-4 domain deletion polypeptides as immunogenic and/or antigenic epitopes as described elsewhere herein.

In preferred embodiments, the following C-terminal LTRPC3b inter TM3-4 domain deletion polypeptides are encompassed by the present invention: I1-G13, I1-D12, I1-S11, I1-R10, I1-F9, I1-P8, and/or I1-Q7 of SEQ ID NO:102. Polynucleotide sequences encoding these polypeptides are also provided. The present invention also encompasses the use of these C-terminal LTRPC3b inter TM3-4 domain deletion polypeptides as immunogenic and/or antigenic epitopes as described elsewhere herein.

In preferred embodiments, the following N-terminal LTRPC3b inter TM4-5 domain deletion polypeptides are encompassed by the present invention: F1-K16, G2-K16, V3-K16, N4-K16, K5-K16, Y6-K16, L7-K16, G8-K16, P9-K16, and/or Y10-K16 of SEQ ID NO:103. Polynucleotide sequences encoding these polypeptides are also provided. The present invention also encompasses the use of these N-terminal LTRPC3b inter TM4-5 domain deletion polypeptides as immunogenic and/or antigenic epitopes as described elsewhere herein.

In preferred embodiments, the following C-terminal LTRPC3b inter TM4-5 domain deletion polypeptides are encompassed by the present invention: F1-K16, F1-G15, F1-I14, F1-M13, F1-M12, F1-V11, F1-Y10, F1-P9, F1-G8, and/or F1-L7 of SEQ ID NO:103. Polynucleotide sequences encoding these polypeptides are also provided. The present invention also encompasses the use of these C-terminal LTRPC3b inter TM4-5 domain deletion polypeptides as immunogenic and/or antigenic epitopes as described elsewhere herein.

In preferred embodiments, the following N-terminal LTRPC3b inter TM5-6 domain deletion polypeptides are encompassed by the present invention: F1-P69, G2-P69, V3-P69, A4-P69, R5-P69, Q6-P69, A7-P69, I8-P69, L9-P69, F10-P69, P11-P69, N12-P69, E13-P69, E14-P69, P15-P69, S16-P69, W17-P69, K18-P69, L19-P69, A20-P69, K21-P69, N22-P69, I23-P69, F24-P69, Y25-P69, M26-P69, P27-P69, Y28-P69, W29-P69, M30-P69, I31-P69, Y32-P69, G33-P69, E34-P69, V35-P69, F36-P69, A37-P69, D38-P69, Q39-P69, I40-P69, D41-P69, P42-P69, P43-P69, C44-P69, G45-P69, Q46-P69, N47-P69, E48-P69, T49-P69, R50-P69, E51-P69, D52-P69, G53-P69, K54-P69, I55-P69, I56-P69, Q57-P69, L58-P69, P59-P69, P60-P69, C61-P69, K62-P69, and/or T63-P69 of SEQ ID NO:104. Polynucleotide sequences encoding these polypeptides are also provided. The present invention also encompasses the use of these N-terminal LTRPC3b inter TM5-6 domain deletion polypeptides as immunogenic and/or antigenic epitopes as described elsewhere herein.

In preferred embodiments, the following C-terminal LTRPC3b inter TM5-6 domain deletion polypeptides are encompassed by the present invention: F1-P69, F1-V68, F1-I67, F1-W66, F1-A65, F1-G64, F1-T63, F1-K62, F1-C61, F1-P60, F1-P59, F1-L58, F1-Q57, F1-I56, F1-I55, F1-K54, F1-G53, F1-D52, F1-E51, F1-R50, F1-T49, F1-E48, F1-N47, F1-Q46, F1-G45, F1-C44, F1-P43, F1-P42, F1-D41, F1-I40, F1-Q39, F1-D38, F1-A37, F1-F36, F1-V35, F1-E34, F1-G33, F1-Y32, F1-I31, F1-M30, F1-W29, F1-Y28, F1-P27, F1-M26, F1-Y25, F1-F24, F1-I23, F1-N22, F1-K21, F1-A20, F1-L19, F1-K18, F1-W17, F1-S16, F1-P15, F1-E14, F1-E13, F1-N12, F1-P11, F1-F10, F1-L9, F1-I8, and/or F1-A7 of SEQ ID NO:104. Polynucleotide sequences encoding these polypeptides are also provided.

The present invention also encompasses the use of these C-terminal LTRPC3b inter TM5-6 domain deletion polypeptides as immunogenic and/or antigenic epitopes as described elsewhere herein.

The LTRPC3b polypeptide was determined to comprise several conserved cysteines, at amino acid 94, 209, 265, 431, 529, 594, 611, 833, 924, 941, 954, 1057, 1148, and 1114 of SEQ ID No: 2 (FIGS. 1A-F). Conservation of cysteines at key amino acid residues is indicative of conserved structural features, which may correlate with conservation of protein function and/or activity.

In confirmation of the LTRPC3b representing a member of the transient receptor channel family, the LTRPC3b polypeptide was determined to comprise a predicted TRP domain (EWKFAR) located from about amino acid 985 to about amino acid 990 of SEQ ID NO:4. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following TRP domain polypeptide is encompassed by the present invention: VWKFQR (SEQ ID NO:105). Polynucleotides encoding this polypeptide are also provided. The present invention also encompasses the use of this LTRPC3b TRP domain polypeptide as an immunogenic and/or antigenic epitope as described elsewhere herein.

In further confirmation of the LTRPC3b representing a member of the transient receptor channel family, the LTRPC3b polypeptide was determined to comprise a predicted ion transport signature domain located at about amino acid 748 to about amino acid 959 of SEQ ID NO:4. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following ion transport signature domain polypeptide is encompassed by the present invention: TQEWIVISYIFTLGIEKMREILMSEPGKLLQKVKVWLQEYWNVTDLIAILLFSV GMILRLQDQPFRSDGRVIYCVNIIYWYIRLL- DIFGVNKYLGPYVMMIGKMMID MMYFVIIMLVVLMSFGVARQAILFP- NEEPSWKLAKNIFYMPYWMIYGEVFAD QIDPPCGQNETREDGKIIQLPPCKTGAWIV- PAIMACYLLVANILLVNLLIAVF (SEQ ID NO:109). Polynucleotides encoding this polypeptide are also provided. The present invention also encompasses the use of this LTRPC3b ion transport signature domain polypeptide as an immunogenic and/or antigenic epitope as described elsewhere herein.

The LTRPC3b polypeptide was determined to comprise a predicted coiled-coil domain located at about amino acid 1075 to about amino acid 1129 of SEQ ID NO:4. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following coiled-coil domain polypeptide is encompassed by the present invention: ERIRVTSERVENMSMRLEEVNEREH- SMKASLQTVDIRLAQLEDLIGRMATAL ERL (SEQ ID NO:106). Polynucleotides encoding this polypeptide are also provided. The present invention also encompasses the use of this LTRPC3b coiled-coil domain polypeptide as an immunogenic and/or antigenic epitope as described elsewhere herein.

The present invention is also directed to polynucleotides comprising at least about 45 nt of the polynucleotide sequence provided as SEQ ID NO:3. Specifically, the present invention is directed to a polynucleotide sequence comprising nucleotides from about nucleotide 1174 to about nucleotide 1212; nucleotides from about nucleotide 1174 to about nucleotide 1215; nucleotides from about nucleotide 1168 to about nucleotide 1209; nucleotides from about nucleotide 1165 to about nucleotide 1209; of SEQ ID NO:3; and/or nucleotides from about nucleotide 1162 to about nucleotide 1209. In this context "about" includes the particularly recited value, a value larger or smaller by several (5, 4, 3, 2, or 1) nucleotides, at either terminus, or at both termini.

The present invention is also directed to polypeptides comprising at least about 15 amino acids of the polypeptides sequence provided as SEQ ID NO:4. Specifically, the present invention is directed to a polypeptides sequence comprising amino acids from about amino acid 392 to about amino acid 404; amino acids from about amino acid 392 to about amino acid 405; amino acids from about amino acid 392 to about amino acid 406; amino acids from about amino acid 390 to about amino acid 403; amino acids from about amino acid 389 to about amino acid 403; and/or amino acids from about amino acid 388 to about amino acid 403 of SEQ ID NO:4. In this context "about" includes the particularly recited value, a value larger or smaller by several (5, 4, 3, 2, or 1) nucleotides, at either terminus, or at both termini.

LTRPC3b polypeptides and polynucleotides are useful for diagnosing diseases related to the over and/or under expression of LTRPC3b by identifying mutations in the LTRPC3b gene using LTRPC3b sequences as probes or by determining LTRPC3b protein or mRNA expression levels. LTRPC3b polypeptides will be useful in screens for compounds that affect the activity of the protein. LTRPC3b peptides can also be used for the generation of specific antibodies and as bait in yeast two hybrid screens to find proteins the specifically interact with LTRPC3b.

Consistent with LTRPC3 representing a transient receptor potential channel, immunohistochemical experiments have shown that LTRPC3 localizes to the cell membrane (see FIG. 17 and Example 6). Specifically, the complete open reading frame of LTRPC3 with a C-terminal HA tag was transiently transfected into HEK 293 cells to assess its cellular localization. The HA-tagged LTRPC3 was detected using a fluorescein-conjugated anti-HA antibody and a laser scanning confocal microscope which produces a green fluorescent signal. The green fluorescent signal was exclusively detected at the subplasma membrane region of the transfected cells (see FIG. 17), which is consistent with LTRPC3 being an integral membrane protein. Under these conditions approximately ~70% of cells are expressing LTRPC3. The expression of full-length protein was accessed with immunoblot using an anti-HA antibody and detected as the expected size of ~170 kD (data not shown). Cellular localization of the LTRPC3b splice variant is expected to be similarly localized to the subplasma membrane region.

Moreover, physiometric studies have shown that LTRPC3 is a functional $Ca^{2+}$ permeable channel (see FIGS. 18 and 19, and Example 7). LTRPC3 function was assessed using a Fluorometric Imaging Plate Reader (FLIPR™) that measures real-time intracellular fluorescence changes. Cells transiently transfected with vector or LTRPC3-HA were loaded with the cytoplasmic $Ca^{2+}$ indicator Fluoro-4 in a 1 mM $Ca^{2+}$ solution. Addition of $Ca^{2+}$ to the media resulted in a concentration-dependent influx of $Ca^{2+}$ into LTRPC3-expressing cells (FIG. 18; right panels), indicating that LTRPC3 is a functional $Ca^{2+}$ channel. In contrast, vector-transfected cells showed minimal $Ca^{2+}$ influx under the same experimental conditions (FIG. 18, left panels). The non-transfected cells were indistinguishable from the vector-transfected cells (data not shown). Therefore, LTRPC3 is a constitutively active channel capable of mediating $Ca^{2+}$ influx. The $Ca^{2+}$ influx activity of the LTRPC3b splice variants is expected to be similar to LTRPC3.

To further address the mechanism of LTRPC3-mediated $Ca^{2+}$ entry, similar $Ca^{2+}$ addition experiments were performed on transfected cells incubated (~30 min) in a nominally $Ca^{2+}$-free solution. Previous studies have shown that lowering extracellular $Ca^{2+}$ concentration below physiological levels can deplete intracellular $Ca^{2+}$ stores in many cell types including HEK 293 (EMBO J. 17, 4274-4282, (1998)). Incubating vector-transfected HEK 293 cells in a nominally $Ca^{2+}$-free solution gave rise to $Ca^{2+}$ entry that was dependent on the concentration of $Ca^{2+}$ added to the buffers, indicating $Ca^{2+}$ influx was mediated through endogenous SOCs in HEK293 cells (FIG. 18, left panels). In LTRPC3 cells, the $Ca^{2+}$ transients triggered by similar $Ca^{2+}$ treatment were much larger (FIG. 18, right panels). This $Ca^{2+}$ entry observed in LTRPC3 cells incubated in $Ca^{2+}$-free media were greater than those observed in 1 mM $Ca^{2+}$ media, indicating that LTRPC3-mediated $Ca^{2+}$ entry can be potentiated by the store-depletion. The store-depletion potentiation of LTRPC3-mediated $Ca^{2+}$ entry is expected to be similar for the LTRPC3b splice variant.

The store-operated mechanism of LTRPC3-mediated $Ca^{2+}$ influx was tested further by passively depleting $Ca^{2+}$ stores with thapsigargin (TG), an inhibitor of microsomal $Ca^{2+}$ ATPases that pumps ions from the cytosol back into the stores. Addition of 2 µM thapsigargin equivalently depleted $Ca^{2+}$ stores in LTRPC3-HA- and vector-transfected cells (FIG. 19A). Following store depletion with TG, addition of $Ca^{2+}$ to the buffer induced a much larger $Ca^{2+}$ entry in LTRPC3 cells compared to the vector control cells. The increased $Ca^{2+}$ entry of LTRPC3 cells, relative to non-LTRPC3 transfected cells, post store depletion with TG is expected to be similar for the LTRPC3b splice variant.

Receptor-mediated $Ca^{2+}$ entry was also more pronounced in LTRPC3-HA-transfected cells. Carbachol (CCh) can activate an endogenous muscarinic receptor and trigger $IP_3$ production, leading to store-depletion in HEK 293 cells. The addition of 50 µM of CCh caused a transient and rapid intracellular $Ca^{2+}$ increase in both LTRPC3- and vector-transfected cells (FIG. 19B). After the store depletion with CCh, adding of $Ca^{2+}$ to the buffer induced a much larger influx of $Ca^{2+}$ into LTRPC3 cells, as compared to vector control cells. These results show that after store depletion with TG or CCh LTRPC3-transfected cells exhibit an increased $Ca^{2+}$ influx when compared to control cells. The increased $Ca^{2+}$ entry of LTRPC3 cells, relative to non-LTRPC3 transfected cells, post store depletion with TG or CCh is expected to be similar for the LTRPC3b splice variant.

The lanthanides, gadolinium ($Gd^{3+}$) and lanthanum ($La^{3+}$), are nonselective $Ca^{2+}$-permeable channel blockers, often used as part of the characterization of overexpressed TRP channels. Both lanthanides blocked LTRPC3 $Ca^{2+}$ conductance, although $La^{3+}$ was more potent (FIG. 19C). In the presence of 1 mM $Ca^{2+}$ in which endogenous SOCs is minimally activated (FIG. 18A), pre-treatment with 100 µM of $La^{3+}$ and $Gd^{3+}$ blocked LTRPC3 $Ca^{2+}$ currents, stimulated by adding 10 mM $Ca^{2+}$, by 67 and 39%, respectively. These results indicated that LTRPC3 mediated currents are not non-specific leak currents resulting from protein overexpression.

LTRPC3 is constitutively active but can be potentiated by store-depletion and is partially sensitive to $La^{3+}$ and $Gd^{3+}$ blockade. LTRPC3 is believed to represent the first member of the TRPM subfamily that exhibits this store-operated mechanism, although some members of TRPC subfamily have been considered for this role. TRPM1 and TRPM4a are constitutive $Ca^{2+}$ permeable channels but it is unclear whether they can be stimulated by store-depletion (*Proc. Natl. Acad. Sci. U.S.A.* 98, 10692-10697, (2001)). Distinct from TRPM4a, TRPM4b is directly activated by changes in intracellular $Ca^{2+}$ without significant permeation of $Ca^{2+}$ (*Cell* 109, 397-401, (2002)). TRPM2 is activated by ADP-ribose, NAD and changes in redox status (*Nature* 411, 595-599, (2001); *Science* 293, 1327-1330, (2001); and *Mol. Cell* 9, 163-173, (2002)). TRPM7 is regulated by $Mg^{2+}$-ATP and/or $PIP_2$ (*Science* 291, 1043-1047, (2001); *Nature* 411, 690-695, (2001); and *Nat. Cell Biol.* 4, 329-36 (2002)). TRPM8 is activated by cold temperatures and cooling agents (*Nature* 416, 52-58, (2002); and *Cell* 108, 705-715, (2002)). Therefore, in conjunction with its fairly restricted tissue expression, which is not observed with any other family members, LTRPC3 may have a unique biological function in human.

Expression profiling designed to measure the steady state mRNA levels encoding the LTRPC3 polypeptide showed predominately high expression levels in kidney. The LTRPC3 polypeptide was also significantly expression in spinal cord, testis, and brain (as shown in FIG. 6). The expression profile of the LTRPC3b splice variant is expected to be similar to LTRPC3.

Moreover, Northern hybridizations of the LTRPC3 mRNA confirmed the predominately high expression levels in kidney, and significant expression levels in testis, and brain (as shown in FIG. 7). The Northern hybridization was not performed on spinal cord tissue.

Expanded analysis of LTRPC3 expression levels by TaqMan™ quantitative PCR (see FIG. 12) confirmed that the LTRPC3 polypeptide is expressed in kidney, brain, testis (FIGS. 6 and 7), although higher expression levels were observed in brain than previously appreciated. LTRPC3 mRNA was expressed predominately in the brain, specifically the cerebellum, choroid plexus, the locus coeruleus, the posterior hypothalamus and the substantia nigra. Expression of LTRPC3 was also significantly expressed in the kidney, with higher levels observed in the cortex than in the medulla or pelvis. LTRPC3 was also significantly expressed in the spinal cord, testis, and to a lesser extent in other tissues as shown.

Therefore, LTRPC3b polynucleotides and polypeptides, including modulators or fragments thereof, may be useful in treating, diagnosing, prognosing, and/or preventing a variety of neurological conditions, in particular various choroid plexus neoplasms, choroid plexus papilloma, Alzheimer's disease, prion disorders and multiple sclerosis and movement disorders that involve the cerebellum. Based upon the expression pattern of LTRPC3 in kidney, this novel TRP family member, or a splice variant or polymorphism thereof, may also be the cause solitary metastasis in the choroid plexus, a rare type of carcinoma. For example, it has been shown that out of 15 cases of solitary metastasis of the choroid plexus, five originated from renal cell carcinoma (Neurol. Med. Chir. (Tokyo) 1997 December; 37(12):916-9). Additionally, given the rather selective expression of LTRPC3 in the choroid plexus and renal tissues, it may be possible that altered function of LTRPC3 or a splice variant or polymorphism thereof, may be responsible for solitary metastasis and renal carcinoma. LTRPC3 polynucleotides and polypeptides, including modulators or fragments thereof, may be useful in treating, diagnosing, prognosing, and/or preventing a variety of renal disorders, particularly solitary metastasis in the choroid plexus, and renal carcinoma.

Moreover, an additional analysis of LTRPC3 expression levels by TaqMan™ quantitative PCR (see FIG. 13) in disease cells and tissues indicated that the LTRPC3 polypeptide is differentially expressed in renal, testicular, and ovarian tumor tissues. In the renal tumor tissue results, an average of 2 out of 3 matched samples, which represent 3 out of 4 samples total, showed a significant decrease in LTRPC3 steady state RNA levels in tumor compared to control samples. In the testicular tumor tissue results, differential expression of LTRPC3 in testicular cancers was observed with all 5 tumor samples showing a significant reduction in steady-state RNA levels compared to two control samples. In the ovarian tumor tissue results, differential expression of LTRPC3 in ovarian cancers was observed with 3 tumor samples showing a significant reduction in steady-state RNA levels compared to five control samples.

The differential expression of LTRPC3 in tumors relative to normal tissues suggests that loss of LTRPC3 expression during tumor progression might contribute to the metastatic process by altering internal calcium stores in a manner that reflects a loss of cellular control on apoptosis. Restoring LTRPC3b function might provide a novel therapeutic approach to treating certain cancers. Therefore, LTRPC3b polynucleotides and polypeptides, including modulators or fragments thereof, particularly agonists of LTRPC3b activity or expression, may be useful in treating, diagnosing, prognosing, ameloriating, and/or preventing a variety of cancers and proliferative conditions, particularly of the kidney, testis, and ovaries.

Characterization of the LTRPC3 polypeptide of the present invention using antisense oligonucleotides led to the determination that LTRPC3 is involved in the negative modulation of the FEN1 DNA base-excision repair/proliferation modulating protein as described in Example 5 herein.

Specifically, antisense inhibition of LTRPC3 resulted in upregulation of Fen1, a marker of proliferation. As such, LTRPC3 behaves in a manner similar to a tumor suppressor, in that loss results in increases in proliferation. While some increases in the proliferation markers p21 and IkB were also observed, they were less significant, and could be a response to the pro-proliferative effect of LTRPC3 antisense inhibition. Interestingly, expression of LTRPC3 was also observed to be significantly reduced in tumor tissues, relative to normal tissues (see FIG. 13). Specifically, renal, testicular, and ovarian tumor samples showed as much as 12 to 30 fold down regulation of LTRPC3 message levels compared to normal tissues. This reduction of LTRPC3 correlating with the tumor state is consistent with the negative FEN1 modulatory activity and suggests this gene may have antiproliferative activities. Therefore, for modulators of LTRPC3 to be useful for treating cancer, it would be necessary to increase the activity of the gene or gene product in order to have the reverse effect on cancerous cells. Thus, an agonist of LTRPC3 activity or a compound that increased LTRPC3 message levels would be a desired invention for cancer therapy. The same regimen may also be applicable to LTRPC3 splice variants and/or polymorphisms, such as LTRPC3b.

In preferred embodiments, LTRPC3b polynucleotides and polypeptides, including fragments and modulators thereof, are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, LTRPC3b polynucleotides and polypeptides, including fragments and modulators thereof, are useful for increasing mammalian base excision repair activity, increasing mammalian single-nucleotide base excision repair activity, and/or increasing mammalian long patch base excision repair activity.

In preferred embodiments, antagonists directed against LTRPC3b are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, antagonists directed against LTRPC3b are useful for increasing mammalian base excision repair activity, increasing mammalian single-nucleotide base excision repair activity, and/or increasing mammalian long patch base excision repair activity.

In preferred embodiments, agonists directed against LTRPC3b are useful for treating, diagnosing, and/or ameliorating, disorders related to aberrant signal transduction, proliferating disorders, and/or cancers, particularly renal cell carcinomas, testicular cancers, and/or ovarian cancers.

The strong homology to human transient receptor potential channels (TRP), combined with the predominate localized expression in kidney tissue of LTRPC3 suggests the LTRPC3b polynucleotides and polypeptides, including modulators or fragments thereof, may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention, slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome.for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H., Willems, P, H., Bindels, R, J. J. Biol, Chem., 274(13):8375-8, (1999)).

Thus, the LTRPC3b polynucleotides and polypeptides are expected to share at least some biological activity with TRP family members expressed in kidney cells and tissues, particularly those specifically referenced herein.

The strong homology to human transient receptor potential channels (TRP) proteins, combined with the localized expression in spinal cord and brain of LTRPC3 suggests the LTRPC3b polynucleotides and polypeptides, including modulators or fragments thereof, may be useful in treating, diagnosing, prognosing, and/or preventing neurodegenerative disease states, behavioral disorders, or inflammatory conditions. Representative uses are described in the "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong homology to human transient receptor potential channels (TRP), combined with the localized expression in testis tissue of LTRPC3 emphasizes the potential utility for LTRPC3b polynucleotides and polypeptides in treating, diagnosing, prognosing, and/or preventing testicular, in addition to reproductive disorders.

In preferred embodiments, LTRPC3b polynucleotides and polypeptides including agonists and fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The LTRPC3b polynucleotides and polypeptides including agonists and fragments thereof, may also have uses related to modulating testicular development, embryogenesis, reproduction, and in ameliorating, treating, and/or preventing testicular proliferative disorders (e.g., cancers, which include, for example, choriocarcinoma, Nonseminoma, seminona, and testicular germ cell tumors).

Likewise, the localized expression in testis tissue also emphasizes the potential utility for LTRPC3b polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Bimbaumer, L, Lett., 373(3):193-8, (1995)); and TRPC1 (Wes, P, D., Chevesich, J., Jeromin, A., Rosenberg, C., Stetten, G., Montell, C, Proc, Natl, Acad, Sci, U,S,A., 92(21):9652-6, (1995)).

Thus, the LTRPC3b polynucleotides and polypeptides are expected to share at least some biological activity with TRP family members expressed in testis cells and tissues, particularly those specifically referenced herein.

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

In preferred embodiments, LTRPC3b polynucleotides and polypeptides of the present invention, including agonists and/or fragments thereof, have uses that include, modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity.

In more preferred embodiments, LTRPC3b polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

LTRPC3b polynucleotides and polypeptides of the present invention, including agonists and/or fragments may be involved in intracellular $Ca^{2+}$ homeostasis which affects various aspects of biological functions including mechano-regulation, pain transduction, vasorelaxation, gene expression, cell cycle and proliferation/apoptosis. Since LTRPC3b is dominantly expressed in kidney, it may particularly play an important role in regulating cytosolic Ca2+ in the renal system, potentially Ca2+ absorption.

The LTRPC3b gene maps to chromosome 9q21.11-21.31 between the two markers D9S1874 and D9S1807. This region is linked to amyotrophic lateral sclerosis with frontotemporal dementia, early-onset pulverulent cataract, infantile nephronophthisis, hypomagnesemia with secondary hypocalcemia (HSH), and familial hemophagocytic lymphohistiocytosis. Therefore, agonists and/or antagonists of the novel LTRPC3b can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in $Ca^{2+}$ homeostasis including osteoporosis, hypercalciuric stone disease, and chronic renal failure.

Moreover, given the selective expression in kidney, LTRPC3b could be considered a candidate gene for HSH, since the phenotype is a renal insufficiency. LTRPC3b chromosomal location is ~600 kb downstream of a X;9 translocation breakpoint interval described for one patient with HSH (*Hum. Mol. Genet.* 6, 1491-1497, (1997)). Recently, two groups reported that a new member of the TRPM subfamily, TRPM6, expressed in both intestinal tissues and kidney, is associated with HSH (*Nat. Genet.* 31, 166-170, (2002); and *Nat. Genet.* 31, 171-174 (2002)). Indeed, LTRPC3 is ~4 mb 5' to TRPM6 on 9q21. Although TRPM6 is the first component identified for HSH, this should not preclude involvement of LTRPC3b in the disease. Therefore, it is possible that LTRPC3b may co-localize with TRPM6 and/or forms a heteromultimer with TRPM6 in the kidney.

The kidney plays a major role in $Ca^{2+}$ homeostasis (reviewed in *Physiol. Rev.* 75, 429-471, (1995)). LTRPC3b may play a direct role in $Ca^{2+}$ absorption due to its constitutive $Ca^{2+}$ permeability. Alternatively, LTRPC3b may be the SOC that regulates $Ca^{2+}$ absorption. In kidney, $Ca^{2+}$ absorption is regulated by agonists such as calcitonin, parathyroid hormone and parathyroid hormone-related peptide through their respective G protein-coupled receptors, and downstream SOCs. Additionally, in kidney a SOC has been described (*J. Biol. Chem.* 276, 25759-25765, (2001)) for the action of angiotensin II, a vasoactive peptide that plays a major role in regulating blood pressure.

In addition, LTRPC3b polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++ sensitive signaling pathways, the activation of kinase-activatible proteins, and the activation of kinase-dependent signaling pathways.

The LTRPC3b polynucleotides and polypeptides of the present invention, including agonists and/or fragments thereof, have uses that include modulating proliferation, differentiation, migration, and activation in various cells, tissues, and organisms, and particularly in mammalian kidney, spinal cord, testis, and brain, preferably human. LTRPC3b polynucleotides and polypeptides of the present invention, including agonists and/or fragments thereof, may be useful in diagnosing, treating, prognosing, and/or preventing renal, neural, and/or proliferative diseases or disorders, particularly of the renal system.

In addition, antagonists of the LTRPC3b polynucleotides and polypeptides, including modulators or fragments thereof, may have uses that include diagnosing, treating, prognosing, and/or preventing diseases or disorders related to transient receptor potential channel activity, which may include renal, neural, reproductive, and/or proliferative diseases or disorders.

Although it is believed the encoded polypeptide may share at least some biological activities with transient receptor potential channel family members, particularly those melastatin1, a number of methods of determining the exact biological function of this clone are either known in the art or are described elsewhere herein. Briefly, the function of this clone may be determined by applying microarray methodology. Nucleic acids corresponding to the LTRPC3b polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known transient potential receptor inhibitors, which include, but are not limited to the drugs listed herein or otherwise known in the art, might indicate a function in modulating transient potential receptor function, for example. In the case of LTRPC3b, kidney, spinal cord, testis, and brain, should be used to extract RNA to prepare the probe.

In addition, the function of the protein may be assessed by applying quantitative PCR methodology, for example. Real time quantitative PCR would provide the capability of following the expression of the LTRPC3b gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:3 (FIGS. 2A-F).

The function of the protein may also be assessed through complementation assays in yeast. For example, in the case of the LTRPC3b, transforming yeast deficient in transient receptor potential channel activity with LTRPC3b and assessing their ability to grow would provide convincing evidence the LTRPC3b polypeptide has transient receptor potential channel activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a kidney, spinal cord, testis, and/or brain-specific promoter), or it can be expressed at a specified time of development using an inducible and/or a developmentally regulated promoter.

In the case of LTRPC3b transgenic mice or rats, if no phenotype is apparent in normal growth conditions, observing the organism under diseased conditions (renal, reproductive, neural, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal LTRPC3b deletion polypeptides are encompassed by the present invention: M1-T1566, Y2-T1566, V3-T1566, R4-T1566, V5-T1566, S6-T1566, F7-T1566, D8-T1566, T9-T1566, K10-T1566, P11-T1566, D12-T1566, L13-T1566, L14-T1566, L15-T1566, H16-T1566, L17-T1566, M18-T1566, T19-T1566, K20-T1566, E21-T1566, W22-T1566, Q23-T1566, L24-T1566, E25-T1566, L26-T1566, P27-T1566, K28-T1566, L29-T1566, L30-T1566, I31-T1566, S32-T1566, V33-T1566, H34-T1566, G35-T1566, G36-T1566, L37-T1566, Q38-T1566, N39-T1566, F40-T1566, E41-T1566, L42-T1566, Q43-T1566, P44-T1566, K45-T1566, L46-T1566, K47-T1566, Q48-T1566, V49-T1566, F50-T1566, G51-T1566, K52-T1566, G53-T1566, L54-T1566, I55-T1566, K56-T1566, A57-T1566, A58-T1566, M59-T1566, T60-T1566, T61-T1566, G62-T1566, A63-T1566, W64-T1566, I65-T1566, F66-T1566, T67-T1566, G68-T1566, G69-T1566, V70-T1566, N71-T1566, T72-T1566, G73-T1566, V74-T1566, I75-T1566, R76-T1566, H77-T1566, V78-T1566, G79-T1566, D80-T1566, A81-T1566, L82-T1566, K83-T1566, D84-T1566, H85-T1566, A86-T1566, S87-T1566, K88-T1566, S89-T1566, R90-T1566, G91-T1566, K92-T1566, I93-T1566, C94-T1566, T95-T1566, I96-T1566, G97-T1566, I98-T1566, A99-T1566, P100-T1566, W101-T1566, G102-T1566, I103-T1566, V104-T1566, E105-T1566, N106-T1566, Q107-T1566, E108-T1566, D109-T1566, L110-T1566, I111-T1566, G112-T1566, R113-T1566, D114-T1566, V115-T1566, V116-T1566, R117-T1566, P118-T1566, Y119-T1566, Q120-T1566, T121-T1566, M122-T1566, S123-T1566, N124-T1566, P125-T1566, M126-T1566, S127-T1566, K128-T1566, L129-T1566, T130-T1566, V131-T1566, L132-T1566, N133-T1566, S134-T1566, M135-T1566, H136-T1566, S137-T1566, H138-T1566, F139-T1566, I140-T1566, L141-T1566, A142-T1566, D143-T1566, N144-T1566, G145-T1566, T146-T1566, T147-T1566, G148-T1566, K149-T1566, Y150-T1566, G151-T1566, A152-T1566, E153-T1566, V154-T1566, K155-T1566, L156-T1566, R157-T1566, R158-T1566, Q159-T1566, L160-T1566, E161-T1566, K162-T1566, H163-T1566, I164-T1566, S165-T1566, L166-T1566, Q167-T1566, K168-T1566, I169-T1566, N170-T1566, T171-T1566, R172-T1566, I173-T1566, G174-T1566, Q175-T1566, G176-T1566, V177-T1566, P178-T1566, V179-T1566, V180-T1566, A181-T1566, L182-T1566, I183-T1566, V184-T1566, E185-T1566, G186-T1566, G187-T1566, P188-T1566, N189-T1566, V190-T1566, I191-T1566, S192-T1566, I193-T1566, V194-T1566, L195-T1566, E196-T1566, Y197-T1566, L198-T1566, R199-T1566, D200-T1566, T201-T1566, P202-T1566, P203-T1566, V204-T1566, P205-T1566, V206-T1566, V207-T1566, V208-T1566, C209-T1566, D210-T1566, G211-T1566, S212-T1566, G213-T1566, R214-T1566, A215-T1566, S216-T1566, D217-T1566, I218-T1566, L219-T1566, A220-T1566, F221-T1566, G222-T1566, H223-T1566, K224-T1566, Y225-T1566, S226-T1566, E227-

T1566, E228-T1566, G229-T1566, G230-T1566, L231-T1566, I232-T1566, N233-T1566, E234-T1566, S235-T1566, L236-T1566, R237-T1566, D238-T1566, Q239-T1566, L240-T1566, L241-T1566, V242-T1566, T243-T1566, I244-T1566, Q245-T1566, K246-T1566, T247-T1566, F248-T1566, T249-T1566, Y250-T1566, T251-T1566, R252-T1566, T253-T1566, Q254-T1566, A255-T1566, Q256-T1566, H257-T1566, L258-T1566, F259-T1566, I260-T1566, I261-T1566, L262-T1566, M263-T1566, E264-T1566, C265-T1566, M266-T1566, K267-T1566, K268-T1566, K269-T1566, E270-T1566, L271-T1566, I272-T1566, T273-T1566, V274-T1566, F275-T1566, R276-T1566, M277-T1566, G278-T1566, S279-T1566, E280-T1566, G281-T1566, H282-T1566, Q283-T1566, D284-T1566, I285-T1566, D286-T1566, L287-T1566, A288-T1566, I289-T1566, L290-T1566, T291-T1566, A292-T1566, L293-T1566, L294-T1566, K295-T1566, G296-T1566, A297-T1566, N298-T1566, A299-T1566, S300-T1566, A301-T1566, P302-T1566, D303-T1566, Q304-T1566, L305-T1566, S306-T1566, L307-T1566, A308-T1566, L309-T1566, A310-T1566, W311-T1566, N312-T1566, R313-T1566, V314-T1566, D315-T1566, I316-T1566, A317-T1566, R318-T1566, S319-T1566, Q320-T1566, I321-T1566, F322-T1566, I323-T1566, Y324-T1566, G325-T1566, Q326-T1566, Q327-T1566, W328-T1566, P329-T1566, V330-T1566, G331-T1566, S332-T1566, L333-T1566, E334-T1566, Q335-T1566, A336-T1566, M337-T1566, L338-T1566, D339-T1566, A340-T1566, L341-T1566, V342-T1566, L343-T1566, D344-T1566, R345-T1566, V346-T1566, D347-T1566, F348-T1566, V349-T1566, K350-T1566, L351-T1566, L352-T1566, I353-T1566, E354-T1566, N355-T1566, G356-T1566, V357-T1566, S358-T1566, M359-T1566, H360-T1566, R361-T1566, F362-T1566, L363-T1566, T364-T1566, I365-T1566, S366-T1566, R367-T1566, L368-T1566, E369-T1566, E370-T1566, L371-T1566, Y372-T1566, N373-T1566, T374-T1566, R375-T1566, H376-T1566, G377-T1566, P378-T1566, S379-T1566, N380-T1566, T381-T1566, L382-T1566, Y383-T1566, H384-T1566, L385-T1566, V386-T1566, R387-T1566, D388-T1566, V389-T1566, K390-T1566, K391-T1566, R392-T1566, E393-T1566, Y394-T1566, P395-T1566, G396-T1566, F397-T1566, G398-T1566, W399-T1566, I400-T1566, Y401-T1566, F402-T1566, and/or K403-T1566 of SEQ ID NO:4. Polynucleotide sequences encoding these polypeptides are also provided. The present invention also encompasses the use of these N-terminal LTRPC3b deletion polypeptides as immunogenic and/or antigenic epitopes as described elsewhere herein.

In preferred embodiments, the following C-terminal LTRPC3b deletion polypeptides are encompassed by the present invention: M1-T1566, M1-H1565, M1-K1564, M1-S1563, M1-E1562, M1-F1561, M1-S1560, M1-Q1559, M1-F1558, M1-A1557, M1-S1556, M1-T1555, M1-R1554, M1-S1553, M1-L1552, M1-R1551, M1-R1550, M1-M1549, M1-S1548, M1-L1547, M1-S1546, M1-D1545, M1-G1544, M1-R1543, M1-G1542, M1-E1541, M1-P1540, M1-K1539, M1-S1538, M1-S1537, M1-K1536, M1-S1535, M1-R1534, M1-Q1533, M1-F1532, M1-P1531, M1-N1530, M1-Q1529, M1-L1528, M1-S1527, M1-A1526, M1-T1525, M1-N1524, M1-R1523, M1-Q1522, M1-R1521, M1-D1520, M1-L1519, M1-K1518, M1-D1517, M1-S1516, M1-I1515, M1-S1514, M1-F1513, M1-S1512, M1-K1511, M1-R1510, M1-T1509, M1-H1508, M1-A1507, M1-Y1506, M1-P1505, M1-A1504, M1-S1503, M1-P1502, M1-E1501, M1-E1500, M1-A1499, M1-S1498, M1-Y1497, M1-S1496, M1-N1495, M1-A1494, M1-R1493, M1-E1492, M1-I1491, M1-K1490, M1-P1489, M1-V1488, M1-T1487, M1-I1486, M1-N1485, M1-N1484, M1-S1483, M1-L1482, M1-T1481, M1-R1480, M1-E1479, M1-S1478, M1-N1477, M1-D1476, M1-G1475, M1-E1474, M1-Q1473, M1-S1472, M1-S1471, M1-I1470, M1-A1469, M1-I1468, M1-T1467, M1-A1466, M1-R1465, M1-R1464, M1-G1463, M1-K1462, M1-A1461, M1-E1460, M1-N1459, M1-E1458, M1-E1457, M1-S1456, M1-D1455, M1-S1454, M1-S1453, M1-P1452, M1-H1451, M1-S1450, M1-L1449, M1-E1448, M1-A1447, M1-E1446, M1-R1445, M1-E1444, M1-P1443, M1-H1442, M1-C1441, M1-C1440, M1-T1439, M1-L1438, M1-D1437, M1-E1436, M1-V1435, M1-K1434, M1-D1433, M1-G1432, M1-L1431, M1-G1430, M1-G1429, M1-P1428, M1-F1427, M1-A1426, M1-A1425, M1-R1424, M1-D1423, M1-A1422, M1-I1421, M1-A1420, M1-Q1419, M1-P1418, M1-A1417, M1-N1416, M1-V1415, M1-C1414, M1-R1413, M1-T1412, M1-D1411, M1-I1410, M1-C1409, M1-D1408, M1-T1407, M1-I1406, M1-S1405, M1-T1404, M1-Y1403, M1-E1402, M1-A1401, M1-T1400, M1-K1399, M1-V1398, M1-P1397, M1-V1396, M1-G1395, M1-F1394, M1-N1393, M1-A1392, M1-Y1391, M1-Y1390, M1-S1389, M1-R1388, M1-S1387, M1-P1386, M1-S1385, M1-F1384, M1-M1383, M1-F1382, M1-S1381, M1-H1380, M1-S1379, M1-K1378, M1-V1377, M1-I1376, M1-P1375, M1-A1374, M1-E1373, M1-E1372, M1-L1371, M1-L1370, M1-F1369, M1-P1368, M1-T1367, M1-T1366, M1-A1365, M1-L1364, M1-Y1363, M1-R1362, M1-S1361, M1-S1360, M1-K1359, M1-S1358, M1-R1357, M1-E1356, M1-I1355, M1-T1354, M1-H1353, M1-Y1352, M1-M1351, M1-P1350, M1-P1349, M1-E1348, M1-S1347, M1-D1346, M1-W1345, M1-P1344, M1-N1343, M1-Q1342, M1-C1341, M1-E1340, M1-P1339, M1-L1338, M1-H1337, M1-T1336, M1-Y1335, M1-D1334, M1-S1333, M1-S1332, M1-F1331, M1-S1330, M1-R1329, M1-T1328, M1-D1327, M1-M1326, M1-S1325, M1-T1324, M1-I1323, M1-D1322, M1-E1321, M1-F1320, M1-D1319, M1-I1318, M1-S1317, M1-R1316, M1-S1315, M1-P1314, M1-P1313, M1-R1312, M1-D1311, M1-T1310, M1-P1309, M1-A1308, M1-L1307, M1-T1306, M1-A1305, M1-Y1304, M1-A1303, M1-S1302, M1-S1301, M1-S1300, M1-P1299, M1-A1298, M1-T1297, M1-S1296, M1-P1295, M1-V1294, M1-P1293, M1-T1292, M1-S1291, M1-F1290, M1-S1289, M1-P1288, M1-E1287, M1-G1286, M1-L1285, M1-G1284, M1-L1283, M1-I1282, M1-N1281, M1-V1280, M1-S1279, M1-N1278, M1-D1277, M1-L1276, M1-P1275, M1-D1274, M1-I1273, M1-D1272, M1-C1271, M1-H1270, M1-L1269, M1-E1268, M1-D1267, M1-M1266, M1-A1265, M1-S1264, M1-V1263, M1-Y1262, M1-I1261, M1-D1260, M1-I1259, M1-C1258, M1-S1257, M1-S1256, M1-P1255, M1-R1254, M1-R1253, M1-S1252, M1-D1251, M1-P1250, M1-V1249, M1-I1248, M1-A1247, M1-L1246, M1-T1245, M1-N1244, M1-A1243, M1-P1242, M1-A1241, M1-A1240, M1-P1239, M1-A1238, M1-K1237, M1-P1236, M1-E1235, M1-K1234, M1-A1233, M1-V1232, M1-S1231, M1-H1230, M1-S1229, M1-S1228, M1-T1227, M1-A1226, M1-R1225, M1-H1224, M1-L1223, M1-S1222, M1-L1221, M1-S1220, M1-R1219, M1-E1218, M1-K1217, M1-F1216, M1-I1215, M1-S1214, M1-E1213, M1-L1212, M1-K1211, M1-E1210, M1-I1209, M1-G1208, M1-G1207, M1-K1206, M1-D1205, M1-K1204, M1-M1203, M1-N1202, M1-V1201, M1-S1200, M1-Y1199, M1-F1198, M1-S1197, M1-H1196, M1-S1195, M1-R1194, M1-M1193, M1-R1192, M1-P191, M1-M1190, M1-L1189, M1-T1188, M1-P1187, M1-S1186, M1-T1185, M1-P1184, M1-S1183, M1-M1182, M1-T1181, M1-E1180, M1-E1179, M1-G1178, M1-A1177, M1-P1176, M1-D1175, M1-I1174, M1-S1173, M1-E1172, M1-Q1171, M1-L1170, M1-K1169, M1-F1168, M1-T1167, M1-N1166, M1-G1165, M1-E1164, M1-Q1163, M1-S1162, M1-N1161, M1-F1160, M1-S1159, M1-S1158, M1-Q1157, M1-R1156, M1-V1155, M1-I1154, M1-Y1153, M1-A1152, M1-A1151, M1-D1150, M1-T1149, M1-C1148, M1-D1147, M1-S1146, M1-S1145, M1-T1144, M1-R1143, M1-S1142, M1-R1141, M1-I1140, M1-K1139, M1-N1138, M1-S1137, M1-E1136, M1-A1135, M1-R1134, M1-E1133, M1-L1132, M1-G1131, M1-T1130, M1-L1129, M1-R1128, M1-E1127, M1-L1126, M1-A1125, M1-T1124, M1-A1123, M1-M1122, M1-R1121, M1-G1120, M1-I1119, M1-L1118, M1-D1117, M1-E1116, M1-L1115, M1-Q1114, M1-A1113, M1-L1112, M1-R1111, M1-I1110, M1-D1109, M1-V1108, M1-T1107, M1-Q1106, M1-L1105, M1-S1104, M1-A1103, M1-K1102, M1-M111, M1-S110, M1-H1099, M1-E1098, M1-R1097, M1-E1096, M1-N1095, M1-V1094, M1-E1093, M1-E1092, M1-L1091, M1-R1090, M1-M1089, M1-S1088, M1-M1087, M1-N1086, M1-E1085, M1-V1084, M1-R1083, M1-E1082, M1-S1081, M1-T1080, M1-V1079, M1-R1078, M1-I1077, M1-R1076, M1-E1075, M1-D1074, M1-N1073, M1-S1072, M1-S1071, M1-N1070, M1-F1069, M1-R1068, M1-D1067, M1-D1066, M1-K1065, M1-E1064, M1-R1063, M1-F1062, M1-Y1061, M1-E1060, M1-E1059, M1-I1058, M1-C1057, M1-Q1056, M1-E1055, M1-E1054, M1-F1053, M1-D1052, M1-H1051, M1-V1050, M1-K1049, M1-K1048, M1-L1047, M1-E1046, M1-D1045, M1-D1044, M1-T1043, M1-I1042, M1-F1041, M1-L1040, M1-K1039, M1-L1038, M1-G1037, M1-Y1036, M1-D1035, M1-R1034, M1-E1033, M1-D1032, M1-P1031, M1-D1030, M1-S1029, M1-E1028, M1-H1027, M1-K1026, M1-R1025, M1-W1024, M1-R1023, M1-C1022, M1-C1021, M1-L1020, M1-H1019, M1-Q1008, M1-F1017, M1-I1016, M1-M1015, M1-T1014, M1-M1013, M1-H1012, M1-S1011, M1-F1010, M1-I1009, M1-I1008, M1-L1007, M1-P1006, M1-P1005, M1-P1004, M1-L1003, M1-V1002, M1-P1001, M1-R1000, M1-E999, M1-H998, M1-F997, M1-T996, M1-M995, M1-I994, M1-L993, M1-Q992, M1-Y991, M1-R990, M1-Q989, M1-F988, M1-K987, M1-W986, M1-V985, M1-Q984, M1-N983, M1-S982, M1-I981, M1-S980, M1-K979, M1-V978, M1-E977, M1-F976, M1-F975, M1-T974, M1-N973, M1-N972, M1-F971, M1-V970, M1-A969, M1-I968, M1-L967, M1-L966, M1-N965, M1-V964, M1-L963, M1-L962, M1-I961, M1-N960, M1-A959, M1-V958, M1-L957, M1-L956, M1-Y955, M1-C954, M1-A953, M1-M952, M1-I951, M1-A950, M1-P949, M1-V948, M1-I947, M1-W946, M1-A945, M1-G944, M1-T943, M1-K942, M1-C941, M1-P940, M1-P939, M1-L938, M1-Q937, M1-I936, M1-I935, M1-K934, M1-G933, M1-D932, M1-E931, M1-R930, M1-T929, M1-E928, M1-N927, M1-Q926, M1-G925, M1-C924, M1-P923, M1-P922, M1-D921, M1-I920, M1-Q919, M1-D918, M1-A917, M1-F916, M1-V915, M1-E914, M1-G913, M1-Y912, M1-I911, M1-M910, M1-W909, M1-Y908, M1-P907, M1-M906, M1-Y905, M1-F904, M1-I903, M1-N902, M1-K901, M1-A900, M1-L899, M1-K898, M1-W897, M1-S896, M1-P895, M1-E894, M1-E893, M1-N892, M1-P891, M1-F890, M1-L889, M1-I888, M1-A887, M1-Q886, M1-R885, M1-A884, M1-V883, M1-G882, M1-F881, M1-S880, M1-M879, M1-L878, M1-V877, M1-V876, M1-L875, M1-M874, M1-I873, M1-I872, M1-V871, M1-F870, M1-Y869, M1-M868, M1-M867, M1-D866, M1-I865, M1-M864, M1-M863, M1-K862, M1-G861, M1-I860, M1-M859, M1-M858, M1-V857, M1-Y856, M1-P855, M1-G854, M1-L853, M1-Y852, M1-K851, M1-N850, M1-V849, M1-G848, M1-F847, M1-I846, M1-D845, M1-L844, M1-L843, M1-R842, M1-I841, M1-Y840, M1-W839, M1-Y838, M1-I837, M1-I836, M1-N835, M1-V834, M1-C833, M1-Y832, M1-I831, M1-V830, M1-R829, M1-G828, M1-D827, M1-S826, M1-R825, M1-F824, M1-P823, M1-Q822, M1-D821, M1-Q820, M1-L819, M1-R818, M1-L817, M1-I816, M1-M815, M1-G814, M1-V813, M1-S812, M1-F811, M1-L810, M1-L809, M1-I808, M1-A807, M1-I806, M1-L805, M1-D804, M1-T803, M1-V802, M1-N801, M1-W800, M1-Y799, M1-E798, M1-Q797, M1-L796, M1-W795, M1-V794, M1-K793, M1-V792, M1-K791, M1-Q790, M1-L789, M1-L788, M1-K787, M1-G786, M1-P785, M1-E784, M1-S783, M1-M782, M1-L781, M1-I780, M1-E779, M1-R778, M1-M777, M1-K776, M1-E775, M1-I774, M1-G773, M1-L772, M1-T771, M1-F770, M1-I769, M1-Y768, M1-S767, M1-I766, M1-V765, M1-I764, M1-W763, M1-E762, M1-Q761, M1-T760, M1-S759, M1-P758, M1-W757, M1-R756, M1-E755, M1-M754, M1-K753, M1-V752, M1-L751, M1-V750, M1-I749, M1-Y748, M1-N747, M1-F746, M1-L745, M1-M744, M1-L743, M1-Y742, M1-G741, M1-I740, M1-Y739, M1-A738, M1-L737, M1-T736, M1-Y735, M1-F734, M1-W733, M1-F732, M1-K731, M1-V730, M1-I729, M1-P728, M1-A727, M1-N726, M1-Y725, M1-F724, M1-E723, M1-Y722, M1-I721, M1-K720, M1-R719, M1-G718, M1-L717, M1-P716, M1-I715, M1-L714, M1-R713, M1-H712, M1-K711, M1-S710, M1-Q709, M1-V708, M1-E707, M1-E706, M1-E705, M1-D704, M1-K703, M1-K702, M1-R701, M1-S700, M1-S699, M1-E698, M1-G697, M1-N696, M1-N695, M1-R694, M1-G693, M1-L692, M1-M691, M1-A690, M1-T689, M1-L688, M1-E687, M1-M686, M1-D685, M1-E684, M1-E683, M1-E682, M1-K681, M1-E680, M1-K679, M1-T678, M1-P677, M1-K676, M1-E675, M1-P674, M1-E673, M1-E672, M1-A671, M1-E670, M1-K669, M1-E668, M1-Q667, M1-L666, M1-H665, M1-I664, M1-E663, M1-Q662, M1-A661, M1-Q660, M1-S659, M1-M658, M1-Y657, M1-P656, M1-M655, M1-D654, M1-D653, M1-K652, M1-N651, M1-K650, M1-F649, M1-E648, M1-L647, M1-S646, M1-L645, M-I644, M1-S643, M1-P642, M1-P641, M1-L640, M1-L639, M1-I638, M1-G637, M1-L636, M1-I635, M1-V634, M1-K633, M1-L632, M1-G631, M1-S630, M1-N629, M1-K628, M1-R627, M1-M626, M1-R625, M1-L624, M1-R623, M1-G622, M1-M621, M1-W620, M1-M619, M1-D618, M1-T617, M1-L616, M1-L615, M1-M614, M1-Q613, M1-S612, M1-C611, M1-T610, M1-H609, M1-A608, M1-I607, M1-F606, M1-D605, M1-R604, M1-H603, M1-K602, M1-A601, M1-A600, M1-V599, M1-A598, M1-L597, M1-Q596, M1-L595, M1-C594, M1-T593, M1-A592, M1-N591, M1-S590, M1-W589, M1-N588, M1-K587, M1-L586, M1-E585, M1-Y584, M1-T583, M1-L582, M1-L581, M1-K580, M1-M579, M1-A578, M1-L577, M1-Q576, M1-E575, M1-D574, M1-Q573, M1-K572, M1-Y571, M1-S570, M1-Q569, M1-D568, M1-L567, M1-L566, M1-E565, M1-V564, M1-A563, M1-L562, M1-Q561, M1-G560, M1-F559, M1-D558, M1-R557, M1-S556, M1-N555, M1-H554, M1-N553, M1-L552, M1-E551, M1-Q550, M1-S549, M1-I548, M1-D547, M1-D546, M1-V545, M1-M544, M1-D543, M1-N542, M1-E541, M1-S540, M1-A539, M1-E538, M1-H537, M1-A536, M1-M535, M1-A534, M1-K533, M1-C532, M1-L531, M1-K530, M1-C529, M1-A528, M1-V527, M1-L526, M1-A525, M1-K524, M1-A523, M1-M522, M1-A521, M1-E520, M1-E519, M1-G518, M1-H517, M1-Q516, M1-W515, M1-F514, M1-F513, M1-L512, M1-A511, M1-K510, M1-K509, M1-Q508, M1-R507, M1-K506, M1-M505, M1-L504, M1-V503, M1-A502, M1-W501, M1-V500, M1-M499, M1-L498, M1-E497, M1-H496, M1-F495, M1-P494, M1-F493, M1-P492, M1-F491, M1-H490, M1-N489, M1-I488, M1-E487, M1-P486, M1-D485, M1-D484, M1-L483, M1-D482, M1-I481, M1-D480, M1-V479, M1-E478, M1-E477, M1-E476, M1-R475, M1-K474, M1-K473, M1-T472, M1-T471, M1-K470, M1-R469, M1-G468, M1-R467, M1-R466, M1-L465, M1-P464, M1-I463, M1-D462, M1-D461, M1-E460, M1-M459, M1-G458, M1-L457, M1-L456, M1-K455, M1-L454, M1-A453, M1-K452, M1-P451, M1-R450, M1-K449, M1-P448, M1-G447, M1-F446, M1-L445, M1-N444, M1-H443, M1-Y442, M1-L441, M1-T440, M1-R439, M1-F438, M1-R437, M1-K436, M1-R435, M1-T434, M1-Y433, M1-N432, M1-C431, M1-R430, M1-Y429, M1-A428, M1-G427, M1-G426, M1-M425, M1-L424, M1-Y423, M1-E422, M1-I421, M1-V420, M1-L419, M1-G418, M1-I417, M1-D416, M1-I415, M1-L414, M1-S413, M1-I412, M1-R411, M1-Y410, M1-D409, M1-P408, M1-P407, M1-L406, M1-N405, M1-G404, M1-K403, M1-F402, M1-Y401, M1-I400, M1-W399, M1-G398, M1-F397, M1-G396, M1-P395, M1-Y394, M1-E393, M1-R392, and/or M1-K391 of SEQ ID NO:4. Polynucleotide sequences encoding these polypeptides are also provided. The present invention also encompasses the use of these C-terminal LTRPC3b deletion polypeptides as immunogenic and/or antigenic epitopes as described elsewhere herein.

Alternatively, preferred polypeptides of the present invention may comprise polypeptide sequences corresponding to, for example, internal regions of the LTRPC3b polypeptide (e.g., any combination of both N- and C-terminal LTRPC3b polypeptide deletions) of SEQ ID NO:4. For example, internal regions could be defined by the equation: amino acid NX to amino acid CX, wherein NX refers to any N-terminal deletion polypeptide amino acid of LTRPC3b (SEQ ID NO:4), and where CX refers to any C-terminal deletion polypeptide amino acid of LTRPC3b (SEQ ID NO:4). Polynucleotides encoding these polypeptides are also provided. The present invention also encompasses the use of these polypeptides as an immunogenic and/or antigenic epitope as described elsewhere herein.

The LTRPC3b polypeptides of the present invention were determined to comprise several phosphorylation sites based upon the Motif algorithm (Genetics Computer Group, Inc.). The phosphorylation of such sites may regulate some biological activity of the LTRPC3b polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the LTRPC3b polypeptide to associate with other potassium channel alpha subunits, beta subunits, or its ability to modulate potassium channel function.

Specifically, the LTRPC3b polypeptide was predicted to comprise two tyrosine phosphorylation sites using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or [RK]-x(3)-[DE]-x(2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Natl. Acad. Sci. U.S.A. 79:973-977 (1982); Hunter T., J. Biol. Chem. 257:4843-4848 (1982), and Cooper J. A., Esch F. S., Taylor S. S., Hunter T., J. Biol. Chem. 259:7835-7841(1984), which are hereby incorporated herein by reference.

In preferred embodiments, the following tyrosine phosphorylation site polypeptides are encompassed by the present invention: LSLEFKNKDDMPYMSQAQ (SEQ ID NO:110), and/or VMMIGKMMIDMMYFVIIM (SEQ ID NO:111). Polynucleotides encoding these polypeptides are also provided. The present invention also encompasses the use of these LTRPC3b tyrosine phosphorylation site polypeptides as immunogenic and/or antigenic epitopes as described elsewhere herein.

The LTRPC3b polypeptide was predicted to comprise twenty three PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. 260: 12492-12499 (1985); which are hereby incorporated by reference herein.

In preferred embodiments, the following PKC phosphorylation site polypeptides are encompassed by the present invention: ADNGTTGKYGAEV (SEQ ID NO:112), VVCDGSGRASDIL (SEQ ID NO:113), GLINESLRDQLLV (SEQ ID NO:114), YRCNYTRKRFRTL (SEQ ID NO:115), RRGRKTTKKREEE (SEQ ID NO:116), RGRKTTKKREEEV (SEQ ID NO:117), ELLDQSYKQDEQL (SEQ ID NO:118), RNNGESSRKKDEE (SEQ ID NO:119), NNGESSRKKDEEE (SEQ ID NO:120), PNEEPSWKLAKNI (SEQ ID NO:121), RIRVTSERVENMS (SEQ ID NO:122), RVENMSMRLEEVN (SEQ ID NO:123), NEREHSMKASLQT (SEQ ID NO:124), LERAESNKIRSRT (SEQ ID NO:125), SQEGNTFKLQESI (SEQ ID NO:126), AIVPDSRRPSSCI (SEQ ID NO:127), ATLAPTDRPPSRS (SEQ ID NO:128), IERSKSSRYLATT (SEQ ID NO:129), QEGDNSERTLSNN (SEQ ID NO:130), APYAHTRKSFSIS (SEQ ID NO:131), KSFSISDKLDRQR (SEQ ID NO:132), FQRSKSSKPEGRG (SEQ ID NO:133), and/or RGDSLSMRRLSRT (SEQ ID NO:134). Polynucleotides encoding these polypeptides are also provided. The present invention also encompasses the use of these LTRPC3b PKC phosphorylation site polypeptides as immunogenic and/or antigenic epitopes as described elsewhere herein.

The present invention also encompasses immunogenic and/or antigenic epitopes of the LTRPC3b polypeptide.

The LTRPC3b polypeptide has been shown to comprise twelve glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine phosphorylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673-702 (1972); Pless D. D., Lennarz W. J., Proc. Natl. Acad. Sci. U.S.A. 74:134-138 (1977); Bause E., Biochem. J. 209:331-336 (1983); Gavel Y., von Heijne G., Protein Eng. 3:433-442 (1990); and Miletich J. P., Broze G. J. Jr., J. Biol. Chem. 265:11397-11404 (1990).

In preferred embodiments, the following asparagine glycosylation site polypeptides are encompassed by the present invention: FILADNGTTGKYGA (SEQ ID NO:135), EGGLINESLRDQLL (SEQ ID NO:136), LLKGANASAPDQLS (SEQ ID NO:137), GAYRCNYTRKRFRT (SEQ ID NO:138), TYELKNWSNATCLQ (SEQ ID NO:139), LKNWSNATCLQLAV (SEQ ID NO:140), LQEYWNVTDLIAIL (SEQ ID NO:141), PPCGQNETREDGKI (SEQ ID NO:142), LIAVFNNTFFEVKS (SEQ ID NO:143), KDDRFNSSNDERIR (SEQ ID NO:144), SERVENMSMRLEEV (SEQ ID NO:145), and/or RTLSNNITVPKIER (SEQ ID NO:146). Polynucleotides encoding these polypeptides are also provided. The present invention also encompasses the use of these LTRPC3b asparagine glycosylation site polypeptides as immunogenic and/or antigenic epitopes as described elsewhere herein.

The LTRPC3b polypeptide has been shown to comprise one RGD cell attachment site domain according to the Motif algorithm (Genetics Computer Group, Inc.). The sequence Arg-Gly-Asp, found in fibronectin, is crucial for its interaction with its cell surface receptor, an integrin. What has been called the 'RGD' tripeptide is also found in the sequences of a number of other proteins, where it has been shown to play a role in cell adhesion. Non-limiting examples of these proteins are the following: some forms of collagens, fibrinogen, vitronectin, von Willebrand factor (VWF), snake disintegrins, and slime mold discoidins. The 'RGD' tripeptide is also found in other proteins where it may serve the same purpose. A consensus pattern for RGD cell attachment sites is the following: R-G-D. Additional information relating to RGD cell attachment site domains may be found in reference to the following publications, which are hereby incorporated by reference herein: Ruoslahti E., Pierschbacher M. D., Cell 44:517-518 (1986); and d'Souza S. E., Ginsberg M. H., Plow E. F., Trends Biochem. Sci. 16:246-250 (1991).

In preferred embodiments, the following RGD cell attachment site domain polypeptide is encompassed by the present invention: SKPEGRGDSLSMR (SEQ ID NO:108). Polynucleotides encoding these polypeptides are also provided. The present invention also encompasses the use of this RGD cell attachment site domain polypeptide as an immunogenic and/or antigenic epitope as described elsewhere herein.

The LTRPC3b polypeptide has been shown to comprise one aminoacyl-transfer RNA synthetases class-II domain according to the Motif algorithm (Genetics Computer Group, Inc.). Aminoacyl-tRNA synthetases (EC 6.1.1.-) are a group of enzymes which activate amino acids and transfer them to specific tRNA molecules as the first step in protein biosynthesis. In prokaryotic organisms there are at least twenty different types of aminoacyl-tRNA synthetases, one for each different amino acid. In eukaryotes there are generally two aminoacyl-tRNA synthetases for each different amino acid: one cytosolic form and a mitochondrial form. While all these enzymes have a common function, they are widely diverse in terms of subunit size and of quaternary structure.

The synthetases specific for alanine, asparagine, aspartic acid, glycine, histidine, lysine, phenylalanine, proline, serine, and threonine are referred to as class-II synthetases and probably have a common folding pattern in their catalytic domain for the binding of ATP and amino acid which is different to the Rossmann fold observed for the class I synthetases.

Class-II tRNA synthetases do not share a high degree of similarity, however at least three conserved regions are present.

The consensus pattern for aminoacyl-transfer RNA synthetases class-II domains are as follows: [FYH]-R-x-[DE]-x(4,12)-[RH]-x(3)-F-x(3)-[DE]; and [GSTALVF]-{DENQHRKP}-[GSTA]-[LIVMF]-[DE]-R-[LIVMF]-x-[LIVMSTAG]-[LIVMFY], where 'x' represents an intervening amino acid residue.

Additional information specific to aminoacyl-transfer RNA synthetases class-II domains may be found in reference to the following publications, Schimmel P., Annu. Rev. Biochem. 56:125-158 (1987); Delarue M., Moras D., BioEssays 15:675-687 (1993); Schimmel P., Trends Biochem. Sci. 16:1-3 (1991); Nagel G. M., Doolittle R. F., Proc. Natl. Acad. Sci. U.S.A. 88:8121-8125 (1991); Cusack S., Haertlein M., Leberman R., Nucleic Acids Res. 19:3489-3498 (1991); Cusack S., Biochimie 75:1077-1081 (1993); Cusack S., Berthet-Colominas C., Haertlein M., Nassar N., Leberman R., Nature 347:249-255 (1990); and Leveque F., Plateau P., Dessen P., Blanquet S., Nucleic Acids Res. 18:305-312 (1990); which are hereby incorporated herein by reference in their entirety.

In preferred embodiments, the following aminoacyl-transfer RNA synthetases class-II domain polypeptide is encompassed by the present invention: LIGRMATALERLTGLERAES (SEQ ID NO:107). Polynucleotides encoding these polypeptides are also provided. The present invention also encompasses the use of this RGD cell attachment site domain polypeptide as an immunogenic and/or antigenic epitope as described elsewhere herein.

The LTRPC3b polypeptide has been shown to comprise three amidation sites according to the Motif algorithm (Genetics Computer Group, Inc.). The precursor of hormones and other active peptides which are C-terminally amidated is always directly followed by a glycine residue which provides the amide group, and most often by at least two consecutive basic residues (Arg or Lys) which generally function as an active peptide precursor cleavage site. Although all amino acids can be amidated, neutral hydrophobic residues such as Val or Phe are good substrates, while charged residues such as Asp or Arg are much less reactive. A consensus pattern for amidation sites is the following: x-G-[RK]-[RK], wherein "X" represents the amidation site. Additional information relating to asparagine glycosylation may be found in reference to the following publications, which are hereby incorporated by reference herein: Kreil G., Meth. Enzymol. 106: 218-223(1984); and Bradbury A. F., Smyth D. G., Biosci. Rep. 7:907-916 (1987).

In preferred embodiments, the following amidation site polypeptides are encompassed by the present invention: DIPLRRGRKTTKKR (SEQ ID NO:147), HRLIPLGRKIYEFY (SEQ ID NO:148), and/or EENEAKGRRATIAI (SEQ ID NO:149). Polynucleotides encoding these polypeptides are also provided. The present invention also encompasses the use of these LTRPC3b amidation site polypeptides as immunogenic and/or antigenic epitopes as described elsewhere herein.

Many polynucleotide sequences, such as EST sequences, are publicly available and accessible through sequence databases. Some of these sequences are related to SEQ ID NO:3 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 4687 of SEQ ID NO:3, b is an integer between 15 to 4701, where both a and b correspond to the positions of nucleotide residues shown in SEQ ID NO:3, and where b is greater than or equal to a+14.

Features of the Polypeptide Encoded by Gene No:3

The polypeptide of this gene provided as SEQ ID NO:6 (FIGS. 3A-F), encoded by the polynucleotide sequence according to SEQ ID NO:5 (FIGS. 3A-F), and/or encoded by the polynucleotide contained within the deposited clone, LTRPC3c, has significant homology at the nucleotide and amino acid level to the human melastatin 1 protein (Melastatin1; Genbank Accession No. gi|3243075; SEQ ID NO:11). An alignment of the LTRPC3c polypeptide with this protein is provided in FIGS. 5A-D.

The LTRPC3c polypeptide was determined to share 65.4% identity and 73.1% similarity with the human melastatin 1 protein (Melastatin1; Genbank Accession No. gi|3243075; SEQ ID NO:11) as shown in FIG. 8.

The LTRPC3c protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain. This family is commonly referred to as the transient receptor potential channel (TRP) family. Melastatin1 defines a separate subfamily of TRP channels referred to as TRPM (melastatin1). TRPM family members are characteristic of their unusually long cytoplasmic tails at both ends of the channel domain and some of the family members contain an enzyme domain at the C-terminal region. Thus, LTRPC3 represents a novel member of the TRPM subfamily.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the melastatin1 protein, in addition to, other transient receptor potential channel family members referenced elsewhere herein or otherwise known in the art.

Most of the known transient receptor potential channel family members, possess one or more transmembrane domains. Likewise, the LTRPC3c polypeptide has been determined to comprise six transmembrane domains (TM1-TM6) as shown in FIGS. 3A-F. The transmembrane domains are located from about amino acid 620 to about amino acid 637 (TM1), from about amino acid 717 to about amino acid 734 (TM2), from about amino acid 790 to about amino acid 803 (TM3), from about amino acid 817 to about amino acid 834 (TM4), from about amino acid 851 to about amino acid 868 (TM5), and/or from about amino acid 950 to about amino acid 970 (TM6) of SEQ ID NO:6. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKVILGILLPPSILSLEF (SEQ ID NO:38), IVKFW-FYTLAYIGYLMLF (SEQ ID NO:39), VTDLIAILLFS-VGM (SEQ ID NO:40), RVIYCVNIIYWYIRLLDI (SEQ ID NO:41), MMIDMMYFVIIMLVVLMS (SEQ ID NO:42), and/or AIMACYLLVANILLVNLLIAV (SEQ ID NO:43). Polynucleotides encoding these polypeptides are also provided. The present invention also encompasses the use of the LTRPC3c transmembrane polypeptides as immunogenic and/or antigenic epitopes as described elsewhere herein.

The present invention also encompasses polypeptides corresponding to the regions between each transmembrane domain of LTRPC3c, referred to herein as inter-transmembrane domain polypeptides (inter TM1-2, inter TM2-3, inter TM3-4, inter TM4-5, and inter TM5-6). Such regions are typically solvent accessible (either extracellularly or intracellularly). Therefore, these regions are amenable to the development of agonists and/or antagonists to the LTRPC3c polypeptide, particularly for the development of antibodies specific to these regions.

In preferred embodiments, the following inter-transmembrane domain polypeptides are encompassed by the present invention: KNKDDMPYMSQAQEIHLQEKEAEEPE-KPTKEKEEEDMELTAMLGRNNGESS RKKDEEEVQSKHRLIPLGRKIYEFYNAP (SEQ ID NO:150), NYIVLVKMERWPSTQEWIVISYIFTLG-IEKMREILMSEPGKLLQKVKVWLQEY WN (SEQ ID NO:151), ILRLQDQPFRSDG (SEQ ID NO:152), FGVNKYLGPYVMMIGK (SEQ ID NO:153), and/or FGVARQAILFPNEEPSWKLAKNIFYMPY-WMIYGEVFADQIDRKQVYDSHTPK SAPCGQN-ETREDGKIIQLPPCKTGAWIVP (SEQ ID NO:154). Polynucleotides encoding these polypeptides are also provided. The present invention also encompasses the use of the LTRPC3c inter-transmembrane polypeptides as immunogenic and/or antigenic epitopes as described elsewhere herein.

In preferred embodiments, the following N-terminal LTRPC3c inter TM1-2 domain deletion polypeptides are encompassed by the present invention: K1-P79, N2-P79, K3-P79, D4-P79, D5-P79, M6-P79, P7-P79, Y8-P79, M9-P79, S10-P79, Q11-P79, A12-P79, Q13-P79, E14-P79, I15-P79, H16-P79, L17-P79, Q18-P79, E19-P79, K20-P79, E21-P79, A22-P79, E23-P79, E24-P79, P25-P79, E26-P79, K27-P79, P28-P79, T29-P79, K30-P79, E31-P79, K32-P79, E33-P79, E34-P79, E35-P79, D36-P79, M37-P79, E38-P79, L39-P79, T40-P79, A41-P79, M42-P79, L43-P79, G44-P79, R45-P79, N46-P79, N47-P79, G48-P79, E49-P79, S50-P79, S51-P79, R52-P79, K53-P79, K54-P79, D55-P79, E56-P79, E57-P79, E58-P79, V59-P79, Q60-P79, S61-P79, K62-P79, H63-P79, R64-P79, L65-P79, I66-P79, P67-P79, L68-P79, G69-P79, R70-P79, K71-P79, I72-P79, and/or Y73-P79 of SEQ ID NO:150. Polynucleotide sequences encoding these polypeptides are also provided. The present invention also encompasses the use of these N-terminal LTRPC3c inter TM1-2 domain deletion polypeptides as immunogenic and/or antigenic epitopes as described elsewhere herein.

In preferred embodiments, the following C-terminal LTRPC3c inter TM1-2 domain deletion polypeptides are encompassed by the present invention: K1-P79, K1-A78, K1-N77, K1-Y76, K1-F75, K1-E74, K1-Y73, K1-I72, K1-K71, K1-R70, K1-G69, K1-L68, K1-P67, K1-I66, K1-L65, K1-R64, K1-H63, K1-K62, K1-S61, K1-Q60, K1-V59, K1-E58, K1-E57, K1-E56, K1-D55, K1-K54, K1-K53, K1-R52, K1-S51, K1-S50, K1-E49, K1-G48, K1-N47, K1-N46, K1-R45, K1-G44, K1-L43, K1-M42, K1-A41, K1-T40, K1-L39, K1-E38, K1-M37, K1-D36, K1-E35, K1-E34, K1-E33, K1-K32, K1-E31, K1-K30, K1-T29, K1-P28, K1-K27, K1-E26, K1-P25, K1-E24, K1-E23, K1-A22, K1-E21, K1-K20, K1-E19, K1-Q18, K1-L17, K1-H16, K1-I15, K1-E14, K1-Q13, K1-A12, K1-Q11, K1-S10, K1-M9, K1-Y8, and/or K1-P7 of SEQ ID NO:150. Polynucleotide sequences encoding these polypeptides are also provided. The present invention also encompasses the use of these C-terminal LTRPC3c inter TM1-2 domain deletion polypeptides as immunogenic and/or antigenic epitopes as described elsewhere herein.

In preferred embodiments, the following N-terminal LTRPC3c inter TM2-3 domain deletion polypeptides are encompassed by the present invention: F1-N56, N2-N56, Y3-N56, I4-N56, V5-N56, L6-N56, V7-N56, K8-N56, M9-N56, E10-N56, R11-N56, W12-N56, P13-N56, S14-N56, T15-N56, Q16-N56, E17-N56, W18-N56, I19-N56, V20-N56, I21-N56, S22-N56, Y23-N56, I24-N56, F25-N56, T26-N56, L27-N56, G28-N56, I29-N56, E30-N56, K31-N56, M32-N56, R33-N56, E34-N56, I35-N56, L36-N56, M37-N56, S38-N56, E39-N56, P40-N56, G41-N56, K42-N56, L43-N56, L44-N56, Q45-N56, K46-N56, V47-N56, K48-N56, V49-N56, and/or W50-N56 of SEQ ID NO:151. Polynucleotide sequences encoding these polypeptides are also provided. The present invention also encompasses the use of these N-terminal LTRPC3c inter TM2-3 domain deletion polypeptides as immunogenic and/or antigenic epitopes as described elsewhere herein.

In preferred embodiments, the following C-terminal LTRPC3c inter TM2-3 domain deletion polypeptides are encompassed by the present invention: F1-N56, F1-W55, F1-Y54, F1-E53, F1-Q52, F1-L51, F1-W50, F1-V49, F1-K48, F1-V47, F1-K46, F1-Q45, F1-L44, F1-L43, F1-K42, F1-G41, F1-P40, F1-E39, F1-S38, F1-M37, F1-L36, F1-I35, F1-E34, F1-R33, F1-M32, F1-K31, F1-E30, F1-I29, F1-G28, F1-L27, F1-T26, F1-F25, F1-I24, F1-Y23, F1-S22, F1-I21, F1-V20, F1-I19, F1-W18, F1-E17, F1-Q16, F1-T15, F1-S14, F1-P13, F1-W12, F1-R11, F1-E10, F1-M9, F1-K8, and/or F1-V7 of SEQ ID NO:151. Polynucleotide sequences encoding these polypeptides are also provided. The present invention also encompasses the use of these C-terminal LTRPC3c inter TM2-3 domain deletion polypeptides as immunogenic and/or antigenic epitopes as described elsewhere herein.

In preferred embodiments, the following N-terminal LTRPC3c inter TM3-4 domain deletion polypeptides are encompassed by the present invention: I1-G13, L2-G13, R3-G13, L4-G13, Q5-G13, D6-G13, and/or Q7-G13 of SEQ ID NO:152. Polynucleotide sequences encoding these polypeptides are also provided. The present invention also encompasses the use of these N-terminal LTRPC3c inter TM3-4 domain deletion polypeptides as immunogenic and/or antigenic epitopes as described elsewhere herein.

In preferred embodiments, the following C-terminal LTRPC3c inter TM3-4 domain deletion polypeptides are encompassed by the present invention: I1-G13, I1-D12, I1-S11, I1-R10, I1-F9, I1-P8, and/or I1-Q7 of SEQ ID NO:152. Polynucleotide sequences encoding these polypeptides are also provided. The present invention also encompasses the use of these C-terminal LTRPC3c inter TM3-4 domain deletion polypeptides as immunogenic and/or antigenic epitopes as described elsewhere herein.

In preferred embodiments, the following N-terminal LTRPC3c inter TM4-5 domain deletion polypeptides are encompassed by the present invention: F1-K16, G2-K16, V3-K16, N4-K16, K5-K16, Y6-K16, L7-K16, G8-K16, P9-K16, and/or Y10-K16 of SEQ ID NO:153. Polynucleotide sequences encoding these polypeptides are also provided. The present invention also encompasses the use of these N-terminal LTRPC3c inter TM4-5 domain deletion polypeptides as immunogenic and/or antigenic epitopes as described elsewhere herein.

In preferred embodiments, the following C-terminal LTRPC3c inter TM4-5 domain deletion polypeptides are encompassed by the present invention: F1-K16, F1-G15, F1-I14, F1-M13, F1-M12, F1-V11, F1-Y10, F1-P9, F1-G8, and/or F1-L7 of SEQ ID NO:153. Polynucleotide sequences encoding these polypeptides are also provided. The present invention also encompasses the use of these C-terminal LTRPC3c inter TM4-5 domain deletion polypeptides as immunogenic and/or antigenic epitopes as described elsewhere herein.

In preferred embodiments, the following N-terminal LTRPC3c inter TM5-6 domain deletion polypeptides are encompassed by the present invention: F1-P81, G2-P81, V3-P81, A4-P81, R5-P81, Q6-P81, A7-P81, I8-P81, L9-P81, F10-P81, P11-P81, N12-P81, E13-P81, E14-P81, P15-P81, S16-P81, W17-P81, K18-P81, L19-P81, A20-P81, K21-P81, N22-P81, I23-P81, F24-P81, Y25-P81, M26-P81, P27-P81, Y28-P81, W29-P81, M30-P81, I31-P81, Y32-P81, G33-P81, E34-P81, V35-P81, F36-P81, A37-P81, D38-P81, Q39-P81, I40-P81, D41-P81, R42-P81, K43-P81, Q44-P81, V45-P81, Y46-P81, D47-P81, S48-P81, H49-P81, T50-P81, P51-P81, K52-P81, S53-P81, A54-P81, P55-P81, C56-P81, G57-P81, Q58-P81, N59-P81, E60-P81, T61-P81, R62-P81, E63-P81, D64-P81, G65-P81, K66-P81, I67-P81, I68-P81, Q69-P81, L70-P81, P71-P81, P72-P81, C73-P81, K74-P81, and/or T75-P81 of SEQ ID NO:154. Polynucleotide sequences encoding these polypeptides are also provided. The present invention also encompasses the use of these N-terminal LTRPC3c inter TM5-6 domain deletion polypeptides as immunogenic and/or antigenic epitopes as described elsewhere herein.

In preferred embodiments, the following C-terminal LTRPC3c inter TM5-6 domain deletion polypeptides are encompassed by the present invention: F1-P81, F1-V80, F1-I79, F1-W78, F1-A77, F1-G76, F1-T75, F1-K74, F1-C73, F1-P72, F1-P71, F1-L70, F1-Q69, F1-I68, F1-I67, F1-K66, F1-G65, F1-D64, F1-E63, F1-R62, F1-T61, F1-E60, F1-N59, F1-Q58, F1-G57, F1-C56, F1-P55, F1-A54, F1-S53, F1-K52, F1-P51, F1-T50, F1-H49, F1-S48, F1-D47, F1-Y46, F1-V45, F1-Q44, F1-K43, F1-R42, F1-D41, F1-I40, F1-Q39, F1-D38, F1-A37, F1-F36, F1-V35, F1-E34, F1-G33, F1-Y32, F1-I31, F1-M30, F1-W29, F1-Y28, F1-P27, F1-M26, F1-Y25, F1-F24, F1-I23, F1-N22, F1-K21, F1-A20, F1-L19, F1-K18, F1-W17, F1-S16, F1-P15, F1-E14, F1-E13, F1-N12, F1-P11, F1-F10, F1-L9, F1-I8, and/or F1-A7 of SEQ ID NO:154. Polynucleotide sequences encoding these polypeptides are also provided. The present invention also encompasses the use of these C-terminal LTRPC3c inter TM5-6 domain deletion polypeptides as immunogenic and/or antigenic epitopes as described elsewhere herein.

The LTRPC3c polypeptide was determined to comprise several conserved cysteines, at amino acid 94, 210, 265, 419, 517, 582, 599. 821, 941, 1057, 1148, and 1414 of SEQ ID No: 2 (FIGS. 1A-F). Conservation of cysteines at key amino acid residues is indicative of conserved structural features, which may correlate with conservation of protein function and/or activity.

In confirmation of the LTRPC3c representing a member of the transient receptor channel family, the LTRPC3c polypeptide was determined to comprise a predicted TRP domain (EWKFAR) located from about amino acid 985 to about amino acid 990 of SEQ ID NO:6. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following TRP domain polypeptide is encompassed by the present invention: VWKFQR (SEQ ID NO:155). Polynucleotides encoding this polypeptide are also provided. The present invention also encompasses the use of this LTRPC3c TRP domain polypeptide as an immunogenic and/or antigenic epitope as described elsewhere herein.

In further confirmation of the LTRPC3c representing a member of the transient receptor channel family, the LTRPC3c polypeptide was determined to comprise a predicted ion transport signature domain located at about amino acid 760 to about amino acid 971 of SEQ ID NO:6. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following ion transport signature domain polypeptide is encompassed by the present invention: LGIEKMREILMSEPGKLLQKVKVWLQEYWNVTDLIAILLFSVGMILRLQDQPF RSDGRVIYCVNIIYWYIRLLDIFGVNKYLGPYVMMIGKM-MIDMMYFVIIMLV VLMSFGVARQAILFPNEEPSWKLAKNI-FYMPYWMIYGEVFADQIDRKQVYDS HTPK-SAPCGQNETREDGKIIQLPPCKTGAWIV-PAIMACYLLVANILLVNLLIAV F (SEQ ID NO:156). Polynucleotides encoding this polypeptide are also provided. The present invention also encompasses the use of this LTRPC3c ion transport signature domain polypeptide as an immunogenic and/or antigenic epitope as described elsewhere herein.

The LTRPC3c polypeptide was determined to comprise a predicted coiled-coil domain located at about amino acid 1075 to about amino acid 1129 of SEQ ID NO:6. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following coiled-coil domain polypeptide is encompassed by the present invention: ERIRVTSERVENMSMRLEEVNEREH-SMKASLQTVDIRLAQLEDLIGRMATAL ERL (SEQ ID NO:157). Polynucleotides encoding this polypeptide are also provided. The present invention also encompasses the use of this LTRPC3c coiled-coil domain polypeptide as an immunogenic and/or antigenic epitope as described elsewhere herein.

The present invention is also directed to polynucleotides comprising at least about 39 nt of the polynucleotide sequence provided as SEQ ID NO:5. Specifically, the present invention is directed to a polynucleotide sequence comprising nucleotides from about nucleotide 1174 to about nucleotide 1212; nucleotides from about nucleotide 1174 to about nucleotide 1215; nucleotides from about nucleotide 1168 to about nucleotide 1209; nucleotides from about nucleotide 1165 to about nucleotide 1209; of SEQ ID NO:5; and/or nucleotides from about nucleotide 1162 to about nucleotide 1209. In this context "about" includes the particularly recited value, a value larger or smaller by several (5, 4, 3, 2, or 1) nucleotides, at either terminus, or at both termini.

The present invention is also directed to polypeptides comprising at least about 13 amino acids of the polypeptides sequence provided as SEQ ID NO:6. Specifically, the present invention is directed to a polypeptides sequence comprising amino acids from about amino acid 2728 to about amino acid 2766; amino acids from about amino acid 2728 to about amino acid 2769; amino acids from about amino acid 2728 to about amino acid 2772; amino acids from about amino acid 2725 to about amino acid 2766; amino acids from about amino acid 2722 to about amino acid 2766; and/or amino acids from about amino acid 2719 to about amino acid 2766 of SEQ ID NO:6. In this context "about" includes the particularly recited value, a value larger or smaller by several (5, 4, 3, 2, or 1) nucleotides, at either terminus, or at both termini.

LTRPC3c polypeptides and polynucleotides are useful for diagnosing diseases related to the over and/or under expression of LTRPC3c by identifying mutations in the LTRPC3c gene using LTRPC3c sequences as probes or by determining LTRPC3c protein or mRNA expression levels. LTRPC3c polypeptides will be useful in screens for compounds that affect the activity of the protein. LTRPC3c peptides can also be used for the generation of specific antibodies and as bait in yeast two hybrid screens to find proteins the specifically interact with LTRPC3c.

LTRPC3b polypeptides and polynucleotides are useful for diagnosing diseases related to the over and/or under expression of LTRPC3b by identifying mutations in the LTRPC3b gene using LTRPC3b sequences as probes or by determining LTRPC3b protein or mRNA expression levels. LTRPC3b polypeptides will be useful in screens for compounds that affect the activity of the protein. LTRPC3b peptides can also be used for the generation of specific antibodies and as bait in yeast two hybrid screens to find proteins the specifically interact with LTRPC3b.

Consistent with LTRPC3 representing a transient receptor potential channel, immunohistochemical experiments have shown that LTRPC3 localizes to the cell membrane (see FIG. 17 and Example 6). Specifically, the complete open reading frame of LTRPC3 with a C-terminal HA tag was transiently transfected into HEK 293 cells to assess its cellular localization. The HA-tagged LTRPC3 was detected using a fluorescein-conjugated anti-HA antibody and a laser scanning confocal microscope which produces a green fluorescent signal. The green fluorescent signal was exclusively detected at the subplasma membrane region of the transfected cells (see FIG. 17), which is consistent with LTRPC3 being an integral membrane protein. Under these conditions approximately ~70% of cells are expressing LTRPC3. The expression of full-length protein was accessed with immunoblot using an anti-HA antibody and detected as the expected size of ~170 kD (data not shown). Cellular localization of the LTRPC3c splice variant is expected to be similarly localized to the subplasma membrane region.

Moreover, physiometric studies have shown that LTRPC3 is a functional $Ca^{2+}$ permeable channel (see FIGS. 18 and 19, and Example 7). LTRPC3 function was assessed using a Fluorometric Imaging Plate Reader (FLIPR™) that measures real-time intracellular fluorescence changes. Cells transiently transfected with vector or LTRPC3-HA were loaded with the cytoplasmic $Ca^{2+}$ indicator Fluoro-4 in a 1 mM $Ca^{2+}$ solution. Addition of $Ca^{2+}$ to the media resulted in a concentration-dependent influx of $Ca^{2+}$ into LTRPC3-expressing cells (FIG. 18; right panels), indicating that LTRPC3 is a functional $Ca^{2+}$ channel. In contrast, vector-transfected cells showed minimal $Ca^{2+}$ influx under the same experimental conditions (FIG. 18, left panels). The non-transfected cells were indistinguishable from the vector-transfected cells (data not shown). Therefore, LTRPC3 is a constitutively active channel capable of mediating $Ca^{2+}$ influx. The $Ca^{2+}$ influx activity of the LTRPC3c splice variants is expected to be similar to LTRPC3.

To further address the mechanism of LTRPC3-mediated $Ca^{2+}$ entry, similar $Ca^{2+}$ addition experiments were performed on transfected cells incubated (~30 min) in a nominally $Ca^{2+}$-free solution. Previous studies have shown that lowering extracellular $Ca^{2+}$ concentration below physiological levels can deplete intracellular $Ca^{2+}$ stores in many cell types including HEK 293 (EMBO J. 17, 4274-4282, (1998)). Incubating vector-transfected HEK 293 cells in a nominally $Ca^{2+}$-free solution gave rise to $Ca^{2+}$ entry that was dependent on the concentration of $Ca^{2+}$ added to the buffers, indicating $Ca^{2+}$ influx was mediated through endogenous SOCs in HEK293 cells (FIG. 18, left panels). In LTRPC3 cells, the $Ca^{2+}$ transients triggered by similar $Ca^{2+}$ treatment were much larger (FIG. 18, right panels). This $Ca^{2+}$ entry observed in LTRPC3 cells incubated in $Ca^{2+}$-free media were greater than those observed in 1 mM $Ca^{2+}$ media, indicating that LTRPC3-mediated $Ca^{2+}$ entry can be potentiated by the store-depletion. The store-depletion potentiation of LTRPC3-mediated $Ca^{2+}$ entry is expected to be similar for the LTRPC3c splice variant.

The store-operated mechanism of LTRPC3-mediated $Ca^{2+}$ influx was tested further by passively depleting $Ca^{2+}$ stores with thapsigargin (TG), an inhibitor of microsomal $Ca^{2+}$ ATPases that pumps ions from the cytosol back into the stores. Addition of 2 µM thapsigargin equivalently depleted $Ca^{2+}$ stores in LTRPC3-HA- and vector-transfected cells (FIG. 19A). Following store depletion with TG, addition of $Ca^{2+}$ to the buffer induced a much larger $Ca^{2+}$ entry in LTRPC3 cells compared to the vector control cells. The increased $Ca^{2+}$ entry of LTRPC3 cells, relative to non-LTRPC3 transfected cells, post store depletion with TG is expected to be similar for the LTRPC3c splice variant.

Receptor-mediated $Ca^{2+}$ entry was also more pronounced in LTRPC3-HA-transfected cells. Carbachol (CCh) can activate an endogenous muscarinic receptor and trigger $IP_3$ production, leading to store-depletion in HEK 293 cells. The addition of 50 µM of CCh caused a transient and rapid intracellular $Ca^{2+}$ increase in both LTRPC3- and vector-transfected cells (FIG. 19B). After the store depletion with CCh, adding of $Ca^{2+}$ to the buffer induced a much larger influx of $Ca^{2+}$ into LTRPC3 cells, as compared to vector control cells. These results show that after store depletion with TG or CCh LTRPC3-transfected cells exhibit an increased $Ca^{2+}$ influx when compared to control cells. The increased $Ca^{2+}$ entry of LTRPC3 cells, relative to non-LTRPC3 transfected cells, post store depletion with TG or CCh is expected to be similar for the LTRPC3c splice variant.

The lanthanides, gadolinium ($Gd^{3+}$) and lanthanum ($La^{3+}$), are nonselective $Ca^{2+}$-permeable channel blockers, often used as part of the characterization of overexpressed TRP channels. Both lanthanides blocked LTRPC3 $Ca^{2+}$ conductance, although $La^{3+}$ was more potent (FIG. 19C). In the presence of 1 mM $Ca^{2+}$ in which endogenous SOCs is minimally activated (FIG. 18A), pre-treatment with 100 µM of $La^{3+}$ and $Gd^{3+}$ blocked LTRPC3 $Ca^{2+}$ currents, stimulated by adding 10 mM $Ca^{2+}$, by 67 and 39%, respectively. These results indicated that LTRPC3 mediated currents are not non-specific leak currents resulting from protein overexpression.

LTRPC3 is constitutively active but can be potentiated by store-depletion and is partially sensitive to $La^{3+}$ and $Gd^{3+}$ blockade. LTRPC3 is believed to represent the first member of the TRPM subfamily that exhibits this store-operated mechanism, although some members of TRPC subfamily have been considered for this role. TRPM1 and TRPM4a are constitutive $Ca^{2+}$ permeable channels but it is unclear whether they can be stimulated by store-depletion (Proc. Natl. Acad. Sci. U.S.A. 98, 10692-10697, (2001)). Distinct from TRPM4a, TRPM4b is directly activated by changes in intracellular $Ca^{2+}$ without significant permeation of $Ca^{2+}$ (Cell 109, 397-401, (2002)). TRPM2 is activated by ADP-ribose, NAD and changes in redox status (Nature 411, 595-599, (2001); Science 293, 1327-1330, (2001); and Mol. Cell 9, 163-173, (2002)). TRPM7 is regulated by $Mg^{2+}$-ATP and/or $PIP_2$ (Science 291, 1043-1047, (2001); Nature 411, 690-695, (2001); and Nat. Cell Biol. 4, 329-36 (2002)). TRPM8 is activated by cold temperatures and cooling agents (Nature 416, 52-58, (2002); and Cell 108, 705-715, (2002)). Therefore, in conjunction with its fairly restricted tissue expression, which is not observed with any other family members, LTRPC3 may have a unique biological function in human.

Expression profiling designed to measure the steady state mRNA levels encoding the LTRPC3 polypeptide showed predominately high expression levels in kidney. The LTRPC3 polypeptide was also significantly expression in spinal cord, testis, and brain (as shown in FIG. 6).

Moreover, Northern hybridizations of the LTRPC3 mRNA confirmed the predominately high expression levels in kidney, and significant expression levels in testis, and brain (as shown in FIG. 7). The Northern hybridization was not performed on spinal cord tissue.

Expanded analysis of LTRPC3 expression levels by Taq-Man™ quantitative PCR (see FIG. 12) confirmed that the LTRPC3 polypeptide is expressed in kidney, brain, testis (FIGS. 6 and 7), although higher expression levels were observed in brain than previously appreciated. LTRPC3 mRNA was expressed predominately in the brain, specifically the cerebellum, choroid plexus, the locus coeruleus, the posterior hypothalamus and the substantia nigra. Expression of LTRPC3 was also significantly expressed in the kidney, with higher levels observed in the cortex than in the medulla or pelvis. LTRPC3 was also significantly expressed in the spinal cord, testis, and to a lesser extent in other tissues as shown.

Therefore, LTRPC3c polynucleotides and polypeptides, including modulators or fragments thereof, may be useful in treating, diagnosing, prognosing, and/or preventing a variety of neurological conditions, in particular various choroid plexus neoplasms, choroid plexus papilloma, Alzheimer's disease, prion disorders and multiple sclerosis and movement disorders that involve the cerebellum. Based upon the expression pattern of LTRPC3 in kidney, this novel TRP family member, or a splice variant or polymorphism thereof, may also be the cause solitary metastasis in the choroid plexus, a rare type of carcinoma. For example, it has been shown that out of 15 cases of solitary metastasis of the choroid plexus, five originated from renal cell carcinoma (Neurol. Med. Chir. (Tokyo) 1997 December; 37(12):916-9). Additionally, given the rather selective expression of LTRPC3 in the choroid plexus and renal tissues, it may be possible that altered function of LTRPC3 or a splice variant or polymorphism thereof, may be responsible for solitary metastasis and renal carcinoma. LTRPC3 polynucleotides and polypeptides, including modulators or fragments thereof, may be useful in treating, diagnosing, prognosing, and/or preventing a variety of renal disorders, particularly solitary metastasis in the choroid plexus, and renal carcinoma.

Moreover, an additional analysis of LTRPC3 expression levels by TaqMan™ quantitative PCR (see FIG. 13) in disease cells and tissues indicated that the LTRPC3 polypeptide is differentially expressed in renal, testicular, and ovarian tumor tissues. In the renal tumor tissue results, an average of 2 out of 3 matched samples, which represent 3 out of 4 samples total, showed a significant decrease in LTRPC3 steady state RNA levels in tumor compared to control samples. In the testicular tumor tissue results, differential expression of LTRPC3 in testicular cancers was observed with all 5 tumor samples showing a significant reduction in steady-state RNA levels compared to two control samples. In the ovarian tumor tissue results, differential expression of LTRPC3 in ovarian cancers was observed with 3 tumor samples showing a significant reduction in steady-state RNA levels compared to five control samples.

The differential expression of LTRPC3 in tumors relative to normal tissues suggests that loss of LTRPC3 expression during tumor progression might contribute to the metastatic process by altering internal calcium stores in a manner that reflects a loss of cellular control on apoptosis. Restoring LTRPC3c function might provide a novel therapeutic approach to treating certain cancers. Therefore, LTRPC3c polynucleotides and polypeptides, including modulators or fragments thereof, particularly agonists of LTRPC3c activity or expression, may be useful in treating, diagnosing, prognosing, ameloriating, and/or preventing a variety of cancers and proliferative conditions, particularly of the kidney, testis, and ovaries.

Characterization of the LTRPC3 polypeptide of the present invention using antisense oligonucleotides led to the determination that LTRPC3 is involved in the negative modulation of the FEN1 DNA base-excision repair/proliferation modulating protein as described in Example 5 herein.

Specifically, antisense inhibition of LTRPC3 resulted in upregulation of Fen1, a marker of proliferation. As such, LTRPC3 behaves in a manner similar to a tumor suppressor, in that loss results in increases in proliferation. While some increases in the proliferation markers p21 and IkB were also observed, they were less significant, and could be a response to the pro-proliferative effect of LTRPC3 antisense inhibition. Interestingly, expression of LTRPC3 was also observed to be significantly reduced in tumor tissues, relative to normal tissues (see FIG. 13). Specifically, renal, testicular, and ovarian tumor samples showed as much as 12 to 30 fold down regulation of LTRPC3 message levels compared to normal tissues. This reduction of LTRPC3 correlating with the tumor state is consistent with the negative FEN1 modulatory activity and suggests this gene may have antiproliferative activities. Therefore, for modulators of LTRPC3 to be useful for treating cancer, it would be necessary to increase the activity of the gene or gene product in order to have the reverse effect on cancerous cells. Thus, an agonist of LTRPC3 activity or a compound that increased LTRPC3 message levels would be a desired invention for cancer therapy. The same regimen may also be applicable to LTRPC3 splice variants and/or polymorphisms, such as LTRPC3c.

In preferred embodiments, LTRPC3c polynucleotides and polypeptides, including fragments and modulators thereof, are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, LTRPC3c polynucleotides and polypeptides, including fragments and modulators thereof, are useful for increasing mammalian base excision repair activity, increasing mammalian single-nucleotide base excision repair activity, and/or increasing mammalian long patch base excision repair activity.

In preferred embodiments, antagonists directed against LTRPC3c are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, antagonists directed against LTRPC3c are useful for increasing mammalian base excision repair activity, increasing mammalian single-nucleotide base excision repair activity, and/or increasing mammalian long patch base excision repair activity.

In preferred embodiments, agonists directed against LTRPC3c are useful for treating, diagnosing, and/or ameliorating, disorders related to aberrant signal transduction, proliferating disorders, and/or cancers, particularly renal cell carcinomas, testicular cancers, and/or ovarian cancers.

The strong homology to human transient receptor potential channels (TRP), combined with the predominate localized expression in kidney tissue of LTRPC3 suggests the LTRPC3c polynucleotides and polypeptides, including modulators or fragments thereof, may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention, slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome.for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H., Willems, P, H., Bindels, R, J. J. Biol, Chem., 274(13):8375-8, (1999)).

Thus, the LTRPC3c polynucleotides and polypeptides are expected to share at least some biological activity with TRP family members expressed in kidney cells and tissues, particularly those specifically referenced herein.

The strong homology to human transient receptor potential channels (TRP) proteins, combined with the localized expression in spinal cord and brain of LTRPC3 suggests the LTRPC3c polynucleotides and polypeptides, including modulators or fragments thereof, may be useful in treating, diagnosing, prognosing, and/or preventing neurodegenerative disease states, behavioral disorders, or inflammatory conditions. Representative uses are described in the "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong homology to human transient receptor potential channels (TRP), combined with the localized expression in testis tissue of LTRPC3 emphasizes the potential utility for LTRPC3c polynucleotides and polypeptides in treating, diagnosing, prognosing, and/or preventing testicular, in addition to reproductive disorders.

In preferred embodiments, LTRPC3c polynucleotides and polypeptides including agonists and fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The LTRPC3c polynucleotides and polypeptides including agonists and fragments thereof, may also have uses related to modulating testicular development, embryogenesis, reproduction, and in ameliorating, treating, and/or preventing testicular proliferative disorders (e.g., cancers, which include, for example, choriocarcinoma, Non-seminoma, seminona, and testicular germ cell tumors).

Likewise, the localized expression in testis tissue also emphasizes the potential utility for LTRPC3c polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Bimbaumer, L, Lett., 373(3):193-8, (1995)); and TRPC1 (Wes, P, D., Chevesich, J., Jeromin, A., Rosenberg, C., Stetten, G., Montell, C, Proc, Natl, Acad, Sci, U,S,A., 92(21):9652-6, (1995)).

Thus, the LTRPC3c polynucleotides and polypeptides are expected to share at least some biological activity with TRP family members expressed in testis cells and tissues, particularly those specifically referenced herein.

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosensitivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

In preferred embodiments, LTRPC3c polynucleotides and polypeptides of the present invention, including agonists and/or fragments thereof, have uses that include, modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity.

In more preferred embodiments, LTRPC3c polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

LTRPC3c polynucleotides and polypeptides of the present invention, including agonists and/or fragments may be involved in intracellular $Ca^{2+}$ homeostasis which affects various aspects of biological functions including mechano-regulation, pain transduction, vasorelaxation, gene expression, cell cycle and proliferation/apoptosis. Since LTRPC3c is dominantly expressed in kidney, it may particularly play an important role in regulating cytosolic Ca2+ in the renal system, potentially $Ca^{2+}$ absorption.

The LTRPC3c gene maps to chromosome 9q21.11-21.31 between the two markers D9S1874 and D9S1807. This region is linked to amyotrophic lateral sclerosis with frontotemporal dementia, early-onset pulverulent cataract, infantile nephronophthisis, hypomagnesemia with secondary hypocalcemia (HSH), and familial hemophagocytic lymphohistiocytosis. Therefore, agonists and/or antagonists of the novel LTRPC3c can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in $Ca^{2+}$ homeostasis including osteoporosis, hypercalciuric stone disease, and chronic renal failure.

Moreover, given the selective expression in kidney, LTRPC3c could be considered a candidate gene for HSH, since the phenotype is a renal insufficiency. LTRPC3c chromosomal location is ~600 kb downstream of a X;9 translocation breakpoint interval described for one patient with HSH (*Hum. Mol. Genet.* 6, 1491-1497, (1997)). Recently, two groups reported that a new member of the TRPM subfamily, TRPM6, expressed in both intestinal tissues and kidney, is associated with HSH (*Nat. Genet.* 31, 166-170, (2002); and *Nat. Genet.* 31, 171-174 (2002)). Indeed, LTRPC3 is ~4 mb 5' to TRPM6 on 9q21. Although TRPM6 is the first component identified for HSH, this should not preclude involvement of LTRPC3c in the disease. Therefore, it is possible that LTRPC3c may co-localize with TRPM6 and/or forms a heteromultimer with TRPM6 in the kidney.

The kidney plays a major role in $Ca^{2+}$ homeostasis (reviewed in *Physiol. Rev.* 75, 429-471, (1995)). LTRPC3c may play a direct role in $Ca^{2+}$ absorption due to its constitutive $Ca^{2+}$ permeability. Alternatively, LTRPC3c may be the SOC that regulates $Ca^{2+}$ absorption. In kidney, $Ca^{2+}$ absorption is regulated by agonists such as calcitonin, parathyroid hormone and parathyroid hormone-related peptide through their respective G protein-coupled receptors, and downstream SOCs. Additionally, in kidney a SOC has been described (*J. Biol. Chem.* 276, 25759-25765, (2001)) for the action of angiotensin II, a vasoactive peptide that plays a major role in regulating blood pressure.

In addition, LTRPC3c polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++ sensitive signaling pathways, the activation of kinase-activatible proteins, and the activation of kinase-dependent signaling pathways.

The LTRPC3c polynucleotides and polypeptides of the present invention, including agonists and/or fragments thereof, have uses that include modulating proliferation, differentiation, migration, and activation in various cells, tissues, and organisms, and particularly in mammalian kidney, spinal cord, testis, and brain, preferably human. LTRPC3c polynucleotides and polypeptides of the present invention, including agonists and/or fragments thereof, may be useful in diagnosing, treating, prognosing, and/or preventing renal, neural, and/or proliferative diseases or disorders, particularly of the renal system.

In addition, antagonists of the LTRPC3c polynucleotides and polypeptides, including modulators or fragments thereof, may have uses that include diagnosing, treating, prognosing, and/or preventing diseases or disorders related to transient receptor potential channel activity, which may include renal, neural, reproductive, and/or proliferative diseases or disorders.

Although it is believed the encoded polypeptide may share at least some biological activities with transient receptor potential channel family members, particularly those melastatin1, a number of methods of determining the exact biological function of this clone are either known in the art or are described elsewhere herein. Briefly, the function of this clone may be determined by applying microarray methodology. Nucleic acids corresponding to the LTRPC3c polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known transient potential receptor inhibitors, which include, but are not limited to the drugs listed herein or otherwise known in the art, might indicate a function in modulating transient potential receptor function, for example. In the case of LTRPC3c, kidney, spinal cord, testis, and brain, should be used to extract RNA to prepare the probe.

In addition, the function of the protein may be assessed by applying quantitative PCR methodology, for example. Real time quantitative PCR would provide the capability of following the expression of the LTRPC3c gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:5 (FIGS. 3A-F).

The function of the protein may also be assessed through complementation assays in yeast. For example, in the case of the LTRPC3c, transforming yeast deficient in transient receptor potential channel activity with LTRPC3c and assessing their ability to grow would provide convincing evidence the LTRPC3c polypeptide has transient receptor potential channel activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a kidney, spinal cord, testis, and/or brain-specific promoter), or it can be expressed at a specified time of development using an inducible and/or a developmentally regulated promoter.

In the case of LTRPC3c transgenic mice or rats, if no phenotype is apparent in normal growth conditions, observing the organism under diseased conditions (renal, reproductive, neural, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal LTRPC3c deletion polypeptides are encompassed by the present invention: M1-T1566, Y2-T1566, V3-T1566, R4-T1566, V5-T1566, S6-T1566, F7-T1566, D8-T1566, T9-T1566, K10-T1566, P11-T1566, D12-T1566, L13-T1566, L14-T1566, L15-T1566, H16-T1566, L17-T1566, M18-T1566, T19-T1566, K20-T1566, E21-T1566, W22-T1566, Q23-T1566, L24-T1566, E25-T1566, L26-T1566, P27-T1566, K28-T1566, L29-T1566, L30-T1566, I31-T1566, S32-T1566, V33-T1566, H34-T1566, G35-T1566, G36-T1566, L37-T1566, Q38-T1566, N39-T1566, F40-T1566, E41-T1566, L42-T1566, Q43-T1566, P44-T1566, K45-T1566, L46-T1566, K47-T1566, Q48-T1566, V49-T1566, F50-T1566, G51-T1566, K52-T1566, G53-T1566, L54-T1566, I55-T1566, K56-T1566, A57-T1566, A58-T1566, M59-T1566, T60-T1566, T61-T1566, G62-T1566, A63-T1566, W64-T1566, I65-T1566, F66-T1566, T67-T1566, G68-T1566, G69-T1566, V70-T1566, N71-T1566, T72-T1566, G73-T1566, V74-T1566, I75-T1566, R76-T1566, H77-T1566, V78-T1566, G79-T1566, D80-T1566, A81-T1566, L82-T1566, K83-T1566, D84-T1566, H85-T1566, A86-T1566, S87-T1566, K88-T1566, S89-T1566, R90-T1566, G91-T1566, K92-T1566, I93-T1566, C94-T1566, T95-T1566, I96-T1566, G97-T1566, I98-T1566, A99-T1566, P100-T1566, W101-T1566, G102-T1566, I103-T1566, V104-T1566, E105-T1566, N106-T1566, Q107-T1566, E108-T1566, D109-T1566, L110110-T1566, I11-T1566, G112-T1566, R113-T1566, D114-T1566, V115-T1566, V116-T1566, R117-T1566, P118-T1566, Y119-T1566, Q120-T1566, T121-T1566, M122-T1566, S123-T1566, N124-T1566, P125-T1566, M126-T1566, S127-T1566, K128-T1566, L129-T1566, T130-T1566, V131-T1566, L132-T1566, N133-T1566, S134-T1566, M135-T1566, H136-T1566, S137-T1566, H138-T1566, F139-T1566, I140-T1566, L141-T1566, A142-T1566, D143-T1566, N144-T1566, G145-T1566, T146-T1566, T147-T1566, G148-T1566, K149-T1566, Y150-T1566, G151-T1566, A152-T1566, E153-T1566, V154-T1566, K155-T1566, L156-T1566, R157-T1566, R158-T1566, Q159-T1566, L160-T1566, E161-T1566, K162-T1566, H163-T1566, I164-T1566, S165-T1566, L166-T1566, Q167-T1566, K168-T1566, I169-T1566, N170-T1566, T171-T1566, R172-T1566, I173-T1566, G174-T1566, Q175-T1566, G176-T1566, V177-T1566, P178-T1566, V179-T1566, V180-T1566, A181-T1566, L182-T1566, I183-T1566, V184-T1566, E185-T1566, G186-T1566, G187-T1566, P188-T1566, N189-T1566, V190-T1566, I191-T1566, S192-T1566, I193-T1566, V194-T1566, L195-T1566, E196-T1566, Y197-T1566, L198-T1566, R199-T1566, D200-T1566, T201-T1566, P202-T1566, P203-T1566, V204-T1566, P205-T1566, V206-T1566, V207-T1566, V208-T1566, C209-T1566, D210-T1566, G211-T1566, S212-T1566, G213-T1566, R214-T1566, A215-T1566, S216-T1566, D217-T1566, I218-T1566, L219-T1566, A220-T1566, F221-T1566, G222-T1566, H223-T1566, K224-T1566, Y225-T1566, S226-T1566, E227-T1566, E228-T1566, G229-T1566, G230-T1566, L231-T1566, I232-T1566, N233-T1566, E234-T1566, S235-T1566, L236-T1566, R237-T1566, D238-T1566, Q239-T1566, L240-T1566, L241-T1566, V242-T1566, T243-T1566, I244-T1566, Q245-T1566, K246-T1566, T247-T1566, F248-T1566, T249-T1566, Y250-T1566, T251-T1566, R252-T1566, T253-T1566, Q254-T1566, A255-T1566, Q256-T1566, H257-T1566, L258-T1566, F259-T1566, I260-T1566, I261-T1566, L262-T1566, M263-T1566, E264-T1566, C265-T1566, M266-T1566, K267-T1566, K268-T1566, K269-T1566, E270-T1566, L271-T1566, I272-T1566, T273-T1566, V274-T1566, F275-T1566, R276-T1566, M277-T1566, G278-T1566, S279-T1566, E280-T1566, G281-T1566, H282-T1566, Q283-T1566, D284-T1566, I285-T1566, D286-T1566, L287-T1566, A288-T1566, I289-T1566, L290-T1566, T291-T1566, A292-T1566, L293-T1566, L294-T1566, K295-T1566, G296-T1566, A297-T1566, N298-T1566, A299-T1566, S300-T1566, A301-T1566, P302-T1566, D303-T1566, Q304-T1566, L305-T1566, S306-T1566, L307-T1566, A308-T1566, L309-T1566, A310-T1566, W311-T1566, N312-T1566, R313-T1566, V314-T1566, D315-T1566, I316-T1566, A317-T1566, R318-T1566, S319-T1566, Q320-T1566, I321-T1566, F322-T1566, I323-T1566, Y324-T1566, G325-T1566, Q326-T1566, Q327-T1566, W328-T1566, P329-T1566, V330-T1566, G331-T1566, S332-T1566, L333-T1566, E334-T1566, Q335-T1566, A336-T1566, M337-T1566, L338-T1566, D339-T1566, A340-T1566, L341-T1566, V342-T1566, L343-T1566, D344-T1566, R345-T1566, V346-T1566, D347-T1566, F348-T1566, V349-T1566, K350-T1566, L351-T1566, L352-T1566, I353-T1566, E354-T1566, N355-T1566, G356-T1566, V357-T1566, S358-T1566, M359-T1566, H360-T1566, R361-T1566, F362-T1566, L363-T1566, T364-T1566, I365-T1566, S366-T1566, R367-T1566, L368-T1566, E369-T1566, E370-T1566, L371-T1566, Y372-T1566, N373-T1566, T374-T1566, R375-T1566, H376-T1566, G377-T1566, P378-T1566, S379-T1566, N380-T1566, T381-T1566, L382-T1566, Y383-T1566, H384-T1566, L385-T1566, V386-T1566, R387-T1566, D388-T1566, V389-T1566, K390-T1566, K391-T1566, G392-T1566, N393-T1566, L394-T1566, P395-T1566, P396-T1566, D397-T1566, Y398-T1566, R399-T1566, I400-T1566, S401-T1566, L402-T1566, I403-T1566, D404-T1566, I405-T1566, G406-T1566, L407-T1566, V408-T1566, I409-T1566, E410-T1566, Y411-T1566, L412-T1566, M413-T1566, G414-T1566, G415-T1566, A416-T1566, Y417-T1566, R418-T1566, C419-T1566, N420-T1566, Y421-T1566, T422-T1566, R423-T1566, K424-T1566, R425-T1566, F426-T1566, R427-T1566, T428-T1566, L429-T1566, Y430-T1566, H431-T1566, N432-T1566, L433-T1566, F434-T1566, G435-T1566, P436-T1566, K437-T1566, R438-T1566, P439-T1566, K440-T1566, A441-T1566, L442-T1566, K443-T1566, L444-T1566, L445-T1566, G446-T1566, M447-T1566, E448-T1566, D449-T1566, D450-T1566, I451-T1566, P452-T1566, L453-T1566, R454-T1566, R455-T1566, G456-T1566, R457-T1566, K458-T1566, T459-T1566, T460-T1566, K461-T1566, K462-T1566, R463-T1566, E464-T1566, E465-T1566, E466-T1566, V467-T1566, D468-T1566, I469-T1566, D470-T1566, L471-T1566, D472-T1566, D473-T1566, P474-T1566, E475-T1566, I476-T1566, N477-T1566, H478-T1566, F479-T1566, P480-T1566, F481-T1566, P482-T1566, F483-T1566, H484-T1566, E485-T1566, L486-T1566, M487-T1566, V488-T1566, W489-T1566, A490-T1566, V491-T1566, L492-T1566, M493-T1566, K494-T1566, R495-

T1566, Q496-T1566, K497-T1566, M498-T1566, A499-T1566, L500-T1566, F501-T1566, F502-T1566, W503-T1566, Q504-T1566, H505-T1566, G506-T1566, E507-T1566, E508-T1566, A509-T1566, M510-T1566, A511-T1566, K512-T1566, A513-T1566, L514-T1566, V515-T1566, A516-T1566, C517-T1566, K518-T1566, L519-T1566, C520-T1566, K521-T1566, A522-T1566, M523-T1566, A524-T1566, H525-T1566, E526-T1566, A527-T1566, S528-T1566, E529-T1566, N530-T1566, D531-T1566, M532-T1566, V533-T1566, D534-T1566, D535-T1566, I536-T1566, S537-T1566, Q538-T1566, E539-T1566, L540-T1566, N541-T1566, H542-T1566, N543-T1566, S544-T1566, R545-T1566, D546-T1566, F547-T1566, G548-T1566, Q549-T1566, L550-T1566, A551-T1566, V552-T1566, E553-T1566, L554-T1566, L555-T1566, D556-T1566, Q557-T1566, S558-T1566, Y559-T1566, K560-T1566, Q561-T1566, D562-T1566, E563-T1566, Q564-T1566, L565-T1566, A566-T1566, M567-T1566, K568-T1566, L569-T1566, L570-T1566, T571-T1566, Y572-T1566, E573-T1566, L574-T1566, K575-T1566, N576-T1566, W577-T1566, S578-T1566, N579-T1566, A580-T1566, T581-T1566, C582-T1566, L583-T1566, Q584-T1566, L585-T1566, A586-T1566, V587-T1566, A588-T1566, A589-T1566, K590-T1566, H591-T1566, R592-T1566, D593-T1566, F594-T1566, I595-T1566, A596-T1566, H597-T1566, T598-T1566, C599-T1566, S600-T1566, Q601-T1566, M602-T1566, L603-T1566, L604-T1566, T605-T1566, D606-T1566, M607-T1566, W608-T1566, M609-T1566, G610-T1566, R611-T1566, L612-T1566, R613-T1566, M614-T1566, R615-T1566, K616-T1566, N617-T1566, S618-T1566, G619-T1566, L620-T1566, K621-T1566, V622-T1566, I623-T1566, L624-T1566, G625-T1566, I626-T1566, L627-T1566, L628-T1566, P629-T1566, P630-T1566, S631-T1566, I632-T1566, L633-T1566, S634-T1566, L635-T1566, E636-T1566, F637-T1566, K638-T1566, N639-T1566, K640-T1566, D641-T1566, D642-T1566, M643-T1566, P644-T1566, Y645-T1566, M646-T1566, S647-T1566, Q648-T1566, A649-T1566, Q650-T1566, E651-T1566, I652-T1566, H653-T1566, L654-T1566, Q655-T1566, E656-T1566, K657-T1566, E658-T1566, A659-T1566, E660-T1566, E661-T1566, P662-T1566, E663-T1566, K664-T1566, P665-T1566, T666-T1566, K667-T1566, E668-T1566, K669-T1566, E670-T1566, E671-T1566, E672-T1566, D673-T1566, M674-T1566, E675-T1566, L676-T1566, T677-T1566, A678-T1566, M679-T1566, L680-T1566, G681-T1566, R682-T1566, N683-T1566, N684-T1566, G685-T1566, E686-T1566, S687-T1566, S688-T1566, R689-T1566, K690-T1566, K691-T1566, D692-T1566, E693-T1566, E694-T1566, E695-T1566, V696-T1566, Q697-T1566, S698-T1566, K699-T1566, H700-T1566, R701-T1566, L702-T1566, I703-T1566, P704-T1566, L705-T1566, G706-T1566, R707-T1566, K708-T1566, I709-T1566, Y710-T1566, E711-T1566, F712-T1566, Y713-T1566, N714-T1566, A715-T1566, P716-T1566, I717-T1566, V718-T1566, K719-T1566, F720-T1566, W721-T1566, F722-T1566, Y723-T1566, T724-T1566, L725-T1566, A726-T1566, Y727-T1566, I728-T1566, G729-T1566, Y730-T1566, L731-T1566, M732-T1566, L733-T1566, F734-T1566, N735-T1566, Y736-T1566, I737-T1566, V738-T1566, L739-T1566, V740-T1566, K741-T1566, M742-T1566, E743-T1566, R744-T1566, W745-T1566, P746-T1566, S747-T1566, T748-T1566, Q749-T1566, E750-T1566, W751-T1566, I752-T1566, V753-T1566, I754-T1566, S755-T1566, Y756-T1566, I757-T1566, F758-T1566, T759-T1566, L760-T1566, G761-T1566, I762-T1566, E763-T1566, K764-T1566, M765-T1566, R766-T1566, E767-T1566, I768-T1566, L769-T1566, M770-T1566, S771-T1566, E772-T1566, P773-T1566, G774-T1566, K775-T1566, L776-T1566, L777-T1566, Q778-T1566, K779-T1566, V780-T1566, K781-T1566, V782-T1566, W783-T1566, L784-T1566, Q785-T1566, E786-T1566, Y787-T1566, W788-T1566, N789-T1566, V790-T1566, T791-T1566, D792-T1566, L793-T1566, I794-T1566, A795-T1566, I796-T1566, L797-T1566, L798-T1566, F799-T1566, S800-T1566, V801-T1566, G802-T1566, M803-T1566, I804-T1566, L805-T1566, R806-T1566, L807-T1566, Q808-T1566, D809-T1566, Q810-T1566, P811-T1566, F812-T1566, R813-T1566, S814-T1566, D815-T1566, G816-T1566, R817-T1566, V818-T1566, I819-T1566, Y820-T1566, C821-T1566, V822-T1566, N823-T1566, I824-T1566, I825-T1566, Y826-T1566, W827-T1566, Y828-T1566, I829-T1566, R830-T1566, L831-T1566, L832-T1566, D833-T1566, I834-T1566, F835-T1566, G836-T1566, V837-T1566, N838-T1566, K839-T1566, Y840-T1566, L841-T1566, G842-T1566, P843-T1566, Y844-T1566, V845-T1566, M846-T1566, M847-T1566, I848-T1566, G849-T1566, K850-T1566, M851-T1566, M852-T1566, I853-T1566, D854-T1566, M855-T1566, M856-T1566, Y857-T1566, F858-T1566, V859-T1566, I860-T1566, I861-T1566, M862-T1566, L863-T1566, V864-T1566, V865-T1566, L866-T1566, M867-T1566, S868-T1566, F869-T1566, G870-T1566, V871-T1566, A872-T1566, R873-T1566, Q874-T1566, A875-T1566, I876-T1566, L877-T1566, F878-T1566, P879-T1566, N880-T1566, E881-T1566, E882-T1566, P883-T1566, S884-T1566, W885-T1566, K886-T1566, L887-T1566, A888-T1566, K889-T1566, N890-T1566, I891-T1566, F892-T1566, Y893-T1566, M894-T1566, P895-T1566, Y896-T1566, W897-T1566, M898-T1566, I899-T1566, Y900-T1566, G901-T1566, E902-T1566, V903-T1566, F904-T1566, A905-T1566, D906-T1566, Q907-T1566, I908-T1566, D909-T1566, R910-T1566, K911-T1566, Q912-T1566, V913-T1566, Y914-T1566, D915-T1566, S916-T1566, H917-T1566, T918-T1566, P919-T1566, K920-T1566, S921-T1566, and/or A922-T1566 of SEQ ID NO:6. Polynucleotide sequences encoding these polypeptides are also provided. The present invention also encompasses the use of these N-terminal LTRPC3c deletion polypeptides as immunogenic and/or antigenic epitopes as described elsewhere herein.

In preferred embodiments, the following C-terminal LTRPC3c deletion polypeptides are encompassed by the present invention: M1-T1566, M1-H1565, M1-K1564, M1-S1563, M1-E1562, M1-F1561, M1-S1560, M1-Q1559, M1-F1558, M1-A1557, M1-S1556, M1-T1555, M1-R1554, M1-S1553, M1-L1552, M1-R1551, M1-R1550, M1-M1549, M1-S1548, M1-L1547, M1-S1546, M1-D1545, M1-G1544, M1-R1543, M1-G1542, M1-E1541, M1-P1540, M1-K1539, M1-S1538, M1-S1537, M1-K1536, M1-S1535, M1-R1534, M1-Q1533, M1-F1532, M1-P1531, M1-N1530, M1-Q1529, M1-L1528, M1-S1527, M1-A1526, M1-T1525, M1-N1524, M1-R1523, M1-Q1522, M1-R1521, M1-D1520, M1-L1519, M1-K1518, M1-D1517, M1-S1516, M1-I1515, M1-S1514, M1-F1513, M1-S1512, M1-K1511, M1-R1510, M1-T1509, M1-H1508, M1-A1507, M1-Y1506, M1-P1505, M1-A1504, M1-S1503, M1-P1502, M1-E1501, M1-E1500, M1-A1499, M1-S1498, M1-Y1497, M1-S1496, M1-N1495, M1-A1494, M1-R1493, M1-E1492, M1-I1491, M1-K1490, M1-P1489, M1-V1488, M1-T1487, M1-I1486, M1-N1485, M1-N1484, M1-S1483, M1-L1482, M1-T1481, M1-R1480, M1-E1479, M1-S1478, M1-N1477, M1-D1476, M1-G1475, M1-E1474, M1-Q1473, M1-S1472, M1-S1471, M1-I1470, M1-A1469, M1-I1468, M1-T1467, M1-A1466, M1-R1465, M1-R1464, M1-G1463, M1-K1462, M1-A1461, M1-E1460, M1-N1459, M1-E1458, M1-E1457, M1-S1456, M1-D1455, M1-S1454, M1-S1453, M1-P1452, M1-H1451, M1-S1450, M1-L1449, M1-E1448, M1-A1447, M1-E1446, M1-R1445, M1-E1444, M1-P1443, M1-H1442, M1-C1441, M1-C1440, M1-T1439, M1-L1438, M1-D1437, M1-E1436, M1-V1435, M1-K1434, M1-D1433, M1-G1432, M1-L1431, M1-G1430, M1-G1429, M1-P1428, M1-F1427, M1-A1426, M1-A1425, M1-R1424, M1-D1423, M1-A1422, M1-I1421, M1-A1420, M1-Q1419, M1-P1418, M1-A1417, M1-N1416, M1-V1415, M1-C1414, M1-R1413, M1-T1412, M1-D1411, M1-I1410, M1-C1409, M1-D1408, M1-T1407, M1-I1406, M1-S1405, M1-T1404, M1-Y1403, M1-E1402, M1-A1401, M1-T1400, M1-K1399, M1-V1398, M1-P1397, M1-V1396, M1-G1395, M1-F1394, M1-N1393, M1-A1392, M1-Y1391, M1-Y1390, M1-S1389, M1-R1388, M1-S1387, M1-P1386, M1-S1385, M1-F1384, M1-M1383, M1-F1382, M1-S1381, M1-H1380, M1-S1379, M1-K1378, M1-V1377, M1-I1376, M1-P1375, M1-A1374, M1-E1373, M1-E1372, M1-L1371, M1-L1370, M1-F1369, M1-P1368, M1-T1367, M1-T1366, M1-A1365, M1-L1364, M1-Y1363, M1-R1362, M1-S1361, M1-S1360, M1-K1359, M1-S1358, M1-R1357, M1-E1356, M1-I1355, M1-T1354, M1-H1353, M1-Y1352, M1-M1351, M1-P1350, M1-P1349, M1-E1348, M1-S1347, M1-D1346, M1-W1345, M1-P1344, M1-N1343, M1-Q1342, M1-C1341, M1-E1340, M1-P1339, M1-L1338, M1-H1337, M1-T1336, M1-Y1335, M1-D1334, M1-S1333, M1-S1332, M1-F1331, M1-S1330, M1-R1329, M1-T1328, M1-D1327, M1-M1326, M1-S1325, M1-T1324, M1-I1323, M1-D1322, M1-E1321, M1-F1320, M1-D1319, M1-I1318, M1-S1317, M1-R1316, M1-S1315, M1-P1314, M1-P1313, M1-R1312, M1-D1311, M1-T1310, M1-P1309, M1-A1308, M1-L1307, M1-T1306, M1-A1305, M1-Y1304, M1-A1303, M1-S1302, M1-S1301, M1-S1300, M1-P1299, M1-A1298, M1-T1297, M1-S1296, M1-P1295, M1-V1294, M1-P1293, M1-T1292, M1-S1291, M1-F1290, M1-S1289, M1-P1288, M1-E1287, M1-G1286, M1-L1285, M1-G1284, M1-L1283, M1-I1282, M1-N1281, M1-V1280, M1-S1279, M1-N1278, M1-D1277, M1-L1276, M1-P1275, M1-D1274, M1-I1273, M1-D1272, M1-C1271, M1-H1270, M1-L1269, M1-E1268, M1-D1267, M1-M1266, M1-A1265, M1-S1264, M1-V1263, M1-Y1262, M1-I1261, M1-D1260, M1-I1259, M1-C1258, M1-S1257, M1-S1256, M1-P1255, M1-R1254, M1-R1253, M1-S1252, M1-D1251, M1-P1250, M1-V1249, M1-I1248, M1-A1247, M1-L1246, M1-T1245, M1-N1244, M1-A1243, M1-P1242, M1-A1241, M1-A1240, M1-P1239, M1-A1238, M1-K1237, M1-P1236, M1-E1235, M1-K1234, M1-A1233, M1-V1232, M1-S1231, M1-H1230, M1-S1229, M1-S1228, M1-T1227, M1-A1226, M1-R1225, M1-H1224, M1-L1223, M1-S1222, M1-L1221, M1-S1220, M1-R1219, M1-E1218, M1-K1217, M1-F1216, M1-I1215, M1-S1214, M1-E1213, M1-L1212, M1-K1211, M1-E1210, M1-I1209, M1-G1208, M1-G1207, M1-K1206, M1-D1205, M1-K1204, M1-M1203, M1-N1202, M1-V1201, M1-S1200, M1-Y1199, M1-F1198, M1-S1197, M1-H1196, M1-S1195, M1-R1194, M1-M1193, M1-R1192, M1-P1191, M1-M1190, M1-L1189, M1-T1188, M1-P1187, M1-S1186, M1-T1185, M1-P1184, M1-S1183, M1-M1182, M1-T1181, M1-E1180, M1-E1179, M1-G1178, M1-A1177, M1-P1176, M1-D1175, M1-I1174, M1-S1173, M1-E1172, M1-Q1171, M1-L1170, M1-K1169, M1-F1168, M1-T1167, M1-N1166, M1-G1165, M1-E1164, M1-Q1163, M1-S1162, M1-N1161, M1-F1160, M1-S1159, M1-S1158, M1-Q1157, M1-R1156, M1-V1155, M1-I1154, M1-Y1153, M1-A1152, M1-A1151, M1-D1150, M1-T1149, M1-C1148, M1-D1147, M1-S1146, M1-S1145, M1-T1144, M1-R1143, M1-S1142, M1-R1141, M1-I1140, M1-K1139, M1-N1138, M1-S1137, M1-E1136, M1-A1135, M1-R1134, M1-E1133, M1-L1132, M1-G1131, M1-T1130, M1-L1129, M1-R1128, M1-E1127, M1-L1126, M1-A1125, M1-T1124, M1-A1123, M1-M1122, M1-R1121, M1-G1120, M1-I1119, M1-L1118, M1-D1117, M1-E1116, M1-L1115, M1-Q1114, M1-A1113, M1-L1112, M1-R1111, M1-I1110, M1-D1109, M1-V1108, M1-T1107, M1-Q1106, M1-L1105, M1-S1104, M1-A1103, M1-K1102, M1-M111, M1-S1100, M1-H1099, M1-E1098, M1-R1097, M1-E1096, M1-N1095, M1-V1094, M1-E1093, M1-E1092, M1-L1091, M1-R1090, M1-M1089, M1-S1088, M1-M1087, M1-N1086, M1-E1085, M1-V1084, M1-R1083, M1-E1082, M1-S1081, M1-T1080, M1-V1079, M1-R1078, M1-I1077, M1-R1076, M1-E1075, M1-D1074, M1-N1073, M1-S1072, M1-S1071, M1-N1070, M1-F1069, M1-R1068, M1-D1067, M1-D1066, M1-K1065, M1-E1064, M1-R1063, M1-F1062, M1-Y1061, M1-E1060, M1-E1059, M1-I1058, M1-C1057, M1-Q1056, M1-E1055, M1-E1054, M1-F1053, M1-D1052, M1-H1051, M1-V1050, M1-K1049, M1-K1048, M1-L1047, M1-E1046, M1-D1045, M1-D1044, M1-T1043, M1-I1042, M1-F1041, M1-L1040, M1-K1039, M1-L1038, M1-G1037, M1-Y1036, M1-D1035, M1-R1034, M1-E1033, M1-D1032, M1-P1031, M1-D1030, M1-S1029, M1-E1028, M1-H1027, M1-K1026, M1-R1025, M1-W1024, M1-R1023, M1-C1022, M1-C1021, M1-L1020, M1-H1019, M1-Q1018, M1-F1017, M1-I1016, M1-M1015, M1-T1014, M1-M1013, M1-H1012, M1-S1011, M1-F1010, M1-I1009, M1-I1008, M1-L1007, M1-P1006, M1-P1005, M1-P1004, M1-L1003, M1-V1002, M1-P1001, M1-R1000, M1-E999, M1-H998, M1-F997, M1-T996, M1-M995, M1-I994, M1-L993, M1-Q992, M1-Y991, M1-R990, M1-Q989, M1-F988, M1-K987, M1-W986, M1-V985, M1-Q984, M1-N983, M1-S982, M1-I981, M1-S980, M1-K979, M1-V978, M1-E977, M1-F976, M1-F975, M1-T974, M1-N973, M1-N972, M1-F971, M1-V970, M1-A969, M1-I968, M1-L967, M1-L966, M1-N965, M1-V964, M1-L963, M1-L962, M1-I961, M1-N960, M1-A959, M1-V958, M1-L957, M1-L956, M1-Y955, M1-C954, M1-A953, M1-M952, M1-I951, M1-A950, M1-P949, M1-V948, M1-I947, M1-W946, M1-A945, M1-G944, M1-T943, M1-K942, M1-C941, M1-P940, M1-P939, M1-L938, M1-Q937, M1-I936, M1-I935, M1-K934, M1-G933, M1-D932, M1-E931, M1-R930, M1-T929, M1-E928, M1-N927, M1-Q926, M1-G925, M1-C924, M1-P923, M1-A922, M1-S921, M1-K920, M1-P919, M1-T918, M1-H917, M1-S916, M1-D915, M1-Y914, M1-V913, M1-Q912, M1-K911, and/or M1-R910 of SEQ ID NO:6. Polynucleotide sequences encoding these polypeptides are also provided. The present invention also encompasses the use of these C-terminal LTRPC3c deletion polypeptides as immunogenic and/or antigenic epitopes as described elsewhere herein.

Alternatively, preferred polypeptides of the present invention may comprise polypeptide sequences corresponding to, for example, internal regions of the LTRPC3c polypeptide (e.g., any combination of both N- and C-terminal LTRPC3c polypeptide deletions) of SEQ ID NO:6. For example, internal regions could be defined by the equation: amino acid NX to amino acid CX, wherein NX refers to any N-terminal deletion polypeptide amino acid of LTRPC3c (SEQ ID NO:6), and where CX refers to any C-terminal deletion polypeptide amino acid of LTRPC3c (SEQ ID NO:6). Polynucleotides encoding these polypeptides are also provided. The present invention also encompasses the use of these polypeptides as an immunogenic and/or antigenic epitope as described elsewhere herein.

The LTRPC3c polypeptides of the present invention were determined to comprise several phosphorylation sites based upon the Motif algorithm (Genetics Computer Group, Inc.). The phosphorylation of such sites may regulate some biological activity of the LTRPC3c polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the LTRPC3c polypeptide to associate with other potassium channel alpha subunits, beta subunits, or its ability to modulate potassium channel function.

Specifically, the LTRPC3c polypeptide was predicted to comprise two tyrosine phosphorylation sites using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or [RK]-x(3)-[DE]-x(2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Natl. Acad. Sci. U.S.A. 79:973-977 (1982); Hunter T., J. Biol. Chem. 257:4843-4848 (1982), and Cooper J. A., Esch F. S., Taylor S. S., Hunter T., J. Biol. Chem. 259:7835-7841(1984), which are hereby incorporated herein by reference.

In preferred embodiments, the following tyrosine phosphorylation site polypeptides are encompassed by the present invention: LSLEFKNKDDMPYMSQAQ (SEQ ID NO:158), and/or VMMIGKMMIDMMYFVIIM (SEQ ID NO:159). Polynucleotides encoding these polypeptides are also provided. The present invention also encompasses the use of these LTRPC3c tyrosine phosphorylation site polypeptides as immunogenic and/or antigenic epitopes as described elsewhere herein.

The LTRPC3c polypeptide was predicted to comprise twenty four PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. 260: 12492-12499 (1985); which are hereby incorporated by reference herein.

In preferred embodiments, the following PKC phosphorylation site polypeptides are encompassed by the present invention: ADNGTTGKYGAEV (SEQ ID NO:160), VVCDGSGRASDIL (SEQ ID NO:161), GLINESLRDQLLV (SEQ ID NO:162), YRCNYTRKRFRTL (SEQ ID NO:163), RRGRKTTKKREEE (SEQ ID NO:164), RGRKTTKKREEEV (SEQ ID NO:165), ELLDQSYKQDEQL (SEQ ID NO:166), RNNGESSRKKDEE (SEQ ID NO:167), NNGESSRKKDEEE (SEQ ID NO:168), PNEEPSWKLAKNI (SEQ ID NO:169), VYDSHTPKSAPCG (SEQ ID NO:170), RIRVTSERVENMS (SEQ ID NO:171), RVENMSMRLEEVN (SEQ ID NO:172), NEREHSMKASLQT (SEQ ID NO:173), LERAESNKIRSRT (SEQ ID NO:174), SQEGNTFKLQESI (SEQ ID NO:175), AIVPDSRRPSSCI (SEQ ID NO:176), ATLAPTDRPPSRS (SEQ ID NO:177), IERSKSSRYLATT (SEQ ID NO:178), QEGDNSERTLSNN (SEQ ID NO:179), APYAHTRKSFSIS (SEQ ID NO:180), KSFSISDKLDRQR (SEQ ID NO:181), FQRSKSSKPEGRG (SEQ ID NO:182), and/or RGDSLSMRRLSRT (SEQ ID NO:183.). Polynucleotides encoding these polypeptides are also provided. The present invention also encompasses the use of these LTRPC3c PKC phosphorylation site polypeptides as immunogenic and/or antigenic epitopes as described elsewhere herein.

The present invention also encompasses immunogenic and/or antigenic epitopes of the LTRPC3c polypeptide.

The LTRPC3c polypeptide has been shown to comprise twelve glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine phosphorylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673-702 (1972); Pless D. D., Lennarz W. J., Proc. Natl. Acad. Sci. U.S.A. 74:134-138 (1977); Bause E., Biochem. J. 209:331-336 (1983); Gavel Y., von Heijne G., Protein Eng. 3:433-442 (1990); and Miletich J. P., Broze G. J. Jr., J. Biol. Chem. 265:11397-11404 (1990).

In preferred embodiments, the following asparagine glycosylation site polypeptides are encompassed by the present invention: FILADNGTTGKYGA (SEQ ID NO:184), EGGLINESLRDQLL (SEQ ID NO:185), LLKGANASAPDQLS (SEQ ID NO:186), GAYRCNYTRKRFRT (SEQ ID NO:187), TYELKNWSNATCLQ (SEQ ID NO:188), LKNWSNATCLQLAV (SEQ ID NO:189), LQEYWNVTDLIAIL (SEQ ID NO:190), APCGQNETREDGKI (SEQ ID NO:191), LIAVFNNTFFEVKS (SEQ ID NO:192), KDDRFNSSNDERIR (SEQ ID NO:193), SERVENMSMRLEEV (SEQ ID NO:194), and/or RTLSNNITVPKIER (SEQ ID NO:195). Polynucleotides encoding these polypeptides are also provided. The present invention also encompasses the use of these LTRPC3c asparagine glycosylation site polypeptides as immunogenic and/or antigenic epitopes as described elsewhere herein.

The LTRPC3c polypeptide has been shown to comprise one RGD cell attachment site domain according to the Motif algorithm (Genetics Computer Group, Inc.). The sequence Arg-Gly-Asp, found in fibronectin, is crucial for its interaction with its cell surface receptor, an integrin. What has been called the 'RGD' tripeptide is also found in the sequences of a number of other proteins, where it has been shown to play a role in cell adhesion. Non-limiting examples of these proteins are the following: some forms of collagens, fibrinogen, vitronectin, von Willebrand factor (VWF), snake disintegrins, and slime mold discoidins. The 'RGD' tripeptide is also found in other proteins where it may serve the same purpose. A consensus pattern for RGD cell attachment sites is the following: R-G-D. Additional information relating to RGD cell attachment site domains may be found in reference to the following publications, which are hereby incorporated by reference herein: Ruoslahti E., Pierschbacher M. D., Cell 44:517-518 (1986); and d'Souza S. E., Ginsberg M. H., Plow E. F., Trends Biochem. Sci. 16:246-250 (1991).

In preferred embodiments, the following RGD cell attachment site domain polypeptide is encompassed by the present invention: SKPEGRGDSLSMR (SEQ ID NO:196). Polynucleotides encoding these polypeptides are also provided. The present invention also encompasses the use of this RGD cell attachment site domain polypeptide as an immunogenic and/or antigenic epitope as described elsewhere herein.

The LTRPC3c polypeptide has been shown to comprise one aminoacyl-transfer RNA synthetases class-II domain according to the Motif algorithm (Genetics Computer Group, Inc.). Aminoacyl-tRNA synthetases (EC 6.1.1.-) are a group of enzymes which activate amino acids and transfer them to specific tRNA molecules as the first step in protein biosynthesis. In prokaryotic organisms there are at least twenty different types of aminoacyl-tRNA synthetases, one for each different amino acid. In eukaryotes there are generally two aminoacyl-tRNA synthetases for each different amino acid: one cytosolic form and a mitochondrial form. While all these enzymes have a common function, they are widely diverse in terms of subunit size and of quaternary structure.

The synthetases specific for alanine, asparagine, aspartic acid, glycine, histidine, lysine, phenylalanine, proline, serine, and threonine are referred to as class-II synthetases and probably have a common folding pattern in their catalytic domain for the binding of ATP and amino acid which is different to the Rossmann fold observed for the class I synthetases.

Class-II tRNA synthetases do not share a high degree of similarity, however at least three conserved regions are present.

The consensus pattern for aminoacyl-transfer RNA synthetases class-II domains are as follows: [FYH]-R-x-[DE]-x (4,12)-[RH]-x(3)-F-x(3)-[DE]; and [GSTALVF]-{DEN-QHRKP}-[GSTA]-[LIVMF]-[DE]-R-[LIVMF]-x-[LIVMSTAG]-[LIVMFY], where 'x' represents an intervening amino acid residue.

Additional information specific to aminoacyl-transfer RNA synthetases class-II domains may be found in reference to the following publications, Schimmel P., Annu. Rev. Biochem. 56:125-158 (1987); Delarue M., Moras D., BioEssays 15:675-687 (1993); Schimmel P., Trends Biochem. Sci. 16:1-3 (1991); Nagel G. M., Doolittle R. F., Proc. Natl. Acad. Sci. U.S.A. 88:8121-8125 (1991); Cusack S., Haertlein M., Leberman R., Nucleic Acids Res. 19:3489-3498 (1991); Cusack S., Biochimie 75:1077-1081 (1993); Cusack S., Berthet-Colominas C., Haertlein M., Nassar N., Leberman R., Nature 347:249-255 (1990); and Leveque F., Plateau P., Dessen P., Blanquet S., Nucleic Acids Res. 18:305-312 (1990); which are hereby incorporated herein by reference in their entirety.

In preferred embodiments, the following aminoacyl-transfer RNA synthetases class-II domain polypeptide is encompassed by the present invention: LIGRMATALERLTGLER-AES (SEQ ID NO:197). Polynucleotides encoding these polypeptides are also provided. The present invention also encompasses the use of this RGD cell attachment site domain polypeptide as an immunogenic and/or antigenic epitope as described elsewhere herein.

The LTRPC3c polypeptide has been shown to comprise three amidation sites according to the Motif algorithm (Genetics Computer Group, Inc.). The precursor of hormones and other active peptides which are C-terminally amidated is always directly followed by a glycine residue which provides the amide group, and most often by at least two consecutive basic residues (Arg or Lys) which generally function as an active peptide precursor cleavage site. Although all amino acids can be amidated, neutral hydrophobic residues such as Val or Phe are good substrates, while charged residues such as Asp or Arg are much less reactive. A consensus pattern for amidation sites is the following: x-G-[RK]-[RK], wherein "X" represents the amidation site. Additional information relating to asparagine glycosylation may be found in reference to the following publications, which are hereby incorporated by reference herein: Kreil G., Meth. Enzymol. 106: 218-223(1984); and Bradbury A. F., Smyth D. G., Biosci. Rep. 7:907-916 (1987).

In preferred embodiments, the following amidation site polypeptides are encompassed by the present invention: DIPLRRGRKTTKKR (SEQ ID NO:198), HRLI-PLGRKIYEFY (SEQ ID NO:199), and/or EENEAKGRRA-TIAI (SEQ ID NO:200). Polynucleotides encoding these polypeptides are also provided. The present invention also encompasses the use of these LTRPC3c amidation site polypeptides as immunogenic and/or antigenic epitopes as described elsewhere herein.

Many polynucleotide sequences, such as EST sequences, are publicly available and accessible through sequence databases. Some of these sequences are related to SEQ ID NO:5 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 4687 of SEQ ID NO:5, b is an integer between 15 to 4701, where both a and b correspond to the positions of nucleotide residues shown in SEQ ID NO:5, and where b is greater than or equal to a+14.

Features of the Polypeptide Encoded by Gene No:4

The polypeptide of this gene provided as SEQ ID NO:10 (FIGS. 4A-F), encoded by the polynucleotide sequence according to SEQ ID NO:8 (FIGS. 4A-F), and/or encoded by the polynucleotide contained within the deposited clone, LTRPC3e, has significant homology at the nucleotide and amino acid level to the human melastatin 1 protein (Melastatin1; Genbank Accession No. gi|3243075; SEQ ID NO:11). An alignment of the LTRPC3e polypeptide with this protein is provided in FIGS. 5A-D.

The LTRPC3e polypeptide was determined to share 65.5% identity and 73.3% similarity with the human melastatin 1 protein (Melastatin1; Genbank Accession No. gi|3243075; SEQ ID NO:11) as shown in FIG. 8.

The LTRPC3e protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain. This family is commonly referred to as the transient receptor potential channel (TRP) family. to Melastatin1 defines a separate subfamily of TRP channels referred to as TRPM (melastatin1). TRPM family members are characteristic of their unusually long cytoplasmic tails at both ends of the channel domain and some of the family members contain an enzyme domain at the C-terminal region. Thus, LTRPC3 represents a novel member of the TRPM subfamily.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the melastatin1 protein, in addition to, other transient receptor potential channel family members referenced elsewhere herein or otherwise known in the art.

Most of the known transient receptor potential channel family members, possess one or more transmembrane domains. Likewise, the LTRPC3e polypeptide has been determined to comprise six transmembrane domains (TM1-TM6) as shown in FIGS. 4A-F. The transmembrane domains are located from about amino acid 622 to about amino acid 639 (TM1), from about amino acid 719 to about amino acid 736 (TM2), from about amino acid 792 to about amino acid 805 (TM3), from about amino acid 819 to about amino acid 836 (TM4), from about amino acid 853 to about amino acid 870 (TM5), and/or from about amino acid 940 to about amino acid 960 (TM6) of SEQ ID NO:9. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKVILGILLPPSILSLEF (SEQ ID NO:44), IVKFWFYTLAYIGYLMLF (SEQ ID NO:45), VTDLIAILLFSVGM (SEQ ID NO:46), RVIYCVNIIYWYIRLLDI (SEQ ID NO:47), MMIDMMYFVIIMLVVLMS (SEQ ID NO:48), and/or AIMACYLLVANILLVNLLIAV (SEQ ID NO:49). Polynucleotides encoding these polypeptides are also provided. The present invention also encompasses the use of the LTRPC3e transmembrane polypeptides as immunogenic and/or antigenic epitopes as described elsewhere herein.

The present invention also encompasses polypeptides corresponding to the regions between each transmembrane domain of LTRPC3e, referred to herein as inter-transmembrane domain polypeptides (inter TM1-2, inter TM2-3, inter TM3-4, inter TM4-5, and inter TM5-6). Such regions are typically solvent accessible (either extracellularly or intracellularly). Therefore, these regions are amenable to the development of agonists and/or antagonists to the LTRPC3e polypeptide, particularly for the development of antibodies specific to these regions.

In preferred embodiments, the following inter-transmembrane domain polypeptides are encompassed by the present invention: KNKDDMPYMSQAQEIHLQEKEAEEPEKPTKEKEEEDMELTAMLGRNNGESSRKKDEEEVQSKHRLIPLGRKIYEFYNAP (SEQ ID NO:201), NYIVLVKMERWPSTQEWIVISYIFTLGIEKMREILMSEPGKLLQKVKVWLQEY WN (SEQ ID NO:202), ILRLQDQPFRSDG (SEQ ID NO:203), FGVNKYLGPYVMMIGK (SEQ ID NO:204), and/or FGVARQAILFPNEEPSWKLAKNIFYMPYWMIYGEVFADQIDPPCGQNETRED GKIIQLPPCKTGAWIVP (SEQ ID NO:205). Polynucleotides encoding these polypeptides are also provided. The present invention also encompasses the use of the LTRPC3e inter-transmembrane polypeptides as immunogenic and/or antigenic epitopes as described elsewhere herein.

In preferred embodiments, the following N-terminal LTRPC3e inter TM1-2 domain deletion polypeptides are encompassed by the present invention: K1-P79, N2-P79, K3-P79, D4-P79, D5-P79, M6-P79, P7-P79, Y8-P79, M9-P79, S10-P79, Q11-P79, A12-P79, Q13-P79, E14-P79, I15-P79, H16-P79, L17-P79, Q18-P79, E19-P79, K20-P79, E21-P79, A22-P79, E23-P79, E24-P79, P25-P79, E26-P79, K27-P79, P28-P79, T29-P79, K30-P79, E31-P79, K32-P79, E33-P79, E34-P79, E35-P79, D36-P79, M37-P79, E38-P79, L39-P79, T40-P79, A41-P79, M42-P79, L43-P79, G44-P79, R45-P79, N46-P79, N47-P79, G48-P79, E49-P79, S50-P79, S51-P79, R52-P79, K53-P79, K54-P79, D55-P79, E56-P79, E57-P79, E58-P79, V59-P79, Q60-P79, S61-P79, K62-P79, H63-P79, R64-P79, L65-P79, I66-P79, P67-P79, L68-P79, G69-P79, R70-P79, K71-P79, I72-P79, and/or Y73-P79 of SEQ ID NO:201. Polynucleotide sequences encoding these polypeptides are also provided. The present invention also encompasses the use of these N-terminal LTRPC3e inter TM1-2 domain deletion polypeptides as immunogenic and/or antigenic epitopes as described elsewhere herein.

In preferred embodiments, the following C-terminal LTRPC3e inter TM1-2 domain deletion polypeptides are encompassed by the present invention: K1-P79, K1-A78, K1-N77, K1-Y76, K1-F75, K1-E74, K1-Y73, K1-I72, K1-K71, K1-R70, K1-G69, K1-L68, K1-P67, K1-I66, K1-L65, K1-R64, K1-H63, K1-K62, K1-S61, K1-Q60, K1-V59, K1-E58, K1-E57, K1-E56, K1-D55, K1-K54, K1-K53, K1-R52, K1-S51, K1-S50, K1-E49, K1-G48, K1-N47, K1-N46, K1-R45, K1-G44, K1-L43, K1-M42, K1-A41, K1-T40, K1-L39, K1-E38, K1-M37, K1-D36, K1-E35, K1-E34, K1-E33, K1-K32, K1-E31, K1-K30, K1-T29, K1-P28, K1-K27, K1-E26, K1-P25, K1-E24, K1-E23, K1-A22, K1-E21, K1-K20, K1-E19, K1-Q18, K1-L17, K1-H16, K1-I15, K1-E14, K1-Q13, K1-A12, K1-Q11, K1-S10, K1-M9, K1-Y8, and/or K1-P7 of SEQ ID NO:201. Polynucleotide sequences encoding these polypeptides are also provided. The present invention also encompasses the use of these C-terminal LTRPC3e inter TM1-2 domain deletion polypeptides as immunogenic and/or antigenic epitopes as described elsewhere herein.

In preferred embodiments, the following N-terminal LTRPC3e inter TM2-3 domain deletion polypeptides are encompassed by the present invention: F1-N56, N2-N56, Y3-N56, I4-N56, V5-N56, L6-N56, V7-N56, K8-N56, M9-N56, E10-N56, R11-N56, W12-N56, P13-N56, S14-N56, T15-N56, Q16-N56, E17-N56, W18-N56, I19-N56, V20-N56, I21-N56, S22-N56, Y23-N56, I24-N56, F25-N56, T26-N56, L27-N56, G28-N56, I29-N56, E30-N56, K31-N56, M32-N56, R33-N56, E34-N56, I35-N56, L36-N56, M37-N56, S38-N56, E39-N56, P40-N56, G41-N56, K42-N56, L43-N56, L44-N56, Q45-N56, K46-N56, V47-N56, K48-N56, V49-N56, and/or W50-N56 of SEQ ID NO:202. Polynucleotide sequences encoding these polypeptides are also provided. The present invention also encompasses the use of these N-terminal LTRPC3e inter TM2-3 domain deletion polypeptides as immunogenic and/or antigenic epitopes as described elsewhere herein.

In preferred embodiments, the following C-terminal LTRPC3e inter TM2-3 domain deletion polypeptides are encompassed by the present invention: F1-N56, F1-W55, F1-Y54, F1-E53, F1-Q52, F1-L51, F1-W50, F1-V49, F1-K48, F1-V47, F1-K46, F1-Q45, F1-L44, F1-L43, F1-K42, F1-G41, F1-P40, F1-E39, F1-S38, F1-M37, F1-L36, F1-I35, F1-E34, F1-R33, F1-M32, F1-K31, F1-E30, F1-I29, F1-G28, F1-L27, F1-T26, F1-F25, F1-I24, F1-Y23, F1-S22, F1-I21, F1-V20, F1-I19, F1-W18, F1-E17, F1-Q16, F1-T15, F1-S14, F1-P13, F1-W12, F1-R11, F1-E10, F1-M9, F1-K8, and/or F1-V7 of SEQ ID NO:202. Polynucleotide sequences encoding these polypeptides are also provided.

The present invention also encompasses the use of these C-terminal LTRPC3e inter TM2-3 domain deletion polypeptides as immunogenic and/or antigenic epitopes as described elsewhere herein.

In preferred embodiments, the following N-terminal LTRPC3e inter TM3-4 domain deletion polypeptides are encompassed by the present invention: I1-G13, L2-G13, R3-G13, L4-G13, Q5-G13, D6-G13, and/or Q7-G13 of SEQ ID NO:203. Polynucleotide sequences encoding these polypeptides are also provided. The present invention also encompasses the use of these N-terminal LTRPC3e inter TM3-4 domain deletion polypeptides as immunogenic and/or antigenic epitopes as described elsewhere herein.

In preferred embodiments, the following C-terminal LTRPC3e inter TM3-4 domain deletion polypeptides are encompassed by the present invention: I1-G13, I1-D12, I1-S11, I1-R10, I1-F9, I1-P8, and/or I1-Q7 of SEQ ID NO:203. Polynucleotide sequences encoding these polypeptides are also provided. The present invention also encompasses the use of these C-terminal LTRPC3e inter TM3-4 domain deletion polypeptides as immunogenic and/or antigenic epitopes as described elsewhere herein.

In preferred embodiments, the following N-terminal LTRPC3e inter TM4-5 domain deletion polypeptides are encompassed by the present invention: F1-K16, G2-K16, V3-K16, N4-K16, K5-K16, Y6-K16, L7-K16, G8-K16, P9-K16, and/or Y10-K16 of SEQ ID NO:204. Polynucleotide sequences encoding these polypeptides are also provided. The present invention also encompasses the use of these N-terminal LTRPC3e inter TM4-5 domain deletion polypeptides as immunogenic and/or antigenic epitopes as described elsewhere herein.

In preferred embodiments, the following C-terminal LTRPC3e inter TM4-5 domain deletion polypeptides are encompassed by the present invention: F1-K16, F1-G15, F1-I14, F1-M13, F1-M12, F1-V11, F1-Y10, F1-P9, F1-G8, and/or F1-L7 of SEQ ID NO:204. Polynucleotide sequences encoding these polypeptides are also provided. The present invention also encompasses the use of these C-terminal LTRPC3e inter TM4-5 domain deletion polypeptides as immunogenic and/or antigenic epitopes as described elsewhere herein.

In preferred embodiments, the following N-terminal LTRPC3e inter TM5-6 domain deletion polypeptides are encompassed by the present invention: F1-P81, G2-P81, V3-P81, A4-P81, R5-P81, Q6-P81, A7-P81, I8-P81, L9-P81, F10-P81, P11-P81, N12-P81, E13-P81, E14-P81, P15-P81, S16-P81, W17-P81, K18-P81, L19-P81, A20-P81, K21-P81, N22-P81, I23-P81, F24-P81, Y25-P81, M26-P81, P27-P81, Y28-P81, W29-P81, M30-P81, I31-P81, Y32-P81, G33-P81, E34-P81, V35-P81, F36-P81, A37-P81, D38-P81, Q39-P81, I40-P81, D41-P81, R42-P81, K43-P81, Q44-P81, V45-P81, Y46-P81, D47-P81, S48-P81, H49-P81, T50-P81, P51-P81, K52-P81, S53-P81, A54-P81, P55-P81, C56-P81, G57-P81, Q58-P81, N59-P81, E60-P81, T61-P81, R62-P81, E63-P81, D64-P81, G65-P81, K66-P81, I67-P81, I68-P81, Q69-P81, L70-P81, P71-P81, P72-P81, C73-P81, K74-P81, and/or T75-P81 of SEQ ID NO:205. Polynucleotide sequences encoding these polypeptides are also provided. The present invention also encompasses the use of these N-terminal LTRPC3e inter TM5-6 domain deletion polypeptides as immunogenic and/or antigenic epitopes as described elsewhere herein.

In preferred embodiments, the following C-terminal LTRPC3e inter TM5-6 domain deletion polypeptides are encompassed by the present invention: F1-P81, F1-V80, F1-I79, F1-W78, F1-A77, F1-G76, F1-T75, F1-K74, F1-C73, F1-P72, F1-P71, F1-L70, F1-Q69, F1-I68, F1-I67, F1-K66, F1-G65, F1-D64, F1-E63, F1-R62, F1-T61, F1-E60, F1-N59, F1-Q58, F1-G57, F1-C56, F1-P55, F1-A54, F1-S53, F1-K52, F1-P51, F1-T50, F1-H49, F1-S48, F1-D47, F1-Y46, F1-V45, F1-Q44, F1-K43, F1-R42, F1-D41, F1-I40, F1-Q39, F1-D38, F1-A37, F1-F36, F1-V35, F1-E34, F1-G33, F1-Y32, F1-I31, F1-M30, F1-W29, F1-Y28, F1-P27, F1-M26, F1-Y25, F1-F24, F1-I23, F1-N22, F1-K21, F1-A20, F1-L19, F1-K18, F1-W17, F1-S16, F1-P15, F1-E14, F1-E13, F1-N12, F1-P11, F1-F10, F1-L9, F1-I8, and/or F1-A7 of SEQ ID NO:205. Polynucleotide sequences encoding these polypeptides are also provided. The present invention also encompasses the use of these C-terminal LTRPC3e inter TM5-6 domain deletion polypeptides as immunogenic and/or antigenic epitopes as described elsewhere herein.

The LTRPC3e polypeptide was determined to comprise several conserved cysteines, at amino acid 94, 209, 265, 431, 519, 584, 601, 823, 914, 931, 944, 1047, 1138, and 1404 of SEQ ID NO:9 (FIGS. 4A-F). Conservation of cysteines at key amino acid residues is indicative of conserved structural features, which may correlate with conservation of protein function and/or activity.

In confirmation of the LTRPC3e representing a member of the transient receptor channel family, the LTRPC3e polypeptide was determined to comprise a predicted TRP domain (EWKFAR) located from about amino acid 975 to about amino acid 980 of SEQ ID NO:9. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following TRP domain polypeptide is encompassed by the present invention: VWKFQR (SEQ ID NO:206). Polynucleotides encoding this polypeptide are also provided. The present invention also encompasses the use of this LTRPC3e TRP domain polypeptide as an immunogenic and/or antigenic epitope as described elsewhere herein.

In further confirmation of the LTRPC3e representing a member of the transient receptor channel family, the LTRPC3e polypeptide was determined to comprise a predicted ion transport signature domain located at about amino acid 750 to about amino acid 961 of SEQ ID NO:9. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following ion transport signature domain polypeptide is encompassed by the present invention: TQEWIVISYIFTLGIEKMREILM-SEPGKLLQKVKVWLQEYWNVTDLIAILLFSV GMIL-RLQDQPFRSDGRVIYCVNIIYWYIRLL-DIFGVNKYLGPYVMMIGKMMID MMYFVIIMLVVLMSFGVARQAILFP-NEEPSWKLAKNIFYMPYWMIYGEVFAD QIDP-PCGQNETREDGKIIQLPPCKTGAWIV-PAIMACYLLVANILLVNLLIAVF (SEQ ID NO:207). Polynucleotides encoding this polypeptide are also provided. The present invention also encompasses the use of this LTRPC3e ion transport signature domain polypeptide as an immunogenic and/or antigenic epitope as described elsewhere herein.

The LTRPC3e polypeptide was determined to comprise a predicted coiled-coil domain located at about amino acid 1065 to about amino acid 1119 of SEQ ID NO:9. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following coiled-coil domain polypeptide is encompassed by the present invention: ERIRVTSERVENMSMRLEEVNEREH-SMKASLQTVDIRLAQLEDLIGRMATAL ERL (SEQ ID NO:208). Polynucleotides encoding this polypeptide are also provided. The present invention also encompasses the use of this LTRPC3e coiled-coil domain polypeptide as an immunogenic and/or antigenic epitope as described elsewhere herein.

The present invention is also directed to polynucleotides comprising at least about 45 nt of the polynucleotide sequence provided as SEQ ID NO:8. Specifically, the present invention is directed to a polynucleotide sequence comprising nucleotides from about nucleotide 1174 to about nucleotide 1212; nucleotides from about nucleotide 1174 to about nucleotide 1215; nucleotides from about nucleotide 1168 to about nucleotide 1209; nucleotides from about nucleotide 1165 to about nucleotide 1209; of SEQ ID NO:8; and/or nucleotides from about nucleotide 1162 to about nucleotide 1209. In this context "about" includes the particularly recited value, a value larger or smaller by several (5, 4, 3, 2, or 1) nucleotides, at either terminus, or at both termini.

The present invention is also directed to polypeptides comprising at least about 15 amino acids of the polypeptides sequence provided as SEQ ID NO:9. Specifically, the present invention is directed to a polypeptides sequence comprising amino acids from about amino acid 392 to about amino acid 404; amino acids from about amino acid 392 to about amino acid 405; amino acids from about amino acid 392 to about amino acid 406; amino acids from about amino acid 390 to about amino acid 403; amino acids from about amino acid 389 to about amino acid 403; and/or amino acids from about amino acid 388 to about amino acid 403 of SEQ ID NO:9. In this context "about" includes the particularly recited value, a value larger or smaller by several (5, 4, 3, 2, or 1) nucleotides, at either terminus, or at both termini.

LTRPC3e polypeptides and polynucleotides are useful for diagnosing diseases related to the over and/or under expression of LTRPC3e by identifying mutations in the LTRPC3e gene using LTRPC3e sequences as probes or by determining LTRPC3e protein or mRNA expression levels. LTRPC3e polypeptides will be useful in screens for compounds that affect the activity of the protein. LTRPC3e peptides can also be used for the generation of specific antibodies and as bait in yeast two hybrid screens to find proteins the specifically interact with LTRPC3e.

Consistent with LTRPC3 representing a transient receptor potential channel, immunohistochemical experiments have shown that LTRPC3 localizes to the cell membrane (see FIG. 17 and Example 6). Specifically, the complete open reading frame of LTRPC3 with a C-terminal HA tag was transiently transfected into HEK 293 cells to assess its cellular localization. The HA-tagged LTRPC3 was detected using a fluorescein-conjugated anti-HA antibody and a laser scanning confocal microscope which produces a green fluorescent signal. The green fluorescent signal was exclusively detected at the subplasma membrane region of the transfected cells (see FIG. 17), which is consistent with LTRPC3 being an integral membrane protein. Under these conditions approximately ~70% of cells are expressing LTRPC3. The expression of full-length protein was accessed with immunoblot using an anti-HA antibody and detected as the expected size of ~170 kD (data not shown). Cellular localization of the LTRPC3d splice variant is expected to be similarly localized to the subplasma membrane region.

Moreover, physiometric studies have shown that LTRPC3 is a functional $Ca^{2+}$ permeable channel (see FIGS. 18 and 19, and Example 7). LTRPC3 function was assessed using a Fluorometric Imaging Plate Reader (FLIPR™) that measures real-time intracellular fluorescence changes. Cells transiently transfected with vector or LTRPC3-HA were loaded with the cytoplasmic $Ca^{2+}$ indicator Fluoro-4 in a 1 mM $Ca^{2+}$ solution. Addition of $Ca^{2+}$ to the media resulted in a concentration-dependent influx of $Ca^{2+}$ into LTRPC3-expressing cells (FIG. 18; right panels), indicating that LTRPC3 is a functional $Ca^{2+}$ channel. In contrast, vector-transfected cells showed minimal $Ca^{2+}$ influx under the same experimental conditions (FIG. 18, left panels). The non-transfected cells were indistinguishable from the vector-transfected cells (data not shown). Therefore, LTRPC3 is a constitutively active channel capable of mediating $Ca^{2+}$ influx. The $Ca^{2+}$ influx activity of the LTRPC3d splice variants is expected to be similar to LTRPC3.

To further address the mechanism of LTRPC3-mediated $Ca^{2+}$ entry, similar $Ca^{2+}$ addition experiments were performed on transfected cells incubated (~30 min) in a nominally $Ca^{2+}$-free solution. Previous studies have shown that lowering extracellular $Ca^{2+}$ concentration below physiological levels can deplete intracellular $Ca^{2+}$ stores in many cell types including HEK 293 (EMBO J. 17, 4274-4282, (1998)). Incubating vector-transfected HEK 293 cells in a nominally $Ca^{2+}$-free solution gave rise to $Ca^{2+}$ entry that was dependent on the concentration of $Ca^{2+}$ added to the buffers, indicating $Ca^{2+}$ influx was mediated through endogenous SOCs in HEK293 cells (FIG. 18, left panels). In LTRPC3 cells, the $Ca^{2+}$ transients triggered by similar $Ca^{2+}$ treatment were much larger (FIG. 18, right panels). This $Ca^{2+}$ entry observed in LTRPC3 cells incubated in $Ca^{2+}$-free media were greater than those observed in 1 mM $Ca^{2+}$ media, indicating that LTRPC3-mediated $Ca^{2+}$ entry can be potentiated by the store-depletion. The store-depletion potentiation of LTRPC3-mediated $Ca^{2+}$ entry is expected to be similar for the LTRPC3d splice variant.

The store-operated mechanism of LTRPC3-mediated $Ca^{2+}$ influx was tested further by passively depleting $Ca^{2+}$ stores with thapsigargin (TG), an inhibitor of microsomal $Ca^{2+}$ ATPases that pumps ions from the cytosol back into the stores. Addition of 2 μM thapsigargin equivalently depleted $Ca^{2+}$ stores in LTRPC3-HA- and vector-transfected cells (FIG. 19A). Following store depletion with TG, addition of $Ca^{2+}$ to the buffer induced a much larger $Ca^{2+}$ entry in LTRPC3 cells compared to the vector control cells. The increased $Ca^{2+}$ entry of LTRPC3 cells, relative to non-LTRPC3 transfected cells, post store depletion with TG is expected to be similar for the LTRPC3d splice variant.

Receptor-mediated $Ca^{2+}$ entry was also more pronounced in LTRPC3-HA-transfected cells. Carbachol (CCh) can activate an endogenous muscarinic receptor and trigger $IP_3$ production, leading to store-depletion in HEK 293 cells. The addition of 50 μM of CCh caused a transient and rapid intracellular $Ca^{2+}$ increase in both LTRPC3- and vector-transfected cells (FIG. 19B). After the store depletion with CCh, adding of $Ca^{2+}$ to the buffer induced a much larger influx of $Ca^{2+}$ into LTRPC3 cells, as compared to vector control cells. These results show that after store depletion with TG or CCh LTRPC3-transfected cells exhibit an increased $Ca^{2+}$ influx when compared to control cells. The increased $Ca^{2+}$ entry of LTRPC3 cells, relative to non-LTRPC3 transfected cells, post store depletion with TG or CCh is expected to be similar for the LTRPC3d splice variant.

The lanthanides, gadolinium ($Gd^{3+}$) and lanthanum ($La^{3+}$), are nonselective $Ca^{2+}$-permeable channel blockers, often used as part of the characterization of overexpressed TRP channels. Both lanthanides blocked LTRPC3 $Ca^{2+}$ conductance, although $La^{3+}$ was more potent (FIG. 19C). In the presence of 1 mM $Ca^{2+}$ in which endogenous SOCs is minimally activated (FIG. 18A), pre-treatment with 100 µM of $La^{3+}$ and $Gd^{3+}$ blocked LTRPC3 $Ca^{2+}$ currents, stimulated by adding 10 mM $Ca^{2+}$, by 67 and 39%, respectively. These results indicated that LTRPC3 mediated currents are not non-specific leak currents resulting from protein overexpression.

LTRPC3 is constitutively active but can be potentiated by store-depletion and is partially sensitive to $La^{3+}$ and $Gd^{3+}$ blockade. LTRPC3 is believed to represent the first member of the TRPM subfamily that exhibits this store-operated mechanism, although some members of TRPC subfamily have been considered for this role. TRPM1 and TRPM4a are constitutive $Ca^{2+}$ permeable channels but it is unclear whether they can be stimulated by store-depletion (*Proc. Natl. Acad. Sci. U.S.A.* 98, 10692-10697, (2001)). Distinct from TRPM4a, TRPM4b is directly activated by changes in intracellular $Ca^{2+}$ without significant permeation of $Ca^{2+}$ (*Cell* 109, 397-401, (2002)). TRPM2 is activated by ADP-ribose, NAD and changes in redox status (*Nature* 411, 595-599, (2001); *Science* 293, 1327-1330, (2001); and *Mol. Cell* 9, 163-173, (2002)). TRPM7 is regulated by $Mg^{2+}$-ATP and/or $PIP_2$ (*Science* 291, 1043-1047, (2001); *Nature* 411, 690-695, (2001); and *Nat. Cell Biol.* 4, 329-36 (2002)). TRPM8 is activated by cold temperatures and cooling agents (*Nature* 416, 52-58, (2002); and *Cell* 108, 705-715, (2002)). Therefore, in conjunction with its fairly restricted tissue expression, which is not observed with any other family members, LTRPC3 may have a unique biological function in human.

Expression profiling designed to measure the steady state mRNA levels encoding the LTRPC3 polypeptide showed predominately high expression levels in kidney. The LTRPC3 polypeptide was also significantly expression in spinal cord, testis, and brain (as shown in FIG. 6).

Moreover, Northern hybridizations of the LTRPC3 mRNA confirmed the predominately high expression levels in kidney, and significant expression levels in testis, and brain (as shown in FIG. 7). The Northern hybridization was not performed on spinal cord tissue.

Expanded analysis of LTRPC3 expression levels by TaqMan™ quantitative PCR (see FIG. 12) confirmed that the LTRPC3 polypeptide is expressed in kidney, brain, testis (FIGS. 6 and 7), although higher expression levels were observed in brain than previously appreciated. LTRPC3 mRNA was expressed predominately in the brain, specifically the cerebellum, choroid plexus, the locus coeruleus, the posterior hypothalamus and the substantia nigra. Expression of LTRPC3 was also significantly expressed in the kidney, with higher levels observed in the cortex than in the medulla or pelvis. LTRPC3 was also significantly expressed in the spinal cord, testis, and to a lesser extent in other tissues as shown.

Therefore, LTRPC3e polynucleotides and polypeptides, including modulators or fragments thereof, may be useful in treating, diagnosing, prognosing, and/or preventing a variety of neurological conditions, in particular various choroid plexus neoplasms, choroid plexus papilloma, Alzheimer's disease, prion disorders and multiple sclerosis and movement disorders that involve the cerebellum. Based upon the expression pattern of LTRPC3 in kidney, this novel TRP family member, or a splice variant or polymorphism thereof, may also be the cause solitary metastasis in the choroid plexus, a rare type of carcinoma. For example, it has been shown that out of 15 cases of solitary metastasis of the choroid plexus, five originated from renal cell carcinoma (Neurol. Med. Chir. (Tokyo) 1997 December; 37(12):916-9). Additionally, given the rather selective expression of LTRPC3 in the choroid plexus and renal tissues, it may be possible that altered function of LTRPC3 or a splice variant or polymorphism thereof, may be responsible for solitary metastasis and renal carcinoma. LTRPC3 polynucleotides and polypeptides, including modulators or fragments thereof, may be useful in treating, diagnosing, prognosing, and/or preventing a variety of renal disorders, particularly solitary metastasis in the choroid plexus, and renal carcinoma.

Moreover, an additional analysis of LTRPC3 expression levels by TaqMan™ quantitative PCR (see FIG. 13) in disease cells and tissues indicated that the LTRPC3 polypeptide is differentially expressed in renal, testicular, and ovarian tumor tissues. In the renal tumor tissue results, an average of 2 out of 3 matched samples, which represent 3 out of 4 samples total, showed a significant decrease in LTRPC3 steady state RNA levels in tumor compared to control samples. In the testicular tumor tissue results, differential expression of LTRPC3 in testicular cancers was observed with all 5 tumor samples showing a significant reduction in steady-state RNA levels compared to two control samples. In the ovarian tumor tissue results, differential expression of LTRPC3 in ovarian cancers was observed with 3 tumor samples showing a significant reduction in steady-state RNA levels compared to five control samples.

The differential expression of LTRPC3 in tumors relative to normal tissues suggests that loss of LTRPC3 expression during tumor progression might contribute to the metastatic process by altering internal calcium stores in a manner that reflects a loss of cellular control on apoptosis. Restoring LTRPC3e function might provide a novel therapeutic approach to treating certain cancers. Therefore, LTRPC3e polynucleotides and polypeptides, including modulators or fragments thereof, particularly agonists of LTRPC3e activity or expression, may be useful in treating, diagnosing, prognosing, ameliorating, and/or preventing a variety of cancers and proliferative conditions, particularly of the kidney, testis, and ovaries.

Characterization of the LTRPC3 polypeptide of the present invention using antisense oligonucleotides led to the determination that LTRPC3 is involved in the negative modulation of the FEN1 DNA base-excision repair/proliferation modulating protein as described in Example 5 herein.

Specifically, antisense inhibition of LTRPC3 resulted in upregulation of Fen1, a marker of proliferation. As such, LTRPC3 behaves in a manner similar to a tumor suppressor, in that loss results in increases in proliferation. While some increases in the proliferation markers p21 and IkB were also observed, they were less significant, and could be a response to the pro-proliferative effect of LTRPC3 antisense inhibition. Interestingly, expression of LTRPC3 was also observed to be significantly reduced in tumor tissues, relative to normal tissues (see FIG. 13). Specifically, renal, testicular, and ovarian tumor samples showed as much as 12 to 30 fold down regulation of LTRPC3 message levels compared to normal tissues. This reduction of LTRPC3 correlating with the tumor state is consistent with the negative FEN1 modulatory activity and suggests this gene may have antiproliferative activities. Therefore, for modulators of LTRPC3 to be useful for treating cancer, it would be necessary to increase the activity of the gene or gene product in order to have the reverse effect on cancerous cells. Thus, an agonist of LTRPC3 activity or a compound that increased LTRPC3 message levels would be a desired invention for cancer therapy. The same regimen may also be applicable to LTRPC3 splice variants and/or polymorphisms, such as LTRPC3e.

In preferred embodiments, LTRPC3e polynucleotides and polypeptides, including fragments and modulators thereof, are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, LTRPC3e polynucleotides and polypeptides, including fragments and modulators thereof, are useful for increasing mammalian base excision repair activity, increasing mammalian single-nucleotide base excision repair activity, and/or increasing mammalian long patch base excision repair activity.

In preferred embodiments, antagonists directed against LTRPC3e are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, antagonists directed against LTRPC3e are useful for increasing mammalian base excision repair activity, increasing mammalian single-nucleotide base excision repair activity, and/or increasing mammalian long patch base excision repair activity.

In preferred embodiments, agonists directed against LTRPC3e are useful for treating, diagnosing, and/or ameliorating, disorders related to aberrant signal transduction, proliferating disorders, and/or cancers, particularly renal cell carcinomas, testicular cancers, and/or ovarian cancers.

The strong homology to human transient receptor potential channels (TRP), combined with the predominate localized expression in kidney tissue of LTRPC3 suggests the LTRPC3e polynucleotides and polypeptides, including modulators or fragments thereof, may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention, slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome.for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H., Willems, P, H., Bindels, R, J. J. Biol, Chem., 274(13):8375-8, (1999)).

Thus, the LTRPC3e polynucleotides and polypeptides are expected to share at least some biological activity with TRP family members expressed in kidney cells and tissues, particularly those specifically referenced herein.

The strong homology to human transient receptor potential channels (TRP) proteins, combined with the localized expression in spinal cord and brain of LTRPC3 suggests the LTRPC3e polynucleotides and polypeptides, including modulators or fragments thereof, may be useful in treating, diagnosing, prognosing, and/or preventing neurodegenerative disease states, behavioral disorders, or inflammatory conditions. Representative uses are described in the "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong homology to human transient receptor potential channels (TRP), combined with the localized expression in testis tissue of LTRPC3 emphasizes the potential utility for LTRPC3e polynucleotides and polypeptides in treating, diagnosing, prognosing, and/or preventing testicular, in addition to reproductive disorders.

In preferred embodiments, LTRPC3e polynucleotides and polypeptides including agonists and fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The LTRPC3e polynucleotides and polypeptides including agonists and fragments thereof, may also have uses related to modulating testicular development, embryogenesis, reproduction, and in ameliorating, treating, and/or preventing testicular proliferative disorders (e.g., cancers, which include, for example, choriocarcinoma, Non-seminoma, seminona, and testicular germ cell tumors).

Likewise, the localized expression in testis tissue also emphasizes the potential utility for LTRPC3e polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Bimbaumer, L, Lett., 373(3):193-8, (1995)); and TRPC1 (Wes, P, D., Chevesich, J., Jeromin, A., Rosenberg, C., Stetten, G., Montell, C, Proc, Natl, Acad, Sci, U,S,A., 92(21):9652-6, (1995)).

Thus, the LTRPC3e polynucleotides and polypeptides are expected to share at least some biological activity with TRP family members expressed in testis cells and tissues, particularly those specifically referenced herein.

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

In preferred embodiments, LTRPC3e polynucleotides and polypeptides of the present invention, including agonists and/or fragments thereof, have uses that include, modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity.

In more preferred embodiments, LTRPC3e polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

LTRPC3e polynucleotides and polypeptides of the present invention, including agonists and/or fragments may be involved in intracellular $Ca^{2+}$ homeostasis which affects various aspects of biological functions including mechano-regulation, pain transduction, vasorelaxation, gene expression, cell cycle and proliferation/apoptosis. Since LTRPC3e is dominantly expressed in kidney, it may particularly play an important role in regulating cytosolic Ca2+ in the renal system, potentially Ca2+ absorption.

The LTRPC3e gene maps to chromosome 9q21.11-21.31 between the two markers D9S1874 and D9S1807. This region is linked to amyotrophic lateral sclerosis with frontotemporal dementia, early-onset pulverulent cataract, infantile nephronophthisis, hypomagnesemia with secondary hypocalcemia (HSH), and familial hemophagocytic lymphohistiocytosis. Therefore, agonists and/or antagonists of the novel LTRPC3e can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in $Ca^{2+}$ homeostasis including osteoporosis, hypercalciuric stone disease, and chronic renal failure.

Moreover, given the selective expression in kidney, LTRPC3e could be considered a candidate gene for HSH, since the phenotype is a renal insufficiency. LTRPC3e chromosomal location is ~600 kb downstream of a X;9 translocation breakpoint interval described for one patient with HSH (*Hum. Mol. Genet.* 6, 1491-1497, (1997)). Recently, two groups reported that a new member of the TRPM subfamily, TRPM6, expressed in both intestinal tissues and kidney, is associated with HSH (*Nat. Genet.* 31, 166-170, (2002); and *Nat. Genet.* 31, 171-174 (2002)). Indeed, LTRPC3 is ~4 mb 5' to TRPM6 on 9q21. Although TRPM6 is the first component identified for HSH, this should not preclude involvement of LTRPC3e in the disease. Therefore, it is possible that LTRPC3e may co-localize with TRPM6 and/or forms a heteromultimer with TRPM6 in the kidney.

The kidney plays a major role in $Ca^{2+}$ homeostasis (reviewed in *Physiol. Rev.* 75, 429-471, (1995)). LTRPC3e may play a direct role in $Ca^{2+}$ absorption due to its constitutive $Ca^{2+}$ permeability. Alternatively, LTRPC3e may be the SOC that regulates $Ca^{2+}$ absorption. In kidney, $Ca^{2+}$ absorption is regulated by agonists such as calcitonin, parathyroid hormone and parathyroid hormone-related peptide through their respective G protein-coupled receptors, and downstream SOCs. Additionally, in kidney a SOC has been described (*J. Biol. Chem.* 276, 25759-25765, (2001)) for the action of angiotensin II, a vasoactive peptide that plays a major role in regulating blood pressure.

In addition, LTRPC3e polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++ sensitive signaling pathways, the activation of kinase-activatible proteins, and the activation of kinase-dependent signaling pathways.

The LTRPC3e polynucleotides and polypeptides of the present invention, including agonists and/or fragments thereof, have uses that include modulating proliferation, differentiation, migration, and activation in various cells, tissues, and organisms, and particularly in mammalian kidney, spinal cord, testis, and brain, preferably human. LTRPC3e polynucleotides and polypeptides of the present invention, including agonists and/or fragments thereof, may be useful in diagnosing, treating, prognosing, and/or preventing renal, neural, and/or proliferative diseases or disorders, particularly of the renal system.

In addition, antagonists of the LTRPC3e polynucleotides and polypeptides, including modulators or fragments thereof, may have uses that include diagnosing, treating, prognosing, and/or preventing diseases or disorders related to transient receptor potential channel activity, which may include renal, neural, reproductive, and/or proliferative diseases or disorders.

Although it is believed the encoded polypeptide may share at least some biological activities with transient receptor potential channel family members, particularly those melastatin1, a number of methods of determining the exact biological function of this clone are either known in the art or are described elsewhere herein. Briefly, the function of this clone may be determined by applying microarray methodology. Nucleic acids corresponding to the LTRPC3e polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known transient potential receptor inhibitors, which include, but are not limited to the drugs listed herein or otherwise known in the art, might indicate a function in modulating transient potential receptor function, for example. In the case of LTRPC3e, kidney, spinal cord, testis, and brain, should be used to extract RNA to prepare the probe.

In addition, the function of the protein may be assessed by applying quantitative PCR methodology, for example. Real time quantitative PCR would provide the capability of following the expression of the LTRPC3e gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:8 (FIGS. 4A-F).

The function of the protein may also be assessed through complementation assays in yeast. For example, in the case of the LTRPC3e, transforming yeast deficient in transient receptor potential channel activity with LTRPC3e and assessing their ability to grow would provide convincing evidence the LTRPC3e polypeptide has transient receptor potential channel activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a kidney, spinal cord, testis, and/or brain-specific promoter), or it can be expressed at a specified time of development using an inducible and/or a developmentally regulated promoter.

In the case of LTRPC3e transgenic mice or rats, if no phenotype is apparent in normal growth conditions, observing the organism under diseased conditions (renal, reproductive, neural, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal LTRPC3e deletion polypeptides are encompassed by the present invention: M1-T1556, Y2-T1556, V3-T1556, R4-T1556, V5-T1556, S6-T1556, F7-T1556, D8-T1556, T9-T1556, K10-T1556, P11-T1556, D12-T1556, L13-T1556, L14-T1556, L15-T1556, H16-T1556, L17-T1556, M18-T1556, T19-T1556, K20-T1556, E21-T1556, W22-T1556, Q23-T1556, L24-T1556, E25-T1556, L26-T1556, P27-T1556, K28-T1556, L29-T1556, L30-T1556, I31-T1556, S32-T1556, V33-T1556, H34-T1556, G35-T1556, G36-T1556, L37-T1556, Q38-T1556, N39-T1556, F40-T1556, E41-T1556, L42-T1556, Q43-T1556, P44-T1556, K45-T1556, L46-T1556, K47-T1556, Q48-T1556, V49-T1556, F50-T1556, G51-T1556, K52-T1556, G53-T1556, L54-T1556, I55-T1556, K56-T1556, A57-T1556, A58-T1556, M59-T1556, T60-T1556, T61-T1556, G62-T1556, A63-T1556, W64-T1556, I65-T1556, F66-T1556, T67-T1556, G68-T1556, G69-T1556, V70-T1556, N71-T1556, T72-T1556, G73-T1556, V74-T1556, I75-T1556, R76-T1556, H77-T1556, V78-T1556, G79-T1556, D80-T1556, A81-T1556, L82-T1556, K83-T1556, D84-T1556, H85-T1556, A86-T1556, S87-T1556, K88-T1556, S89-T1556, R90-T1556, G91-T1556, K92-T1556, I93-T1556, C94-T1556, T95-T1556, I96-T1556, G97-T1556, I98-T1556, A99-T1556, P100-T1556, W101-T1556, G102-T1556, I103-T1556, V104-T1556, E105-T1556, N106-T1556, Q107-T1556, E108-T1556, D109-T1556, L110-T1556, I111-T1556, G112-T1556, R113-T1556, D114-T1556, V115-T1556, V116-T1556, R117-T1556, P118-T1556, Y119-T1556, Q120-T1556, T121-T1556, M122-T1556, S123-T1556, N124-T1556, P125-T1556, M126-T1556, S127-T1556, K128-T1556, L129-T1556, T130-T1556, V131-T1556, L132-T1556, N133-T1556, S134-T1556, M135-T1556, H136-T1556, S137-T1556, H138-T1556, F139-T1556, I140-T1556, L141-T1556, A142-T1556, D143-T1556, N144-T1556, G145-T1556, T146-T1556, T147-T1556, G148-T1556, K149-T1556, Y150-T1556, G151-T1556, A152-T1556, E153-T1556, V154-T1556, K155-T1556, L156-T1556, R157-T1556, R158-T1556, Q159-T1556, L160-T1556, E161-T1556, K162-T1556, H163-T1556, I164-T1556, S165-T1556, L166-T1556, Q167-T1556, K168-T1556, I169-T1556, N170-T1556, T171-T1556, R172-T1556, I173-T1556, G174-T1556, Q175-T1556, G176-T1556, V177-T1556, P178-T1556, V179-T1556, V180-T1556, A181-T1556, L182-T1556, I183-

T1556, V184-T1556, E185-T1556, G186-T1556, G187-T1556, P188-T1556, N189-T1556, V190-T1556, I191-T1556, S192-T1556, I193-T1556, V194-T1556, L195-T1556, E196-T1556, Y197-T1556, L198-T1556, R199-T1556, D200-T1556, T201-T1556, P202-T1556, P203-T1556, V204-T1556, P205-T1556, V206-T1556, V207-T1556, V208-T1556, C209-T1556, D210-T1556, G211-T1556, S212-T1556, G213-T1556, R214-T1556, A215-T1556, S216-T1556, D217-T1556, I218-T1556, L219-T1556, A220-T1556, F221-T1556, G222-T1556, H223-T1556, K224-T1556, Y225-T1556, S226-T1556, E227-T1556, E228-T1556, G229-T1556, G230-T1556, L231-T1556, I232-T1556, N233-T1556, E234-T1556, S235-T1556, L236-T1556, R237-T1556, D238-T1556, Q239-T1556, L240-T1556, L241-T1556, V242-T1556, T243-T1556, I244-T1556, Q245-T1556, K246-T1556, T247-T1556, F248-T1556, T249-T1556, Y250-T1556, T251-T1556, R252-T1556, T253-T1556, Q254-T1556, A255-T1556, Q256-T1556, H257-T1556, L258-T1556, F259-T1556, I260-T1556, I261-T1556, L262-T1556, M263-T1556, E264-T1556, C265-T1556, M266-T1556, K267-T1556, K268-T1556, K269-T1556, E270-T1556, L271-T1556, I272-T1556, T273-T1556, V274-T1556, F275-T1556, R276-T1556, M277-T1556, G278-T1556, S279-T1556, E280-T1556, G281-T1556, H282-T1556, Q283-T1556, D284-T1556, I285-T1556, D286-T1556, L287-T1556, A288-T1556, I289-T1556, L290-T1556, T291-T1556, A292-T1556, L293-T1556, L294-T1556, K295-T1556, G296-T1556, A297-T1556, N298-T1556, A299-T1556, S300-T1556, A301-T1556, P302-T1556, D303-T1556, Q304-T1556, L305-T1556, S306-T1556, L307-T1556, A308-T1556, L309-T1556, A310-T1556, W311-T1556, N312-T1556, R313-T1556, V314-T1556, D315-T1556, I316-T1556, A317-T1556, R318-T1556, S319-T1556, Q320-T1556, I321-T1556, F322-T1556, I323-T1556, Y324-T1556, G325-T1556, Q326-T1556, Q327-T1556, W328-T1556, P329-T1556, V330-T1556, G331-T1556, S332-T1556, L333-T1556, E334-T1556, Q335-T1556, A336-T1556, M337-T1556, L338-T1556, D339-T1556, A340-T1556, L341-T1556, V342-T1556, L343-T1556, D344-T1556, R345-T1556, V346-T1556, D347-T1556, F348-T1556, V349-T1556, K350-T1556, L351-T1556, L352-T1556, I353-T1556, E354-T1556, N355-T1556, G356-T1556, V357-T1556, S358-T1556, M359-T1556, H360-T1556, R361-T1556, F362-T1556, L363-T1556, T364-T1556, I365-T1556, S366-T1556, R367-T1556, L368-T1556, E369-T1556, E370-T1556, L371-T1556, Y372-T1556, N373-T1556, T374-T1556, R375-T1556, H376-T1556, G377-T1556, P378-T1556, S379-T1556, N380-T1556, T381-T1556, L382-T1556, Y383-T1556, H384-T1556, L385-T1556, V386-T1556, R387-T1556, D388-T1556, V389-T1556, K390-T1556, K391-T1556, R392-T1556, E393-T1556, Y394-T1556, P395-T1556, G396-T1556, F397-T1556, G398-T1556, W399-T1556, I400-T1556, Y401-T1556, F402-T1556, K403-T1556, G404-T1556, N405-T1556, L406-T1556, P407-T1556, P408-T1556, D409-T1556, Y410-T1556, R411-T1556, I412-T1556, S413-T1556, L414-T1556, I415-T1556, D416-T1556, I417-T1556, G418-T1556, L419-T1556, V420-T1556, I421-T1556, E422-T1556, Y423-T1556, L424-T1556, M425-T1556, G426-T1556, G427-T1556, A428-T1556, Y429-T1556, R430-T1556, C431-T1556, N432-T1556, Y433-T1556, T434-T1556, R435-T1556, K436-T1556, R437-T1556, F438-T1556, R439-T1556, T440-T1556, L441-T1556, Y442-T1556, H443-T1556, N444-T1556, L445-T1556, F446-T1556, G447-T1556, P448-T1556, K449-T1556, and/or R450-T1556 of SEQ ID NO:9. Polynucleotide sequences encoding these polypeptides are also provided. The present invention also encompasses the use of these N-terminal LTRPC3e deletion polypeptides as immunogenic and/or antigenic epitopes as described elsewhere herein.

In preferred embodiments, the following C-terminal LTRPC3e deletion polypeptides are encompassed by the present invention: M1-T1556, M1-H1555, M1-K1554, M1-S1553, M1-E1552, M1-F1551, M1-S1550, M1-Q1549, M1-F1548, M1-A1547, M1-S1546, M1-T1545, M1-R1544, M1-S1543, M1-L1542, M1-R1541, M1-R1540, M1-M1539, M1-S1538, M1-L1537, M1-S1536, M1-D1535, M1-G1534, M1-R1533, M1-G1532, M1-E1531, M1-P1530, M1-K1529, M1-S1528, M1-S1527, M1-K1526, M1-S1525, M1-R1524, M1-Q1523, M1-F1522, M1-P1521, M1-N1520, M1-Q1519, M1-L1518, M1-S1517, M1-A1516, M1-T1515, M1-N1514, M1-R1513, M1-Q1512, M1-R1511, M1-D1510, M1-L1509, M1-K1508, M1-D1507, M1-S1506, M1-I1505, M1-S1504, M1-F1503, M1-S1502, M1-K1501, M1-R1500, M1-T1499, M1-H1498, M1-A1497, M1-Y1496, M1-P1495, M1-A1494, M1-S1493, M1-P1492, M1-E1491, M1-E1490, M1-A1489, M1-S1488, M1-Y1487, M1-S1486, M1-N1485, M1-A1484, M1-R1483, M1-E1482, M1-I1481, M1-K1480, M1-P1479, M1-V1478, M1-T1477, M1-I1476, M1-N1475, M1-N1474, M1-S1473, M1-L1472, M1-T1471, M1-R1470, M1-E1469, M1-S1468, M1-N1467, M1-D1466, M1-G1465, M1-E1464, M1-Q1463, M1-S1462, M1-S1461, M1-I1460, M1-A1459, M1-I1458, M1-T1457, M1-A1456, M1-R1455, M1-R1454, M1-G1453, M1-K1452, M1-A1451, M1-E1450, M1-N1449, M1-E1448, M1-E1447, M1-S1446, M1-D1445, M1-S1444, M1-S1443, M1-P1442, M1-H1441, M1-S1440, M1-L1439, M1-E1438, M1-A1437, M1-E1436, M1-R1435, M1-E1434, M1-P1433, M1-H1432, M1-C1431, M1-C1430, M1-T1429, M1-L1428, M1-D1427, M1-E1426, M1-V1425, M1-K1424, M1-D1423, M1-G1422, M1-L1421, M1-G1420, M1-G1419, M1-P1418, M1-F1417, M1-A1416, M1-A1415, M1-R1414, M1-D1413, M1-A1412, M1-I1411, M1-A1410, M1-Q1409, M1-P1408, M1-A1407, M1-N1406, M1-V1405, M1-C1404, M1-R1403, M1-T1402, M1-D1401, M1-I1400, M1-C1399, M1-D1398, M1-T1397, M1-I1396, M1-S1395, M1-T1394, M1-Y1393, M1-E1392, M1-A1391, M1-T1390, M1-K1389, M1-V1388, M1-P1387, M1-V1386, M1-G1385, M1-F1384, M1-N1383, M1-A1382, M1-Y1381, M1-Y1380, M1-S1379, M1-R1378, M1-S1377, M1-P1376, M1-S1375, M1-F1374, M1-M1373, M1-F1372, M1-S1371, M1-H1370, M1-S1369, M1-K1368, M1-V1367, M1-I1366, M1-P1365, M1-A1364, M1-E1363, M1-E1362, M1-L1361, M1-L1360, M1-F1359, M1-P1358, M1-T1357, M1-T1356, M1-A1355, M1-L1354, M1-Y1353, M1-R1352, M1-S1351, M1-S1350, M1-K1349, M1-S1348, M1-R1347, M1-E1346, M1-I1345, M1-T1344, M1-H1343, M1-Y1342, M1-M1341, M1-P1340, M1-P1339, M1-E1338, M1-S1337, M1-D1336, M1-W1335, M1-P1334, M1-N1333, M1-Q1332, M1-C1331, M1-E1330, M1-P1329, M1-L1328, M1-H1327, M1-T1326, M1-Y1325, M1-D1324, M1-S1323, M1-S1322, M1-F1321, M1-S1320, M1-R1319, M1-T1318, M1-D1317, M1-M1316, M1-S1315, M1-T1314, M1-I1313, M1-D1312, M1-E1311, M1-F1310, M1-D1309, M1-I1308, M1-S1307, M1-R1306, M1-S1305, M1-P1304, M1-P1303, M1-R1302, M1-D1301, M1-T1300, M1-P1299, M1-A1298, M1-L1297, M1-T1296, M1-A1295, M1-Y1294, M1-A1293, M1-S1292, M1-S1291, M1-S1290, M1-P1289, M1-A1288, M1-T1287, M1-S1286, M1-P1285, M1-V1284, M1-P1283, M1-S1282, M1-S1281, M1-F1280, M1-S1279, M1-P1278, M1-E1277, M1-G1276, M1-L1275, M1-G1274, M1-L1273, M1-I1272, M1-N1271, M1-V1270, M1-S1269, M1-N1268, M1-D1267, M1-L1266, M1-P1265, M1-D1264, M1-I1263, M1-D1262, M1-C1261, M1-H1260, M1-L1259, M1-E1258, M1-D1257, M1-M1256, M1-A1255, M1-S1254,
M1-V1253, M1-Y1252, M1-I1251, M1-D1250, M1-I1249,
M1-C1248, M1-S1247, M1-S1246, M1-P1245, M1-R1244,
M1-R1243, M1-S1242, M1-D1241, M1-P1240, M1-V1239,
M1-I1238, M1-A1237, M1-L1236, M1-T1235, M1-N1234,
M1-A1233, M1-P1232, M1-A1231, M1-A1230, M1-P1229,
M1-A1228, M1-K1227, M1-P1226, M1-E1225, M1-K1224,
M1-A1223, M1-V1222, M1-S1221, M1-H1220, M1-S1219,
M1-S1218, M1-T1217, M1-A1216, M1-R1215, M1-H1214,
M1-L1213, M1-S1212, M1-L1211, M1-S1210, M1-R1209,
M1-E1208, M1-K1207, M1-F1206, M1-I1205, M1-S1204,
M1-E1203, M1-L1202, M1-K1201, M1-E1200, M1-I1199,
M1-G1198, M1-G1197, M1-K1196, M1-D1195,
M1-K1194, M1-M1193, M1-N1192, M1-V1191,
M1-S1190, M1-Y1189, M1-F1188, M1-S1187, M1-H1186,
M1-S1185, M1-R1184, M1-M1183, M1-R1182, M1-P1181,
M1-M1180, M1-L1179, M1-T1178, M1-P1177, M1-S1176,
M1-T1175, M1-P1174, M1-S1173, M1-M1172, M1-T1171,
M1-E1170, M1-E1169, M1-G1168, M1-A1167, M1-P1166,
M1-D1165, M1-I1164, M1-S1163, M1-E1162, M1-Q161,
M1-L1160, M1-K1159, M1-F1158, M1-T1157, M1-N1156,
M1-G1155, M1-E1154, M1-Q1153, M1-S1152, M1-N1151,
M1-F1150, M1-S1149, M1-S1148, M1-Q1147, M1-R1146,
M1-V1145, M1-I1144, M1-Y1143, M1-A1142, M1-A1141,
M1-D1140, M1-T1139, M1-C1138, M1-D1137, M1-S1136,
M1-S1135, M1-T1134, M1-R1133, M1-S1132, M1-R1131,
M1-I130, M1-K1129, M1-N1128, M1-S1127, M1-E1126,
M1-A1125, M1-R1124, M1-E1123, M1-L1122, M1-G1121,
M1-T1120, M1-L1119, M1-R1118, M1-E1117, M1-L1116,
M1-A1115, M1-T1114, M1-A1113, M1-M1112,
M1-R1111, M1-G1110, M1-I1109, M1-L1108, M1-D1107,
M1-E1106, M1-L1105, M1-Q1104, M1-A1103, M1-L1102,
M1-R1101, M1-I1100, M1-D1099, M1-V1098, M1-T1097,
M1-Q1096, M1-L1095, M1-S1094, M1-A1093, M1-K1092,
M1-M1091, M1-S1090, M1-H1089, M1-E1088, M1-R1087,
M1-E1086, M1-N1085, M1-V1084, M1-E1083, M1-E1082,
M1-L1081, M1-R1080, M1-M1079, M1-S1078,
M1-M1077, M1-N1076, M1-E1075, M1-V1074,
M1-R1073, M1-E1072, M1-S1071, M1-T1070, M1-V1069,
M1-R1068, M1-I1067, M1-R1066, M1-E1065, M1-D1064,
M1-N1063, M1-S1062, M1-S1061, M1-N1060, M1-F1059,
M1-R1058, M1-D1057, M1-D1056, M1-K1055, M1-E1054,
M1-R1053, M1-F1052, M1-Y1051, M1-E1050, M1-E1049,
M1-I1048, M1-C1047, M1-Q1046, M1-E1045, M1-E1044,
M1-F1043, M1-D1042, M1-H1041, M1-V1040, M1-K1039,
M1-K1038, M1-L1037, M1-E1036, M1-D1035, M1-D1034,
M1-T1033, M1-I1032, M1-F1031, M1-L1030, M1-K1029,
M1-L1028, M1-G1027, M1-Y1026, M1-D1025, M1-R1024,
M1-E1023, M1-D1022, M1-P1021, M1-D1020, M1-S1019,
M1-E1018, M1-H1017, M1-K1016, M1-R1015,
M1-W1014, M1-R1013, M1-C1012, M1-C1011,
M1-L1010, M1-H1009, M1-Q1008, M1-F1007, M1-I1006,
M1-M1005, M1-T1004, M1-M1003, M1-H1002,
M1-S1001, M1-F1000, M1-I999, M1-I998, M1-L997,
M1-P996, M1-P995, M1-P994, M1-L993, M1-V992,
M1-P991, M1-R990, M1-E989, M1-H988, M1-F987,
M1-T986, M1-M985, M1-I984, M1-L983, M1-Q982,
M1-Y981, M1-R980, M1-Q979, M1-F978, M1-K977,
M1-W976, M1-V975, M1-Q974, M1-N973, M1-S972,
M1-I971, M1-S970, M1-K969, M1-V968, M1-E967,
M1-F966, M1-F965, M1-T964, M1-N963, M1-N962,
M1-F961, M1-V960, M1-A959, M1-I958, M1-L957,
M1-L956, M1-N955, M1-V954, M1-L953, M1-L952,
M1-I951, M1-N950, M1-A949, M1-W948, M1-L947,
M1-L946, M1-Y945, M1-C944, M1-A943, M1-M942,
M1-I941, M1-A940, M1-P939, M1-V938, M1-I937,
M1-W936, M1-A935, M1-G934, M1-T933, M1-K932,
M1-C931, M1-P930, M1-P929, M1-L928, M1-Q927,
M1-I926, M1-I925, M1-K924, M1-G923, M1-D922,
M1-E921, M1-R920, M1-T919, M1-E918, M1-N917,
M1-Q916, M1-G915, M1-C914, M1-P913, M1-P912,
M1-D911, M1-I910, M1-Q909, M1-D908, M1-A907,
M1-F906, M1-V905, M1-E904, M1-G903, M1-Y902,
M1-I901, M1-M900, M1-W899, M1-Y898, M1-P897,
M1-M896, M1-Y895, M1-F894, M1-I893, M1-N892,
M1-K891, M1-A890, M1-L889, M1-K888, M1-W887,
M1-S886, M1-P885, M1-E884, M1-E883, M1-N882,
M1-P881, M1-F880, M1-L879, M1-I878, M1-A877,
M1-Q876, M1-R875, M1-A874, M1-V873, M1-G872,
M1-F871, M1-S870, M1-M869, M1-L868, M1-V867,
M1-V866, M1-L865, M1-M864, M1-I863, M1-I862,
M1-V861, M1-F860, M1-Y859, M1-M858, M1-M857,
M1-D856, M1-I855, M1-M854, M1-M853, M1-K852,
M1-G851, M1-I850, M1-M849, M1-M848, M1-V847,
M1-Y846, M1-P845, M1-G844, M1-L843, M1-Y842,
M1-K841, M1-N840, M1-V839, M1-G838, M1-F837,
M1-I836, M1-D835, M1-L834, M1-L833, M1-R832,
M1-I831, M1-Y830, M1-W829, M1-Y828, M1-I827,
M1-I826, M1-N825, M1-V824, M1-C823, M1-Y822,
M1-I821, M1-V820, M1-R819, M1-G818, M1-D817,
M1-S816, M1-R815, M1-F814, M1-P813, M1-Q812,
M1-D811, M1-Q810, M1-L809, M1-R808, M1-L807,
M1-I806, M1-M805, M1-G804, M1-V803, M1-S802,
M1-F801, M1-L800, M1-L799, M1-I798, M1-A797,
M1-I796, M1-L795, M1-D794, M1-T793, M1-V792,
M1-N791, M1-W790, M1-Y789, M1-E788, M1-Q787,
M1-L786, M1-W785, M1-V784, M1-K783, M1-V782,
M1-K781, M1-Q780, M1-L779, M1-L778, M1-K777,
M1-G776, M1-P775, M1-E774, M1-S773, M1-M772,
M1-L771, M1-I770, M1-E769, M1-R768, M1-M767,
M1-K766, M1-E765, M1-I764, M1-G763, M1-L762,
M1-T761, M1-F760, M1-I759, M1-Y758, M1-S757,
M1-I756, M1-V755, M1-I754, M1-W753, M1-E752,
M1-Q751, M1-T750, M1-S749, M1-P748, M1-W747,
M1-R746, M1-E745, M1-M744, M1-K743, M1-V742,
M1-L741, M1-V740, M1-I739, M1-Y738, M1-N737,
M1-F736, M1-L735, M1-M734, M1-L733, M1-Y732,
M1-G731, M1-I730, M1-Y729, M1-A728, M1-L727,
M1-T726, M1-Y725, M1-F724, M1-W723, M1-F722,
M1-K721, M1-V720, M1-I719, M1-P718, M1-A717,
M1-N716, M1-Y715, M1-F714, M1-E713, M1-Y712,
M1-I711, M1-K710, M1-R709, M1-G708, M1-L707,
M1-P706, M1-I705, M1-L704, M1-R703, M1-H702,
M1-K701, M1-S700, M1-Q699, M1-V698, M1-E697,
M1-E696, M1-E695, M1-D694, M1-K693, M1-K692,
M1-R691, M1-S690, M1-S689, M1-E688, M1-G687,
M1-N686, M1-N685, M1-R684, M1-G683, M1-L682,
M1-M681, M1-A680, M1-T679, M1-L678, M1-E677,
M1-M676, M1-D675, M1-E674, M1-E673, M1-E672,
M1-K671, M1-E670, M1-K669, M1-T668, M1-P667,
M1-K666, M1-E665, M1-P664, M1-E663, M1-E662,
M1-A661, M1-E660, M1-K659, M1-E658, M1-Q657,
M1-L656, M1-H655, M1-I654, M1-E653, M1-Q652,
M1-A651, M1-Q650, M1-S649, M1-M648, M1-Y647,
M1-P646, M1-M645, M1-D644, M1-D643, M1-K642,
M1-N641, M1-K640, M1-F639, M1-E638, M1-L637,
M1-S636, M1-L635, M1-I634, M1-S633, M1-P632,
M1-P631, M1-L630, M1-L629, M1-I628, M1-G627,
M1-L626, M1-I625, M1-V624, M1-K623, M1-L622,
M1-G621, M1-S620, M1-N619, M1-K618, M1-R617,
M1-M616, M1-R615, M1-L614, M1-R613, M1-G612,
M1-M611, M1-W610, M1-M609, M1-D608, M1-T607,
M1-L606, M1-L605, M1-M604, M1-Q603, M1-S602,
M1-C601, M1-T600, M1-H599, M1-A598, M1-I597, M1-F596, M1-D595, M1-R594, M1-H593, M1-K592, M1-A591, M1-A590, M1-V589, M1-A588, M1-L587, M1-Q586, M1-L585, M1-C584, M1-T583, M1-A582, M1-N581, M1-S580, M1-W579, M1-N578, M1-K577, M1-L576, M1-E575, M1-Y574, M1-T573, M1-L572, M1-L571, M1-K570, M1-M569, M1-A568, M1-L567, M1-Q566, M1-E565, M1-D564, M1-Q563, M1-K562, M1-Y561, M1-S560, M1-Q559, M1-D558, M1-L557, M1-L556, M1-E555, M1-V554, M1-A553, M1-L552, M1-Q551, M1-G550, M1-F549, M1-D548, M1-R547, M1-S546, M1-N545, M1-H544, M1-N543, M1-L542, M1-E541, M1-Q540, M1-S539, M1-I538, M1-D537, M1-D536, M1-V535, M1-M534, M1-D533, M1-N532, M1-E531, M1-S530, M1-A529, M1-E528, M1-H527, M1-A526, M1-M525, M1-A524, M1-K523, M1-C522, M1-L521, M1-K520, M1-C519, M1-A518, M1-V517, M1-L516, M1-A515, M1-K514, M1-A513, M1-M512, M1-A511, M1-E510, M1-E509, M1-G508, M1-H507, M1-Q506, M1-W505, M1-F504, M1-F503, M1-L502, M1-A501, M1-M500, M1-K499, M1-Q498, M1-R497, M1-K496, M1-M495, M1-L494, M1-V493, M1-A492, M1-W491, M1-V490, M1-M489, M1-L488, M1-E487, M1-H486, M1-F485, M1-P484, M1-F483, M1-P482, M1-F481, M1-H480, M1-N479, M1-I478, M1-E477, M1-P476, M1-D475, M1-D474, M1-L473, M1-D472, M1-I471, M1-D470, M1-V469, M1-E468, M1-E467, M1-E466, M1-R465, M1-K464, M1-K463, M1-T462, M1-T461, M1-K460, M1-R459, M1-G458, M1-R457, M1-R456, M1-L455, M1-P454, M1-I453, M1-D452, and/or M1-D451 of SEQ ID NO:9. Polynucleotide sequences encoding these polypeptides are also provided. The present invention also encompasses the use of these C-terminal LTRPC3e deletion polypeptides as immunogenic and/or antigenic epitopes as described elsewhere herein.

Alternatively, preferred polypeptides of the present invention may comprise polypeptide sequences corresponding to, for example, internal regions of the LTRPC3e polypeptide (e.g., any combination of both N- and C-terminal LTRPC3e polypeptide deletions) of SEQ ID NO:9. For example, internal regions could be defined by the equation: amino acid NX to amino acid CX, wherein NX refers to any N-terminal deletion polypeptide amino acid of LTRPC3e (SEQ ID NO:9), and where CX refers to any C-terminal deletion polypeptide amino acid of LTRPC3e (SEQ ID NO:9). Polynucleotides encoding these polypeptides are also provided. The present invention also encompasses the use of these polypeptides as an immunogenic and/or antigenic epitope as described elsewhere herein.

The LTRPC3e polypeptides of the present invention were determined to comprise several phosphorylation sites based upon the Motif algorithm (Genetics Computer Group, Inc.). The phosphorylation of such sites may regulate some biological activity of the LTRPC3e polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the LTRPC3e polypeptide to associate with other potassium channel alpha subunits, beta subunits, or its ability to modulate potassium channel function.

Specifically, the LTRPC3e polypeptide was predicted to comprise two tyrosine phosphorylation sites using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or [RK]-x(3)-[DE]-x(2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Natl. Acad. Sci. U.S.A. 79:973-977 (1982); Hunter T., J. Biol. Chem. 257:4843-4848 (1982), and Cooper J. A., Esch F. S., Taylor S. S., Hunter T., J. Biol. Chem. 259:7835-7841(1984), which are hereby incorporated herein by reference.

In preferred embodiments, the following tyrosine phosphorylation site polypeptides are encompassed by the present invention: LSLEFKNKDDMPYMSQAQ (SEQ ID NO:209), and/or VMMIGKMMIDMMYFVIIM (SEQ ID NO:210). Polynucleotides encoding these polypeptides are also provided. The present invention also encompasses the use of these LTRPC3e tyrosine phosphorylation site polypeptides as immunogenic and/or antigenic epitopes as described elsewhere herein.

The LTRPC3e polypeptide was predicted to comprise twenty three PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. 260: 12492-12499 (1985); which are hereby incorporated by reference herein.

In preferred embodiments, the following PKC phosphorylation site polypeptides are encompassed by the present invention: ADNGTTGKYGAEV (SEQ ID NO:211), VVCDGSGRASDIL (SEQ ID NO:212), GLINESLRDQLLV (SEQ ID NO:213), YRCNYTRKRFRTL (SEQ ID NO:214), RRGRKTTKKREEE (SEQ ID NO:215), RGRKTTKKREEEV (SEQ ID NO:216), ELLDQSYKQDEQL (SEQ ID NO:217), RNNGESSRKKDEE (SEQ ID NO:218), NNGESSRKKDEEE (SEQ ID NO:219), PNEEPSWKLAKNI (SEQ ID NO:220), RIRVTSERVENMS (SEQ ID NO:221), RVENMSMRLEEVN (SEQ ID NO:222), NEREHSMKASLQT (SEQ ID NO:223), LERAESNKIRSRT (SEQ ID NO:224), SQEGNTFKLQESI (SEQ ID NO:225), AIVPDSRRPSSCI (SEQ ID NO:226), ATLAPTDRPPSRS (SEQ ID NO:227), IERSKSSRYLATT (SEQ ID NO:228), QEGDNSERTLSNN (SEQ ID NO:229), APYAHTRKSFSIS (SEQ ID NO:230), KSFSISDKLDRQR (SEQ ID NO:231), FQRSKSSKPEGRG (SEQ ID NO:232), and/or RGDSLSMRRLSRT (SEQ ID NO:233). Polynucleotides encoding these polypeptides are also provided. The present invention also encompasses the use of these LTRPC3e PKC phosphorylation site polypeptides as immunogenic and/or antigenic epitopes as described elsewhere herein.

The present invention also encompasses immunogenic and/or antigenic epitopes of the LTRPC3e polypeptide.

The LTRPC3e polypeptide has been shown to comprise twelve glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine phosphorylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673-702 (1972); Pless D. D., Lennarz W. J., Proc. Natl. Acad. Sci. U.S.A. 74:134-138 (1977); Bause E., Biochem. J. 209:331-336 (1983); Gavel Y., von Heijne G., Protein Eng. 3:433-442 (1990); and Miletich J. P., Broze G. J. Jr., J. Biol. Chem. 265:11397-11404 (1990).

In preferred embodiments, the following asparagine glycosylation site polypeptides are encompassed by the present invention: FILADNGTTGKYGA (SEQ ID NO:234), EGGLINESLRDQLL (SEQ ID NO:235), LLKGANASAPDQLS (SEQ ID NO:236), GAYRCNYTRKRFRT (SEQ ID NO:237), TYELKNWSNATCLQ (SEQ ID NO:238), LKNWSNATCLQLAV (SEQ ID NO:239), LQEYWNVTDLIAIL (SEQ ID NO:240), PPCGQNETREDGKI (SEQ ID NO:241), LIAVFNNTFFEVKS (SEQ ID NO:242), KDDRFNSSNDERIR (SEQ ID NO:243), SERVENMSMRLEEV (SEQ ID NO:244), and/or RTLSNNITVPKIER (SEQ ID NO:245). Polynucleotides encoding these polypeptides are also provided. The present invention also encompasses the use of these LTRPC3e asparagine glycosylation site polypeptides as immunogenic and/or antigenic epitopes as described elsewhere herein.

The LTRPC3e polypeptide has been shown to comprise one RGD cell attachment site domain according to the Motif algorithm (Genetics Computer Group, Inc.). The sequence Arg-Gly-Asp, found in fibronectin, is crucial for its interaction with its cell surface receptor, an integrin. What has been called the 'RGD' tripeptide is also found in the sequences of a number of other proteins, where it has been shown to play a role in cell adhesion. Non-limiting examples of these proteins are the following: some forms of collagens, fibrinogen, vitronectin, von Willebrand factor (VWF), snake disintegrins, and slime mold discoidins. The 'RGD' tripeptide is also found in other proteins where it may serve the same purpose. A consensus pattern for RGD cell attachment sites is the following: R-G-D. Additional information relating to RGD cell attachment site domains may be found in reference to the following publications, which are hereby incorporated by reference herein: Ruoslahti E., Pierschbacher M. D., Cell 44:517-518 (1986); and d'Souza S. E., Ginsberg M. H., Plow E. F., Trends Biochem. Sci. 16:246-250 (1991).

In preferred embodiments, the following RGD cell attachment site domain polypeptide is encompassed by the present invention: SKPEGRGDSLSMR (SEQ ID NO:246). Polynucleotides encoding these polypeptides are also provided. The present invention also encompasses the use of this RGD cell attachment site domain polypeptide as an immunogenic and/or antigenic epitope as described elsewhere herein.

The LTRPC3e polypeptide has been shown to comprise one aminoacyl-transfer RNA synthetases class-II domain according to the Motif algorithm (Genetics Computer Group, Inc.). Aminoacyl-tRNA synthetases (EC 6.1.1.-) are a group of enzymes which activate amino acids and transfer them to specific tRNA molecules as the first step in protein biosynthesis. In prokaryotic organisms there are at least twenty different types of aminoacyl-tRNA synthetases, one for each different amino acid. In eukaryotes there are generally two aminoacyl-tRNA synthetases for each different amino acid: one cytosolic form and a mitochondrial form. While all these enzymes have a common function, they are widely diverse in terms of subunit size and of quaternary structure.

The synthetases specific for alanine, asparagine, aspartic acid, glycine, histidine, lysine, phenylalanine, proline, serine, and threonine are referred to as class-II synthetases and probably have a common folding pattern in their catalytic domain for the binding of ATP and amino acid which is different to the Rossmann fold observed for the class I synthetases.

Class-II tRNA synthetases do not share a high degree of similarity, however at least three conserved regions are present.

The consensus pattern for aminoacyl-transfer RNA synthetases class-II domains are as follows: [FYH]-R-x-[DE]-x(4,12)-[RH]-x(3)-F-x(3)-[DE]; and [GSTALVF]-{DENQHRKP}-[GSTA]-[LIVMF]-[DE]-R-[LIVMF]-x-[LIVMSTAG]-[LIVMFY], where 'x' represents an intervening amino acid residue.

Additional information specific to aminoacyl-transfer RNA synthetases class-II domains may be found in reference to the following publications, Schimmel P., Annu. Rev. Biochem. 56:125-158 (1987); Delarue M., Moras D., BioEssays 15:675-687 (1993); Schimmel P., Trends Biochem. Sci. 16:1-3 (1991); Nagel G. M., Doolittle R. F., Proc. Natl. Acad. Sci. U.S.A. 88:8121-8125 (1991); Cusack S., Haertlein M., Leberman R., Nucleic Acids Res. 19:3489-3498 (1991); Cusack S., Biochimie 75:1077-1081 (1993); Cusack S., Berthet-Colominas C., Haertlein M., Nassar N., Leberman R., Nature 347:249-255 (1990); and Leveque F., Plateau P., Dessen P., Blanquet S., Nucleic Acids Res. 18:305-312 (1990); which are hereby incorporated herein by reference in their entirety.

In preferred embodiments, the following aminoacyl-transfer RNA synthetases class-II domain polypeptide is encompassed by the present invention: LIGRMATALERLTGLERAES (SEQ ID NO:247). Polynucleotides encoding these polypeptides are also provided. The present invention also encompasses the use of this RGD cell attachment site domain polypeptide as an immunogenic and/or antigenic epitope as described elsewhere herein.

The LTRPC3e polypeptide has been shown to comprise three amidation sites according to the Motif algorithm (Genetics Computer Group, Inc.). The precursor of hormones and other active peptides which are C-terminally amidated is always directly followed by a glycine residue which provides the amide group, and most often by at least two consecutive basic residues (Arg or Lys) which generally function as an active peptide precursor cleavage site. Although all amino acids can be amidated, neutral hydrophobic residues such as Val or Phe are good substrates, while charged residues such as Asp or Arg are much less reactive. A consensus pattern for amidation sites is the following: x-G-[RK]-[RK], wherein "X" represents the amidation site. Additional information relating to asparagine glycosylation may be found in reference to the following publications, which are hereby incorporated by reference herein: Kreil G., Meth. Enzymol. 106: 218-223(1984); and Bradbury A. F., Smyth D. G., Biosci. Rep. 7:907-916 (1987).

In preferred embodiments, the following amidation site polypeptides are encompassed by the present invention:

DIPLRRGRKTTKKR (SEQ ID NO:248), HRLI-PLGRKIYEFY (SEQ ID NO:249), and/or EENEAKGRRA-TIAI (SEQ ID NO:250). Polynucleotides encoding these polypeptides are also provided. The present invention also encompasses the use of these LTRPC3e amidation site polypeptides as immunogenic and/or antigenic epitopes as described elsewhere herein.

Many polynucleotide sequences, such as EST sequences, are publicly available and accessible through sequence databases. Some of these sequences are related to SEQ ID NO:8 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 4657 of SEQ ID NO:8, b is an integer between 15 to 4671, where both a and b correspond to the positions of nucleotide residues shown in SEQ ID NO:8, and where b is greater than or equal to a+14.

sequences were assembled into a single contiguous sequence of high redundancy (usually several overlapping sequences at each nucleotide position), resulting in a final sequence identified as SEQ ID NO:X.

The cDNA Clone ID was deposited on the date and given the corresponding deposit number listed in "ATCC Deposit No:Z and Date." "Vector" refers to the type of vector contained in the cDNA Clone ID.

"Total NT Seq. Of Clone" refers to the total number of nucleotides in the clone contig identified by "Gene No." The deposited clone may contain all or most of the sequence of SEQ ID NO:X. The nucleotide position of SEQ ID NO:X of the putative start codon (methionine) is identified as "5' NT of Start Codon of ORF."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

TABLE I

| Gene No. | CDNA CloneID | ATCC Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 1. | LTRPC3 (AL358786, NT_008306, clone 86, TRPM3, and/or LTRPC6) | PTA-4175 Mar. 21, 2002 | PBSII-SKSΔP-XB | 1 | 4665 | 1 | 4662 | 2 | 1554 |
| 2 | LTRPC3b (AL358786, NT_008306, clone 86, TRPM3, and/or LTRPC6 splice variant) | N/A | N/A | 3 | 4701 | 1 | 4698 | 4 | 1566 |
| 3. | LTRPC3c (AL358786, NT_008306, clone 86, TRPM3, and/or LTRPC6 splice variant) | N/A | N/A | 5 | 4701 | 1 | 4698 | 6 | 1566 |
| 4 | LTRPC3e (AL358786, NT_008306, clone 86, TRPM3, and/or LTRPC6 splice variant) | N/A | N/A | 8 | 4671 | 1 | 4668 | 9 | 1556 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping The total number of amino acids within the open reading frame of SEQ ID NO:Y is identified as "Total AA of ORF".

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further herein. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1, 3, 5, 8, 317, and/or 318 and the predicted translated amino acid sequence identified as SEQ ID NO:2, 4, 6, 7, 9, and/or 10. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell, collecting the protein, and determining its sequence.

The present invention also relates to the genes corresponding to SEQ ID NO:1, 3, 5, 8, 317, and/or 318, SEQ ID NO:2, 4, 6, 7, 9, and/or 10. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologues of genes corresponding to SEQ ID NO:1, 3, 5, 8, 317, and/or 318, SEQ ID NO:2, 4, 6, 7, 9, and/or 10, or a deposited clone, relying on the sequence from the sequences disclosed herein. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Gene 67:31-40 (1988). Polypeptides of the invention also can be purified from natural, synthetic or recombinant sources using protocols described herein or otherwise known in the art, such as, for example, antibodies of the invention raised against the full-length form of the protein.

The present invention provides a polynucleotide comprising, or alternatively consisting of, the sequence identified as SEQ ID NO:1, 3, 5, 8, 317, and/or 318. The present invention also provides a polypeptide comprising, or alternatively consisting of, the sequence identified as SEQ ID NO:2, 4, 6, 7, 9, and/or 10. The present invention also provides polynucleotides encoding a polypeptide comprising, or alternatively consisting of the polypeptide sequence of SEQ ID NO:2, 4, 6, 7, 9, and/or 10.

Preferably, the present invention is directed to a polynucleotide comprising, or alternatively consisting of, the sequence identified as SEQ ID NO:1, 3, 5, 8, 317, and/or 318 that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention also encompasses polynucleotides capable of hybridizing, preferably under reduced stringency conditions, more preferably under stringent conditions, and most preferably under highly stringent conditions, to polynucleotides described herein. Examples of stringency conditions are shown in Table 2 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 2

| Stringency Condition | Polynucleotide Hybrid± | Hybrid Length (bp)‡ | Hyridization Temperature and Buffer† | Wash Temperature and Buffer† |
|---|---|---|---|---|
| A | DNA:DNA | > or equal to 50 | 65° C.; 1xSSC -or- 42° C.; 1xSSC, 50% formamide | 65° C.; 0.3xSSC |

TABLE 2-continued

| Stringency Condition | Polynucleotide Hybrid± | Hybrid Length (bp)‡ | Hyridization Temperature and Buffer† | Wash Temperature and Buffer† |
|---|---|---|---|---|
| B | DNA:DNA | <50 | Tb*; 1xSSC | Tb*; 1xSSC |
| C | DNA:RNA | > or equal to 50 | 67° C.; 1xSSC -or- 45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC -or- 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC -or- 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC -or- 45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC -or- 40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC -or- 40° C. 6xSSC, 50% formamide | 50° C.; 2xSSC |
| N | DNA:DNA | <50 | Tn*; 6xSSC | Tn*; 6xSSC |
| O | DNA:RNA | > or equal to 50 | 55° C.; 4xSSC -or- 42° C.; 6xSSC, 50% formamide | 55° C.; 2xSSC |
| P | DNA:RNA | <50 | Tp*; 6xSSC | Tp*; 6xSSC |
| Q | RNA:RNA | > or equal to 50 | 60° C.; 4xSSC -or- 45° C.; 6xSSC, 50% formamide | 60° C.; 2xSSC |
| R | RNA:RNA | <50 | Tr*; 4xSSC | Tr*; 4xSSC |

‡The "hybrid length" is the anticipated length for the hybridized region(s) of the hybridizing polynucleotides. When hybridizing a polynucletotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MegAlign program of the DNA*Star suite of programs, etc).
†SSPE (1xSSPE is 0.15 M NaCl, 10 mM NaH2PO4, and 1.25 mM EDTA, pH 7.4) can be substituted for SSC (1xSSC is 0.15 M NaCl anmd 15 mM sodium citrate) in the hybridization and wash buffers; washes are performed for 15 minutes after hybridization is complete. The hydridizations and washes may additionally include 5X Denhardt's reagent, .5-1.0% SDS, 100 ug/ml denatured, fragmented salmon sperm DNA, 0.5% sodium pyrophosphate, and up to 50% formamide.
*Tb – Tr: The hybridization temperature for hybrids anticipated to be less than 50 base pairs in length should be 5-10° C. less than the melting temperature Tm of the hybrids there Tm is determined according to the following equations. For hybrids less than 18 base pairs in length, $Tm(° C.) = 2(\# \text{ of } A + T \text{ bases}) + 4(\# \text{ of } G + C \text{ bases})$. For hybrids between 18 and 49 base pairs in length, $Tm(° C.) = 81.5 + 16.6(\log_{10}[Na+]) + 0.41 (\% G + C) - (600/N)$, where N is the number of bases in the hybrid, and [Na+] is the concentration of sodium ions in the hybridization buffer ([NA+] for 1xSSC = .165 M).
±The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3-6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The invention encompasses the application of PCR methodology to the polynucleotide sequences of the present invention, and/or the cDNA encoding the polypeptides of the present invention. PCR techniques for the amplification of nucleic acids are described in U.S. Pat. No. 4,683,195 and Saiki et al., Science, 239:487-491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643-1650, (1991); and "PCR Protocols, A Guide to Methods and Applications", Eds., Innis et al., Academic Press, New York, (1990).

Polynucleotide and Polypeptide Variants

The present invention also encompasses variants (e.g., allelic variants, orthologs, etc.) of the polynucleotide sequence disclosed herein in SEQ ID NO:1, 3, 5, 8, 317, and/or 318, the complementary strand thereto, and/or the cDNA sequence contained in the deposited clone.

The present invention also encompasses variants of the polypeptide sequence, and/or fragments therein, disclosed in SEQ ID NO:2, 4, 6, 7, 9, and/or 10, a polypeptide encoded by the polynucleotide sequence in SEQ ID NO:1, 3, 5, 8, 317, and/or 318, and/or a polypeptide encoded by a cDNA in the deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a LTRPC3 related polypeptide having an amino acid.- sequence as shown in the sequence listing and described in SEQ ID NO:1, 3, 5, 8, 317, and/or 318; (b) a nucleotide sequence encoding a mature LTRPC3 related polypeptide having the amino acid sequence as shown in the sequence listing and described in SEQ ID NO:1, 3, 5, 8, 317, and/or 318; (c) a nucleotide sequence encoding a biologically active fragment of a LTRPC3 related polypeptide having an amino acid sequence shown in the sequence listing and described in SEQ ID NO:1, 3, 5, 8, 317, and/or 318; (d) a nucleotide sequence encoding an antigenic fragment of a LTRPC3 related polypeptide having an amino acid sequence shown in the sequence listing and described in SEQ ID NO:1, 3, 5, 8, 317, and/or 318; (e) a nucleotide sequence encoding a LTRPC3 related polypeptide comprising the complete amino acid sequence encoded by a human cDNA plasmid containined in SEQ ID NO:1, 3, 5, 8, 317, and/or 318; (f) a nucleotide sequence encoding a mature LTRPC3 realted polypeptide having an amino acid sequence encoded by a human cDNA plasmid contained in SEQ ID NO:1, 3, 5, 8, 317, and/or 318; (g) a nucleotide sequence encoding a biologically active fragement of a LTRPC3 related polypeptide having an amino acid sequence encoded by a human cDNA plasmid contained in SEQ ID NO:1, 3, 5, 8, 317, and/or 318; (h) a nucleotide sequence encoding an antigenic fragment of a LTRPC3 related polypeptide having an amino acid sequence encoded by a human cDNA plasmid contained in SEQ ID NO:1, 3, 5, 8, 317, and/or 318; (I) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above.

Polynucleotides encoded by these nucleic acid molecules are also encompassed by the invention. In another embodiment, the invention encompasses nucleic acid molecule which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

Another aspect of the invention provides an isolated nucleic acid molecule comprising, or alternatively, consisting of, a polynucleotide having a nucleotide sequence selected from the group consisting of: (a) a nucleotide sequence encoding a LTRPC3 related polypeptide having an amino acid sequence as shown in the sequence listing and described in Table 1; (b) a nucleotide sequence encoding a mature LTRPC3 related polypeptide having the amino acid sequence as shown in the sequence listing and described in Table 1; (c) a nucleotide sequence encoding a biologically active fragment of a LTRPC3 related polypeptide having an amino acid sequence as shown in the sequence listing and described in Table 1; (d) a nucleotide sequence encoding an antigenic fragment of a LTRPC3 related polypeptide having an amino acid sequence as shown in the sequence listing and described in Table 1; (e) a nucleotide sequence encoding a biologically active fragment of a LTRPC3 related polypeptide having an amino acid sequence encoded by a human cDNA (f) a nucleotide sequence encoding an antigenic fragment of a LTRPC3 related polypeptide.

The present invention is also directed to nucleic acid molecules which comprise, or alternatively, consist of, a nucleotide sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, the following non-limited examples, the polypeptide sequence identified as SEQ ID NO:2, 4, 6, 7, 9, and/or 10, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecule which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, the polypeptide sequence shown in SEQ ID NO:2, 4, 6, 7, 9, and/or 10, a polypeptide sequence encoded by the nucleotide sequence in SEQ ID NO:1, 3, 5, 8, 317, and/or 318,and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table 1, the ORF (open reading frame), or any fragment specified as described herein.

As a practical matter, whether any particular nucleic acid molecule or polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multiple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for instance, an amino acid sequence referenced in Table 1 (SEQ ID NO:2), can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both amino acid sequences. The result of said global sequence alignment is in percent identity. Preferred parameters used in a CLUSTALW alignment of DNA sequences to calculate percent identity via pairwise alignments are: Matrix=BLOSUM, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multiple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of N- or C-terminal deletions, not because of internal deletions. If only the local pairwise percent identity is required, no manual correction is needed. However, a manual correction may be applied to determine the global percent identity from a global polypeptide alignment. Percent identity calculations based upon global polypeptide alignments are often preferred since they reflect the percent identity between the polypeptide molecules as a whole (i.e., including any polypeptide overhangs, not just overlapping regions), as opposed to, only local matching polypeptides. Manual corrections for global percent identity determinations are required since the CLUSTALW program does not account for N- and C-terminal truncations of the subject sequence when calculating percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the CLUSTALW sequence alignment. This percentage is then subtracted from the percent identity, calculated by the above CLUSTALW program using the specified parameters, to arrive at a final percent identity score. This final percent identity score is what may be used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the CLUSTALW alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the CLUSTALW program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence, which are not matched/aligned with the query. In this case the percent identity calculated by CLUSTALW is not manually corrected. Once again, only residue positions outside the N- and C-terminal ends of the subject sequence, as displayed in the CLUSTALW alignment, which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modified CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268: 2984-2988 (1993), reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein (Dobeli et al., J. Biotechnology 7:199-216 (1988)).

Moreover, ample evidence demonstrates that variants often retain a biological activity similar to that of the naturally occurring protein. For example, Gayle and coworkers (J. Biol. Chem. 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

The invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081-1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306-1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table III below.

TABLE III

| For Amino Acid | Code | Replace with any of: |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S—Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |

TABLE III-continued

| For Amino Acid | Code | Replace with any of: |
|---|---|---|
| Methionine | M | D-Met, S—Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1-5, 5-10, 5-25, 5-50, 10-50 or 50-150, conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:1, 3, 5, 8, 317, and/or 318 or the complementary strand thereto, or is a portion of a polynucleotide sequence encoding the polypeptide of SEQ ID NO:2, 4, 6, 7, 9, and/or 10. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:1, 3, 5, 8, 317, and/or 318. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001 to the end of SEQ ID NO:1, 3, 5, 8, 317, and/or 318. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:2, 4, 6, 7, 9, and/or 10. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1-20, 21-40, 41-60, 61-80, 81-100, 102-120, 121-140, 141-160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1-60, can be deleted from the amino terminus of the full-length polypeptide. Similarly, any number of amino acids, ranging from 1-30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2, 4, 6, 7, 9, and/or 10 falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at least one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NO:2, 4, 6, 7, 9, and/or 10 or encoded by a polynucleotide that hybridizes to the complement of the sequence of SEQ ID NO:1, 3, 5, 8, 317, and/or 318 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length, or longer. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811, 238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:1, 3, 5, 8, 317, and/or 318 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced in-between such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958-3964 (1995).)

Similarly, EP-A-O 464 533 (Canadian counterpart 2045869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existence of other "tags" which could be readily substituted for the tags referred to supra for purification and/or identification of polypeptides of the present invention (Jones C., et al., J Chromatogr A. 707(1):3-22 (1995)). For example, the c-myc tag and the 8F9, 3 C7, 6E10, G4m B7 and 9E10 antibodies thereto (Evan et al., Molecular and Cellular Biology 5:3610-3616 (1985)); the Herpes Simplex virus glycoprotein D (gD) tag and its antibody (Paborsky et al., Protein Engineering, 3(6):547-553 (1990), the Flag-peptide—i.e., the octapeptide sequence DYKDDDDK (SEQ ID NO:251), (Hopp et al., Biotech. 6:1204-1210 (1988); the KT3 epitope peptide (Martin et al., Science, 255:192-194 (1992)); a-tubulin epitope peptide (Skinner et al., J. Biol. Chem., 266:15136-15166, (1991)); the T7 gene 10 protein peptide tag (Lutz-Freyermuth et al., Proc. Natl. Sci. USA, 87:6363-6397 (1990)), the FITC epitope (Zymed, Inc.), the GFP epitope (Zymed, Inc.), and the Rhodamine epitope (Zymed, Inc.).

The present invention also encompasses the attachment of up to nine codons encoding a repeating series of up to nine arginine amino acids to the coding region of a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc.)). Due to the availability of monoclonal antibodies specific to such haptens, the protein could be readily purified using immunoprecipation, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann. N.Y. Acad. Sci. 1999; 886:233-5), or HC toxin (Tonukari N J, et al., Plant Cell. 2000 February; 12(2):237-248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In. Imm. 11:548-557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast Pichia pastoris is used to express the polypeptide of the present invention in a eukaryotic system. Pichia pastoris is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, Pichia pastoris must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in Pichia pastoris. See, Ellis, S. B., et al., Mol. Cell. Biol. 5:1111-21 (1985); Koutz, P. J, et al., Yeast 5:167-77 (1989); Tschopp, J. F., et al., Nucl. Acids Res. 15:3859-76 (1987). Thus, a heterologous coding sequence, such as, for example, a polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the Pichia pastoris alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105-111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.). stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics®, commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2, 4, 6, 7, 9, and/or 10 or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15-25 bp) from the sequences shown in SEQ ID NO:1, 3, 5, 8, 317, and/or 318. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:1, 3, 5, 8, 317, and/or 318 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000-4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one gene per 20 kb, a cDNA precisely localized to a chromosomal region associated with the disease could be one of 50-500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may Preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The US patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point (T.sub.m) by 8°-20° C., vs. 4°-16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., Nat. Biotech., 18:300-303, (2000); which is hereby incorporated herein by reference.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615-622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976-985 (1985); Jalkanen, M., et al., J. Cell. Biol. 105:3087-3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Having generally described the invention, the same will be more readily understood by reference to the following examples, which are provided by way of illustration and are not intended as limiting.

REFERENCES

Caterina, M. J., Leffler, A, Malmberg, A. B., Martin, W. J., Trafton, J, Petersen-Zeitz, K. R., Koltzenburg, M, Basbaum, A. I. & Julius, D. Impaired nociception and pain sensation in mice lacking the capsaicin receptor. *Science.* 288, 306-313 (2000).

Caterina, M. J., Rosen, T. A., Tominaga, M., Brake, A. J. & Julius, D. A capsaicin-receptor homologue with a high threshold for noxious heat. *Nature.* 398, 436-41 (1999).

Duncan, L. M., Deeds, J., Hunter, J., Shao, J., Holmgren, L. M., Woolf, E. A., Tepper, R. I. & Shyjan, A. W. Downregulation of the novel gene melastatin correlates with potential for melanoma metastasis. *Cancer Res.* 58, 1515-1520 (1998).

Freichel, M., Suh, S. H., Pfeifer, A., Schweig, U., Trost, C., Weissgerber, P., Biel, M., Philipp, S., Freise, D., Droogmans, G., Hofmann, F., Flockerzi, V. & Nilius, B. Lack of an endothelial store-operated Ca2+ current impairs agonist-dependent vasorelaxation in TRP4−/− mice. *Nat. Cell Biol.* 3, 121-127 (2001).

Harteneck, C., Plant T. D. & Schultz, G. From worm to man: three subfamilies of TRP channels. *Trends Neurosci.* 23, 159-166 (2000).

Inoue, R., Okada, T., Onoue, H., Hara, Y., Shimizu, S., Naitoh, S., Ito, Y. & Mori, Y. The transient receptor potential protein homologue TRP6 is the essential component of vascular alpha(1)-adrenoceptor-activated Ca(2+)-permeable cation channel. *Circ Res.* 88, 325-332 (2001).

Liman, E. R., Corey, D. P. & Dulac, C. TRP2: a candidate transduction channel for mammalian pheromone sensory signaling. *Proc Natl Acad Sci USA.* 96, 5791-5796 (1999).

Missiaen, L., Robberecht, W., van den Bosch, L., Callewaert, G., Parys, J. B., Wuytack, F., Raeymaekers, L., Nilius, B., Eggermont, J. & De Smedt, H. Abnormal intracellular $Ca^{2+}$ homeostasis and disease. *Cell Calcium.* 28, 1-21 (2000).

Nagamine, K., Kudoh, J., Minoshima, S., Kawasaki, K., Asakawa, S., Ito F. & Shimizu, N. Molecular cloning of a novel putative Ca2+ channel protein (TRPC7) highly expressed in brain. *Genomics* 54, 124-131 (1998)

Peng, J. B., Chen, X. Z., Berger, U. V., Vassilev, P. M., Tsukaguchi, H., Brown, E. M. & Hediger, M. A. Molecular cloning and characterization of a channel-like transporter mediating intestinal calcium absorption. *J. Biol. Chem.* 274, 22739-22746 (1999).

Prawitt, D., Enklaar, T., Klemm, G., Gartner, B., Spangenberg, C., Winterpacht, A., Higgins, M., Pelletier, J. & Zabel, B. Identification and characterization of MTR1, a novel gene with homology to melastatin (MLSN1) and the trp family located in the BWS-WT2 critical region on chromosome 11p15.5 and showing allele-specific expression. *Hum Mol. Genet.* 9, 203-16 (2000).

Runnels, L. W., Yue, L. & Clapham, D. E. TRP-PLIK, a bifunctional protein kinase and ion channel activities. *Science* 291, 1043-1047 (2001).

Strotmann, R., Harteneck, C., Nunnenmacher, K., Schultz, G. & Plant, T. D. OTRPC4, a nonselective cation channel that confers sensitivity to extracellular osmolarity. *Nat. Cell Biol.* 2, 695-702 (2000).

Tsavaler, L., Shapero, M. H., Morkowski, S. & Laus R. TRP-P8, a novel prostate-specific gene, is up-regulated in prostate cancer and other malignancies and shares high homology with transient receptor potential calcium channel proteins. *Cancer Res.* 61, 3760-3769 (2001).

Walker, R. G., Willingham, A. T. & Zuker, C. S. A *Drosophila* mechanosensory transduction channel. *Science.* 287, 2229-34 (2000).

Xu, S. Z. & Beech, D. J. TrpC1 is a membrane-spanning subunit of store-operated $Ca^{2+}$ channels in native vascular smooth muscle. *Circ Res.* 88, 84-7 (2001).

Yue, L., Peng, J. B., Hediger, M. A., Clapham, D. E. CaT1 manifests the pore properties of the calcium-release-activated calcium channel. *Nature.* 410, 705-709 (2001).

Zygmunt, P. M., Petersson, J., Andersson, D. A., Chuang, H., Sorgard, M., Di Marzo V., Julius, D. & Hogestatt, E. D. Vanilloid receptors on sensory nerves mediate the vasodilator action of anandamide. *Nature.* 400, 452-457 (1999).

EXAMPLES

Description of the Preferred Embodiments

Example 1

Method Used to Identify the Novel LTRPC3 Polynucleotide of the Present Invention—Bioinformatics Analysis Ion channel sequences (mouse TRP1a, gi|1911245, SEQ ID NO:27; mouse TRP2, gi|4324938, SEQ ID NO:26; mouse TRP4, gi|4200415, SEQ ID NO:25; mouse TRP5, gi|6048344, SEQ ID NO:24; human TRP7, gi|13928756, SEQ ID NO:23; mouse TRP3, gi|6014703, SEQ ID NO:22; mouse TRP6, gi|2979524, SEQ ID NO:21; mouse TRP8, gi|5326854, SEQ ID NO:20; *Drosophila* NOMPC, gi|7328583, SEQ ID NO:19; *C. elegans* Y71A12B.4, gi|1065673, SEQ ID NO:18) in the TRP/NOMPC family were used as probes to search the human genomic sequence database (see FIGS. 13A-C). The search program used was the gapped BLAST program TBLASTN (Altschul et al., 1997). A multiple sequence alignment of TRP/NOMPC family members was generated using the Align program in software Vector NTI 5.5, using the ClustalW algorithm. A Hidden Markov Model (HMM) specific for NOMPC family was constructed using the HMMERBUILD program in the Genewise/Wise2 package from the above multiple sequence alignment (Bateman et al., 2000). This HMM model was then used to search the human genomic sequence database using the software program GENEWISEDB in the Genewise/Wise2 package (http://www.sanger.ac.uk/Software/Wise2/index.shtml). Results from the TBLASTN and GENEWISEDB searches were pooled and a potential TRP family member was identified in human BAC AL358786 (Genbank Accession No. gi|AL358786). The high scoring hit segments from the genomic sequence hits from BAC AL358786 were extracted and searched back against non-redundant protein and patent sequence databases. The most similar protein sequence for each genomic sequence hit was used as a template to predict putative exons from the BAC AL358786 genomic sequence using the GENEWISEDB program in the Genewise/Wise2 package (trpc7; SEQ ID NO:23). From this analysis, exons encoding the potential novel ion channel, LTRPC3, was identified based upon sequence homology. To extend the 5' and 3' sequences of putative novel ion channel molecules, the genomic regions surrounding the matching exons in genomic sequence NT_008306 (SEQ ID NO:17) using GENSCAN and FGENESH programs to generate de novo exons. Based on these analysis, partial sequences of novel human ion channel related genes were identified (shown in FIG. 10; SEQ ID NO:12, 13, and 14). The full-length clone of one novel ion channel gene LTRPC3 was experimentally obtained by using the putative exon sequences as templates to design PCR cloning primers as described below.

Example 2

Cloning the Novel Transient Receptor Potential Channel Member, LTRPC3

Probe Design

Using the predicted exon genomic sequence from BAC AL358786 (FIG. 10; SEQ ID NO:12, 13, and 14), oligonucleotides with the following sequences was used to amplify fragments from the human kidney Marathon-Ready cDNA library (Clontech). The reaction mixture in 50 ul containing 5 ul cDNA library, 0.5 mM each primer, 5 mM dNTPs (1.25 mM each), 5 ul of 10×PCR and 0.5 unit of TaqPlus Precision polymerase (Stratagene). The reaction was repeated for 30 cycles (94° C. for 45 seconds, 55° C. for 45 seconds, and 72° C. for 4 minutes). The amplified fragments were cloned into the sequencing vector pCR4 Blunt-TOPO (Invitrogen) for sequence analysis. For functional studies the cDNA was fused in-frame with an HA epitope at its C terminus and subcloned into the mammalian expression vector pcDNA3.1/Hygro (Invitrogen).

| Primer Name | Primer Sequence | |
|---|---|---|
| 86-N2-C | ATGTATGTGCGAGTATCTTTTGATACAAAACCT | (SEQ ID NO:253) |
| 86-1-NC | AGCCAAATCAATGTCCTGGTGTCC | (SEQ ID NO:254) |
| 86-1-C | GAAGGACACCAGGACATTGATTTG | (SEQ ID NO:255) |
| 86-2-NC | GTCACTCCTGAAGGGCTGGTCTTG | (SEQ ID NO:256) |
| 86-2-C | CAAGACCAGCCCTTCAGGAGTGAC | (SEQ ID NO:257) |
| 86-3-NC | CGCCCGATAAGGTCTTCCAGCTG | (SEQ ID NO:258) |
| 86-3-C | CAGCTGGAAGACCTTATCGGGCG | (SEQ ID NO:259) |
| 86-END-NC | TTAGGTGTGCTTGCTTTCAAAGCT | (SEQ ID NO:260) |

The resulting full-length encoding polynucleotide sequence for LTRPC3 is shown in FIGS. 1A-F (SEQ ID NO:1).

Additional clones corresponding to the LTRPC3 splice variants of the present invention were isolated according to the above methods. The full-length polynucleotide sequence of each of the LTRPC3 splice variants are provided in FIGS. 2A-F (SEQ ID NO:3), FIGS. 3A-F (SEQ ID NO:5), FIGS. 4A-F (SEQ ID NO:8), for LTRPC3b, LTRPC3c, and LTRPC3e, respectively. Additional splice variants of LTRPC3 were also isolated corresponding to LTRPC3d and LTRPC3f. The amino acid sequences of these splice variants are provided in FIGS. 9A-E (SEQ ID NO:7 and 10, respectively), while the polynucleotide sequences of these splice variants are provided in FIG. 14 (LTRPC3d, SEQ ID NO:281) and FIG. 15 (LTRPC3f, SEQ ID NO:282).

Example 3

Expression Profiling of Novel Human Immunoglobulin Protein, LTRPC3

RT-PCR

A PCR primer pair was designed to measure the steady state levels of the LTRPC3 mRNA by quantitative RT-PCR.

| LTRP6.tp1s | CGCAGCTGGAAGACCTTATC | (SEQ ID NO:261) |
|---|---|---|
| LTRP6.tp1a | AAGCTGCTCTGACGGACAAT | (SEQ ID NO:262) |

Briefly, first strand cDNA was made from commercially available mRNA. The relative amount of cDNA used in each assay was determined by performing a parallel experiment using a primer pair for a gene expressed in equal amounts in all tissues, cyclophilin. The cyclophilin primer pair detected small variations in the amount of cDNA in each sample and these data were used for normalization of the data obtained with the primer pair for the LTRPC3 transcript. The PCR data was converted into a relative assessment of the difference in transcript abundance amongst the tissues tested and the data is presented in FIG. 8. Transcripts corresponding to the LTRPC3 transcript were found to be highly expressed in the kidney; and significantly in spinal cord, testis, and brain.

Northern Blot Analysis

Human tissue Northern blots (Clontech) were probed with an RNA probe derived from a 645-bp DNA fragment amplified from the primer pair 86-1-C (SEQ ID NO:255) and 86-5-NC (5'-AGGGAAGGGGAAGTGGTTGATCTC-3', SEQ ID NO:263). Hybridization of the blot was performed at 68° C. in ExpressHyb (Clontech) for 6 hours, with 1×10$^6$ cpm/ml of $^{32}$P-labeled probe. Autoradiography was performed for 1 week at −70° C.

The results of the Northern hybridization are shown in FIG. 9. As shown, Transcripts corresponding to the LTRPC3 transcript were found to be highly expressed in kidney, and to a lesser extent in brain, and testis.

Example 4

Method of Assessing the Expression Profile of the Novel LTRPC3 Polypeptides of the Present Invention Using Expanded mRNA Tissue and Cell Sources Total RNA from tissues was isolated using the TriZol protocol (Invitrogen) and quantified by determining its absorbance at 260 nM. An assessment of the 18s and 28s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI. For LTRPC3, the primer probe sequences were as follows

| Forward Primer | | |
|---|---|---|
| 5'-TCAGAGAATGGGCCAACAAGA-3' | | (SEQ ID NO:270) |
| Reverse Primer | | |
| 5'-CGAAAACGCTCGAGGAATGA-3' | | (SEQ ID NO:271) |
| TaqMan Probe | | |
| 5'-CAGGCCTAGGTTCCTCCTCTCGGAAA-3' | | (SEQ ID NO:272) |

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TaqMan assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+RNA. If not the RNA was not used in actual experiments.

Reverse Transcription Reaction and Sequence Detection 100 ng of Dnase-treated total RNA was annealed to 2.5 µM of the respective gene-specific reverse primer in the presence of 5.5 mM Magnesium Chloride by heating the sample to 72° C. for 2 min and then cooling to 55° C. for 30 min. 1.25 U/µl of MuLv reverse transcriptase and 500 µM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 µM forward and reverse primers, 500 µM of each dNTP, buffer and 5 U AmpliTaq Gold™. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$ The expanded expression profile of the LTRPC3 polypeptide is provided in FIGS. 12 and 13 and described elsewhere herein.

Example 5

Complementary Oligonucleotides to the LTRPC3 Polynucleotide

Antisense molecules or nucleic acid sequences complementary to the LTRPC3 protein-encoding sequence, or any part thereof, was used to decrease or to inhibit the expression of naturally occurring LTRPC3. Although the use of antisense or complementary oligonucleotides comprising about 15 to 35 base-pairs is described, essentially the same procedure is used with smaller or larger nucleic acid sequence fragments. An oligonucleotide based on the coding sequence of LTRPC3 protein, as shown in FIGS. 1A-F, or as depicted in SEQ ID NO:1, for example, is used to inhibit expression of naturally occurring LTRPC3. The complementary oligonucleotide is typically designed from the most unique 5′ sequence and is used either to inhibit transcription by preventing promoter binding to the coding sequence, or to inhibit translation by preventing the ribosome from binding to the LTRPC3 protein-encoding transcript. However, other regions may also be targeted.

Using an appropriate portion of a 5′ sequence of SEQ ID NO:1, an effective antisense oligonucleotide includes any of about 15-35 nucleotides spanning the region which translates into the signal or 5′ coding sequence, among other regions, of the polypeptide as shown in FIGS. 1A-F (SEQ ID NO:2). Appropriate oligonucleotides are designed using OLIGO 4.06 software and the LTRPC3 protein coding sequence (SEQ ID NO:1). Preferred oligonucleotides are deoxynucleotide, or chimeric deoxynucleotide/ribonucleotide based and are provided below. The oligonucleotides were synthesized using chemistry essentially as described in U.S. Pat. No. 5,849,902; which is hereby incorporated herein by reference in its entirety.

| ID#   | Sequence                        |                  |
|-------|---------------------------------|------------------|
| 15737 | CCAUGGACAGAGAUGAGAAGCUUGGU      | (SEQ ID NO:276)  |
| 15738 | AGUGGUCCCGUUGUCAGCCAGAAUGU      | (SEQ ID NO:277)  |
| 15739 | CCUUCCACUAUGAGUGCCACCACAGU      | (SEQ ID NO:278)  |
| 15740 | GUGUCCUUCUGAUCCCAUCCGAAAUU      | (SEQ ID NO:279)  |
| 15741 | UGGUAUGGCCGGACAACAUCUCUUCU      | (SEQ ID NO:280)  |

The LTRPC3 polypeptide has been shown to be involved in the regulation of mammalian base-excision repair. Subjecting cells with an effective amount of a pool of all five of the above antisense oligonucleotides resulted in a significant increase in FEN1 expression/activity providing convincing evidence that LTRPC3 at least regulates the activity and/or expression of FEN1 either directly, or indirectly. Moreover, the results suggest that LTRPC3 is involved in the negative regulation of FEN1 activity and/or expression, either directly or indirectly. The FEN1 assay used is described below and was based upon the analysis of FEN1 activity as a downstream marker for proliferative signal transduction events.

Transfection of Post-Quiescent A549 Cells with AntiSense Oligonucleotides.

Materials needed:
    A549 cells maintained in DMEM with high glucose (Gibco-BRL) supplemented with 10% Fetal Bovine Serum, 2 mM L-Glutamine, and 1× penicillin/streptomycin.
    Opti-MEM (Gibco-BRL)
    Lipofectamine 2000 (Invitrogen)
    Antisense oligomers (Sequitur)
    Polystyrene tubes.
    Tissue culture treated plates.
    Quiescent cells were prepared as follows:
Day 0: 300,000 A549 cells were seeded in a T75 tissue culture flask in 10 ml of A549 media (as specified above), and incubated in at 37° C., 5% $CO_2$ in a humidified incubator for 48 hours.
Day 2: The T75 flasks were rocked to remove any loosely adherent cells, and the A549 growth media removed and replenished with 10 ml of fresh A549 media. The cells were cultured for six days without changing the media to create a quiescent cell population.
Day 8: Quiescent cells were plated in multi-well format and transfected with antisense oligonucleotides.
    A549 cells were transfected according to the following:
    1. Trypsinize T75 flask containing quiescent population of A549 cells.
    2. Count the cells and seed 24-well plates with 60K quiescent A549 cells per well.
    3. Allow the cells to adhere to the tissue culture plate (approximately 4 hours).

4. Transfect the cells with antisense and control oligonucleotides according to the following:
   a. A 10× stock of lipofectamine 2000 (10 ug/ml is 10×) was prepared, and diluted lipid was allowed to stand at RT for 15 minutes.
      Stock solution of lipofectamine 2000 was 1 mg/ml.
      10× solution for transfection was 10 ug/ml.
      To prepare 10× solution, dilute 10 ul of lipofectamine 2000 stock per 1 ml of Opti-MEM (serum free media).
   b. A 10× stock of each oligomer was prepared to be used in the transfection.
      Stock solutions of oligomers were at 100 uM in 20 mM HEPES, pH 7.5.
      10× concentration of oligomer was 0.25 uM.
      To prepare the 10× solutions, dilute 2.5 ul of oligomer per 1 ml of Opti-MEM.
   c. Equal volumes of the 10× lipofectamine 2000 stock and the 10× oligomer solutions were mixed well, and incubated for 15 minutes at RT to allow complexation of the oligomer and lipid. The resulting mixture was 5×.
   d. After the 15 minute complexation, 4 volumes of full growth media was added to the oligomer/lipid complexes (solution was 1×).
   e. The media was aspirated from the cells, and 0.5 ml of the 1× oligomer/lipid complexes added to each well.
   f. The cells were incubated for 16-24 hours at 37° C. in a humidified $CO_2$ incubator.
   g. Cell pellets were harvested for RNA isolation and TaqMan analysis of downstream marker genes.

TaqMan Reactions

Quantitative RT-PCR analysis was performed on total RNA preps that had been treated with DNaseI or poly A selected RNA. The Dnase treatment may be performed using methods known in the art, though preferably using a Qiagen Rneasy kit to purify the RNA samples, wherein DNAse I treatment is performed on the column.

Briefly, a master mix of reagents was prepared according to the following table:

| Dnase I Treatment | |
| --- | --- |
| Reagent | Per r'xn (in uL) |
| 10 × Buffer | 2.5 |
| Dnase I (1 unit/ul @1 unit per ug sample) | 2 |
| DEPC $H_2O$ | 0.5 |
| RNA sample @ 0.1 ug/ul (2-3 ug total) | 20 |
| Total | 25 |

Next, 5 ul of master mix was aliquoted per well of a 96-well PCR reaction plate (PE part #N801-0560). RNA samples were adjusted to 0.1 ug/ul with DEPC treated $H_2O$ (if necessary), and 20 ul was added to the aliquoted master mix for a final reaction volume of 25 ul.

The wells were capped using strip well caps (PE part #N801-0935), placed in a plate, and briefly spun in a plate centrifuge (Beckman) to collect all volume in the bottom of the tubes. Generally, a short spin up to 500 rpm in a Sorvall RT is sufficient.

The plates were incubated at 37° C. for 30 mins. Then, an equal volume of 0.1 mM EDTA in 10 mM Tris was added to each well, and heat inactivated at 70° C. for 5 min. The plates were stored at −80° C. upon completion.

RT Reaction

A master mix of reagents was prepared according to the following table:

| | RT reaction | |
| --- | --- | --- |
| Reagent | RT Per Rx'n (in ul) | No RT Per Rx'n (in ul) |
| 10 × RT buffer | 5 | 2.5 |
| $MgCl_2$ | 11 | 5.5 |
| DNTP mixture | 10 | 5 |
| Random Hexamers | 2.5 | 1.25 |
| Rnase inhibitors | 1.25 | 0.625 |
| RT enzyme | 1.25 | — |
| Total RNA 500 ng (100 ng no RT) | 19.0 max | 10.125 max |
| DEPC $H_2O$ | — | — |
| Total | 50 uL | 25 uL |

Samples were adjusted to a concentration so that 500 ng of RNA was added to each RT rx'n (100 ng for the no RT). A maximum of 19 ul can be added to the RT rx'n mixture (10.125 ul for the no RT.) Any remaining volume up to the maximum values was filled with DEPC treated $H_2O$, so that the total reaction volume was 50 ul (RT) or 25 ul (no RT).

On a 96-well PCR reaction plate (PE part #N801-0560), 37.5 ul of master mix was aliquoted (22.5 ul of no RT master mix), and the RNA sample added for a total reaction volume of 50 ul (25 ul, no RT). Control samples were loaded into two or even three different wells in order to have enough template for generation of a standard curve.

The wells were capped using strip well caps (PE part #N801-0935), placed in a plate, and spin briefly in a plate centrifuge (Beckman) to collect all volume in the bottom of the tubes. Generally, a short spin up to 500 rpm in a Sorvall RT is sufficient.

For the RT-PCR reaction, the following thermal profile was used:
25° C. for 10 min
48° C. for 30 min
95° C. for 5 min
4° C. hold (for 1 hour)
Store plate @-20° C. or lower upon completion.

TaqMan Reaction (Template Comes from RT Plate.)

A master mix was prepared according to the following table:

| TaqMan reaction (per well) | |
| --- | --- |
| Reagent | Per Rx'n (in ul) |
| TaqMan Master Mix | 4.17 |
| 100 uM Probe (SEQ ID NO: 311) | .025 |
| 100 uM Forward primer (SEQ ID NO: 309) | .05 |
| 100 uM Reverse primer (SEQ ID NO: 310) | .05 |
| Template | — |
| DEPC $H_2O$ | 18.21 |
| Total | 22.5 |

The primers used for the RT-PCR reaction is as follows:

```
FEN1 primer and probes:
Forward Primer:
CCACCTGATGGGCATGTTCT         (SEQ ID NO:273)

Reverse Primer:
CGGCTTGCCATCAAAGACATA        (SEQ ID NO:274)

TaqMan Probe:
CCGCACCATTCGCATGATGGAG       (SEQ ID NO:275)
```

Using a Gilson P-10 repeat pipetter, 22.5 ul of master mix was aliquouted per well of a 96-well optical plate. Then, using P-10 pipetter, 2.5 ul of sample was added to individual wells. Generally, RT samples are run in triplicate with each primer/probe set used, and no RT samples are run once and only with one primer/probe set, often gapdh (or other internal control).

A standard curve is then constructed and loaded onto the plate. The curve has five points plus one no template control (NTC, =DEPC treated $H_2O$). The curve was made with a high point of 50 ng of sample (twice the amount of RNA in unknowns), and successive samples of 25, 10, 5, and 1 ng. The curve was made from a control sample(s) (see above).

The wells were capped using optical strip well caps (PE part #N801-0935), placed in a plate, and spun in a centrifuge to collect all volume in the bottom of the tubes. Generally, a short spin up to 500 rpm in a Sorvall RT is sufficient.

Plates were loaded onto a PE 5700 sequence detector making sure the plate is aligned properly with the notch in the upper right hand corner. The lid was tightened down and run using the 5700 and 5700 quantitation programs and the SYBR probe using the following thermal profile:
50° C. for 2 min
95° C. for 10 min
and the following for 40 cycles:
  95° C. for 15 sec
  60° C. for 1 min
Change the reaction volume to 25 ul.

Once the reaction was complete, a manual threshold of around 0.1 was set to minimize the background signal. Additional information relative to operation of the GeneAmp 5700 machine may be found in reference to the following manuals: "GeneAmp 5700 Sequence Detection System Operator Training CD"; and the "User's Manual for 5700 Sequence Detection System"; available from Perkin-Elmer and hereby incorporated by reference herein in their entirety.

Example 6

Method of Assessing the Cellular Localization of the LTRPC3 Polypeptide

HEK 293 cells were cultured in Dulbecco's modified medium containing 10% heat-inactivated fetal bovine serum and grown on the poly-D-lysine-coated glass coverslips. The cells were transiently transfected with the pcDNA3.1/Hygro-LTRPC3-HA vector with Fugene (Roche). Forty-eight hours later, cells were fixed with 4% paraformaldehyde in PBS, permeabilized with 0.1% Triton X-100, blocked in PBS containing 5% FBS and 5% normal goat serum, and stained with 10 µg/ml Fluorescein-conjugated anti-HA High Affinity antibody (3F10, Roche) and DAPI (0.5 µg/ml; Molecular Probes). Immunostained cell cultures were examined using a laser scanning confocal microscope (ZEISS LSM510). A 63× oil immersion objective was used with appropriate filter sets. Images were reconstructed from confocal stacks of Z-series scans of 10-20 optical sections through a depth of 5-15 µM.

The cellular localization of HA-tagged LTRPC3 was exclusively detected at the subplasma membrane region of the transfected cells (see FIG. 18), which is consistent with LTRPC3 being an integral membrane protein. Under these conditions approximately ~70% of cells were expressing LTRPC3.

Example 7

Method of Assessing the Ion Channel Activity of the LTRPC3 Polypeptide

The cytoplasmic $Ca^{2+}$ indicator Fluo-4-AM (Molecular Probe) and the Fluorometric Imaging Plate Reader (FLIPR™, Molecular Devices) instrument were used to detect changes in intracellular $Ca^{2+}$. The pcDNA3.1/Hygro-LTRPC3-HA transfected cells were seeded on PDL-coated 96-well plates at a density of 70,000 cells/well 24 hours after transfection and used 24 hours after plating. Transfected cells were loaded with 4 µM Fluo-4-AM at 37° C. for 30 min in a nominally $Ca^{2+}$-free or 1 mM $CaCl_2$ buffer containing 140 mM NaCl, 4.7 mM KCl, 1 mM $MgCl_2$, 10M HEPES, 10 mM Glucose, and 2.5 mM Probenecid (Sigma), pH 7.4. Extracellular Fluo-4-AM was removed and cells were maintained in either $Ca^{2+}$-free buffer or buffer containing 1 mM $Ca^{2+}$ at room temperature prior to the experiments, which were conducted within 30 min after dye removal. Fluo-4 was excited at 488 nm using an argon laser and emitted light was selected using a 510-570 nm bandpass filter. Baseline intracellular fluorescence was established during the initial 50 seconds of the FLIPR read, then 1, 3 or 10 mM $Ca^{2+}$ was added to each well and subsequent changes in the intracellular $Ca^{2+}$ were monitored for 8 minutes. For store-depletion studies, 2 µM thapsigargin or 100 µM carbachol was added to Fluo-4-loaded cells in $Ca^{2+}$-free buffer before adding $Ca^{2+}$ on FLIPR. For pharmacology studies, 100 µM $LaCl_3$ or 100 µM $GdCl_3$ were added to Fluo-4-loaded cells in 1 mM $Ca^{2+}$ buffer before adding $Ca^{2+}$ on FLIPR. Experiments were carried out at room temperature. The results of these physiometric studies are shown in FIGS. 18 and 19.

The addition of $Ca^{2+}$ to the media resulted in a concentration-dependent influx of $Ca^{2+}$ into LTRPC3-expressing cells (as shown in FIG. 18, right panels), indicating that LTRPC3 is a functional $Ca^{2+}$ channel. In contrast, vector-transfected cells showed minimal $Ca^{2+}$ influx under the same experimental conditions (as shown in FIG. 18, left panels). The non-transfected cells were indistinguishable from the vector-transfected cells (data not shown). Therefore, LTRPC3 is a constitutively active channel capable of mediating $Ca^{2+}$ influx.

To further address the mechanism of LTRPC3-mediated $Ca^{2+}$ entry, similar $Ca^{2+}$ addition experiments were performed on transfected cells incubated (~30 min) in a nominally $Ca^{2+}$-free solution. Previous studies have shown that lowering extracellular $Ca^{2+}$ concentration below physiological levels can deplete intracellular $Ca^{2+}$ stores in many cell types including HEK 293 (*EMBO J.* 17, 4274-4282 (1998)). Incubating vector-transfected HEK 293 cells in a nominally $Ca^{2+}$-free solution gave rise to $Ca^{2+}$ entry that was dependent on the concentration of $Ca^{2+}$ added to the buffers, indicating $Ca^{2+}$ influx was mediated through endogenous SOCs in HEK293 cells (as shown in FIG. 19; left panel). In LTRPC3 cells, the $Ca^{2+}$ transients triggered by similar $Ca^{2+}$ treatment were much larger (as shown in FIG. 19, right panel). This $Ca^{2+}$ entry observed in LTRPC3 cells incubated in $Ca^{2+}$-free media were greater than in 1 mM $Ca^{2+}$ media, indicating that LTRPC3-mediated $Ca^{2+}$ entry can be potentiated by the store-depletion.

Example 8

Method of Assessing the Expression Profile of the Ion Channel Activity of the LTRPC3 Polypeptide Using In Situ Hybridization Human Kidney was collected and received from the National Disease Research Interchange (Philadelphia, Pa.) according to IRB approved protocol. Tissue sections were embedded in OCT compound (Miles) and snap-frozen by immersion in 2-methylbutane cooled in dry ice and subsequently stored at −70° C.

Templates for LTRPC3 cRNA probes were derived from a 678-bp LTRPC3 fragment, cloned in a pCR-BluntII-TOPO vector (Invitrogen) utilizing the primer pair: (forward: 5'-CAGCTGGAAGACCTTATCGGG-3' (SEQ ID NO:285); reverse: 5'-TGGGAGGTGGGTGTAGTCTGAAGA-3' (SEQ ID NO:286)). The template for positive control cRNA human lysozyme probe was derived from a 638 bp EST (Incyte Genomics, GenBank Accession No:AA588081). $^{35}$S-labeled riboprobes were synthesized via in vitro transcription utilizing the Riboprobe®Combination System (Promega) where T7 and Sp6 RNA polymerase yielded sense and antisense probes respectively for LTRPC3 while T7 and T3 RNA polymerases yielded antisense and sense probes respectively for human lysozyme. Cryostat tissue sections cut at 10 µm and fixed in 4.0% formalin were used for in situ hybridization as previously described (Dambach, D. M., et al., (2002) Hepatology 35, 1093-1103.): Briefly, tissue sections were acetylated; dehydrated in a graded ethanol series; immersed in chloroform; alcohol rinsed; air dried and then hybridized with sense and antisense $^{35}$S RNA probes (1.5×10$^6$ cpm/slide) for 16-20 hours at 60° C. Following hybridization, slides were rinsed in 4×SSC/50% formamide and 4×SSC; treated with RNAse A (20 µg/ml; Invitrogen) at 37° C.; washed through increasing stringent solutions to final high stringency wash in 0.1×SSC at 60° C.; dehydrated; air dried and then coated with NTB-2 emulsion (Eastman Kodak). Slides were placed in a dark box with desiccant at 4° C. and developed after one and four weeks exposure. Sections were stained with hematoxylin and eosin, and coverslipped. Expression signals were detected by dark phase microscopy. Cellular phenotype identification was by bright field microscopy.

The In situ hybridization results of the LTRPC3 polypeptide is provided in FIG. 20 and described elsewhere herein.

Example 9

Method of Further Assessing Cellular Localization of the LTRPC3 Polypeptide

HEK 293 cells were cultured in Dulbecco's Modified Eagle Medium (DMEM) containing 10% heat-inactivated fetal bovine serum and grown on poly-D-lysine-coated (PDL) glass coverslips. The cells were transiently transfected with hLTRPC3-HA with FuGENE 6 (Roche Molecular Biochemicals). Forty-eight hours later, cells were stained in culture media with the membrane probe Vybrant™ CM-DiI (5 µl/ml; Molecular Probes) at 37° C. for 5 min and 4° C. for 15 min. After washing with PBS, cells were fixed with 4% paraformaldehyde in PBS, permeabilized with 0.1% Triton X-100, blocked in PBS containing 5% FBS and 5% normal goat serum, and stained with 10 µg/ml Fluorescein-conjugated anti-HA High Affinity antibody (3F10; Roche Molecular Biochemicals) and DAPI (0.5 µg/ml; Molecular Probes). Immunostained cell cultures were examined using a laser scanning confocal microscope (ZEISS LSM510), a 63× oil immersion objective, and appropriate filter sets. Images shown are of a single optical section approximately 1 µm thick.

The expanded confocal microscopy results of the LTRPC3 polypeptide is provided in FIG. 21 and described elsewhere herein.

Example 10

Method of Further Assessing the Ion Channel Activity of the LTRPC3 Polypeptide

The cytoplasmic $Ca^{2+}$ indicator Fluo-4-AM (Molecular Probes) and a Fluorometric Imaging Plate Reader (FLIPR™; Molecular Devices) instrument were used to detect changes in intracellular $Ca^{2+}$ concentration. The hLTRPC3-transfected cells were seeded on PDL-coated 96-well plates at a density of 70,000 cells/well 24 hours after transfection and used 24 hours after plating. Cells were loaded with 4 µM Fluo-4-AM at 37° C. for 30 min in a nominally $Ca^{2+}$-free or 1 mM $CaCl_2$ buffer containing (in mM): 140 NaCl, 4.7 KCl, 1 $MgCl_2$, 10 HEPES, 10 Glucose, and 2.5 Probenecid (Sigma), pH 7.4. Extracellular Fluo-4-AM was removed and cells were maintained in either $Ca^{2+}$-free buffer or buffer containing 1 mM $Ca^{2+}$ at room temperature prior to the experiments, which were conducted within 30 min after dye removal. Fluo-4 was excited at 488 nm using an argon laser and emitted light was selected using a 510-570 nm bandpass filter. Baseline intracellular fluorescence was established during the initial 50 seconds of the FLIPR read, then 1, 3, or 10 mM $Ca^{2+}$ was added to each well and subsequent changes in the intracellular $Ca^{2+}$ were monitored for 8 minutes. For store-depletion or receptor activation studies, 2 µM thapsigargin or 50 µM carbachol, respectively, was added to Fluo-4-loaded cells in $Ca^{2+}$-free buffer before adding 2 mM $Ca^{2+}$ on FLIPR. For pharmacology studies, 100 µM $GdCl_3$ was added to Fluo-4-loaded cells in 0 or 1 mM $Ca^{2+}$ buffer, as described in herein, prior to the start of the FLIPR recordings. Experiments were carried out at room temperature.

The results of the expanded physiometric experiments are provided in FIG. 22 and described herein.

Example 11

Method of Assessing the Putative Kinase Activity of the LTRPC3 Polypeptide

A number of methods may be employed to assess the potential kinase activity of the LTRPC3 polypeptides. One preferred method is described below. A fusion construct is made whereby the LTRPC3 encoding polynucleotide is operably linked to the coding region of the HA protein. CHO-K1 or HEK-293 cells grown on 100-mm dishes are transiently transfected with 8 µg of novel LTRPC3-HA cDNA construct in the pTracer-CMV2 (Invitrogen) vector with LipofectAMINE 2000 (Gibco). Cells are harvested after 48 hours with 3 ml of RIPA buffer [50 mM Tris (pH 7.4), 150 mM NaCl, 1 mM EDTA, 1% IGEPAL CA-630, 0.5% (w/v) deoxycholate, 0.1% (w/v) SDS, and 10 mM iodoacetamide]. LTRPC3-HA is immunoprecipitated with mouse monoclonal immunoglobulin G2a (IgG2a) HA probe (F-7) coupled to agarose (Santa Cruz Biotechnology). The agarose is sedimented and washed three times with RIPA buffer, and 2×SDS sample buffer is added. The samples may be resolved by SDS-PAGE and Western blotting following standard methods. HA probe Y-11 antibody could be the primary antibody (Santa Cruz Biotechnology), and horseradish peroxidase-linked antibody to rabbit Ig (Amersham Pharmacia Biotech) could be the secondary antibody. The SuperSignal West Dura substrate may be used for chemiluminescent detection (Pierce)

For phosphorylation experiments, purified GST-kinase fusion proteins and mutants are incubated at 37° C. for 30 min in the presence or absence of MBP as a test substrate in a 50-μl reaction. These reactions are performed in KIN buffer {50 mM Mops (pH 7.2), 100 mM NaCl, 20 mM MgCl2, 0.5 mM ATP, and 2 μCi of [-32P]ATP}. Immunokinase reactions containing immunopurified LTRPC3—HA are incubated at 37° C. for 30 min in a 50-μl reaction containing KIN buffer with 75 mM n-octyl—D-glucopyranoside. The reactions are terminated by the addition of 2×SDS sample buffer, and the proteins were resolved by SDS-PAGE and Coomassie staining for the GST-kinase experiment or by SDS-PAGE and Western blotting for the immunokinase assay. The gels are dried, and 32P incorporation is visualized by autoradiography for the GST-kinase experiment. For the immunokinase experiment, 32P incorporation may be visualized by autoradiography of the transferred proteins on polyvinylidene difluoride membrane (Bio-Rad) before Western blotting.

Example 12

Bacterial Expression of a Polypeptide

A polynucleotide encoding a polypeptide of the present invention is amplified using PCR oligonucleotide primers corresponding to the 5' and 3' ends of the DNA sequence, as outlined in Example 15, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3-4 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 13

Purification of a Polypeptide from an Inclusion Body

The following alternative method can be used to purify a polypeptide expressed in E coli when it is present in the form of inclusion bodies. Unless otherwise specified, all of the following steps are conducted at 4-10 degree C.

Upon completion of the production phase of the E. coli fermentation, the cell culture is cooled to 4-10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perceptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perceptive Biosystems) and weak anion (Poros CM-20, Perceptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 14

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

A polynucleotide encoding a polypeptide of the present invention is amplified using PCR oligonucleotide primers corresponding to the 5' and 3' ends of the DNA sequence, as outlined in Example 15, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described in Example 15. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413-7417 (1987). One ug of BaculoGold™ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 15

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357-1370 (1978); Hamlin, J. L. and Ma, C., Biochem. et Biophys. Acta, 1097:107-143 (1990); Page, M. J. and Sydenham, M. A., Biotechnology 9:64-68 (1991).) Another useful selection marker is the enzyme glutamine synthase (GS) (Murphy et al., Biochem J. 227:277-279 (1991); Bebbington et al., Bio/Technology 10:169-175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five μg of an expression plasmid is cotransformed with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100-200 uM. Expression of the desired gene product is analyzed, for instance, by SDS-PAGE and Western blot or by reversed phase HPLC analysis.

Example 16

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84-86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

```
Human IgG Fc region:
                                                 (SEQ ID NO:252)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT
```

Example 17

Method of Creating N- and C-Terminal Deletion Mutants Corresponding to the LTRPC3 Polypeptide of the Present Invention As described elsewhere herein, the present invention encompasses the creation of N- and C-terminal deletion mutants, in addition to any combination of N- and C-terminal deletions thereof, corresponding to the LTRPC3 polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length LTRPC3 polypeptide sequence (as described in Example 15, for example), appropriate primers of about 15-25 nucleotides derived from the desired 5' and 3' positions of SEQ ID NO:1, SEQ ID NO:3, SEQ ID NO:5, SEQ ID NO:8, SEQ ID NO:281, or SEQ ID NO:282 may be designed to PCR amplify, and subsequently clone, the intended N- and/or C-terminal deletion mutant. Such primers could comprise, for example, an initiation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the G620 to T1554 LTRPC3 N-terminal deletion mutant, the following primers could be used to amplify a cDNA fragment corresponding to this deletion mutant:

```
5' Primer 5'-GCAGCA GCGGCCGC CTCAAGGTAATTCTGGGAATTCTAC-3'  (SEQ ID NO:378)
                    NotI 3' Primer 5'-GCAGCA GTCGAC GGTGTGCTTGCTTTCAAAGCTTTGG-3'   (SEQ ID NO:379)
                    SalI
```

For example, in the case of the M1 to N960 LTRPC3 C-terminal deletion mutant, the following primers could be used to amplify a cDNA fragment corresponding to this deletion mutant:

```
5' Primer 5'-GCAGCA GCGGCCGC ATGTATGTGCGAGTATCTTTTG-3'   (SEQ ID NO:380)
                    NotI 3' Primer 5'-GCAGCA GTCGAC GTTAAAGACAGCAATGAGGAGGTTG-3'  (SEQ ID NO:381)
                    SalI
```

The resulting C-terminal deletion mutant could be used as a potential, membrane bound, LTRPC3 decoy receptor.

For example, in the case of the M1 to N1061 LTRPC3 C-terminal deletion mutant, the following primers could be used to amplify a cDNA fragment corresponding to this deletion mutant:

```
5' Primer 5'-GCAGCA GCGGCCGC ATGTATGTGCGAGTATCTTTTG-3'   (SEQ ID NO:382)
                   NotI 3' Primer 5'-GCAGCA GTCGAC ATTAGATGAGTTGAACCGATCATCC-3'  (SEQ ID NO:383)
                   SalI
```

The resulting C-terminal deletion mutant could be used as a potential, membrane bound, LTRPC3 decoy receptor.

Representative PCR amplification conditions are provided below, although the skilled artisan would appreciate that other conditions may be required for efficient amplification. A 100 ul PCR reaction mixture may be prepared using 10 ng of the template DNA (cDNA clone of LTRPC3, LTRPC3b, LTRPC3c, LTRPC3d, LTRPC3e, or LTRPC3f), 200 uM 4dNTPs, 1 uM primers, 0.25 U Taq DNA polymerase (PE), and standard Taq DNA polymerase buffer. Typical PCR cycling condition are as follows:

20-25 cycles: 45 sec, 93 degrees 2 min, 50 degrees 2 min, 72 degrees 1 cycle: 10 min, 72 degrees After the final extension step of PCR, 5 U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent E. coli cells using methods provided herein and/or otherwise known in the art.

The 5' primer sequence for amplifying any additional N-terminal deletion mutants may be determined by reference to the following formula:

$$(S+(X*3)) \text{ to } ((S+(X*3))+25),$$

wherein 'S' is equal to the nucleotide position of the initiating start codon of the LTRPC3 gene (SEQ ID NO:1), LTRPC3b gene (SEQ ID NO:3), LTRPC3c gene (SEQ ID NO:5), LTRPC3d gene (SEQ ID NO:281), LTRPC3e gene (SEQ ID NO:8), LTRPC3f gene (SEQ ID NO:282) and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1, SEQ ID NO:3, SEQ ID NO:5, SEQ ID NO:8, SEQ ID NO:281, or SEQ ID NO:282. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula:

$$(S+(X*3)) \text{ to } ((S+(X*3))-25),$$

wherein 'S' is equal to the nucleotide position of the initiating start codon of the LTRPC3 gene (SEQ ID NO:1), LTRPC3b gene (SEQ ID NO:3), LTRPC3c gene (SEQ ID NO:5), LTRPC3d gene (SEQ ID NO:281), LTRPC3e gene (SEQ ID NO:8), LTRPC3f gene (SEQ ID NO:282) and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1, SEQ ID NO:3, SEQ ID NO:5, SEQ ID NO:8, SEQ ID NO:281, or SEQ ID NO:282. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

One skilled in the art could easily modify the exemplified studies to test the activity of polynucleotides of the invention (e.g., gene therapy), agonists, and/or antagonists of polynucleotides or polypeptides of the invention.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated polynucleotide comprising a sequence selected from the group consisting of:
   (a) an isolated polynucleotide comprising the sequence encoding amino acids 1 to 1556 of SEQ ID NO: 9; and
   (b) an isolated polynucleotide comprising the sequence encoding amino acids 2 to 1556 of SEQ ID NO: 9.

2. The isolated polynucleotide of claim 1, wherein said polynucleotide is (a).

3. The isolated polynucleotide of claim 1, wherein said polynucleotide comprises nucleotides 1 to 4668 of SEQ ID NO:8.

4. The isolated nucleic acid molecule of claim 1, wherein said polynucleotide is (b).

5. The isolated nucleic acid molecule of claim 4, wherein said polynucleotide comprises nucleotides 4 to 4668 of SEQ ID NO:8.

6. The isolated polynucleotide of claim 1 wherein said nucleic acid sequence further comprises a heterologous nucleic acid sequence.

7. The isolated polynucleotide of claim 6 wherein said heterologous nucleic acid sequence encodes a heterologous polypeptide.

8. The isolated polynucleotide of claim 7 wherein said heterologous polypeptide is the Fc domain of immunoglobulin.

9. An isolated polynucleotide comprising a polynucleotide that encodes a polypeptide sequence having at least 99.0% identity to amino acids 1 to 1556 of SEQ ID NO:9, wherein percent identity is calculated using a CLUSTLAW global sequence alignment, and wherein said polynucleotide is a transient receptor potential channel having $Ca^{++}$ flux activity.

10. The isolated polynucleotide of claim 9 further comprising a heterologous polynucleotide.

11. The isolated polynucleotide of claim 10 wherein said heterologous polynucleotide is the Fc domain of immunoglobulin.

12. An isolated polynucleotide comprising a polynucleotide sequence that encodes at least 1116 contiguous amino acids of SEQ ID NO:9, wherein said polynucleotide is a transient receptor potential channel having $Ca^{++}$ flux activity.

13. The isolated polynucleotide of claim 12, wherein said polynucleotide comprises at least 3348 contiguous nucleotides of SEQ ID NO:8.

14. A recombinant vector comprising the isolated nucleic acid molecule of claim 1.

15. An isolated recombinant host cell comprising the recombinant vector of claim 14.

16. A method of making an isolated polypeptide comprising:
   (a) culturing the isolated recombinant host cell of claim 15 under conditions such that a polypeptide comprising either amino acids 1 to 1556 of SEQ ID NO:9 or amino acids 2 to 1556 of SEQ ID NO:9 is expressed; and
   (b) recovering said polypeptide.

* * * * *

UNITED STATES PATENT AND TRADEMARK OFFICE
CERTIFICATE OF CORRECTION

PATENT NO. : 7,767,418 B2  
APPLICATION NO. : 12/152547  
DATED : August 3, 2010  
INVENTOR(S) : Liana Lee et al.

Page 1 of 1

It is certified that error appears in the above-identified patent and that said Letters Patent is hereby corrected as shown below:

Item (63) should read:

This application is a divisional application of non-provisional application U.S. Serial No. 10/405,793, filed March 3, 2003, which is a continuation-in-part application of non-provisional application U.S. Serial No. 10/210,152, filed August 1, 2002, which claims benefit to provisional application U.S. Serial No. 60/309,544 filed August 2, 2001.

Column 1 - Line 5, should read:

This application is a divisional application of non-provisional application U.S. Serial No. 10/405,793, filed March 3, 2003, which is a continuation-in-part application of non-provisional application U.S. Serial No. 10/210,152, filed August 1, 2002, which claims benefit to provisional application U.S. Serial No. 60/309,544 filed August 2, 2001, under 35 U.S.C 119(e).

Signed and Sealed this
First Day of March, 2011

David J. Kappos
*Director of the United States Patent and Trademark Office*

SEQUENCE LISTING

<160> NUMBER OF SEQ ID NOS: 286

<210> SEQ ID NO 1
<211> LENGTH: 4665
<212> TYPE: DNA
<213> ORGANISM: Homo sapiens
<220> FEATURE:
<221> NAME/KEY: CDS
<222> LOCATION: (1)..(4662)

<400> SEQUENCE: 1

```
atg tat gtg cga gta tct ttt gat aca aaa cct gat ctc ctc tta cac      48
Met Tyr Val Arg Val Ser Phe Asp Thr Lys Pro Asp Leu Leu Leu His
 1               5                  10                  15 ctg atg acc aag gaa tgg cag ttg gag ctt ccc aag ctt ctc atc tct      96
Leu Met Thr Lys Glu Trp Gln Leu Glu Leu Pro Lys Leu Leu Ile Ser
             20                  25                  30 gtc cat ggg ggc ctg cag aac ttt gaa ctc cag cca aaa ctc aag caa     144
Val His Gly Gly Leu Gln Asn Phe Glu Leu Gln Pro Lys Leu Lys Gln
         35                  40                  45 gtc ttt ggg aaa ggg ctc atc aaa gca gca atg aca act gga gcg tgg     192
Val Phe Gly Lys Gly Leu Ile Lys Ala Ala Met Thr Thr Gly Ala Trp
     50                  55                  60 ata ttc act gga ggg gtt aac aca ggt gtt att cgt cat gtt ggc gat     240
Ile Phe Thr Gly Gly Val Asn Thr Gly Val Ile Arg His Val Gly Asp
 65                  70                  75                  80 gcc ttg aag gat cat gcc tct aag tct cga gga aag ata tgc acc ata     288
Ala Leu Lys Asp His Ala Ser Lys Ser Arg Gly Lys Ile Cys Thr Ile
                 85                  90                  95 ggt att gcc ccc tgg gga att gtg gaa aac cag gag gac ctc att gga     336
Gly Ile Ala Pro Trp Gly Ile Val Glu Asn Gln Glu Asp Leu Ile Gly
            100                 105                 110 aga gat gtt gtc cgg cca tac cag acc atg tcc aat ccc atg agc aag     384
Arg Asp Val Val Arg Pro Tyr Gln Thr Met Ser Asn Pro Met Ser Lys
        115                 120                 125 ctc act gtt ctc aac agc atg cat tcc cac ttc att ctg gct gac aac     432
Leu Thr Val Leu Asn Ser Met His Ser His Phe Ile Leu Ala Asp Asn
    130                 135                 140 ggg acc act gga aaa tat gga gca gag gtg aaa ctt cga aga caa ctg     480
Gly Thr Thr Gly Lys Tyr Gly Ala Glu Val Lys Leu Arg Arg Gln Leu
145                 150                 155                 160 gaa aag cat att tca ctc cag aag ata aac aca aga atc ggt caa ggt     528
Glu Lys His Ile Ser Leu Gln Lys Ile Asn Thr Arg Ile Gly Gln Gly
                165                 170                 175 gtt cct gtg gtg gca ctc ata gtg gaa gga gga ccc aat gtg atc tcg     576
Val Pro Val Val Ala Leu Ile Val Glu Gly Gly Pro Asn Val Ile Ser
            180                 185                 190 att gtt ttg gag tac ctt cga gac acc cct ccc gtg cca gtg gtt gtc     624
Ile Val Leu Glu Tyr Leu Arg Asp Thr Pro Pro Val Pro Val Val Val
        195                 200                 205 tgt gat ggg agt gga cgg gca tcg gac atc ctg gcc ttt ggg cat aaa     672
Cys Asp Gly Ser Gly Arg Ala Ser Asp Ile Leu Ala Phe Gly His Lys
    210                 215                 220 tac tca gaa gaa ggc gga ctg ata aat gaa tct ttg agg gac cag ctg     720
Tyr Ser Glu Glu Gly Gly Leu Ile Asn Glu Ser Leu Arg Asp Gln Leu
225                 230                 235                 240 ttg gtg act ata cag aag act ttc aca tac act cga acc caa gct cag     768
Leu Val Thr Ile Gln Lys Thr Phe Thr Tyr Thr Arg Thr Gln Ala Gln
                245                 250                 255
```

```
cat ctg ttc atc atc ctc atg gag tgc atg aag aag aag gaa ttg att       816
His Leu Phe Ile Ile Leu Met Glu Cys Met Lys Lys Lys Glu Leu Ile
            260                 265                 270 acg gta ttt cgg atg gga tca gaa gga cac cag gac att gat ttg gct       864
Thr Val Phe Arg Met Gly Ser Glu Gly His Gln Asp Ile Asp Leu Ala
                275                 280                 285 atc ctg aca gct tta ctc aaa gga gcc aat gcc tcg gcc cca gac caa       912
Ile Leu Thr Ala Leu Leu Lys Gly Ala Asn Ala Ser Ala Pro Asp Gln
        290                 295                 300 ctg agc tta gct tta gcc tgg aac aga gtc gac atc gct cgc agc cag       960
Leu Ser Leu Ala Leu Ala Trp Asn Arg Val Asp Ile Ala Arg Ser Gln
305                 310                 315                 320 atc ttt att tac ggg caa cag tgg ccg gtg gga tct ctg gag caa gcc      1008
Ile Phe Ile Tyr Gly Gln Gln Trp Pro Val Gly Ser Leu Glu Gln Ala
                325                 330                 335 atg ttg gat gcc tta gtt ctg gac aga gtg gat ttt gtg aaa tta ctc      1056
Met Leu Asp Ala Leu Val Leu Asp Arg Val Asp Phe Val Lys Leu Leu
        340                 345                 350 ata gag aat gga gta agc atg cac cgt ttt ctc acc atc tcc aga cta      1104
Ile Glu Asn Gly Val Ser Met His Arg Phe Leu Thr Ile Ser Arg Leu
    355                 360                 365 gag gaa ttg tac aat acg aga cat ggg ccc tca aat aca ttg tac cac      1152
Glu Glu Leu Tyr Asn Thr Arg His Gly Pro Ser Asn Thr Leu Tyr His
370                 375                 380 ttg gtc agg gat gtc aaa aag ggg aac ctg ccc cca gac tac aga atc      1200
Leu Val Arg Asp Val Lys Lys Gly Asn Leu Pro Pro Asp Tyr Arg Ile
385                 390                 395                 400 agc ctg att gac atc ggc ctg gtg atc gag tac ctg atg ggc ggg gct      1248
Ser Leu Ile Asp Ile Gly Leu Val Ile Glu Tyr Leu Met Gly Gly Ala
                405                 410                 415 tat cgc tgc aac tac acg cgc aag cgc ttc cgg acc ctc tac cac aac      1296
Tyr Arg Cys Asn Tyr Thr Arg Lys Arg Phe Arg Thr Leu Tyr His Asn
            420                 425                 430 ctc ttc ggc ccc aag agg ccc aaa gcc ttg aaa ctg ctg gga atg gag      1344
Leu Phe Gly Pro Lys Arg Pro Lys Ala Leu Lys Leu Leu Gly Met Glu
        435                 440                 445 gat gat att ccc ttg agg cga gga aga aag aca acc aag aaa cgt gaa      1392
Asp Asp Ile Pro Leu Arg Arg Gly Arg Lys Thr Thr Lys Lys Arg Glu
450                 455                 460 gaa gag gtg gac att gac ttg gat gat cct gag atc aac cac ttc ccc      1440
Glu Glu Val Asp Ile Asp Leu Asp Asp Pro Glu Ile Asn His Phe Pro
465                 470                 475                 480 ttc cct ttc cat gag ctc atg gtg tgg gct gtt ctc atg aag cgg cag      1488
Phe Pro Phe His Glu Leu Met Val Trp Ala Val Leu Met Lys Arg Gln
                485                 490                 495 aag atg gcc ctg ttc ttc tgg cag cac ggt gag gag gcc atg gcc aag      1536
Lys Met Ala Leu Phe Phe Trp Gln His Gly Glu Glu Ala Met Ala Lys
            500                 505                 510 gcc ctg gtg gcc tgc aag ctc tgc aaa gcc atg gct cat gag gcc tct      1584
Ala Leu Val Ala Cys Lys Leu Cys Lys Ala Met Ala His Glu Ala Ser
        515                 520                 525 gag aac gac atg gtt gac gac att tcc cag gag ctg aat cac aat tcc      1632
Glu Asn Asp Met Val Asp Asp Ile Ser Gln Glu Leu Asn His Asn Ser
530                 535                 540 aga gac ttt ggc cag ctg gct gtg gag ctc ctg gac cag tcc tac aag      1680
Arg Asp Phe Gly Gln Leu Ala Val Glu Leu Leu Asp Gln Ser Tyr Lys
545                 550                 555                 560 cag gac gaa cag ctg gcc atg aaa ctg ctg acg tat gag ctg aag aac      1728
Gln Asp Glu Gln Leu Ala Met Lys Leu Leu Thr Tyr Glu Leu Lys Asn
                565                 570                 575
```

```
                                                     -continued tgg agc aac gcc acg tgc ctg cag ctt gcc gtg gct gcc aaa cac cgc    1776
Trp Ser Asn Ala Thr Cys Leu Gln Leu Ala Val Ala Ala Lys His Arg
            580                 585                 590 gac ttc atc gcg cac acg tgc agc cag atg ctg ctc acc gac atg tgg    1824
Asp Phe Ile Ala His Thr Cys Ser Gln Met Leu Leu Thr Asp Met Trp
                595                 600                 605 atg ggc cgg ctc cgc atg cgc aag aac tca ggc ctc aag gta att ctg    1872
Met Gly Arg Leu Arg Met Arg Lys Asn Ser Gly Leu Lys Val Ile Leu
    610                 615                 620 gga att cta ctt cct cct tca att ctc agc ttg gag ttc aag aac aaa    1920
Gly Ile Leu Leu Pro Pro Ser Ile Leu Ser Leu Glu Phe Lys Asn Lys
625                 630                 635                 640 gac gac atg ccc tat atg tct cag gcc cag gaa atc cac ctc caa gag    1968
Asp Asp Met Pro Tyr Met Ser Gln Ala Gln Glu Ile His Leu Gln Glu
                645                 650                 655 aag gag gca gaa gaa cca gag aag ccc aca aag gaa aaa gag gaa gag    2016
Lys Glu Ala Glu Glu Pro Glu Lys Pro Thr Lys Glu Lys Glu Glu Glu
            660                 665                 670 gac atg gag ctc aca gca atg ttg gga cga aac aac ggg gag tcc tcc    2064
Asp Met Glu Leu Thr Ala Met Leu Gly Arg Asn Asn Gly Glu Ser Ser
    675                 680                 685 agg aag aag gat gaa gag gaa gtt cag agc aag cac cgg tta atc ccc    2112
Arg Lys Lys Asp Glu Glu Glu Val Gln Ser Lys His Arg Leu Ile Pro
690                 695                 700 ctc ggc aga aaa atc tat gaa ttc tac aat gca ccc atc gtg aag ttc    2160
Leu Gly Arg Lys Ile Tyr Glu Phe Tyr Asn Ala Pro Ile Val Lys Phe
705                 710                 715                 720 tgg ttc tac aca ctg gcg tat atc gga tac ctg atg ctc ttc aac tat    2208
Trp Phe Tyr Thr Leu Ala Tyr Ile Gly Tyr Leu Met Leu Phe Asn Tyr
                725                 730                 735 atc gtg tta gtg aag atg gaa cgc tgg ccg tcc acc cag gaa tgg atc    2256
Ile Val Leu Val Lys Met Glu Arg Trp Pro Ser Thr Gln Glu Trp Ile
            740                 745                 750 gta atc tcc tat att ttc acc ctg gga ata gaa aag atg aga gag att    2304
Val Ile Ser Tyr Ile Phe Thr Leu Gly Ile Glu Lys Met Arg Glu Ile
    755                 760                 765 ctg atg tca gag cca ggg aag ttg cta cag aaa gtg aag gta tgg ctg    2352
Leu Met Ser Glu Pro Gly Lys Leu Leu Gln Lys Val Lys Val Trp Leu
770                 775                 780 cag gag tac tgg aat gtc acg gac ctc atc gcc atc ctt ctg ttt tct    2400
Gln Glu Tyr Trp Asn Val Thr Asp Leu Ile Ala Ile Leu Leu Phe Ser
785                 790                 795                 800 gtc gga atg atc ctt cgt ctc caa gac cag ccc ttc agg agt gac ggg    2448
Val Gly Met Ile Leu Arg Leu Gln Asp Gln Pro Phe Arg Ser Asp Gly
                805                 810                 815 agg gtc atc tac tgc gtg aac atc att tac tgg tat atc cgt ctc cta    2496
Arg Val Ile Tyr Cys Val Asn Ile Ile Tyr Trp Tyr Ile Arg Leu Leu
            820                 825                 830 gac atc ttc ggc gtg aac aag tat ttg ggc ccg tat gta atg atg att    2544
Asp Ile Phe Gly Val Asn Lys Tyr Leu Gly Pro Tyr Val Met Met Ile
    835                 840                 845 gga aaa atg atg ata gac atg atg tac ttt gtc atc att atg ctg gtg    2592
Gly Lys Met Met Ile Asp Met Met Tyr Phe Val Ile Ile Met Leu Val
850                 855                 860 gtt ctg atg agc ttt ggg gtc gcc agg caa gcc atc ctt ttt ccc aat    2640
Val Leu Met Ser Phe Gly Val Ala Arg Gln Ala Ile Leu Phe Pro Asn
865                 870                 875                 880 gag gag cca tca tgg aaa ctg gcc aag aac atc ttc tac atg ccc tat    2688
Glu Glu Pro Ser Trp Lys Leu Ala Lys Asn Ile Phe Tyr Met Pro Tyr
```

-continued

|  |  |  |  |  |  |  |  |  |  |  |  |  |  |  |  |
|---|---|---|---|---|---|---|---|---|---|---|---|---|---|---|---|
|  |  | 885 |  |  |  | 890 |  |  |  | 895 |  |  |  |  |  |
| tgg | atg | att | tat | ggg | gaa | gtg | ttt | gcg | gac | cag | ata | gac | cct | ccc | tgt | 2736 |
| Trp | Met | Ile | Tyr | Gly | Glu | Val | Phe | Ala | Asp | Gln | Ile | Asp | Pro | Pro | Cys |  |
|  | 900 |  |  |  |  | 905 |  |  |  |  | 910 |  |  |  |  |  |
| gga | cag | aat | gag | acc | cga | gag | gat | ggt | aaa | ata | atc | cag | ctg | cct | ccc | 2784 |
| Gly | Gln | Asn | Glu | Thr | Arg | Glu | Asp | Gly | Lys | Ile | Ile | Gln | Leu | Pro | Pro |  |
|  |  | 915 |  |  |  |  | 920 |  |  |  |  | 925 |  |  |  |  |
| tgc | aag | aca | gga | gct | tgg | atc | gtg | ccg | gcc | atc | atg | gcc | tgc | tac | ctc | 2832 |
| Cys | Lys | Thr | Gly | Ala | Trp | Ile | Val | Pro | Ala | Ile | Met | Ala | Cys | Tyr | Leu |  |
|  | 930 |  |  |  |  | 935 |  |  |  |  | 940 |  |  |  |  |  |
| tta | gtg | gca | aac | atc | ttg | ctg | gtc | aac | ctc | ctc | att | gct | gtc | ttt | aac | 2880 |
| Leu | Val | Ala | Asn | Ile | Leu | Leu | Val | Asn | Leu | Leu | Ile | Ala | Val | Phe | Asn |  |
| 945 |  |  |  |  | 950 |  |  |  |  | 955 |  |  |  |  | 960 |  |
| aat | aca | ttt | ttt | gaa | gta | aaa | tcg | ata | tcc | aac | caa | gtc | tgg | aag | ttt | 2928 |
| Asn | Thr | Phe | Phe | Glu | Val | Lys | Ser | Ile | Ser | Asn | Gln | Val | Trp | Lys | Phe |  |
|  |  |  |  | 965 |  |  |  |  | 970 |  |  |  |  | 975 |  |  |
| cag | agg | tat | cag | ctc | atc | atg | act | ttc | cat | gaa | agg | cca | gtt | ctg | ccc | 2976 |
| Gln | Arg | Tyr | Gln | Leu | Ile | Met | Thr | Phe | His | Glu | Arg | Pro | Val | Leu | Pro |  |
|  |  |  | 980 |  |  |  |  | 985 |  |  |  |  | 990 |  |  |  |
| cca | cca | ctg | atc | atc | ttc | agc | cac | atg | acc | atg | ata | ttc | cag | cac | ctg | 3024 |
| Pro | Pro | Leu | Ile | Ile | Phe | Ser | His | Met | Thr | Met | Ile | Phe | Gln | His | Leu |  |
|  |  | 995 |  |  |  |  | 1000 |  |  |  |  | 1005 |  |  |  |  |
| tgc | tgc | cga | tgg | agg | aaa | cac | gag | agc | gac | ccg | gat | gaa | agg | gac |  | 3069 |
| Cys | Cys | Arg | Trp | Arg | Lys | His | Glu | Ser | Asp | Pro | Asp | Glu | Arg | Asp |  |  |
| 1010 |  |  |  |  | 1015 |  |  |  |  | 1020 |  |  |  |  |  |  |
| tac | ggc | ctg | aaa | ctc | ttc | ata | acc | gat | gat | gag | ctc | aag | aaa | gta |  | 3114 |
| Tyr | Gly | Leu | Lys | Leu | Phe | Ile | Thr | Asp | Asp | Glu | Leu | Lys | Lys | Val |  |  |
| 1025 |  |  |  |  | 1030 |  |  |  |  | 1035 |  |  |  |  |  |  |
| cat | gac | ttt | gaa | gag | caa | tgc | ata | gaa | gaa | tac | ttc | aga | gaa | aag |  | 3159 |
| His | Asp | Phe | Glu | Glu | Gln | Cys | Ile | Glu | Glu | Tyr | Phe | Arg | Glu | Lys |  |  |
| 1040 |  |  |  |  | 1045 |  |  |  |  | 1050 |  |  |  |  |  |  |
| gat | gat | cgg | ttc | aac | tca | tct | aat | gat | gag | agg | ata | cgg | gtg | act |  | 3204 |
| Asp | Asp | Arg | Phe | Asn | Ser | Ser | Asn | Asp | Glu | Arg | Ile | Arg | Val | Thr |  |  |
| 1055 |  |  |  |  | 1060 |  |  |  |  | 1065 |  |  |  |  |  |  |
| tca | gaa | agg | gtg | gag | aac | atg | tct | atg | cgg | ctg | gag | gaa | gtc | aac |  | 3249 |
| Ser | Glu | Arg | Val | Glu | Asn | Met | Ser | Met | Arg | Leu | Glu | Glu | Val | Asn |  |  |
| 1070 |  |  |  |  | 1075 |  |  |  |  | 1080 |  |  |  |  |  |  |
| gag | aga | gag | cac | tcc | atg | aag | gct | tca | ctc | cag | acc | gtg | gac | atc |  | 3294 |
| Glu | Arg | Glu | His | Ser | Met | Lys | Ala | Ser | Leu | Gln | Thr | Val | Asp | Ile |  |  |
| 1085 |  |  |  |  | 1090 |  |  |  |  | 1095 |  |  |  |  |  |  |
| cgg | ctg | gcg | cag | ctg | gaa | gac | ctt | atc | ggg | cgc | atg | gcc | acg | gcc |  | 3339 |
| Arg | Leu | Ala | Gln | Leu | Glu | Asp | Leu | Ile | Gly | Arg | Met | Ala | Thr | Ala |  |  |
| 1100 |  |  |  |  | 1105 |  |  |  |  | 1110 |  |  |  |  |  |  |
| ctg | gag | cgc | ctg | aca | ggt | ctg | gag | cgg | gcc | gag | tcc | aac | aaa | atc |  | 3384 |
| Leu | Glu | Arg | Leu | Thr | Gly | Leu | Glu | Arg | Ala | Glu | Ser | Asn | Lys | Ile |  |  |
| 1115 |  |  |  |  | 1120 |  |  |  |  | 1125 |  |  |  |  |  |  |
| cgc | tcg | agg | acc | tcg | tca | gac | tgc | acg | gac | gcc | gcc | tac | att | gtc |  | 3429 |
| Arg | Ser | Arg | Thr | Ser | Ser | Asp | Cys | Thr | Asp | Ala | Ala | Tyr | Ile | Val |  |  |
| 1130 |  |  |  |  | 1135 |  |  |  |  | 1140 |  |  |  |  |  |  |
| cgt | cag | agc | agc | ttc | aac | agc | cag | gaa | ggg | aac | acc | ttc | aag | ctc |  | 3474 |
| Arg | Gln | Ser | Ser | Phe | Asn | Ser | Gln | Glu | Gly | Asn | Thr | Phe | Lys | Leu |  |  |
| 1145 |  |  |  |  | 1150 |  |  |  |  | 1155 |  |  |  |  |  |  |
| caa | gag | agt | ata | gac | cct | gca | ggt | gag | gag | acc | atg | tcc | cca | act |  | 3519 |
| Gln | Glu | Ser | Ile | Asp | Pro | Ala | Gly | Glu | Glu | Thr | Met | Ser | Pro | Thr |  |  |
| 1160 |  |  |  |  | 1165 |  |  |  |  | 1170 |  |  |  |  |  |  |
| tct | cca | acc | tta | atg | ccc | cgt | atg | cga | agc | cat | tct | ttc | tat | tca |  | 3564 |
| Ser | Pro | Thr | Leu | Met | Pro | Arg | Met | Arg | Ser | His | Ser | Phe | Tyr | Ser |  |  |
| 1175 |  |  |  |  | 1180 |  |  |  |  | 1185 |  |  |  |  |  |  |
| gtc | aat | atg | aaa | gac | aaa | ggt | ggt | ata | gaa | aag | ttg | gaa | agt | att |  | 3609 |

```
Val Asn Met Lys Asp Lys Gly Gly Ile Glu Lys Leu Glu Ser Ile
    1190            1195                1200 ttt aaa gaa agg tcc ctg agc cta cac cgg gct act agt tcc cac    3654
Phe Lys Glu Arg Ser Leu Ser Leu His Arg Ala Thr Ser Ser His
    1205            1210                1215 tct gta gca aaa gaa ccc aaa gct cct gca gcc cct gcc aac acc    3699
Ser Val Ala Lys Glu Pro Lys Ala Pro Ala Ala Pro Ala Asn Thr
    1220            1225                1230 ttg gcc att gtt cct gat tcc aga aga cca tca tcg tgt ata gac    3744
Leu Ala Ile Val Pro Asp Ser Arg Arg Pro Ser Ser Cys Ile Asp
    1235            1240                1245 atc tat gtc tct gct atg gat gag ctc cac tgt gat ata gac cct    3789
Ile Tyr Val Ser Ala Met Asp Glu Leu His Cys Asp Ile Asp Pro
    1250            1255                1260 ctg gac aat tcc gtg aac atc ctt ggg cta ggc gag cca agc ttt    3834
Leu Asp Asn Ser Val Asn Ile Leu Gly Leu Gly Glu Pro Ser Phe
    1265            1270                1275 tca act cca gta cct tcc aca gcc cct tca agt agt gcc tat gca    3879
Ser Thr Pro Val Pro Ser Thr Ala Pro Ser Ser Ser Ala Tyr Ala
    1280            1285                1290 aca ctt gca ccc aca gac aga cct cca agc cgg agc att gat ttt    3924
Thr Leu Ala Pro Thr Asp Arg Pro Pro Ser Arg Ser Ile Asp Phe
    1295            1300                1305 gag gac atc acc tcc atg gac act aga tct ttt tct tca gac tac    3969
Glu Asp Ile Thr Ser Met Asp Thr Arg Ser Phe Ser Ser Asp Tyr
    1310            1315                1320 acc cac ctc cca gaa tgc caa aac ccc tgg gac tca gag cct ccg    4014
Thr His Leu Pro Glu Cys Gln Asn Pro Trp Asp Ser Glu Pro Pro
    1325            1330                1335 atg tac cac acc att gag cgt tcc aaa agt agc cgc tac cta gcc    4059
Met Tyr His Thr Ile Glu Arg Ser Lys Ser Ser Arg Tyr Leu Ala
    1340            1345                1350 acc aca ccc ttt ctt cta gaa gag gct ccc att gtg aaa tct cat    4104
Thr Thr Pro Phe Leu Leu Glu Glu Ala Pro Ile Val Lys Ser His
    1355            1360                1365 agc ttt atg ttt tcc ccc tca agg agc tat tat gcc aac ttt ggg    4149
Ser Phe Met Phe Ser Pro Ser Arg Ser Tyr Tyr Ala Asn Phe Gly
    1370            1375                1380 gtg cct gta aaa aca gca gaa tac aca agt att aca gac tgt att    4194
Val Pro Val Lys Thr Ala Glu Tyr Thr Ser Ile Thr Asp Cys Ile
    1385            1390                1395 gac aca agg tgt gtc aat gcc cct caa gca att gcg gac aga gct    4239
Asp Thr Arg Cys Val Asn Ala Pro Gln Ala Ile Ala Asp Arg Ala
    1400            1405                1410 gcc ttc cct gga ggt ctt gga gac aaa gtg gag gac tta act tgc    4284
Ala Phe Pro Gly Gly Leu Gly Asp Lys Val Glu Asp Leu Thr Cys
    1415            1420                1425 tgc cat cca gag cga gaa gca gaa ctg agt cac ccc agc tct gac    4329
Cys His Pro Glu Arg Glu Ala Glu Leu Ser His Pro Ser Ser Asp
    1430            1435                1440 agt gag gag aat gag gcc aaa ggc cgc aga gcc acc att gca ata    4374
Ser Glu Glu Asn Glu Ala Lys Gly Arg Arg Ala Thr Ile Ala Ile
    1445            1450                1455 tcc tcc cag gag ggt gat aac tca gag aga acc ctg tcc aac aac    4419
Ser Ser Gln Glu Gly Asp Asn Ser Glu Arg Thr Leu Ser Asn Asn
    1460            1465                1470 atc act gtt ccc aag ata gag cgc gcc aac agc tac tcg gca gag    4464
Ile Thr Val Pro Lys Ile Glu Arg Ala Asn Ser Tyr Ser Ala Glu
    1475            1480                1485
```

-continued

| | | | | | | | | | | | | |
|---|---|---|---|---|---|---|---|---|---|---|---|---|
| gag | cca | agt | gcg | cca | tat | gca | cac | acc | agg | aag | agc | ttc tcc atc |
| Glu | Pro | Ser | Ala | Pro | Tyr | Ala | His | Thr | Arg | Lys | Ser | Phe Ser Ile |
| | 1490 | | | | 1495 | | | | | 1500 | | |

4509

| | | | | | | | | | | | | |
|---|---|---|---|---|---|---|---|---|---|---|---|---|
| agt | gac | aaa | ctc | gac | agg | cag | cgg | aac | aca | gca | agc | ctg caa aat |
| Ser | Asp | Lys | Leu | Asp | Arg | Gln | Arg | Asn | Thr | Ala | Ser | Leu Gln Asn |
| 1505 | | | | | 1510 | | | | | 1515 | | |

4554

| | | | | | | | | | | | | |
|---|---|---|---|---|---|---|---|---|---|---|---|---|
| ccc | ttc | cag | aga | agc | aag | tcc | tcc | aag | ccg | gag | ggc | cga ggg gac |
| Pro | Phe | Gln | Arg | Ser | Lys | Ser | Ser | Lys | Pro | Glu | Gly | Arg Gly Asp |
| | 1520 | | | | 1525 | | | | | 1530 | | |

4599

| | | | | | | | | | | | | |
|---|---|---|---|---|---|---|---|---|---|---|---|---|
| agc | ctg | tcc | atg | agg | aga | ctg | tcc | aga | aca | tcg | gct | ttc caa agc |
| Ser | Leu | Ser | Met | Arg | Arg | Leu | Ser | Arg | Thr | Ser | Ala | Phe Gln Ser |
| 1535 | | | | | 1540 | | | | | 1545 | | |

4644

| | | | | |
|---|---|---|---|---|
| ttt | gaa | agc | aag | cac acc taa |
| Phe | Glu | Ser | Lys | His Thr |
| | 1550 | | | |

4665

<210> SEQ ID NO 2
<211> LENGTH: 1554
<212> TYPE: PRT
<213> ORGANISM: Homo sapiens

<400> SEQUENCE: 2

Met Tyr Val Arg Val Ser Phe Asp Thr Lys Pro Asp Leu Leu Leu His
1               5                   10                  15

Leu Met Thr Lys Glu Trp Gln Leu Glu Leu Pro Lys Leu Leu Ile Ser
            20                  25                  30

Val His Gly Gly Leu Gln Asn Phe Glu Leu Gln Pro Lys Leu Lys Gln
        35                  40                  45

Val Phe Gly Lys Gly Leu Ile Lys Ala Ala Met Thr Thr Gly Ala Trp
    50                  55                  60

Ile Phe Thr Gly Gly Val Asn Thr Gly Val Ile Arg His Val Gly Asp
65                  70                  75                  80

Ala Leu Lys Asp His Ala Ser Lys Ser Arg Gly Lys Ile Cys Thr Ile
                85                  90                  95

Gly Ile Ala Pro Trp Gly Ile Val Glu Asn Gln Glu Asp Leu Ile Gly
            100                 105                 110

Arg Asp Val Val Arg Pro Tyr Gln Thr Met Ser Asn Pro Met Ser Lys
        115                 120                 125

Leu Thr Val Leu Asn Ser Met His Ser His Phe Ile Leu Ala Asp Asn
    130                 135                 140

Gly Thr Thr Gly Lys Tyr Gly Ala Glu Val Lys Leu Arg Arg Gln Leu
145                 150                 155                 160

Glu Lys His Ile Ser Leu Gln Lys Ile Asn Thr Arg Ile Gly Gln Gly
                165                 170                 175

Val Pro Val Val Ala Leu Ile Val Glu Gly Gly Pro Asn Val Ile Ser
            180                 185                 190

Ile Val Leu Glu Tyr Leu Arg Asp Thr Pro Pro Val Pro Val Val Val
        195                 200                 205

Cys Asp Gly Ser Gly Arg Ala Ser Asp Ile Leu Ala Phe Gly His Lys
    210                 215                 220

Tyr Ser Glu Glu Gly Gly Leu Ile Asn Glu Ser Leu Arg Asp Gln Leu
225                 230                 235                 240

Leu Val Thr Ile Gln Lys Thr Phe Thr Tyr Thr Arg Thr Gln Ala Gln
                245                 250                 255

His Leu Phe Ile Ile Leu Met Glu Cys Met Lys Lys Lys Glu Leu Ile
            260                 265                 270

```
Thr Val Phe Arg Met Gly Ser Glu Gly His Gln Asp Ile Asp Leu Ala
        275                 280                 285

Ile Leu Thr Ala Leu Leu Lys Gly Ala Asn Ala Ser Ala Pro Asp Gln
        290                 295                 300

Leu Ser Leu Ala Leu Ala Trp Asn Arg Val Asp Ile Ala Arg Ser Gln
305                 310                 315                 320

Ile Phe Ile Tyr Gly Gln Gln Trp Pro Val Gly Ser Leu Glu Gln Ala
                325                 330                 335

Met Leu Asp Ala Leu Val Leu Asp Arg Val Asp Phe Val Lys Leu Leu
                340                 345                 350

Ile Glu Asn Gly Val Ser Met His Arg Phe Leu Thr Ile Ser Arg Leu
                355                 360                 365

Glu Glu Leu Tyr Asn Thr Arg His Gly Pro Ser Asn Thr Leu Tyr His
        370                 375                 380

Leu Val Arg Asp Val Lys Lys Gly Asn Leu Pro Pro Asp Tyr Arg Ile
385                 390                 395                 400

Ser Leu Ile Asp Ile Gly Leu Val Ile Glu Tyr Leu Met Gly Gly Ala
                405                 410                 415

Tyr Arg Cys Asn Tyr Thr Arg Lys Arg Phe Arg Thr Leu Tyr His Asn
                420                 425                 430

Leu Phe Gly Pro Lys Arg Pro Lys Ala Leu Lys Leu Leu Gly Met Glu
                435                 440                 445

Asp Asp Ile Pro Leu Arg Arg Gly Arg Lys Thr Thr Lys Lys Arg Glu
                450                 455                 460

Glu Glu Val Asp Ile Asp Leu Asp Asp Pro Glu Ile Asn His Phe Pro
465                 470                 475                 480

Phe Pro Phe His Glu Leu Met Val Trp Ala Val Leu Met Lys Arg Gln
                485                 490                 495

Lys Met Ala Leu Phe Phe Trp Gln His Gly Glu Glu Ala Met Ala Lys
                500                 505                 510

Ala Leu Val Ala Cys Lys Leu Cys Lys Ala Met Ala His Glu Ala Ser
                515                 520                 525

Glu Asn Asp Met Val Asp Asp Ile Ser Gln Glu Leu Asn His Asn Ser
        530                 535                 540

Arg Asp Phe Gly Gln Leu Ala Val Glu Leu Leu Asp Gln Ser Tyr Lys
545                 550                 555                 560

Gln Asp Glu Gln Leu Ala Met Lys Leu Leu Thr Tyr Glu Leu Lys Asn
                565                 570                 575

Trp Ser Asn Ala Thr Cys Leu Gln Leu Ala Val Ala Ala Lys His Arg
                580                 585                 590

Asp Phe Ile Ala His Thr Cys Ser Gln Met Leu Leu Thr Asp Met Trp
                595                 600                 605

Met Gly Arg Leu Arg Met Arg Lys Asn Ser Gly Leu Lys Val Ile Leu
        610                 615                 620

Gly Ile Leu Leu Pro Pro Ser Ile Leu Ser Leu Glu Phe Lys Asn Lys
625                 630                 635                 640

Asp Asp Met Pro Tyr Met Ser Gln Ala Gln Glu Ile His Leu Gln Glu
                645                 650                 655

Lys Glu Ala Glu Glu Pro Glu Lys Pro Thr Lys Glu Lys Glu Glu Glu
                660                 665                 670

Asp Met Glu Leu Thr Ala Met Leu Gly Arg Asn Asn Gly Glu Ser Ser
                675                 680                 685

Arg Lys Lys Asp Glu Glu Glu Val Gln Ser Lys His Arg Leu Ile Pro
```

```
            690            695            700
Leu Gly Arg Lys Ile Tyr Glu Phe Tyr Asn Ala Pro Ile Val Lys Phe
705                710                715                720

Trp Phe Tyr Thr Leu Ala Tyr Ile Gly Tyr Leu Met Leu Phe Asn Tyr
                725                730                735

Ile Val Leu Val Lys Met Glu Arg Trp Pro Ser Thr Gln Glu Trp Ile
                740                745                750

Val Ile Ser Tyr Ile Phe Thr Leu Gly Ile Glu Lys Met Arg Glu Ile
                755                760                765

Leu Met Ser Glu Pro Gly Lys Leu Leu Gln Lys Val Lys Val Trp Leu
770                775                780

Gln Glu Tyr Trp Asn Val Thr Asp Leu Ile Ala Ile Leu Leu Phe Ser
785                790                795                800

Val Gly Met Ile Leu Arg Leu Gln Asp Gln Pro Phe Arg Ser Asp Gly
                805                810                815

Arg Val Ile Tyr Cys Val Asn Ile Ile Tyr Trp Tyr Ile Arg Leu Leu
                820                825                830

Asp Ile Phe Gly Val Asn Lys Tyr Leu Gly Pro Tyr Val Met Met Ile
                835                840                845

Gly Lys Met Met Ile Asp Met Met Tyr Phe Val Ile Ile Met Leu Val
850                855                860

Val Leu Met Ser Phe Gly Val Ala Arg Gln Ala Ile Leu Phe Pro Asn
865                870                875                880

Glu Glu Pro Ser Trp Lys Leu Ala Lys Asn Ile Phe Tyr Met Pro Tyr
                885                890                895

Trp Met Ile Tyr Gly Glu Val Phe Ala Asp Gln Ile Asp Pro Pro Cys
                900                905                910

Gly Gln Asn Glu Thr Arg Glu Asp Gly Lys Ile Ile Gln Leu Pro Pro
                915                920                925

Cys Lys Thr Gly Ala Trp Ile Val Pro Ala Ile Met Ala Cys Tyr Leu
                930                935                940

Leu Val Ala Asn Ile Leu Leu Val Asn Leu Leu Ile Ala Val Phe Asn
945                950                955                960

Asn Thr Phe Phe Glu Val Lys Ser Ile Ser Asn Gln Val Trp Lys Phe
                965                970                975

Gln Arg Tyr Gln Leu Ile Met Thr Phe His Glu Arg Pro Val Leu Pro
                980                985                990

Pro Pro Leu Ile Ile Phe Ser His Met Thr Met Ile Phe Gln His Leu
                995                1000               1005

Cys Cys Arg Trp Arg Lys His Glu Ser Asp Pro Asp Glu Arg Asp
    1010               1015               1020

Tyr Gly Leu Lys Leu Phe Ile Thr Asp Asp Glu Leu Lys Lys Val
    1025               1030               1035

His Asp Phe Glu Glu Gln Cys Ile Glu Glu Tyr Phe Arg Glu Lys
    1040               1045               1050

Asp Asp Arg Phe Asn Ser Ser Asn Asp Glu Arg Ile Arg Val Thr
    1055               1060               1065

Ser Glu Arg Val Glu Asn Met Ser Met Arg Leu Glu Glu Val Asn
    1070               1075               1080

Glu Arg Glu His Ser Met Lys Ala Ser Leu Gln Thr Val Asp Ile
    1085               1090               1095

Arg Leu Ala Gln Leu Glu Asp Leu Ile Gly Arg Met Ala Thr Ala
    1100               1105               1110
```

-continued

```
Leu Glu Arg Leu Thr Gly Leu Glu Arg Ala Glu Ser Asn Lys Ile
    1115                1120                1125

Arg Ser Arg Thr Ser Ser Asp Cys Thr Asp Ala Ala Tyr Ile Val
    1130                1135                1140

Arg Gln Ser Ser Phe Asn Ser Gln Glu Gly Asn Thr Phe Lys Leu
    1145                1150                1155

Gln Glu Ser Ile Asp Pro Ala Gly Glu Glu Thr Met Ser Pro Thr
    1160                1165                1170

Ser Pro Thr Leu Met Pro Arg Met Arg Ser His Ser Phe Tyr Ser
    1175                1180                1185

Val Asn Met Lys Asp Lys Gly Gly Ile Glu Lys Leu Glu Ser Ile
    1190                1195                1200

Phe Lys Glu Arg Ser Leu Leu His Arg Ala Thr Ser Ser His
    1205                1210                1215

Ser Val Ala Lys Glu Pro Lys Ala Pro Ala Ala Pro Ala Asn Thr
    1220                1225                1230

Leu Ala Ile Val Pro Asp Ser Arg Arg Pro Ser Ser Cys Ile Asp
    1235                1240                1245

Ile Tyr Val Ser Ala Met Asp Glu Leu His Cys Asp Ile Asp Pro
    1250                1255                1260

Leu Asp Asn Ser Val Asn Ile Leu Gly Leu Gly Glu Pro Ser Phe
    1265                1270                1275

Ser Thr Pro Val Pro Ser Thr Ala Pro Ser Ser Ala Tyr Ala
    1280                1285                1290

Thr Leu Ala Pro Thr Asp Arg Pro Pro Ser Arg Ser Ile Asp Phe
    1295                1300                1305

Glu Asp Ile Thr Ser Met Asp Thr Arg Ser Phe Ser Ser Asp Tyr
    1310                1315                1320

Thr His Leu Pro Glu Cys Gln Asn Pro Trp Asp Ser Glu Pro Pro
    1325                1330                1335

Met Tyr His Thr Ile Glu Arg Ser Lys Ser Ser Arg Tyr Leu Ala
    1340                1345                1350

Thr Thr Pro Phe Leu Leu Glu Glu Ala Pro Ile Val Lys Ser His
    1355                1360                1365

Ser Phe Met Phe Ser Pro Ser Arg Ser Tyr Tyr Ala Asn Phe Gly
    1370                1375                1380

Val Pro Val Lys Thr Ala Glu Tyr Thr Ser Ile Thr Asp Cys Ile
    1385                1390                1395

Asp Thr Arg Cys Val Asn Ala Pro Gln Ala Ile Ala Asp Arg Ala
    1400                1405                1410

Ala Phe Pro Gly Gly Leu Gly Asp Lys Val Glu Asp Leu Thr Cys
    1415                1420                1425

Cys His Pro Glu Arg Glu Ala Glu Leu Ser His Pro Ser Ser Asp
    1430                1435                1440

Ser Glu Glu Asn Glu Ala Lys Gly Arg Arg Ala Thr Ile Ala Ile
    1445                1450                1455

Ser Ser Gln Glu Gly Asp Asn Ser Glu Arg Thr Leu Ser Asn Asn
    1460                1465                1470

Ile Thr Val Pro Lys Ile Glu Arg Ala Asn Ser Tyr Ser Ala Glu
    1475                1480                1485

Glu Pro Ser Ala Pro Tyr Ala His Thr Arg Lys Ser Phe Ser Ile
    1490                1495                1500
```

| | | | | | | | | | | | |
|---|---|---|---|---|---|---|---|---|---|---|---|
| Ser | Asp | Lys | Leu | Asp | Arg | Gln | Arg | Asn | Thr | Ala | Ser | Leu | Gln | Asn |
| | 1505 | | | | 1510 | | | | 1515 | | |

Pro Phe Gln Arg Ser Lys Ser Ser Lys Pro Glu Gly Arg Gly Asp
    1520                1525                1530

Ser Leu Ser Met Arg Arg Leu Ser Arg Thr Ser Ala Phe Gln Ser
    1535                1540                1545

Phe Glu Ser Lys His Thr
    1550

<210> SEQ ID NO 3
<211> LENGTH: 4701
<212> TYPE: DNA
<213> ORGANISM: Homo sapiens
<220> FEATURE:
<221> NAME/KEY: CDS
<222> LOCATION: (1)..(4698)

<400> SEQUENCE: 3

```
atg tat gtg cga gta tct ttt gat aca aaa cct gat ctc ctc tta cac      48
Met Tyr Val Arg Val Ser Phe Asp Thr Lys Pro Asp Leu Leu Leu His
1               5                   10                  15 ctg atg acc aag gaa tgg cag ttg gag ctt ccc aag ctt ctc atc tct      96
Leu Met Thr Lys Glu Trp Gln Leu Glu Leu Pro Lys Leu Leu Ile Ser
            20                  25                  30 gtc cat ggg ggc ctg cag aac ttt gaa ctc cag cca aaa ctc aag caa     144
Val His Gly Gly Leu Gln Asn Phe Glu Leu Gln Pro Lys Leu Lys Gln
        35                  40                  45 gtc ttt ggg aaa ggg ctc atc aaa gca gca atg aca act gga gcg tgg     192
Val Phe Gly Lys Gly Leu Ile Lys Ala Ala Met Thr Thr Gly Ala Trp
    50                  55                  60 ata ttc act gga ggg gtt aac aca ggt gtt att cgt cat gtt ggc gat     240
Ile Phe Thr Gly Gly Val Asn Thr Gly Val Ile Arg His Val Gly Asp
65                  70                  75                  80 gcc ttg aag gat cat gcc tct aag tct cga gga aag ata tgc acc ata     288
Ala Leu Lys Asp His Ala Ser Lys Ser Arg Gly Lys Ile Cys Thr Ile
                85                  90                  95 ggt att gcc ccc tgg gga att gtg gaa aac cag gag gac ctc att gga     336
Gly Ile Ala Pro Trp Gly Ile Val Glu Asn Gln Glu Asp Leu Ile Gly
            100                 105                 110 aga gat gtt gtc cgg cca tac cag acc atg tcc aat ccc atg agc aag     384
Arg Asp Val Val Arg Pro Tyr Gln Thr Met Ser Asn Pro Met Ser Lys
        115                 120                 125 ctc act gtt ctc aac agc atg cat tcc cac ttc att ctg gct gac aac     432
Leu Thr Val Leu Asn Ser Met His Ser His Phe Ile Leu Ala Asp Asn
    130                 135                 140 ggg acc act gga aaa tat gga gca gag gtg aaa ctt cga aga caa ctg     480
Gly Thr Thr Gly Lys Tyr Gly Ala Glu Val Lys Leu Arg Arg Gln Leu
145                 150                 155                 160 gaa aag cat att tca ctc cag aag ata aac aca aga atc ggt caa ggt     528
Glu Lys His Ile Ser Leu Gln Lys Ile Asn Thr Arg Ile Gly Gln Gly
                165                 170                 175 gtt cct gtg gtg gca ctc ata gtg gaa gga gga ccc aat gtg atc tcg     576
Val Pro Val Val Ala Leu Ile Val Glu Gly Gly Pro Asn Val Ile Ser
            180                 185                 190 att gtt ttg gag tac ctt cga gac acc cct ccc gtg cca gtg gtt gtc     624
Ile Val Leu Glu Tyr Leu Arg Asp Thr Pro Pro Val Pro Val Val Val
        195                 200                 205 tgt gat ggg agt gga cgg gca tcg gac atc ctg gcc ttt ggg cat aaa     672
Cys Asp Gly Ser Gly Arg Ala Ser Asp Ile Leu Ala Phe Gly His Lys
    210                 215                 220
```

-continued

| | | |
|---|---|---|
| tac tca gaa gaa ggc gga ctg ata aat gaa tct ttg agg gac cag ctg<br>Tyr Ser Glu Glu Gly Gly Leu Ile Asn Glu Ser Leu Arg Asp Gln Leu<br>225                    230                    235                    240 | 720 |
| ttg gtg act ata cag aag act ttc aca tac act cga acc caa gct cag<br>Leu Val Thr Ile Gln Lys Thr Phe Thr Tyr Thr Arg Thr Gln Ala Gln<br>                245                    250                    255 | 768 |
| cat ctg ttc atc atc ctc atg gag tgc atg aag aag aag gaa ttg att<br>His Leu Phe Ile Ile Leu Met Glu Cys Met Lys Lys Lys Glu Leu Ile<br>            260                    265                    270 | 816 |
| acg gta ttt cgg atg gga tca gaa gga cac cag gac att gat ttg gct<br>Thr Val Phe Arg Met Gly Ser Glu Gly His Gln Asp Ile Asp Leu Ala<br>                275                    280                    285 | 864 |
| atc ctg aca gct tta ctc aaa gga gcc aat gcc tcg gcc cca gac caa<br>Ile Leu Thr Ala Leu Leu Lys Gly Ala Asn Ala Ser Ala Pro Asp Gln<br>290                    295                    300 | 912 |
| ctg agc tta gct tta gcc tgg aac aga gtc gac atc gct cgc agc cag<br>Leu Ser Leu Ala Leu Ala Trp Asn Arg Val Asp Ile Ala Arg Ser Gln<br>305                    310                    315                    320 | 960 |
| atc ttt att tac ggg caa cag tgg ccg gtg gga tct ctg gag caa gcc<br>Ile Phe Ile Tyr Gly Gln Gln Trp Pro Val Gly Ser Leu Glu Gln Ala<br>                325                    330                    335 | 1008 |
| atg ttg gat gcc tta gtt ctg gac aga gtg gat ttt gtg aaa tta ctc<br>Met Leu Asp Ala Leu Val Leu Asp Arg Val Asp Phe Val Lys Leu Leu<br>            340                    345                    350 | 1056 |
| ata gag aat gga gta agc atg cac cgt ttt ctc acc atc tcc aga cta<br>Ile Glu Asn Gly Val Ser Met His Arg Phe Leu Thr Ile Ser Arg Leu<br>                355                    360                    365 | 1104 |
| gag gaa ttg tac aat acg aga cat ggg ccc tca aat aca ttg tac cac<br>Glu Glu Leu Tyr Asn Thr Arg His Gly Pro Ser Asn Thr Leu Tyr His<br>370                    375                    380 | 1152 |
| ttg gtc agg gat gtc aaa aag cga gag tat cca ggt ttc ggt tgg atc<br>Leu Val Arg Asp Val Lys Lys Arg Glu Tyr Pro Gly Phe Gly Trp Ile<br>385                    390                    395                    400 | 1200 |
| tat ttt aag ggg aac ctg ccc cca gac tac aga atc agc ctg att gac<br>Tyr Phe Lys Gly Asn Leu Pro Pro Asp Tyr Arg Ile Ser Leu Ile Asp<br>                    405                    410                    415 | 1248 |
| atc ggc ctg gtg atc gag tac ctg atg ggc ggg gct tat cgc tgc aac<br>Ile Gly Leu Val Ile Glu Tyr Leu Met Gly Gly Ala Tyr Arg Cys Asn<br>            420                    425                    430 | 1296 |
| tac acg cgc aag cgc ttc cgg acc ctc tac cac aac ctc ttc ggc ccc<br>Tyr Thr Arg Lys Arg Phe Arg Thr Leu Tyr His Asn Leu Phe Gly Pro<br>                435                    440                    445 | 1344 |
| aag agg ccc aaa gcc ttg aaa ctg ctg gga atg gag gat gat att ccc<br>Lys Arg Pro Lys Ala Leu Lys Leu Leu Gly Met Glu Asp Asp Ile Pro<br>450                    455                    460 | 1392 |
| ttg agg cga gga aga aag aca acc aag aaa cgt gaa gaa gag gtg gac<br>Leu Arg Arg Gly Arg Lys Thr Thr Lys Lys Arg Glu Glu Glu Val Asp<br>465                    470                    475                    480 | 1440 |
| att gac ttg gat gat cct gag atc aac cac ttc ccc ttc cct ttc cat<br>Ile Asp Leu Asp Asp Pro Glu Ile Asn His Phe Pro Phe Pro Phe His<br>                    485                    490                    495 | 1488 |
| gag ctc atg gtg tgg gct gtt ctc atg aag cgg cag aag atg gcc ctg<br>Glu Leu Met Val Trp Ala Val Leu Met Lys Arg Gln Lys Met Ala Leu<br>            500                    505                    510 | 1536 |
| ttc ttc tgg cag cac ggt gag gag gcc atg gcc aag gcc ctg gtg gcc<br>Phe Phe Trp Gln His Gly Glu Glu Ala Met Ala Lys Ala Leu Val Ala<br>                515                    520                    525 | 1584 |
| tgc aag ctc tgc aaa gcc atg gct cat gag gcc tct gag aac gac atg<br>Cys Lys Leu Cys Lys Ala Met Ala His Glu Ala Ser Glu Asn Asp Met<br>530                    535                    540 | 1632 |

```
gtt gac gac att tcc cag gag ctg aat cac aat tcc aga gac ttt ggc      1680
Val Asp Asp Ile Ser Gln Glu Leu Asn His Asn Ser Arg Asp Phe Gly
545                 550                 555                 560 cag ctg gct gtg gag ctc ctg gac cag tcc tac aag cag gac gaa cag      1728
Gln Leu Ala Val Glu Leu Leu Asp Gln Ser Tyr Lys Gln Asp Glu Gln
                565                 570                 575 ctg gcc atg aaa ctg ctg acg tat gag ctg aag aac tgg agc aac gcc      1776
Leu Ala Met Lys Leu Leu Thr Tyr Glu Leu Lys Asn Trp Ser Asn Ala
            580                 585                 590 acg tgc ctg cag ctt gcc gtg gct gcc aaa cac cgc gac ttc atc gcg      1824
Thr Cys Leu Gln Leu Ala Val Ala Ala Lys His Arg Asp Phe Ile Ala
        595                 600                 605 cac acg tgc agc cag atg ctg ctc acc gac atg tgg atg ggc cgg ctc      1872
His Thr Cys Ser Gln Met Leu Leu Thr Asp Met Trp Met Gly Arg Leu
    610                 615                 620 cgc atg cgc aag aac tca ggc ctc aag gta att ctg gga att cta ctt      1920
Arg Met Arg Lys Asn Ser Gly Leu Lys Val Ile Leu Gly Ile Leu Leu
625                 630                 635                 640 cct cct tca att ctc agc ttg gag ttc aag aac aaa gac gac atg ccc      1968
Pro Pro Ser Ile Leu Ser Leu Glu Phe Lys Asn Lys Asp Asp Met Pro
                645                 650                 655 tat atg tct cag gcc cag gaa atc cac ctc caa gag aag gag gca gaa      2016
Tyr Met Ser Gln Ala Gln Glu Ile His Leu Gln Glu Lys Glu Ala Glu
            660                 665                 670 gaa cca gag aag ccc aca aag gaa aaa gag gaa gag gac atg gag ctc      2064
Glu Pro Glu Lys Pro Thr Lys Glu Lys Glu Glu Glu Asp Met Glu Leu
        675                 680                 685 aca gca atg ttg gga cga aac aac ggg gag tcc tcc agg aag aag gat      2112
Thr Ala Met Leu Gly Arg Asn Asn Gly Glu Ser Ser Arg Lys Lys Asp
    690                 695                 700 gaa gag gaa gtt cag agc aag cac cgg tta atc ccc ctc ggc aga aaa      2160
Glu Glu Glu Val Gln Ser Lys His Arg Leu Ile Pro Leu Gly Arg Lys
705                 710                 715                 720 atc tat gaa ttc tac aat gca ccc atc gtg aag ttc tgg ttc tac aca      2208
Ile Tyr Glu Phe Tyr Asn Ala Pro Ile Val Lys Phe Trp Phe Tyr Thr
                725                 730                 735 ctg gcg tat atc gga tac ctg atg ctc ttc aac tat atc gtg tta gtg      2256
Leu Ala Tyr Ile Gly Tyr Leu Met Leu Phe Asn Tyr Ile Val Leu Val
            740                 745                 750 aag atg gaa cgc tgg ccg tcc acc cag gaa tgg atc gta atc tcc tat      2304
Lys Met Glu Arg Trp Pro Ser Thr Gln Glu Trp Ile Val Ile Ser Tyr
        755                 760                 765 att ttc acc ctg gga ata gaa aag atg aga gag att ctg atg tca gag      2352
Ile Phe Thr Leu Gly Ile Glu Lys Met Arg Glu Ile Leu Met Ser Glu
    770                 775                 780 cca ggg aag ttg cta cag aaa gtg aag gta tgg ctg cag gag tac tgg      2400
Pro Gly Lys Leu Leu Gln Lys Val Lys Val Trp Leu Gln Glu Tyr Trp
785                 790                 795                 800 aat gtc acg gac ctc atc gcc atc ctt ctg ttt tct gtc gga atg atc      2448
Asn Val Thr Asp Leu Ile Ala Ile Leu Leu Phe Ser Val Gly Met Ile
                805                 810                 815 ctt cgt ctc caa gac cag ccc ttc agg agt gac ggg agg gtc atc tac      2496
Leu Arg Leu Gln Asp Gln Pro Phe Arg Ser Asp Gly Arg Val Ile Tyr
            820                 825                 830 tgc gtg aac atc att tac tgg tat atc cgt ctc cta gac atc ttc ggc      2544
Cys Val Asn Ile Ile Tyr Trp Tyr Ile Arg Leu Leu Asp Ile Phe Gly
        835                 840                 845 gtg aac aag tat ttg ggc ccg tat gta atg atg att gga aaa atg atg      2592
Val Asn Lys Tyr Leu Gly Pro Tyr Val Met Met Ile Gly Lys Met Met
```

-continued

| | | |
|---|---|---|
| 850 | 855 | 860 |

| | |
|---|---|
| ata gac atg atg tac ttt gtc atc att atg ctg gtg gtt ctg atg agc<br>Ile Asp Met Met Tyr Phe Val Ile Ile Met Leu Val Val Leu Met Ser<br>865                         870                       875                   880 | 2640 |
| ttt ggg gtc gcc agg caa gcc atc ctt ttt ccc aat gag gag cca tca<br>Phe Gly Val Ala Arg Gln Ala Ile Leu Phe Pro Asn Glu Glu Pro Ser<br>                    885                       890                       895 | 2688 |
| tgg aaa ctg gcc aag aac atc ttc tac atg ccc tat tgg atg att tat<br>Trp Lys Leu Ala Lys Asn Ile Phe Tyr Met Pro Tyr Trp Met Ile Tyr<br>                900                       905                      910 | 2736 |
| ggg gaa gtg ttt gcg gac cag ata gac cct ccc tgt gga cag aat gag<br>Gly Glu Val Phe Ala Asp Gln Ile Asp Pro Pro Cys Gly Gln Asn Glu<br>             915                       920                    925 | 2784 |
| acc cga gag gat ggt aaa ata atc cag ctg cct ccc tgc aag aca gga<br>Thr Arg Glu Asp Gly Lys Ile Ile Gln Leu Pro Pro Cys Lys Thr Gly<br>930                         935                       940 | 2832 |
| gct tgg atc gtg ccg gcc atc atg gcc tgc tac ctc tta gtg gca aac<br>Ala Trp Ile Val Pro Ala Ile Met Ala Cys Tyr Leu Leu Val Ala Asn<br>945                         950                       955                    960 | 2880 |
| atc ttg ctg gtc aac ctc ctc att gct gtc ttt aac aat aca ttt ttt<br>Ile Leu Leu Val Asn Leu Leu Ile Ala Val Phe Asn Asn Thr Phe Phe<br>                965                       970                      975 | 2928 |
| gaa gta aaa tcg ata tcc aac caa gtc tgg aag ttt cag agg tat cag<br>Glu Val Lys Ser Ile Ser Asn Gln Val Trp Lys Phe Gln Arg Tyr Gln<br>             980                       985                    990 | 2976 |
| ctc atc atg act ttc cat gaa agg  cca gtt ctg ccc cca  cca ctg atc<br>Leu Ile Met Thr Phe His Glu Arg  Pro Val Leu Pro Pro  Pro Leu Ile<br>          995                      1000                    1005 | 3024 |
| atc ttc agc cac atg acc atg  ata ttc cag cac ctg  tgc tgc cga<br>Ile Phe Ser His Met Thr Met  Ile Phe Gln His Leu  Cys Cys Arg<br>         1010                      1015                    1020 | 3069 |
| tgg agg aaa cac gag agc gac  ccg gat gaa agg gac  tac ggc ctg<br>Trp Arg Lys His Glu Ser Asp  Pro Asp Glu Arg Asp  Tyr Gly Leu<br>         1025                      1030                    1035 | 3114 |
| aaa ctc ttc ata acc gat gat  gag ctc aag aaa gta  cat gac ttt<br>Lys Leu Phe Ile Thr Asp Asp  Glu Leu Lys Lys Val  His Asp Phe<br>         1040                      1045                    1050 | 3159 |
| gaa gag caa tgc ata gaa gaa  tac ttc aga gaa aag  gat gat cgg<br>Glu Glu Gln Cys Ile Glu Glu  Tyr Phe Arg Glu Lys  Asp Asp Arg<br>         1055                      1060                    1065 | 3204 |
| ttc aac tca tct aat gat gag  agg ata cgg gtg act  tca gaa agg<br>Phe Asn Ser Ser Asn Asp Glu  Arg Ile Arg Val Thr  Ser Glu Arg<br>         1070                      1075                    1080 | 3249 |
| gtg gag aac atg tct atg cgg  ctg gag gaa gtc aac  gag aga gag<br>Val Glu Asn Met Ser Met Arg  Leu Glu Glu Val Asn  Glu Arg Glu<br>         1085                      1090                    1095 | 3294 |
| cac tcc atg aag gct tca ctc  cag acc gtg gac atc  cgg ctg gcg<br>His Ser Met Lys Ala Ser Leu  Gln Thr Val Asp Ile  Arg Leu Ala<br>         1100                      1105                    1110 | 3339 |
| cag ctg gaa gac ctt atc ggg  cgc atg gcc acg gcc  ctg gag cgc<br>Gln Leu Glu Asp Leu Ile Gly  Arg Met Ala Thr Ala  Leu Glu Arg<br>         1115                      1120                    1125 | 3384 |
| ctg aca ggt ctg gag cgg gcc  gag tcc aac aaa atc  cgc tcg agg<br>Leu Thr Gly Leu Glu Arg Ala  Glu Ser Asn Lys Ile  Arg Ser Arg<br>         1130                      1135                    1140 | 3429 |
| acc tcg tca gac tgc acg gac  gcc gcc tac att gtc  cgt cag agc<br>Thr Ser Ser Asp Cys Thr Asp  Ala Ala Tyr Ile Val  Arg Gln Ser<br>         1145                      1150                    1155 | 3474 |
| agc ttc aac agc cag gaa ggg  aac acc ttc aag ctc  caa gag agt<br>| 3519 |

```
Ser Phe Asn Ser Gln Glu Gly Asn Thr Phe Lys Leu Gln Glu Ser
    1160            1165                1170 ata gac cct gca ggt gag gag acc atg tcc cca act tct cca acc         3564
Ile Asp Pro Ala Gly Glu Glu Thr Met Ser Pro Thr Ser Pro Thr
    1175            1180                1185 tta atg ccc cgt atg cga agc cat tct ttc tat tca gtc aat atg         3609
Leu Met Pro Arg Met Arg Ser His Ser Phe Tyr Ser Val Asn Met
    1190            1195                1200 aaa gac aaa ggt ggt ata gaa aag ttg gaa agt att ttt aaa gaa         3654
Lys Asp Lys Gly Gly Ile Glu Lys Leu Glu Ser Ile Phe Lys Glu
    1205            1210                1215 agg tcc ctg agc cta cac cgg gct act agt tcc cac tct gta gca         3699
Arg Ser Leu Ser Leu His Arg Ala Thr Ser Ser His Ser Val Ala
    1220            1225                1230 aaa gaa ccc aaa gct cct gca gcc cct gcc aac acc ttg gcc att         3744
Lys Glu Pro Lys Ala Pro Ala Ala Pro Ala Asn Thr Leu Ala Ile
    1235            1240                1245 gtt cct gat tcc aga aga cca tca tcg tgt ata gac atc tat gtc         3789
Val Pro Asp Ser Arg Arg Pro Ser Ser Cys Ile Asp Ile Tyr Val
    1250            1255                1260 tct gct atg gat gag ctc cac tgt gat ata gac cct ctg gac aat         3834
Ser Ala Met Asp Glu Leu His Cys Asp Ile Asp Pro Leu Asp Asn
    1265            1270                1275 tcc gtg aac atc ctt ggg cta ggc gag cca agc ttt tca act cca         3879
Ser Val Asn Ile Leu Gly Leu Gly Glu Pro Ser Phe Ser Thr Pro
    1280            1285                1290 gta cct tcc aca gcc cct tca agt agt gcc tat gca aca ctt gca         3924
Val Pro Ser Thr Ala Pro Ser Ser Ser Ala Tyr Ala Thr Leu Ala
    1295            1300                1305 ccc aca gac aga cct cca agc cgg agc att gat ttt gag gac atc         3969
Pro Thr Asp Arg Pro Pro Ser Arg Ser Ile Asp Phe Glu Asp Ile
    1310            1315                1320 acc tcc atg gac act aga tct ttt tct tca gac tac acc cac ctc         4014
Thr Ser Met Asp Thr Arg Ser Phe Ser Ser Asp Tyr Thr His Leu
    1325            1330                1335 cca gaa tgc caa aac ccc tgg gac tca gag cct ccg atg tac cac         4059
Pro Glu Cys Gln Asn Pro Trp Asp Ser Glu Pro Pro Met Tyr His
    1340            1345                1350 acc att gag cgt tcc aaa agt agc cgc tac cta gcc acc aca ccc         4104
Thr Ile Glu Arg Ser Lys Ser Ser Arg Tyr Leu Ala Thr Thr Pro
    1355            1360                1365 ttt ctt cta gaa gag gct ccc att gtg aaa tct cat agc ttt atg         4149
Phe Leu Leu Glu Glu Ala Pro Ile Val Lys Ser His Ser Phe Met
    1370            1375                1380 ttt tcc ccc tca agg agc tat tat gcc aac ttt ggg gtg cct gta         4194
Phe Ser Pro Ser Arg Ser Tyr Tyr Ala Asn Phe Gly Val Pro Val
    1385            1390                1395 aaa aca gca gaa tac aca agt att aca gac tgt att gac aca agg         4239
Lys Thr Ala Glu Tyr Thr Ser Ile Thr Asp Cys Ile Asp Thr Arg
    1400            1405                1410 tgt gtc aat gcc cct caa gca att gcg gac aga gct gcc ttc cct         4284
Cys Val Asn Ala Pro Gln Ala Ile Ala Asp Arg Ala Ala Phe Pro
    1415            1420                1425 gga ggt ctt gga gac aaa gtg gag gac tta act tgc tgc cat cca         4329
Gly Gly Leu Gly Asp Lys Val Glu Asp Leu Thr Cys Cys His Pro
    1430            1435                1440 gag cga gaa gca gaa ctg agt cac ccc agc tct gac agt gag gag         4374
Glu Arg Glu Ala Glu Leu Ser His Pro Ser Ser Asp Ser Glu Glu
    1445            1450                1455
```

```
aat gag gcc aaa ggc cgc aga gcc acc att gca ata tcc tcc cag      4419
Asn Glu Ala Lys Gly Arg Arg Ala Thr Ile Ala Ile Ser Ser Gln
    1460                1465                1470 gag ggt gat aac tca gag aga acc ctg tcc aac aac atc act gtt      4464
Glu Gly Asp Asn Ser Glu Arg Thr Leu Ser Asn Asn Ile Thr Val
1475                1480                1485 ccc aag ata gag cgc gcc aac agc tac tcg gca gag gag cca agt      4509
Pro Lys Ile Glu Arg Ala Asn Ser Tyr Ser Ala Glu Glu Pro Ser
    1490                1495                1500 gcg cca tat gca cac acc agg aag agc ttc tcc atc agt gac aaa      4554
Ala Pro Tyr Ala His Thr Arg Lys Ser Phe Ser Ile Ser Asp Lys
1505                1510                1515 ctc gac agg cag cgg aac aca gca agc ctg caa aat ccc ttc cag      4599
Leu Asp Arg Gln Arg Asn Thr Ala Ser Leu Gln Asn Pro Phe Gln
    1520                1525                1530 aga agc aag tcc tcc aag ccg gag ggc cga ggg gac agc ctg tcc      4644
Arg Ser Lys Ser Ser Lys Pro Glu Gly Arg Gly Asp Ser Leu Ser
1535                1540                1545 atg agg aga ctg tcc aga aca tcg gct ttc caa agc ttt gaa agc      4689
Met Arg Arg Leu Ser Arg Thr Ser Ala Phe Gln Ser Phe Glu Ser
    1550                1555                1560 aag cac acc taa                                                  4701
Lys His Thr
1565

<210> SEQ ID NO 4
<211> LENGTH: 1566
<212> TYPE: PRT
<213> ORGANISM: Homo sapiens

<400> SEQUENCE: 4

Met Tyr Val Arg Val Ser Phe Asp Thr Lys Pro Asp Leu Leu His
1               5                   10                  15

Leu Met Thr Lys Glu Trp Gln Leu Glu Leu Pro Lys Leu Leu Ile Ser
            20                  25                  30

Val His Gly Gly Leu Gln Asn Phe Glu Leu Gln Pro Lys Leu Lys Gln
        35                  40                  45

Val Phe Gly Lys Gly Leu Ile Lys Ala Ala Met Thr Thr Gly Ala Trp
    50                  55                  60

Ile Phe Thr Gly Gly Val Asn Thr Gly Val Ile Arg His Val Gly Asp
65                  70                  75                  80

Ala Leu Lys Asp His Ala Ser Lys Ser Arg Gly Lys Ile Cys Thr Ile
                85                  90                  95

Gly Ile Ala Pro Trp Gly Ile Val Glu Asn Gln Glu Asp Leu Ile Gly
            100                 105                 110

Arg Asp Val Val Arg Pro Tyr Gln Thr Met Ser Asn Pro Met Ser Lys
        115                 120                 125

Leu Thr Val Leu Asn Ser Met His Ser His Phe Ile Leu Ala Asp Asn
    130                 135                 140

Gly Thr Thr Gly Lys Tyr Gly Ala Glu Val Lys Leu Arg Arg Gln Leu
145                 150                 155                 160

Glu Lys His Ile Ser Leu Gln Lys Ile Asn Thr Arg Ile Gly Gln Gly
                165                 170                 175

Val Pro Val Val Ala Leu Ile Val Glu Gly Gly Pro Asn Val Ile Ser
            180                 185                 190

Ile Val Leu Glu Tyr Leu Arg Asp Thr Pro Pro Val Pro Val Val Val
        195                 200                 205
```

-continued

```
Cys Asp Gly Ser Gly Arg Ala Ser Asp Ile Leu Ala Phe Gly His Lys
    210                 215                 220

Tyr Ser Glu Glu Gly Gly Leu Ile Asn Glu Ser Leu Arg Asp Gln Leu
225                 230                 235                 240

Leu Val Thr Ile Gln Lys Thr Phe Thr Tyr Thr Arg Thr Gln Ala Gln
                245                 250                 255

His Leu Phe Ile Ile Leu Met Glu Cys Met Lys Lys Lys Glu Leu Ile
                260                 265                 270

Thr Val Phe Arg Met Gly Ser Glu Gly His Gln Asp Ile Asp Leu Ala
                275                 280                 285

Ile Leu Thr Ala Leu Leu Lys Gly Ala Asn Ala Ser Ala Pro Asp Gln
    290                 295                 300

Leu Ser Leu Ala Leu Ala Trp Asn Arg Val Asp Ile Ala Arg Ser Gln
305                 310                 315                 320

Ile Phe Ile Tyr Gly Gln Gln Trp Pro Val Gly Ser Leu Glu Gln Ala
                325                 330                 335

Met Leu Asp Ala Leu Val Leu Asp Arg Val Asp Phe Val Lys Leu Leu
                340                 345                 350

Ile Glu Asn Gly Val Ser Met His Arg Phe Leu Thr Ile Ser Arg Leu
                355                 360                 365

Glu Glu Leu Tyr Asn Thr Arg His Gly Pro Ser Asn Thr Leu Tyr His
370                 375                 380

Leu Val Arg Asp Val Lys Lys Arg Glu Tyr Pro Gly Phe Gly Trp Ile
385                 390                 395                 400

Tyr Phe Lys Gly Asn Leu Pro Pro Asp Tyr Arg Ile Ser Leu Ile Asp
                405                 410                 415

Ile Gly Leu Val Ile Glu Tyr Leu Met Gly Gly Ala Tyr Arg Cys Asn
                420                 425                 430

Tyr Thr Arg Lys Arg Phe Arg Thr Leu Tyr His Asn Leu Phe Gly Pro
                435                 440                 445

Lys Arg Pro Lys Ala Leu Lys Leu Leu Gly Met Glu Asp Asp Ile Pro
    450                 455                 460

Leu Arg Arg Gly Arg Lys Thr Thr Lys Lys Arg Glu Glu Glu Val Asp
465                 470                 475                 480

Ile Asp Leu Asp Asp Pro Glu Ile Asn His Phe Pro Phe Pro Phe His
                485                 490                 495

Glu Leu Met Val Trp Ala Val Leu Met Lys Arg Gln Lys Met Ala Leu
                500                 505                 510

Phe Phe Trp Gln His Gly Glu Glu Ala Met Ala Lys Ala Leu Val Ala
    515                 520                 525

Cys Lys Leu Cys Lys Ala Met Ala His Glu Ala Ser Glu Asn Asp Met
530                 535                 540

Val Asp Asp Ile Ser Gln Glu Leu Asn His Asn Ser Arg Asp Phe Gly
545                 550                 555                 560

Gln Leu Ala Val Glu Leu Leu Asp Gln Ser Tyr Lys Gln Asp Glu Gln
                565                 570                 575

Leu Ala Met Lys Leu Leu Thr Tyr Glu Leu Lys Asn Trp Ser Asn Ala
                580                 585                 590

Thr Cys Leu Gln Leu Ala Val Ala Ala Lys His Arg Asp Phe Ile Ala
    595                 600                 605

His Thr Cys Ser Gln Met Leu Leu Thr Asp Met Trp Met Gly Arg Leu
    610                 615                 620

Arg Met Arg Lys Asn Ser Gly Leu Lys Val Ile Leu Gly Ile Leu Leu
```

```
                625               630               635               640
Pro Pro Ser Ile Leu Ser Leu Glu Phe Lys Asn Lys Asp Asp Met Pro
                645               650               655

Tyr Met Ser Gln Ala Gln Glu Ile His Leu Gln Glu Lys Glu Ala Glu
                660               665               670

Glu Pro Glu Lys Pro Thr Lys Glu Lys Glu Glu Asp Met Glu Leu
                675               680               685

Thr Ala Met Leu Gly Arg Asn Asn Gly Glu Ser Ser Arg Lys Lys Asp
                690               695               700

Glu Glu Glu Val Gln Ser Lys His Arg Leu Ile Pro Leu Gly Arg Lys
705               710               715               720

Ile Tyr Glu Phe Tyr Asn Ala Pro Ile Val Lys Phe Trp Phe Tyr Thr
                725               730               735

Leu Ala Tyr Ile Gly Tyr Leu Met Leu Phe Asn Tyr Ile Val Leu Val
                740               745               750

Lys Met Glu Arg Trp Pro Ser Thr Gln Glu Trp Ile Val Ile Ser Tyr
                755               760               765

Ile Phe Thr Leu Gly Ile Glu Lys Met Arg Glu Ile Leu Met Ser Glu
                770               775               780

Pro Gly Lys Leu Leu Gln Lys Val Lys Val Trp Leu Gln Glu Tyr Trp
785               790               795               800

Asn Val Thr Asp Leu Ile Ala Ile Leu Leu Phe Ser Val Gly Met Ile
                805               810               815

Leu Arg Leu Gln Asp Gln Pro Phe Arg Ser Asp Gly Arg Val Ile Tyr
                820               825               830

Cys Val Asn Ile Ile Tyr Trp Tyr Ile Arg Leu Leu Asp Ile Phe Gly
                835               840               845

Val Asn Lys Tyr Leu Gly Pro Tyr Val Met Met Ile Gly Lys Met Met
850               855               860

Ile Asp Met Met Tyr Phe Val Ile Ile Met Leu Val Val Leu Met Ser
865               870               875               880

Phe Gly Val Ala Arg Gln Ala Ile Leu Phe Pro Asn Glu Glu Pro Ser
                885               890               895

Trp Lys Leu Ala Lys Asn Ile Phe Tyr Met Pro Tyr Trp Met Ile Tyr
                900               905               910

Gly Glu Val Phe Ala Asp Gln Ile Asp Pro Pro Cys Gly Gln Asn Glu
                915               920               925

Thr Arg Glu Asp Gly Lys Ile Ile Gln Leu Pro Pro Cys Lys Thr Gly
                930               935               940

Ala Trp Ile Val Pro Ala Ile Met Ala Cys Tyr Leu Leu Val Ala Asn
945               950               955               960

Ile Leu Leu Val Asn Leu Leu Ile Ala Val Phe Asn Asn Thr Phe Phe
                965               970               975

Glu Val Lys Ser Ile Ser Asn Gln Val Trp Lys Phe Gln Arg Tyr Gln
                980               985               990

Leu Ile Met Thr Phe His Glu Arg Pro Val Leu Pro Pro Pro Leu Ile
                995               1000              1005

Ile Phe Ser His Met Thr Met Ile Phe Gln His Leu Cys Cys Arg
                1010              1015              1020

Trp Arg Lys His Glu Ser Asp Pro Asp Glu Arg Asp Tyr Gly Leu
                1025              1030              1035

Lys Leu Phe Ile Thr Asp Asp Glu Leu Lys Lys Val His Asp Phe
                1040              1045              1050
```

-continued

```
Glu Glu Gln Cys Ile Glu Glu Tyr Phe Arg Glu Lys Asp Asp Arg
    1055                1060                1065

Phe Asn Ser Ser Asn Asp Glu Arg Ile Arg Val Thr Ser Glu Arg
    1070                1075                1080

Val Glu Asn Met Ser Met Arg Leu Glu Glu Val Asn Glu Arg Glu
    1085                1090                1095

His Ser Met Lys Ala Ser Leu Gln Thr Val Asp Ile Arg Leu Ala
    1100                1105                1110

Gln Leu Glu Asp Leu Ile Gly Arg Met Ala Thr Ala Leu Glu Arg
    1115                1120                1125

Leu Thr Gly Leu Glu Arg Ala Glu Ser Asn Lys Ile Arg Ser Arg
    1130                1135                1140

Thr Ser Ser Asp Cys Thr Asp Ala Ala Tyr Ile Val Arg Gln Ser
    1145                1150                1155

Ser Phe Asn Ser Gln Glu Gly Asn Thr Phe Lys Leu Gln Glu Ser
    1160                1165                1170

Ile Asp Pro Ala Gly Glu Glu Thr Met Ser Pro Thr Ser Pro Thr
    1175                1180                1185

Leu Met Pro Arg Met Arg Ser His Ser Phe Tyr Ser Val Asn Met
    1190                1195                1200

Lys Asp Lys Gly Gly Ile Glu Lys Leu Glu Ser Ile Phe Lys Glu
    1205                1210                1215

Arg Ser Leu Ser Leu His Arg Ala Thr Ser Ser His Ser Val Ala
    1220                1225                1230

Lys Glu Pro Lys Ala Pro Ala Ala Pro Ala Asn Thr Leu Ala Ile
    1235                1240                1245

Val Pro Asp Ser Arg Arg Pro Ser Ser Cys Ile Asp Ile Tyr Val
    1250                1255                1260

Ser Ala Met Asp Glu Leu His Cys Asp Ile Asp Pro Leu Asp Asn
    1265                1270                1275

Ser Val Asn Ile Leu Gly Leu Gly Glu Pro Ser Phe Ser Thr Pro
    1280                1285                1290

Val Pro Ser Thr Ala Pro Ser Ser Ala Tyr Ala Thr Leu Ala
    1295                1300                1305

Pro Thr Asp Arg Pro Pro Ser Arg Ser Ile Asp Phe Glu Asp Ile
    1310                1315                1320

Thr Ser Met Asp Thr Arg Ser Phe Ser Ser Asp Tyr Thr His Leu
    1325                1330                1335

Pro Glu Cys Gln Asn Pro Trp Asp Ser Glu Pro Met Tyr His
    1340                1345                1350

Thr Ile Glu Arg Ser Lys Ser Ser Arg Tyr Leu Ala Thr Thr Pro
    1355                1360                1365

Phe Leu Leu Glu Glu Ala Pro Ile Val Lys Ser His Ser Phe Met
    1370                1375                1380

Phe Ser Pro Ser Arg Ser Tyr Tyr Ala Asn Phe Gly Val Pro Val
    1385                1390                1395

Lys Thr Ala Glu Tyr Thr Ser Ile Thr Asp Cys Ile Asp Thr Arg
    1400                1405                1410

Cys Val Asn Ala Pro Gln Ala Ile Ala Asp Arg Ala Ala Phe Pro
    1415                1420                1425

Gly Gly Leu Gly Asp Lys Val Glu Asp Leu Thr Cys Cys His Pro
    1430                1435                1440
```

```
Glu Arg Glu Ala Glu Leu Ser His Pro Ser Ser Asp Ser Glu Glu
    1445                1450                1455

Asn Glu Ala Lys Gly Arg Arg Ala Thr Ile Ala Ile Ser Ser Gln
1460                1465                1470

Glu Gly Asp Asn Ser Glu Arg Thr Leu Ser Asn Asn Ile Thr Val
    1475                1480                1485

Pro Lys Ile Glu Arg Ala Asn Ser Tyr Ser Ala Glu Glu Pro Ser
1490                1495                1500

Ala Pro Tyr Ala His Thr Arg Lys Ser Phe Ser Ile Ser Asp Lys
    1505                1510                1515

Leu Asp Arg Gln Arg Asn Thr Ala Ser Leu Gln Asn Pro Phe Gln
1520                1525                1530

Arg Ser Lys Ser Ser Lys Pro Glu Gly Arg Gly Asp Ser Leu Ser
    1535                1540                1545

Met Arg Arg Leu Ser Arg Thr Ser Ala Phe Gln Ser Phe Glu Ser
1550                1555                1560

Lys His Thr
    1565

<210> SEQ ID NO 5
<211> LENGTH: 4701
<212> TYPE: DNA
<213> ORGANISM: Homo sapiens
<220> FEATURE:
<221> NAME/KEY: CDS
<222> LOCATION: (1)..(4698)

<400> SEQUENCE: 5 atg tat gtg cga gta tct ttt gat aca aaa cct gat ctc ctc tta cac    48
Met Tyr Val Arg Val Ser Phe Asp Thr Lys Pro Asp Leu Leu Leu His
1               5                   10                  15 ctg atg acc aag gaa tgg cag ttg gag ctt ccc aag ctt ctc atc tct    96
Leu Met Thr Lys Glu Trp Gln Leu Glu Leu Pro Lys Leu Leu Ile Ser
            20                  25                  30 gtc cat ggg ggc ctg cag aac ttt gaa ctc cag cca aaa ctc aag caa   144
Val His Gly Gly Leu Gln Asn Phe Glu Leu Gln Pro Lys Leu Lys Gln
        35                  40                  45 gtc ttt ggg aaa ggg ctc atc aaa gca gca atg aca act gga gcg tgg   192
Val Phe Gly Lys Gly Leu Ile Lys Ala Ala Met Thr Thr Gly Ala Trp
    50                  55                  60 ata ttc act gga ggg gtt aac aca ggt gtt att cgt cat gtt ggc gat   240
Ile Phe Thr Gly Gly Val Asn Thr Gly Val Ile Arg His Val Gly Asp
65                  70                  75                  80 gcc ttg aag gat cat gcc tct aag tct cga gga aag ata tgc acc ata   288
Ala Leu Lys Asp His Ala Ser Lys Ser Arg Gly Lys Ile Cys Thr Ile
                85                  90                  95 ggt att gcc ccc tgg gga att gtg gaa aac cag gag gac ctc att gga   336
Gly Ile Ala Pro Trp Gly Ile Val Glu Asn Gln Glu Asp Leu Ile Gly
            100                 105                 110 aga gat gtt gtc cgg cca tac cag acc atg tcc aat ccc atg agc aag   384
Arg Asp Val Val Arg Pro Tyr Gln Thr Met Ser Asn Pro Met Ser Lys
        115                 120                 125 ctc act gtt ctc aac agc atg cat tcc cac ttc att ctg gct gac aac   432
Leu Thr Val Leu Asn Ser Met His Ser His Phe Ile Leu Ala Asp Asn
    130                 135                 140 ggg acc act gga aaa tat gga gca gag gtg aaa ctt cga aga caa ctg   480
Gly Thr Thr Gly Lys Tyr Gly Ala Glu Val Lys Leu Arg Arg Gln Leu
145                 150                 155                 160 gaa aag cat att tca ctc cag aag ata aac aca aga atc ggt caa ggt   528
```

```
Glu Lys His Ile Ser Leu Gln Lys Ile Asn Thr Arg Ile Gly Gln Gly
            165                 170                 175 gtt cct gtg gtg gca ctc ata gtg gaa gga gga ccc aat gtg atc tcg        576
Val Pro Val Val Ala Leu Ile Val Glu Gly Gly Pro Asn Val Ile Ser
            180                 185                 190 att gtt ttg gag tac ctt cga gac acc cct ccc gtg cca gtg gtt gtc        624
Ile Val Leu Glu Tyr Leu Arg Asp Thr Pro Pro Val Pro Val Val Val
            195                 200                 205 tgt gat ggg agt gga cgg gca tcg gac atc ctg gcc ttt ggg cat aaa        672
Cys Asp Gly Ser Gly Arg Ala Ser Asp Ile Leu Ala Phe Gly His Lys
            210                 215                 220 tac tca gaa gaa ggc gga ctg ata aat gaa tct ttg agg gac cag ctg        720
Tyr Ser Glu Glu Gly Gly Leu Ile Asn Glu Ser Leu Arg Asp Gln Leu
225                 230                 235                 240 ttg gtg act ata cag aag act ttc aca tac act cga acc caa gct cag        768
Leu Val Thr Ile Gln Lys Thr Phe Thr Tyr Thr Arg Thr Gln Ala Gln
            245                 250                 255 cat ctg ttc atc atc ctc atg gag tgc atg aag aag aag gaa ttg att        816
His Leu Phe Ile Ile Leu Met Glu Cys Met Lys Lys Lys Glu Leu Ile
            260                 265                 270 acg gta ttt cgg atg gga tca gaa gga cac cag gac att gat ttg gct        864
Thr Val Phe Arg Met Gly Ser Glu Gly His Gln Asp Ile Asp Leu Ala
            275                 280                 285 atc ctg aca gct tta ctc aaa gga gcc aat gcc tcg gcc cca gac caa        912
Ile Leu Thr Ala Leu Leu Lys Gly Ala Asn Ala Ser Ala Pro Asp Gln
            290                 295                 300 ctg agc tta gct tta gcc tgg aac aga gtc gac atc gct cgc agc cag        960
Leu Ser Leu Ala Leu Ala Trp Asn Arg Val Asp Ile Ala Arg Ser Gln
305                 310                 315                 320 atc ttt att tac ggg caa cag tgg ccg gtg gga tct ctg gag caa gcc       1008
Ile Phe Ile Tyr Gly Gln Gln Trp Pro Val Gly Ser Leu Glu Gln Ala
            325                 330                 335 atg ttg gat gcc tta gtt ctg gac aga gtg gat ttt gtg aaa tta ctc       1056
Met Leu Asp Ala Leu Val Leu Asp Arg Val Asp Phe Val Lys Leu Leu
            340                 345                 350 ata gag aat gga gta agc atg cac cgt ttt ctc acc atc tcc aga cta       1104
Ile Glu Asn Gly Val Ser Met His Arg Phe Leu Thr Ile Ser Arg Leu
            355                 360                 365 gag gaa ttg tac aat acg aga cat ggg ccc tca aat aca ttg tac cac       1152
Glu Glu Leu Tyr Asn Thr Arg His Gly Pro Ser Asn Thr Leu Tyr His
            370                 375                 380 ttg gtc agg gat gtc aaa aag ggg aac ctg ccc cca gac tac aga atc       1200
Leu Val Arg Asp Val Lys Lys Gly Asn Leu Pro Pro Asp Tyr Arg Ile
385                 390                 395                 400 agc ctg att gac atc ggc ctg gtg atc gag tac ctg atg ggc ggg gct       1248
Ser Leu Ile Asp Ile Gly Leu Val Ile Glu Tyr Leu Met Gly Gly Ala
            405                 410                 415 tat cgc tgc aac tac acg cgc aag cgc ttc cgg acc ctc tac cac aac       1296
Tyr Arg Cys Asn Tyr Thr Arg Lys Arg Phe Arg Thr Leu Tyr His Asn
            420                 425                 430 ctc ttc ggc ccc aag agg ccc aaa gcc ttg aaa ctg ctg gga atg gag       1344
Leu Phe Gly Pro Lys Arg Pro Lys Ala Leu Lys Leu Leu Gly Met Glu
            435                 440                 445 gat gat att ccc ttg agg cga gga aga aag aca acc aag aaa cgt gaa       1392
Asp Asp Ile Pro Leu Arg Arg Gly Arg Lys Thr Thr Lys Lys Arg Glu
450                 455                 460 gaa gag gtg gac att gac ttg gat gat cct gag atc aac cac ttc ccc       1440
Glu Glu Val Asp Ile Asp Leu Asp Asp Pro Glu Ile Asn His Phe Pro
465                 470                 475                 480
```

```
ttc cct ttc cat gag ctc atg gtg tgg gct gtt ctc atg aag cgg cag      1488
Phe Pro Phe His Glu Leu Met Val Trp Ala Val Leu Met Lys Arg Gln
                485                 490                 495 aag atg gcc ctg ttc ttc tgg cag cac ggt gag gag gcc atg gcc aag      1536
Lys Met Ala Leu Phe Phe Trp Gln His Gly Glu Glu Ala Met Ala Lys
            500                 505                 510 gcc ctg gtg gcc tgc aag ctc tgc aaa gcc atg gct cat gag gcc tct      1584
Ala Leu Val Ala Cys Lys Leu Cys Lys Ala Met Ala His Glu Ala Ser
        515                 520                 525 gag aac gac atg gtt gac gac att tcc cag gag ctg aat cac aat tcc      1632
Glu Asn Asp Met Val Asp Asp Ile Ser Gln Glu Leu Asn His Asn Ser
    530                 535                 540 aga gac ttt ggc cag ctg gct gtg gag ctc ctg gac cag tcc tac aag      1680
Arg Asp Phe Gly Gln Leu Ala Val Glu Leu Leu Asp Gln Ser Tyr Lys
545                 550                 555                 560 cag gac gaa cag ctg gcc atg aaa ctg ctg acg tat gag ctg aag aac      1728
Gln Asp Glu Gln Leu Ala Met Lys Leu Leu Thr Tyr Glu Leu Lys Asn
                565                 570                 575 tgg agc aac gcc acg tgc ctg cag ctt gcc gtg gct gcc aaa cac cgc      1776
Trp Ser Asn Ala Thr Cys Leu Gln Leu Ala Val Ala Ala Lys His Arg
            580                 585                 590 gac ttc atc gcg cac acg tgc agc cag atg ctg ctc acc gac atg tgg      1824
Asp Phe Ile Ala His Thr Cys Ser Gln Met Leu Leu Thr Asp Met Trp
        595                 600                 605 atg ggc cgg ctc cgc atg cgc aag aac tca ggc ctc aag gta att ctg      1872
Met Gly Arg Leu Arg Met Arg Lys Asn Ser Gly Leu Lys Val Ile Leu
    610                 615                 620 gga att cta ctt cct cct tca att ctc agc ttg gag ttc aag aac aaa      1920
Gly Ile Leu Leu Pro Pro Ser Ile Leu Ser Leu Glu Phe Lys Asn Lys
625                 630                 635                 640 gac gac atg ccc tat atg tct cag gcc cag gaa atc cac ctc caa gag      1968
Asp Asp Met Pro Tyr Met Ser Gln Ala Gln Glu Ile His Leu Gln Glu
                645                 650                 655 aag gag gca gaa gaa cca gag aag ccc aca aag gaa aaa gag gaa gag      2016
Lys Glu Ala Glu Glu Pro Glu Lys Pro Thr Lys Glu Lys Glu Glu Glu
            660                 665                 670 gac atg gag ctc aca gca atg ttg gga cga aac aac ggg gag tcc tcc      2064
Asp Met Glu Leu Thr Ala Met Leu Gly Arg Asn Asn Gly Glu Ser Ser
        675                 680                 685 agg aag aag gat gaa gag gaa gtt cag agc aag cac cgg tta atc ccc      2112
Arg Lys Lys Asp Glu Glu Glu Val Gln Ser Lys His Arg Leu Ile Pro
    690                 695                 700 ctc ggc aga aaa atc tat gaa ttc tac aat gca ccc atc gtg aag ttc      2160
Leu Gly Arg Lys Ile Tyr Glu Phe Tyr Asn Ala Pro Ile Val Lys Phe
705                 710                 715                 720 tgg ttc tac aca ctg gcg tat atc gga tac ctg atg ctc ttc aac tat      2208
Trp Phe Tyr Thr Leu Ala Tyr Ile Gly Tyr Leu Met Leu Phe Asn Tyr
                725                 730                 735 atc gtg tta gtg aag atg gaa cgc tgg ccg tcc acc cag gaa tgg atc      2256
Ile Val Leu Val Lys Met Glu Arg Trp Pro Ser Thr Gln Glu Trp Ile
            740                 745                 750 gta atc tcc tat att ttc acc ctg gga ata gaa aag atg aga gag att      2304
Val Ile Ser Tyr Ile Phe Thr Leu Gly Ile Glu Lys Met Arg Glu Ile
        755                 760                 765 ctg atg tca gag cca ggg aag ttg cta cag aaa gtg aag gta tgg ctg      2352
Leu Met Ser Glu Pro Gly Lys Leu Leu Gln Lys Val Lys Val Trp Leu
    770                 775                 780 cag gag tac tgg aat gtc acg gac ctc atc gcc atc ctt ctg ttt tct      2400
Gln Glu Tyr Trp Asn Val Thr Asp Leu Ile Ala Ile Leu Leu Phe Ser
785                 790                 795                 800
```

-continued

| | |
|---|---|
| gtc gga atg atc ctt cgt ctc caa gac cag ccc ttc agg agt gac ggg<br>Val Gly Met Ile Leu Arg Leu Gln Asp Gln Pro Phe Arg Ser Asp Gly<br>805   810   815 | 2448 |
| agg gtc atc tac tgc gtg aac atc att tac tgg tat atc cgt ctc cta<br>Arg Val Ile Tyr Cys Val Asn Ile Ile Tyr Trp Tyr Ile Arg Leu Leu<br>820   825   830 | 2496 |
| gac atc ttc ggc gtg aac aag tat ttg ggc ccg tat gta atg atg att<br>Asp Ile Phe Gly Val Asn Lys Tyr Leu Gly Pro Tyr Val Met Met Ile<br>835   840   845 | 2544 |
| gga aaa atg atg ata gac atg atg tac ttt gtc atc att atg ctg gtg<br>Gly Lys Met Met Ile Asp Met Met Tyr Phe Val Ile Ile Met Leu Val<br>850   855   860 | 2592 |
| gtt ctg atg agc ttt ggg gtc gcc agg caa gcc atc ctt ttt ccc aat<br>Val Leu Met Ser Phe Gly Val Ala Arg Gln Ala Ile Leu Phe Pro Asn<br>865   870   875   880 | 2640 |
| gag gag cca tca tgg aaa ctg gcc aag aac atc ttc tac atg ccc tat<br>Glu Glu Pro Ser Trp Lys Leu Ala Lys Asn Ile Phe Tyr Met Pro Tyr<br>885   890   895 | 2688 |
| tgg atg att tat ggg gaa gtg ttt gcg gac cag ata gac cgt aag caa<br>Trp Met Ile Tyr Gly Glu Val Phe Ala Asp Gln Ile Asp Arg Lys Gln<br>900   905   910 | 2736 |
| gtt tat gat tct cat aca cca aag tca gct ccc tgt gga cag aat gag<br>Val Tyr Asp Ser His Thr Pro Lys Ser Ala Pro Cys Gly Gln Asn Glu<br>915   920   925 | 2784 |
| acc cga gag gat ggt aaa ata atc cag ctg cct ccc tgc aag aca gga<br>Thr Arg Glu Asp Gly Lys Ile Ile Gln Leu Pro Pro Cys Lys Thr Gly<br>930   935   940 | 2832 |
| gct tgg atc gtg ccg gcc atc atg gcc tgc tac ctc tta gtg gca aac<br>Ala Trp Ile Val Pro Ala Ile Met Ala Cys Tyr Leu Leu Val Ala Asn<br>945   950   955   960 | 2880 |
| atc ttg ctg gtc aac ctc ctc att gct gtc ttt aac aat aca ttt ttt<br>Ile Leu Leu Val Asn Leu Leu Ile Ala Val Phe Asn Asn Thr Phe Phe<br>965   970   975 | 2928 |
| gaa gta aaa tcg ata tcc aac caa gtc tgg aag ttt cag agg tat cag<br>Glu Val Lys Ser Ile Ser Asn Gln Val Trp Lys Phe Gln Arg Tyr Gln<br>980   985   990 | 2976 |
| ctc atc atg act ttc cat gaa agg cca gtt ctg ccc cca cca ctg atc<br>Leu Ile Met Thr Phe His Glu Arg Pro Val Leu Pro Pro Pro Leu Ile<br>995   1000   1005 | 3024 |
| atc ttc agc cac atg acc atg ata ttc cag cac ctg tgc tgc cga<br>Ile Phe Ser His Met Thr Met Ile Phe Gln His Leu Cys Cys Arg<br>1010   1015   1020 | 3069 |
| tgg agg aaa cac gag agc gac ccg gat gaa agg gac tac ggc ctg<br>Trp Arg Lys His Glu Ser Asp Pro Asp Glu Arg Asp Tyr Gly Leu<br>1025   1030   1035 | 3114 |
| aaa ctc ttc ata acc gat gat gag ctc aag aaa gta cat gac ttt<br>Lys Leu Phe Ile Thr Asp Asp Glu Leu Lys Lys Val His Asp Phe<br>1040   1045   1050 | 3159 |
| gaa gag caa tgc ata gaa gaa tac ttc aga gaa aag gat gat cgg<br>Glu Glu Gln Cys Ile Glu Glu Tyr Phe Arg Glu Lys Asp Asp Arg<br>1055   1060   1065 | 3204 |
| ttc aac tca tct aat gat gag agg ata cgg gtg act tca gaa agg<br>Phe Asn Ser Ser Asn Asp Glu Arg Ile Arg Val Thr Ser Glu Arg<br>1070   1075   1080 | 3249 |
| gtg gag aac atg tct atg cgg ctg gag gaa gtc aac gag aga gag<br>Val Glu Asn Met Ser Met Arg Leu Glu Glu Val Asn Glu Arg Glu<br>1085   1090   1095 | 3294 |
| cac tcc atg aag gct tca ctc cag acc gtg gac atc cgg ctg gcg<br>His Ser Met Lys Ala Ser Leu Gln Thr Val Asp Ile Arg Leu Ala | 3339 |

```
                    1100                1105                1110 cag ctg gaa gac ctt atc ggg cgc atg gcc acg gcc ctg gag cgc        3384
Gln Leu Glu Asp Leu Ile Gly Arg Met Ala Thr Ala Leu Glu Arg
    1115                1120                1125 ctg aca ggt ctg gag cgg gcc gag tcc aac aaa atc cgc tcg agg        3429
Leu Thr Gly Leu Glu Arg Ala Glu Ser Asn Lys Ile Arg Ser Arg
    1130                1135                1140 acc tcg tca gac tgc acg gac gcc gcc tac att gtc cgt cag agc        3474
Thr Ser Ser Asp Cys Thr Asp Ala Ala Tyr Ile Val Arg Gln Ser
    1145                1150                1155 agc ttc aac agc cag gaa ggg aac acc ttc aag ctc caa gag agt        3519
Ser Phe Asn Ser Gln Glu Gly Asn Thr Phe Lys Leu Gln Glu Ser
    1160                1165                1170 ata gac cct gca ggt gag gag acc atg tcc cca act tct cca acc        3564
Ile Asp Pro Ala Gly Glu Glu Thr Met Ser Pro Thr Ser Pro Thr
    1175                1180                1185 tta atg ccc cgt atg cga agc cat tct ttc tat tca gtc aat atg        3609
Leu Met Pro Arg Met Arg Ser His Ser Phe Tyr Ser Val Asn Met
    1190                1195                1200 aaa gac aaa ggt ggt ata gaa aag ttg gaa agt att ttt aaa gaa        3654
Lys Asp Lys Gly Gly Ile Glu Lys Leu Glu Ser Ile Phe Lys Glu
    1205                1210                1215 agg tcc ctg agc cta cac cgg gct act agt tcc cac tct gta gca        3699
Arg Ser Leu Ser Leu His Arg Ala Thr Ser Ser His Ser Val Ala
    1220                1225                1230 aaa gaa ccc aaa gct cct gca gcc cct gcc aac acc ttg gcc att        3744
Lys Glu Pro Lys Ala Pro Ala Ala Pro Ala Asn Thr Leu Ala Ile
    1235                1240                1245 gtt cct gat tcc aga aga cca tca tcg tgt ata gac atc tat gtc        3789
Val Pro Asp Ser Arg Arg Pro Ser Ser Cys Ile Asp Ile Tyr Val
    1250                1255                1260 tct gct atg gat gag ctc cac tgt gat ata gac cct ctg gac aat        3834
Ser Ala Met Asp Glu Leu His Cys Asp Ile Asp Pro Leu Asp Asn
    1265                1270                1275 tcc gtg aac atc ctt ggg cta ggc gag cca agc ttt tca act cca        3879
Ser Val Asn Ile Leu Gly Leu Gly Glu Pro Ser Phe Ser Thr Pro
    1280                1285                1290 gta cct tcc aca gcc cct tca agt agt gcc tat gca aca ctt gca        3924
Val Pro Ser Thr Ala Pro Ser Ser Ser Ala Tyr Ala Thr Leu Ala
    1295                1300                1305 ccc aca gac aga cct cca agc cgg agc att gat ttt gag gac atc        3969
Pro Thr Asp Arg Pro Pro Ser Arg Ser Ile Asp Phe Glu Asp Ile
    1310                1315                1320 acc tcc atg gac act aga tct ttt tct tca gac tac acc cac ctc        4014
Thr Ser Met Asp Thr Arg Ser Phe Ser Ser Asp Tyr Thr His Leu
    1325                1330                1335 cca gaa tgc caa aac ccc tgg gac tca gag cct ccg atg tac cac        4059
Pro Glu Cys Gln Asn Pro Trp Asp Ser Glu Pro Pro Met Tyr His
    1340                1345                1350 acc att gag cgt tcc aaa agt agc cgc tac cta gcc acc aca ccc        4104
Thr Ile Glu Arg Ser Lys Ser Ser Arg Tyr Leu Ala Thr Thr Pro
    1355                1360                1365 ttt ctt cta gaa gag gct ccc att gtg aaa tct cat agc ttt atg        4149
Phe Leu Leu Glu Glu Ala Pro Ile Val Lys Ser His Ser Phe Met
    1370                1375                1380 ttt tcc ccc tca agg agc tat tat gcc aac ttt ggg gtg cct gta        4194
Phe Ser Pro Ser Arg Ser Tyr Tyr Ala Asn Phe Gly Val Pro Val
    1385                1390                1395 aaa aca gca gaa tac aca agt att aca gac tgt att gac aca agg        4239
```

-continued

```
Lys Thr Ala Glu Tyr Thr Ser Ile Thr Asp Cys Ile Asp Thr Arg
1400                1405                1410 tgt gtc aat gcc cct caa gca att gcg gac aga gct gcc ttc cct       4284
Cys Val Asn Ala Pro Gln Ala Ile Ala Asp Arg Ala Ala Phe Pro
    1415                1420                1425 gga ggt ctt gga gac aaa gtg gag gac tta act tgc tgc cat cca       4329
Gly Gly Leu Gly Asp Lys Val Glu Asp Leu Thr Cys Cys His Pro
1430                1435                1440 gag cga gaa gca gaa ctg agt cac ccc agc tct gac agt gag gag       4374
Glu Arg Glu Ala Glu Leu Ser His Pro Ser Ser Asp Ser Glu Glu
    1445                1450                1455 aat gag gcc aaa ggc cgc aga gcc acc att gca ata tcc tcc cag       4419
Asn Glu Ala Lys Gly Arg Arg Ala Thr Ile Ala Ile Ser Ser Gln
1460                1465                1470 gag ggt gat aac tca gag aga acc ctg tcc aac aac atc act gtt       4464
Glu Gly Asp Asn Ser Glu Arg Thr Leu Ser Asn Asn Ile Thr Val
    1475                1480                1485 ccc aag ata gag cgc gcc aac agc tac tcg gca gag gag cca agt       4509
Pro Lys Ile Glu Arg Ala Asn Ser Tyr Ser Ala Glu Glu Pro Ser
1490                1495                1500 gcg cca tat gca cac acc agg aag agc ttc tcc atc agt gac aaa       4554
Ala Pro Tyr Ala His Thr Arg Lys Ser Phe Ser Ile Ser Asp Lys
    1505                1510                1515 ctc gac agg cag cgg aac aca gca agc ctg caa aat ccc ttc cag       4599
Leu Asp Arg Gln Arg Asn Thr Ala Ser Leu Gln Asn Pro Phe Gln
1520                1525                1530 aga agc aag tcc tcc aag ccg gag ggc cga ggg gac agc ctg tcc       4644
Arg Ser Lys Ser Ser Lys Pro Glu Gly Arg Gly Asp Ser Leu Ser
    1535                1540                1545 atg agg aga ctg tcc aga aca tcg gct ttc caa agc ttt gaa agc       4689
Met Arg Arg Leu Ser Arg Thr Ser Ala Phe Gln Ser Phe Glu Ser
1550                1555                1560 aag cac acc taa                                                    4701
Lys His Thr
    1565

<210> SEQ ID NO 6
<211> LENGTH: 1566
<212> TYPE: PRT
<213> ORGANISM: Homo sapiens

<400> SEQUENCE: 6

Met Tyr Val Arg Val Ser Phe Asp Thr Lys Pro Asp Leu Leu His
1               5                   10                  15

Leu Met Thr Lys Glu Trp Gln Leu Glu Leu Pro Lys Leu Leu Ile Ser
            20                  25                  30

Val His Gly Gly Leu Gln Asn Phe Glu Leu Gln Pro Lys Leu Lys Gln
        35                  40                  45

Val Phe Gly Lys Gly Leu Ile Lys Ala Ala Met Thr Thr Gly Ala Trp
    50                  55                  60

Ile Phe Thr Gly Gly Val Asn Thr Gly Val Ile Arg His Val Gly Asp
65                  70                  75                  80

Ala Leu Lys Asp His Ala Ser Lys Ser Arg Gly Lys Ile Cys Thr Ile
                85                  90                  95

Gly Ile Ala Pro Trp Gly Ile Val Glu Asn Gln Glu Asp Leu Ile Gly
            100                 105                 110

Arg Asp Val Val Arg Pro Tyr Gln Thr Met Ser Asn Pro Met Ser Lys
        115                 120                 125
```

-continued

```
Leu Thr Val Leu Asn Ser Met His Ser His Phe Ile Leu Ala Asp Asn
    130                 135                 140
Gly Thr Thr Gly Lys Tyr Gly Ala Glu Val Lys Leu Arg Arg Gln Leu
145                 150                 155                 160
Glu Lys His Ile Ser Leu Gln Lys Ile Asn Thr Arg Ile Gly Gln Gly
            165                 170                 175
Val Pro Val Val Ala Leu Ile Val Glu Gly Gly Pro Asn Val Ile Ser
                180                 185                 190
Ile Val Leu Glu Tyr Leu Arg Asp Thr Pro Val Pro Val Val Val
        195                 200                 205
Cys Asp Gly Ser Gly Arg Ala Ser Asp Ile Leu Ala Phe Gly His Lys
    210                 215                 220
Tyr Ser Glu Glu Gly Gly Leu Ile Asn Glu Ser Leu Arg Asp Gln Leu
225                 230                 235                 240
Leu Val Thr Ile Gln Lys Thr Phe Thr Tyr Thr Arg Thr Gln Ala Gln
            245                 250                 255
His Leu Phe Ile Ile Leu Met Glu Cys Met Lys Lys Glu Leu Ile
                260                 265                 270
Thr Val Phe Arg Met Gly Ser Glu Gly His Gln Asp Ile Asp Leu Ala
        275                 280                 285
Ile Leu Thr Ala Leu Leu Lys Gly Ala Asn Ala Ser Ala Pro Asp Gln
    290                 295                 300
Leu Ser Leu Ala Leu Ala Trp Asn Arg Val Asp Ile Ala Arg Ser Gln
305                 310                 315                 320
Ile Phe Ile Tyr Gly Gln Gln Trp Pro Val Gly Ser Leu Glu Gln Ala
            325                 330                 335
Met Leu Asp Ala Leu Val Leu Asp Arg Val Asp Phe Val Lys Leu Leu
                340                 345                 350
Ile Glu Asn Gly Val Ser Met His Arg Phe Leu Thr Ile Ser Arg Leu
        355                 360                 365
Glu Glu Leu Tyr Asn Thr Arg His Gly Pro Ser Asn Thr Leu Tyr His
    370                 375                 380
Leu Val Arg Asp Val Lys Lys Gly Asn Leu Pro Pro Asp Tyr Arg Ile
385                 390                 395                 400
Ser Leu Ile Asp Ile Gly Leu Val Ile Glu Tyr Leu Met Gly Gly Ala
            405                 410                 415
Tyr Arg Cys Asn Tyr Thr Arg Lys Arg Phe Arg Thr Leu Tyr His Asn
                420                 425                 430
Leu Phe Gly Pro Lys Arg Pro Lys Ala Leu Lys Leu Leu Gly Met Glu
        435                 440                 445
Asp Asp Ile Pro Leu Arg Arg Gly Arg Lys Thr Thr Lys Lys Arg Glu
    450                 455                 460
Glu Glu Val Asp Ile Asp Leu Asp Asp Pro Glu Ile Asn His Phe Pro
465                 470                 475                 480
Phe Pro Phe His Glu Leu Met Val Trp Ala Val Leu Met Lys Arg Gln
            485                 490                 495
Lys Met Ala Leu Phe Phe Trp Gln His Gly Glu Glu Ala Met Ala Lys
                500                 505                 510
Ala Leu Val Ala Cys Lys Leu Cys Lys Ala Met Ala His Glu Ala Ser
        515                 520                 525
Glu Asn Asp Met Val Asp Ile Ser Gln Glu Leu Asn His Asn Ser
    530                 535                 540
Arg Asp Phe Gly Gln Leu Ala Val Glu Leu Leu Asp Gln Ser Tyr Lys
```

-continued

```
            545                 550                 555                 560
Gln Asp Glu Gln Leu Ala Met Lys Leu Leu Thr Tyr Glu Leu Lys Asn
                565                 570                 575
Trp Ser Asn Ala Thr Cys Leu Gln Leu Ala Val Ala Ala Lys His Arg
                580                 585                 590
Asp Phe Ile Ala His Thr Cys Ser Gln Met Leu Leu Thr Asp Met Trp
                595                 600                 605
Met Gly Arg Leu Arg Met Arg Lys Asn Ser Gly Leu Lys Val Ile Leu
                610                 615                 620
Gly Ile Leu Leu Pro Pro Ser Ile Leu Ser Leu Glu Phe Lys Asn Lys
625                 630                 635                 640
Asp Asp Met Pro Tyr Met Ser Gln Ala Gln Glu Ile His Leu Gln Glu
                645                 650                 655
Lys Glu Ala Glu Glu Pro Glu Lys Pro Thr Lys Glu Lys Glu Glu Glu
                660                 665                 670
Asp Met Glu Leu Thr Ala Met Leu Gly Arg Asn Asn Gly Glu Ser Ser
                675                 680                 685
Arg Lys Lys Asp Glu Glu Glu Val Gln Ser Lys His Arg Leu Ile Pro
                690                 695                 700
Leu Gly Arg Lys Ile Tyr Glu Phe Tyr Asn Ala Pro Ile Val Lys Phe
705                 710                 715                 720
Trp Phe Tyr Thr Leu Ala Tyr Ile Gly Tyr Leu Met Leu Phe Asn Tyr
                725                 730                 735
Ile Val Leu Val Lys Met Glu Arg Trp Pro Ser Thr Gln Glu Trp Ile
                740                 745                 750
Val Ile Ser Tyr Ile Phe Thr Leu Gly Ile Glu Lys Met Arg Glu Ile
                755                 760                 765
Leu Met Ser Glu Pro Gly Lys Leu Leu Gln Lys Val Lys Val Trp Leu
                770                 775                 780
Gln Glu Tyr Trp Asn Val Thr Asp Leu Ile Ala Ile Leu Leu Phe Ser
785                 790                 795                 800
Val Gly Met Ile Leu Arg Leu Gln Asp Gln Pro Phe Arg Ser Asp Gly
                805                 810                 815
Arg Val Ile Tyr Cys Val Asn Ile Ile Tyr Trp Tyr Ile Arg Leu Leu
                820                 825                 830
Asp Ile Phe Gly Val Asn Lys Tyr Leu Gly Pro Tyr Val Met Met Ile
                835                 840                 845
Gly Lys Met Met Ile Asp Met Met Tyr Phe Val Ile Ile Met Leu Val
                850                 855                 860
Val Leu Met Ser Phe Gly Val Ala Arg Gln Ala Ile Leu Phe Pro Asn
865                 870                 875                 880
Glu Glu Pro Ser Trp Lys Leu Ala Lys Asn Ile Phe Tyr Met Pro Tyr
                885                 890                 895
Trp Met Ile Tyr Gly Glu Val Phe Ala Asp Gln Ile Asp Arg Lys Gln
                900                 905                 910
Val Tyr Asp Ser His Thr Pro Lys Ser Ala Pro Cys Gly Gln Asn Glu
                915                 920                 925
Thr Arg Glu Asp Gly Lys Ile Ile Gln Leu Pro Pro Cys Lys Thr Gly
                930                 935                 940
Ala Trp Ile Val Pro Ala Ile Met Ala Cys Tyr Leu Leu Val Ala Asn
945                 950                 955                 960
Ile Leu Leu Val Asn Leu Leu Ile Ala Val Phe Asn Asn Thr Phe Phe
                965                 970                 975
```

```
Glu Val Lys Ser Ile Ser Asn Gln Val Trp Lys Phe Gln Arg Tyr Gln
                980                 985                 990

Leu Ile Met Thr Phe His Glu Arg  Pro Val Leu Pro Pro  Pro Leu Ile
        995                 1000                 1005

Ile Phe  Ser His Met Thr Met  Ile Phe Gln His Leu  Cys Cys Arg
        1010                 1015                 1020

Trp Arg  Lys His Glu Ser Asp  Pro Asp Glu Arg Asp  Tyr Gly Leu
        1025                 1030                 1035

Lys Leu  Phe Ile Thr Asp Asp  Glu Leu Lys Lys Val  His Asp Phe
        1040                 1045                 1050

Glu Glu  Gln Cys Ile Glu Glu  Tyr Phe Arg Glu Lys  Asp Asp Arg
        1055                 1060                 1065

Phe Asn  Ser Ser Asn Asp Glu  Arg Ile Arg Val Thr  Ser Glu Arg
        1070                 1075                 1080

Val Glu  Asn Met Ser Met Arg  Leu Glu Glu Val Asn  Glu Arg Glu
        1085                 1090                 1095

His Ser  Met Lys Ala Ser Leu  Gln Thr Val Asp Ile  Arg Leu Ala
        1100                 1105                 1110

Gln Leu  Glu Asp Leu Ile Gly  Arg Met Ala Thr Ala  Leu Glu Arg
        1115                 1120                 1125

Leu Thr  Gly Leu Glu Arg Ala  Glu Ser Asn Lys Ile  Arg Ser Arg
        1130                 1135                 1140

Thr Ser  Ser Asp Cys Thr Asp  Ala Ala Tyr Ile Val  Arg Gln Ser
        1145                 1150                 1155

Ser Phe  Asn Ser Gln Glu Gly  Asn Thr Phe Lys Leu  Gln Glu Ser
        1160                 1165                 1170

Ile Asp  Pro Ala Gly Glu Glu  Thr Met Ser Pro Thr  Ser Pro Thr
        1175                 1180                 1185

Leu Met  Pro Arg Met Arg Ser  His Ser Phe Tyr Ser  Val Asn Met
        1190                 1195                 1200

Lys Asp  Lys Gly Gly Ile Glu  Lys Leu Glu Ser Ile  Phe Lys Glu
        1205                 1210                 1215

Arg Ser  Leu Ser Leu His Arg  Ala Thr Ser Ser His  Ser Val Ala
        1220                 1225                 1230

Lys Glu  Pro Lys Ala Pro Ala  Ala Pro Ala Asn Thr  Leu Ala Ile
        1235                 1240                 1245

Val Pro  Asp Ser Arg Arg Pro  Ser Ser Cys Ile Asp  Ile Tyr Val
        1250                 1255                 1260

Ser Ala  Met Asp Glu Leu His  Cys Asp Ile Asp Pro  Leu Asp Asn
        1265                 1270                 1275

Ser Val  Asn Ile Leu Gly Leu  Gly Glu Pro Ser Phe  Ser Thr Pro
        1280                 1285                 1290

Val Pro  Ser Thr Ala Pro Ser  Ser Ser Ala Tyr Ala  Thr Leu Ala
        1295                 1300                 1305

Pro Thr  Asp Arg Pro Pro Ser  Arg Ser Ile Asp Phe  Glu Asp Ile
        1310                 1315                 1320

Thr Ser  Met Asp Thr Arg Ser  Phe Ser Ser Asp Tyr  Thr His Leu
        1325                 1330                 1335

Pro Glu  Cys Gln Asn Pro Trp  Asp Ser Glu Pro Pro  Met Tyr His
        1340                 1345                 1350

Thr Ile  Glu Arg Ser Lys Ser  Ser Arg Tyr Leu Ala  Thr Thr Pro
        1355                 1360                 1365
```

-continued

```
Phe Leu Leu Glu Glu Ala Pro Ile Val Lys Ser His Ser Phe Met
    1370                1375                1380

Phe Ser Pro Ser Arg Ser Tyr Tyr Ala Asn Phe Gly Val Pro Val
    1385                1390                1395

Lys Thr Ala Glu Tyr Thr Ser Ile Thr Asp Cys Ile Asp Thr Arg
    1400                1405                1410

Cys Val Asn Ala Pro Gln Ala Ile Ala Asp Arg Ala Ala Phe Pro
    1415                1420                1425

Gly Gly Leu Gly Asp Lys Val Glu Asp Leu Thr Cys Cys His Pro
    1430                1435                1440

Glu Arg Glu Ala Glu Leu Ser His Pro Ser Ser Asp Ser Glu Glu
    1445                1450                1455

Asn Glu Ala Lys Gly Arg Arg Ala Thr Ile Ala Ile Ser Ser Gln
    1460                1465                1470

Glu Gly Asp Asn Ser Glu Arg Thr Leu Ser Asn Asn Ile Thr Val
    1475                1480                1485

Pro Lys Ile Glu Arg Ala Asn Ser Tyr Ser Ala Glu Glu Pro Ser
    1490                1495                1500

Ala Pro Tyr Ala His Thr Arg Lys Ser Phe Ser Ile Ser Asp Lys
    1505                1510                1515

Leu Asp Arg Gln Arg Asn Thr Ala Ser Leu Gln Asn Pro Phe Gln
    1520                1525                1530

Arg Ser Lys Ser Ser Lys Pro Glu Gly Arg Gly Asp Ser Leu Ser
    1535                1540                1545

Met Arg Arg Leu Ser Arg Thr Ser Ala Phe Gln Ser Phe Glu Ser
    1550                1555                1560

Lys His Thr
    1565

<210> SEQ ID NO 7
<211> LENGTH: 1544
<212> TYPE: PRT
<213> ORGANISM: Homo sapiens

<400> SEQUENCE: 7

Met Tyr Val Arg Val Ser Phe Asp Thr Lys Pro Asp Leu Leu Leu His
1               5                   10                  15

Leu Met Thr Lys Glu Trp Gln Leu Glu Leu Pro Lys Leu Leu Ile Ser
            20                  25                  30

Val His Gly Gly Leu Gln Asn Phe Glu Leu Gln Pro Lys Leu Lys Gln
        35                  40                  45

Val Phe Gly Lys Gly Leu Ile Lys Ala Ala Met Thr Thr Gly Ala Trp
    50                  55                  60

Ile Phe Thr Gly Gly Val Asn Thr Gly Val Ile Arg His Val Gly Asp
65                  70                  75                  80

Ala Leu Lys Asp His Ala Ser Lys Ser Arg Gly Lys Ile Cys Thr Ile
                85                  90                  95

Gly Ile Ala Pro Trp Gly Ile Val Glu Asn Gln Glu Asp Leu Ile Gly
            100                 105                 110

Arg Asp Val Val Arg Pro Tyr Gln Thr Met Ser Asn Pro Met Ser Lys
        115                 120                 125

Leu Thr Val Leu Asn Ser Met His Ser His Phe Ile Leu Ala Asp Asn
    130                 135                 140

Gly Thr Thr Gly Lys Tyr Gly Ala Glu Val Lys Leu Arg Arg Gln Leu
145                 150                 155                 160
```

-continued

```
Glu Lys His Ile Ser Leu Gln Lys Ile Asn Thr Arg Ile Gly Gln Gly
                165                 170                 175
Val Pro Val Ala Leu Ile Val Glu Gly Gly Pro Asn Val Ile Ser
        180                 185                 190
Ile Val Leu Glu Tyr Leu Arg Asp Thr Pro Val Pro Val Val Val
        195                 200                 205
Cys Asp Gly Ser Gly Arg Ala Ser Asp Ile Leu Ala Phe Gly His Lys
        210                 215                 220
Tyr Ser Glu Glu Gly Gly Leu Ile Asn Glu Ser Leu Arg Asp Gln Leu
225                 230                 235                 240
Leu Val Thr Ile Gln Lys Thr Phe Thr Tyr Thr Arg Thr Gln Ala Gln
                245                 250                 255
His Leu Phe Ile Ile Leu Met Glu Cys Met Lys Lys Glu Leu Ile
                260                 265                 270
Thr Val Phe Arg Met Gly Ser Glu Gly His Gln Asp Ile Asp Leu Ala
            275                 280                 285
Ile Leu Thr Ala Leu Leu Lys Gly Ala Asn Ala Ser Ala Pro Asp Gln
        290                 295                 300
Leu Ser Leu Ala Leu Ala Trp Asn Arg Val Asp Ile Ala Arg Ser Gln
305                 310                 315                 320
Ile Phe Ile Tyr Gly Gln Gln Trp Pro Val Gly Ser Leu Glu Gln Ala
                325                 330                 335
Met Leu Asp Ala Leu Val Leu Asp Arg Val Asp Phe Val Lys Leu Leu
            340                 345                 350
Ile Glu Asn Gly Val Ser Met His Arg Phe Leu Thr Ile Ser Arg Leu
        355                 360                 365
Glu Glu Leu Tyr Asn Thr Arg His Gly Pro Ser Asn Thr Leu Tyr His
            370                 375                 380
Leu Val Arg Asp Val Lys Lys Gly Asn Leu Pro Pro Asp Tyr Arg Ile
385                 390                 395                 400
Ser Leu Ile Asp Ile Gly Leu Val Ile Glu Tyr Leu Met Gly Gly Ala
                405                 410                 415
Tyr Arg Cys Asn Tyr Thr Arg Lys Arg Phe Arg Thr Leu Tyr His Asn
            420                 425                 430
Leu Phe Gly Pro Lys Arg Asp Asp Ile Pro Leu Arg Arg Gly Arg Lys
        435                 440                 445
Thr Thr Lys Lys Arg Glu Glu Glu Val Asp Ile Asp Leu Asp Asp Pro
450                 455                 460
Glu Ile Asn His Phe Pro Phe Pro Phe His Glu Leu Met Val Trp Ala
465                 470                 475                 480
Val Leu Met Lys Arg Gln Lys Met Ala Leu Phe Phe Trp Gln His Gly
                485                 490                 495
Glu Glu Ala Met Ala Lys Ala Leu Val Ala Cys Lys Leu Cys Lys Ala
            500                 505                 510
Met Ala His Glu Ala Ser Glu Asn Asp Met Val Asp Ile Ser Gln
        515                 520                 525
Glu Leu Asn His Asn Ser Arg Asp Phe Gly Gln Leu Ala Val Glu Leu
        530                 535                 540
Leu Asp Gln Ser Tyr Lys Gln Asp Glu Gln Leu Ala Met Lys Leu Leu
545                 550                 555                 560
Thr Tyr Glu Leu Lys Asn Trp Ser Asn Ala Thr Cys Leu Gln Leu Ala
                565                 570                 575
```

-continued

```
Val Ala Ala Lys His Arg Asp Phe Ile Ala His Thr Cys Ser Gln Met
            580                 585                 590
Leu Leu Thr Asp Met Trp Met Gly Arg Leu Arg Met Arg Lys Asn Ser
        595                 600                 605
Gly Leu Lys Val Ile Leu Gly Ile Leu Leu Pro Ser Ile Leu Ser
    610                 615                 620
Leu Glu Phe Lys Asn Lys Asp Asp Met Pro Tyr Met Ser Gln Ala Gln
625                 630                 635                 640
Glu Ile His Leu Gln Glu Lys Ala Glu Glu Pro Glu Lys Pro Thr
                645                 650                 655
Lys Glu Lys Glu Glu Asp Met Glu Leu Thr Ala Met Leu Gly Arg
            660                 665                 670
Asn Asn Gly Glu Ser Ser Arg Lys Lys Asp Glu Glu Val Gln Ser
        675                 680                 685
Lys His Arg Leu Ile Pro Leu Gly Arg Lys Ile Tyr Glu Phe Tyr Asn
    690                 695                 700
Ala Pro Ile Val Lys Phe Trp Phe Tyr Thr Leu Ala Tyr Ile Gly Tyr
705                 710                 715                 720
Leu Met Leu Phe Asn Tyr Ile Val Leu Val Lys Met Glu Arg Trp Pro
                725                 730                 735
Ser Thr Gln Glu Trp Ile Val Ile Ser Tyr Ile Phe Thr Leu Gly Ile
            740                 745                 750
Glu Lys Met Arg Glu Ile Leu Met Ser Glu Pro Gly Lys Leu Leu Gln
        755                 760                 765
Lys Val Lys Val Trp Leu Gln Glu Tyr Trp Asn Val Thr Asp Leu Ile
    770                 775                 780
Ala Ile Leu Leu Phe Ser Val Gly Met Ile Leu Arg Leu Gln Asp Gln
785                 790                 795                 800
Pro Phe Arg Ser Asp Gly Arg Val Ile Tyr Cys Val Asn Ile Ile Tyr
                805                 810                 815
Trp Tyr Ile Arg Leu Leu Asp Ile Phe Gly Val Asn Lys Tyr Leu Gly
            820                 825                 830
Pro Tyr Val Met Met Ile Gly Lys Met Met Ile Asp Met Met Tyr Phe
        835                 840                 845
Val Ile Ile Met Leu Val Val Leu Met Ser Phe Gly Val Ala Arg Gln
    850                 855                 860
Ala Ile Leu Phe Pro Asn Glu Glu Pro Ser Trp Lys Leu Ala Lys Asn
865                 870                 875                 880
Ile Phe Tyr Met Pro Tyr Trp Met Ile Tyr Gly Glu Val Phe Ala Asp
                885                 890                 895
Gln Ile Asp Pro Pro Cys Gly Asn Glu Thr Arg Glu Asp Gly Lys
            900                 905                 910
Ile Ile Gln Leu Pro Pro Cys Lys Thr Gly Ala Trp Ile Val Pro Ala
        915                 920                 925
Ile Met Ala Cys Tyr Leu Leu Val Ala Asn Ile Leu Leu Val Asn Leu
    930                 935                 940
Leu Ile Ala Val Phe Asn Asn Thr Phe Phe Glu Val Lys Ser Ile Ser
945                 950                 955                 960
Asn Gln Val Trp Lys Phe Gln Arg Tyr Gln Leu Ile Met Thr Phe His
                965                 970                 975
Glu Arg Pro Val Leu Pro Pro Leu Ile Ile Phe Ser His Met Thr
            980                 985                 990
Met Ile Phe Gln His Leu Cys Cys  Arg Trp Arg Lys His  Glu Ser Asp
```

-continued

```
            995                 1000                1005
Pro Asp Glu Arg Asp Tyr Gly Leu Lys Leu Phe Ile Thr Asp Asp
    1010                1015                1020
Glu Leu Lys Lys Val His Asp Phe Glu Glu Gln Cys Ile Glu Glu
    1025                1030                1035
Tyr Phe Arg Glu Lys Asp Arg Phe Asn Ser Ser Asn Asp Glu
    1040                1045                1050
Arg Ile Arg Val Thr Ser Glu Arg Val Glu Asn Met Ser Met Arg
    1055                1060                1065
Leu Glu Glu Val Asn Glu Arg Glu His Ser Met Lys Ala Ser Leu
    1070                1075                1080
Gln Thr Val Asp Ile Arg Leu Ala Gln Leu Glu Asp Leu Ile Gly
    1085                1090                1095
Arg Met Ala Thr Ala Leu Glu Arg Leu Thr Gly Leu Glu Arg Ala
    1100                1105                1110
Glu Ser Asn Lys Ile Arg Ser Arg Thr Ser Ser Asp Cys Thr Asp
    1115                1120                1125
Ala Ala Tyr Ile Val Arg Gln Ser Ser Phe Asn Ser Gln Glu Gly
    1130                1135                1140
Asn Thr Phe Lys Leu Gln Glu Ser Ile Asp Pro Ala Gly Glu Glu
    1145                1150                1155
Thr Met Ser Pro Thr Ser Pro Thr Leu Met Pro Arg Met Arg Ser
    1160                1165                1170
His Ser Phe Tyr Ser Val Asn Met Lys Asp Lys Gly Gly Ile Glu
    1175                1180                1185
Lys Leu Glu Ser Ile Phe Lys Glu Arg Ser Leu Ser Leu His Arg
    1190                1195                1200
Ala Thr Ser Ser His Ser Val Ala Lys Glu Pro Lys Ala Pro Ala
    1205                1210                1215
Ala Pro Ala Asn Thr Leu Ala Ile Val Pro Asp Ser Arg Arg Pro
    1220                1225                1230
Ser Ser Cys Ile Asp Ile Tyr Val Ser Ala Met Asp Glu Leu His
    1235                1240                1245
Cys Asp Ile Asp Pro Leu Asp Asn Ser Val Asn Ile Leu Gly Leu
    1250                1255                1260
Gly Glu Pro Ser Phe Ser Thr Pro Val Pro Ser Thr Ala Pro Ser
    1265                1270                1275
Ser Ser Ala Tyr Ala Thr Leu Ala Pro Thr Asp Arg Pro Pro Ser
    1280                1285                1290
Arg Ser Ile Asp Phe Glu Ile Thr Ser Met Asp Thr Arg Ser
    1295                1300                1305
Phe Ser Ser Asp Tyr Thr His Leu Pro Glu Cys Gln Asn Pro Trp
    1310                1315                1320
Asp Ser Glu Pro Pro Met Tyr His Thr Ile Glu Arg Ser Lys Ser
    1325                1330                1335
Ser Arg Tyr Leu Ala Thr Thr Pro Phe Leu Leu Glu Glu Ala Pro
    1340                1345                1350
Ile Val Lys Ser His Ser Phe Met Phe Ser Pro Ser Arg Ser Tyr
    1355                1360                1365
Tyr Ala Asn Phe Gly Val Pro Val Lys Thr Ala Glu Tyr Thr Ser
    1370                1375                1380
Ile Thr Asp Cys Ile Asp Thr Arg Cys Val Asn Ala Pro Gln Ala
    1385                1390                1395
```

```
Ile Ala  Asp Arg Ala Ala  Phe Pro Gly Gly Leu  Gly Asp Lys Val
    1400             1405                 1410

Glu Asp  Leu Thr Cys Cys  His Pro Glu Arg Glu  Ala Glu Leu Ser
    1415             1420                 1425

His Pro  Ser Ser Asp Ser  Glu Glu Asn Glu Ala  Lys Gly Arg Arg
    1430             1435                 1440

Ala Thr  Ile Ala Ile Ser  Ser Gln Glu Gly Asp  Asn Ser Glu Arg
    1445             1450                 1455

Thr Leu  Ser Asn Asn Ile  Thr Val Pro Lys Ile  Glu Arg Ala Asn
    1460             1465                 1470

Ser Tyr  Ser Ala Glu Glu  Pro Ser Ala Pro Tyr  Ala His Thr Arg
    1475             1480                 1485

Lys Ser  Phe Ser Ile Ser  Asp Lys Leu Asp Arg  Gln Arg Asn Thr
    1490             1495                 1500

Ala Ser  Leu Gln Asn Pro  Phe Gln Arg Ser Lys  Ser Ser Lys Pro
    1505             1510                 1515

Glu Gly  Arg Gly Asp Ser  Leu Ser Met Arg Arg  Leu Ser Arg Thr
    1520             1525                 1530

Ser Ala  Phe Gln Ser Phe  Glu Ser Lys His Thr
    1535             1540

<210> SEQ ID NO 8
<211> LENGTH: 4671
<212> TYPE: DNA
<213> ORGANISM: Homo sapiens
<220> FEATURE:
<221> NAME/KEY: CDS
<222> LOCATION: (1)..(4668)

<400> SEQUENCE: 8 atg tat gtg cga gta tct ttt gat aca aaa cct gat ctc ctc tta cac     48
Met Tyr Val Arg Val Ser Phe Asp Thr Lys Pro Asp Leu Leu Leu His
1               5                   10                  15 ctg atg acc aag gaa tgg cag ttg gag ctt ccc aag ctt ctc atc tct     96
Leu Met Thr Lys Glu Trp Gln Leu Glu Leu Pro Lys Leu Leu Ile Ser
            20                  25                  30 gtc cat ggg ggc ctg cag aac ttt gaa ctc cag cca aaa ctc aag caa    144
Val His Gly Gly Leu Gln Asn Phe Glu Leu Gln Pro Lys Leu Lys Gln
        35                  40                  45 gtc ttt ggg aaa ggg ctc atc aaa gca gca atg aca act gga gcg tgg    192
Val Phe Gly Lys Gly Leu Ile Lys Ala Ala Met Thr Thr Gly Ala Trp
    50                  55                  60 ata ttc act gga ggg gtt aac aca ggt gtt att cgt cat gtt ggc gat    240
Ile Phe Thr Gly Gly Val Asn Thr Gly Val Ile Arg His Val Gly Asp
65                  70                  75                  80 gcc ttg aag gat cat gcc tct aag tct cga gga aag ata tgc acc ata    288
Ala Leu Lys Asp His Ala Ser Lys Ser Arg Gly Lys Ile Cys Thr Ile
                85                  90                  95 ggt att gcc ccc tgg gga att gtg gaa aac cag gag gac ctc att gga    336
Gly Ile Ala Pro Trp Gly Ile Val Glu Asn Gln Glu Asp Leu Ile Gly
            100                 105                 110 aga gat gtt gtc cgg cca tac cag acc atg tcc aat ccc atg agc aag    384
Arg Asp Val Val Arg Pro Tyr Gln Thr Met Ser Asn Pro Met Ser Lys
        115                 120                 125 ctc act gtt ctc aac agc atg cat tcc cac ttc att ctg gct gac aac    432
Leu Thr Val Leu Asn Ser Met His Ser His Phe Ile Leu Ala Asp Asn
    130                 135                 140 ggg acc act gga aaa tat gga gca gag gtg aaa ctt cga aga caa ctg    480
```

```
Gly Thr Thr Gly Lys Tyr Gly Ala Glu Val Lys Leu Arg Arg Gln Leu
145                 150                 155                 160 gaa aag cat att tca ctc cag aag ata aac aca aga atc ggt caa ggt        528
Glu Lys His Ile Ser Leu Gln Lys Ile Asn Thr Arg Ile Gly Gln Gly
                165                 170                 175 gtt cct gtg gtg gca ctc ata gtg gaa gga gga ccc aat gtg atc tcg        576
Val Pro Val Val Ala Leu Ile Val Glu Gly Gly Pro Asn Val Ile Ser
            180                 185                 190 att gtt ttg gag tac ctt cga gac acc cct ccc gtg cca gtg gtt gtc        624
Ile Val Leu Glu Tyr Leu Arg Asp Thr Pro Pro Val Pro Val Val Val
        195                 200                 205 tgt gat ggg agt gga cgg gca tcg gac atc ctg gcc ttt ggg cat aaa        672
Cys Asp Gly Ser Gly Arg Ala Ser Asp Ile Leu Ala Phe Gly His Lys
    210                 215                 220 tac tca gaa gaa ggc gga ctg ata aat gaa tct ttg agg gac cag ctg        720
Tyr Ser Glu Glu Gly Gly Leu Ile Asn Glu Ser Leu Arg Asp Gln Leu
225                 230                 235                 240 ttg gtg act ata cag aag act ttc aca tac act cga acc caa gct cag        768
Leu Val Thr Ile Gln Lys Thr Phe Thr Tyr Thr Arg Thr Gln Ala Gln
                245                 250                 255 cat ctg ttc atc atc ctc atg gag tgc atg aag aag aag gaa ttg att        816
His Leu Phe Ile Ile Leu Met Glu Cys Met Lys Lys Lys Glu Leu Ile
            260                 265                 270 acg gta ttt cgg atg gga tca gaa gga cac cag gac att gat ttg gct        864
Thr Val Phe Arg Met Gly Ser Glu Gly His Gln Asp Ile Asp Leu Ala
        275                 280                 285 atc ctg aca gct tta ctc aaa gga gcc aat gcc tcg gcc cca gac caa        912
Ile Leu Thr Ala Leu Leu Lys Gly Ala Asn Ala Ser Ala Pro Asp Gln
    290                 295                 300 ctg agc tta gct tta gcc tgg aac aga gtc gac atc gct cgc agc cag        960
Leu Ser Leu Ala Leu Ala Trp Asn Arg Val Asp Ile Ala Arg Ser Gln
305                 310                 315                 320 atc ttt att tac ggg caa cag tgg ccg gtg gga tct ctg gag caa gcc       1008
Ile Phe Ile Tyr Gly Gln Gln Trp Pro Val Gly Ser Leu Glu Gln Ala
                325                 330                 335 atg ttg gat gcc tta gtt ctg gac aga gtg gat ttt gtg aaa tta ctc       1056
Met Leu Asp Ala Leu Val Leu Asp Arg Val Asp Phe Val Lys Leu Leu
            340                 345                 350 ata gag aat gga gta agc atg cac cgt ttt ctc acc atc tcc aga cta       1104
Ile Glu Asn Gly Val Ser Met His Arg Phe Leu Thr Ile Ser Arg Leu
        355                 360                 365 gag gaa ttg tac aat acg aga cat ggg ccc tca aat aca ttg tac cac       1152
Glu Glu Leu Tyr Asn Thr Arg His Gly Pro Ser Asn Thr Leu Tyr His
    370                 375                 380 ttg gtc agg gat gtc aaa aag cga gag tat cca ggt ttc ggt tgg atc       1200
Leu Val Arg Asp Val Lys Lys Arg Glu Tyr Pro Gly Phe Gly Trp Ile
385                 390                 395                 400 tat ttt aag ggg aac ctg ccc cca gac tac aga atc agc ctg att gac       1248
Tyr Phe Lys Gly Asn Leu Pro Pro Asp Tyr Arg Ile Ser Leu Ile Asp
                405                 410                 415 atc ggc ctg gtg atc gag tac ctg atg ggc ggg gct tat cgc tgc aac       1296
Ile Gly Leu Val Ile Glu Tyr Leu Met Gly Gly Ala Tyr Arg Cys Asn
            420                 425                 430 tac acg cgc aag cgc ttc cgg acc ctc tac cac aac ctc ttc ggc ccc       1344
Tyr Thr Arg Lys Arg Phe Arg Thr Leu Tyr His Asn Leu Phe Gly Pro
        435                 440                 445 aag agg gat gat att ccc ttg agg cga gga aga aag aca acc aag aaa       1392
Lys Arg Asp Asp Ile Pro Leu Arg Arg Gly Arg Lys Thr Thr Lys Lys
    450                 455                 460
```

```
cgt gaa gaa gag gtg gac att gac ttg gat gat cct gag atc aac cac      1440
Arg Glu Glu Glu Val Asp Ile Asp Leu Asp Asp Pro Glu Ile Asn His
465                 470                 475                 480 ttc ccc ttc cct ttc cat gag ctc atg gtg tgg gct gtt ctc atg aag      1488
Phe Pro Phe Pro Phe His Glu Leu Met Val Trp Ala Val Leu Met Lys
                    485                 490                 495 cgg cag aag atg gcc ctg ttc ttc tgg cag cac ggt gag gag gcc atg      1536
Arg Gln Lys Met Ala Leu Phe Phe Trp Gln His Gly Glu Glu Ala Met
                500                 505                 510 gcc aag gcc ctg gtg gcc tgc aag ctc tgc aaa gcc atg gct cat gag      1584
Ala Lys Ala Leu Val Ala Cys Lys Leu Cys Lys Ala Met Ala His Glu
            515                 520                 525 gcc tct gag aac gac atg gtt gac gac att tcc cag gag ctg aat cac      1632
Ala Ser Glu Asn Asp Met Val Asp Asp Ile Ser Gln Glu Leu Asn His
530                 535                 540 aat tcc aga gac ttt ggc cag ctg gct gtg gag ctc ctg gac cag tcc      1680
Asn Ser Arg Asp Phe Gly Gln Leu Ala Val Glu Leu Leu Asp Gln Ser
545                 550                 555                 560 tac aag cag gac gaa cag ctg gcc atg aaa ctg ctg acg tat gag ctg      1728
Tyr Lys Gln Asp Glu Gln Leu Ala Met Lys Leu Leu Thr Tyr Glu Leu
                565                 570                 575 aag aac tgg agc aac gcc acg tgc ctg cag ctt gcc gtg gct gcc aaa      1776
Lys Asn Trp Ser Asn Ala Thr Cys Leu Gln Leu Ala Val Ala Ala Lys
                580                 585                 590 cac cgc gac ttc atc gcg cac acg tgc agc cag atg ctg ctc acc gac      1824
His Arg Asp Phe Ile Ala His Thr Cys Ser Gln Met Leu Leu Thr Asp
            595                 600                 605 atg tgg atg ggc cgg ctc cgc atg cgc aag aac tca ggc ctc aag gta      1872
Met Trp Met Gly Arg Leu Arg Met Arg Lys Asn Ser Gly Leu Lys Val
610                 615                 620 att ctg gga att cta ctt cct cct tca att ctc agc ttg gag ttc aag      1920
Ile Leu Gly Ile Leu Leu Pro Pro Ser Ile Leu Ser Leu Glu Phe Lys
625                 630                 635                 640 aac aaa gac gac atg ccc tat atg tct cag gcc cag gaa atc cac ctc      1968
Asn Lys Asp Asp Met Pro Tyr Met Ser Gln Ala Gln Glu Ile His Leu
                645                 650                 655 caa gag aag gag gca gaa gaa cca gag aag ccc aca aag gaa aaa gag      2016
Gln Glu Lys Glu Ala Glu Glu Pro Glu Lys Pro Thr Lys Glu Lys Glu
                660                 665                 670 gaa gag gac atg gag ctc aca gca atg ttg gga cga aac aac ggg gag      2064
Glu Glu Asp Met Glu Leu Thr Ala Met Leu Gly Arg Asn Asn Gly Glu
            675                 680                 685 tcc tcc agg aag aag gat gaa gag gaa gtt cag agc aag cac cgg tta      2112
Ser Ser Arg Lys Lys Asp Glu Glu Glu Val Gln Ser Lys His Arg Leu
690                 695                 700 atc ccc ctc ggc aga aaa atc tat gaa ttc tac aat gca ccc atc gtg      2160
Ile Pro Leu Gly Arg Lys Ile Tyr Glu Phe Tyr Asn Ala Pro Ile Val
705                 710                 715                 720 aag ttc tgg ttc tac aca ctg gcg tat atc gga tac ctg atg ctc ttc      2208
Lys Phe Trp Phe Tyr Thr Leu Ala Tyr Ile Gly Tyr Leu Met Leu Phe
                725                 730                 735 aac tat atc gtg tta gtg aag atg gaa cgc tgg ccg tcc acc cag gaa      2256
Asn Tyr Ile Val Leu Val Lys Met Glu Arg Trp Pro Ser Thr Gln Glu
                740                 745                 750 tgg atc gta atc tcc tat att ttc acc ctg gga ata gaa aag atg aga      2304
Trp Ile Val Ile Ser Tyr Ile Phe Thr Leu Gly Ile Glu Lys Met Arg
            755                 760                 765 gag att ctg atg tca gag cca ggg aag ttg cta cag aaa gtg aag gta      2352
Glu Ile Leu Met Ser Glu Pro Gly Lys Leu Leu Gln Lys Val Lys Val
770                 775                 780
```

```
tgg ctg cag gag tac tgg aat gtc acg gac ctc atc gcc atc ctt ctg      2400
Trp Leu Gln Glu Tyr Trp Asn Val Thr Asp Leu Ile Ala Ile Leu Leu
785                 790                 795                 800 ttt tct gtc gga atg atc ctt cgt ctc caa gac cag ccc ttc agg agt      2448
Phe Ser Val Gly Met Ile Leu Arg Leu Gln Asp Gln Pro Phe Arg Ser
            805                 810                 815 gac ggg agg gtc atc tac tgc gtg aac atc att tac tgg tat atc cgt      2496
Asp Gly Arg Val Ile Tyr Cys Val Asn Ile Ile Tyr Trp Tyr Ile Arg
        820                 825                 830 ctc cta gac atc ttc ggc gtg aac aag tat ttg ggc ccg tat gta atg      2544
Leu Leu Asp Ile Phe Gly Val Asn Lys Tyr Leu Gly Pro Tyr Val Met
    835                 840                 845 atg att gga aaa atg atg ata gac atg atg tac ttt gtc atc att atg      2592
Met Ile Gly Lys Met Met Ile Asp Met Met Tyr Phe Val Ile Ile Met
850                 855                 860 ctg gtg gtt ctg atg agc ttt ggg gtc gcc agg caa gcc atc ctt ttt      2640
Leu Val Val Leu Met Ser Phe Gly Val Ala Arg Gln Ala Ile Leu Phe
865                 870                 875                 880 ccc aat gag gag cca tca tgg aaa ctg gcc aag aac atc ttc tac atg      2688
Pro Asn Glu Glu Pro Ser Trp Lys Leu Ala Lys Asn Ile Phe Tyr Met
            885                 890                 895 ccc tat tgg atg att tat ggg gaa gtg ttt gcg gac cag ata gac cct      2736
Pro Tyr Trp Met Ile Tyr Gly Glu Val Phe Ala Asp Gln Ile Asp Pro
        900                 905                 910 ccc tgt gga cag aat gag acc cga gag gat ggt aaa ata atc cag ctg      2784
Pro Cys Gly Gln Asn Glu Thr Arg Glu Asp Gly Lys Ile Ile Gln Leu
    915                 920                 925 cct ccc tgc aag aca gga gct tgg atc gtg ccg gcc atc atg gcc tgc      2832
Pro Pro Cys Lys Thr Gly Ala Trp Ile Val Pro Ala Ile Met Ala Cys
930                 935                 940 tac ctc tta gtg gca aac atc ttg ctg gtc aac ctc ctc att gct gtc      2880
Tyr Leu Leu Val Ala Asn Ile Leu Leu Val Asn Leu Leu Ile Ala Val
945                 950                 955                 960 ttt aac aat aca ttt ttt gaa gta aaa tcg ata tcc aac caa gtc tgg      2928
Phe Asn Asn Thr Phe Phe Glu Val Lys Ser Ile Ser Asn Gln Val Trp
            965                 970                 975 aag ttt cag agg tat cag ctc atc atg act ttc cat gaa agg cca gtt      2976
Lys Phe Gln Arg Tyr Gln Leu Ile Met Thr Phe His Glu Arg Pro Val
        980                 985                 990 ctg ccc cca cca ctg atc atc ttc agc cac atg acc atg ata ttc cag     3024
Leu Pro Pro Pro Leu Ile Ile Phe Ser His Met Thr Met Ile Phe Gln
    995                 1000                1005 cac ctg tgc tgc cga tgg agg aaa cac gag agc gac ccg gat gaa         3069
His Leu Cys Cys Arg Trp Arg Lys His Glu Ser Asp Pro Asp Glu
    1010                1015                1020 agg gac tac ggc ctg aaa ctc ttc ata acc gat gat gag ctc aag         3114
Arg Asp Tyr Gly Leu Lys Leu Phe Ile Thr Asp Asp Glu Leu Lys
    1025                1030                1035 aaa gta cat gac ttt gaa gag caa tgc ata gaa gaa tac ttc aga         3159
Lys Val His Asp Phe Glu Glu Gln Cys Ile Glu Glu Tyr Phe Arg
    1040                1045                1050 gaa aag gat gat cgg ttc aac tca tct aat gat gag agg ata cgg         3204
Glu Lys Asp Asp Arg Phe Asn Ser Ser Asn Asp Glu Arg Ile Arg
    1055                1060                1065 gtg act tca gaa agg gtg gag aac atg tct atg cgg ctg gag gaa         3249
Val Thr Ser Glu Arg Val Glu Asn Met Ser Met Arg Leu Glu Glu
    1070                1075                1080 gtc aac gag aga gag cac tcc atg aag gct tca ctc cag acc gtg         3294
Val Asn Glu Arg Glu His Ser Met Lys Ala Ser Leu Gln Thr Val
```

-continued

| | | | | | | | | | | | |
|---|---|---|---|---|---|---|---|---|---|---|---|
| | 1085 | | | 1090 | | | | 1095 | | | |
| gac | atc | cgg | ctg | gcg | cag | ctg | gaa | gac | ctt | atc | ggg | cgc | atg | gcc | 3339 |
| Asp | Ile | Arg | Leu | Ala | Gln | Leu | Glu | Asp | Leu | Ile | Gly | Arg | Met | Ala | |
| | 1100 | | | | 1105 | | | | | 1110 | | | | | |
| acg | gcc | ctg | gag | cgc | ctg | aca | ggt | ctg | gag | cgg | gcc | gag | tcc | aac | 3384 |
| Thr | Ala | Leu | Glu | Arg | Leu | Thr | Gly | Leu | Glu | Arg | Ala | Glu | Ser | Asn | |
| | 1115 | | | | | 1120 | | | | | 1125 | | | | |
| aaa | atc | cgc | tcg | agg | acc | tcg | tca | gac | tgc | acg | gac | gcc | gcc | tac | 3429 |
| Lys | Ile | Arg | Ser | Arg | Thr | Ser | Ser | Asp | Cys | Thr | Asp | Ala | Ala | Tyr | |
| | 1130 | | | | | 1135 | | | | | 1140 | | | | |
| att | gtc | cgt | cag | agc | agc | ttc | aac | agc | cag | gaa | ggg | aac | acc | ttc | 3474 |
| Ile | Val | Arg | Gln | Ser | Ser | Phe | Asn | Ser | Gln | Glu | Gly | Asn | Thr | Phe | |
| | 1145 | | | | | 1150 | | | | | 1155 | | | | |
| aag | ctc | caa | gag | agt | ata | gac | cct | gca | ggt | gag | gag | acc | atg | tcc | 3519 |
| Lys | Leu | Gln | Glu | Ser | Ile | Asp | Pro | Ala | Gly | Glu | Glu | Thr | Met | Ser | |
| | 1160 | | | | | 1165 | | | | | 1170 | | | | |
| cca | act | tct | cca | acc | tta | atg | ccc | cgt | atg | cga | agc | cat | tct | ttc | 3564 |
| Pro | Thr | Ser | Pro | Thr | Leu | Met | Pro | Arg | Met | Arg | Ser | His | Ser | Phe | |
| | 1175 | | | | | 1180 | | | | | 1185 | | | | |
| tat | tca | gtc | aat | atg | aaa | gac | aaa | ggt | ggt | ata | gaa | aag | ttg | gaa | 3609 |
| Tyr | Ser | Val | Asn | Met | Lys | Asp | Lys | Gly | Gly | Ile | Glu | Lys | Leu | Glu | |
| | 1190 | | | | | 1195 | | | | | 1200 | | | | |
| agt | att | ttt | aaa | gaa | agg | tcc | ctg | agc | cta | cac | cgg | gct | act | agt | 3654 |
| Ser | Ile | Phe | Lys | Glu | Arg | Ser | Leu | Ser | Leu | His | Arg | Ala | Thr | Ser | |
| | 1205 | | | | | 1210 | | | | | 1215 | | | | |
| tcc | cac | tct | gta | gca | aaa | gaa | ccc | aaa | gct | cct | gca | gcc | cct | gca | 3699 |
| Ser | His | Ser | Val | Ala | Lys | Glu | Pro | Lys | Ala | Pro | Ala | Ala | Pro | Ala | |
| | 1220 | | | | | 1225 | | | | | 1230 | | | | |
| aac | acc | ttg | gcc | att | gtt | cct | gat | tcc | aga | aga | cca | tca | tcg | tgt | 3744 |
| Asn | Thr | Leu | Ala | Ile | Val | Pro | Asp | Ser | Arg | Arg | Pro | Ser | Ser | Cys | |
| | 1235 | | | | | 1240 | | | | | 1245 | | | | |
| ata | gac | atc | tat | gtc | tct | gct | atg | gat | gag | ctc | cac | tgt | gat | ata | 3789 |
| Ile | Asp | Ile | Tyr | Val | Ser | Ala | Met | Asp | Glu | Leu | His | Cys | Asp | Ile | |
| | 1250 | | | | | 1255 | | | | | 1260 | | | | |
| gac | cct | ctg | gac | aat | tcc | gtg | aac | atc | ctt | ggg | cta | ggc | gag | cca | 3834 |
| Asp | Pro | Leu | Asp | Asn | Ser | Val | Asn | Ile | Leu | Gly | Leu | Gly | Glu | Pro | |
| | 1265 | | | | | 1270 | | | | | 1275 | | | | |
| agc | ttt | tca | act | cca | gta | cct | tcc | aca | gcc | cct | tca | agt | agt | gcc | 3879 |
| Ser | Phe | Ser | Thr | Pro | Val | Pro | Ser | Thr | Ala | Pro | Ser | Ser | Ser | Ala | |
| | 1280 | | | | | 1285 | | | | | 1290 | | | | |
| tat | gca | aca | ctt | gca | ccc | aca | gac | aga | cct | cca | agc | cgg | agc | att | 3924 |
| Tyr | Ala | Thr | Leu | Ala | Pro | Thr | Asp | Arg | Pro | Pro | Ser | Arg | Ser | Ile | |
| | 1295 | | | | | 1300 | | | | | 1305 | | | | |
| gat | ttt | gag | gac | atc | acc | tcc | atg | gac | act | aga | tct | ttt | tct | tca | 3969 |
| Asp | Phe | Glu | Asp | Ile | Thr | Ser | Met | Asp | Thr | Arg | Ser | Phe | Ser | Ser | |
| | 1310 | | | | | 1315 | | | | | 1320 | | | | |
| gac | tac | acc | cac | ctc | cca | gaa | tgc | caa | aac | ccc | tgg | gac | tca | gag | 4014 |
| Asp | Tyr | Thr | His | Leu | Pro | Glu | Cys | Gln | Asn | Pro | Trp | Asp | Ser | Glu | |
| | 1325 | | | | | 1330 | | | | | 1335 | | | | |
| cct | ccg | atg | tac | cac | acc | att | gag | cgt | tcc | aaa | agt | agc | cgc | tac | 4059 |
| Pro | Pro | Met | Tyr | His | Thr | Ile | Glu | Arg | Ser | Lys | Ser | Ser | Arg | Tyr | |
| | 1340 | | | | | 1345 | | | | | 1350 | | | | |
| cta | gcc | acc | aca | ccc | ttt | ctt | cta | gaa | gag | gct | ccc | att | gtg | aaa | 4104 |
| Leu | Ala | Thr | Thr | Pro | Phe | Leu | Leu | Glu | Glu | Ala | Pro | Ile | Val | Lys | |
| | 1355 | | | | | 1360 | | | | | 1365 | | | | |
| tct | cat | agc | ttt | atg | ttt | tcc | ccc | tca | agg | agc | tat | tat | gcc | aac | 4149 |
| Ser | His | Ser | Phe | Met | Phe | Ser | Pro | Ser | Arg | Ser | Tyr | Tyr | Ala | Asn | |
| | 1370 | | | | | 1375 | | | | | 1380 | | | | |
| ttt | ggg | gtg | cct | gta | aaa | aca | gca | gaa | tac | aca | agt | att | aca | gac | 4194 |

```
                                                                                -continued Phe Gly Val Pro Val Lys Thr Ala Glu Tyr Thr Ser Ile Thr Asp
    1385                1390                1395 tgt att gac aca agg tgt gtc aat gcc cct caa gca att gcg gac        4239
Cys Ile Asp Thr Arg Cys Val Asn Ala Pro Gln Ala Ile Ala Asp
    1400                1405                1410 aga gct gcc ttc cct gga ggt ctt gga gac aaa gtg gag gac tta        4284
Arg Ala Ala Phe Pro Gly Gly Leu Gly Asp Lys Val Glu Asp Leu
    1415                1420                1425 act tgc tgc cat cca gag cga gaa gca gaa ctg agt cac ccc agc        4329
Thr Cys Cys His Pro Glu Arg Glu Ala Glu Leu Ser His Pro Ser
    1430                1435                1440 tct gac agt gag gag aat gag gcc aaa ggc cgc aga gcc acc att        4374
Ser Asp Ser Glu Glu Asn Glu Ala Lys Gly Arg Arg Ala Thr Ile
    1445                1450                1455 gca ata tcc tcc cag gag ggt gat aac tca gag aga acc ctg tcc        4419
Ala Ile Ser Ser Gln Glu Gly Asp Asn Ser Glu Arg Thr Leu Ser
    1460                1465                1470 aac aac atc act gtt ccc aag ata gag cgc gcc aac agc tac tcg        4464
Asn Asn Ile Thr Val Pro Lys Ile Glu Arg Ala Asn Ser Tyr Ser
    1475                1480                1485 gca gag gag cca agt gcg cca tat gca cac acc agg aag agc ttc        4509
Ala Glu Glu Pro Ser Ala Pro Tyr Ala His Thr Arg Lys Ser Phe
    1490                1495                1500 tcc atc agt gac aaa ctc gac agg cag cgg aac aca gca agc ctg        4554
Ser Ile Ser Asp Lys Leu Asp Arg Gln Arg Asn Thr Ala Ser Leu
    1505                1510                1515 caa aat ccc ttc cag aga agc aag tcc tcc aag ccg gag ggc cga        4599
Gln Asn Pro Phe Gln Arg Ser Lys Ser Ser Lys Pro Glu Gly Arg
    1520                1525                1530 ggg gac agc ctg tcc atg agg aga ctg tcc aga aca tcg gct ttc        4644
Gly Asp Ser Leu Ser Met Arg Arg Leu Ser Arg Thr Ser Ala Phe
    1535                1540                1545 caa agc ttt gaa agc aag cac acc taa                                4671
Gln Ser Phe Glu Ser Lys His Thr
    1550                1555

<210> SEQ ID NO 9
<211> LENGTH: 1556
<212> TYPE: PRT
<213> ORGANISM: Homo sapiens

<400> SEQUENCE: 9

Met Tyr Val Arg Val Ser Phe Asp Thr Lys Pro Asp Leu Leu His
1               5                   10                  15

Leu Met Thr Lys Glu Trp Gln Leu Glu Leu Pro Lys Leu Leu Ile Ser
                20                  25                  30

Val His Gly Gly Leu Gln Asn Phe Glu Leu Gln Pro Lys Leu Lys Gln
            35                  40                  45

Val Phe Gly Lys Gly Leu Ile Lys Ala Ala Met Thr Thr Gly Ala Trp
        50                  55                  60

Ile Phe Thr Gly Gly Val Asn Thr Gly Val Ile Arg His Val Gly Asp
65                  70                  75                  80

Ala Leu Lys Asp His Ala Ser Lys Ser Arg Gly Lys Ile Cys Thr Ile
                85                  90                  95

Gly Ile Ala Pro Trp Gly Ile Val Glu Asn Gln Glu Asp Leu Ile Gly
            100                 105                 110

Arg Asp Val Val Arg Pro Tyr Gln Thr Met Ser Asn Pro Met Ser Lys
        115                 120                 125
```

-continued

```
Leu Thr Val Leu Asn Ser Met His Ser His Phe Ile Leu Ala Asp Asn
    130                 135                 140

Gly Thr Thr Gly Lys Tyr Gly Ala Glu Val Lys Leu Arg Arg Gln Leu
145                 150                 155                 160

Glu Lys His Ile Ser Leu Gln Lys Ile Asn Thr Arg Ile Gly Gln Gly
                165                 170                 175

Val Pro Val Val Ala Leu Ile Val Glu Gly Gly Pro Asn Val Ile Ser
                180                 185                 190

Ile Val Leu Glu Tyr Leu Arg Asp Thr Pro Val Pro Val Val Val
        195                 200                 205

Cys Asp Gly Ser Gly Arg Ala Ser Asp Ile Leu Ala Phe Gly His Lys
    210                 215                 220

Tyr Ser Glu Glu Gly Gly Leu Ile Asn Glu Ser Leu Arg Asp Gln Leu
225                 230                 235                 240

Leu Val Thr Ile Gln Lys Thr Phe Thr Tyr Thr Arg Thr Gln Ala Gln
                245                 250                 255

His Leu Phe Ile Ile Leu Met Glu Cys Met Lys Lys Glu Leu Ile
    260                 265                 270

Thr Val Phe Arg Met Gly Ser Glu Gly His Gln Asp Ile Asp Leu Ala
    275                 280                 285

Ile Leu Thr Ala Leu Leu Lys Gly Ala Asn Ala Ser Ala Pro Asp Gln
    290                 295                 300

Leu Ser Leu Ala Leu Ala Trp Asn Arg Val Asp Ile Ala Arg Ser Gln
305                 310                 315                 320

Ile Phe Ile Tyr Gly Gln Gln Trp Pro Val Gly Ser Leu Glu Gln Ala
                325                 330                 335

Met Leu Asp Ala Leu Val Leu Asp Arg Val Asp Phe Val Lys Leu Leu
            340                 345                 350

Ile Glu Asn Gly Val Ser Met His Arg Phe Leu Thr Ile Ser Arg Leu
            355                 360                 365

Glu Glu Leu Tyr Asn Thr Arg His Gly Pro Ser Asn Thr Leu Tyr His
    370                 375                 380

Leu Val Arg Asp Val Lys Lys Arg Glu Tyr Pro Gly Phe Gly Trp Ile
385                 390                 395                 400

Tyr Phe Lys Gly Asn Leu Pro Pro Asp Tyr Arg Ile Ser Leu Ile Asp
                405                 410                 415

Ile Gly Leu Val Ile Glu Tyr Leu Met Gly Gly Ala Tyr Arg Cys Asn
            420                 425                 430

Tyr Thr Arg Lys Arg Phe Arg Thr Leu Tyr His Asn Leu Phe Gly Pro
    435                 440                 445

Lys Arg Asp Asp Ile Pro Leu Arg Arg Gly Arg Lys Thr Thr Lys Lys
    450                 455                 460

Arg Glu Glu Glu Val Asp Ile Asp Leu Asp Asp Pro Glu Ile Asn His
465                 470                 475                 480

Phe Pro Phe Pro Phe His Glu Leu Met Val Trp Ala Val Leu Met Lys
                485                 490                 495

Arg Gln Lys Met Ala Leu Phe Phe Trp Gln His Gly Glu Glu Ala Met
                500                 505                 510

Ala Lys Ala Leu Val Ala Cys Lys Leu Cys Lys Ala Met Ala His Glu
            515                 520                 525

Ala Ser Glu Asn Asp Met Val Asp Asp Ile Ser Gln Glu Leu Asn His
    530                 535                 540

Asn Ser Arg Asp Phe Gly Gln Leu Ala Val Glu Leu Leu Asp Gln Ser
```

-continued

```
            545                 550                 555                 560
        Tyr Lys Gln Asp Glu Gln Leu Ala Met Lys Leu Leu Thr Tyr Glu Leu
                        565                 570                 575
        Lys Asn Trp Ser Asn Ala Thr Cys Leu Gln Leu Ala Val Ala Ala Lys
                    580                 585                 590
        His Arg Asp Phe Ile Ala His Thr Cys Ser Gln Met Leu Leu Thr Asp
                595                 600                 605
        Met Trp Met Gly Arg Leu Arg Met Arg Lys Asn Ser Gly Leu Lys Val
            610                 615                 620
        Ile Leu Gly Ile Leu Leu Pro Pro Ser Ile Leu Ser Leu Glu Phe Lys
        625                 630                 635                 640
        Asn Lys Asp Asp Met Pro Tyr Met Ser Gln Ala Gln Glu Ile His Leu
                        645                 650                 655
        Gln Glu Lys Glu Ala Glu Pro Glu Lys Pro Thr Lys Glu Lys Glu
                    660                 665                 670
        Glu Glu Asp Met Glu Leu Thr Ala Met Leu Gly Arg Asn Asn Gly Glu
                675                 680                 685
        Ser Ser Arg Lys Lys Asp Glu Glu Val Gln Ser Lys His Arg Leu
            690                 695                 700
        Ile Pro Leu Gly Arg Lys Ile Tyr Glu Phe Tyr Asn Ala Pro Ile Val
        705                 710                 715                 720
        Lys Phe Trp Phe Tyr Thr Leu Ala Tyr Ile Gly Tyr Leu Met Leu Phe
                        725                 730                 735
        Asn Tyr Ile Val Leu Val Lys Met Glu Arg Trp Pro Ser Thr Gln Glu
                    740                 745                 750
        Trp Ile Val Ile Ser Tyr Ile Phe Thr Leu Gly Ile Glu Lys Met Arg
                755                 760                 765
        Glu Ile Leu Met Ser Glu Pro Gly Lys Leu Leu Gln Lys Val Lys Val
            770                 775                 780
        Trp Leu Gln Glu Tyr Trp Asn Val Thr Asp Leu Ile Ala Ile Leu Leu
        785                 790                 795                 800
        Phe Ser Val Gly Met Ile Leu Arg Leu Gln Asp Gln Pro Phe Arg Ser
                        805                 810                 815
        Asp Gly Arg Val Ile Tyr Cys Val Asn Ile Ile Tyr Trp Tyr Ile Arg
                    820                 825                 830
        Leu Leu Asp Ile Phe Gly Val Asn Lys Tyr Leu Gly Pro Tyr Val Met
                835                 840                 845
        Met Ile Gly Lys Met Met Ile Asp Met Met Tyr Phe Val Ile Ile Met
            850                 855                 860
        Leu Val Val Leu Met Ser Phe Gly Val Ala Arg Gln Ala Ile Leu Phe
        865                 870                 875                 880
        Pro Asn Glu Glu Pro Ser Trp Lys Leu Ala Lys Asn Ile Phe Tyr Met
                        885                 890                 895
        Pro Tyr Trp Met Ile Tyr Gly Glu Val Phe Ala Asp Gln Ile Asp Pro
                    900                 905                 910
        Pro Cys Gly Gln Asn Glu Thr Arg Glu Asp Gly Lys Ile Ile Gln Leu
                915                 920                 925
        Pro Pro Cys Lys Thr Gly Ala Trp Ile Val Pro Ala Ile Met Ala Cys
            930                 935                 940
        Tyr Leu Leu Val Ala Asn Ile Leu Leu Val Asn Leu Leu Ile Ala Val
        945                 950                 955                 960
        Phe Asn Asn Thr Phe Phe Glu Val Lys Ser Ile Ser Asn Gln Val Trp
                        965                 970                 975
```

-continued

```
Lys Phe Gln Arg Tyr Gln Leu Ile Met Thr Phe His Glu Arg Pro Val
            980                 985                 990

Leu Pro Pro Pro Leu Ile Ile Phe Ser His Met Thr Met Ile Phe Gln
        995                 1000                1005

His Leu Cys Cys Arg Trp Arg Lys His Glu Ser Asp Pro Asp Glu
    1010                1015                1020

Arg Asp Tyr Gly Leu Lys Leu Phe Ile Thr Asp Asp Glu Leu Lys
    1025                1030                1035

Lys Val His Asp Phe Glu Glu Gln Cys Ile Glu Tyr Phe Arg
    1040                1045                1050

Glu Lys Asp Asp Arg Phe Asn Ser Ser Asn Asp Glu Arg Ile Arg
    1055                1060                1065

Val Thr Ser Glu Arg Val Glu Asn Met Ser Met Arg Leu Glu Glu
    1070                1075                1080

Val Asn Glu Arg Glu His Ser Met Lys Ala Ser Leu Gln Thr Val
    1085                1090                1095

Asp Ile Arg Leu Ala Gln Leu Glu Asp Leu Ile Gly Arg Met Ala
    1100                1105                1110

Thr Ala Leu Glu Arg Leu Thr Gly Leu Glu Arg Ala Glu Ser Asn
    1115                1120                1125

Lys Ile Arg Ser Arg Thr Ser Ser Asp Cys Thr Asp Ala Ala Tyr
    1130                1135                1140

Ile Val Arg Gln Ser Ser Phe Asn Ser Gln Glu Gly Asn Thr Phe
    1145                1150                1155

Lys Leu Gln Glu Ser Ile Asp Pro Ala Gly Glu Glu Thr Met Ser
    1160                1165                1170

Pro Thr Ser Pro Thr Leu Met Pro Arg Met Arg Ser His Ser Phe
    1175                1180                1185

Tyr Ser Val Asn Met Lys Asp Lys Gly Gly Ile Glu Lys Leu Glu
    1190                1195                1200

Ser Ile Phe Lys Glu Arg Ser Leu Ser Leu His Arg Ala Thr Ser
    1205                1210                1215

Ser His Ser Val Ala Lys Glu Pro Lys Ala Pro Ala Ala Pro Ala
    1220                1225                1230

Asn Thr Leu Ala Ile Val Pro Asp Ser Arg Arg Pro Ser Ser Cys
    1235                1240                1245

Ile Asp Ile Tyr Val Ser Ala Met Asp Glu Leu His Cys Asp Ile
    1250                1255                1260

Asp Pro Leu Asp Asn Ser Val Asn Ile Leu Gly Leu Gly Glu Pro
    1265                1270                1275

Ser Phe Ser Thr Pro Val Pro Ser Thr Ala Pro Ser Ser Ala
    1280                1285                1290

Tyr Ala Thr Leu Ala Pro Thr Asp Arg Pro Pro Ser Arg Ser Ile
    1295                1300                1305

Asp Phe Glu Asp Ile Thr Ser Met Asp Thr Arg Ser Phe Ser Ser
    1310                1315                1320

Asp Tyr Thr His Leu Pro Glu Cys Gln Asn Pro Trp Asp Ser Glu
    1325                1330                1335

Pro Pro Met Tyr His Thr Ile Glu Arg Ser Lys Ser Ser Arg Tyr
    1340                1345                1350

Leu Ala Thr Thr Pro Phe Leu Leu Glu Glu Ala Pro Ile Val Lys
    1355                1360                1365
```

```
Ser His Ser Phe Met Phe Ser Pro Ser Arg Ser Tyr Tyr Ala Asn
    1370                1375                1380

Phe Gly Val Pro Val Lys Thr Ala Glu Tyr Thr Ser Ile Thr Asp
1385                1390                1395

Cys Ile Asp Thr Arg Cys Val Asn Ala Pro Gln Ala Ile Ala Asp
1400                1405                1410

Arg Ala Ala Phe Pro Gly Gly Leu Gly Asp Lys Val Glu Asp Leu
    1415                1420                1425

Thr Cys Cys His Pro Glu Arg Glu Ala Glu Leu Ser His Pro Ser
1430                1435                1440

Ser Asp Ser Glu Glu Asn Glu Ala Lys Gly Arg Arg Ala Thr Ile
    1445                1450                1455

Ala Ile Ser Ser Gln Glu Gly Asp Asn Ser Glu Arg Thr Leu Ser
1460                1465                1470

Asn Asn Ile Thr Val Pro Lys Ile Glu Arg Ala Asn Ser Tyr Ser
1475                1480                1485

Ala Glu Glu Pro Ser Ala Pro Tyr Ala His Thr Arg Lys Ser Phe
    1490                1495                1500

Ser Ile Ser Asp Lys Leu Asp Arg Gln Arg Asn Thr Ala Ser Leu
1505                1510                1515

Gln Asn Pro Phe Gln Arg Ser Lys Ser Ser Lys Pro Glu Gly Arg
    1520                1525                1530

Gly Asp Ser Leu Ser Met Arg Arg Leu Ser Arg Thr Ser Ala Phe
1535                1540                1545

Gln Ser Phe Glu Ser Lys His Thr
    1550                1555

<210> SEQ ID NO 10
<211> LENGTH: 1579
<212> TYPE: PRT
<213> ORGANISM: Homo sapiens

<400> SEQUENCE: 10

Met Tyr Val Arg Val Ser Phe Asp Thr Lys Pro Asp Leu Leu His
1               5                   10                  15

Leu Met Thr Lys Glu Trp Gln Leu Glu Leu Pro Lys Leu Ile Ser
                20                  25                  30

Val His Gly Gly Leu Gln Asn Phe Glu Leu Gln Pro Lys Leu Lys Gln
            35                  40                  45

Val Phe Gly Lys Gly Leu Ile Lys Ala Ala Met Thr Thr Gly Ala Trp
    50                  55                  60

Ile Phe Thr Gly Gly Val Asn Thr Gly Val Ile Arg His Val Gly Asp
65                  70                  75                  80

Ala Leu Lys Asp His Ala Ser Lys Ser Arg Gly Lys Ile Cys Thr Ile
                85                  90                  95

Gly Ile Ala Pro Trp Gly Ile Val Glu Asn Gln Glu Asp Leu Ile Gly
            100                 105                 110

Arg Asp Val Val Arg Pro Tyr Gln Thr Met Ser Asn Pro Met Ser Lys
        115                 120                 125

Leu Thr Val Leu Asn Ser Met His Ser His Phe Ile Leu Ala Asp Asn
    130                 135                 140

Gly Thr Thr Gly Lys Tyr Gly Ala Glu Val Lys Leu Arg Arg Gln Leu
145                 150                 155                 160

Glu Lys His Ile Ser Leu Gln Lys Ile Asn Thr Arg Cys Leu Pro Phe
                165                 170                 175
```

-continued

```
Phe Ser Leu Asp Ser Arg Leu Phe Tyr Ser Phe Trp Gly Ser Cys Gln
            180                 185                 190
Leu Asp Ser Val Gly Ile Gly Gln Gly Val Pro Val Ala Leu Ile
            195                 200                 205
Val Glu Gly Gly Pro Asn Val Ile Ser Ile Val Leu Glu Tyr Leu Arg
            210                 215                 220
Asp Thr Pro Pro Val Pro Val Val Cys Asp Gly Ser Gly Arg Ala
225                 230                 235                 240
Ser Asp Ile Leu Ala Phe Gly His Lys Tyr Ser Glu Glu Gly Leu
            245                 250                 255
Ile Asn Glu Ser Leu Arg Asp Gln Leu Leu Val Thr Ile Gln Lys Thr
            260                 265                 270
Phe Thr Tyr Thr Arg Thr Gln Ala Gln His Leu Phe Ile Ile Leu Met
            275                 280                 285
Glu Cys Met Lys Lys Lys Glu Leu Ile Thr Val Phe Arg Met Gly Ser
            290                 295                 300
Glu Gly His Gln Asp Ile Asp Leu Ala Ile Leu Thr Ala Leu Leu Lys
305                 310                 315                 320
Gly Ala Asn Ala Ser Ala Pro Asp Gln Leu Ser Leu Ala Leu Ala Trp
            325                 330                 335
Asn Arg Val Asp Ile Ala Arg Ser Gln Ile Phe Ile Tyr Gly Gln Gln
            340                 345                 350
Trp Pro Val Gly Ser Leu Glu Gln Ala Met Leu Asp Ala Leu Val Leu
            355                 360                 365
Asp Arg Val Asp Phe Val Lys Leu Leu Ile Glu Asn Gly Val Ser Met
            370                 375                 380
His Arg Phe Leu Thr Ile Ser Arg Leu Glu Glu Leu Tyr Asn Thr Arg
385                 390                 395                 400
His Gly Pro Ser Asn Thr Leu Tyr His Leu Val Arg Asp Val Lys Lys
            405                 410                 415
Gly Asn Leu Pro Pro Asp Tyr Arg Ile Ser Leu Ile Asp Ile Gly Leu
            420                 425                 430
Val Ile Glu Tyr Leu Met Gly Gly Ala Tyr Arg Cys Asn Tyr Thr Arg
            435                 440                 445
Lys Arg Phe Arg Thr Leu Tyr His Asn Leu Phe Gly Pro Lys Arg Pro
            450                 455                 460
Lys Ala Leu Lys Leu Leu Gly Met Glu Asp Asp Ile Pro Leu Arg Arg
465                 470                 475                 480
Gly Arg Lys Thr Thr Lys Lys Arg Glu Glu Val Asp Ile Asp Leu
            485                 490                 495
Asp Asp Pro Glu Ile Asn His Phe Pro Phe Pro Phe His Glu Leu Met
            500                 505                 510
Val Trp Ala Val Leu Met Lys Arg Gln Lys Met Ala Leu Phe Phe Trp
            515                 520                 525
Gln His Gly Glu Glu Ala Met Ala Lys Ala Leu Val Ala Cys Lys Leu
            530                 535                 540
Cys Lys Ala Met Ala His Glu Ala Ser Glu Asn Asp Met Val Asp Asp
545                 550                 555                 560
Ile Ser Gln Glu Leu Asn His Asn Ser Arg Asp Phe Gly Gln Leu Ala
            565                 570                 575
Val Glu Leu Leu Asp Gln Ser Tyr Lys Gln Asp Glu Gln Leu Ala Met
            580                 585                 590
```

```
Lys Leu Leu Thr Tyr Glu Leu Lys Asn Trp Ser Asn Ala Thr Cys Leu
                595                 600                 605

Gln Leu Ala Val Ala Ala Lys His Arg Asp Phe Ile Ala His Thr Cys
            610                 615                 620

Ser Gln Met Leu Leu Thr Asp Met Trp Met Gly Arg Leu Arg Met Arg
625                 630                 635                 640

Lys Asn Ser Gly Leu Lys Val Ile Leu Gly Ile Leu Leu Pro Pro Ser
                645                 650                 655

Ile Leu Ser Leu Glu Phe Lys Asn Lys Asp Met Pro Tyr Met Ser
                660                 665                 670

Gln Ala Gln Glu Ile His Leu Gln Glu Lys Glu Ala Glu Glu Pro Glu
            675                 680                 685

Lys Pro Thr Lys Glu Lys Glu Glu Glu Asp Met Glu Leu Thr Ala Met
690                 695                 700

Leu Gly Arg Asn Asn Gly Glu Ser Ser Arg Lys Lys Asp Glu Glu
705                 710                 715                 720

Val Gln Ser Lys His Arg Leu Ile Pro Leu Gly Arg Lys Ile Tyr Glu
                725                 730                 735

Phe Tyr Asn Ala Pro Ile Val Lys Phe Trp Phe Tyr Thr Leu Ala Tyr
                740                 745                 750

Ile Gly Tyr Leu Met Leu Phe Asn Tyr Ile Val Leu Val Lys Met Glu
                755                 760                 765

Arg Trp Pro Ser Thr Gln Glu Trp Ile Val Ile Ser Tyr Ile Phe Thr
                770                 775                 780

Leu Gly Ile Glu Lys Met Arg Glu Ile Leu Met Ser Glu Pro Gly Lys
785                 790                 795                 800

Leu Leu Gln Lys Val Lys Val Trp Leu Gln Glu Tyr Trp Asn Val Thr
                805                 810                 815

Asp Leu Ile Ala Ile Leu Leu Phe Ser Val Gly Met Ile Leu Arg Leu
                820                 825                 830

Gln Asp Gln Pro Phe Arg Ser Asp Gly Arg Val Ile Tyr Cys Val Asn
            835                 840                 845

Ile Ile Tyr Trp Tyr Ile Arg Leu Leu Asp Ile Phe Gly Val Asn Lys
            850                 855                 860

Tyr Leu Gly Pro Tyr Val Met Met Ile Gly Lys Met Met Ile Asp Met
865                 870                 875                 880

Met Tyr Phe Val Ile Ile Met Leu Val Val Leu Met Ser Phe Gly Val
                885                 890                 895

Ala Arg Gln Ala Ile Leu Phe Pro Asn Glu Glu Pro Ser Trp Lys Leu
            900                 905                 910

Ala Lys Asn Ile Phe Tyr Met Pro Tyr Trp Met Ile Tyr Gly Glu Val
            915                 920                 925

Phe Ala Asp Gln Ile Asp Pro Pro Cys Gly Gln Asn Glu Thr Arg Glu
930                 935                 940

Asp Gly Lys Ile Ile Gln Leu Pro Pro Cys Lys Thr Gly Ala Trp Ile
945                 950                 955                 960

Val Pro Ala Ile Met Ala Cys Tyr Leu Leu Val Ala Asn Ile Leu Leu
                965                 970                 975

Val Asn Leu Leu Ile Ala Val Phe Asn Asn Thr Phe Phe Glu Val Lys
            980                 985                 990

Ser Ile Ser Asn Gln Val Trp Lys Phe Gln Arg Tyr Gln Leu Ile Met
            995                 1000                1005

Thr Phe His Glu Arg Pro Val Leu Pro Pro Pro Leu Ile Ile Phe
```

-continued

```
                1010                1015                1020
Ser His Met Thr Met Ile Phe Gln His Leu Cys Cys Arg Trp Arg
    1025                1030                1035

Lys His Glu Ser Asp Pro Asp Glu Arg Asp Tyr Gly Leu Lys Leu
    1040                1045                1050

Phe Ile Thr Asp Asp Glu Leu Lys Lys Val His Asp Phe Glu Glu
    1055                1060                1065

Gln Cys Ile Glu Glu Tyr Phe Arg Glu Lys Asp Asp Arg Phe Asn
    1070                1075                1080

Ser Ser Asn Asp Glu Arg Ile Arg Val Thr Ser Glu Arg Val Glu
    1085                1090                1095

Asn Met Ser Met Arg Leu Glu Glu Val Asn Glu Arg Glu His Ser
    1100                1105                1110

Met Lys Ala Ser Leu Gln Thr Val Asp Ile Arg Leu Ala Gln Leu
    1115                1120                1125

Glu Asp Leu Ile Gly Arg Met Ala Thr Ala Leu Glu Arg Leu Thr
    1130                1135                1140

Gly Leu Glu Arg Ala Glu Ser Asn Lys Ile Arg Ser Arg Thr Ser
    1145                1150                1155

Ser Asp Cys Thr Asp Ala Ala Tyr Ile Val Arg Gln Ser Ser Phe
    1160                1165                1170

Asn Ser Gln Glu Gly Asn Thr Phe Lys Leu Gln Glu Ser Ile Asp
    1175                1180                1185

Pro Ala Gly Glu Glu Thr Met Ser Pro Thr Ser Pro Thr Leu Met
    1190                1195                1200

Pro Arg Met Arg Ser His Ser Phe Tyr Ser Val Asn Met Lys Asp
    1205                1210                1215

Lys Gly Gly Ile Glu Lys Leu Glu Ser Ile Phe Lys Glu Arg Ser
    1220                1225                1230

Leu Ser Leu His Arg Ala Thr Ser Ser His Ser Val Ala Lys Glu
    1235                1240                1245

Pro Lys Ala Pro Ala Ala Pro Ala Asn Thr Leu Ala Ile Val Pro
    1250                1255                1260

Asp Ser Arg Arg Pro Ser Ser Cys Ile Asp Ile Tyr Val Ser Ala
    1265                1270                1275

Met Asp Glu Leu His Cys Asp Ile Asp Pro Leu Asp Asn Ser Val
    1280                1285                1290

Asn Ile Leu Gly Leu Gly Glu Pro Ser Phe Ser Thr Pro Val Pro
    1295                1300                1305

Ser Thr Ala Pro Ser Ser Ser Ala Tyr Ala Thr Leu Ala Pro Thr
    1310                1315                1320

Asp Arg Pro Pro Ser Arg Ser Ile Asp Phe Glu Asp Ile Thr Ser
    1325                1330                1335

Met Asp Thr Arg Ser Phe Ser Ser Asp Tyr Thr His Leu Pro Glu
    1340                1345                1350

Cys Gln Asn Pro Trp Asp Ser Glu Pro Pro Met Tyr His Thr Ile
    1355                1360                1365

Glu Arg Ser Lys Ser Ser Arg Tyr Leu Ala Thr Thr Pro Phe Leu
    1370                1375                1380

Leu Glu Glu Ala Pro Ile Val Lys Ser His Ser Phe Met Phe Ser
    1385                1390                1395

Pro Ser Arg Ser Tyr Tyr Ala Asn Phe Gly Val Pro Val Lys Thr
    1400                1405                1410
```

-continued

```
Ala Glu Tyr Thr Ser Ile Thr Asp Cys Ile Asp Thr Arg Cys Val
    1415                1420                1425

Asn Ala Pro Gln Ala Ile Ala Asp Arg Ala Ala Phe Pro Gly Gly
    1430                1435                1440

Leu Gly Asp Lys Val Glu Asp Leu Thr Cys Cys His Pro Glu Arg
    1445                1450                1455

Glu Ala Glu Leu Ser His Pro Ser Ser Asp Ser Glu Glu Asn Glu
    1460                1465                1470

Ala Lys Gly Arg Arg Ala Thr Ile Ala Ile Ser Gln Glu Gly
    1475                1480                1485

Asp Asn Ser Glu Arg Thr Leu Ser Asn Asn Ile Thr Val Pro Lys
    1490                1495                1500

Ile Glu Arg Ala Asn Ser Tyr Ser Ala Glu Glu Pro Ser Ala Pro
    1505                1510                1515

Tyr Ala His Thr Arg Lys Ser Phe Ser Ile Ser Asp Lys Leu Asp
    1520                1525                1530

Arg Gln Arg Asn Thr Ala Ser Leu Gln Asn Pro Phe Gln Arg Ser
    1535                1540                1545

Lys Ser Ser Lys Pro Glu Gly Arg Gly Asp Ser Leu Ser Met Arg
    1550                1555                1560

Arg Leu Ser Arg Thr Ser Ala Phe Gln Ser Phe Glu Ser Lys His
    1565                1570                1575

Thr

<210> SEQ ID NO 11
<211> LENGTH: 1533
<212> TYPE: PRT
<213> ORGANISM: Homo sapiens

<400> SEQUENCE: 11

Met Tyr Ile Arg Val Ser Tyr Asp Thr Lys Pro Asp Ser Leu Leu His
1               5                   10                  15

Leu Met Val Lys Asp Trp Gln Leu Glu Leu Pro Lys Leu Leu Ile Ser
            20                  25                  30

Val His Gly Gly Leu Gln Asn Phe Glu Met Gln Pro Lys Leu Lys Gln
        35                  40                  45

Val Phe Gly Lys Gly Leu Ile Lys Ala Ala Met Thr Thr Gly Ala Trp
    50                  55                  60

Ile Phe Thr Gly Gly Val Ser Thr Gly Val Ile Ser His Val Gly Asp
65                  70                  75                  80

Ala Leu Lys Asp His Ser Ser Lys Ser Arg Gly Arg Val Cys Ala Ile
                85                  90                  95

Gly Ile Ala Pro Trp Gly Ile Val Glu Asn Lys Glu Asp Leu Val Gly
            100                 105                 110

Lys Asp Val Thr Arg Val Tyr Gln Thr Met Ser Asn Pro Leu Ser Lys
        115                 120                 125

Leu Ser Val Leu Asn Asn Ser His Thr His Phe Ile Leu Ala Asp Asn
    130                 135                 140

Gly Thr Leu Gly Lys Tyr Gly Ala Glu Val Lys Leu Arg Arg Leu Leu
145                 150                 155                 160

Glu Lys His Ile Ser Leu Gln Lys Ile Asn Thr Arg Leu Gly Gln Gly
                165                 170                 175

Val Pro Leu Val Gly Leu Val Val Glu Gly Gly Pro Asn Val Val Ser
            180                 185                 190
```

```
Ile Val Leu Glu Tyr Leu Gln Glu Glu Pro Pro Ile Pro Val Val Ile
            195                 200                 205

Cys Asp Gly Ser Gly Arg Ala Ser Asp Ile Leu Ser Phe Ala His Lys
        210                 215                 220

Tyr Cys Glu Glu Gly Gly Ile Ile Asn Glu Ser Leu Arg Glu Gln Leu
225                 230                 235                 240

Leu Val Thr Ile Gln Lys Thr Phe Asn Tyr Asn Lys Ala Gln Ser His
                245                 250                 255

Gln Leu Phe Ala Ile Ile Met Glu Cys Met Lys Lys Lys Glu Leu Val
            260                 265                 270

Thr Val Phe Arg Met Gly Ser Glu Gly Gln Gln Asp Ile Glu Met Ala
        275                 280                 285

Ile Leu Thr Ala Leu Leu Lys Gly Thr Asn Val Ser Ala Pro Asp Gln
        290                 295                 300

Leu Ser Leu Ala Leu Ala Trp Asn Arg Val Asp Ile Ala Arg Ser Gln
305                 310                 315                 320

Ile Phe Val Phe Gly Pro His Trp Thr Pro Leu Gly Ser Leu Ala Pro
                325                 330                 335

Pro Thr Asp Ser Lys Ala Thr Glu Lys Glu Lys Lys Pro Pro Met Ala
            340                 345                 350

Thr Thr Lys Gly Gly Arg Gly Lys Gly Lys Gly Lys Lys Lys Gly Lys
        355                 360                 365

Val Lys Glu Glu Val Glu Glu Glu Thr Asp Pro Arg Lys Ile Glu Leu
        370                 375                 380

Leu Asn Trp Val Asn Ala Leu Glu Gln Ala Met Leu Asp Ala Leu Val
385                 390                 395                 400

Leu Asp Arg Val Asp Phe Val Lys Leu Leu Ile Glu Asn Gly Val Asn
                405                 410                 415

Met Gln His Phe Leu Thr Ile Pro Arg Leu Glu Glu Leu Tyr Asn Thr
            420                 425                 430

Arg Leu Gly Pro Pro Asn Thr Leu His Leu Leu Val Arg Asp Val Lys
        435                 440                 445

Lys Ser Asn Leu Pro Pro Asp Tyr His Ile Ser Leu Ile Asp Ile Gly
        450                 455                 460

Leu Val Leu Glu Tyr Leu Met Gly Gly Ala Tyr Arg Cys Asn Tyr Thr
465                 470                 475                 480

Arg Lys Asn Phe Arg Thr Leu Tyr Asn Asn Leu Phe Gly Pro Lys Arg
                485                 490                 495

Pro Lys Ala Leu Lys Leu Leu Gly Met Glu Asp Asp Glu Pro Pro Ala
            500                 505                 510

Lys Gly Lys Lys Lys Lys Lys Lys Lys Glu Glu Glu Ile Asp Ile
        515                 520                 525

Asp Val Asp Asp Pro Ala Val Ser Arg Phe Gln Tyr Pro Phe His Glu
        530                 535                 540

Leu Met Val Trp Ala Val Leu Met Lys Arg Gln Lys Met Ala Val Phe
545                 550                 555                 560

Leu Trp Gln Arg Gly Glu Glu Ser Met Ala Lys Ala Leu Val Ala Cys
                565                 570                 575

Lys Leu Tyr Lys Ala Met Ala His Glu Ser Ser Glu Ser Asp Leu Val
            580                 585                 590

Asp Asp Ile Ser Gln Asp Leu Asp Asn Asn Ser Lys Asp Phe Gly Gln
        595                 600                 605
```

-continued

```
Leu Ala Leu Glu Leu Asp Gln Ser Tyr Lys His Asp Glu Gln Ile
    610             615                 620
Ala Met Lys Leu Leu Thr Tyr Glu Leu Lys Asn Trp Ser Asn Ser Thr
625                 630                 635                 640
Cys Leu Lys Leu Ala Val Ala Ala Lys His Arg Asp Phe Ile Ala His
                645                 650                 655
Thr Cys Ser Gln Met Leu Leu Thr Asp Met Trp Met Gly Arg Leu Arg
            660                 665                 670
Met Arg Lys Asn Pro Gly Leu Lys Val Ile Met Gly Ile Leu Leu Pro
        675                 680                 685
Pro Thr Ile Leu Phe Leu Glu Phe Arg Thr Tyr Asp Asp Phe Ser Tyr
    690                 695                 700
Gln Thr Ser Lys Glu Asn Glu Asp Gly Lys Glu Lys Glu Glu Asn
705                 710                 715                 720
Thr Asp Ala Asn Ala Asp Ala Gly Ser Arg Lys Gly Asp Glu Asn
                725                 730                 735
Glu His Lys Lys Gln Arg Ser Ile Pro Ile Gly Thr Lys Ile Cys Glu
            740                 745                 750
Phe Tyr Asn Ala Pro Ile Val Lys Phe Trp Phe Tyr Thr Ile Ser Tyr
            755                 760                 765
Leu Gly Tyr Leu Leu Phe Asn Tyr Val Ile Leu Val Arg Met Asp
770                 775                 780
Gly Trp Pro Ser Leu Gln Glu Trp Ile Val Ile Ser Tyr Ile Val Ser
785                 790                 795                 800
Leu Ala Leu Glu Lys Ile Arg Glu Ile Leu Met Ser Glu Pro Gly Lys
                805                 810                 815
Leu Ser Gln Lys Ile Lys Val Trp Leu Gln Glu Tyr Trp Asn Ile Thr
            820                 825                 830
Asp Leu Val Ala Ile Ser Thr Phe Met Ile Gly Ala Ile Leu Arg Leu
        835                 840                 845
Gln Asn Gln Pro Tyr Met Gly Tyr Gly Arg Val Ile Tyr Cys Val Asp
    850                 855                 860
Ile Ile Phe Trp Tyr Ile Arg Val Leu Asp Ile Phe Gly Val Asn Lys
865                 870                 875                 880
Tyr Leu Gly Pro Tyr Val Met Met Ile Gly Lys Met Met Ile Asp Met
                885                 890                 895
Leu Tyr Phe Val Val Ile Met Leu Val Val Leu Met Ser Phe Gly Val
            900                 905                 910
Ala Arg Gln Ala Ile Leu His Pro Glu Glu Lys Pro Ser Trp Lys Leu
        915                 920                 925
Ala Arg Asn Ile Phe Tyr Met Pro Tyr Trp Met Ile Tyr Gly Glu Val
    930                 935                 940
Phe Ala Asp Gln Ile Asp Leu Tyr Ala Met Glu Ile Asn Pro Pro Cys
945                 950                 955                 960
Gly Glu Asn Leu Tyr Asp Glu Glu Gly Lys Arg Leu Pro Pro Cys Ile
                965                 970                 975
Pro Gly Ala Trp Leu Thr Pro Ala Leu Met Ala Cys Tyr Leu Leu Val
            980                 985                 990
Ala Asn Ile Leu Leu Val Asn Leu Leu Ile Ala Val Phe Asn Asn Thr
        995                 1000                1005
Phe Phe Glu Val Lys Ser Ile Ser Asn Gln Val Trp Lys Phe Gln
    1010                1015                1020
Arg Tyr Gln Leu Ile Met Thr Phe His Asp Arg Pro Val Leu Pro
```

```
                    1025                1030                1035

Pro Pro Met Ile Ile Leu Ser His Ile Tyr Ile Ile Met Arg
    1040                1045                1050

Leu Ser Gly Arg Cys Arg Lys Lys Arg Glu Gly Asp Gln Glu Glu
    1055                1060                1065

Arg Asp Arg Gly Leu Lys Leu Phe Leu Ser Asp Glu Glu Leu Lys
    1070                1075                1080

Arg Leu His Glu Phe Glu Glu Gln Cys Val Gln Glu His Phe Arg
    1085                1090                1095

Glu Lys Glu Asp Glu Gln Gln Ser Ser Ser Asp Glu Arg Ile Arg
    1100                1105                1110

Val Thr Ser Glu Arg Val Glu Asn Met Ser Met Arg Leu Glu Glu
    1115                1120                1125

Ile Asn Glu Arg Glu Thr Phe Met Lys Thr Ser Leu Gln Thr Val
    1130                1135                1140

Asp Leu Arg Leu Ala Gln Leu Glu Glu Leu Ser Asn Arg Met Val
    1145                1150                1155

Asn Ala Leu Glu Asn Leu Ala Gly Ile Asp Arg Ser Asp Leu Ile
    1160                1165                1170

Gln Ala Arg Ser Arg Ala Ser Ser Glu Cys Glu Ala Thr Tyr Leu
    1175                1180                1185

Leu Arg Gln Ser Ser Ile Asn Ser Ala Asp Gly Tyr Ser Leu Tyr
    1190                1195                1200

Arg Tyr His Phe Asn Gly Glu Glu Leu Leu Phe Glu Asp Thr Ser
    1205                1210                1215

Leu Ser Thr Ser Pro Gly Thr Gly Val Arg Lys Lys Thr Cys Ser
    1220                1225                1230

Phe Arg Ile Lys Glu Glu Lys Asp Val Lys Thr His Leu Val Pro
    1235                1240                1245

Glu Cys Gln Asn Ser Leu His Leu Ser Leu Gly Thr Ser Thr Ser
    1250                1255                1260

Ala Thr Pro Asp Gly Ser His Leu Ala Val Asp Asp Leu Lys Asn
    1265                1270                1275

Ala Glu Glu Ser Lys Leu Gly Pro Asp Ile Gly Ile Ser Lys Glu
    1280                1285                1290

Asp Asp Glu Arg Gln Thr Asp Ser Lys Lys Glu Glu Thr Ile Ser
    1295                1300                1305

Pro Ser Leu Asn Lys Thr Asp Val Ile His Gly Gln Asp Lys Ser
    1310                1315                1320

Asp Val Gln Asn Thr Gln Leu Thr Val Glu Thr Thr Asn Ile Glu
    1325                1330                1335

Gly Thr Ile Ser Tyr Pro Leu Glu Glu Thr Lys Ile Thr Arg Tyr
    1340                1345                1350

Phe Pro Asp Glu Thr Ile Asn Ala Cys Lys Thr Met Lys Ser Arg
    1355                1360                1365

Ser Phe Val Tyr Ser Arg Gly Arg Lys Leu Val Gly Gly Val Asn
    1370                1375                1380

Gln Asp Val Glu Tyr Ser Ser Ile Thr Asp Gln Leu Thr Thr
    1385                1390                1395

Glu Trp Gln Cys Gln Val Gln Lys Ile Thr Arg Ser His Ser Thr
    1400                1405                1410

Asp Ile Pro Tyr Ile Val Ser Glu Ala Ala Val Gln Ala Glu Gln
    1415                1420                1425
```

```
Lys Glu  Gln Phe Ala Asp Met  Gln Asp Glu His  His Val Ala Glu
    1430             1435              1440

Ala Ile  Pro Arg Ile Pro Arg  Leu Ser Leu Thr  Ile Thr Asp Arg
    1445             1450              1455

Asn Gly  Met Glu Asn Leu Leu  Ser Val Lys Pro  Asp Gln Thr Leu
    1460             1465              1470

Gly Phe  Pro Ser Leu Arg Ser  Lys Ser Leu His  Gly His Pro Arg
    1475             1480              1485

Asn Val  Lys Ser Ile Gln Gly  Lys Leu Asp Arg  Ser Gly His Ala
    1490             1495              1500

Ser Ser  Val Ser Ser Leu Val  Ile Val Ser Gly  Met Thr Ala Glu
    1505             1510              1515

Glu Lys  Lys Val Lys Lys Glu  Lys Ala Ser Thr  Glu Thr Glu Cys
    1520             1525              1530

<210> SEQ ID NO 12
<211> LENGTH: 84
<212> TYPE: DNA
<213> ORGANISM: Homo sapiens
<220> FEATURE:
<221> NAME/KEY: misc_feature
<222> LOCATION: (82)..(84)
<223> OTHER INFORMATION: wherein "n" equals A, C, G, or T.

<400> SEQUENCE: 12
attacggtat tcggatggga atcagaagga caccaggaca ttgatttggc tatcctgaca      60
gctttactca aaggtaaaag annn                                            84

<210> SEQ ID NO 13
<211> LENGTH: 396
<212> TYPE: DNA
<213> ORGANISM: Homo sapiens
<220> FEATURE:
<221> NAME/KEY: misc_feature
<222> LOCATION: (394)..(396)
<223> OTHER INFORMATION: wherein "n" equals A, C, G, or T.

<400> SEQUENCE: 13
cctttccatg agctcatggt gtgggctgtt ctcatgaagc ggcagaagat ggccctgttc      60
ttctggcagc acggtgagga ggccatggcc aaggccctgg tggcctgcaa gctctgcaaa    120
gccatggctc atgaggcctc tgagaacgac atggttgacg acatttccca ggagctgaat    180
cacaattcca gagactttgg ccagctggct gtggagctcc tggaccagtc ctacaagcag    240
gacgaacagc tggccatgaa actgctgacg tatgagctga gaactggag caacgccacg     300 tgcctgcagc ttgccgtggc tgccaaacac cgcgacttca tcgcgcacac gtgcagccag    360
atgctgctca ccgacatgtg gatgggccgg ctcnnn                              396

<210> SEQ ID NO 14
<211> LENGTH: 537
<212> TYPE: DNA
<213> ORGANISM: Homo sapiens

<400> SEQUENCE: 14
ctggcgtata tcggatacct gatgctcttc aactatatcg tgttagtgaa gatggaacgc      60
tggccgtcca cccaggaatg gatcgtaatc tcctatattt tcaccctggg aatagaaaag    120
atgagagaga ttctgatgtc agagccaggg aagttgctac agaaagtgaa ggtatggctg    180
caggagtact ggaatgtcac ggacctcatc gccatccttc tgttttctgt cggaatgatc    240
```

```
cttcgtctcc aagaccagcc cttcaggagt gacgggaggg tcatctactg cgtgaacatc      300
atttactggt atatccgtct cctagacatc ttcggcgtga acaagtattt gggcccgtat      360
gtaatgatga ttggaaaaat gatgatagac atgatgtact ttgtcatcat tatgctggtg      420
gttctgatga gctttggggt cgccaggcaa gccatccttt tcccaatga ggagccatca       480 tggaaactgg ccaagaacat cttctacatg ccctattgga tgatttatgg ggaagtg         537
```

<210> SEQ ID NO 15
<211> LENGTH: 1463
<212> TYPE: DNA
<213> ORGANISM: Homo sapiens

<400> SEQUENCE: 15

```
atatttaatc acttaaatta gcagaataca tgccctctag ctctatgaag caggaacatg      60
aaccaaacac atttaggatg ttgcaaaaac taaaggcata gctgtataca gagactgttc      120
ggagttattt acataaaatg caaagctgac ttctgtagac tgttcggagt tatttccata     180
aaacacaaag tttacttctg taataagaag cagctttgcc acatgccaca cacacacgca     240
cactttgccc catgctgggg ccatcgccag ttctgcccct gcttgcctgg tgttgctgtg     300
ggcgtctgat aggccagcat gttggcctca cccccagtat ctccgtgctt cagaatgaga     360
aaaatgaaag tcgcctctcc cgaaatgaca tccagtctga aaagtggtcc atcagcaaac     420
acactcaact cagccctacg gatgcttttg ggaccattga gttccaagga ggtggccatt     480
ccaacaaagc catgtatgtg cgagtatctt ttgatacaaa acctgatctc ctcttacacc     540
tgatgaccaa ggaatggcag ttggagcttc ccaagcttct catctctgtc catggggcc      600 tgcagaactt tgaactccag ccaaaactca agcaagtctt tgggaaaggg ctcatcaaag     660
cagcaatgac aactggagcg tggatattca ctggaggggt taacacaggt gttattcgtc     720
atgttggcga tgccttgaag gatcatgcct ctaagtctcg aggaaagata tgcaccatag     780
gtattgcccc ctggggaatt gtggaaaacc aggaggacct cattggaaga gatgttgtcc     840
ggccatacca gaccatgtcc aatcccatga gcaagctcac tgttctcaac agcatgcatt     900
cccacttcat tctggctgac aacgggacca ctggaaaata tggagcagag gtgaaacttc     960
gaagacaact ggaaaagcat atttcactcc agaaagataaa cacaagatgc ctgccgtttt    1020
tctctcttga ctcccgcttg ttttattcat tttggggtag ttgccagtta gactcagttg     1080
gaatcggtca aggtgttcct gtggtggcac tcatagtgga aggaggaccc aatgtgatct     1140
cgattgtttt ggagtaccct cgagacaccc ctcccgtgcc agtggttgtc tgtgatggga     1200
gtggacgggc atcggacatc ctggccttg ggcataaata ctcagaagaa gcggactga      1260 taaatgaatc tttgagggac cagctgttgg tgactataca gaagactttc acatacactc     1320
gaacccaagc tcagcatctg ttcatcatcc tcatggagtg catgaagaag aaggaattga    1380
ttacggtatt tcggatggga tcagaaggac accaggacat tgatttggct atcctgacag     1440
ctttactcaa aggtaaaaga gtc                                              1463
```

<210> SEQ ID NO 16
<211> LENGTH: 461
<212> TYPE: PRT
<213> ORGANISM: Caenorhabditis elegans

<400> SEQUENCE: 16

```
Lys Phe Ile Phe Asp Leu Met Val Cys Gly Lys Thr Asn Asp Asn Glu
1               5                   10                  15
```

-continued

```
Pro Leu Gln Glu Phe Ile Leu Gln Ser Pro Ala Pro Ile Glu Thr Ala
             20                  25                  30
Val Lys Leu Ser Ala Leu Tyr Arg Asp Met Ser Glu Lys Glu Lys Glu
         35                  40                  45
Arg Ala Lys Asp Leu Leu Asn Val Ala Val Phe Ser Glu Asn Met Ala
     50                  55                  60
Val Glu Leu Leu Gly Ile Thr Ala Thr Glu Tyr Asn Ala Ala Leu Leu
 65                  70                  75                  80
Leu Lys Ala Lys Asp Asn Arg Gly Arg Pro Leu Leu Asp Val Leu Ile
                 85                  90                  95
Glu Asn Glu Gln Lys Glu Val Val Ser Tyr Ala Ser Val Gln Arg Tyr
            100                 105                 110
Leu Thr Glu Val Trp Thr Ala Arg Val Asp Trp Ser Phe Gly Lys Phe
        115                 120                 125
Val Ala Phe Ser Leu Phe Val Leu Ile Cys Pro Pro Ala Trp Phe Tyr
    130                 135                 140
Phe Ser Leu Pro Leu Asp Ser Arg Ile Gly Arg Ala Pro Ile Ile Lys
145                 150                 155                 160
Phe Val Cys His Ile Val Ser His Val Tyr Phe Thr Ile Leu Leu Thr
                165                 170                 175
Ile Val Val Leu Asn Ile Thr His Lys Met Tyr Glu Val Thr Ser Val
            180                 185                 190
Val Pro Asn Pro Val Glu Trp Leu Leu Leu Trp Leu Ser Gly Asn
        195                 200                 205
Leu Val Ser Glu Leu Ser Thr Val Gly Gly Ser Gly Leu Gly Ile
    210                 215                 220
Val Lys Val Leu Ile Leu Val Leu Ser Ala Met Ala Ile Ala Val His
225                 230                 235                 240
Val Leu Ala Phe Leu Leu Pro Ala Val Phe Leu Thr His Leu Asp Asn
                245                 250                 255
Asp Glu Lys Leu His Phe Ala Arg Thr Met Leu Tyr Leu Lys Asn Gln
            260                 265                 270
Leu Phe Ala Phe Ala Leu Leu Phe Ala Phe Val Glu Tyr Leu Asp Phe
        275                 280                 285
Leu Thr Val His His Leu Phe Gly Pro Trp Ala Ile Ile Ile Arg Asp
    290                 295                 300
Leu Met Tyr Asp Leu Ala Arg Phe Leu Val Ile Leu Met Leu Phe Val
305                 310                 315                 320
Ala Gly Phe Thr Leu His Val Thr Ser Ile Phe Gln Pro Ala Tyr Gln
                325                 330                 335
Pro Val Asp Glu Asp Ser Ala Glu Leu Met Arg Leu Ala Ser Pro Ser
            340                 345                 350
Gln Thr Leu Glu Met Leu Phe Phe Ser Leu Phe Gly Leu Val Glu Pro
        355                 360                 365
Asp Ser Met Pro Pro Leu His Leu Val Pro Asp Phe Ala Lys Ile Ile
    370                 375                 380
Leu Lys Leu Leu Phe Gly Ile Tyr Met Met Val Thr Leu Ile Val Leu
385                 390                 395                 400
Ile Asn Leu Leu Ile Ala Met Met Ser Asp Thr Tyr Gln Arg Ile Gln
                405                 410                 415
Ala Gln Ser Asp Lys Glu Trp Lys Phe Gly Arg Ala Ile Leu Ile Arg
            420                 425                 430
```

```
Gln Met Asn Lys Lys Ser Ala Thr Pro Ser Pro Ile Asn Met Leu Thr
        435                 440                 445

Lys Leu Ile Ile Val Leu Arg Val Ala Trp Arg Asn Arg
450                 455                 460
```

<210> SEQ ID NO 17
<211> LENGTH: 476
<212> TYPE: PRT
<213> ORGANISM: Drosophila melanogaster

<400> SEQUENCE: 17

```
Arg Phe Val Tyr Asn Leu Met Val Val Ser Lys Asn His Asn Asn Lys
1               5                   10                  15

Pro Ile Gln Glu Phe Val Leu Val Ser Pro Ala Pro Val Asp Thr Ala
            20                  25                  30

Ala Lys Leu Ser Asn Ile Tyr Ile Val Leu Ser Thr Lys Glu Lys Glu
        35                  40                  45

Arg Ala Lys Asp Leu Val Ala Ala Gly Lys Gln Cys Glu Ala Met Ala
    50                  55                  60

Thr Glu Leu Leu Ala Leu Ala Ala Gly Ser Asp Ser Ala Gly Lys Ile
65                  70                  75                  80

Leu Gln Ala Thr Asp Lys Arg Asn Val Glu Phe Leu Asp Val Leu Ile
                85                  90                  95

Glu Asn Glu Gln Lys Glu Val Ile Ala His Thr Val Val Gln Arg Tyr
            100                 105                 110

Leu Gln Glu Leu Trp His Gly Ser Leu Thr Trp Ala Ser Trp Lys Ile
        115                 120                 125

Leu Leu Leu Leu Val Ala Phe Ile Val Cys Pro Pro Val Trp Ile Gly
    130                 135                 140

Phe Thr Phe Pro Met Gly His Lys Phe Asn Lys Val Pro Ile Ile Lys
145                 150                 155                 160

Phe Met Ser Tyr Leu Thr Ser His Ile Tyr Leu Met Ile His Leu Ser
                165                 170                 175

Ile Val Gly Ile Thr Pro Ile Tyr Pro Val Leu Arg Leu Ser Leu Val
            180                 185                 190

Pro Tyr Trp Tyr Glu Val Gly Leu Leu Ile Trp Leu Ser Gly Leu Leu
        195                 200                 205

Leu Phe Glu Leu Thr Asn Pro Ser Asp Lys Ser Gly Leu Gly Ser Ile
    210                 215                 220

Lys Val Leu Val Leu Leu Leu Gly Met Ala Gly Val Gly Val His Val
225                 230                 235                 240

Ser Ala Phe Leu Phe Val Ser Lys Glu Tyr Trp Pro Thr Leu Val Tyr
                245                 250                 255

Cys Arg Asn Gln Cys Phe Ala Leu Ala Phe Leu Leu Ala Cys Val Gln
            260                 265                 270

Ile Leu Asp Phe Leu Ser Phe His His Leu Phe Gly Pro Trp Ala Ile
        275                 280                 285

Ile Ile Gly Asp Leu Leu Lys Asp Leu Ala Arg Phe Leu Ala Val Leu
    290                 295                 300

Ala Ile Phe Val Phe Gly Phe Ser Met His Ile Val Ala Leu Asn Gln
305                 310                 315                 320

Ser Phe Ala Asn Phe Ser Pro Glu Asp Leu Arg Ser Phe Glu Lys Lys
                325                 330                 335

Asn Arg Asn Arg Gly Tyr Phe Ser Asp Val Arg Met His Pro Ile Asn
            340                 345                 350
```

```
Ser Phe Glu Leu Leu Phe Phe Ala Val Phe Gly Gln Thr Thr Thr Glu
            355                 360                 365

Gln Thr Gln Val Asp Lys Ile Lys Asn Val Ala Thr Pro Thr Gln Pro
        370                 375                 380

Tyr Trp Val Glu Tyr Leu Phe Lys Ile Val Phe Gly Ile Tyr Met Leu
385                 390                 395                 400

Val Ser Val Val Val Leu Ile Asn Leu Leu Ile Ala Met Met Ser Asp
                405                 410                 415

Thr Tyr Gln Arg Ile Gln Val Val Leu Leu Asn Ala Leu Leu Ser Asn
            420                 425                 430

Ser Thr Leu Phe Ile Asn Ser Tyr Phe Asn His Lys Tyr Ile Asn Phe
        435                 440                 445

Ile Leu His Cys Val Leu Ile Ile Leu Tyr Phe Ser Ile Arg Ser Lys
    450                 455                 460

Phe Thr Tyr Glu Asp Asp Leu Tyr Phe Leu Asp Ile
465                 470                 475
```

<210> SEQ ID NO 18
<211> LENGTH: 862
<212> TYPE: PRT
<213> ORGANISM: Mus musculus

<400> SEQUENCE: 18

```
Met Leu Gly Ser Asn Thr Phe Lys Asn Met Gln Arg Arg His Thr Thr
1               5                   10                  15

Leu Arg Glu Lys Gly Arg Arg Gln Ala Ile Arg Gly Pro Ala Tyr Met
            20                  25                  30

Phe Asn Glu Lys Gly Thr Ser Leu Thr Pro Glu Glu Glu Arg Phe Leu
        35                  40                  45

Asp Ser Ala Glu Tyr Gly Asn Ile Pro Val Val Arg Lys Met Leu Glu
    50                  55                  60

Glu Ser Lys Thr Leu Asn Phe Asn Cys Val Asp Tyr Met Gly Gln Asn
65                  70                  75                  80

Ala Leu Gln Leu Ala Val Gly Asn Glu His Leu Glu Val Thr Glu Leu
                85                  90                  95

Leu Leu Lys Lys Glu Asn Leu Ala Arg Val Gly Asp Ala Leu Leu Leu
            100                 105                 110

Ala Ile Ser Lys Gly Tyr Val Arg Ile Val Glu Ala Ile Leu Ser His
        115                 120                 125

Pro Ala Phe Ala Gln Gly Gln Arg Leu Thr Leu Ser Pro Leu Glu Gln
    130                 135                 140

Glu Leu Arg Asp Asp Asp Phe Tyr Ala Tyr Asp Glu Asp Gly Thr Arg
145                 150                 155                 160

Phe Ser His Asp Ile Thr Pro Ile Ile Leu Ala Ala His Cys Gln Glu
                165                 170                 175

Tyr Glu Ile Val His Ile Leu Leu Lys Gly Ala Arg Ile Glu Arg
            180                 185                 190

Pro His Asp Tyr Phe Cys Lys Cys Asn Glu Cys Thr Glu Lys Gln Arg
        195                 200                 205

Lys Asp Ser Phe Ser His Ser Arg Ser Arg Met Asn Ala Tyr Lys Gly
    210                 215                 220

Leu Ala Ser Ala Ala Tyr Leu Ser Leu Ser Ser Glu Asp Pro Val Leu
225                 230                 235                 240

Thr Ala Leu Glu Leu Ser Asn Glu Leu Ala Arg Leu Ala Asn Ile Glu
```

-continued

```
                245                 250                 255
Thr Glu Phe Lys Asn Asp Tyr Arg Lys Leu Ser Met Gln Cys Lys Asp
                260                 265                 270
Phe Val Val Gly Val Leu Asp Leu Cys Arg Asp Thr Glu Glu Val Glu
                275                 280                 285
Ala Ile Leu Asn Gly Asp Val Asn Leu Gln Val Trp Ser Asp His His
                290                 295                 300
Arg Pro Ser Leu Ser Arg Ile Lys Leu Ala Ile Lys Tyr Glu Val Lys
305                 310                 315                 320
Lys Phe Val Ala His Pro Asn Cys Gln Gln Leu Leu Thr Met Trp
                325                 330                 335
Tyr Glu Asn Leu Ser Gly Leu Arg Gln Gln Ser Ile Ala Val Lys Phe
                340                 345                 350
Leu Ala Val Phe Gly Val Ser Ile Gly Leu Pro Phe Leu Ala Ile Ala
                355                 360                 365
Tyr Trp Ile Ala Pro Cys Ser Lys Leu Gly Gln Thr Leu Arg Ser Pro
                370                 375                 380
Phe Met Lys Phe Val Ala His Ala Val Ser Phe Thr Ile Phe Leu Gly
385                 390                 395                 400
Leu Leu Val Val Asn Ala Ser Asp Arg Phe Glu Gly Val Lys Thr Leu
                405                 410                 415
Pro Asn Glu Thr Phe Thr Asp Tyr Pro Lys Gln Ile Phe Arg Val Lys
                420                 425                 430
Thr Thr Gln Phe Ser Trp Thr Glu Met Leu Ile Met Lys Trp Val Leu
                435                 440                 445
Gly Met Ile Trp Ser Glu Cys Lys Glu Ile Trp Glu Glu Gly Pro Arg
                450                 455                 460
Glu Tyr Val Leu His Leu Trp Asn Leu Leu Asp Phe Gly Met Leu Ser
465                 470                 475                 480
Ile Phe Val Ala Ser Phe Thr Ala Arg Phe Met Ala Phe Leu Lys Ala
                485                 490                 495
Ser Glu Ala Gln Leu Tyr Val Asp Gln Tyr Val Gln Asp Val Thr Leu
                500                 505                 510
His Asn Val Ser Leu Pro Pro Glu Val Ala Tyr Phe Thr Tyr Ala Arg
                515                 520                 525
Asp Lys Trp Trp Pro Ser Asp Pro Gln Ile Ile Ser Glu Gly Leu Tyr
                530                 535                 540
Ala Ile Ala Val Val Leu Ser Phe Ser Arg Ile Ala Tyr Ile Leu Pro
545                 550                 555                 560
Ala Asn Glu Ser Phe Gly Pro Leu Gln Ile Ser Leu Gly Arg Thr Val
                565                 570                 575
Lys Asp Ile Phe Lys Phe Met Val Ile Phe Ile Met Val Phe Val Ala
                580                 585                 590
Phe Met Ile Gly Met Phe Asn Leu Tyr Ser Tyr Arg Gly Ala Lys
                595                 600                 605
Tyr Asn Pro Ala Phe Thr Thr Val Glu Glu Ser Phe Lys Thr Leu Phe
                610                 615                 620
Trp Ser Ile Phe Gly Leu Ser Glu Val Ile Ser Val Val Leu Lys Tyr
625                 630                 635                 640
Asp His Lys Phe Ile Glu Asn Ile Gly Tyr Val Leu Tyr Gly Val Tyr
                645                 650                 655
Asn Val Thr Met Val Val Val Leu Leu Asn Met Leu Ile Ala Met Ile
                660                 665                 670
```

-continued

```
Asn Asn Ser Tyr Gln Glu Ile Glu Glu Asp Ala Asp Val Glu Trp Lys
            675                 680                 685

Phe Ala Arg Ala Lys Leu Trp Leu Ser Tyr Phe Asp Glu Gly Arg Thr
        690                 695                 700

Leu Pro Ala Pro Phe Asn Leu Val Pro Ser Pro Lys Ser Phe Tyr Tyr
705                 710                 715                 720

Leu Ile Met Arg Ile Lys Met Cys Leu Ile Glu Leu Cys Gln Ser Lys
                725                 730                 735

Ala Lys Arg Cys Glu Asn Asp Leu Glu Met Gly Met Leu Asn Ser Lys
            740                 745                 750

Phe Arg Lys Thr Arg Tyr Gln Ala Gly Met Arg Asn Ser Glu Asn Leu
        755                 760                 765

Thr Ala Asn Ser Thr Phe Ser Lys Pro Thr Arg Tyr Gln Lys Ile Met
770                 775                 780

Lys Arg Leu Ile Lys Arg Tyr Val Leu Lys Ala Gln Val Asp Arg Glu
785                 790                 795                 800

Asn Asp Glu Val Asn Glu Gly Glu Leu Lys Glu Ile Lys Gln Asp Ile
                805                 810                 815

Ser Ser Leu Arg Tyr Glu Leu Leu Glu Glu Lys Ser Gln Ala Thr Gly
            820                 825                 830

Glu Leu Ala Asp Leu Ile Gln Gln Leu Ser Glu Lys Phe Gly Lys Asn
        835                 840                 845

Leu Asn Lys Asp His Leu Arg Val Asn Gln Gly Lys Asp Ile
850                 855                 860

<210> SEQ ID NO 19
<211> LENGTH: 930
<212> TYPE: PRT
<213> ORGANISM: Mus musculus

<400> SEQUENCE: 19

Met Ser Gln Ser Pro Arg Phe Val Thr Arg Arg Gly Gly Ser Leu Lys
1               5                   10                  15

Ala Ala Pro Gly Ala Gly Thr Arg Arg Asn Glu Ser Gln Asp Tyr Leu
            20                  25                  30

Leu Met Asp Glu Leu Gly Asp Asp Gly Tyr Pro Gln Leu Pro Leu Pro
        35                  40                  45

Pro Tyr Gly Tyr Tyr Pro Ser Phe Arg Gly Asn Glu Asn Arg Leu Thr
    50                  55                  60

His Arg Arg Gln Thr Ile Leu Arg Glu Lys Gly Arg Arg Leu Ala Asn
65                  70                  75                  80

Arg Gly Pro Ala Tyr Met Phe Asn Asp His Ser Thr Ser Leu Ser Ile
                85                  90                  95

Glu Glu Glu Arg Phe Leu Asp Ala Val Glu Tyr Gly Asn Ile Pro Val
            100                 105                 110

Val Trp Lys Met Leu Glu Glu Cys His Ser Leu Asn Val Asn Cys Val
        115                 120                 125

Asp Tyr Met Gly Gln Asn Ala Leu Gln Leu Ala Val Ala Asn Glu His
    130                 135                 140

Leu Glu Ile Thr Glu Leu Leu Leu Lys Lys Glu Asn Leu Ser Arg Val
145                 150                 155                 160

Gly Asp Ala Leu Leu Leu Ala Ile Ser Lys Gly Tyr Val Arg Ile Val
                165                 170                 175

Glu Ala Ile Leu Asn His Pro Ser Phe Ala Glu Gly Lys Arg Leu Ala
```

-continued

```
                180                 185                 190
Thr Ser Pro Ser Gln Ser Glu Leu Gln Gln Asp Asp Phe Tyr Ala Tyr
            195                 200                 205
Asp Glu Asp Gly Thr Arg Phe Ser His Asp Val Thr Pro Ile Ile Leu
210                 215                 220
Ala Ala His Cys Gln Glu Tyr Glu Ile Val His Thr Leu Leu Arg Lys
225                 230                 235                 240
Gly Ala Arg Ile Glu Arg Pro His Asp Tyr Phe Cys Lys Cys Thr Glu
                245                 250                 255
Cys Ser Gln Lys Gln Lys His Asp Ser Phe Ser His Ser Arg Ser Arg
            260                 265                 270
Ile Asn Ala Tyr Lys Gly Leu Ala Ser Pro Ala Tyr Leu Ser Leu Ser
        275                 280                 285
Ser Glu Asp Pro Val Met Thr Ala Leu Glu Leu Ser Asn Glu Leu Ala
    290                 295                 300
Val Leu Ala Asn Ile Glu Lys Glu Phe Lys Asn Asp Tyr Arg Lys Leu
305                 310                 315                 320
Ser Met Gln Cys Lys Asp Phe Val Val Gly Leu Leu Asp Leu Cys Arg
                325                 330                 335
Asn Thr Glu Glu Val Glu Ala Ile Leu Asn Gly Asp Ala Glu Thr Arg
            340                 345                 350
Gln Pro Gly Asp Phe Gly Arg Pro Asn Leu Ser Arg Leu Lys Leu Ala
        355                 360                 365
Ile Lys Asp Glu Val Lys Lys Phe Val Ala His Pro Asn Cys Gln Gln
    370                 375                 380
Gln Leu Leu Ser Ile Trp Tyr Glu Asn Leu Ser Gly Leu Arg Gln Gln
385                 390                 395                 400
Thr Met Ala Val Lys Phe Leu Val Leu Ala Val Ala Ile Gly Leu
                405                 410                 415
Pro Phe Leu Ala Leu Ile Tyr Trp Cys Ala Pro Cys Ser Lys Met Gly
            420                 425                 430
Lys Ile Leu Pro Arg Pro Phe Met Lys Phe Val Ala His Ala Ala Ser
        435                 440                 445
Phe Thr Ile Phe Leu Gly Leu Leu Val Met Asn Ala Ala Asp Arg Phe
    450                 455                 460
Glu Gly Thr Lys Leu Leu Pro Asn Glu Thr Ser Thr Asp Asn Ala Arg
465                 470                 475                 480
Gln Leu Phe Arg Met Lys Thr Ser Cys Phe Ser Trp Met Glu Met Leu
                485                 490                 495
Ile Ile Ser Trp Val Ile Gly Met Ile Trp Ala Glu Cys Lys Glu Ile
            500                 505                 510
Trp Thr Gln Gly Pro Lys Glu Tyr Leu Phe Glu Leu Trp Asn Met Leu
        515                 520                 525
Asp Phe Gly Met Leu Ala Ile Phe Ala Ala Ser Phe Ile Ala Arg Phe
    530                 535                 540
Met Ala Phe Trp His Ala Ser Lys Ala Gln Ser Ile Ile Asp Ala Asn
545                 550                 555                 560
Asp Thr Leu Lys Asp Leu Thr Lys Val Thr Leu Gly Asp Asn Val Lys
                565                 570                 575
Tyr Tyr Asn Leu Ala Arg Ile Lys Trp Asp Pro Thr Asp Pro Gln Ile
            580                 585                 590
Ile Ser Glu Gly Leu Tyr Ala Ile Ala Val Val Leu Ser Phe Ser Arg
        595                 600                 605
```

Ile Ala Tyr Ile Leu Pro Ala Asn Glu Ser Phe Gly Pro Leu Gln Ile
    610                 615                 620

Ser Leu Gly Arg Thr Val Lys Asp Ile Phe Lys Phe Met Val Ile Phe
625                 630                 635                 640

Ile Met Val Phe Val Ala Phe Met Ile Gly Met Phe Asn Leu Tyr Ser
                645                 650                 655

Tyr Tyr Ile Gly Ala Lys Gln Asn Glu Ala Phe Thr Thr Val Glu Glu
            660                 665                 670

Ser Phe Lys Thr Leu Phe Trp Ala Ile Phe Gly Leu Ser Glu Val Lys
        675                 680                 685

Ser Val Val Ile Asn Tyr Asn His Lys Phe Ile Glu Asn Ile Gly Tyr
    690                 695                 700

Val Leu Tyr Gly Val Tyr Asn Val Thr Met Val Ile Val Leu Leu Asn
705                 710                 715                 720

Met Leu Ile Ala Met Ile Asn Ser Ser Phe Gln Glu Ile Glu Asp Asp
                725                 730                 735

Ala Asp Val Glu Trp Lys Phe Ala Arg Ala Lys Leu Trp Phe Ser Tyr
            740                 745                 750

Phe Glu Glu Gly Arg Thr Leu Pro Val Pro Phe Asn Leu Val Pro Ser
        755                 760                 765

Pro Lys Ser Leu Leu Tyr Leu Leu Leu Lys Phe Lys Lys Trp Met Cys
    770                 775                 780

Glu Leu Ile Gln Gly Gln Lys Gln Gly Phe Gln Glu Asp Ala Glu Met
785                 790                 795                 800

Asn Lys Arg Asn Glu Glu Lys Lys Phe Gly Ile Ser Gly Ser His Glu
                805                 810                 815

Asp Leu Ser Lys Phe Ser Leu Asp Lys Asn Gln Leu Ala His Asn Lys
            820                 825                 830

Gln Ser Ser Thr Arg Ser Ser Glu Asp Tyr His Leu Asn Ser Phe Ser
        835                 840                 845

Asn Pro Pro Arg Gln Tyr Gln Lys Ile Met Lys Arg Leu Ile Lys Arg
    850                 855                 860

Tyr Val Leu Gln Ala Gln Ile Asp Lys Glu Ser Asp Glu Val Asn Glu
865                 870                 875                 880

Gly Glu Leu Lys Glu Ile Lys Gln Asp Ile Ser Ser Leu Arg Tyr Glu
                885                 890                 895

Leu Leu Glu Glu Lys Ser Gln Asn Ser Glu Asp Leu Ala Glu Leu Ile
            900                 905                 910

Arg Lys Leu Gly Glu Arg Leu Ser Leu Glu Pro Lys Leu Glu Glu Ser
        915                 920                 925

Arg Arg
    930

<210> SEQ ID NO 20
<211> LENGTH: 836
<212> TYPE: PRT
<213> ORGANISM: Mus musculus

<400> SEQUENCE: 20

Met Arg Asp Lys Gly Arg Arg Gln Ala Val Arg Gly Pro Ala Phe Met
1               5                   10                  15

Phe Gly Ala Arg Gly Pro Ser Leu Thr Ala Glu Glu Arg Phe Leu
            20                  25                  30

Asp Ala Ala Glu Tyr Gly Asn Ile Pro Val Val Arg Lys Met Leu Glu

-continued

```
                35                  40                  45
Glu Ser Arg Thr Leu Asn Val Asn Cys Val Asp Tyr Met Gly Gln Asn
 50                  55                  60

Ala Leu Gln Leu Ala Val Gly Asn Glu His Leu Glu Val Thr Glu Leu
65                  70                  75                  80

Leu Leu Lys Lys Glu Asn Leu Ala Arg Ile Gly Asp Ala Leu Leu Leu
                85                  90                  95

Ala Ile Ser Lys Gly Tyr Val Arg Ile Val Glu Ala Ile Leu Gly His
                100                 105                 110

Pro Gly Phe Ala Ala Ser Arg Arg Leu Thr Leu Ser Pro Cys Glu Gln
                115                 120                 125

Glu Leu Arg Asp Asp Asp Phe Tyr Ala Tyr Asp Glu Asp Gly Thr Arg
        130                 135                 140

Phe Ser Pro Asp Ile Thr Pro Ile Ile Leu Ala Ala His Cys His Lys
145                 150                 155                 160

Tyr Glu Val Val His Leu Leu Leu Lys Gly Ala Arg Ile Glu Arg
                165                 170                 175

Ala His Asp Tyr Phe Cys Arg Cys Ser Asp Cys Ala Glu Lys Gln Arg
                180                 185                 190

Leu Asp Ala Phe Ser His Ser Arg Ser Arg Ile Asn Ala Tyr Lys Gly
        195                 200                 205

Leu Ala Ser Pro Ala Tyr Leu Ser Leu Ser Ser Glu Asp Pro Val Leu
210                 215                 220

Thr Ala Leu Glu Leu Ser Asn Glu Leu Ala Lys Leu Ala Asn Ile Glu
225                 230                 235                 240

Lys Glu Phe Lys Asn Asp Tyr Arg Lys Leu Ser Met Gln Cys Lys Asp
                245                 250                 255

Phe Val Val Gly Val Leu Asp Leu Cys Arg Asp Ser Glu Glu Val Glu
                260                 265                 270

Ala Ile Leu Asn Gly Asp Leu Glu Ser Ala Glu Pro Leu Glu Arg His
        275                 280                 285

Gly His Lys Ala Ser Leu Ser Arg Val Lys Leu Ala Ile Lys Tyr Glu
        290                 295                 300

Val Lys Lys Phe Val Ala His Pro Asn Cys Gln Gln Gln Leu Leu Thr
305                 310                 315                 320

Ile Trp Tyr Glu Asn Leu Ser Gly Leu Arg Glu Gln Thr Ile Ala Ile
                325                 330                 335

Lys Cys Leu Val Val Leu Val Val Ala Leu Gly Leu Pro Phe Leu Ala
                340                 345                 350

Ile Gly Tyr Trp Ile Ala Pro Cys Ser Arg Leu Gly Lys Ile Leu Arg
                355                 360                 365

Ser Pro Phe Met Lys Phe Val Ala His Ala Ala Ser Phe Ile Ile Phe
        370                 375                 380

Leu Gly Leu Leu Val Phe Asn Ala Ser Asp Arg Phe Glu Gly Ile Thr
385                 390                 395                 400

Thr Leu Pro Asn Ile Thr Val Ile Asp Tyr Pro Lys Gln Ile Phe Arg
                405                 410                 415

Val Lys Thr Thr Gln Phe Thr Trp Thr Glu Met Leu Ile Met Val Trp
                420                 425                 430

Val Leu Gly Met Met Trp Ser Glu Cys Lys Glu Leu Trp Leu Glu Gly
        435                 440                 445

Pro Arg Glu Tyr Ile Val Gln Leu Trp Asn Val Leu Asp Phe Gly Met
450                 455                 460
```

```
Leu Ser Ile Phe Ile Ala Ala Phe Thr Ala Arg Phe Leu Ala Phe Leu
465                 470                 475                 480

Gln Ala Thr Lys Ala Gln Gln Tyr Val Asp Ser His Val Gln Glu Ser
                485                 490                 495

Asp Leu Ser Glu Val Thr Leu Pro Pro Glu Val Gln Tyr Phe Thr Tyr
            500                 505                 510

Ala Arg Asp Lys Trp Leu Pro Ser Asp Pro Gln Ile Ile Ser Glu Gly
            515                 520                 525

Leu Tyr Ala Ile Ala Val Val Leu Ser Phe Ser Arg Ile Ala Tyr Ile
530                 535                 540

Leu Pro Ala Asn Glu Ser Phe Gly Pro Leu Gln Ile Ser Leu Gly Arg
545                 550                 555                 560

Thr Val Lys Asp Ile Phe Lys Phe Met Val Leu Phe Ile Met Val Phe
                565                 570                 575

Leu Ala Phe Met Ile Gly Met Phe Ile Leu Tyr Ser Tyr Tyr Leu Gly
                580                 585                 590

Ala Lys Val Asn Pro Ala Phe Thr Thr Val Glu Glu Ser Phe Lys Thr
                595                 600                 605

Leu Phe Trp Ser Ile Phe Gly Leu Ser Glu Val Thr Ser Val Val Leu
610                 615                 620

Lys Tyr Asp His Lys Phe Ile Glu Asn Ile Gly Tyr Val Leu Tyr Gly
625                 630                 635                 640

Ile Tyr Asn Val Thr Met Val Val Leu Leu Asn Met Leu Ile Ala
                645                 650                 655

Met Ile Asn Ser Ser Tyr Gln Glu Ile Glu Asp Asp Ser Asp Val Glu
                660                 665                 670

Trp Lys Phe Ala Arg Ser Lys Leu Trp Leu Ser Tyr Phe Asp Asp Gly
                675                 680                 685

Lys Thr Leu Pro Pro Pro Phe Ser Leu Val Pro Ser Pro Lys Ser Phe
            690                 695                 700

Val Tyr Phe Ile Met Arg Ile Thr Asn Phe Ser Lys Cys Arg Arg Arg
705                 710                 715                 720

Arg Leu Gln Lys Asp Leu Glu Leu Gly Met Gly Asn Ser Lys Ser Arg
                725                 730                 735

Leu Asn Leu Phe Thr Gln Ser Asn Ser Arg Val Phe Glu Ser His Ser
                740                 745                 750

Phe Asn Ser Ile Leu Asn Gln Pro Thr Arg Tyr Gln Gln Ile Met Lys
                755                 760                 765

Arg Leu Ile Lys Arg Tyr Val Leu Lys Ala Gln Val Asp Lys Glu Asn
            770                 775                 780

Asp Glu Val Asn Glu Gly Glu Leu Lys Glu Ile Lys Gln Asp Ile Ser
785                 790                 795                 800

Ser Leu Arg Tyr Glu Leu Leu Glu Asp Lys Ser Gln Ala Thr Glu Glu
                805                 810                 815

Leu Ala Ile Leu Ile His Lys Leu Ser Glu Lys Leu Asn Pro Ser Val
                820                 825                 830

Leu Arg Cys Glu
            835

<210> SEQ ID NO 21
<211> LENGTH: 1503
<212> TYPE: PRT
<213> ORGANISM: Homo sapiens
```

```
<400> SEQUENCE: 21

Met Glu Pro Ser Ala Leu Arg Lys Ala Gly Ser Glu Gln Glu Glu Gly
1               5                   10                  15

Phe Glu Gly Leu Pro Arg Arg Val Thr Asp Leu Gly Met Val Ser Asn
            20                  25                  30

Leu Arg Arg Ser Asn Ser Ser Leu Phe Lys Ser Trp Arg Leu Gln Cys
        35                  40                  45

Pro Phe Gly Asn Asn Asp Lys Gln Glu Ser Leu Ser Ser Trp Ile Pro
    50                  55                  60

Glu Asn Ile Lys Lys Glu Cys Val Tyr Phe Val Glu Ser Ser Lys
65                  70                  75                  80

Leu Ser Asp Ala Gly Lys Val Val Cys Gln Cys Gly Tyr Thr His Glu
                85                  90                  95

Gln His Leu Glu Glu Ala Thr Lys Pro His Thr Phe Gln Gly Thr Gln
            100                 105                 110

Trp Asp Pro Lys Lys His Val Gln Glu Met Pro Thr Asp Ala Phe Gly
        115                 120                 125

Asp Ile Val Phe Thr Gly Leu Ser Gln Lys Val Lys Lys Tyr Val Arg
    130                 135                 140

Val Ser Gln Asp Thr Pro Ser Ser Val Ile Tyr His Leu Met Thr Gln
145                 150                 155                 160

His Trp Gly Leu Asp Val Pro Asn Leu Leu Ile Ser Val Thr Gly Gly
                165                 170                 175

Ala Lys Asn Phe Asn Met Lys Pro Arg Leu Lys Ser Ile Phe Arg Arg
            180                 185                 190

Gly Leu Val Lys Val Ala Gln Thr Thr Gly Ala Trp Ile Ile Thr Gly
        195                 200                 205

Gly Ser His Thr Gly Val Met Lys Gln Val Gly Glu Ala Val Arg Asp
    210                 215                 220

Phe Ser Leu Ser Ser Ser Tyr Lys Glu Gly Glu Leu Ile Thr Ile Gly
225                 230                 235                 240

Val Ala Thr Trp Gly Thr Val His Arg Arg Glu Gly Leu Ile His Pro
                245                 250                 255

Thr Gly Ser Phe Pro Ala Glu Tyr Ile Leu Asp Glu Asp Gly Gln Gly
            260                 265                 270

Asn Leu Thr Cys Leu Asp Ser Asn His Ser His Phe Ile Leu Val Asp
        275                 280                 285

Asp Gly Thr His Gly Gln Tyr Gly Val Glu Ile Pro Leu Arg Thr Arg
    290                 295                 300

Leu Glu Lys Phe Ile Ser Glu Gln Thr Lys Glu Arg Gly Gly Val Ala
305                 310                 315                 320

Ile Lys Ile Pro Ile Val Cys Val Val Leu Glu Gly Gly Pro Gly Thr
                325                 330                 335

Leu His Thr Ile Asp Asn Ala Thr Thr Asn Gly Thr Pro Cys Val Val
            340                 345                 350

Val Glu Gly Ser Gly Arg Val Ala Asp Val Ile Ala Gln Val Ala Asn
        355                 360                 365

Leu Pro Val Ser Asp Ile Thr Ile Ser Leu Ile Gln Gln Lys Leu Ser
    370                 375                 380

Val Phe Phe Gln Glu Met Phe Glu Thr Phe Thr Glu Ser Arg Ile Val
385                 390                 395                 400

Glu Trp Thr Lys Lys Ile Gln Asp Ile Val Arg Arg Arg Gln Leu Leu
                405                 410                 415
```

-continued

```
Thr Val Phe Arg Glu Gly Lys Asp Gly Gln Gln Asp Val Asp Val Ala
            420                 425                 430

Ile Leu Gln Ala Leu Leu Lys Ala Ser Arg Ser Gln Asp His Phe Gly
            435                 440                 445

His Glu Asn Trp Asp His Gln Leu Lys Leu Ala Val Ala Trp Asn Arg
        450                 455                 460

Val Asp Ile Ala Arg Ser Glu Ile Phe Met Asp Glu Trp Gln Trp Lys
465                 470                 475                 480

Pro Ser Asp Leu His Pro Thr Met Thr Ala Ala Leu Ile Ser Asn Lys
                485                 490                 495

Pro Glu Phe Val Lys Leu Phe Leu Glu Asn Gly Val Gln Leu Lys Glu
            500                 505                 510

Phe Val Thr Trp Asp Thr Leu Leu Tyr Leu Tyr Glu Asn Leu Asp Pro
            515                 520                 525

Ser Cys Leu Phe His Ser Lys Leu Gln Lys Val Leu Val Glu Asp Pro
        530                 535                 540

Glu Arg Pro Ala Cys Ala Pro Ala Ala Pro Arg Leu Gln Met His His
545                 550                 555                 560

Val Ala Gln Val Leu Arg Glu Leu Leu Gly Asp Phe Thr Gln Pro Leu
                565                 570                 575

Tyr Pro Arg Pro Arg His Asn Asp Arg Leu Arg Leu Leu Leu Pro Val
            580                 585                 590

Pro His Val Lys Leu Asn Val Gln Gly Val Ser Leu Arg Ser Leu Tyr
        595                 600                 605

Lys Arg Ser Ser Gly His Val Thr Phe Thr Met Asp Pro Ile Arg Asp
        610                 615                 620

Leu Leu Ile Trp Ala Ile Val Gln Asn Arg Arg Glu Leu Ala Gly Ile
625                 630                 635                 640

Ile Trp Ala Gln Ser Gln Asp Cys Ile Ala Ala Leu Ala Cys Ser
                645                 650                 655

Lys Ile Leu Lys Glu Leu Ser Lys Glu Glu Asp Thr Asp Ser Ser
            660                 665                 670

Glu Glu Met Leu Ala Leu Ala Glu Glu Tyr Glu His Arg Ala Ile Gly
            675                 680                 685

Val Phe Thr Glu Cys Tyr Arg Lys Asp Glu Glu Arg Ala Gln Lys Leu
        690                 695                 700

Leu Thr Arg Val Ser Glu Ala Trp Gly Lys Thr Thr Cys Leu Gln Leu
705                 710                 715                 720

Ala Leu Glu Ala Lys Asp Met Lys Phe Val Ser His Gly Gly Ile Gln
                725                 730                 735

Ala Phe Leu Thr Lys Val Trp Trp Gly Gln Leu Ser Val Asp Asn Gly
            740                 745                 750

Leu Trp Arg Val Thr Leu Cys Met Leu Ala Phe Pro Leu Leu Leu Thr
            755                 760                 765

Gly Leu Ile Ser Phe Arg Glu Lys Arg Leu Gln Asp Val Gly Thr Pro
        770                 775                 780

Ala Ala Arg Ala Arg Ala Phe Phe Thr Ala Pro Val Val Phe His
785                 790                 795                 800

Leu Asn Ile Leu Ser Tyr Phe Ala Phe Leu Cys Leu Phe Ala Tyr Val
                805                 810                 815

Leu Met Val Asp Phe Gln Pro Val Pro Ser Trp Cys Glu Cys Ala Ile
            820                 825                 830
```

-continued

```
Tyr Leu Trp Leu Phe Ser Leu Val Cys Glu Glu Met Arg Gln Leu Phe
        835                 840                 845

Tyr Asp Pro Asp Glu Cys Gly Leu Met Lys Lys Ala Ala Leu Tyr Phe
    850                 855                 860

Ser Asp Phe Trp Asn Lys Leu Asp Val Gly Ala Ile Leu Leu Phe Val
865                 870                 875                 880

Ala Gly Leu Thr Cys Arg Leu Ile Pro Ala Thr Leu Tyr Pro Gly Arg
                885                 890                 895

Val Ile Leu Ser Leu Asp Phe Ile Leu Phe Cys Leu Arg Leu Met His
            900                 905                 910

Ile Phe Thr Ile Ser Lys Thr Leu Gly Pro Lys Ile Ile Val Lys
        915                 920                 925

Arg Met Met Lys Asp Val Phe Phe Leu Phe Leu Leu Ala Val Trp
    930                 935                 940

Val Val Ser Phe Gly Val Ala Lys Gln Ala Ile Leu Ile His Asn Glu
945                 950                 955                 960

Arg Arg Val Asp Trp Leu Phe Arg Gly Ala Val Tyr His Ser Tyr Leu
                965                 970                 975

Thr Ile Phe Gly Gln Ile Pro Gly Tyr Ile Asp Gly Val Asn Phe Asn
            980                 985                 990

Pro Glu His Cys Ser Pro Asn Gly  Thr Asp Pro Tyr Lys  Pro Lys Cys
            995                 1000                1005

Pro Glu  Ser Asp Ala Thr Gln  Gln Arg Pro Ala Phe  Pro Glu Trp
    1010                1015                1020

Leu Thr  Val Leu Leu Leu Cys  Leu Tyr Leu Leu Phe  Thr Asn Ile
    1025                1030                1035

Leu Leu  Leu Asn Leu Leu Ile  Ala Met Phe Asn Tyr  Thr Phe Gln
    1040                1045                1050

Gln Val  Gln Glu His Thr Asp  Gln Ile Trp Lys Phe  Gln Arg His
    1055                1060                1065

Asp Leu  Ile Glu Glu Tyr His  Gly Arg Pro Ala Ala  Pro Pro Pro
    1070                1075                1080

Phe Ile  Leu Leu Ser His Leu  Gln Leu Phe Ile Lys  Arg Val Val
    1085                1090                1095

Leu Lys  Thr Pro Ala Lys Arg  His Lys Gln Leu Lys  Asn Lys Leu
    1100                1105                1110

Glu Lys  Asn Glu Glu Ala Ala  Leu Leu Ser Trp Glu  Ile Tyr Leu
    1115                1120                1125

Lys Glu  Asn Tyr Leu Gln Asn  Arg Gln Phe Gln Gln  Lys Gln Arg
    1130                1135                1140

Pro Glu  Gln Lys Ile Glu Asp  Ile Ser Asn Lys Val  Asp Ala Met
    1145                1150                1155

Val Asp  Leu Leu Asp Leu Asp  Pro Leu Lys Arg Ser  Gly Ser Met
    1160                1165                1170

Glu Gln  Arg Leu Ala Ser Leu  Glu Glu Gln Val Ala  Gln Thr Ala
    1175                1180                1185

Arg Ala  Leu His Trp Ile Val  Arg Thr Leu Arg Ala  Ser Gly Phe
    1190                1195                1200

Ser Ser  Glu Ala Asp Val Pro  Thr Leu Ala Ser Gln  Lys Ala Ala
    1205                1210                1215

Glu Glu  Pro Asp Ala Glu Pro  Gly Gly Arg Lys Lys  Thr Glu Glu
    1220                1225                1230

Pro Gly  Asp Ser Tyr His Val  Asn Ala Arg His Leu  Leu Tyr Pro
```

-continued 1235                1240              1245

Asn Cys Pro Val Thr Arg Phe Pro Val Pro Asn Glu Lys Val Pro
    1250                1255              1260

Trp Glu Thr Glu Phe Leu Ile Tyr Asp Pro Pro Phe Tyr Thr Ala
    1265                1270              1275

Glu Arg Lys Asp Ala Ala Ala Met Asp Pro Met Gly Asp Thr Leu
    1280                1285              1290

Glu Pro Leu Ser Thr Ile Gln Tyr Asn Val Val Asp Gly Leu Arg
    1295                1300              1305

Asp Arg Arg Ser Phe His Gly Pro Tyr Thr Val Gln Ala Gly Leu
    1310                1315              1320

Pro Leu Asn Pro Met Gly Arg Thr Gly Leu Arg Gly Arg Gly Ser
    1325                1330              1335

Leu Ser Cys Phe Gly Pro Asn His Thr Leu Tyr Pro Met Val Thr
    1340                1345              1350

Arg Trp Arg Arg Asn Glu Asp Gly Ala Ile Cys Arg Lys Ser Ile
    1355                1360              1365

Lys Lys Met Leu Glu Val Leu Val Val Lys Leu Pro Leu Ser Glu
    1370                1375              1380

His Trp Ala Leu Pro Gly Gly Ser Arg Glu Pro Gly Glu Met Leu
    1385                1390              1395

Pro Arg Lys Leu Lys Arg Ile Leu Arg Gln Glu His Trp Pro Ser
    1400                1405              1410

Phe Glu Asn Leu Leu Lys Cys Gly Met Glu Val Tyr Lys Gly Tyr
    1415                1420              1425

Met Asp Asp Pro Arg Asn Thr Asp Asn Ala Trp Ile Glu Thr Val
    1430                1435              1440

Ala Val Ser Val His Phe Gln Asp Gln Asn Asp Val Glu Leu Asn
    1445                1450              1455

Arg Leu Asn Ser Asn Leu His Ala Cys Asp Ser Gly Ala Ser Ile
    1460                1465              1470

Arg Trp Gln Val Val Asp Arg Arg Ile Pro Leu Tyr Ala Asn His
    1475                1480              1485

Lys Thr Leu Leu Gln Lys Ala Ala Glu Phe Gly Ala His Tyr
    1490                1495              1500

<210> SEQ ID NO 22
<211> LENGTH: 966
<212> TYPE: PRT
<213> ORGANISM: Mus musculus

<400> SEQUENCE: 22

Met Ala Gln Leu Tyr Tyr Lys Lys Val Asn Tyr Ser Pro Tyr Arg Asp
1               5                   10                  15

Arg Ile Pro Leu Gln Ile Val Arg Ala Glu Thr Glu Leu Ser Ala Glu
            20                  25                  30

Glu Lys Ala Phe Leu Ser Ala Val Glu Lys Gly Asp Tyr Ala Thr Val
        35                  40                  45

Lys Gln Ala Leu Gln Glu Ala Glu Ile Tyr Tyr Asn Val Asn Ile Asn
    50                  55                  60

Cys Met Asp Pro Leu Gly Arg Ser Ala Leu Leu Ile Ala Ile Glu Asn
65                  70                  75                  80

Glu Asn Leu Glu Ile Met Glu Leu Leu Leu Asn His Ser Val Tyr Val
                85                  90                  95

-continued

```
Gly Asp Ala Leu Leu Tyr Ala Ile Arg Lys Glu Val Gly Ala Val
            100                 105                 110

Glu Leu Leu Leu Ser Tyr Arg Lys Pro Ser Gly Glu Lys Gln Val Pro
            115                 120                 125

Thr Leu Met Met Asp Thr Gln Phe Ser Glu Phe Thr Pro Asp Ile Thr
        130                 135                 140

Pro Ile Met Leu Ala Ala His Thr Asn Asn Tyr Glu Ile Ile Lys Leu
145                 150                 155                 160

Leu Val Gln Lys Arg Val Thr Ile Pro Arg Pro His Gln Ile Arg Cys
                165                 170                 175

Asn Cys Val Glu Cys Val Ser Ser Glu Val Asp Ser Leu Arg His
                180                 185                 190

Ser Arg Ser Arg Leu Asn Ile Tyr Lys Ala Leu Ala Ser Pro Ser Leu
            195                 200                 205

Ile Ala Leu Ser Ser Glu Asp Pro Ile Leu Thr Ala Phe Arg Leu Gly
        210                 215                 220

Trp Glu Leu Lys Glu Leu Ser Lys Val Glu Asn Glu Phe Lys Ala Glu
225                 230                 235                 240

Tyr Glu Glu Leu Ser Gln Gln Cys Lys Leu Phe Ala Lys Asp Leu Leu
                245                 250                 255

Asp Gln Ala Arg Ser Ser Arg Glu Leu Glu Ile Ile Leu Asn His Arg
            260                 265                 270

Asp Asp His Ser Glu Glu Leu Asp Pro Gln Lys Tyr His Asp Leu Ala
        275                 280                 285

Lys Leu Lys Val Ala Ile Lys Tyr His Gln Lys Glu Phe Val Ala Gln
290                 295                 300

Pro Asn Cys Gln Gln Leu Leu Ala Thr Leu Trp Tyr Asp Gly Phe Pro
305                 310                 315                 320

Gly Trp Arg Arg Lys His Trp Val Val Lys Leu Leu Thr Cys Met Thr
                325                 330                 335

Ile Gly Phe Leu Phe Pro Met Leu Ser Ile Ala Tyr Leu Ile Ser Pro
            340                 345                 350

Arg Ser Asn Leu Gly Leu Phe Ile Lys Lys Pro Phe Ile Lys Phe Ile
        355                 360                 365

Cys His Thr Ala Ser Tyr Leu Thr Phe Leu Phe Met Leu Leu Leu Ala
            370                 375                 380

Ser Gln His Ile Val Arg Thr Asp Leu His Val Gln Gly Pro Pro Pro
385                 390                 395                 400

Thr Val Val Glu Trp Met Ile Leu Pro Trp Val Leu Gly Phe Ile Trp
                405                 410                 415

Gly Glu Ile Lys Glu Met Trp Asp Gly Gly Phe Thr Glu Tyr Ile His
            420                 425                 430

Asp Trp Trp Asn Leu Met Asp Phe Ala Met Asn Ser Leu Tyr Leu Ala
        435                 440                 445

Thr Ile Ser Leu Lys Ile Val Ala Tyr Val Lys Tyr Asn Gly Ser Arg
450                 455                 460

Pro Arg Glu Glu Trp Glu Met Trp His Pro Thr Leu Ile Ala Glu Ala
465                 470                 475                 480

Leu Phe Ala Ile Ser Asn Ile Leu Ser Ser Leu Arg Leu Ile Ser Leu
                485                 490                 495

Phe Thr Ala Asn Ser His Leu Gly Pro Leu Gln Ile Ser Leu Gly Arg
            500                 505                 510

Met Leu Leu Asp Ile Leu Lys Phe Leu Phe Ile Tyr Cys Leu Val Leu
```

-continued

```
                515                 520                 525
Leu Ala Phe Ala Asn Gly Leu Asn Gln Leu Tyr Phe Tyr Tyr Glu Thr
            530                 535                 540

Arg Ala Ile Asp Glu Pro Asn Asn Cys Lys Gly Ile Arg Cys Glu Lys
545                 550                 555                 560

Gln Asn Asn Ala Phe Ser Thr Leu Phe Glu Thr Leu Gln Ser Leu Phe
                        565                 570                 575

Trp Ser Val Phe Gly Leu Leu Asn Leu Tyr Val Thr Asn Val Lys Ala
                580                 585                 590

Arg His Glu Phe Thr Glu Phe Val Gly Ala Thr Met Phe Gly Thr Tyr
            595                 600                 605

Asn Val Ile Ser Leu Val Val Leu Leu Asn Met Leu Ile Ala Met Met
        610                 615                 620

Asn Asn Ser Tyr Gln Leu Ile Ala Asp His Ala Asp Ile Glu Trp Lys
625                 630                 635                 640

Phe Ala Arg Thr Lys Leu Trp Met Ser Tyr Phe Asp Glu Gly Gly Thr
                    645                 650                 655

Leu Pro Pro Pro Phe Asn Ile Ile Pro Ser Pro Lys Ser Phe Leu Tyr
                660                 665                 670

Leu Gly Asn Trp Phe Asn Asn Thr Phe Cys Pro Lys Arg Asp Pro Asp
            675                 680                 685

Gly Arg Arg Arg Arg His Asn Leu Arg Ser Phe Thr Glu Arg His Ala
690                 695                 700

Asp Ser Leu Ile Gln Asn Gln His Tyr Gln Glu Val Ile Arg Asn Leu
705                 710                 715                 720

Val Lys Arg Tyr Val Ala Ala Met Ile Arg Asn Ser Lys Thr Asn Glu
                725                 730                 735

Gly Leu Thr Glu Glu Asn Phe Lys Glu Leu Lys Gln Asp Ile Ser Ser
            740                 745                 750

Phe Arg Tyr Glu Val Leu Asp Leu Leu Gly Asn Arg Lys His Pro Arg
        755                 760                 765

Arg Ser Leu Ser Thr Ser Ser Ala Asp Phe Ser Gln Arg Asp Asp Thr
770                 775                 780

Asn Asp Gly Ser Gly Gly Ala Arg Ala Lys Ser Lys Ser Val Ser Phe
785                 790                 795                 800

Asn Val Gly Cys Lys Lys Lys Ala Cys His Gly Ala Pro Leu Ile Arg
                    805                 810                 815

Thr Val Pro Arg Ala Ser Gly Ala Gln Gly Lys Pro Lys Ser Glu Ser
                820                 825                 830

Ser Ser Lys Arg Ser Phe Met Gly Pro Ser Phe Lys Lys Leu Gly Leu
            835                 840                 845

Phe Phe Ser Lys Phe Asn Gly Gln Thr Ser Glu Pro Thr Ser Glu Pro
850                 855                 860

Met Tyr Thr Ile Ser Asp Gly Ile Ala Gln His Cys Met Trp Gln
865                 870                 875                 880

Asp Ile Arg Tyr Ser Gln Met Glu Lys Gly Lys Ala Glu Ala Cys Ser
                    885                 890                 895

Gln Ser Gln Met Asn Leu Gly Glu Val Glu Leu Gly Glu Ile Arg Gly
                900                 905                 910

Ala Ala Ala Arg Ser Ser Glu Cys Pro Leu Ala Cys Ser Ser Ser Leu
            915                 920                 925

His Cys Ala Ser Gly Ile Cys Ser Ser Asn Ser Lys Leu Leu Asp Ser
930                 935                 940
```

Ser Glu Asp Val Phe Glu Thr Trp Gly Glu Ala Cys Asp Leu Leu Met
945                 950                 955                 960

His Lys Trp Gly Asp Gly
                965

<210> SEQ ID NO 23
<211> LENGTH: 974
<212> TYPE: PRT
<213> ORGANISM: Mus musculus

<400> SEQUENCE: 23

Met Ala Gln Phe Tyr Tyr Lys Arg Asn Val Asn Ala Pro Tyr Arg Asp
1               5                   10                  15

Arg Ile Pro Leu Arg Ile Val Arg Ala Glu Ser Glu Leu Ser Pro Ser
            20                  25                  30

Glu Lys Ala Tyr Leu Asn Ala Val Glu Lys Gly Asp Tyr Ala Ser Val
        35                  40                  45

Lys Lys Ser Leu Glu Glu Ala Glu Ile Tyr Phe Lys Ile Asn Ile Asn
    50                  55                  60

Cys Ile Asp Pro Leu Gly Arg Thr Ala Leu Leu Ile Ala Ile Glu Asn
65                  70                  75                  80

Glu Asn Leu Glu Leu Ile Glu Leu Leu Leu Ser Phe Asn Val Tyr Val
                85                  90                  95

Gly Asp Ala Leu Leu His Ala Ile Arg Lys Glu Val Val Gly Ala Val
            100                 105                 110

Glu Leu Leu Leu Asn His Lys Lys Pro Ser Gly Glu Lys Gln Val Pro
        115                 120                 125

Pro Ile Leu Leu Asp Lys Gln Phe Ser Glu Phe Thr Pro Asp Ile Thr
    130                 135                 140

Pro Ile Ile Leu Ala Ala His Thr Asn Asn Tyr Glu Ile Ile Lys Leu
145                 150                 155                 160

Leu Val Gln Lys Gly Val Ser Val Pro Arg Pro His Glu Val Arg Cys
                165                 170                 175

Asn Cys Val Glu Cys Val Ser Ser Ser Asp Val Asp Ser Leu Arg His
            180                 185                 190

Ser Arg Ser Arg Leu Asn Ile Tyr Lys Ala Leu Ala Ser Pro Ser Leu
        195                 200                 205

Ile Ala Leu Ser Ser Glu Asp Pro Phe Leu Thr Ala Phe Gln Leu Ser
    210                 215                 220

Trp Glu Leu Gln Glu Leu Ser Lys Val Glu Asn Glu Phe Lys Ser Glu
225                 230                 235                 240

Tyr Glu Glu Leu Ser Arg Gln Cys Lys Gln Phe Ala Lys Asp Leu Leu
                245                 250                 255

Asp Gln Thr Arg Ser Ser Arg Glu Leu Glu Ile Ile Leu Asn Tyr Arg
            260                 265                 270

Asp Asp Asn Ser Leu Ile Glu Glu Gln Ser Gly Asn Asp Leu Ala Arg
        275                 280                 285

Leu Lys Leu Ala Ile Lys Tyr Arg Gln Lys Glu Phe Val Ala Gln Pro
    290                 295                 300

Asn Cys Gln Gln Leu Leu Ala Ser Arg Trp Tyr Asp Glu Phe Pro Gly
305                 310                 315                 320

Trp Arg Arg Arg His Trp Ala Val Lys Met Val Thr Cys Phe Ile Ile
                325                 330                 335

Gly Leu Leu Phe Pro Val Phe Ser Val Cys Tyr Leu Ile Ala Pro Lys

-continued

```
                340                 345                 350
Ser Pro Leu Gly Leu Phe Ile Arg Lys Pro Phe Ile Lys Phe Ile Cys
            355                 360                 365
His Thr Ala Ser Tyr Leu Thr Phe Leu Phe Leu Leu Leu Leu Ala Ser
        370                 375                 380
Gln His Ile Asp Arg Ser Asp Leu Asn Arg Gln Gly Pro Pro Pro Thr
385                 390                 395                 400
Ile Val Glu Trp Met Ile Leu Pro Trp Val Leu Gly Phe Ile Trp Gly
                405                 410                 415
Glu Ile Lys Gln Met Trp Asp Gly Gly Leu Gln Asp Tyr Ile His Asp
            420                 425                 430
Trp Trp Asn Leu Met Asp Phe Val Met Asn Ser Leu Tyr Leu Ala Thr
        435                 440                 445
Ile Ser Leu Lys Ile Val Ala Phe Val Lys Tyr Ser Ala Leu Asn Pro
    450                 455                 460
Arg Glu Ser Trp Asp Met Trp His Pro Thr Leu Val Ala Glu Ala Leu
465                 470                 475                 480
Phe Ala Ile Ala Asn Ile Phe Ser Ser Leu Arg Leu Ile Ser Leu Phe
                485                 490                 495
Thr Ala Asn Ser His Leu Gly Pro Leu Gln Ile Ser Leu Gly Arg Met
            500                 505                 510
Leu Leu Asp Ile Leu Lys Phe Leu Phe Ile Tyr Cys Leu Val Leu Leu
        515                 520                 525
Ala Phe Ala Asn Gly Leu Asn Gln Leu Tyr Phe Tyr Tyr Glu Glu Thr
    530                 535                 540
Lys Gly Leu Ser Cys Lys Gly Ile Arg Cys Glu Lys Gln Asn Asn Ala
545                 550                 555                 560
Phe Ser Thr Leu Phe Glu Thr Leu Gln Ser Leu Phe Trp Ser Ile Phe
                565                 570                 575
Gly Leu Ile Asn Leu Tyr Val Thr Asn Val Lys Ala Gln His Glu Phe
            580                 585                 590
Thr Glu Phe Val Gly Ala Thr Met Phe Gly Thr Tyr Asn Val Ile Ser
        595                 600                 605
Leu Val Val Leu Leu Asn Met Leu Ile Ala Met Met Asn Asn Ser Tyr
    610                 615                 620
Gln Leu Ile Ala Asp His Ala Asp Ile Glu Trp Lys Phe Ala Arg Thr
625                 630                 635                 640
Lys Leu Trp Met Ser Tyr Phe Glu Glu Gly Gly Thr Leu Pro Thr Pro
                645                 650                 655
Phe Asn Val Ile Pro Ser Pro Lys Ser Leu Trp Tyr Leu Val Lys Trp
            660                 665                 670
Ile Trp Thr His Leu Cys Lys Lys Met Arg Arg Lys Pro Glu Ser
        675                 680                 685
Phe Gly Thr Ile Gly Arg Arg Ala Ala Asp Asn Leu Arg Arg His His
    690                 695                 700
Gln Tyr Gln Glu Val Met Arg Asn Leu Val Lys Arg Tyr Val Ala Ala
705                 710                 715                 720
Met Ile Arg Glu Ala Lys Thr Glu Glu Gly Leu Thr Glu Glu Asn Val
                725                 730                 735
Lys Glu Leu Lys Gln Asp Ile Ser Ser Phe Arg Phe Glu Val Leu Gly
            740                 745                 750
Leu Leu Arg Gly Ser Lys Leu Ser Thr Ile Gln Ser Ala Asn Ala Ala
        755                 760                 765
```

-continued

Ser Ser Ala Asp Ser Asp Glu Lys Ser Gln Ser Glu Gly Asn Gly Lys
      770                 775                 780

Asp Lys Arg Lys Asn Leu Ser Leu Phe Asp Leu Thr Thr Leu Ile His
785                 790                 795                 800

Pro Arg Ser Ala Ala Ile Ala Ser Glu Arg His Asn Leu Ser Asn Gly
                    805                 810                 815

Ser Ala Leu Val Val Gln Glu Pro Arg Glu Lys Gln Arg Lys Val
                820                 825                 830

Asn Phe Val Ala Asp Ile Lys Asn Phe Gly Leu Phe His Arg Arg Ser
            835                 840                 845

Lys Gln Asn Ala Ala Glu Gln Asn Ala Asn Gln Ile Phe Ser Val Ser
    850                 855                 860

Glu Ile Thr Arg Gln Gln Ala Ala Gly Ala Leu Glu Arg Asn Ile
865                 870                 875                 880

Glu Leu Glu Ser Lys Gly Leu Ala Ser Arg Gly Asp Arg Ser Ile Pro
                885                 890                 895

Gly Leu Asn Glu Gln Cys Val Leu Val Asp His Arg Glu Arg Asn Thr
                900                 905                 910

Asp Thr Leu Gly Leu Gln Val Gly Lys Arg Val Cys Ser Thr Phe Lys
            915                 920                 925

Ser Glu Lys Val Val Glu Asp Thr Val Pro Ile Ile Pro Lys Glu
    930                 935                 940

Lys His Ala His Glu Glu Asp Ser Ser Ile Asp Tyr Asp Leu Ser Pro
945                 950                 955                 960

Thr Asp Thr Ala Ala His Glu Asp Tyr Val Thr Thr Arg Leu
                    965                 970

<210> SEQ ID NO 24
<211> LENGTH: 1072
<212> TYPE: PRT
<213> ORGANISM: Mus musculus

<400> SEQUENCE: 24

Met Gly Thr Lys Thr His Pro Val Val Pro Trp Ser Thr Lys Glu Ile
1               5                   10                  15

Ser Glu Leu Lys Gly Met Leu Lys Gln Leu Gln Pro Gly Pro Leu Gly
            20                  25                  30

Arg Ala Ala Arg Met Val Leu Ser Ala Arg Lys Ala Pro Pro Ala
        35                  40                  45

Ser Val Val Ser Pro Asn Asn Ser His Gly Glu Pro Gly Pro Ser Arg
    50                  55                  60

Ala Glu Ser Ala Glu Pro Arg Ala Glu Pro Asn Arg Lys Thr Ala
65                  70                  75                  80

Val Gly Arg Arg Lys Arg Arg Lys Val Gln Glu Pro Arg Arg Ser Leu
                85                  90                  95

Ser Asn Ser Ser Ser Gln Pro Asn Arg Arg Thr Gly Arg Thr Arg Gln
            100                 105                 110

Arg Gln His Arg Pro Gln Thr Lys Ser Asp Asp Gly Val Gln Ala
        115                 120                 125

Ala Gly Gln Cys Pro Ile Cys Ala Gly Phe Phe Ser Ile Glu Thr Leu
    130                 135                 140

Pro Gln His Ala Ala Thr Cys Gly Glu Ser Pro Pro Gln Pro Ala
145                 150                 155                 160

Ser Pro Ala Ser Leu Ser Ser Ser Glu Ser Val Leu Arg Arg His His

-continued

```
                165                 170                 175
Val Ala Leu Thr Pro Val Pro Leu Val Pro Lys Pro Gln Pro Asn Trp
            180                 185                 190
Thr Glu Ile Val Asn Lys Lys Leu Lys Phe Pro Pro Thr Leu Leu Arg
        195                 200                 205
Ala Ile Gln Glu Gly Gln Leu Gly Leu Val Gln Gln Leu Leu Glu Ser
    210                 215                 220
Ser Ser Asp Ala Ser Gly Ala Gly Pro Gly Gly Pro Leu Arg Asn Val
225                 230                 235                 240
Glu Glu Ser Glu Asp Arg Ser Trp Arg Glu Ala Leu Asn Leu Ala Ile
                245                 250                 255
Arg Leu Gly His Glu Val Ile Thr Asp Val Leu Leu Ala Asn Val Lys
            260                 265                 270
Phe Asp Phe Arg Gln Ile His Glu Ala Leu Leu Val Ala Val Asp Thr
        275                 280                 285
Asn Gln Pro Ala Val Val Arg Arg Leu Leu Ala Arg Leu Glu Arg Glu
    290                 295                 300
Lys Gly Arg Lys Val Asp Thr Lys Ser Phe Ser Leu Ala Phe Asp
305                 310                 315                 320
Ser Ser Ile Asp Gly Ser Arg Phe Ala Pro Gly Val Thr Pro Leu Thr
                325                 330                 335
Leu Ala Cys Gln Lys Asp Leu Tyr Glu Ile Ala Gln Leu Leu Met Asp
            340                 345                 350
Gln Gly His Thr Ile Ala Arg Pro His Pro Val Ser Cys Ala Cys Leu
        355                 360                 365
Glu Cys Ser Asn Ala Arg Arg Tyr Asp Leu Leu Lys Phe Ser Leu Ser
    370                 375                 380
Arg Ile Asn Thr Tyr Arg Gly Ile Ala Ser Arg Ala His Leu Ser Leu
385                 390                 395                 400
Ala Ser Glu Asp Ala Met Leu Ala Ala Phe Gln Leu Ser Arg Glu Leu
                405                 410                 415
Arg Arg Leu Ala Arg Lys Glu Pro Glu Phe Lys Pro Gln Tyr Ile Ala
            420                 425                 430
Leu Glu Ser Leu Cys Gln Asp Tyr Gly Phe Glu Leu Leu Gly Met Cys
        435                 440                 445
Arg Asn Gln Ser Glu Val Thr Ala Val Leu Asn Asp Leu Gly Glu Asp
    450                 455                 460
Ser Glu Thr Glu Pro Glu Ala Glu Gly Leu Gly Gln Ala Phe Glu Glu
465                 470                 475                 480
Gly Ile Pro Asn Leu Ala Arg Leu Arg Leu Ala Val Asn Tyr Asn Gln
                485                 490                 495
Lys Gln Phe Val Ala His Pro Ile Cys Gln Gln Val Leu Ser Ser Ile
            500                 505                 510
Trp Cys Gly Asn Leu Ala Gly Trp Arg Gly Ser Thr Thr Ile Trp Arg
        515                 520                 525
Leu Phe Val Ala Ser Leu Ile Phe Leu Thr Met Pro Phe Leu Cys Ile
    530                 535                 540
Gly Tyr Trp Leu Ala Pro Lys Ser Gln Leu Gly Arg Leu Leu Lys Ile
545                 550                 555                 560
Pro Val Leu Lys Phe Leu Leu His Ser Ala Ser Tyr Leu Trp Phe Leu
                565                 570                 575
Ile Phe Leu Leu Gly Glu Ser Leu Val Met Glu Thr Gln Leu Ser Thr
            580                 585                 590
```

-continued

```
Phe Lys Gly Arg Ser Gln Ser Val Trp Glu Thr Ser Leu His Met Ile
        595                 600                 605
Trp Val Thr Gly Phe Leu Trp Phe Glu Cys Lys Glu Val Trp Ile Glu
    610                 615                 620
Gly Leu Arg Ser Tyr Leu Leu Asp Trp Trp Asn Phe Leu Asp Val Val
625                 630                 635                 640
Ile Leu Ser Leu Tyr Leu Ala Ser Phe Ala Leu Arg Leu Leu Leu Ala
                645                 650                 655
Gly Leu Ala Tyr Met His Cys Arg Asp Ala Ser Asp Ser Thr Thr Cys
                660                 665                 670
Arg Cys Phe Thr Thr Ala Glu Arg Ser Glu Trp Arg Thr Glu Asp Pro
            675                 680                 685
Gln Phe Leu Ala Glu Val Leu Phe Thr Val Thr Ser Met Leu Ser Phe
        690                 695                 700
Thr Arg Leu Ala Tyr Ile Leu Pro Ala His Glu Ser Leu Gly Thr Leu
705                 710                 715                 720
Gln Ile Ser Ile Gly Lys Met Ile Asp Asp Met Ile Arg Phe Met Phe
                725                 730                 735
Ile Leu Met Ile Ile Leu Thr Ala Phe Leu Cys Gly Leu Asn Asn Ile
                740                 745                 750
Tyr Val Pro Tyr Gln Glu Ser Glu Lys Leu Gly Asn Phe Asn Glu Thr
            755                 760                 765
Phe Gln Phe Leu Phe Trp Thr Met Phe Gly Met Glu Glu His Thr Val
        770                 775                 780
Val Asp Met Pro Gln Phe Leu Val Pro Glu Phe Val Gly Arg Ala Met
785                 790                 795                 800
Tyr Gly Ile Phe Thr Ile Val Met Val Ile Leu Leu Asn Met Leu
                805                 810                 815
Ile Ala Met Ile Thr Asn Ser Phe Gln Lys Ile Glu Asp Asp Ala Asp
                820                 825                 830
Val Glu Trp Lys Phe Ala Arg Ser Lys Leu Tyr Leu Ser Tyr Phe Arg
            835                 840                 845
Glu Gly Leu Thr Leu Pro Val Pro Phe Asn Ile Leu Pro Ser Pro Lys
        850                 855                 860
Ala Ala Phe Tyr Leu Val Arg Arg Ile Phe Arg Phe Leu Cys Cys Gly
865                 870                 875                 880
Ser Ser Cys Cys Lys Ala Lys Lys Ser Asp Tyr Pro Pro Ile Gly Thr
                885                 890                 895
Phe Thr Asn Pro Gly Ala Arg Ala Gly Ser Ala Gly Glu Gly Glu Arg
            900                 905                 910
Val Ser Tyr Arg Leu Arg Val Ile Lys Ala Leu Val Gln Arg Tyr Ile
        915                 920                 925
Glu Thr Ala Arg Arg Glu Phe Glu Glu Thr Arg Arg Lys Asp Leu Gly
        930                 935                 940
Asn Arg Leu Thr Glu Leu Thr Lys Thr Val Ser Arg Leu Gln Ser Glu
945                 950                 955                 960
Val Ala Ser Val Gln Lys Asn Leu Ala Ala Gly Gly Ala Pro Arg Pro
                965                 970                 975
Pro Asp Gly Ala Ser Ile Leu Ser Arg Tyr Ile Thr Arg Val Arg Asn
            980                 985                 990
Ser Phe Gln Asn Leu Gly Pro Pro  Thr Ser Asp Thr Pro  Ala Glu Leu
        995                 1000                 1005
```

```
Thr Met Pro Gly Ile Val Glu Thr Glu Val Ser Leu Gly Asp Gly
    1010                1015                1020

Leu Asp Gly Thr Gly Glu Ala Gly Ala Pro Ala Pro Gly Glu Pro
    1025                1030                1035

Gly Ser Ser Ser Ser Ala His Val Leu Val His Arg Glu Gln Glu
    1040                1045                1050

Ala Glu Gly Ser Gly Asp Leu Leu Glu Gly Asp Leu Glu Thr
    1055                1060                1065

Lys Gly Glu Ser
    1070

<210> SEQ ID NO 25
<211> LENGTH: 809
<212> TYPE: PRT
<213> ORGANISM: Mus musculus

<400> SEQUENCE: 25

Met Gly Ala Pro Pro Ser Pro Gly Leu Pro Ser Trp Ala Ala
1               5                   10              15

Met Met Ala Ala Leu Tyr Pro Ser Thr Asp Leu Ser Gly Val Ser Ser
            20                  25                  30

Ser Ser Leu Pro Ser Ser Pro Ser Ser Ser Pro Asn Glu Val Met
        35                  40                  45

Ala Leu Lys Asp Val Arg Glu Val Lys Glu Glu Asn Thr Leu Asn Glu
    50                  55                  60

Lys Leu Phe Leu Leu Ala Cys Asp Lys Gly Asp Tyr Tyr Met Val Lys
65                  70                  75                  80

Lys Ile Leu Glu Glu Asn Ser Ser Gly Asp Leu Asn Ile Asn Cys Val
                85                  90                  95

Asp Val Leu Gly Arg Asn Ala Val Thr Ile Thr Ile Glu Asn Glu Ser
            100                 105                 110

Leu Asp Ile Leu Gln Leu Leu Asp Tyr Gly Cys Gln Ser Ala Asp
        115                 120                 125

Ala Leu Leu Val Ala Ile Asp Ser Glu Val Val Gly Ala Val Asp Ile
    130                 135                 140

Leu Leu Asn His Arg Pro Lys Arg Ser Ser Arg Pro Thr Ile Val Lys
145                 150                 155                 160

Leu Met Glu Arg Ile Gln Asn Pro Glu Tyr Ser Thr Thr Met Asp Val
                165                 170                 175

Ala Pro Val Ile Leu Ala Ala His Arg Asn Asn Tyr Glu Ile Leu Thr
            180                 185                 190

Met Leu Leu Lys Gln Asp Val Ser Leu Pro Lys Pro His Ala Val Gly
        195                 200                 205

Cys Glu Cys Thr Leu Cys Ser Ala Lys Asn Lys Lys Asp Ser Leu Arg
    210                 215                 220

His Ser Arg Phe Arg Leu Asp Ile Tyr Arg Cys Leu Ala Ser Pro Ala
225                 230                 235                 240

Leu Ile Met Leu Thr Glu Glu Asp Pro Ile Leu Arg Ala Phe Glu Leu
                245                 250                 255

Ser Ala Asp Leu Lys Glu Leu Ser Leu Val Glu Val Glu Phe Arg Asn
            260                 265                 270

Asp Tyr Glu Glu Leu Ala Arg Gln Cys Lys Met Phe Ala Lys Asp Leu
        275                 280                 285

Leu Ala Gln Ala Arg Asn Ser Arg Glu Leu Glu Val Ile Leu Asn His
    290                 295                 300
```

-continued

```
Thr Ser Ser Asp Glu Pro Leu Asp Lys Arg Gly Leu Leu Glu Arg
305                 310                 315                 320

Met Asn Leu Ser Arg Leu Lys Leu Ala Ile Lys Tyr Asn Gln Lys Glu
            325                 330                 335

Phe Val Ser Gln Ser Asn Cys Gln Gln Phe Leu Asn Thr Val Trp Phe
                340                 345                 350

Gly Gln Met Ser Gly Tyr Arg Arg Lys Pro Thr Cys Lys Lys Ile Met
            355                 360                 365

Thr Val Leu Thr Val Gly Ile Phe Trp Pro Val Leu Ser Leu Cys Tyr
370                 375                 380

Leu Ile Ala Pro Lys Ser Gln Phe Gly Arg Ile Ile His Thr Pro Phe
385                 390                 395                 400

Met Lys Phe Ile Ile His Gly Ala Ser Tyr Phe Thr Phe Leu Leu Leu
                405                 410                 415

Leu Asn Leu Tyr Ser Leu Val Tyr Asn Glu Asp Lys Lys Asn Thr Met
                420                 425                 430

Gly Pro Ala Leu Glu Arg Ile Asp Tyr Leu Leu Ile Leu Trp Ile Ile
            435                 440                 445

Gly Met Ile Trp Ser Asp Ile Lys Arg Leu Trp Tyr Glu Gly Leu Glu
450                 455                 460

Asp Phe Leu Glu Glu Ser Arg Asn Gln Leu Ser Phe Val Met Asn Ser
465                 470                 475                 480

Leu Tyr Leu Ala Thr Phe Ala Leu Lys Val Val Ala His Asn Lys Phe
                485                 490                 495

His Asp Phe Ala Asp Arg Lys Asp Trp Asp Ala Phe His Pro Thr Leu
            500                 505                 510

Val Ala Glu Gly Leu Phe Ala Phe Ala Asn Val Leu Ser Tyr Leu Arg
            515                 520                 525

Leu Phe Phe Met Tyr Thr Thr Ser Ser Ile Leu Gly Pro Leu Gln Ile
530                 535                 540

Ser Met Gly Gln Met Leu Gln Asp Phe Gly Lys Phe Leu Gly Met Phe
545                 550                 555                 560

Leu Leu Val Leu Phe Ser Phe Thr Ile Gly Leu Thr Gln Leu Tyr Asp
                565                 570                 575

Lys Gly Tyr Thr Ser Lys Glu Gln Lys Asp Cys Val Gly Ile Phe Cys
            580                 585                 590

Glu Gln Gln Ser Asn Asp Thr Phe His Ser Phe Ile Gly Thr Cys Phe
            595                 600                 605

Ala Leu Phe Trp Tyr Ile Phe Ser Leu Ala His Val Ala Ile Phe Val
610                 615                 620

Thr Arg Phe Ser Tyr Gly Glu Glu Leu Gln Ser Phe Val Gly Ala Val
625                 630                 635                 640

Ile Val Gly Thr Tyr Asn Val Val Val Ile Val Leu Thr Lys Leu
                645                 650                 655

Leu Val Ala Met Leu His Lys Ser Phe Gln Leu Ile Ala Asn His Glu
                660                 665                 670

Asp Lys Glu Trp Lys Phe Ala Arg Ala Lys Leu Trp Leu Ser Tyr Phe
            675                 680                 685

Asp Asp Lys Cys Thr Leu Pro Pro Pro Phe Asn Ile Ile Pro Ser Pro
            690                 695                 700

Lys Thr Ile Cys Tyr Met Ile Ser Ser Leu Ser Lys Trp Ile Cys Ser
705                 710                 715                 720
```

```
His Thr Ser Lys Gly Lys Val Lys Arg Gln Asn Ser Leu Lys Glu Trp
            725                 730                 735

Arg Asn Leu Lys Gln Lys Arg Asp Glu Asn Tyr Gln Lys Val Met Cys
            740                 745                 750

Cys Leu Val His Arg Tyr Leu Thr Ser Met Arg Gln Lys Met Gln Ser
            755                 760                 765

Thr Asp Gln Ala Thr Val Glu Asn Leu Asn Glu Leu Arg Gln Asp Leu
            770                 775                 780

Ser Lys Phe Arg Asn Glu Ile Arg Asp Leu Leu Gly Phe Arg Thr Ser
785                 790                 795                 800

Lys Tyr Ala Met Phe Tyr Pro Arg Asn
            805

<210> SEQ ID NO 26
<211> LENGTH: 18
<212> TYPE: PRT
<213> ORGANISM: Homo sapiens

<400> SEQUENCE: 26

Leu Lys Val Ile Leu Gly Ile Leu Leu Pro Pro Ser Ile Leu Ser Leu
1               5                   10                  15

Glu Phe

<210> SEQ ID NO 27
<211> LENGTH: 18
<212> TYPE: PRT
<213> ORGANISM: Homo sapiens

<400> SEQUENCE: 27

Ile Val Lys Phe Trp Phe Tyr Thr Leu Ala Tyr Ile Gly Tyr Leu Met
1               5                   10                  15

Leu Phe

<210> SEQ ID NO 28
<211> LENGTH: 14
<212> TYPE: PRT
<213> ORGANISM: Homo sapiens

<400> SEQUENCE: 28

Val Thr Asp Leu Ile Ala Ile Leu Leu Phe Ser Val Gly Met
1               5                   10

<210> SEQ ID NO 29
<211> LENGTH: 18
<212> TYPE: PRT
<213> ORGANISM: Homo sapiens

<400> SEQUENCE: 29

Arg Val Ile Tyr Cys Val Asn Ile Ile Tyr Trp Tyr Ile Arg Leu Leu
1               5                   10                  15

Asp Ile

<210> SEQ ID NO 30
<211> LENGTH: 18
<212> TYPE: PRT
<213> ORGANISM: Homo sapiens

<400> SEQUENCE: 30

Met Met Ile Asp Met Met Tyr Phe Val Ile Ile Met Leu Val Val Leu
1               5                   10                  15
```

Met Ser

<210> SEQ ID NO 31
<211> LENGTH: 21
<212> TYPE: PRT
<213> ORGANISM: Homo sapiens

<400> SEQUENCE: 31

Ala Ile Met Ala Cys Tyr Leu Leu Val Ala Asn Ile Leu Leu Val Asn
1               5                   10                  15

Leu Leu Ile Ala Val
            20

<210> SEQ ID NO 32
<211> LENGTH: 18
<212> TYPE: PRT
<213> ORGANISM: Homo sapiens

<400> SEQUENCE: 32

Leu Lys Val Ile Leu Gly Ile Leu Leu Pro Pro Ser Ile Leu Ser Leu
1               5                   10                  15

Glu Phe

<210> SEQ ID NO 33
<211> LENGTH: 18
<212> TYPE: PRT
<213> ORGANISM: Homo sapiens

<400> SEQUENCE: 33

Ile Val Lys Phe Trp Phe Tyr Thr Leu Ala Tyr Ile Gly Tyr Leu Met
1               5                   10                  15

Leu Phe

<210> SEQ ID NO 34
<211> LENGTH: 14
<212> TYPE: PRT
<213> ORGANISM: Homo sapiens

<400> SEQUENCE: 34

Val Thr Asp Leu Ile Ala Ile Leu Leu Phe Ser Val Gly Met
1               5                   10

<210> SEQ ID NO 35
<211> LENGTH: 18
<212> TYPE: PRT
<213> ORGANISM: Homo sapiens

<400> SEQUENCE: 35

Arg Val Ile Tyr Cys Val Asn Ile Ile Tyr Trp Tyr Ile Arg Leu Leu
1               5                   10                  15

Asp Ile

<210> SEQ ID NO 36
<211> LENGTH: 18
<212> TYPE: PRT
<213> ORGANISM: Homo sapiens

<400> SEQUENCE: 36

Met Met Ile Asp Met Met Tyr Phe Val Ile Met Leu Val Val Leu
1               5                   10                  15

Met Ser

```
<210> SEQ ID NO 37
<211> LENGTH: 21
<212> TYPE: PRT
<213> ORGANISM: Homo sapiens

<400> SEQUENCE: 37

Ala Ile Met Ala Cys Tyr Leu Leu Val Ala Asn Ile Leu Leu Val Asn
1               5                   10                  15

Leu Leu Ile Ala Val
            20

<210> SEQ ID NO 38
<211> LENGTH: 18
<212> TYPE: PRT
<213> ORGANISM: Homo sapiens

<400> SEQUENCE: 38

Leu Lys Val Ile Leu Gly Ile Leu Leu Pro Pro Ser Ile Leu Ser Leu
1               5                   10                  15

Glu Phe

<210> SEQ ID NO 39
<211> LENGTH: 18
<212> TYPE: PRT
<213> ORGANISM: Homo sapiens

<400> SEQUENCE: 39

Ile Val Lys Phe Trp Phe Tyr Thr Leu Ala Tyr Ile Gly Tyr Leu Met
1               5                   10                  15

Leu Phe

<210> SEQ ID NO 40
<211> LENGTH: 14
<212> TYPE: PRT
<213> ORGANISM: Homo sapiens

<400> SEQUENCE: 40

Val Thr Asp Leu Ile Ala Ile Leu Leu Phe Ser Val Gly Met
1               5                   10

<210> SEQ ID NO 41
<211> LENGTH: 18
<212> TYPE: PRT
<213> ORGANISM: Homo sapiens

<400> SEQUENCE: 41

Arg Val Ile Tyr Cys Val Asn Ile Ile Tyr Trp Tyr Ile Arg Leu Leu
1               5                   10                  15

Asp Ile

<210> SEQ ID NO 42
<211> LENGTH: 18
<212> TYPE: PRT
<213> ORGANISM: Homo sapiens

<400> SEQUENCE: 42

Met Met Ile Asp Met Met Tyr Phe Val Ile Ile Met Leu Val Val Leu
1               5                   10                  15

Met Ser

<210> SEQ ID NO 43
```

```
<211> LENGTH: 21
<212> TYPE: PRT
<213> ORGANISM: Homo sapiens

<400> SEQUENCE: 43

Ala Ile Met Ala Cys Tyr Leu Leu Val Ala Asn Ile Leu Leu Val Asn
1               5                   10                  15

Leu Leu Ile Ala Val
            20

<210> SEQ ID NO 44
<211> LENGTH: 18
<212> TYPE: PRT
<213> ORGANISM: Homo sapiens

<400> SEQUENCE: 44

Leu Lys Val Ile Leu Gly Ile Leu Leu Pro Pro Ser Ile Leu Ser Leu
1               5                   10                  15

Glu Phe

<210> SEQ ID NO 45
<211> LENGTH: 18
<212> TYPE: PRT
<213> ORGANISM: Homo sapiens

<400> SEQUENCE: 45

Ile Val Lys Phe Trp Phe Tyr Thr Leu Ala Tyr Ile Gly Tyr Leu Met
1               5                   10                  15

Leu Phe

<210> SEQ ID NO 46
<211> LENGTH: 14
<212> TYPE: PRT
<213> ORGANISM: Homo sapiens

<400> SEQUENCE: 46

Val Thr Asp Leu Ile Ala Ile Leu Leu Phe Ser Val Gly Met
1               5                   10

<210> SEQ ID NO 47
<211> LENGTH: 18
<212> TYPE: PRT
<213> ORGANISM: Homo sapiens

<400> SEQUENCE: 47

Arg Val Ile Tyr Cys Val Asn Ile Ile Tyr Trp Tyr Ile Arg Leu Leu
1               5                   10                  15

Asp Ile

<210> SEQ ID NO 48
<211> LENGTH: 18
<212> TYPE: PRT
<213> ORGANISM: Homo sapiens

<400> SEQUENCE: 48

Met Met Ile Asp Met Met Tyr Phe Val Ile Ile Met Leu Val Val Leu
1               5                   10                  15

Met Ser

<210> SEQ ID NO 49
<211> LENGTH: 21
<212> TYPE: PRT
```

<213> ORGANISM: Homo sapiens

<400> SEQUENCE: 49

Ala Ile Met Ala Cys Tyr Leu Leu Val Ala Asn Ile Leu Leu Val Asn
1               5                   10                  15

Leu Leu Ile Ala Val
            20

<210> SEQ ID NO 50
<211> LENGTH: 79
<212> TYPE: PRT
<213> ORGANISM: Homo sapiens

<400> SEQUENCE: 50

Lys Asn Lys Asp Asp Met Pro Tyr Met Ser Gln Ala Gln Glu Ile His
1               5                   10                  15

Leu Gln Glu Lys Glu Ala Glu Glu Pro Glu Lys Pro Thr Lys Glu Lys
            20                  25                  30

Glu Glu Glu Asp Met Glu Leu Thr Ala Met Leu Gly Arg Asn Asn Gly
        35                  40                  45

Glu Ser Ser Arg Lys Lys Asp Glu Glu Val Gln Ser Lys His Arg
    50                  55                  60

Leu Ile Pro Leu Gly Arg Lys Ile Tyr Glu Phe Tyr Asn Ala Pro
65                  70                  75

<210> SEQ ID NO 51
<211> LENGTH: 55
<212> TYPE: PRT
<213> ORGANISM: Homo sapiens

<400> SEQUENCE: 51

Asn Tyr Ile Val Leu Val Lys Met Glu Arg Trp Pro Ser Thr Gln Glu
1               5                   10                  15

Trp Ile Val Ile Ser Tyr Ile Phe Thr Leu Gly Ile Glu Lys Met Arg
            20                  25                  30

Glu Ile Leu Met Ser Glu Pro Gly Lys Leu Leu Gln Lys Val Lys Val
        35                  40                  45

Trp Leu Gln Glu Tyr Trp Asn
    50                  55

<210> SEQ ID NO 52
<211> LENGTH: 13
<212> TYPE: PRT
<213> ORGANISM: Homo sapiens

<400> SEQUENCE: 52

Ile Leu Arg Leu Gln Asp Gln Pro Phe Arg Ser Asp Gly
1               5                   10

<210> SEQ ID NO 53
<211> LENGTH: 16
<212> TYPE: PRT
<213> ORGANISM: Homo sapiens

<400> SEQUENCE: 53

Phe Gly Val Asn Lys Tyr Leu Gly Pro Tyr Val Met Met Ile Gly Lys
1               5                   10                  15

<210> SEQ ID NO 54
<211> LENGTH: 69
<212> TYPE: PRT

-continued

```
<213> ORGANISM: Homo sapiens

<400> SEQUENCE: 54

Phe Gly Val Ala Arg Gln Ala Ile Leu Phe Pro Asn Glu Glu Pro Ser
1               5                   10                  15

Trp Lys Leu Ala Lys Asn Ile Phe Tyr Met Pro Tyr Trp Met Ile Tyr
                20                  25                  30

Gly Glu Val Phe Ala Asp Gln Ile Asp Pro Pro Cys Gly Gln Asn Glu
                35                  40                  45

Thr Arg Glu Asp Gly Lys Ile Ile Gln Leu Pro Pro Cys Lys Thr Gly
            50                  55                  60

Ala Trp Ile Val Pro
65

<210> SEQ ID NO 55
<211> LENGTH: 6
<212> TYPE: PRT
<213> ORGANISM: Homo sapiens

<400> SEQUENCE: 55

Val Trp Lys Phe Gln Arg
1               5

<210> SEQ ID NO 56
<211> LENGTH: 212
<212> TYPE: PRT
<213> ORGANISM: Homo sapiens

<400> SEQUENCE: 56

Thr Gln Glu Trp Ile Val Ile Ser Tyr Ile Phe Thr Leu Gly Ile Glu
1               5                   10                  15

Lys Met Arg Glu Ile Leu Met Ser Glu Pro Gly Lys Leu Leu Gln Lys
                20                  25                  30

Val Lys Val Trp Leu Gln Glu Tyr Trp Asn Val Thr Asp Leu Ile Ala
                35                  40                  45

Ile Leu Leu Phe Ser Val Gly Met Ile Leu Arg Leu Gln Asp Gln Pro
            50                  55                  60

Phe Arg Ser Asp Gly Arg Val Ile Tyr Cys Val Asn Ile Ile Tyr Trp
65                  70                  75                  80

Tyr Ile Arg Leu Leu Asp Ile Phe Gly Val Asn Lys Tyr Leu Gly Pro
                85                  90                  95

Tyr Val Met Met Ile Gly Lys Met Met Ile Asp Met Met Tyr Phe Val
                100                 105                 110

Ile Ile Met Leu Val Val Leu Met Ser Phe Gly Val Ala Arg Gln Ala
            115                 120                 125

Ile Leu Phe Pro Asn Glu Glu Pro Ser Trp Lys Leu Ala Lys Asn Ile
            130                 135                 140

Phe Tyr Met Pro Tyr Trp Met Ile Tyr Gly Glu Val Phe Ala Asp Gln
145                 150                 155                 160

Ile Asp Pro Pro Cys Gly Gln Asn Glu Thr Arg Glu Asp Gly Lys Ile
                165                 170                 175

Ile Gln Leu Pro Pro Cys Lys Thr Gly Ala Trp Ile Val Pro Ala Ile
                180                 185                 190

Met Ala Cys Tyr Leu Leu Val Ala Asn Ile Leu Leu Val Asn Leu Leu
            195                 200                 205

Ile Ala Val Phe
            210
```

<210> SEQ ID NO 57
<211> LENGTH: 56
<212> TYPE: PRT
<213> ORGANISM: Homo sapiens

<400> SEQUENCE: 57

Glu Arg Ile Arg Val Thr Ser Glu Arg Val Glu Asn Met Ser Met Arg
1               5                   10                  15

Leu Glu Glu Val Asn Glu Arg Glu His Ser Met Lys Ala Ser Leu Gln
            20                  25                  30

Thr Val Asp Ile Arg Leu Ala Gln Leu Glu Asp Leu Ile Gly Arg Met
        35                  40                  45

Ala Thr Ala Leu Glu Arg Leu Thr
    50                  55

<210> SEQ ID NO 58
<211> LENGTH: 18
<212> TYPE: PRT
<213> ORGANISM: Homo sapiens

<400> SEQUENCE: 58

Leu Ser Leu Glu Phe Lys Asn Lys Asp Asp Met Pro Tyr Met Ser Gln
1               5                   10                  15

Ala Gln

<210> SEQ ID NO 59
<211> LENGTH: 18
<212> TYPE: PRT
<213> ORGANISM: Homo sapiens

<400> SEQUENCE: 59

Val Met Met Ile Gly Lys Met Met Ile Asp Met Met Tyr Phe Val Ile
1               5                   10                  15

Ile Met

<210> SEQ ID NO 60
<211> LENGTH: 13
<212> TYPE: PRT
<213> ORGANISM: Homo sapiens

<400> SEQUENCE: 60

Ala Asp Asn Gly Thr Thr Gly Lys Tyr Gly Ala Glu Val
1               5                   10

<210> SEQ ID NO 61
<211> LENGTH: 13
<212> TYPE: PRT
<213> ORGANISM: Homo sapiens

<400> SEQUENCE: 61

Val Val Cys Asp Gly Ser Gly Arg Ala Ser Asp Ile Leu
1               5                   10

<210> SEQ ID NO 62
<211> LENGTH: 13
<212> TYPE: PRT
<213> ORGANISM: Homo sapiens

<400> SEQUENCE: 62

Gly Leu Ile Asn Glu Ser Leu Arg Asp Gln Leu Leu Val
1               5                   10

<210> SEQ ID NO 63
<211> LENGTH: 13
<212> TYPE: PRT
<213> ORGANISM: Homo sapiens

<400> SEQUENCE: 63

Tyr Arg Cys Asn Tyr Thr Arg Lys Arg Phe Arg Thr Leu
1               5                   10

<210> SEQ ID NO 64
<211> LENGTH: 13
<212> TYPE: PRT
<213> ORGANISM: Homo sapiens

<400> SEQUENCE: 64

Arg Arg Gly Arg Lys Thr Thr Lys Lys Arg Glu Glu Glu
1               5                   10

<210> SEQ ID NO 65
<211> LENGTH: 13
<212> TYPE: PRT
<213> ORGANISM: Homo sapiens

<400> SEQUENCE: 65

Arg Gly Arg Lys Thr Thr Lys Lys Arg Glu Glu Glu Val
1               5                   10

<210> SEQ ID NO 66
<211> LENGTH: 13
<212> TYPE: PRT
<213> ORGANISM: Homo sapiens

<400> SEQUENCE: 66

Glu Leu Leu Asp Gln Ser Tyr Lys Gln Asp Glu Gln Leu
1               5                   10

<210> SEQ ID NO 67
<211> LENGTH: 13
<212> TYPE: PRT
<213> ORGANISM: Homo sapiens

<400> SEQUENCE: 67

Arg Asn Asn Gly Glu Ser Ser Arg Lys Lys Asp Glu Glu
1               5                   10

<210> SEQ ID NO 68
<211> LENGTH: 13
<212> TYPE: PRT
<213> ORGANISM: Homo sapiens

<400> SEQUENCE: 68

Asn Asn Gly Glu Ser Ser Arg Lys Lys Asp Glu Glu Glu
1               5                   10

<210> SEQ ID NO 69
<211> LENGTH: 13
<212> TYPE: PRT
<213> ORGANISM: Homo sapiens

<400> SEQUENCE: 69

Pro Asn Glu Glu Pro Ser Trp Lys Leu Ala Lys Asn Ile
1               5                   10

```
<210> SEQ ID NO 70
<211> LENGTH: 13
<212> TYPE: PRT
<213> ORGANISM: Homo sapiens

<400> SEQUENCE: 70

Arg Ile Arg Val Thr Ser Glu Arg Val Glu Asn Met Ser
1               5                   10

<210> SEQ ID NO 71
<211> LENGTH: 13
<212> TYPE: PRT
<213> ORGANISM: Homo sapiens

<400> SEQUENCE: 71

Arg Val Glu Asn Met Ser Met Arg Leu Glu Glu Val Asn
1               5                   10

<210> SEQ ID NO 72
<211> LENGTH: 13
<212> TYPE: PRT
<213> ORGANISM: Homo sapiens

<400> SEQUENCE: 72

Asn Glu Arg Glu His Ser Met Lys Ala Ser Leu Gln Thr
1               5                   10

<210> SEQ ID NO 73
<211> LENGTH: 13
<212> TYPE: PRT
<213> ORGANISM: Homo sapiens

<400> SEQUENCE: 73

Leu Glu Arg Ala Glu Ser Asn Lys Ile Arg Ser Arg Thr
1               5                   10

<210> SEQ ID NO 74
<211> LENGTH: 13
<212> TYPE: PRT
<213> ORGANISM: Homo sapiens

<400> SEQUENCE: 74

Ser Gln Glu Gly Asn Thr Phe Lys Leu Gln Glu Ser Ile
1               5                   10

<210> SEQ ID NO 75
<211> LENGTH: 13
<212> TYPE: PRT
<213> ORGANISM: Homo sapiens

<400> SEQUENCE: 75

Ala Ile Val Pro Asp Ser Arg Arg Pro Ser Ser Cys Ile
1               5                   10

<210> SEQ ID NO 76
<211> LENGTH: 13
<212> TYPE: PRT
<213> ORGANISM: Homo sapiens

<400> SEQUENCE: 76

Ala Thr Leu Ala Pro Thr Asp Arg Pro Pro Ser Arg Ser
1               5                   10

<210> SEQ ID NO 77
<211> LENGTH: 13
```

```
<212> TYPE: PRT
<213> ORGANISM: Homo sapiens

<400> SEQUENCE: 77

Ile Glu Arg Ser Lys Ser Ser Arg Tyr Leu Ala Thr Thr
1               5                   10

<210> SEQ ID NO 78
<211> LENGTH: 13
<212> TYPE: PRT
<213> ORGANISM: Homo sapiens

<400> SEQUENCE: 78

Gln Glu Gly Asp Asn Ser Glu Arg Thr Leu Ser Asn Asn
1               5                   10

<210> SEQ ID NO 79
<211> LENGTH: 13
<212> TYPE: PRT
<213> ORGANISM: Homo sapiens

<400> SEQUENCE: 79

Ala Pro Tyr Ala His Thr Arg Lys Ser Phe Ser Ile Ser
1               5                   10

<210> SEQ ID NO 80
<211> LENGTH: 13
<212> TYPE: PRT
<213> ORGANISM: Homo sapiens

<400> SEQUENCE: 80

Lys Ser Phe Ser Ile Ser Asp Lys Leu Asp Arg Gln Arg
1               5                   10

<210> SEQ ID NO 81
<211> LENGTH: 13
<212> TYPE: PRT
<213> ORGANISM: Homo sapiens

<400> SEQUENCE: 81

Phe Gln Arg Ser Lys Ser Ser Lys Pro Glu Gly Arg Gly
1               5                   10

<210> SEQ ID NO 82
<211> LENGTH: 13
<212> TYPE: PRT
<213> ORGANISM: Homo sapiens

<400> SEQUENCE: 82

Arg Gly Asp Ser Leu Ser Met Arg Arg Leu Ser Arg Thr
1               5                   10

<210> SEQ ID NO 83
<211> LENGTH: 14
<212> TYPE: PRT
<213> ORGANISM: Homo sapiens

<400> SEQUENCE: 83

Phe Ile Leu Ala Asp Asn Gly Thr Thr Gly Lys Tyr Gly Ala
1               5                   10

<210> SEQ ID NO 84
<211> LENGTH: 14
<212> TYPE: PRT
<213> ORGANISM: Homo sapiens
```

```
<400> SEQUENCE: 84

Glu Gly Gly Leu Ile Asn Glu Ser Leu Arg Asp Gln Leu Leu
1               5                   10

<210> SEQ ID NO 85
<211> LENGTH: 14
<212> TYPE: PRT
<213> ORGANISM: Homo sapiens

<400> SEQUENCE: 85

Leu Leu Lys Gly Ala Asn Ala Ser Ala Pro Asp Gln Leu Ser
1               5                   10

<210> SEQ ID NO 86
<211> LENGTH: 14
<212> TYPE: PRT
<213> ORGANISM: Homo sapiens

<400> SEQUENCE: 86

Gly Ala Tyr Arg Cys Asn Tyr Thr Arg Lys Arg Phe Arg Thr
1               5                   10

<210> SEQ ID NO 87
<211> LENGTH: 14
<212> TYPE: PRT
<213> ORGANISM: Homo sapiens

<400> SEQUENCE: 87

Thr Tyr Glu Leu Lys Asn Trp Ser Asn Ala Thr Cys Leu Gln
1               5                   10

<210> SEQ ID NO 88
<211> LENGTH: 14
<212> TYPE: PRT
<213> ORGANISM: Homo sapiens

<400> SEQUENCE: 88

Leu Lys Asn Trp Ser Asn Ala Thr Cys Leu Gln Leu Ala Val
1               5                   10

<210> SEQ ID NO 89
<211> LENGTH: 14
<212> TYPE: PRT
<213> ORGANISM: Homo sapiens

<400> SEQUENCE: 89

Leu Gln Glu Tyr Trp Asn Val Thr Asp Leu Ile Ala Ile Leu
1               5                   10

<210> SEQ ID NO 90
<211> LENGTH: 14
<212> TYPE: PRT
<213> ORGANISM: Homo sapiens

<400> SEQUENCE: 90

Pro Pro Cys Gly Gln Asn Glu Thr Arg Glu Asp Gly Lys Ile
1               5                   10

<210> SEQ ID NO 91
<211> LENGTH: 14
<212> TYPE: PRT
<213> ORGANISM: Homo sapiens

<400> SEQUENCE: 91
```

```
Leu Ile Ala Val Phe Asn Asn Thr Phe Phe Glu Val Lys Ser
1               5                   10

<210> SEQ ID NO 92
<211> LENGTH: 14
<212> TYPE: PRT
<213> ORGANISM: Homo sapiens

<400> SEQUENCE: 92

Lys Asp Asp Arg Phe Asn Ser Ser Asn Asp Glu Arg Ile Arg
1               5                   10

<210> SEQ ID NO 93
<211> LENGTH: 14
<212> TYPE: PRT
<213> ORGANISM: Homo sapiens

<400> SEQUENCE: 93

Ser Glu Arg Val Glu Asn Met Ser Met Arg Leu Glu Glu Val
1               5                   10

<210> SEQ ID NO 94
<211> LENGTH: 14
<212> TYPE: PRT
<213> ORGANISM: Homo sapiens

<400> SEQUENCE: 94

Arg Thr Leu Ser Asn Asn Ile Thr Val Pro Lys Ile Glu Arg
1               5                   10

<210> SEQ ID NO 95
<211> LENGTH: 13
<212> TYPE: PRT
<213> ORGANISM: Homo sapiens

<400> SEQUENCE: 95

Ser Lys Pro Glu Gly Arg Gly Asp Ser Leu Ser Met Arg
1               5                   10

<210> SEQ ID NO 96
<211> LENGTH: 20
<212> TYPE: PRT
<213> ORGANISM: Homo sapiens

<400> SEQUENCE: 96

Leu Ile Gly Arg Met Ala Thr Ala Leu Glu Arg Leu Thr Gly Leu Glu
1               5                   10                  15

Arg Ala Glu Ser
            20

<210> SEQ ID NO 97
<211> LENGTH: 15
<212> TYPE: PRT
<213> ORGANISM: Homo sapiens

<400> SEQUENCE: 97

Asp Ile Pro Leu Arg Arg Gly Arg Lys Thr Thr Lys Arg Gly
1               5                   10                  15

<210> SEQ ID NO 98
<211> LENGTH: 15
<212> TYPE: PRT
<213> ORGANISM: Homo sapiens
```

```
<400> SEQUENCE: 98

His Arg Leu Ile Pro Leu Gly Arg Lys Ile Tyr Glu Phe Tyr Gly
 1               5                  10                  15

<210> SEQ ID NO 99
<211> LENGTH: 14
<212> TYPE: PRT
<213> ORGANISM: Homo sapiens

<400> SEQUENCE: 99

Glu Glu Asn Glu Ala Lys Gly Arg Arg Ala Thr Ile Ala Ile
 1               5                  10

<210> SEQ ID NO 100
<211> LENGTH: 79
<212> TYPE: PRT
<213> ORGANISM: Homo sapiens

<400> SEQUENCE: 100

Lys Asn Lys Asp Asp Met Pro Tyr Met Ser Gln Ala Gln Glu Ile His
 1               5                  10                  15

Leu Gln Glu Lys Glu Ala Glu Glu Pro Glu Lys Pro Thr Lys Glu Lys
            20                  25                  30

Glu Glu Glu Asp Met Glu Leu Thr Ala Met Leu Gly Arg Asn Asn Gly
        35                  40                  45

Glu Ser Ser Arg Lys Lys Asp Glu Glu Val Gln Ser Lys His Arg
    50                  55                  60

Leu Ile Pro Leu Gly Arg Lys Ile Tyr Glu Phe Tyr Asn Ala Pro
65                  70                  75

<210> SEQ ID NO 101
<211> LENGTH: 55
<212> TYPE: PRT
<213> ORGANISM: Homo sapiens

<400> SEQUENCE: 101

Asn Tyr Ile Val Leu Val Lys Met Glu Arg Trp Pro Ser Thr Gln Glu
 1               5                  10                  15

Trp Ile Val Ile Ser Tyr Ile Phe Thr Leu Gly Ile Glu Lys Met Arg
            20                  25                  30

Glu Ile Leu Met Ser Glu Pro Gly Lys Leu Leu Gln Lys Val Lys Val
        35                  40                  45

Trp Leu Gln Glu Tyr Trp Asn
    50                  55

<210> SEQ ID NO 102
<211> LENGTH: 13
<212> TYPE: PRT
<213> ORGANISM: Homo sapiens

<400> SEQUENCE: 102

Ile Leu Arg Leu Gln Asp Gln Pro Phe Arg Ser Asp Gly
 1               5                  10

<210> SEQ ID NO 103
<211> LENGTH: 16
<212> TYPE: PRT
<213> ORGANISM: Homo sapiens

<400> SEQUENCE: 103

Phe Gly Val Asn Lys Tyr Leu Gly Pro Tyr Val Met Met Ile Gly Lys
```

<210> SEQ ID NO 104
<211> LENGTH: 69
<212> TYPE: PRT
<213> ORGANISM: Homo sapiens

<400> SEQUENCE: 104

Phe Gly Val Ala Arg Gln Ala Ile Leu Phe Pro Asn Glu Glu Pro Ser
1               5                   10                  15

Trp Lys Leu Ala Lys Asn Ile Phe Tyr Met Pro Tyr Trp Met Ile Tyr
                20                  25                  30

Gly Glu Val Phe Ala Asp Gln Ile Asp Pro Pro Cys Gly Gln Asn Glu
            35                  40                  45

Thr Arg Glu Asp Gly Lys Ile Ile Gln Leu Pro Pro Cys Lys Thr Gly
        50                  55                  60

Ala Trp Ile Val Pro
65

<210> SEQ ID NO 105
<211> LENGTH: 6
<212> TYPE: PRT
<213> ORGANISM: Homo sapiens

<400> SEQUENCE: 105

Val Trp Lys Phe Gln Arg
1               5

<210> SEQ ID NO 106
<211> LENGTH: 55
<212> TYPE: PRT
<213> ORGANISM: Homo sapiens

<400> SEQUENCE: 106

Glu Arg Ile Arg Val Thr Ser Glu Arg Val Glu Asn Met Ser Met Arg
1               5                   10                  15

Leu Glu Glu Val Asn Glu Arg Glu His Ser Met Lys Ala Ser Leu Gln
                20                  25                  30

Thr Val Asp Ile Arg Leu Ala Gln Leu Glu Asp Leu Ile Gly Arg Met
            35                  40                  45

Ala Thr Ala Leu Glu Arg Leu
        50                  55

<210> SEQ ID NO 107
<211> LENGTH: 20
<212> TYPE: PRT
<213> ORGANISM: Homo sapiens

<400> SEQUENCE: 107

Leu Ile Gly Arg Met Ala Thr Ala Leu Glu Arg Leu Thr Gly Leu Glu
1               5                   10                  15

Arg Ala Glu Ser
            20

<210> SEQ ID NO 108
<211> LENGTH: 13
<212> TYPE: PRT
<213> ORGANISM: Homo sapiens

<400> SEQUENCE: 108

Ser Lys Pro Glu Gly Arg Gly Asp Ser Leu Ser Met Arg

```
<210> SEQ ID NO 109
<211> LENGTH: 212
<212> TYPE: PRT
<213> ORGANISM: Homo sapiens

<400> SEQUENCE: 109

Thr Gln Glu Trp Ile Val Ile Ser Tyr Ile Phe Thr Leu Gly Ile Glu
 1               5                  10                  15

Lys Met Arg Glu Ile Leu Met Ser Glu Pro Gly Lys Leu Leu Gln Lys
            20                  25                  30

Val Lys Val Trp Leu Gln Glu Tyr Trp Asn Val Thr Asp Leu Ile Ala
        35                  40                  45

Ile Leu Leu Phe Ser Val Gly Met Ile Leu Arg Leu Gln Asp Gln Pro
    50                  55                  60

Phe Arg Ser Asp Gly Arg Val Ile Tyr Cys Val Asn Ile Ile Tyr Trp
65                  70                  75                  80

Tyr Ile Arg Leu Leu Asp Ile Phe Gly Val Asn Lys Tyr Leu Gly Pro
                85                  90                  95

Tyr Val Met Met Ile Gly Lys Met Met Ile Asp Met Met Tyr Phe Val
            100                 105                 110

Ile Ile Met Leu Val Val Leu Met Ser Phe Gly Val Ala Arg Gln Ala
        115                 120                 125

Ile Leu Phe Pro Asn Glu Glu Pro Ser Trp Lys Leu Ala Lys Asn Ile
    130                 135                 140

Phe Tyr Met Pro Tyr Trp Met Ile Tyr Gly Glu Val Phe Ala Asp Gln
145                 150                 155                 160

Ile Asp Pro Pro Cys Gly Gln Asn Glu Thr Arg Glu Asp Gly Lys Ile
                165                 170                 175

Ile Gln Leu Pro Pro Cys Lys Thr Gly Ala Trp Ile Val Pro Ala Ile
            180                 185                 190

Met Ala Cys Tyr Leu Leu Val Ala Asn Ile Leu Leu Val Asn Leu Leu
        195                 200                 205

Ile Ala Val Phe
    210

<210> SEQ ID NO 110
<211> LENGTH: 18
<212> TYPE: PRT
<213> ORGANISM: Homo sapiens

<400> SEQUENCE: 110

Leu Ser Leu Glu Phe Lys Asn Lys Asp Asp Met Pro Tyr Met Ser Gln
 1               5                  10                  15

Ala Gln

<210> SEQ ID NO 111
<211> LENGTH: 18
<212> TYPE: PRT
<213> ORGANISM: Homo sapiens

<400> SEQUENCE: 111

Val Met Met Ile Gly Lys Met Met Ile Asp Met Met Tyr Phe Val Ile
 1               5                  10                  15

Ile Met
```

```
<210> SEQ ID NO 112
<211> LENGTH: 13
<212> TYPE: PRT
<213> ORGANISM: Homo sapiens

<400> SEQUENCE: 112

Ala Asp Asn Gly Thr Thr Gly Lys Tyr Gly Ala Glu Val
1               5                   10

<210> SEQ ID NO 113
<211> LENGTH: 13
<212> TYPE: PRT
<213> ORGANISM: Homo sapiens

<400> SEQUENCE: 113

Val Val Cys Asp Gly Ser Gly Arg Ala Ser Asp Ile Leu
1               5                   10

<210> SEQ ID NO 114
<211> LENGTH: 13
<212> TYPE: PRT
<213> ORGANISM: Homo sapiens

<400> SEQUENCE: 114

Gly Leu Ile Asn Glu Ser Leu Arg Asp Gln Leu Leu Val
1               5                   10

<210> SEQ ID NO 115
<211> LENGTH: 13
<212> TYPE: PRT
<213> ORGANISM: Homo sapiens

<400> SEQUENCE: 115

Tyr Arg Cys Asn Tyr Thr Arg Lys Arg Phe Arg Thr Leu
1               5                   10

<210> SEQ ID NO 116
<211> LENGTH: 13
<212> TYPE: PRT
<213> ORGANISM: Homo sapiens

<400> SEQUENCE: 116

Arg Arg Gly Arg Lys Thr Thr Lys Lys Arg Glu Glu Glu
1               5                   10

<210> SEQ ID NO 117
<211> LENGTH: 13
<212> TYPE: PRT
<213> ORGANISM: Homo sapiens

<400> SEQUENCE: 117

Arg Gly Arg Lys Thr Thr Lys Lys Arg Glu Glu Glu Val
1               5                   10

<210> SEQ ID NO 118
<211> LENGTH: 13
<212> TYPE: PRT
<213> ORGANISM: Homo sapiens

<400> SEQUENCE: 118

Glu Leu Leu Asp Gln Ser Tyr Lys Gln Asp Gln Leu
1               5                   10

<210> SEQ ID NO 119
<211> LENGTH: 13
```

```
<212> TYPE: PRT
<213> ORGANISM: Homo sapiens

<400> SEQUENCE: 119

Arg Asn Asn Gly Glu Ser Ser Arg Lys Lys Asp Glu Glu
1               5                   10

<210> SEQ ID NO 120
<211> LENGTH: 13
<212> TYPE: PRT
<213> ORGANISM: Homo sapiens

<400> SEQUENCE: 120

Asn Asn Gly Glu Ser Ser Arg Lys Lys Asp Glu Glu Glu
1               5                   10

<210> SEQ ID NO 121
<211> LENGTH: 13
<212> TYPE: PRT
<213> ORGANISM: Homo sapiens

<400> SEQUENCE: 121

Pro Asn Glu Glu Pro Ser Trp Lys Leu Ala Lys Asn Ile
1               5                   10

<210> SEQ ID NO 122
<211> LENGTH: 13
<212> TYPE: PRT
<213> ORGANISM: Homo sapiens

<400> SEQUENCE: 122

Arg Ile Arg Val Thr Ser Glu Arg Val Glu Asn Met Ser
1               5                   10

<210> SEQ ID NO 123
<211> LENGTH: 13
<212> TYPE: PRT
<213> ORGANISM: Homo sapiens

<400> SEQUENCE: 123

Arg Val Glu Asn Met Ser Met Arg Leu Glu Glu Val Asn
1               5                   10

<210> SEQ ID NO 124
<211> LENGTH: 13
<212> TYPE: PRT
<213> ORGANISM: Homo sapiens

<400> SEQUENCE: 124

Asn Glu Arg Glu His Ser Met Lys Ala Ser Leu Gln Thr
1               5                   10

<210> SEQ ID NO 125
<211> LENGTH: 13
<212> TYPE: PRT
<213> ORGANISM: Homo sapiens

<400> SEQUENCE: 125

Leu Glu Arg Ala Glu Ser Asn Lys Ile Arg Ser Arg Thr
1               5                   10

<210> SEQ ID NO 126
<211> LENGTH: 13
<212> TYPE: PRT
<213> ORGANISM: Homo sapiens
```

```
<400> SEQUENCE: 126

Ser Gln Glu Gly Asn Thr Phe Lys Leu Gln Glu Ser Ile
1               5                   10

<210> SEQ ID NO 127
<211> LENGTH: 13
<212> TYPE: PRT
<213> ORGANISM: Homo sapiens

<400> SEQUENCE: 127

Ala Ile Val Pro Asp Ser Arg Arg Pro Ser Ser Cys Ile
1               5                   10

<210> SEQ ID NO 128
<211> LENGTH: 13
<212> TYPE: PRT
<213> ORGANISM: Homo sapiens

<400> SEQUENCE: 128

Ala Thr Leu Ala Pro Thr Asp Arg Pro Pro Ser Arg Ser
1               5                   10

<210> SEQ ID NO 129
<211> LENGTH: 13
<212> TYPE: PRT
<213> ORGANISM: Homo sapiens

<400> SEQUENCE: 129

Ile Glu Arg Ser Lys Ser Ser Arg Tyr Leu Ala Thr Thr
1               5                   10

<210> SEQ ID NO 130
<211> LENGTH: 13
<212> TYPE: PRT
<213> ORGANISM: Homo sapiens

<400> SEQUENCE: 130

Gln Glu Gly Asp Asn Ser Glu Arg Thr Leu Ser Asn Asn
1               5                   10

<210> SEQ ID NO 131
<211> LENGTH: 13
<212> TYPE: PRT
<213> ORGANISM: Homo sapiens

<400> SEQUENCE: 131

Ala Pro Tyr Ala His Thr Arg Lys Ser Phe Ser Ile Ser
1               5                   10

<210> SEQ ID NO 132
<211> LENGTH: 13
<212> TYPE: PRT
<213> ORGANISM: Homo sapiens

<400> SEQUENCE: 132

Lys Ser Phe Ser Ile Ser Asp Lys Leu Asp Arg Gln Arg
1               5                   10

<210> SEQ ID NO 133
<211> LENGTH: 13
<212> TYPE: PRT
<213> ORGANISM: Homo sapiens

<400> SEQUENCE: 133
```

Phe Gln Arg Ser Lys Ser Lys Pro Glu Gly Arg Gly
1               5                   10

<210> SEQ ID NO 134
<211> LENGTH: 13
<212> TYPE: PRT
<213> ORGANISM: Homo sapiens

<400> SEQUENCE: 134

Arg Gly Asp Ser Leu Ser Met Arg Arg Leu Ser Arg Thr
1               5                   10

<210> SEQ ID NO 135
<211> LENGTH: 14
<212> TYPE: PRT
<213> ORGANISM: Homo sapiens

<400> SEQUENCE: 135

Phe Ile Leu Ala Asp Asn Gly Thr Thr Gly Lys Tyr Gly Ala
1               5                   10

<210> SEQ ID NO 136
<211> LENGTH: 14
<212> TYPE: PRT
<213> ORGANISM: Homo sapiens

<400> SEQUENCE: 136

Glu Gly Gly Leu Ile Asn Glu Ser Leu Arg Asp Gln Leu Leu
1               5                   10

<210> SEQ ID NO 137
<211> LENGTH: 14
<212> TYPE: PRT
<213> ORGANISM: Homo sapiens

<400> SEQUENCE: 137

Leu Leu Lys Gly Ala Asn Ala Ser Ala Pro Asp Gln Leu Ser
1               5                   10

<210> SEQ ID NO 138
<211> LENGTH: 14
<212> TYPE: PRT
<213> ORGANISM: Homo sapiens

<400> SEQUENCE: 138

Gly Ala Tyr Arg Cys Asn Tyr Thr Arg Lys Arg Phe Arg Thr
1               5                   10

<210> SEQ ID NO 139
<211> LENGTH: 14
<212> TYPE: PRT
<213> ORGANISM: Homo sapiens

<400> SEQUENCE: 139

Thr Tyr Glu Leu Lys Asn Trp Ser Asn Ala Thr Cys Leu Gln
1               5                   10

<210> SEQ ID NO 140
<211> LENGTH: 14
<212> TYPE: PRT
<213> ORGANISM: Homo sapiens

<400> SEQUENCE: 140

Leu Lys Asn Trp Ser Asn Ala Thr Cys Leu Gln Leu Ala Val

-continued

```
1               5                   10

<210> SEQ ID NO 141
<211> LENGTH: 14
<212> TYPE: PRT
<213> ORGANISM: Homo sapiens

<400> SEQUENCE: 141

Leu Gln Glu Tyr Trp Asn Val Thr Asp Leu Ile Ala Ile Leu
1               5                   10

<210> SEQ ID NO 142
<211> LENGTH: 14
<212> TYPE: PRT
<213> ORGANISM: Homo sapiens

<400> SEQUENCE: 142

Pro Pro Cys Gly Gln Asn Glu Thr Arg Glu Asp Gly Lys Ile
1               5                   10

<210> SEQ ID NO 143
<211> LENGTH: 14
<212> TYPE: PRT
<213> ORGANISM: Homo sapiens

<400> SEQUENCE: 143

Leu Ile Ala Val Phe Asn Asn Thr Phe Phe Glu Val Lys Ser
1               5                   10

<210> SEQ ID NO 144
<211> LENGTH: 14
<212> TYPE: PRT
<213> ORGANISM: Homo sapiens

<400> SEQUENCE: 144

Lys Asp Asp Arg Phe Asn Ser Ser Asn Asp Glu Arg Ile Arg
1               5                   10

<210> SEQ ID NO 145
<211> LENGTH: 14
<212> TYPE: PRT
<213> ORGANISM: Homo sapiens

<400> SEQUENCE: 145

Ser Glu Arg Val Glu Asn Met Ser Met Arg Leu Glu Glu Val
1               5                   10

<210> SEQ ID NO 146
<211> LENGTH: 14
<212> TYPE: PRT
<213> ORGANISM: Homo sapiens

<400> SEQUENCE: 146

Arg Thr Leu Ser Asn Asn Ile Thr Val Pro Lys Ile Glu Arg
1               5                   10

<210> SEQ ID NO 147
<211> LENGTH: 14
<212> TYPE: PRT
<213> ORGANISM: Homo sapiens

<400> SEQUENCE: 147

Asp Ile Pro Leu Arg Arg Gly Arg Lys Thr Thr Lys Lys Arg
1               5                   10
```

```
<210> SEQ ID NO 148
<211> LENGTH: 14
<212> TYPE: PRT
<213> ORGANISM: Homo sapiens

<400> SEQUENCE: 148

His Arg Leu Ile Pro Leu Gly Arg Lys Ile Tyr Glu Phe Tyr
1               5                   10

<210> SEQ ID NO 149
<211> LENGTH: 14
<212> TYPE: PRT
<213> ORGANISM: Homo sapiens

<400> SEQUENCE: 149

Glu Glu Asn Glu Ala Lys Gly Arg Arg Ala Thr Ile Ala Ile
1               5                   10

<210> SEQ ID NO 150
<211> LENGTH: 79
<212> TYPE: PRT
<213> ORGANISM: Homo sapiens

<400> SEQUENCE: 150

Lys Asn Lys Asp Asp Met Pro Tyr Met Ser Gln Ala Gln Glu Ile His
1               5                   10                  15

Leu Gln Glu Lys Glu Ala Glu Glu Pro Glu Lys Pro Thr Lys Glu Lys
                20                  25                  30

Glu Glu Glu Asp Met Glu Leu Thr Ala Met Leu Gly Arg Asn Asn Gly
            35                  40                  45

Glu Ser Ser Arg Lys Lys Asp Glu Glu Val Gln Ser Lys His Arg
        50                  55                  60

Leu Ile Pro Leu Gly Arg Lys Ile Tyr Glu Phe Tyr Asn Ala Pro
65                  70                  75

<210> SEQ ID NO 151
<211> LENGTH: 55
<212> TYPE: PRT
<213> ORGANISM: Homo sapiens

<400> SEQUENCE: 151

Asn Tyr Ile Val Leu Val Lys Met Glu Arg Trp Pro Ser Thr Gln Glu
1               5                   10                  15

Trp Ile Val Ile Ser Tyr Ile Phe Thr Leu Gly Ile Glu Lys Met Arg
                20                  25                  30

Glu Ile Leu Met Ser Glu Pro Gly Lys Leu Leu Gln Lys Val Lys Val
            35                  40                  45

Trp Leu Gln Glu Tyr Trp Asn
        50                  55

<210> SEQ ID NO 152
<211> LENGTH: 13
<212> TYPE: PRT
<213> ORGANISM: Homo sapiens

<400> SEQUENCE: 152

Ile Leu Arg Leu Gln Asp Gln Pro Phe Arg Ser Asp Gly
1               5                   10

<210> SEQ ID NO 153
<211> LENGTH: 16
```

```
<212> TYPE: PRT
<213> ORGANISM: Homo sapiens

<400> SEQUENCE: 153

Phe Gly Val Asn Lys Tyr Leu Gly Pro Tyr Val Met Met Ile Gly Lys
1               5                   10                  15

<210> SEQ ID NO 154
<211> LENGTH: 81
<212> TYPE: PRT
<213> ORGANISM: Homo sapiens

<400> SEQUENCE: 154

Phe Gly Val Ala Arg Gln Ala Ile Leu Phe Pro Asn Glu Glu Pro Ser
1               5                   10                  15

Trp Lys Leu Ala Lys Asn Ile Phe Tyr Met Pro Tyr Trp Met Ile Tyr
            20                  25                  30

Gly Glu Val Phe Ala Asp Gln Ile Asp Arg Lys Gln Val Tyr Asp Ser
        35                  40                  45

His Thr Pro Lys Ser Ala Pro Cys Gly Gln Asn Glu Thr Arg Glu Asp
    50                  55                  60

Gly Lys Ile Ile Gln Leu Pro Pro Cys Lys Thr Gly Ala Trp Ile Val
65                  70                  75                  80

Pro

<210> SEQ ID NO 155
<211> LENGTH: 6
<212> TYPE: PRT
<213> ORGANISM: Homo sapiens

<400> SEQUENCE: 155

Val Trp Lys Phe Gln Arg
1               5

<210> SEQ ID NO 156
<211> LENGTH: 212
<212> TYPE: PRT
<213> ORGANISM: Homo sapiens

<400> SEQUENCE: 156

Leu Gly Ile Glu Lys Met Arg Glu Ile Leu Met Ser Glu Pro Gly Lys
1               5                   10                  15

Leu Leu Gln Lys Val Lys Val Trp Leu Gln Glu Tyr Trp Asn Val Thr
            20                  25                  30

Asp Leu Ile Ala Ile Leu Leu Phe Ser Val Gly Met Ile Leu Arg Leu
        35                  40                  45

Gln Asp Gln Pro Phe Arg Ser Asp Gly Arg Val Ile Tyr Cys Val Asn
    50                  55                  60

Ile Ile Tyr Trp Tyr Ile Arg Leu Leu Asp Ile Phe Gly Val Asn Lys
65                  70                  75                  80

Tyr Leu Gly Pro Tyr Val Met Met Ile Gly Lys Met Met Ile Asp Met
                85                  90                  95

Met Tyr Phe Val Ile Ile Met Leu Val Val Leu Met Ser Phe Gly Val
                100                 105                 110

Ala Arg Gln Ala Ile Leu Phe Pro Asn Glu Glu Pro Ser Trp Lys Leu
            115                 120                 125

Ala Lys Asn Ile Phe Tyr Met Pro Tyr Trp Met Ile Tyr Gly Glu Val
        130                 135                 140
```

Phe Ala Asp Gln Ile Asp Arg Lys Gln Val Tyr Asp Ser His Thr Pro
145                 150                 155                 160

Lys Ser Ala Pro Cys Gly Gln Asn Glu Thr Arg Glu Asp Gly Lys Ile
                165                 170                 175

Ile Gln Leu Pro Pro Cys Lys Thr Gly Ala Trp Ile Val Pro Ala Ile
            180                 185                 190

Met Ala Cys Tyr Leu Leu Val Ala Asn Ile Leu Leu Val Asn Leu Leu
        195                 200                 205

Ile Ala Val Phe
    210

<210> SEQ ID NO 157
<211> LENGTH: 55
<212> TYPE: PRT
<213> ORGANISM: Homo sapiens

<400> SEQUENCE: 157

Glu Arg Ile Arg Val Thr Ser Glu Arg Val Glu Asn Met Ser Met Arg
1               5                   10                  15

Leu Glu Glu Val Asn Glu Arg Glu His Ser Met Lys Ala Ser Leu Gln
            20                  25                  30

Thr Val Asp Ile Arg Leu Ala Gln Leu Glu Asp Leu Ile Gly Arg Met
        35                  40                  45

Ala Thr Ala Leu Glu Arg Leu
    50                  55

<210> SEQ ID NO 158
<211> LENGTH: 18
<212> TYPE: PRT
<213> ORGANISM: Homo sapiens

<400> SEQUENCE: 158

Leu Ser Leu Glu Phe Lys Asn Lys Asp Met Pro Tyr Met Ser Gln
1               5                   10                  15

Ala Gln

<210> SEQ ID NO 159
<211> LENGTH: 18
<212> TYPE: PRT
<213> ORGANISM: Homo sapiens

<400> SEQUENCE: 159

Val Met Met Ile Gly Lys Met Met Ile Asp Met Met Tyr Phe Val Ile
1               5                   10                  15

Ile Met

<210> SEQ ID NO 160
<211> LENGTH: 13
<212> TYPE: PRT
<213> ORGANISM: Homo sapiens

<400> SEQUENCE: 160

Ala Asp Asn Gly Thr Thr Gly Lys Tyr Gly Ala Glu Val
1               5                   10

<210> SEQ ID NO 161
<211> LENGTH: 13
<212> TYPE: PRT
<213> ORGANISM: Homo sapiens

<400> SEQUENCE: 161

Val Val Cys Asp Gly Ser Gly Arg Ala Ser Asp Ile Leu
1               5                   10

<210> SEQ ID NO 162
<211> LENGTH: 13
<212> TYPE: PRT
<213> ORGANISM: Homo sapiens

<400> SEQUENCE: 162

Gly Leu Ile Asn Glu Ser Leu Arg Asp Gln Leu Leu Val
1               5                   10

<210> SEQ ID NO 163
<211> LENGTH: 13
<212> TYPE: PRT
<213> ORGANISM: Homo sapiens

<400> SEQUENCE: 163

Tyr Arg Cys Asn Tyr Thr Arg Lys Arg Phe Arg Thr Leu
1               5                   10

<210> SEQ ID NO 164
<211> LENGTH: 13
<212> TYPE: PRT
<213> ORGANISM: Homo sapiens

<400> SEQUENCE: 164

Arg Arg Gly Arg Lys Thr Thr Lys Lys Arg Glu Glu Glu
1               5                   10

<210> SEQ ID NO 165
<211> LENGTH: 13
<212> TYPE: PRT
<213> ORGANISM: Homo sapiens

<400> SEQUENCE: 165

Arg Gly Arg Lys Thr Thr Lys Lys Arg Glu Glu Glu Val
1               5                   10

<210> SEQ ID NO 166
<211> LENGTH: 13
<212> TYPE: PRT
<213> ORGANISM: Homo sapiens

<400> SEQUENCE: 166

Glu Leu Leu Asp Gln Ser Tyr Lys Gln Asp Gln Leu
1               5                   10

<210> SEQ ID NO 167
<211> LENGTH: 13
<212> TYPE: PRT
<213> ORGANISM: Homo sapiens

<400> SEQUENCE: 167

Arg Asn Asn Gly Glu Ser Ser Arg Lys Lys Asp Glu Glu
1               5                   10

<210> SEQ ID NO 168
<211> LENGTH: 13
<212> TYPE: PRT
<213> ORGANISM: Homo sapiens

<400> SEQUENCE: 168

Asn Asn Gly Glu Ser Ser Arg Lys Lys Asp Glu Glu Glu

```
                1               5                   10
```

<210> SEQ ID NO 169
<211> LENGTH: 13
<212> TYPE: PRT
<213> ORGANISM: Homo sapiens

<400> SEQUENCE: 169

```
Pro Asn Glu Glu Pro Ser Trp Lys Leu Ala Lys Asn Ile
1               5                   10
```

<210> SEQ ID NO 170
<211> LENGTH: 13
<212> TYPE: PRT
<213> ORGANISM: Homo sapiens

<400> SEQUENCE: 170

```
Val Tyr Asp Ser His Thr Pro Lys Ser Ala Pro Cys Gly
1               5                   10
```

<210> SEQ ID NO 171
<211> LENGTH: 13
<212> TYPE: PRT
<213> ORGANISM: Homo sapiens

<400> SEQUENCE: 171

```
Arg Ile Arg Val Thr Ser Glu Arg Val Glu Asn Met Ser
1               5                   10
```

<210> SEQ ID NO 172
<211> LENGTH: 13
<212> TYPE: PRT
<213> ORGANISM: Homo sapiens

<400> SEQUENCE: 172

```
Arg Val Glu Asn Met Ser Met Arg Leu Glu Glu Val Asn
1               5                   10
```

<210> SEQ ID NO 173
<211> LENGTH: 13
<212> TYPE: PRT
<213> ORGANISM: Homo sapiens

<400> SEQUENCE: 173

```
Asn Glu Arg Glu His Ser Met Lys Ala Ser Leu Gln Thr
1               5                   10
```

<210> SEQ ID NO 174
<211> LENGTH: 13
<212> TYPE: PRT
<213> ORGANISM: Homo sapiens

<400> SEQUENCE: 174

```
Leu Glu Arg Ala Glu Ser Asn Lys Ile Arg Ser Arg Thr
1               5                   10
```

<210> SEQ ID NO 175
<211> LENGTH: 13
<212> TYPE: PRT
<213> ORGANISM: Homo sapiens

<400> SEQUENCE: 175

```
Ser Gln Glu Gly Asn Thr Phe Lys Leu Gln Glu Ser Ile
1               5                   10
```

```
<210> SEQ ID NO 176
<211> LENGTH: 13
<212> TYPE: PRT
<213> ORGANISM: Homo sapiens

<400> SEQUENCE: 176

Ala Ile Val Pro Asp Ser Arg Arg Pro Ser Ser Cys Ile
1               5                   10

<210> SEQ ID NO 177
<211> LENGTH: 13
<212> TYPE: PRT
<213> ORGANISM: Homo sapiens

<400> SEQUENCE: 177

Ala Thr Leu Ala Pro Thr Asp Arg Pro Pro Ser Arg Ser
1               5                   10

<210> SEQ ID NO 178
<211> LENGTH: 13
<212> TYPE: PRT
<213> ORGANISM: Homo sapiens

<400> SEQUENCE: 178

Ile Glu Arg Ser Lys Ser Ser Arg Tyr Leu Ala Thr Thr
1               5                   10

<210> SEQ ID NO 179
<211> LENGTH: 13
<212> TYPE: PRT
<213> ORGANISM: Homo sapiens

<400> SEQUENCE: 179

Gln Glu Gly Asp Asn Ser Glu Arg Thr Leu Ser Asn Asn
1               5                   10

<210> SEQ ID NO 180
<211> LENGTH: 13
<212> TYPE: PRT
<213> ORGANISM: Homo sapiens

<400> SEQUENCE: 180

Ala Pro Tyr Ala His Thr Arg Lys Ser Phe Ser Ile Ser
1               5                   10

<210> SEQ ID NO 181
<211> LENGTH: 13
<212> TYPE: PRT
<213> ORGANISM: Homo sapiens

<400> SEQUENCE: 181

Lys Ser Phe Ser Ile Ser Asp Lys Leu Asp Arg Gln Arg
1               5                   10

<210> SEQ ID NO 182
<211> LENGTH: 13
<212> TYPE: PRT
<213> ORGANISM: Homo sapiens

<400> SEQUENCE: 182

Phe Gln Arg Ser Lys Ser Ser Lys Pro Glu Gly Arg Gly
1               5                   10

<210> SEQ ID NO 183
```

-continued

```
<211> LENGTH: 13
<212> TYPE: PRT
<213> ORGANISM: Homo sapiens

<400> SEQUENCE: 183

Arg Gly Asp Ser Leu Ser Met Arg Arg Leu Ser Arg Thr
1               5                   10

<210> SEQ ID NO 184
<211> LENGTH: 14
<212> TYPE: PRT
<213> ORGANISM: Homo sapiens

<400> SEQUENCE: 184

Phe Ile Leu Ala Asp Asn Gly Thr Thr Gly Lys Tyr Gly Ala
1               5                   10

<210> SEQ ID NO 185
<211> LENGTH: 14
<212> TYPE: PRT
<213> ORGANISM: Homo sapiens

<400> SEQUENCE: 185

Glu Gly Gly Leu Ile Asn Glu Ser Leu Arg Asp Gln Leu Leu
1               5                   10

<210> SEQ ID NO 186
<211> LENGTH: 14
<212> TYPE: PRT
<213> ORGANISM: Homo sapiens

<400> SEQUENCE: 186

Leu Leu Lys Gly Ala Asn Ala Ser Ala Pro Asp Gln Leu Ser
1               5                   10

<210> SEQ ID NO 187
<211> LENGTH: 14
<212> TYPE: PRT
<213> ORGANISM: Homo sapiens

<400> SEQUENCE: 187

Gly Ala Tyr Arg Cys Asn Tyr Thr Arg Lys Arg Phe Arg Thr
1               5                   10

<210> SEQ ID NO 188
<211> LENGTH: 14
<212> TYPE: PRT
<213> ORGANISM: Homo sapiens

<400> SEQUENCE: 188

Thr Tyr Glu Leu Lys Asn Trp Ser Asn Ala Thr Cys Leu Gln
1               5                   10

<210> SEQ ID NO 189
<211> LENGTH: 14
<212> TYPE: PRT
<213> ORGANISM: Homo sapiens

<400> SEQUENCE: 189

Leu Lys Asn Trp Ser Asn Ala Thr Cys Leu Gln Leu Ala Val
1               5                   10

<210> SEQ ID NO 190
<211> LENGTH: 14
<212> TYPE: PRT
```

-continued

<213> ORGANISM: Homo sapiens

<400> SEQUENCE: 190

Leu Gln Glu Tyr Trp Asn Val Thr Asp Leu Ile Ala Ile Leu
1               5                   10

<210> SEQ ID NO 191
<211> LENGTH: 14
<212> TYPE: PRT
<213> ORGANISM: Homo sapiens

<400> SEQUENCE: 191

Ala Pro Cys Gly Gln Asn Glu Thr Arg Glu Asp Gly Lys Ile
1               5                   10

<210> SEQ ID NO 192
<211> LENGTH: 14
<212> TYPE: PRT
<213> ORGANISM: Homo sapiens

<400> SEQUENCE: 192

Leu Ile Ala Val Phe Asn Asn Thr Phe Phe Glu Val Lys Ser
1               5                   10

<210> SEQ ID NO 193
<211> LENGTH: 14
<212> TYPE: PRT
<213> ORGANISM: Homo sapiens

<400> SEQUENCE: 193

Lys Asp Asp Arg Phe Asn Ser Ser Asn Asp Glu Arg Ile Arg
1               5                   10

<210> SEQ ID NO 194
<211> LENGTH: 14
<212> TYPE: PRT
<213> ORGANISM: Homo sapiens

<400> SEQUENCE: 194

Ser Glu Arg Val Glu Asn Met Ser Met Arg Leu Glu Glu Val
1               5                   10

<210> SEQ ID NO 195
<211> LENGTH: 14
<212> TYPE: PRT
<213> ORGANISM: Homo sapiens

<400> SEQUENCE: 195

Arg Thr Leu Ser Asn Asn Ile Thr Val Pro Lys Ile Glu Arg
1               5                   10

<210> SEQ ID NO 196
<211> LENGTH: 13
<212> TYPE: PRT
<213> ORGANISM: Homo sapiens

<400> SEQUENCE: 196

Ser Lys Pro Glu Gly Arg Gly Asp Ser Leu Ser Met Arg
1               5                   10

<210> SEQ ID NO 197
<211> LENGTH: 20
<212> TYPE: PRT
<213> ORGANISM: Homo sapiens

<400> SEQUENCE: 197

Leu Ile Gly Arg Met Ala Thr Ala Leu Glu Arg Leu Thr Gly Leu Glu
1               5                   10                  15

Arg Ala Glu Ser
            20

<210> SEQ ID NO 198
<211> LENGTH: 14
<212> TYPE: PRT
<213> ORGANISM: Homo sapiens

<400> SEQUENCE: 198

Asp Ile Pro Leu Arg Arg Gly Arg Lys Thr Thr Lys Lys Arg
1               5                   10

<210> SEQ ID NO 199
<211> LENGTH: 14
<212> TYPE: PRT
<213> ORGANISM: Homo sapiens

<400> SEQUENCE: 199

His Arg Leu Ile Pro Leu Gly Arg Lys Ile Tyr Glu Phe Tyr
1               5                   10

<210> SEQ ID NO 200
<211> LENGTH: 14
<212> TYPE: PRT
<213> ORGANISM: Homo sapiens

<400> SEQUENCE: 200

Glu Glu Asn Glu Ala Lys Gly Arg Arg Ala Thr Ile Ala Ile
1               5                   10

<210> SEQ ID NO 201
<211> LENGTH: 79
<212> TYPE: PRT
<213> ORGANISM: Homo sapiens

<400> SEQUENCE: 201

Lys Asn Lys Asp Asp Met Pro Tyr Met Ser Gln Ala Gln Glu Ile His
1               5                   10                  15

Leu Gln Glu Lys Glu Ala Glu Glu Pro Glu Lys Pro Thr Lys Glu Lys
            20                  25                  30

Glu Glu Glu Asp Met Glu Leu Thr Ala Met Leu Gly Arg Asn Asn Gly
        35                  40                  45

Glu Ser Ser Arg Lys Lys Asp Glu Glu Val Gln Ser Lys His Arg
    50                  55                  60

Leu Ile Pro Leu Gly Arg Lys Ile Tyr Glu Phe Tyr Asn Ala Pro
65                  70                  75

<210> SEQ ID NO 202
<211> LENGTH: 55
<212> TYPE: PRT
<213> ORGANISM: Homo sapiens

<400> SEQUENCE: 202

Asn Tyr Ile Val Leu Val Lys Met Glu Arg Trp Pro Ser Thr Gln Glu
1               5                   10                  15

Trp Ile Val Ile Ser Tyr Ile Phe Thr Leu Gly Ile Glu Lys Met Arg
            20                  25                  30

Glu Ile Leu Met Ser Glu Pro Gly Lys Leu Leu Gln Lys Val Lys Val

```
                35                  40                  45

Trp Leu Gln Glu Tyr Trp Asn
     50                  55

<210> SEQ ID NO 203
<211> LENGTH: 13
<212> TYPE: PRT
<213> ORGANISM: Homo sapiens

<400> SEQUENCE: 203

Ile Leu Arg Leu Gln Asp Gln Pro Phe Arg Ser Asp Gly
1               5                  10

<210> SEQ ID NO 204
<211> LENGTH: 16
<212> TYPE: PRT
<213> ORGANISM: Homo sapiens

<400> SEQUENCE: 204

Phe Gly Val Asn Lys Tyr Leu Gly Pro Tyr Val Met Met Ile Gly Lys
1               5                  10                  15

<210> SEQ ID NO 205
<211> LENGTH: 69
<212> TYPE: PRT
<213> ORGANISM: Homo sapiens

<400> SEQUENCE: 205

Phe Gly Val Ala Arg Gln Ala Ile Leu Phe Pro Asn Glu Glu Pro Ser
1               5                  10                  15

Trp Lys Leu Ala Lys Asn Ile Phe Tyr Met Pro Tyr Trp Met Ile Tyr
            20                  25                  30

Gly Glu Val Phe Ala Asp Gln Ile Asp Pro Pro Cys Gly Gln Asn Glu
        35                  40                  45

Thr Arg Glu Asp Gly Lys Ile Ile Gln Leu Pro Pro Cys Lys Thr Gly
    50                  55                  60

Ala Trp Ile Val Pro
65

<210> SEQ ID NO 206
<211> LENGTH: 6
<212> TYPE: PRT
<213> ORGANISM: Homo sapiens

<400> SEQUENCE: 206

Val Trp Lys Phe Gln Arg
1               5

<210> SEQ ID NO 207
<211> LENGTH: 212
<212> TYPE: PRT
<213> ORGANISM: Homo sapiens

<400> SEQUENCE: 207

Thr Gln Glu Trp Ile Val Ile Ser Tyr Ile Phe Thr Leu Gly Ile Glu
1               5                  10                  15

Lys Met Arg Glu Ile Leu Met Ser Glu Pro Gly Lys Leu Leu Gln Lys
            20                  25                  30

Val Lys Val Trp Leu Gln Glu Tyr Trp Asn Val Thr Asp Leu Ile Ala
        35                  40                  45

Ile Leu Leu Phe Ser Val Gly Met Ile Leu Arg Leu Gln Asp Gln Pro
```

```
                   50                 55                 60
Phe Arg Ser Asp Gly Arg Val Ile Tyr Cys Val Asn Ile Ile Tyr Trp
 65                  70                  75                  80

Tyr Ile Arg Leu Leu Asp Ile Phe Gly Val Asn Lys Tyr Leu Gly Pro
                 85                  90                  95

Tyr Val Met Met Ile Gly Lys Met Met Ile Asp Met Met Tyr Phe Val
                100                 105                 110

Ile Ile Met Leu Val Val Leu Met Ser Phe Gly Val Ala Arg Gln Ala
                115                 120                 125

Ile Leu Phe Pro Asn Glu Glu Pro Ser Trp Lys Leu Ala Lys Asn Ile
                130                 135                 140

Phe Tyr Met Pro Tyr Trp Met Ile Tyr Gly Glu Val Phe Ala Asp Gln
145                 150                 155                 160

Ile Asp Pro Pro Cys Gly Gln Asn Glu Thr Arg Glu Asp Gly Lys Ile
                165                 170                 175

Ile Gln Leu Pro Pro Cys Lys Thr Gly Ala Trp Ile Val Pro Ala Ile
                180                 185                 190

Met Ala Cys Tyr Leu Leu Val Ala Asn Ile Leu Leu Val Asn Leu Leu
                195                 200                 205

Ile Ala Val Phe
            210

<210> SEQ ID NO 208
<211> LENGTH: 55
<212> TYPE: PRT
<213> ORGANISM: Homo sapiens

<400> SEQUENCE: 208

Glu Arg Ile Arg Val Thr Ser Glu Arg Val Glu Asn Met Ser Met Arg
 1               5                  10                  15

Leu Glu Glu Val Asn Glu Arg Glu His Ser Met Lys Ala Ser Leu Gln
                20                  25                  30

Thr Val Asp Ile Arg Leu Ala Gln Leu Glu Asp Leu Ile Gly Arg Met
                35                  40                  45

Ala Thr Ala Leu Glu Arg Leu
            50                  55

<210> SEQ ID NO 209
<211> LENGTH: 18
<212> TYPE: PRT
<213> ORGANISM: Homo sapiens

<400> SEQUENCE: 209

Leu Ser Leu Glu Phe Lys Asn Lys Asp Asp Met Pro Tyr Met Ser Gln
 1               5                  10                  15

Ala Gln

<210> SEQ ID NO 210
<211> LENGTH: 18
<212> TYPE: PRT
<213> ORGANISM: Homo sapiens

<400> SEQUENCE: 210

Val Met Met Ile Gly Lys Met Met Ile Asp Met Met Tyr Phe Val Ile
 1               5                  10                  15

Ile Met
```

```
<210> SEQ ID NO 211
<211> LENGTH: 13
<212> TYPE: PRT
<213> ORGANISM: Homo sapiens

<400> SEQUENCE: 211

Ala Asp Asn Gly Thr Thr Gly Lys Tyr Gly Ala Glu Val
1               5                   10

<210> SEQ ID NO 212
<211> LENGTH: 13
<212> TYPE: PRT
<213> ORGANISM: Homo sapiens

<400> SEQUENCE: 212

Val Val Cys Asp Gly Ser Gly Arg Ala Ser Asp Ile Leu
1               5                   10

<210> SEQ ID NO 213
<211> LENGTH: 13
<212> TYPE: PRT
<213> ORGANISM: Homo sapiens

<400> SEQUENCE: 213

Gly Leu Ile Asn Glu Ser Leu Arg Asp Gln Leu Leu Val
1               5                   10

<210> SEQ ID NO 214
<211> LENGTH: 13
<212> TYPE: PRT
<213> ORGANISM: Homo sapiens

<400> SEQUENCE: 214

Tyr Arg Cys Asn Tyr Thr Arg Lys Arg Phe Arg Thr Leu
1               5                   10

<210> SEQ ID NO 215
<211> LENGTH: 13
<212> TYPE: PRT
<213> ORGANISM: Homo sapiens

<400> SEQUENCE: 215

Arg Arg Gly Arg Lys Thr Thr Lys Lys Arg Glu Glu Glu
1               5                   10

<210> SEQ ID NO 216
<211> LENGTH: 13
<212> TYPE: PRT
<213> ORGANISM: Homo sapiens

<400> SEQUENCE: 216

Arg Gly Arg Lys Thr Thr Lys Lys Arg Glu Glu Glu Val
1               5                   10

<210> SEQ ID NO 217
<211> LENGTH: 13
<212> TYPE: PRT
<213> ORGANISM: Homo sapiens

<400> SEQUENCE: 217

Glu Leu Leu Asp Gln Ser Tyr Lys Gln Asp Gln Leu
1               5                   10

<210> SEQ ID NO 218
<211> LENGTH: 13
```

-continued

<212> TYPE: PRT
<213> ORGANISM: Homo sapiens

<400> SEQUENCE: 218

Arg Asn Asn Gly Glu Ser Ser Arg Lys Lys Asp Glu Glu
1               5                   10

<210> SEQ ID NO 219
<211> LENGTH: 13
<212> TYPE: PRT
<213> ORGANISM: Homo sapiens

<400> SEQUENCE: 219

Asn Asn Gly Glu Ser Ser Arg Lys Lys Asp Glu Glu Glu
1               5                   10

<210> SEQ ID NO 220
<211> LENGTH: 13
<212> TYPE: PRT
<213> ORGANISM: Homo sapiens

<400> SEQUENCE: 220

Pro Asn Glu Glu Pro Ser Trp Lys Leu Ala Lys Asn Ile
1               5                   10

<210> SEQ ID NO 221
<211> LENGTH: 13
<212> TYPE: PRT
<213> ORGANISM: Homo sapiens

<400> SEQUENCE: 221

Arg Ile Arg Val Thr Ser Glu Arg Val Glu Asn Met Ser
1               5                   10

<210> SEQ ID NO 222
<211> LENGTH: 13
<212> TYPE: PRT
<213> ORGANISM: Homo sapiens

<400> SEQUENCE: 222

Arg Val Glu Asn Met Ser Met Arg Leu Glu Glu Val Asn
1               5                   10

<210> SEQ ID NO 223
<211> LENGTH: 13
<212> TYPE: PRT
<213> ORGANISM: Homo sapiens

<400> SEQUENCE: 223

Asn Glu Arg Glu His Ser Met Lys Ala Ser Leu Gln Thr
1               5                   10

<210> SEQ ID NO 224
<211> LENGTH: 13
<212> TYPE: PRT
<213> ORGANISM: Homo sapiens

<400> SEQUENCE: 224

Leu Glu Arg Ala Glu Ser Asn Lys Ile Arg Ser Arg Thr
1               5                   10

<210> SEQ ID NO 225
<211> LENGTH: 13
<212> TYPE: PRT
<213> ORGANISM: Homo sapiens

<400> SEQUENCE: 225

Ser Gln Glu Gly Asn Thr Phe Lys Leu Gln Glu Ser Ile
1               5                   10

<210> SEQ ID NO 226
<211> LENGTH: 13
<212> TYPE: PRT
<213> ORGANISM: Homo sapiens

<400> SEQUENCE: 226

Ala Ile Val Pro Asp Ser Arg Arg Pro Ser Ser Cys Ile
1               5                   10

<210> SEQ ID NO 227
<211> LENGTH: 13
<212> TYPE: PRT
<213> ORGANISM: Homo sapiens

<400> SEQUENCE: 227

Ala Thr Leu Ala Pro Thr Asp Arg Pro Pro Ser Arg Ser
1               5                   10

<210> SEQ ID NO 228
<211> LENGTH: 13
<212> TYPE: PRT
<213> ORGANISM: Homo sapiens

<400> SEQUENCE: 228

Ile Glu Arg Ser Lys Ser Ser Arg Tyr Leu Ala Thr Thr
1               5                   10

<210> SEQ ID NO 229
<211> LENGTH: 13
<212> TYPE: PRT
<213> ORGANISM: Homo sapiens

<400> SEQUENCE: 229

Gln Glu Gly Asp Asn Ser Glu Arg Thr Leu Ser Asn Asn
1               5                   10

<210> SEQ ID NO 230
<211> LENGTH: 13
<212> TYPE: PRT
<213> ORGANISM: Homo sapiens

<400> SEQUENCE: 230

Ala Pro Tyr Ala His Thr Arg Lys Ser Phe Ser Ile Ser
1               5                   10

<210> SEQ ID NO 231
<211> LENGTH: 13
<212> TYPE: PRT
<213> ORGANISM: Homo sapiens

<400> SEQUENCE: 231

Lys Ser Phe Ser Ile Ser Asp Lys Leu Asp Arg Gln Arg
1               5                   10

<210> SEQ ID NO 232
<211> LENGTH: 13
<212> TYPE: PRT
<213> ORGANISM: Homo sapiens

<400> SEQUENCE: 232

```
Phe Gln Arg Ser Lys Ser Ser Lys Pro Glu Gly Arg Gly
1               5                   10
```

<210> SEQ ID NO 233
<211> LENGTH: 13
<212> TYPE: PRT
<213> ORGANISM: Homo sapiens

<400> SEQUENCE: 233

```
Arg Gly Asp Ser Leu Ser Met Arg Arg Leu Ser Arg Thr
1               5                   10
```

<210> SEQ ID NO 234
<211> LENGTH: 14
<212> TYPE: PRT
<213> ORGANISM: Homo sapiens

<400> SEQUENCE: 234

```
Phe Ile Leu Ala Asp Asn Gly Thr Thr Gly Lys Tyr Gly Ala
1               5                   10
```

<210> SEQ ID NO 235
<211> LENGTH: 14
<212> TYPE: PRT
<213> ORGANISM: Homo sapiens

<400> SEQUENCE: 235

```
Glu Gly Gly Leu Ile Asn Glu Ser Leu Arg Asp Gln Leu Leu
1               5                   10
```

<210> SEQ ID NO 236
<211> LENGTH: 14
<212> TYPE: PRT
<213> ORGANISM: Homo sapiens

<400> SEQUENCE: 236

```
Leu Leu Lys Gly Ala Asn Ala Ser Ala Pro Asp Gln Leu Ser
1               5                   10
```

<210> SEQ ID NO 237
<211> LENGTH: 14
<212> TYPE: PRT
<213> ORGANISM: Homo sapiens

<400> SEQUENCE: 237

```
Gly Ala Tyr Arg Cys Asn Tyr Thr Arg Lys Arg Phe Arg Thr
1               5                   10
```

<210> SEQ ID NO 238
<211> LENGTH: 14
<212> TYPE: PRT
<213> ORGANISM: Homo sapiens

<400> SEQUENCE: 238

```
Thr Tyr Glu Leu Lys Asn Trp Ser Asn Ala Thr Cys Leu Gln
1               5                   10
```

<210> SEQ ID NO 239
<211> LENGTH: 14
<212> TYPE: PRT
<213> ORGANISM: Homo sapiens

<400> SEQUENCE: 239

```
Leu Lys Asn Trp Ser Asn Ala Thr Cys Leu Gln Leu Ala Val
```

-continued

```
1               5                   10

<210> SEQ ID NO 240
<211> LENGTH: 14
<212> TYPE: PRT
<213> ORGANISM: Homo sapiens

<400> SEQUENCE: 240

Leu Gln Glu Tyr Trp Asn Val Thr Asp Leu Ile Ala Ile Leu
1               5                   10

<210> SEQ ID NO 241
<211> LENGTH: 14
<212> TYPE: PRT
<213> ORGANISM: Homo sapiens

<400> SEQUENCE: 241

Pro Pro Cys Gly Gln Asn Glu Thr Arg Glu Asp Gly Lys Ile
1               5                   10

<210> SEQ ID NO 242
<211> LENGTH: 14
<212> TYPE: PRT
<213> ORGANISM: Homo sapiens

<400> SEQUENCE: 242

Leu Ile Ala Val Phe Asn Asn Thr Phe Phe Glu Val Lys Ser
1               5                   10

<210> SEQ ID NO 243
<211> LENGTH: 14
<212> TYPE: PRT
<213> ORGANISM: Homo sapiens

<400> SEQUENCE: 243

Lys Asp Asp Arg Phe Asn Ser Ser Asn Asp Glu Arg Ile Arg
1               5                   10

<210> SEQ ID NO 244
<211> LENGTH: 14
<212> TYPE: PRT
<213> ORGANISM: Homo sapiens

<400> SEQUENCE: 244

Ser Glu Arg Val Glu Asn Met Ser Met Arg Leu Glu Glu Val
1               5                   10

<210> SEQ ID NO 245
<211> LENGTH: 14
<212> TYPE: PRT
<213> ORGANISM: Homo sapiens

<400> SEQUENCE: 245

Arg Thr Leu Ser Asn Asn Ile Thr Val Pro Lys Ile Glu Arg
1               5                   10

<210> SEQ ID NO 246
<211> LENGTH: 13
<212> TYPE: PRT
<213> ORGANISM: Homo sapiens

<400> SEQUENCE: 246

Ser Lys Pro Glu Gly Arg Gly Asp Ser Leu Ser Met Arg
1               5                   10
```

```
<210> SEQ ID NO 247
<211> LENGTH: 20
<212> TYPE: PRT
<213> ORGANISM: Homo sapiens

<400> SEQUENCE: 247

Leu Ile Gly Arg Met Ala Thr Ala Leu Glu Arg Leu Thr Gly Leu Glu
1               5                   10                  15
Arg Ala Glu Ser
            20

<210> SEQ ID NO 248
<211> LENGTH: 14
<212> TYPE: PRT
<213> ORGANISM: Homo sapiens

<400> SEQUENCE: 248

Asp Ile Pro Leu Arg Arg Gly Arg Lys Thr Thr Lys Lys Arg
1               5                   10

<210> SEQ ID NO 249
<211> LENGTH: 14
<212> TYPE: PRT
<213> ORGANISM: Homo sapiens

<400> SEQUENCE: 249

His Arg Leu Ile Pro Leu Gly Arg Lys Ile Tyr Glu Phe Tyr
1               5                   10

<210> SEQ ID NO 250
<211> LENGTH: 14
<212> TYPE: PRT
<213> ORGANISM: Homo sapiens

<400> SEQUENCE: 250

Glu Glu Asn Glu Ala Lys Gly Arg Arg Ala Thr Ile Ala Ile
1               5                   10

<210> SEQ ID NO 251
<211> LENGTH: 8
<212> TYPE: PRT
<213> ORGANISM: bacteriophage T7

<400> SEQUENCE: 251

Asp Tyr Lys Asp Asp Asp Asp Lys
1               5

<210> SEQ ID NO 252
<211> LENGTH: 733
<212> TYPE: DNA
<213> ORGANISM: homo sapiens

<400> SEQUENCE: 252
gggatccgga gcccaaatct tctgacaaaa ctcacacatg cccaccgtgc ccagcacctg      60
aattcgaggg tgcaccgtca gtcttcctct tccccccaaa acccaaggac accctcatga     120
tctcccggac tcctgaggtc acatgcgtgg tggtggacgt aagccacgaa gaccctgagg     180
tcaagttcaa ctggtacgtg gacggcgtgg aggtgcataa tgccaagaca aagccgcggg     240
aggagcagta caacagcacg taccgtgtgg tcagcgtcct caccgtcctg caccaggact     300
ggctgaatgg caaggagtac aagtgcaagg tctccaacaa agcccctccca accccatcg     360 agaaaaccat ctccaaagcc aaagggcagc ccgagaacc acaggtgtac accctgcccc     420
```

```
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                      733

<210> SEQ ID NO 253
<211> LENGTH: 33
<212> TYPE: DNA
<213> ORGANISM: homo sapiens

<400> SEQUENCE: 253
atgtatgtgc gagtatcttt tgatacaaaa cct                                 33

<210> SEQ ID NO 254
<211> LENGTH: 24
<212> TYPE: DNA
<213> ORGANISM: homo sapiens

<400> SEQUENCE: 254
agccaaatca atgtcctggt gtcc                                           24

<210> SEQ ID NO 255
<211> LENGTH: 24
<212> TYPE: DNA
<213> ORGANISM: homo sapiens

<400> SEQUENCE: 255
gaaggacacc aggacattga tttg                                           24

<210> SEQ ID NO 256
<211> LENGTH: 24
<212> TYPE: DNA
<213> ORGANISM: homo sapiens

<400> SEQUENCE: 256
gtcactcctg aagggctggt cttg                                           24

<210> SEQ ID NO 257
<211> LENGTH: 24
<212> TYPE: DNA
<213> ORGANISM: homo sapiens

<400> SEQUENCE: 257
caagaccagc ccttcaggag tgac                                           24

<210> SEQ ID NO 258
<211> LENGTH: 23
<212> TYPE: DNA
<213> ORGANISM: homo sapiens

<400> SEQUENCE: 258
cgcccgataa ggtcttccag ctg                                            23

<210> SEQ ID NO 259
<211> LENGTH: 23
<212> TYPE: DNA
<213> ORGANISM: homo sapiens
```

-continued

<400> SEQUENCE: 259
cagctggaag accttatcgg gcg                                      23

<210> SEQ ID NO 260
<211> LENGTH: 24
<212> TYPE: DNA
<213> ORGANISM: homo sapiens

<400> SEQUENCE: 260
ttaggtgtgc ttgctttcaa agct                                     24

<210> SEQ ID NO 261
<211> LENGTH: 20
<212> TYPE: DNA
<213> ORGANISM: homo sapiens

<400> SEQUENCE: 261
cgcagctgga agaccttatc                                          20

<210> SEQ ID NO 262
<211> LENGTH: 20
<212> TYPE: DNA
<213> ORGANISM: homo sapiens

<400> SEQUENCE: 262
aagctgctct gacggacaat                                          20

<210> SEQ ID NO 263
<211> LENGTH: 24
<212> TYPE: DNA
<213> ORGANISM: homo sapiens

<400> SEQUENCE: 263
agggaagggg aagtggttga tctc                                     24

<210> SEQ ID NO 264
<211> LENGTH: 39
<212> TYPE: DNA
<213> ORGANISM: Homo sapiens

<400> SEQUENCE: 264
gcagcagcgg ccgcctcaag gtaattctgg gaattctac                     39

<210> SEQ ID NO 265
<211> LENGTH: 37
<212> TYPE: DNA
<213> ORGANISM: Homo sapiens

<400> SEQUENCE: 265
gcagcagtcg acggtgtgct tgctttcaaa gctttgg                       37

<210> SEQ ID NO 266
<211> LENGTH: 36
<212> TYPE: DNA
<213> ORGANISM: Homo sapiens

<400> SEQUENCE: 266
gcagcagcgg ccgcatgtat gtgcgagtat cttttg                        36

<210> SEQ ID NO 267
<211> LENGTH: 37
<212> TYPE: DNA
<213> ORGANISM: Homo sapiens -continued

<400> SEQUENCE: 267
gcagcagtcg acgttaaaga cagcaatgag gaggttg　　　　　　　　　　　37

<210> SEQ ID NO 268
<211> LENGTH: 36
<212> TYPE: DNA
<213> ORGANISM: Homo sapiens

<400> SEQUENCE: 268
gcagcagcgg ccgcatgtat gtgcgagtat cttttg　　　　　　　　　　　　36

<210> SEQ ID NO 269
<211> LENGTH: 37
<212> TYPE: DNA
<213> ORGANISM: Homo sapiens

<400> SEQUENCE: 269
gcagcagtcg acattagatg agttgaaccg atcatcc　　　　　　　　　　　37

<210> SEQ ID NO 270
<211> LENGTH: 23
<212> TYPE: DNA
<213> ORGANISM: Homo sapiens

<400> SEQUENCE: 270
gcttagcttt agcctggaac aga　　　　　　　　　　　　　　　　　　　23

<210> SEQ ID NO 271
<211> LENGTH: 21
<212> TYPE: DNA
<213> ORGANISM: Homo sapiens

<400> SEQUENCE: 271
gccactgttg cccgtaaata a　　　　　　　　　　　　　　　　　　　　21

<210> SEQ ID NO 272
<211> LENGTH: 21
<212> TYPE: DNA
<213> ORGANISM: Homo sapiens

<400> SEQUENCE: 272
tcgacatcgc tcgcagccag a　　　　　　　　　　　　　　　　　　　　21

<210> SEQ ID NO 273
<211> LENGTH: 20
<212> TYPE: DNA
<213> ORGANISM: Homo sapiens

<400> SEQUENCE: 273
ccacctgatg ggcatgttct　　　　　　　　　　　　　　　　　　　　　20

<210> SEQ ID NO 274
<211> LENGTH: 21
<212> TYPE: DNA
<213> ORGANISM: Homo sapiens

<400> SEQUENCE: 274
cggcttgcca tcaaagacat a　　　　　　　　　　　　　　　　　　　　21

<210> SEQ ID NO 275
<211> LENGTH: 22
<212> TYPE: DNA

-continued

```
<213> ORGANISM: Homo sapiens

<400> SEQUENCE: 275
ccgcaccatt cgcatgatgg ag                                              22

<210> SEQ ID NO 276
<211> LENGTH: 26
<212> TYPE: DNA
<213> ORGANISM: Artificial Sequence
<220> FEATURE:
<223> OTHER INFORMATION: Synthesized Oligonucleotide.

<400> SEQUENCE: 276
ccauggacag agaugagaag cuuggu                                          26

<210> SEQ ID NO 277
<211> LENGTH: 26
<212> TYPE: DNA
<213> ORGANISM: Artificial Sequence
<220> FEATURE:
<223> OTHER INFORMATION: Synthesized Oligonucleotide.

<400> SEQUENCE: 277
aguggucccg uugucagcca gaaugu                                          26

<210> SEQ ID NO 278
<211> LENGTH: 26
<212> TYPE: DNA
<213> ORGANISM: Artificial Sequence
<220> FEATURE:
<223> OTHER INFORMATION: Synthesized Oligonucleotide.

<400> SEQUENCE: 278
ccuuccacua ugagugccac cacagu                                          26

<210> SEQ ID NO 279
<211> LENGTH: 26
<212> TYPE: DNA
<213> ORGANISM: Artificial Sequence
<220> FEATURE:
<223> OTHER INFORMATION: Synthesized Oligonucleotide.

<400> SEQUENCE: 279
guguccuucu gaucccaucc gaaauu                                          26

<210> SEQ ID NO 280
<211> LENGTH: 26
<212> TYPE: DNA
<213> ORGANISM: Artificial Sequence
<220> FEATURE:
<223> OTHER INFORMATION: Synthesized Oligonucleotide.

<400> SEQUENCE: 280
ugguauggcc ggacaacauc ucuucu                                          26

<210> SEQ ID NO 281
<211> LENGTH: 4635
<212> TYPE: DNA
<213> ORGANISM: Homo sapiens

<400> SEQUENCE: 281
atgtatgtgc gagtatcttt tgatacaaaa cctgatctcc tcttacacct gatgaccaag     60
gaatggcagt tggagcttcc caagcttctc atctctgtcc atgggggcct gcagaacttt    120
gaactccagc caaaactcaa gcaagtcttt gggaaagggc tcatcaaagc agcaatgaca    180
```

-continued

```
actggagcgt ggatattcac tggaggggtt aacacaggtg ttattcgtca tgttggcgat    240
gccttgaagg atcatgcctc taagtctcga ggaaagatat gcaccatagg tattgccccc    300
tggggaattg tggaaaacca ggaggacctc attggaagag atgttgtccg gccataccag    360
accatgtcca atcccatgag caagctcact gttctcaaca gcatgcattc ccacttcatt    420
ctggctgaca acgggaccac tggaaaatat ggagcagagg tgaaacttcg aagcaaactg    480
gaaaagcata tttcactcca gaagataaac acaagaatcg gtcaaggtgt tcctgtggtg    540
gcactcatag tggaaggagg acccaatgtg atctcgattg ttttggagta ccttcgagac    600
acccctcccg tgccagtggt tgtctgtgat gggagtggac gggcatcgga catcctggcc    660
tttgggcata atactcaga agaaggcgga ctgataaatg aatctttgag ggaccagctg    720
ttggtgacta tacagaagac tttcacatac actcgaaccc aagctcagca tctgttcatc    780
atcctcatgg agtgcatgaa gaagaaggaa ttgattacgg tatttcggat gggatcagaa    840
ggacaccagg acattgattt ggctatcctg acagctttac tcaaaggagc caatgcctcg    900
gccccagacc aactgagctt agctttagcc tggaacagag tcgacatcgc tcgcagccag    960 atctttatt acgggcaaca gtggccggtg ggatctctgg agcaagccat gttggatgcc   1020
ttagttctgg acagagtgga ttttgtgaaa ttactcatag agaatggagt aagcatgcac   1080
cgttttctca ccatctccag actagaggaa ttgtacaata cgagacatgg gccctcaaat   1140
acattgtacc acttggtcag ggatgtcaaa aaggggaacc tgcccccaga ctacagaatc   1200
agcctgattg acatcggcct ggtgatcgag tacctgatgg cgggggctta tcgctgcaac   1260
tacacgcgca agcgcttccg gaccctctac cacaacctct tcggccccaa gagggatgat   1320
attcccttga ggcgaggaag aaagacaacc aagaaacgtg aagaagaggt ggacattgac   1380
ttggatgatc ctgagatcaa ccacttcccc ttcccttttcc atgagctcat ggtgtgggct   1440
gttctcatga agcggcagaa gatggccctg ttcttctggc agcacggtga ggaggccatg   1500
gccaaggccc tggtggcctg caagctctgc aaagccatgg ctcatgaggc ctctgagaac   1560
gacatggttg acgacatttc ccaggagctg aatcacaatt ccagagactt ggccagctg    1620 gctgtggagc tcctggacca gtcctacaag caggacgaac agctggccat gaaactgctg   1680
acgtatgagc tgaagaactg gagcaacgcc acgtgcctgc agcttgccgt ggctgccaaa   1740
caccgcgact tcatcgcgca cacgtgcagc cagatgctgc tcaccgacat gtggatgggc   1800
cggctccgca tgcgcaagaa ctcaggcctc aaggtaattc tgggaattct acttcctcct   1860
tcaattctca gcttggagtt caagaacaaa gacgacatgc cctatatgtc tcaggcccag   1920
gaaatccacc tccaagagaa ggaggcagaa gaaccagaga gcccacaaa ggaaaaagag    1980 gaagaggaca tggagctcac agcaatgttg gacgaaaaca acgggggagtc ctccaggaag   2040 aaggatgaag aggaagttca gagcaagcac cggttaatcc ccctcggcag aaaaatctat   2100
gaattctaca atgcacccat cgtgaagttc tggttctaca cactggcgta tatcggatac   2160
ctgatgctct tcaactatat cgtgttagtg aagatggaac gctggccgtc cacccaggaa   2220
tggatcgtaa tctcctatat tttcacccct ggaatagaaa agatgagaga gattctgatg   2280
tcagagccag ggaagttgct acagaaagtg aaggtatggc tgcaggagta ctggaatgtc   2340
acggacctca tcgccatcct tctgtttttct gtcggaatga tccttcgtct ccaagaccag   2400
cccttcagga gtgacgggag ggtcatctac tgcgtgaaca tcatttactg gtatatccgt   2460
ctcctagaca tcttcggcgt gaacaagtat ttgggcccgt atgtaatgat gattggaaaa   2520
```

```
atgatgatag acatgatgta ctttgtcatc attatgctgg tggttctgat gagctttggg    2580
gtcgccaggc aagccatcct tttcccaat gaggagccat catggaaact ggccaagaac     2640
atcttctaca tgccctattg gatgattat gggggaagtgt ttgcggacca gatagaccct    2700
ccctgtggac agaatgagac ccgagaggat ggtaaaataa tccagctgcc tccctgcaag    2760
acaggagctt ggatcgtgcc ggccatcatg gcctgctacc tcttagtggc aaacatcttg    2820
ctggtcaacc tcctcattgc tgtctttaac aatacatttt ttgaagtaaa atcgatatcc    2880
aaccaagtct ggaagtttca gaggtatcag ctcatcatga ctttccatga aaggccagtt    2940
ctgcccccac cactgatcat cttcagccac atgaccatga tattccagca cctgtgctgc    3000
cgatggagga aacacgagag cgacccggat gaaagggact acggcctgaa actcttcata    3060
accgatgatg agctcaagaa agtacatgac tttgagagc aatgcataga agaatacttc    3120
agagaaaagg atgatcggtt caactcatct aatgatgaga ggatacgggt gacttcagaa    3180
agggtggaga acatgtctat gcggctggag gaagtcaacg agagagagca ctccatgaag    3240
gcttcactcc agaccgtgga catccggctg gcgcagctgg aagacttat cgggcgcatg    3300
gccacggccc tggagcgcct gacaggtctg gagcgggccg agtccaacaa aatccgctcg    3360
aggacctcgt cagactgcac ggacgccgcc tacattgtcc gtcagagcag cttcaacagc    3420
caggaaggga acaccttcaa gctccaagag agtatagacc ctgcaggtga ggagaccatg    3480
tccccaactt ctccaaccct taatgccccgt atgcgaagcc attctttcta ttcagtcaat    3540
atgaaagaca aggtggtat agaaaagttg gaaagtattt ttaaagaaag gtccctgagc    3600
ctacaccggg ctactagttc ccactctgta gcaaaagaac ccaaagctcc tgcagcccct    3660
gccaacacct tggccattgt tcctgattcc agaagaccat catcgtgtat agacatctat    3720
gtctctgcta tggatgagct ccactgtgat atagaccctc tggacaattc cgtgaacatc    3780
cttgggctag gcgagccaag cttttcaact ccagtacctt ccacagcccc ttcaagtagt    3840
gcctatgcaa cacttgcacc cacagacaga cctccaagcc ggagcattga tttgaggac    3900
atcacctcca tggacactag atcttttttct tcagactaca cccacctccc agaatgccaa    3960
aaccctggg actcagagcc tccgatgtac cacaccattg agcgttccaa aagtagccgc    4020
tacctagcca ccacaccctt tcttctagaa gaggctccca ttgtgaaatc tcatagcttt    4080
atgttttccc cctcaaggag ctattatgcc aactttgggg tgcctgtaaa aacagcagaa    4140
tacacaagta ttacagactg tattgacaca aggtgtgtca atgcccctca agcaattgcg    4200
gacagagctg ccttccctgg aggtcttgga gacaaagtgg aggacttaac ttgctgccat    4260
ccagagcgag aagcagaact gagtcacccc agctctgaca gtgaggagaa tgaggccaaa    4320
ggccgcagag ccaccattgc aatatcctcc caggagggtg ataactcaga gagaaccctg    4380
tccaacaaca tcactgttcc caagatagag cgcgccaaca gctactcggc agaggagcca    4440
agtgcgccat atgcacacac caggaagagc ttctccatca gtgacaaact cgacaggcag    4500
cggaacacag caagcctgca aaatcccttc cagagaagca agtcctccaa gccggagggc    4560
cgaggggaca gcctgtccat gaggagactg tccagaacat cggctttcca aagctttgaa    4620
agcaagcaca cctaa                                                      4635
```

<210> SEQ ID NO 282
<211> LENGTH: 4740
<212> TYPE: DNA
<213> ORGANISM: Homo sapiens

<400> SEQUENCE: 282

```
atgtatgtgc gagtatcttt tgatacaaaa cctgatctcc tcttacacct gatgaccaag    60
gaatggcagt tggagcttcc caagcttctc atctctgtcc atgggggcct gcagaacttt   120
gaactccagc caaaactcaa gcaagtcttt gggaaagggc tcatcaaagc agcaatgaca   180
actggagcgt ggatattcac tggagggtt aacacaggtg ttattcgtca tgttggcgat   240
gccttgaagg atcatgcctc taagtctcga ggaaagatat gcaccatagg tattgccccc   300
tgggaattg tggaaaacca ggaggacctc attggaagag atgttgtccg gccataccag   360
accatgtcca atcccatgag caagctcact gttctcaaca gcatgcattc ccacttcatt   420
ctggctgaca acgggaccac tggaaaatat ggagcagagg tgaaacttcg aagacaactg   480
gaaaagcata tttcactcca gaagataaac acaagatgcc tgccgttttt ctctcttgac   540
tcccgcttgt tttattcatt tgggggtagt tgccagctag actcagttgg aatcggtcaa   600
ggtgttcctg tggtggcact catagtgaa ggaggaccca atgtgatctc gattgttttg   660
gagtaccttc gagacacccc tcccgtgcca gtggttgtct gtgatgggag tggacgggca   720
tcggacatcc tggcctttgg gcataaatac tcagaagaag gcggactgat aaatgaatct   780
ttgagggacc agctgttggt gactatacag aagactttca catacactcg aacccaagct   840
cagcatctgt tcatcatcct catggagtgc atgaagaaga aggaattgat tacggtattt   900
cggatgggat cagaaggaca ccaggacatt gatttggcta tcctgacagc tttactcaaa   960
ggagccaatg cctcggcccc agaccaactg agcttagctt tagcctggaa cagagtcgac  1020
atcgctcgca gccagatctt tatttacggg caacagtggc cggtgggatc tctggagcaa  1080
gccatgttgg atgccttagt tctggacaga gtggatttg tgaaattact catagagaat  1140
ggagtaagca tgcaccgttt tctcaccatc tccagactag aggaattgta caatacgaga  1200
catgggccct caaatacatt gtaccacttg gtcagggatg tcaaaaaggg gaacctgccc  1260
ccagactaca gaatcagcct gattgacatc ggcctggtga tcgagtacct gatgggcggg  1320
gcttatcgct gcaactacac gcgcaagcgc ttccggaccc tctaccacaa cctcttcggc  1380
cccaagaggc ccaaagcctt gaaactgctg gaatgaggg atgatattcc cttgaggcga  1440
ggaagaaaga caaccaagaa acgtgaagaa gaggtggaca ttgacttgga tgatcctgag  1500
atcaaccact tccccttccc tttccatgag ctcatggtgt gggctgttct catgaagcgg  1560
cagaagatgg ccctgttctt ctggcagcac ggtgaggagg ccatggccaa ggccctggtg  1620
gcctgcaagc tctgcaaagc catggctcat gaggcctctg agaacgacat ggttgacgac  1680
atttcccagg agctgaatca caattccaga gactttggcc agctggctgt ggagctcctg  1740
gaccagtcct acaagcagga cgaacagctg gccatgaaac tgctgacgta tgagctgaag  1800
aactggagca acgccacgtg cctgcagctt gccgtggctg ccaaacaccg cgacttcatc  1860
gcgcacacgt gcagccagat gctgctcacc gacatgtgga tgggccggct ccgcatgcgc  1920
aagaactcag gcctcaaggt aattctggga attctacttc ctccttcaat tctcagcttg  1980
gagttcaaga caaagacga catgcccttat atgtctcagg cccaggaaat ccacctccaa  2040
gagaaggagg cagaagaacc agagaagccc acaaaggaaa agaggaaga ggacatggag  2100
ctcacagcaa tgttgggacg aaacaacggg gagtcctcca ggaagaagga tgaagaggaa  2160
gttcagagca agcaccggtt aatccccctc ggcagaaaaa tctatgaatt ctacaatgca  2220
cccatcgtga agttctggtt ctacacactg cgctatatcg ataccctgat gctcttcaac  2280
tatatcgtgt tagtgaagat ggaacgctgg ccgtccaccc aggaatggat cgtaatctcc  2340
```

```
tatattttca ccctgggaat agaaaagatg agagagattc tgatgtcaga gccagggaag    2400
ttgctacaga aagtgaaggt atggctgcag gagtactgga atgtcacgga cctcatcgcc    2460
atccttctgt tttctgtcgg aatgatcctt cgtctccaag accagcccct caggagtgac    2520
gggagggtca tctactgcgt gaacatcatt tactggtata tccgtctcct agacatcttc    2580
ggcgtgaaca agtatttggg cccgtatgta atgatgattg gaaaaatgat gatagacatg    2640
atgtactttg tcatcattat gctggtggtt ctgatgagct ttggggtcgc caggcaagcc    2700
atccttttc  ccaatgagga gccatcatgg aaactggcca gaacatcttc ctacatgccc    2760
tattggatga tttatgggga agtgtttgcg gaccagatag accctccctg tggacagaat    2820
gagacccgag aggatggtaa ataatccag ctgcctccct gcaagacagg agcttggatc     2880
gtgccggcca tcatggcctg ctacctctta gtggcaaaca tcttgctggt caacctcctc    2940
attgctgtct ttaacaatac attttttgaa gtaaaatcga tatccaacca agtctggaag    3000
tttcagaggt atcagctcat catgactttc catgaaaggc cagttctgcc cccaccactg    3060
atcatcttca gccacatgac catgatattc cagcacctgt gctgccgatg gaggaaacac    3120
gagagcgacc cggatgaaag ggactacggc ctgaaactct tcataaccga tgatgagctc    3180
aagaaagtac atgactttga agagcaatgc atagaagaat acttcagaga aaaggatgat    3240
cggttcaact catctaatga tgagaggata cgggtgactt cagaaagggt ggagaacatg    3300
tctatgcggc tggaggaagt caacgagaga gagcactcca tgaaggcttc actccagacc    3360
gtggacatcc ggctggcgca gctggaagac cttatcgggc gcatggccac ggccctggag    3420
cgcctgacag gtctggagcg ggccgagtcc aacaaaatcc gctcgaggac ctcgtcagac    3480
tgcacggacg ccgcctacat tgtccgtcag agcagcttca acagccagga agggaacacc    3540
ttcaagctcc aagagagtat agaccctgca ggtgaggaga ccatgtcccc aacttctcca    3600
accttaatgc cccgtatgcg aagccattct ttctattcag tcaatatgaa agacaaaggt    3660
ggtatagaaa agttggaaag tatttttaaa gaaaggtccc tgagcctaca ccgggctact    3720
agttcccact ctgtagcaaa agaacccaaa gctcctgcag cccctgccaa caccttggcc    3780
attgttcctg attccagaag accatcatcg tgtatagaca tctatgtctc tgctatggat    3840
gagctccact gtgatataga ccctctggac aattccgtga acatccttgg gctaggcgag    3900
ccaagctttt caactccagt accttccaca gccccttcaa gtagtgccta tgcaacactt    3960
gcacccacag acagacctcc aagccggagc attgattttg aggacatcac ctccatggac    4020
actagatctt tttcttcaga ctacacccac ctcccagaat gccaaaaccc ctgggactca    4080
gagcctccga tgtaccacac cattgagcgt tccaaaagta gccgctacct agccaccaca    4140
cccttttcttc tagaagaggc tcccattgtg aaatctcata gctttatgtt ttccccctca    4200
aggagctatt atgccaactt tgggggtgcct gtaaaaacag cagaatacac aagtattaca    4260
gactgtattg acacaaggtg tgtcaatgcc cctcaagcat tgcggacag agctgccttc    4320
cctggaggtc ttgagacaa agtggaggac ttaacttgct gccatccaga gcgagaagca    4380
gaactgagtc accccagctc tgacagtgag gagaatgagg ccaaaggccg cagagccacc    4440
attgcaatat cctcccagga gggtgataac tcagagagaa ccctgtccaa caacatcact    4500
gttcccaaga tagagcgcgc caacagctac tcggcagagg agccaagtgc gccatatgca    4560
cacaccagga agagcttctc catcagtgac aaaactcgaca ggcagcggaa cacagcaagc    4620
ctgcaaaatc ccttccagag aagcaagtcc tccaagccgg agggcgagg gacagcctg     4680
tccatgagga gactgtccag aacatcggct ttccaaagct ttgaaagcaa gcacacctaa    4740
```

<210> SEQ ID NO 283
<211> LENGTH: 988
<212> TYPE: PRT
<213> ORGANISM: Homo sapiens

<400> SEQUENCE: 283

```
Met Lys Leu Leu Thr Tyr Glu Leu Lys Asn Trp Ser Asn Ala Thr Cys
1               5                   10                  15

Leu Gln Leu Ala Val Ala Ala Lys His Arg Asp Phe Ile Ala His Thr
            20                  25                  30

Cys Ser Gln Met Leu Leu Thr Asp Met Trp Met Gly Arg Leu Arg Met
        35                  40                  45

Arg Lys Asn Ser Gly Leu Lys Val Ile Leu Gly Ile Leu Leu Pro Pro
    50                  55                  60

Ser Ile Leu Ser Leu Glu Phe Lys Asn Lys Asp Asp Met Pro Tyr Met
65                  70                  75                  80

Ser Gln Ala Gln Glu Ile His Leu Gln Glu Lys Ala Glu Glu Pro
            85                  90                  95

Glu Lys Pro Thr Lys Glu Lys Glu Glu Asp Met Glu Leu Thr Ala
            100                 105                 110

Met Leu Gly Arg Asn Asn Gly Glu Ser Ser Arg Lys Lys Asp Glu Glu
        115                 120                 125

Glu Val Gln Ser Lys His Arg Leu Ile Pro Leu Gly Arg Lys Ile Tyr
    130                 135                 140

Glu Phe Tyr Asn Ala Pro Ile Val Lys Phe Trp Phe Tyr Thr Leu Ala
145                 150                 155                 160

Tyr Ile Gly Tyr Leu Met Leu Phe Asn Tyr Ile Val Leu Val Lys Met
                165                 170                 175

Glu Arg Trp Pro Ser Thr Gln Glu Trp Ile Val Ile Ser Tyr Ile Phe
            180                 185                 190

Thr Leu Gly Ile Glu Lys Met Arg Glu Ile Leu Met Ser Glu Pro Gly
        195                 200                 205

Lys Leu Leu Gln Lys Val Lys Val Trp Leu Gln Glu Tyr Trp Asn Val
    210                 215                 220

Thr Asp Leu Ile Ala Ile Leu Leu Phe Ser Val Gly Met Ile Leu Arg
225                 230                 235                 240

Leu Gln Asp Gln Pro Phe Arg Ser Asp Gly Arg Val Ile Tyr Cys Val
            245                 250                 255

Asn Ile Ile Tyr Trp Tyr Ile Arg Leu Leu Asp Ile Phe Gly Val Asn
            260                 265                 270

Lys Tyr Leu Gly Pro Tyr Val Met Met Ile Gly Lys Met Met Ile Asp
        275                 280                 285

Met Met Tyr Phe Val Ile Ile Met Leu Val Val Leu Met Ser Phe Gly
    290                 295                 300

Val Ala Arg Gln Ala Ile Leu Phe Pro Asn Glu Glu Pro Ser Trp Lys
305                 310                 315                 320

Leu Ala Lys Asn Ile Phe Tyr Met Pro Tyr Trp Met Ile Tyr Gly Glu
                325                 330                 335

Val Phe Ala Asp Gln Ile Asp Pro Pro Cys Gly Gln Asn Glu Thr Arg
            340                 345                 350

Glu Asp Gly Lys Ile Ile Gln Leu Pro Pro Cys Lys Thr Gly Ala Trp
        355                 360                 365

Ile Val Pro Ala Ile Met Ala Cys Tyr Leu Leu Val Ala Asn Ile Leu
```

-continued

```
            370             375             380
Leu Val Asn Leu Leu Ile Ala Val Phe Asn Asn Thr Phe Phe Glu Val
385                 390                 395                 400

Lys Ser Ile Ser Asn Gln Val Trp Lys Phe Gln Arg Tyr Gln Leu Ile
                405                 410                 415

Met Thr Phe His Glu Arg Pro Val Leu Pro Pro Leu Ile Ile Phe
            420                 425                 430

Ser His Met Thr Met Ile Phe Gln His Leu Cys Cys Arg Trp Arg Lys
        435                 440                 445

His Glu Ser Asp Pro Asp Glu Arg Asp Tyr Gly Leu Lys Leu Phe Ile
450                 455                 460

Thr Asp Asp Glu Leu Lys Lys Val His Asp Phe Glu Glu Gln Cys Ile
465                 470                 475                 480

Glu Glu Tyr Phe Arg Glu Lys Asp Asp Arg Phe Asn Ser Ser Asn Asp
                485                 490                 495

Glu Arg Ile Arg Val Thr Ser Glu Arg Val Glu Asn Met Ser Met Arg
                500                 505                 510

Leu Glu Glu Val Asn Glu Arg Glu His Ser Met Lys Ala Ser Leu Gln
            515                 520                 525

Thr Val Asp Ile Arg Leu Ala Gln Leu Glu Asp Leu Ile Gly Arg Met
        530                 535                 540

Ala Thr Ala Leu Glu Arg Leu Thr Gly Leu Glu Arg Ala Glu Ser Asn
545                 550                 555                 560

Lys Ile Arg Ser Arg Thr Ser Ser Asp Cys Thr Asp Ala Ala Tyr Ile
                565                 570                 575

Val Arg Gln Ser Ser Phe Asn Ser Gln Glu Gly Asn Thr Phe Lys Leu
                580                 585                 590

Gln Glu Ser Ile Asp Pro Ala Gly Glu Glu Thr Met Ser Pro Thr Ser
            595                 600                 605

Pro Thr Leu Met Pro Arg Met Arg Ser His Ser Phe Tyr Ser Val Asn
        610                 615                 620

Met Lys Asp Lys Gly Gly Ile Glu Lys Leu Glu Ser Ile Phe Lys Glu
625                 630                 635                 640

Arg Ser Leu Ser Leu His Arg Ala Thr Ser Ser His Ser Val Ala Lys
                645                 650                 655

Glu Pro Lys Ala Pro Ala Ala Pro Ala Asn Thr Leu Ala Ile Val Pro
                660                 665                 670

Asp Ser Arg Arg Pro Ser Ser Cys Ile Asp Ile Tyr Val Ser Ala Met
            675                 680                 685

Asp Glu Leu His Cys Asp Ile Asp Pro Leu Asp Asn Ser Val Asn Ile
        690                 695                 700

Leu Gly Leu Gly Glu Pro Ser Phe Ser Thr Pro Val Pro Ser Thr Ala
705                 710                 715                 720

Pro Ser Ser Ser Ala Tyr Ala Thr Leu Ala Pro Thr Asp Arg Pro Pro
                725                 730                 735

Ser Arg Ser Ile Asp Phe Glu Asp Ile Thr Ser Met Asp Thr Arg Ser
                740                 745                 750

Phe Ser Ser Asp Tyr Thr His Leu Pro Glu Cys Gln Asn Pro Trp Asp
            755                 760                 765

Ser Glu Pro Pro Met Tyr His Thr Ile Glu Arg Ser Lys Ser Ser Arg
        770                 775                 780

Tyr Leu Ala Thr Thr Pro Phe Leu Leu Glu Glu Ala Pro Ile Val Lys
785                 790                 795                 800
```

-continued

```
Ser His Ser Phe Met Phe Ser Pro Ser Arg Ser Tyr Tyr Ala Asn Phe
            805                 810                 815

Gly Val Pro Val Lys Thr Ala Glu Tyr Thr Ser Ile Thr Asp Cys Ile
            820                 825                 830

Asp Thr Arg Cys Val Asn Ala Pro Gln Ala Ile Ala Asp Arg Ala Ala
            835                 840                 845

Phe Pro Gly Gly Leu Gly Asp Lys Val Glu Asp Leu Thr Cys Cys His
            850                 855                 860

Pro Glu Arg Glu Ala Glu Leu Ser His Pro Ser Ser Asp Ser Glu Glu
865                 870                 875                 880

Asn Glu Ala Lys Gly Arg Arg Ala Thr Ile Ala Ile Ser Ser Gln Glu
            885                 890                 895

Gly Asp Asn Ser Glu Arg Thr Leu Ser Asn Asn Ile Thr Val Pro Lys
            900                 905                 910

Ile Glu Arg Ala Asn Ser Tyr Ser Ala Glu Glu Pro Ser Ala Pro Tyr
            915                 920                 925

Ala His Thr Arg Lys Ser Phe Ser Ile Ser Asp Lys Leu Asp Arg Gln
            930                 935                 940

Arg Asn Thr Ala Ser Leu Arg Asn Pro Phe Gln Arg Ser Lys Ser Ser
945                 950                 955                 960

Lys Pro Glu Gly Arg Gly Asp Ser Leu Ser Met Arg Arg Leu Ser Arg
            965                 970                 975

Thr Ser Ala Phe Gln Ser Phe Glu Ser Lys His Asn
            980                 985

<210> SEQ ID NO 284
<211> LENGTH: 6
<212> TYPE: PRT
<213> ORGANISM: Artificial Sequence
<220> FEATURE:
<223> OTHER INFORMATION: TRP Concensus Sequence.
<220> FEATURE:
<221> NAME/KEY: MISC_FEATURE
<222> LOCATION: (1)..(1)
<223> OTHER INFORMATION: wherein "X" equals any amino acid.
<220> FEATURE:
<221> NAME/KEY: MISC_FEATURE
<222> LOCATION: (5)..(5)
<223> OTHER INFORMATION: wherein "X" equals any amino acid.

<400> SEQUENCE: 284

Xaa Trp Lys Phe Xaa Arg
1               5

<210> SEQ ID NO 285
<211> LENGTH: 21
<212> TYPE: DNA
<213> ORGANISM: Homo sapiens

<400> SEQUENCE: 285
cagctggaag accttatcgg g                                          21

<210> SEQ ID NO 286
<211> LENGTH: 24
<212> TYPE: DNA
<213> ORGANISM: Homo sapiens

<400> SEQUENCE: 286
tgggaggtgg gtgtagtctg aaga                                       24
```